(12) United States Patent
Short et al.

(10) Patent No.: US 10,532,995 B2
(45) Date of Patent: Jan. 14, 2020

(54) SUBSTITUTED PYRAZOLE COMPOUNDS AS SERINE PROTEASE INHIBITORS

(71) Applicant: VERSEON CORPORATION, Fremont, CA (US)

(72) Inventors: Kevin Michael Short, Fremont, CA (US); Maria de los Angeles Estiarte-Martinez, Fremont, CA (US); David Ben Kita, Fremont, CA (US); Timothy Philip Shiau, Fremont, CA (US)

(73) Assignee: VERSEON CORPORATION, Fremont, CA (US)

( * ) Notice: Subject to any disclaimer, the term of this patent is extended or adjusted under 35 U.S.C. 154(b) by 0 days.

(21) Appl. No.: 15/553,540

(22) PCT Filed: Feb. 29, 2016

(86) PCT No.: PCT/US2016/020116
§ 371 (c)(1),
(2) Date: Aug. 24, 2017

(87) PCT Pub. No.: WO2016/138532
PCT Pub. Date: Sep. 1, 2016

(65) Prior Publication Data
US 2018/0237421 A1    Aug. 23, 2018

Related U.S. Application Data

(60) Provisional application No. 62/126,424, filed on Feb. 27, 2015.

(51) Int. Cl.
| | | |
|---|---|---|
| *C07D 403/04* | (2006.01) |
| *C07D 409/14* | (2006.01) |
| *C07D 417/14* | (2006.01) |
| *A61K 9/00*   | (2006.01) |
| *A61K 31/4155*| (2006.01) |
| *A61K 31/454* | (2006.01) |
| *A61K 31/4545*| (2006.01) |
| *A61K 31/5377*| (2006.01) |
| *A61K 31/55*  | (2006.01) |
| *A61K 45/06*  | (2006.01) |
| *C07D 401/04* | (2006.01) |
| *C07D 405/04* | (2006.01) |
| *C07D 405/14* | (2006.01) |

(52) U.S. Cl.
CPC .......... *C07D 403/04* (2013.01); *A61K 9/0019* (2013.01); *A61K 9/0048* (2013.01); *A61K 31/4155* (2013.01); *A61K 31/454* (2013.01); *A61K 31/4545* (2013.01); *A61K 31/5377* (2013.01); *A61K 31/55* (2013.01); *A61K 45/06* (2013.01); *C07D 401/04* (2013.01); *C07D 405/04* (2013.01); *C07D 405/14* (2013.01); *C07D 409/14* (2013.01); *C07D 417/14* (2013.01)

(58) Field of Classification Search
CPC ................................................. C07D 403/04
USPC .......................................................... 514/210
See application file for complete search history.

(56) References Cited

U.S. PATENT DOCUMENTS

| | | |
|---|---|---|
| 3,250,761 A | 5/1966 | Schmidt et al. |
| 3,926,999 A | 12/1975 | Poetsch |
| 4,008,249 A | 2/1977 | Fischer et al. |
| 4,160,452 A | 7/1979 | Theeuwes |
| 4,256,108 A | 3/1981 | Theeuwes |
| 4,265,874 A | 5/1981 | Bonsen et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,466,823 A | 11/1995 | Talley et al. |
| 5,547,978 A | 8/1996 | Christensen et al. |
| 5,739,083 A | 4/1998 | Endo et al. |
| 5,753,688 A | 5/1998 | Talley et al. |
| 5,792,761 A | 8/1998 | Fraley et al. |
| 5,902,852 A | 5/1999 | Schulz et al. |
| 5,916,908 A | 6/1999 | Giese et al. |
| 6,114,358 A | 9/2000 | Baucke et al. |
| 6,589,997 B2 | 7/2003 | Pillarisetti et al. |
| 6,962,905 B1 | 11/2005 | Gustafsson |
| 7,429,604 B2 | 9/2008 | Corte et al. |
| 7,625,944 B2 | 12/2009 | Sinha et al. |

(Continued)

FOREIGN PATENT DOCUMENTS

| | | |
|---|---|---|
| CN | 101851207 A | 10/2010 |
| EP | 0246888 A2 | 11/1987 |

(Continued)

OTHER PUBLICATIONS

Miller Keane et al., Miller-Keane Encyclopedia & Dictionary of Medicine, Nursing & Allied Health, 5th Ed. pp. 1651 and 1708. O'Toole (ed.). W.B. Saunders, Philadephia, PA. 1992.
Miura "Transactivation of KDR/Flk-1 by the B2 receptor induces tube formation in human coronary endothelial cells," Hypertension 41(5):1118-1123, published ahead of print Mar. 24, 2003.
Montoya et al., "Regioselective formation of N-alkyl-3,5-pyrazole derived ligands. A synthetic and computational study," Tetrahedron, 61(52). pp. 12377-12385. Dec. 26, 2005.
Moreau et al., "The kallikrein-kinin system: current and future pharmacological targets," Journal of Pharmacological Sciences 99(1):6-38, Sep. 22, 2005.

(Continued)

*Primary Examiner* — Taofiq A Solola
(74) *Attorney, Agent, or Firm* — Davis Wright Tremaine LLP

(57) ABSTRACT

There are provided inter alia multisubstituted aromatic compounds useful for the inhibition of thrombin and/or kallikrein, which compounds include substituted pyrazolyl. There are additionally provided pharmaceutical compositions. There are additionally provided methods of treating and preventing certain diseases or disorders, which diseases or disorders are amenable to treatment or prevention by the inhibition of thrombin and/or kallikrein.

37 Claims, No Drawings

(56) References Cited

U.S. PATENT DOCUMENTS

| | | | |
|---|---|---|---|
| 8,188,045 B2 | 5/2012 | Blair et al. | |
| 9,371,307 B2 | 6/2016 | Freire et al. | |
| 2002/0055639 A1 | 5/2002 | Nebel et al. | |
| 2002/0091116 A1 | 7/2002 | Zhu et al. | |
| 2003/0144309 A1 | 7/2003 | Choon-Moon | |
| 2004/0132726 A1 | 7/2004 | Arora et al. | |
| 2005/0009827 A1 | 1/2005 | Nazare et al. | |
| 2005/0065144 A1 | 3/2005 | Feng et al. | |
| 2005/0203127 A1 | 9/2005 | Cezanne et al. | |
| 2008/0188527 A1 | 8/2008 | Cashman | |
| 2008/0269293 A1 | 10/2008 | Chi et al. | |
| 2008/0275070 A1 | 11/2008 | Liu et al. | |
| 2009/0105253 A1 | 4/2009 | Kubo et al. | |
| 2009/0163545 A1 | 6/2009 | Goldfarb | |
| 2010/0016320 A1 | 1/2010 | Dyckman et al. | |
| 2010/0130474 A1 | 5/2010 | Bothmann et al. | |
| 2010/0210696 A1 | 8/2010 | Nishida et al. | |
| 2011/0071182 A1 | 3/2011 | Seefeld et al. | |
| 2011/0071289 A1 | 3/2011 | Horiuchi et al. | |
| 2012/0110702 A1 | 5/2012 | Yap et al. | |
| 2012/0264798 A1 | 10/2012 | Sinha et al. | |
| 2013/0040950 A1 | 2/2013 | Short et al. | |

FOREIGN PATENT DOCUMENTS

| | | |
|---|---|---|
| EP | 0854723 A1 | 7/1998 |
| EP | 0788358 B1 | 3/2004 |
| JP | S50-117936 A | 9/1975 |
| JP | H01226815 A | 9/1989 |
| JP | H02300173 A | 12/1990 |
| JP | H09059113 A | 3/1997 |
| JP | H10-509708 A | 9/1998 |
| JP | 2003313103 A | 11/2003 |
| JP | 2004231528 A | 8/2004 |
| JP | 2006506340 A | 2/2006 |
| JP | 2006511608 A | 4/2006 |
| JP | 2007506741 A | 3/2007 |
| JP | 2007511485 A | 5/2007 |
| JP | 2007513058 A | 5/2007 |
| JP | 2007530459 A | 11/2007 |
| JP | 2009543818 A | 12/2009 |
| JP | 2011520967 A | 7/2011 |
| JP | 2011529944 A | 12/2011 |
| JP | 2011530548 A | 12/2011 |
| RU | 2221808 C2 | 1/2004 |
| WO | 9605309 A2 | 2/1996 |
| WO | 1996014843 A2 | 5/1996 |
| WO | 1998018792 A1 | 5/1998 |
| WO | 1998025930 A2 | 6/1998 |
| WO | 9828269 A1 | 7/1998 |
| WO | 199842698 A1 | 10/1998 |
| WO | 2000009500 A2 | 2/2000 |
| WO | 00041716 A1 | 7/2000 |
| WO | 2000071536 A1 | 11/2000 |
| WO | 0112189 A1 | 2/2001 |
| WO | 2001019798 A2 | 3/2001 |
| WO | 2001040223 A2 | 6/2001 |
| WO | 2002000651 A2 | 1/2002 |
| WO | 02092573 A2 | 11/2002 |
| WO | 03048155 A1 | 6/2003 |
| WO | 03061682 A1 | 7/2003 |
| WO | 03062206 A2 | 7/2003 |
| WO | 2004000785 A2 | 12/2003 |
| WO | 2004035564 A1 | 4/2004 |
| WO | 2004058721 A2 | 7/2004 |
| WO | 2004058722 A1 | 7/2004 |
| WO | 2004060890 A1 | 7/2004 |
| WO | 2004089911 A1 | 10/2004 |
| WO | 2004098589 A1 | 11/2004 |
| WO | 2004101555 A1 | 11/2004 |
| WO | 2005023761 A2 | 3/2005 |
| WO | 2006074445 A2 | 7/2006 |
| WO | 2006108643 A2 | 10/2006 |
| WO | 2007067836 A2 | 6/2007 |
| WO | 2007129052 A1 | 11/2007 |
| WO | 2007146712 A2 | 12/2007 |
| WO | 2008009638 A2 | 1/2008 |
| WO | 2008016883 A2 | 2/2008 |
| WO | 2008062739 A1 | 5/2008 |
| WO | 2008064265 A2 | 5/2008 |
| WO | 2008079277 A1 | 7/2008 |
| WO | 2008105383 A1 | 9/2008 |
| WO | 2009010560 A1 | 1/2009 |
| WO | 2009041447 A1 | 4/2009 |
| WO | 2008061796 A3 | 7/2009 |
| WO | 2009097141 A1 | 8/2009 |
| WO | 2009100438 A2 | 8/2009 |
| WO | 2009140621 A2 | 11/2009 |
| WO | 2010005580 A2 | 1/2010 |
| WO | 2010020600 A1 | 2/2010 |
| WO | 2010020601 A1 | 2/2010 |
| WO | 2010020602 A1 | 2/2010 |
| WO | 2010127855 A1 | 11/2010 |
| WO | 2011163518 A1 | 12/2011 |
| WO | 2012020820 A1 | 2/2012 |
| WO | 2012065019 A2 | 5/2012 |
| WO | 2012129258 A1 | 9/2012 |
| WO | 2012154880 A1 | 11/2012 |
| WO | 2012158957 A2 | 11/2012 |
| WO | 2013039985 A2 | 3/2013 |
| WO | 2013049591 A2 | 4/2013 |
| WO | 2013101830 A1 | 7/2013 |
| WO | 2013111108 A1 | 8/2013 |
| WO | 2013187462 A1 | 12/2013 |
| WO | 2014111496 A1 | 7/2014 |
| WO | 2014145986 A1 | 9/2014 |
| WO | 2014149139 A2 | 9/2014 |
| WO | 2015087995 A1 | 6/2015 |
| WO | 2015118342 A1 | 8/2015 |
| WO | 2017072020 A1 | 5/2017 |

OTHER PUBLICATIONS

Narita et al., "Protease-activated receptor-1 and platelet-derived growth factor in spinal cord neurons are implicated in neuropathic pain after nerve injury," The Journal of Neuroscience 25(43):10000-10009, Oct. 26, 2005.

Nieman et al., "Oral thrombostatin FM19 inhibits prostate cancer," Thrombosis and Haemostasis, 104(5):1044-1048, published ahead of print Sep. 30, 2010, print publication Nov. 2010.

Nieman et al., "Thrombostatin FM compounds: direct thrombin inhibitors—mechanism of action in vitro and in vivo," Journal of Thrombosis and Haemostasis, 6(5):837-845, published ahead of print Feb. 26, 2008, print publication May 2008.

Olsson et al., "Stroke prevention with the oral direct thrombin inhibitor ximelagatran compared with warfarin in patients with non-valvular atrial fibrillation (SPORTIF III): randomised controlled trial.," Lancet, 362(9397): 1691-1698, Nov. 22, 2003.

Pinto et al., "Discovery of 1-[3-(Aminomethyl)phenyl]-N-[3-fluoro-2'-(methylsulfonyl)- [1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa," Journal of Medicinal Chemistry, 44(4). pp. 566-578. Jan. 24, 2001.

Prezelj et al., "Recent Advances in Serine Protease Inhibitors as Anticoagulant Agents," Current Pharmaceutical Design, 13(3):287-312, Jan. 2007.

Ramalakshmi et al., "Synthesis, Characterization and Biological Screening of Some Novel 1,3,5 Trisubstituted 2-Pyrazolines," Rasayan Journal of Chemistry 2(2):393-396, Apr. 2009.

Reiter et al., "On Triazoles. VI. The acylation of 5-amino-1,2,4-triazoles," Journal of Heterocyclic Chemistry, 24(1). pp. 127-142. Jan. 1987.

Rennéet al., "Plasma kallikrein: Novel functions for an old protease," Thrombosis and Haemostasis 107(6):1012-1013, Jun. 2012.

Saalfrank et al., "Geminale Vinyldiazide, VI. 4,5-Dihydro-1H-tetrazol-5-ylidene aus 3,3-Diazido-2-cyanacrylsäureestern und Hydrazinen, Hydraziden sowie O-substituierten Hydroxylaminen," Chemische Berichte, 122(3). pp. 519-522. Mar. 1989.

Schepetkin et al., "N-Benzoylpyrazoles Are Novel Small-Molecule Inhibitors of Human Neutrophil Elastase," Journal of Medicinal Chemistry, 50(20). pp. 4928-4938. Oct. 4, 2007. Published ahead of print Sep. 12, 2007.

(56) References Cited

OTHER PUBLICATIONS

Schmidt et al., "Thrombin Inhibitors Reduce Intrapulmonary Accumulation of Fibrinogen and Procoagulant Activity of Bronchoalveolar Lavage Fluid During Acute Lung Injury Induced by Pulmonary Overdistention in Newborn Piglets1," Pediatric Research 39(5):798-804, May 1, 1996.
Schmitt et al., "The kallikreins: old proteases with new clinical potentials," Thrombosis and Haemostasis, 110(3):396-398, Sep. 1, 2013.
Schneider et al., "Critical role of kallikrein in hereditary angioedema pathogenesis: a clinical trial of ecallantide, a novel kallikrein inhibitor," Journal of Allergy and Clinical Immunology 120(2):416-422, Aug. 2007.
Schulman et al., "Dabigatran versus warfarin in the treatment of acute venous thromboembolism," New England Journal of Medicine 361(24):2342-52, Dec. 10, 2009.
Silver et al., "Dabigatran Etexilate, an Oral Direct Thrombin Inhibitor, Represses Fibrotic Changes in a Murine Model of Pulmonary Fibrosis." American Journal of Respiratory and Critical Care Medicine 181:A6780, May 2010.
Simiti et al., "Kondensation von 3-Merkapto-5-phenyl-1,2,4-triazole mit Monochloracetaldehyd," Archiv Der Pharmazie, 320(1). pp. 528-534. Jan. 1, 1987.
Smorenburg et al., "The effects of unfractionated heparin on survival in patients with malignancy—a systematic review," Thrombosis and Haemostasis 82(6):1600-1604, Dec. 1, 1999.
Sotiropoulou et al., "Targeting the kallikrein-related peptidases for drug development," Trends in Pharmacological Sciences 33(12):623-634, Dec. 2012.
Stella, "Prodrugs: An Overview and Definition." Pro-drugs as Novel Drug Delivery Systems, vol. 14, Chapter 1. 115 pages. American Chemical Society. Jun. 1, 1975.
STN International File caplus [Online], AN 2007:157737, DN 147:385893, SO: Zhurnal Organichnoi ta Farmatsevtichnoi Kimii 2006, 4(1), p. 32-37, CAS registration No. RN:882238-17-7, 882238-21-3, 882238-25-7, 882239-13-6, 882239-17-0, 882239-21-6.
STN International File Registry [Online]. CAS registration No. RN: 1189909-54-3, 1007171-70-1, 956442-20-9, 956441-56-8, 956375-74-9, 882239-05-6.
STN International Registry File [Online] May 14, 2008, CAS Registration No. RN 1020709-18-5.
Syed et al., "Wet AMD market," Nature Reviews Drug Discovery 11:827-828, Nov. 2012.
Telander, "Inflammation and age-related macular degeneration (AMD)," Seminars in Ophthalmology 26(3):192-197, published online May 24, 2011.
The National Formulary, 14th Ed. American Pharmaceutical Association. Washington, D.C. pp. 1-5. Jul. 1, 1975.
The National Formulary, 14th Ed. American Pharmaceutical Association. Washington, D.C. pp. 6-19. Jul. 1, 1975.
Tripathy et al., "Thrombin, a mediator of cerebrovascular inflammation in AD and hypoxia," Frontiers in Aging Neuroscience 5(19):1-9, May 9, 2013.
Van Noorden et al., "Experimental and clinical effects of anticoagulants on cancer progression," Thrombosis Search, 125 Supplement 2:S77-S79, Apr. 2010.
Varnes et al., "Design, structure-activity relationship, and pharmacokinetic profile of pyrazole-based indoline factor Xa inhibitors," Bioorganic & Medicinal Chemistry Letters 17(1):6481-6488, available online Oct. 1, 2007, print publication Dec. 2007.
Varnes et al., "Structure-activity relationship and pharmacokinetic profile of 5-ketopyrazole factor Xa inhibitors," Bioorganic & Medicinal Chemistry Letters 18(2):749-754, available online Nov. 17, 2007, print publication Jan. 15, 2008.
Vaughan et al., "Protease nexin-1, a potent thrombin inhibitor, is reduced around cerebral blood vessels in Alzheimer's disease," Brain Research 668(1-2):160-170, Dec. 30, 1994.
Wardakhan et al., "Synthesis of novel pyrazole, coumarin, and pyridazine derivatives evaluated as potential antimicrobial and antifungal agents," Journal of the Chilean Chemical Society, 52(2). pp. 1145-1149. Jun. 2007.
Weitz et al., "Direct Thrombin Inhibitors in Acute Coronary Syndromes: Present and Future," Circulation 105(8):1004-1011, Feb. 26, 2002.
Wiedermann et al., "The anti-inflammatory actions of antithrombin—a review," Acta Medica Austriaca 29(3):89-92, Jul. 29, 2002.
Wieland et al., "Approaches in anticoagulation: rationales for target positiong," Current Opinion in Investigational Drugs 4(3):264-271, Mar. 2003.
Wolfram et al., "Update on Pharmacologic Approaches to Prevent Thromboembolism in Atrial Fibrillation: Are Thrombin and Factor Xa Inhibitors the Ultimate Answer?," Current Vascular Pharmacology 9(3):350-357, May 2011.
Wong et al., "Nonpeptide Factor Xa Inhibitors III: Effects of DPC423, an Orally-Active Pyrazole Antithrombotic Agent, on Arterial Thrombosis in Rabbits." The Journal of Pharmacolor and Experimental Therapeutics, 303(3). pp. 993-1000. Dec. 1, 2002.
Wåhlander et al., "Pharmacokinetics, pharmacodynamics and clinical effects of the oral direct thrombin inhibitor ximelagatran in acute treatment of patients with pulmonary embolism and deep vein thrombosis," Thrombosis Research 107(3-4):93-99, Aug. 15, 2002.
Xiong et al., "Discovery and Structure-Activity Relationship of 3-Methoxy- N -(3-(1-methyl-1 H -pyrazol -5-y-1)-4-(2-morpholinoethoxy)phenyl)benzamide (APD791): A Highly Selective 5-Hydroxytryptamine 2A Receptor Inverse Agonist for the Treatment of Arterial Thrombosis," Journal of Medicinal Chemistry 53(11):4412-4421, Jun. 10, 2010, ISSN: 0022-2623, DOI: 10.1021/jm100044a.
Yin et al., "Brain endothelial cells synthesize neurotoxic thrombin in Alzheimer's disease," The American Journal of Pathology 176(4):1600-1606, Apr. 2010.
Young et al., "Selective and dual action orally active inhibitors of thrombin and factor Xa" Bioorganic & Medicinal Chemistry Letters, 17(10). pp. 2927-2930. May 15, 2007.
Yu et al., "Synthesis and biological activities of 5-substituted benzamide triazole," Journal of Central China Normal University, Natural Sciences Edition, 37(4). pp. 503-505. 2003. Accessed from Database CAPLUS. Database accession No. 2004:240714.
Zacharski et al., "Heparin as an anticancer therapeutic," Expert Opinion on Investigational Drugs, 17(7):1029-1037, Jun. 12, 2008.
Surmont et al., "Synthesis of 3-Amino-4-fluoropyrazoles," The Journal of Organic Chemistry 76(10):4105-4111, Apr. 29, 2011.
"Medication Guide: PRADAXA (pra dax' a) (dabigatran etexilate mesylate) capsules," Boehringer Ingelheim Pharmaceuticals, Inc., copyright 2010, FDA approval Sep. 20, 2010, four pages.
Abdel-Salam et al., "A study of unfractionated and low molecular weight heparins in a model of cholestatic liver injury in the rat," Pharmacological Research 51(1):59-67, Jan. 2005.
Abe et al., "Low molecular weight heparin prevents hepatic fibrogenesis caused by carbon tetrachloride in the rat," Journal of Hepatology, 46(2):286-294, Feb. 2007.
Akerblom et al., "Nitrofuryltriazole derivatives as potential urinary tract antibacterial agents," Journal of Medicinal Chemistry, 16(4). pp. 312-319. Apr. 1973.
Akiyama et al., "Thrombin accumulation in brains of patients with Alzheimer's disease," Neuroscience Letters 146 (2):152-154, Nov. 9, 1992.
Akl et al., "Parenteral anticoagulation may prolong the survival of patients with limited small cell lung cancer: a Cochrane systematic review," Journal of Experimental & Clinical Cancer Research 27(4), May 15, 2008, 10 pages.
Albers et al., "Ximelagatran vs warfarin for stroke prevention in patients with nonvalvular atrial fibrillation: a randomized trial," JAMA 293(6):690-8, Feb. 2005.
Albert-Weißenberger et al., "Ischemic stroke and traumatic brain injury: The role of the kallikrein-kinin system," Progress in Neurobiology 101-102:65-82, Feb.-Mar. 2013.

(56) References Cited

OTHER PUBLICATIONS

Altinbas et al., "A randomized clinical trial of combination chemotherapy with and without low-molecular-weight heparin in small cell lung cancer," Journal of Thrombosis and Haemostasis 2(8):1266-1271, Aug. 2004.
Assy et al., "The beneficial effect of aspirin and enoxaparin on fibrosis progression and regenerative activity in a rat model of cirrhosis," Digestive Diseases and Sciences 52(5):1187-1193, May 2007.
Bader, "Kallikrein-Kinin System in Neovascularization," Arteriosclerosis, Thombosis, and Vascular Biology 29(5):617-619, May 2009.
Becker et al., "Why Do So Many Drugs for Alzheimer's Disease Fail in Development? Time for New Methods and New Practices?" Journal of Alzheimer's Disease 15(2):303-325, Oct. 2008.
Beilin et al., "Increased Thrombin Inhibition in Experimental Autoimmune Encephalomyelitis," Journal of Neuroscience Research 79(3):351-359, published online Dec. 16, 2004, print publication Feb. 1, 2005.
Berge et al., "Pharmaceutical Salts," Journal of Pharmaceutical Sciences 66(1):1-19, Jan. 1977.
Bird et al., "Effects of plasma kallikrein deficiency on haemostasis and thrombosis in mice: Murine Ortholog of the Fletcher Trait," Thrombosis and Haemostasis, 107(6):1141-1150, Jun. 2012.
Bogatkevich et al., "Dabigatran, a direct thrombin inhibitor, demonstrates antifibrotic effects on lung fibroblasts," Arthritis & Rheumatism 60(11):3455-3464, published ahead of print Oct. 29, 2009, print publication Nov. 2009.
Brent et al., "Fomepizole for the treatment of ethylene glycol poisoning," The New England Journal of Medicine, 340(11). pp. 832-838. Mar. 18, 1999.
Brown, "A New Era of Anticoagulation: Factor Xa and Direct Thrombin Inhibitors," U.S. Pharmacist 32(3):HS-35-H-48, Mar. 21, 2007, 25 pages.
Calabresi et al., "Section IX Chemotherapy of Neoplastic Diseases Introduction," Goodman & Gilman's The Pharmacological Basis of Therapeutics Tenth Edition: 1381-1388, 2001.
Caliendo et al., "Kallikrein Protease Activated Receptor (PAR) Axis: An Attractive Target for Drug Development," Journal of Medicinal Chemistry 55(15):6669-6686, May 18, 2012.
Calvaruso et al., "Cogaulation and fibrosis in chronic liver disease," Gut 57(12):1722-1727, Dec. 2008.
Chambers et al., "Coagulation cascade proteases and tissue fibrosis," Biochemical Society Transactions 30(2):194-200, Apr. 2002.
Chambers et al., "Procoagulant signalling mechanisms in lung inflammation and fibrosis: novel opportunities for pharmacological intervention?" British Journal of Pharmacology 153(S1):S367-S378, published ahead of print Jan. 28, 2008, print publication Mar. 2008.
Chang et al., "Synthesis and structure-activity relationships of quaternary ammonium cephalosporins with 3-pyrazolylpyridinium derivatives," Bioorganic & Medicinal Chemistry Letters, 10(11). pp. 1211-1214. Jun. 5, 2000.
Chelmicka-Szorc et al., "Partial suppression of experimental allergic encephalomyelitis with heparin," Archives of Neurology 27(2):153-158, Aug. 1972.
Chen et al., "Interaction of Novel Positive Allosteric Modulators of Metabotropic Glutamate Receptor 5 with the Negative Allosteric Antagonist Site is Required for Potentiation of Receptor Responses," Molecular Pharmacology, 71(5). pp. 1389-1398. May 2007. Published ahead of print Feb. 15, 2007.
Cherton et al., "Réactivitédu nucléophile azoture vis-à-vis de cations hétérocycliques aromatiques. VIII. Réarrangement de ß-tétrazolo-trans-benzalacétophénones," Canadian Journal of Chemistry, 63(10). pp. 2601-2607. Oct. 1985.
Cipens et al., "Aminoguanidine derivatives and their transformations. V. Alkyl- and arylamino substituted 1,2,4-triazoles and," Proceedings of the Academy of Science of Latvian SSR, Chemistry Series, 2. pp. 255-261. 1962. Accessed through CAPLUS. Database accession No. 1963:469125.

Colman et al., "The plasma kallikrein-kinin system in sepsis, inflammatory arthritis, and enterocolitis," Clinical Reviews in Allergy and Immunology 16(4):365-384, Dec. 1998.
Connolly et al., "Dabigatran versus warfarin in patients with atrial fibrillation," New England Journal of Medicine 361(12):1139-51, Sep. 17, 2009.
Database Registry Chemical Abstracts Service, Columbus, Ohio, Accession No. RN 67897-88-5, Entered STN: Nov. 16, 1984.
Defeo et al., "Dabigatran etexilate blocks breast cancer progression in vitro and in a 4T1 breast cancer tumor model in mice," Thrombosis Research, 125, Supplement 2, S188, Apr. 2010.
Defeo et al., "Use of dabigatran etexilate to reduce breast cancer progression," Cancer Biology & Therapy, 10(10):1001-1008, Nov. 15, 2010.
Deng et al., "Development of an oxazolopyridine series of dual thrombin/factor Xa inhibitors via structure-guided lead optimization," Bioorganic & Medicinal Chemistry Letters, 15(20). pp. 4411-4416. Oct. 15, 2005.
Diener et al., "Stroke prevention using the oral direct thrombin inhibitor ximelagatran in patients with non-valvular atrial fibrillation. Pooled analysis from the SPORTIF III and V studies," Cerebrovascular Diseases 21(4):279-293, Mar. 2006.
Dubau et al., "Malonylierungsreaktionen an 4-monosubstituierten Pyrazolidin-3,5-dionen," Chemische Berichte, 108(7). pp. 2189-2201. Jul. 1975.
Duplantier et al., "A role for thrombin in liver fibrosis," Gut, 53(11):1682-1687, Nov. 2004.
Dzygiel et al., "Synthesis, Structure and Properties of N-Acetylated Derivatives of Methyl 5-Amino-1H-[1,2,4] triazole-3-carboxylate," Chemical and Pharaceutical Bulletin, 52(2). pp. 192-198. Feb. 1, 2004.
Eliel et al., Stereochemistry of Organic Compounds, Chapter 1. pp. 1-16. Wiley. Sep. 1994.
Eriksson et al., "A Dose-ranging Study of the Oral Direct Thrombin Inhibitor, Ximelagatran, and Its Subcutaneous Form, Melagatran, Compared with Dalteparin in the Prophylaxis of Thromboembolism after Hip or Knee Replacement: METHRO I," Thrombosis and Haemostasis 87(2):231-237, Feb. 2002.
Eriksson et al., "Dabigatran etexilate versus enoxaparin for prevention of venous thromboembolism after total hip replacement: a randomised, double-blind, non-inferiority trial," The Lancet 370(9591):949-56, Sep. 21, 2007.
Eriksson et al., "Direct thrombin inhibitor melagatran followed by oral ximelagatran in comparison with enoxaparin for prevention of venous thromboembolism after total hip or knee replacement." Thrombosis and Haemostasis, 89(2):288-296. Feb. 2003.
Eriksson et al., "Oral dabigatran etexilate vs. subcutaneous enoxaparin for the prevention of venous thromboembolism after total knee replacement: the RE-MODEL randomized trial," Journal of Thrombosis and Haemostasis 5(11):2178-85, Nov. 1, 2007.
Eriksson et al., "Oral dabigatran versus enoxaparin for thromboprophylaxis after primary total hip arthroplasty (RE-NOVATE II)," Thrombosis and Haemostasis 105(4):721-729, Apr. 2011.
Eriksson et al., "The direct thrombin inhibitor melagatran followed by oral ximelagatran compared with enoxaparin for the prevention of venous thromboembolism after total hip or knee replacement: the EXPRESS study," Journal of Thrombosis and Haemostasis, 1(12):2490-6, Dec. 1, 2003.
Falanga et al., "Effect of anticoagulant drugs in cancer," Current Opinion in Pulmonary Medicine, 11(5):403-407, Sep. 2005.
Farghaly et al., "Synthesis of some new azoles with antiviral protential," ARKIVOC XI. pp. 76-90. 2006.
Favreau et al., "Anti-thrombin therapy during warm ischemia and cold preservation prevents chronic kidney graft fibrosis in a DCD model," American Journal of Transplantation 10(1):30-39, published ahead of print Dec. 2, 2009, print publication Jan. 2010.
Feener et al., "Plasma Kallikrein and Diabetic Macular Edema," Current Diabetes Reports, 10(4):270-275, published ahead of print Jun. 10, 2010, print publication Aug. 1, 2010.
Feener et al., "Plasma Kallikrein Kinin System and Diabetic Retinopathy," Biological Chemistry 394(3):319-328, published online Feb. 2, 2013, print publication Mar. 1, 2013.

(56) References Cited

OTHER PUBLICATIONS

Ferrera, "VEGF: an update on biological and therapeutic aspects," Current Opinion in Biotechnology 11(6):617-624, Dec. 1, 2000.
Fiessinger et al., "Ximelagatran vs low-molecular-weight heparin and warfarin for the treatment of deep vein thrombosis: a randomized trial," JAMA 293(6):681-9, Feb. 9, 2005.
Francis et al., "Comparison of ximelagatran with warfarin for the prevention of venous thromboembolism after total knee replacement," New England Journal of Medicine, 349(18):1703-12, Oct. 30, 2001.
Francis et al., "Ximelagatran versus warfarin for the prevention of venous thromboembolism after total knee arthroplasty. A randomized, double-blind trial." Annals of Internal Medicine, 137(8):648-655. Oct. 15, 2002.
Freitas et al., "Isomannide derivatives as new class of inhibitors for human kallikrein 7," Bioorganic & Medicinal Chemistry Letters 22(19):6072-6075, Oct. 1, 2012.
Galanud et al., "The history and historical treatments of deep vein thrombosis," Journal of Thrombosis and Heamostasis 11(3):402-411, Mar. 13, 2011.
Garcia et al., "The role of thrombin and protease-activated receptors in pain mechanisms," Thrombosis and Haemostasis 103(6):1145-1151, published ahead of print Apr. 29, 2010, print publication Jun. 2010.
Gasparini et al., "Peripheral markers in testing pathophysiological hypotheses and diagnosing Alzheimer's disease," The FASEB Journal 12(1):17-34, Jan. 1998.
Giardino, E. C., et al., "Cooperative antithrombotic effect from the simultaneous inhibition of thrombin and factor Xa", Blood Coagulation and Fibrinolysis, 21(2). pp. 128-134. Mar. 2010.
Ginsberg et al., "Oral Thrombin Inhibitor Dabigatran Etexilate vs North American Enoxaparin Regimen for Prevention of Venous Thromboembolism After Knee Arthroplasty Surgery," The Journal of Arthroplasty 24(1):1-9, Jan. 2009.
Goding, "Monoclonal Antibodies: Prinicples and Practice," Academic Press, p. 104, copyright 1986.
Greicius et al., "Presenile dementia syndromes: an update on taxonomy and diagnosis," Journal of Neurology, Neurosurgery, and Psychiatry 72(6):691-700, Jun. 2002.
Gross et al., "New anticoagulants for treatment of venous thromboembolism," Arteriosclerosis, Thrombosis, and Vascular Biology 28(3):380-386, Mar. 2008.
Hallet, "Acute Peripheral Arterial Occulusion," Merck Manual, Professional/Cardiovascular Disorders/Peripheral Arterial Disorders, two pages, May 2014.
Han et al., "Proteomic analysis of active multiple sclerosis lesions reveals therapeutic targets," Nature 451(7182):1076-1081, published ahead of print Feb. 17, 2008, print publication Feb. 28, 2008.
Hankey et al, "Antithrombotic Drugs for Patients with Ischaemic Stroke and Transient Ischaemic Attack to Prevent Recurrent Major Vascular Events," The Lancet Neurology 9(3):273-284, Mar. 2010.
Heit et al., "Comparison of the Oral Direct Thrombin Inhibitor Ximelagatran With Enoxaparin as Prophylaxis Against Venous Thromboembolism After Total Knee Replacement: A Phase 2 Dose-Finding Study," Archives of Internal Medicine 161(18): 2215-2221, Oct. 8, 2001.
Herrera et al., "Regio- and Stereoselectivity of Captodative Olefins in 1,3-Dipolar Cycloadditions. A DFT/HSAB Theory Rationale for the Observed Regiochemistry of Nitrones," The Journal of Organic Chemistry, 66(4). pp. 1252-1263. Feb. 9, 2001. Published ahead of print Jan. 27, 2001.
Hettiarachchi et al., "Do Heparins Do More Than Just Treat Thrombosis? The Influence of Heparins on Cancer Spread," Thrombosis and Haemostasis, 82(2):947-952, Aug. 1, 1999.
Hirsh et al., "New anticoagulants," Blood, 105(2):453-463, published ahead of print Jun. 10, 2004, print publication Jan. 2005.
Howell et al., "Direct thrombin inhibition reduces lung collagen, accumulation, and connective tissue growth factor mRNA levels in bleomycin-induced pulmonary fibrosis.," American Journal of Pathology 159(4):1383-1395, Oct. 2001.

Hu et al., "Role of endogenous thrombin in tumor implantation, seeding, and spontaneous metastasis," Blood, 104(9):2746-2751, Nov. 1, 2004.
Hua et al., "Systemic use of argatroban reduces tumor mass, attenuates neurological deficits and prolongs survival time in rat glioma models," Acta Neurochirurgica Supplement, 95:403-406, date of conference Aug. 2004, print publication 2005.
Hua et al., "The role of thrombin in gliomas," Journal of Thrombosis and Haemostasis, 3(9):1917-1923, published ahead of print Jun. 24, 2005, print publication Sep. 2005.
Hughes, "First oral warfarin alternative approved in the US," Nature Reviews Drug Discovery, 9(12):903-906, published ahead of print Oct. 29, 2010, print publication Dec. 2010.
Inaba et al., "Suppression of experimental autoimmune encephalomyelitis by dermatan sulfate," Cellular Immunology 198(2):96-102, Dec. 15, 1999.
International Search Report and Written Opinion dated Dec. 18, 2015, International Patent Application PCT/US2015/050809, filed Sep. 17, 2015.
International Search Report and Written Opinion dated Jul. 17, 2014, International Patent Application No. PCT/US2014/030853, filed Mar. 17, 2014.
International Search Report and Written Opinion dated May 17, 2016 in International Patent Application No. PCT/US2016/20116, filed Feb. 29, 2016.
Kaiser et al., "Synthetic and recombinant antithrombin drugs," Expert Opinion on Investigational Drugs 7(6):963-985, Jun. 1, 1998.
Kakkar et al., "Low Molecular Weight Heparin, Therapy With Dalteparin, and Survival in Advanced Cancer: The Fragmin Advanced Malignancy Outcome Study (FAMOUS)," Journal of Clinical Oncology 22(10):1944-1948, May 15, 2004.
Kantlehner et al., "Orthoamide, XXXII. Umsetzungen von tert-Butoxy-N,N,N',N'-tetramethylmethandiamin mit NH-und CH-aciden Verbindungen," Liebigs Annalen der Chemie, 1980(3). pp. 372-388. Mar. 1980.
Katritzky et al. "Selective Reactivity of sp3 and sp2 Carbanions of 1-Substituted 1,2,4-Triazoles. A Comparative Approach," Journal of Organic Chemsitry, 63(13). pp. 4323-4331. Jun. 5, 1998.
Keel et al., "Pathophysiology of polytrauma," Injury, 36(6):691-709, Jun. 2005.
Klerk et al., "The Effect of Low Molecular Weight Heparin on Survival in Patients With Advanced Malignancy," Journal of Clinical Oncology, 23(10):2130-2135, Apr. 1, 2005.
Kokolis et al., "Anticoagulation strategies for patients undergoing percutaneous coronary intervention: unfractionated heparin, low-molecular-weight heparins, and direct thrombin inhibitors." Progress in Cardiovascular Disease 46(6):506-523, May-Jun. 2004.
Kolte et al., "PF-04886847 (an Inhibitor of Plasma Kallikrein) Attenuates Inflammatory Mediators and Activation of Blood Coagulation in Rat Model of Lipopolysaccharide (LPS)—Induced Sepsis," Cardiovascular & Hematological Agents in Medicinal Chemistry 10(2):154-66, Feb. 2012.
Kranjc et al., "Dual Inhibitors of the Blood Coagulation Enzymes" Current Medicinal Chemistry, 11(19). pp. 2535-2547. Oct. 2004.
Kumar et al., "Efficient Routes to Pyrazolo[3,4-b]indoles and Pyrazolo[1,5-a]benzimidazoles via Palladium- and Copper-Catalyzed Intramolecular C-C and C-N Bond Formation", The Journal of Organic Chemistry, 74(18). pp. 7046-7051. Sep. 18, 2009. Published ahead of print Aug. 11, 2009.
Kumar, A. et al., "Synthesis of some newer 2-substituted-5-methoxyindolyl pyrazolines as potent anti-inflammatory and analgesic agents," Organic Chemistry: An Indian Journal 5(1):73-79, Mar. 2009.
Labanauskas et al., "Synthesis of 3-(3,4-Dimethoxyphenyl)-1H-1,2,4,-Triazole-5-Thiol and 2-Amino-5-(3,4-Dimethoxypheny)-1,3,4-Thiadiazole Derivatives Exhibiting Anti-Inflammatory Activity," Die Pharmazie, 56(8). pp. 617-619. Aug. 2001.
Langer et al., "New methods of drug delivery," Science, 249(4976). pp. 1527-1533. Sep. 28, 1990.
Lee et al., "Randomized comparison of low molecular weight heparin and coumarin derivatives on the survival of patients with

(56) References Cited

OTHER PUBLICATIONS cancer and venous thromboembolism," Journal of Clinical Oncology, 23(10):2123-2129, Apr. 1, 2005.

Lehman et al., "Bivalirudin in percutaneous coronary intervention," Vascular Health and Risk Management 2(4):357-363, Dec. 2006.

Lewis et al., "Argatroban anticoagulation during percutaneous coronary intervention in patients with heparin-induced thrombocytopenia." Catheterization & Cardiovascular Interventions 57(2):177-184, published ahead of print Sep. 30, 2002, print publication Oct. 2002.

Lloyd et al., "Benzopyran sulfonamides as Kv1.5 potassium channel blockers," Bioorganic & Medicinal Chemistry Letters, 17(12). pp. 3271-3275. Jun. 15, 2007.

Lopez et al., "Transdifferentiated retinal pigment epithelial cells are immunoreactive for vascular endothelial growth factor in surgically excised age-related macular degeneration-related choroidal neovascular membranes," Investigative Ophthalmology & Visual Science 37(5):855-868, Apr. 1996.

Lottenberg et al., "The action of thrombin on peptide p-Nitroanilide substrates: Substrate selectivity and examination of hydrolysis under different reaction condtions," Biochimica et Biophysica Acta (BBA)—Protein Structure and Molecular Enzymology, 742(3). pp. 539-557. Feb. 15, 1983.

Luo et al., "The Role of Thrombin and Thrombin Receptors in the Brain," Chapter 8 in Thrombin: Physiology and Disease, XII. Maragoudakis et al. (eds.). pp. 133-159. 2009.

Mehta et al., "An update on recent patents on thrombin inhibitors (2010-2013)," Expert Opinion on Therapeutic Patents 24(1):47-67, published online Oct. 8, 2013, print publication Jan. 1, 2014.

Wang et al., "Synthesis and biological activity of 1-[2-(2,4-dichlorophenoxyl)acetyl]-5-amino-IH-pyrazole derivatives," Youji Huaxue (Chinese Journal of Organic Chemistry) 24(7):797-801, Jul. 1, 2004.

Database Registry Chemical Abstracts Service, Columbus, Ohio, Accession No. RN 1323438-99-8, Entered STN: Aug. 25, 2011.

Database Registry Chemical Abstracts Service, Columbus, Ohio, Accession No. RN 188918-54-9, Entered STN: May 9, 1997.

SUBSTITUTED PYRAZOLE COMPOUNDS AS SERINE PROTEASE INHIBITORS

CROSS-REFERENCE TO RELATED APPLICATIONS

The present application is a U.S. National Stage entry under 35 U.S.C. § 371 of International Application No. PCT/US2016/020116, filed on Feb. 29, 2016, designating the United States of America and published in English on Sep. 1, 2016, which in turn claims priority to U.S. Provisional Application No. 62/126,424, filed on Feb. 27, 2015, each of which is hereby incorporated by reference in its entirety.

BACKGROUND OF THE INVENTION

The present disclosure relates to compounds, e.g., certain substituted pyrazole compounds, which exhibit biological activity, e.g., inhibitory action, against serine proteases, including thrombin and plasma kallikrein.

Serine proteases are a large family of enzymes with diverse biological functions, their commonality being the presence and critical function of the active-site serine residue. Their central function is the catalytic scission of peptide bond substrates via a Ser, His, Asp triad within the active site (Kraut, J. Annual Review of *Biochemistry* 1977, 46, 331-358). The present disclosure relates to compounds, e.g., heterocycloalkyl-substituted pyrazolyl compounds, which exhibit biological activity, e.g., inhibitory action, against serine proteases, including thrombin and various kallikreins.

In mammalian systems, blood vessel injuries result in bleeding events, which are dealt with by the blood coagulation cascade. The cascade includes the Extrinsic and Intrinsic pathways, involving the activation of at least 13 interconnected factors and a variety of co-factors and other regulatory proteins. Upon vascular injury, plasma factor VII interacts with exposed Tissue Factor (TF), and the resultant TF-fVIIa complex initiates a complex series of events. Factor fXa is produced directly 'downstream' from the TF-fVIIa complex, and amplified manifold via the Intrinsic Pathway. FXa then serves as the catalyst for formation of thrombin (fIIa), which in turn is the direct precursor to fibrinolysis. The outcome is a fibrinolytic clot, which stops the bleeding. Fibrinolysis of the polymeric clot into fibrin monomers leads to dissolution and a return of the system to the pre-clot state. The cascade is a complex balance of factors and co-factors and is tightly regulated.

In disease states, undesired up- or down-regulation of any factor leads to conditions such as bleeding or thrombosis. Historically, anticoagulants have been used in patients at risk of suffering from thrombotic complications, such as angina, stroke and heart attack. Warfarin has enjoyed dominance as a first-in-line anticoagulant therapeutic. Developed in the 1940s, it is a Vitamin K antagonist and inhibits factors II, VII, IX and X, amongst others. It is administered orally, but its ease of use is tempered by other effects: it has a very long half life (>2 days) and has serious drug-drug interactions. Importantly, since Vitamin K is a ubiquitous cofactor within the coagulation cascade, antagonism results in the simultaneous inhibition of many clotting factors and thus can lead to significant bleeding complications.

Much attention has been focused on heparin, the naturally-occurring polysaccharide that activates AT III, the endogenous inhibitor of many of the factors in the coagulation cascade. The need for parenteral administration for the heparin-derived therapeutics, and the inconvenient requirements for close supervision for the orally available warfarin, has resulted in a drive to discover and develop orally available drugs with wide therapeutic windows for safety and efficacy.

Indeed, the position of thrombin in the coagulation cascade has made it a popular target for drug discovery. Thrombin is a central protein in the coagulation process, which is activated and amplified upon vascular injury. Thrombin generation prompts a cascade in various factors in the coagulation cascade, ultimately depositing fibrin, the framework for a clot. The clot causes cessation of the bleeding event accompanying the vascular injury. Thrombin and associated protein ultimately cause dissolution of the clot through 'fibrinolysis', returning the system back to the pre-injury state. In a 'normal' state of injury, this thrombin generation and clot deposition is desired. In a disease state, clot deposition is undesired. General thrombotic events are the clinical result of clot deposition and accumulation in the arteries, veins or within the heart. Eventual break-off of the accumulated clot structure into the vascular system causes the clot to travel to the brain and/or lungs, resulting in a stroke, myocardial infarction (heart attack), pulmonary embolism, paralysis and consequent death. Compounds that inhibit thrombin have been shown in the literature to be useful as anticoagulants in vitro and in vivo, and in the clinic in patients have been shown to fulfil a critically unmet medical need. A thorough discussion of thrombin and its roles in the coagulation process can be found in a variety of references, including the following which are incorporated herein by reference in their entireties and for all purposes: Wieland, H. A., et al., 2003, *Curr Opin Investig Drugs*, 4:264-71; Gross, P. L. & Weitz, J. I., 2008, *Arterioscler Thromb Vasc Biol*, 28:380-6; Hirsh, J., et al., 2005, *Blood*, 105:453-63; Prezelj, A., et al., 2007, *Curr Pharm Des*, 13:287-312. Without further wishing to be bound by any theory, it is believed that the use of direct thrombin inhibitors (DTIs) is very well precedented, such as with the hirudin-based anticoagulants, and thus there is strong interest in the discovery and development of novel DTIs, particularly those with selectivity for inhibiting thrombin over other related serine proteases. Kallikreins are a subgroup of serine proteases, divided into plasma kallikrein and tissue kallikreins. Plasma kallikrein (KLKB1) liberates kinins (bradykinin and kallidin) from the kininogens, peptides responsible for the regulation of blood pressure and activation of inflammation. In the contact activation pathway of the coagulation cascade, plasma kallikrein assists in the conversion of factor XII to factor XIIa (Keel, M.; Trentz, O. *Injury* 2005, 36, 691-709). Factor XIIa converts factor XI into factor XIa, which in turn activates factor IX, which with its co-factor factor VIIIa forms the tenase complex, which finally activates factor X to factor Xa. In the fibrinolysis part of the coagulation cascade, plasma kallikrein serves to convert plasminogen to plasmin. Thus, it has been proposed that plasma kallikrein inhibitors can be useful in the treatment of thrombotic and fibrinolytic diseases and disease conditions (U.S. Pat. No. 7,625,944; Bird et al. *Thrombosis and Hemostasis* 2012, 107, Dhaval Kolte, M D. et al., Cardiology in Review, 2015).

Tissue kallikreins (KLKs, for example, KLK1) are subdivided into various types, and have been extensively investigated in cancer and inflammation biology. Various kallikrein KLKs have been found to be up- or down-regulated in various cancer types, such as cervical-, testicular-, and non-small-cell lung adenocarcinoma (Caliendo et al. *J. Med. Chem.*, 2012, 55, 6669). Furthermore, overexpression of various KLKs in the skin has led to the recognition that certain kallikrein inhibitors can be useful for certain dermatological conditions, including atopic dermatitis, psoriasis and rare skin diseases such as Netherton Syndrome (Freitas et al. *Bioorganic & Medicinal Chemistry Letters* 2012, 22, 6072-6075). A thorough discussion of tissue kallikreins, plasma kallikrein, their functions and potential roles in various diseases can be found in a variety of references, including the following which are incorporated herein by reference in their entireties and for all purposes: Renné, T.; Gruber, A. *Thromb Haemost* 2012, 107, 1012-3; Sotiropoulou, G.; Pampalakis, G. *Trends in Pharmacological Sciences* 2012, 33, 623-634; Pampalakis, G.; Sotiropoulou, G. *Chapter 9 Pharmacological Targeting of Human Tissue Kallikrein-Related Peptidases. In Proteinases as Drug Targets*, Dunn, B., Ed. The Royal Society of Chemistry: 2012; pp 199-228; Caliendo, G.; Santagada, V.; Perissutti, E.; Severino, B.; Fiorino, F.; Frecentese, F.; Juliano, L. *J Med Chem* 2012, 55, 6669-86.

BRIEF SUMMARY OF THE INVENTION

Embodiments of the invention encompass compounds with the following structure:

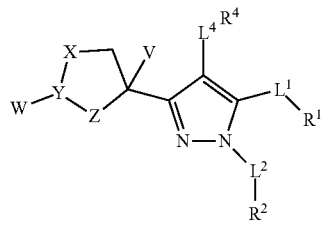

or pharmaceutically acceptable salt, ester, solvate, or prodrug thereof, wherein:

$L^1$, $L^2$, and $L^4$ are independently a bond, substituted or unsubstituted alkylene, substituted or unsubstituted heteroalkylene, —C(O)—, —S—, —SO—, —SO$_2$—, —O—, —NHSO$_2$—, —NHC(O)—, or —NR$^5$—;

$R^1$, $R^2$, and $R^4$ are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted fused ring aryl, or substituted or unsubstituted heteroaryl;

$R^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted fused ring aryl, or substituted or unsubstituted heteroaryl;

V is hydrogen or substituted or unsubstituted alkyl;

W is absent, hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted heteroaryl, —C(O)R$^6$, —C(O)OR$^6$, —C(O)NR$^6$R$^7$, —SR$^6$, —SOR$^6$, —SO$_2$R$^6$, —SO$_2$NR$^6$R$^7$, —OR$^6$, —NHSO$_2$R$^6$, or —NR$^6$R$^7$, where R$^6$ and R$^7$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, or substituted or unsubstituted heteroaryl, wherein R$^6$ and R$^7$ can be combined if both are present to form a substituted or unsubstituted alkylene, or substituted or unsubstituted heteroalkylene;

X is a bond, substituted or unsubstituted alkylene, —O—, or —NR$^8$—;

Y is a bond, substituted or unsubstituted alkylene, —O—, or —N—, provided that when Y is —O—, W is absent; and Z is a bond, —C(O)—, substituted or unsubstituted alkylene, —O—, or —NR$^9$—;

wherein R$^8$ and R$^9$ are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted heteroaryl, —C(O)R$^6$, —C(O)OR$^6$, —C(O)NR$^6$R$^7$, —SR$^6$, —SOR$^6$, —SO$_2$R$^6$, —SO$_2$NR$^6$R$^7$, —OR$^6$, —NHSO$_2$R$^6$, or —NR$^6$R$^7$, wherein R$^6$ and R$^7$ are as defined above; and provided that either at least one of X is —O— or —NR$^8$—, Y is —O— or —N—, or Z is —O— or —NR$^9$—.

In some embodiments, the compound can be a pharmaceutically acceptable salt, ester, solvate, or prodrug of a compound of Formula (IV). In some embodiments, the compound is not an ester, not a solvate, and not a prodrug.

In some embodiments, X can be a bond or substituted or unsubstituted alkylene. In some embodiments, Z can be a bond or substituted or unsubstituted alkylene. In some embodiments, X can be a bond or substituted or unsubstituted alkylene, and Z can be a bond or substituted or unsubstituted alkylene.

Some embodiments include compounds where X is a bond or substituted or unsubstituted alkylene and Z is a bond or substituted or unsubstituted alkylene, Y can be —N—, and W can be hydrogen, substituted or unsubstituted alkyl, substituted or unsubstituted heteroalkyl, substituted or unsubstituted aryl, —C(O)R$^6$, —C(O)OR$^6$, —C(O)NR$^6$R$^{7'}$ —SO$_2$R$^6$, or SO$_2$NR$^6$R$^7$, wherein R$^6$ and R$^7$ can be independently substituted or unsubstituted alkyl, substituted or unsubstituted cycloalkyl, or substituted or unsubstituted heterocycloalkyl, or R$^6$ and R$^7$ can be combined if both are present to form a substituted or unsubstituted alkylene, or substituted or unsubstituted heteroalkylene.

Some embodiments include compounds where X can be substituted or unsubstituted methylene, substituted or unsubstituted ethylene, substituted or unsubstituted propylene, substituted or unsubstituted butylene, or substituted or unsubstituted pentylene, and Z can be a bond. In some embodiments, X can be a bond, and Z can be substituted or unsubstituted methylene, substituted or unsubstituted ethylene, substituted or unsubstituted propylene, substituted or unsubstituted butylene, or substituted or unsubstituted pentylene. In some embodiments, X can be substituted or unsubstituted methylene, substituted or unsubstituted ethylene, substituted or unsubstituted propylene, substituted or unsubstituted butylene, or substituted or unsubstituted pentylene, and Z can be substituted or unsubstituted methylene, substituted or unsubstituted ethylene, substituted or unsubstituted propylene, substituted or unsubstituted butylene, or substituted or unsubstituted pentylene. In some embodiments, X and Z can both be branched alkylene, and X and Z can be covalently attached. In some embodiments, Z can be substituted methylene, substituted ethylene, substituted propylene, substituted butylene, or substituted pentylene, having one or more substituent groups which can be —OH, —$NH_2$, —SH, —CN, —$CF_3$, —$NO_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Some embodiments include compounds where X can be substituted or unsubstituted methylene, substituted or unsubstituted ethylene, substituted or unsubstituted propylene, substituted or unsubstituted butylene, or substituted or unsubstituted pentylene, and Z can be —C(O)—. In some embodiments, W can be hydrogen. In some embodiments, W can be substituted or unsubstituted alkyl, substituted or unsubstituted heteroalkyl, substituted or unsubstituted alkenyl, substituted or unsubstituted heteroalkenyl, substituted or unsubstituted cycloalkyl, substituted or unsubstituted heterocycloalkyl, —C(O)$R^6$, —C(O)O$R^6$, —C(O)N$R^6R^{7'}$ —S$R^6$, —SO$R^6$, —$SO_2R^6$, or —$SO_2$N$R^6$. In some embodiments, W can be substituted alkyl, substituted heteroalkyl, substituted alkenyl, substituted heteroalkenyl, substituted cycloalkyl, or substituted heterocycloalkyl, having one or more substituent which can be —OH, —$NH_2$, —SH, —CN, —$CF_3$, —$NO_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, W can be —CO$R^6$, —C(O)O$R^6$, —C(O)N$R^6R^7$, —$SO_2R^6$ or —$SO_2$N$R^6R^7$, where $R^6$ and $R^7$ can be selected from the group consisting of substituted or unsubstituted alkyl, substituted or unsubstituted heteroalkyl, substituted or unsubstituted aryl, or substituted or unsubstituted heteroaryl, or $R^6$ and $R^7$ can be combined to form a substituted or unsubstituted alkylene.

Some embodiments include compounds where W can be absent, X can be —$NR^8$—, Y can be a bond or substituted or unsubstituted alkylene, and Z can be —$NR^9$—. In some embodiments wherein W can be absent, X can be —$NR^8$—, Y can be a bond or substituted or unsubstituted alkylene, and Z can be —$NR^9$—, Y can be substituted or unsubstituted methylene, substituted or unsubstituted ethylene, substituted or unsubstituted propylene, substituted or unsubstituted butylene, or substituted or unsubstituted pentylene. In some embodiments, $R^8$ can be substituted or unsubstituted alkyl, substituted or unsubstituted heteroalkyl, substituted or unsubstituted alkenyl, substituted or unsubstituted heteroalkenyl, —CO$R^6$, —C(O)O$R^6$, —C(O)N$R^6R^7$, —S$R^6$, —SO$R^6$, —$SO_2R^6$, or —$SO_2$N$R^6R^7$, and wherein $R^9$ can be substituted or unsubstituted alkyl, substituted or unsubstituted heteroalkyl, substituted or unsubstituted alkenyl, substituted or unsubstituted heteroalkenyl, —CO$R^6$, —C(O)O$R^6$, —C(O)N$R^6R^7$, —S$R^6$, —SO$R^6$, —$SO_2R^6$, or —$SO_2$N$R^6R^7$.

Some embodiments include compounds where Y can be —O—, and W can be absent. In some embodiments wherein Y can be —O—, and W can be absent, X can be substituted or unsubstituted methylene, substituted or unsubstituted ethylene, substituted or unsubstituted propylene, substituted or unsubstituted butylene, or substituted or unsubstituted pentylene, and Z can be a bond. In some embodiments, X can be a bond, and Z can be substituted or unsubstituted methylene, substituted or unsubstituted ethylene, substituted or unsubstituted propylene, substituted or unsubstituted butylene, or substituted or unsubstituted pentylene. In some embodiments, X can be substituted or unsubstituted methylene, substituted or unsubstituted ethylene, substituted or unsubstituted propylene, substituted or unsubstituted butylene, or substituted or unsubstituted pentylene, and wherein Z can be substituted or unsubstituted methylene, substituted or unsubstituted ethylene, substituted or unsubstituted propylene, substituted or unsubstituted butylene, or substituted or unsubstituted pentylene.

In some embodiments, V can be hydrogen or substituted or unsubstituted methyl.

In some embodiments, L can be —S—, —O—, —$NR^5$—, substituted or unsubstituted alkylene, or substituted or unsubstituted heteroalkylene; $R^1$ can be substituted or unsubstituted alkyl, substituted or unsubstituted aryl, substituted or unsubstituted fused ring aryl, substituted or unsubstituted heteroaryl, or substituted or unsubstituted heterocycloalkyl; and $R^5$ can be hydrogen, substituted or unsubstituted alkyl, or substituted or unsubstituted heterocycloalkyl. In some embodiments, $L^1$ can be —$NR^5$— or substituted or unsubstituted heteroalkyl, and $R^1$ can be substituted or unsubstituted alkyl or substituted or unsubstituted heteroaryl. In some embodiments, $L^1$ can be —$NR^5$—, and $R^1$ can be substituted alkyl having one or more substituent groups which can be substituted or unsubstituted heteroaryl or substituted or unsubstituted heterocycloalkyl. In some embodiments, $R^1$ can be substituted alkyl substituted by chloro-substituted thiophenyl. In some embodiments, $L^1$ can be substituted or unsubstituted heteroalkyl, and $R^1$ can be substituted or unsubstituted heteroaryl.

In some embodiments, $L^2$ can be bond, substituted or unsubstituted alkylene, —C(O)—, or —$SO_2$—, and $R^2$ can be hydrogen, substituted or unsubstituted alkyl, substituted or unsubstituted heteroalkyl, substituted or unsubstituted cycloalkyl, substituted or unsubstituted aryl, substituted or unsubstituted fused ring aryl, substituted or unsubstituted heteroaryl, or substituted or unsubstituted heterocycloalkyl. In some embodiments, $L^2$ can be bond, and $R^2$ is hydrogen. In some embodiments, $L^2$ can be —C(O)—, and $R^2$ can be substituted or unsubstituted alkyl, substituted or unsubstituted heteroalkyl, substituted or unsubstituted cycloalkyl, substituted or unsubstituted aryl, substituted or unsubstituted fused ring aryl, substituted or unsubstituted heteroaryl, or substituted or unsubstituted heterocycloalkyl.

In some embodiments, $L^4$ can be a bond, and $R^4$ can be hydrogen, halogen, substituted or unsubstituted alkyl, substituted or unsubstituted heteroalkyl, substituted or unsubstituted aryl, or substituted or unsubstituted heteroaryl.

In some embodiments, the compound(s) can be included among those set forth in Table A, Table B, Table C, or Table D.

Embodiments of the invention also relate to pharmaceutical compositions comprising one or more compounds as set forth above, or one or more compound(s) included among those set forth in Table A, Table B, Table C, or Table D, and a pharmaceutically acceptable excipient.

Embodiments of the invention also include methods for treating and/or preventing one or more diseases or disorders in a subject, comprising administering a compound as set forth above, or a pharmaceutical composition including such a compound, to a subject in need thereof in an amount effective to treat or prevent said disease(s) or disorder(s).

In some embodiments of the methods described herein, the disease or disorder to be treated can include one or more thrombotic diseases or disorders and/or can involve a blood clot thrombus or the potential formation of a blood clot thrombus. In some embodiments, the thrombotic disease or disorder can be acute coronary syndrome, thromboembolism, and/or thrombosis. In some embodiments, the thromboembolism can be venous thromboembolism, arterial thromboembolism, and/or cardiogenic thromboembolism. In some embodiments, the venous thromboembolism can include deep vein thrombosis and/or pulmonary embolism. In some embodiments, the deep vein thrombosis and/or pulmonary embolism can occur following a medical procedure. In some embodiments, the thrombotic disease or disorder can involve dysfunctional coagulation or disseminated intravascular coagulation. In some embodiments, the subject with dysfunctional coagulation can be undergoing percutaneous coronary intervention (PCI). In some embodiments, the thrombotic disease or disorder can involve a blood clot thrombus or the potential formation of a blood clot thrombus and further can involve stroke and/or one or more transient ischemic attacks (TIA). In some embodiments, the thrombotic disease or disorder involving a blood clot thrombus or the potential formation of a blood clot thrombus can further involve stroke, wherein the subject can have non-valvular atrial fibrillation. In some embodiments, the thrombotic disease or disorder can involve a blood clot thrombus or the potential formation of a blood clot thrombus and further can involve pulmonary hypertension. In some embodiments, the pulmonary hypertension can be caused by one or more left heart disorder and/or chronic thromboembolic disease. In some embodiments, the pulmonary hypertension can be associated with one or more lung disease, including pulmonary fibrosis (idiopathic or otherwise), and/or hypoxia.

In some embodiments, the venous thromboembolism can be associated with formation of a thrombus within a vein associated with one or more acquired or inherited risk factors and/or embolism of peripheral veins caused by a detached thrombus. In some embodiments, the one or more risk factors can include a previous venous thromboembolism. In some embodiments, the cardiogenic thromboembolism can be due to formation of a thrombus in the heart associated with cardiac arrhythmia, heart valve defect, prosthetic heart valves or heart disease, and/or embolism of peripheral arteries caused by a detached thrombus. In some embodiments, the detached thrombus can be in the brain (ischemic stroke). In some embodiments, the detached thrombus can cause a transient ischemic attack (TIA). In some embodiments, the cardiogenic thromboembolism can be due to non-valvular atrial fibrillation. In some embodiments, the thrombosis can be arterial thrombosis. In some embodiments, the arterial thrombosis can be due to one or more underlying atherosclerotic processes in the arteries. In some embodiments, the one or more underlying atherosclerotic processes in the arteries can obstruct or occlude an artery, cause myocardial ischemia (angina pectoris, acute coronary syndrome), cause myocardial infarction, obstruct or occlude a peripheral artery (ischemic peripheral artery disease), and/or obstruct or occlude the artery after a procedure on a blood vessel (reocclusion or restenosis after transluminal coronary angioplasty, reocclusion or restenosis after percutaneous transluminal angioplasty of peripheral arteries).

In some embodiments, the disease or disorder can include fibrosis, Alzheimer's Disease, multiple sclerosis, pain, cancer, inflammation, and/or Type I diabetes mellitus. In some embodiments, the disease or disorder can involve recurrent cardiac events after myocardial infarction.

In some embodiments, the treatment or prevention can include an adjunct therapy. In some embodiments, the subject can have myocardial infarction, and the adjunct therapy can be in conjunction with thrombolytic therapy. In some embodiments, the subject can have unstable angina pectoris, thrombosis, and/or heparin-induced thrombocytopenia, and the adjunct therapy can be in combination with antiplatelet therapy. In some embodiments, the subject can have non-valvular atrial fibrillation, and the adjunct therapy can be in conjunction with one or more other therapies.

In some embodiments of the methods described herein, the disease or disorder can be a kallikrein-related disorder. In some embodiments, the kallikrein-related disorder can be a thrombotic disease, a fibrinolytic disease, a fibrotic disorder, a type of cancer, an inflammatory condition, or a dermatological condition.

In some embodiments, the kallikrein-related disorder can be an ophthalmic disease. In some embodiments, the compound or pharmaceutical composition can be administered in the form of an ophthalmic composition applied topically to the eye. In some embodiments, the ophthalmic composition can be in the form of eye drops. In some embodiments, the compound or pharmaceutical composition can be administered in the form of an ophthalmic composition via intravitreal injection. In some embodiments, the ophthalmic disease can be diabetic macular edema, hereditary angioedema, age-related macular degeneration, or diabetic retinopathy.

In some embodiments wherein the disease or disorder can be a type of cancer, said type of cancer can be cervical-, testicular-, or non-small-cell lung adenocarcinoma. In some embodiments, the cancer can be limited small cell lung cancer. In some embodiments, the cancer can be a glioma. In some embodiments, the cancer can be malignant breast cancer. In some embodiments, the cancer can be a micrometastasis. In some embodiments, the micrometastasis can be of the blood or liver. In some embodiments, the cancer can be a lung metastasis. In some embodiments, the cancer can be prostatic cancer.

In some embodiments wherein the disease or disorder can be an inflammatory condition, said inflammatory condition can be sepsis, inflammatory bowel disease, systemic inflammatory response syndrome, inflammatory arthritis, or rheumatoid arthritis.

In some embodiments wherein the disease or disorder can be a dermatological condition, said dermatological condition can be atopic dermatitis, psoriasis, or Netherton Syndrome.

In some embodiments, the compound can act by inhibiting thrombin and/or kallikrein. In some embodiments, the compound can act by inhibiting tissue kallikrein and/or plasma kallikrein. In some embodiments, the compound can have inhibitory activity against thrombin and/or plasma kallikrein within a range of 1-10 nM, 10-100 nM, 0.1-1 µM, 1-10 µM, 10-100 µM, 100-200 µM, 200-500 µM, or 500-1000 µM, or greater.

In some embodiments, the amount of compound administered can be a therapeutically effective dose sufficient to achieve a plasma concentration of the compound or its active metabolite(s) within a range of 1-10 nM, 10-100 nM, 0.1-1 µM, 1-10 µM, 10-100 µM, 100-200 µM, 200-500 µM, or 500-1000 µM, or greater.

Embodiments of the invention also relate to compounds or pharmaceutical compositions as described herein, for use in methods for treating and/or preventing one or more diseases or disorders in a subject, as described herein.

BRIEF DESCRIPTION OF THE DRAWINGS

Not applicable.

DETAILED DESCRIPTION OF THE INVENTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the term "attached" signifies a stable covalent bond, certain preferred points of attachment being apparent to those of ordinary skill in the art.

The terms "halogen" or "halo" include fluorine, chlorine, bromine, and iodine. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "alkyl," by itself or as part of another substituent, means, unless otherwise stated, a straight (i.e., unbranched) or branched chain, or combination thereof, which can be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Accordingly, the term "alkyl" can refer to C$_1$-C$_{16}$ straight chain saturated, C$_1$-C$_{16}$ branched saturated, C$_3$-C$_8$ cyclic saturated, C$_3$-C$_8$ cyclic unsaturated, and C$_1$-C$_{16}$ straight chain or branched saturated or unsaturated aliphatic hydrocarbon groups substituted with C$_3$-C$_8$ cyclic saturated or unsaturated aliphatic hydrocarbon groups having the specified number of carbon atoms, and the like. Examples of cyclic alkyl groups include, but are not limited to, cyclopropyl, cyclobutyl, cyclopentyl, cyclohexyl, cycloheptyl, cyclooctyl, cyclopropylmethyl, and the like.

The term "alkylene," by itself or as part of another substituent, means, unless otherwise stated, a divalent radical derived from a saturated or unsaturated alkyl, as defined above and as exemplified, but not limited by, —CH$_2$CH$_2$CH$_2$CH$_2$—, and the like. Typically, an alkyl (or alkylene) group will have from 1 to 24 carbon atoms, with those groups having 10 or fewer carbon atoms being preferred in the compounds disclosed herein. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms can optionally be oxidized, and the nitrogen heteroatom can optionally be quaternized. The heteroatom(s) O, N, P, S, and Si can be placed at any interior position of the heteroalkyl group or at the position at which the alkyl group is attached to the remainder of the molecule. The heteroalkyl group can be fully saturated, mono- or polyunsaturated and can include di- and multivalent radicals, having the number of atoms designated. Accordingly, the term "heteroalkyl" can refer to saturated or unsaturated straight or branched chains containing two through 16 atoms along the chain, cyclic saturated or unsaturated groups containing 3-8 atoms in the cycle, and the like. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—C—H═N—OCH$_3$, —CH═CH—N(CH$_3$)—CH$_3$, —O—CH$_3$, —O—CH$_2$—CH$_3$, —CN, and the like. Up to two heteroatoms can be consecutive, such as, for example, —CH$_2$—NH—OCH$_3$.

Similarly, the term "heteroalkylene," by itself or as part of another substituent, means, unless otherwise stated, a divalent radical derived from heteroalkyl, as defined above and as exemplified, but not limited by, —CH$_2$—CH$_2$—S—CH$_2$—CH$_2$— and —CH$_2$—S—CH$_2$—CH$_2$—NH—CH$_2$—, and the like. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. The "cycloalkyl" and "heterocycloalkyl" groups include, for example, monocyclic rings having 3-8 ring members, as well as bicyclic rings having 4-16 ring members, tricyclic rings having 5-24 ring members, and so on. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "alkenyl" includes $C_2$-$C_{16}$ straight chain unsaturated, $C_2$-$C_{11}$ branched unsaturated, $C_5$-$C_8$ unsaturated cyclic, and $C_2$-$C_{16}$ straight chain or branched unsaturated aliphatic hydrocarbon groups substituted with $C_3$-$C_8$ cyclic saturated and unsaturated aliphatic hydrocarbon groups having the specified number of carbon atoms. Double bonds can occur in any stable point along the chain and the carbon-carbon double bonds can have either the cis or trans configuration. For example, this definition shall include but is not limited to ethenyl, propenyl, butenyl, pentenyl, hexenyl, heptenyl, octenyl, nonenyl, decenyl, undecenyl, 1,5-octadienyl, 1,4,7-nonatrienyl, cyclopentenyl, cyclohexenyl, cycloheptenyl, cyclooctenyl, ethylcyclohexenyl, butenylcyclopentyl, 1-pentenyl-3-cyclohexenyl, and the like. Similarly, "heteroalkenyl" refers to heteroalkyl having one or more double bonds, wherein heteroalkyl is as defined above.

The term "alkynyl" refers in the customary sense to alkyl, as defined above, additionally having one or more triple bonds. The term "cycloalkenyl" refers to cycloalkyl, as defined above, additionally having one or more double bonds. The term "heterocycloalkenyl" refers to heterocycloalkyl, as defined above, additionally having one or more double bonds.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently, wherein each ring contains between 4-20 atoms, and preferably between 5-10 atoms. A fused ring aryl refers to multiple rings fused together wherein at least one of the fused rings is an aryl ring. The term "heteroaryl" refers to aryl groups (or rings), as defined above, that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, and the like. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Accordingly, the term "aryl" can represent an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e. g. 3-indolyl, 4-imidazolyl). The aryl substituents are independently selected from the group consisting of halo, nitro, cyano, trihalomethyl, $C_{1-16}$alkyl, aryl$C_{1-16}$alkyl, $C_{0-16}$alkyloxy$C_{0-16}$alkyl, aryl$C_{0-16}$alkyloxy$C_{0-16}$alkyl, $C_{0-16}$alkylthio$C_{0-16}$alkyl, aryl$C_{0-16}$alkylthio$C_{0-16}$alkyl, $C_{0-16}$alkylamino$C_{0-16}$alkyl, aryl$C_{0-16}$alkylamino$C_{0-16}$alkyl, di(aryl$C_{1-16}$alkyl)amino$C_{0-16}$alkyl, $C_{1-16}$alkylcarbonyl$C_{0-16}$alkyl, aryl$C_{1-16}$alkylcarbonyl$C_{0-16}$alkyl, $C_{1-16}$alkylcarboxy$C_{0-16}$alkyl, aryl$C_{1-16}$alkylcarboxy$C_{0-16}$alkyl, $C_{1-16}$ alkylcarbonylamino$C_{0-16}$alkyl, aryl$C_{1-16}$alkylcarbonylamino$C_{0-16}$alkyl, —$C_{0-16}$alkyl-COOR$_4$, —$C_{0-16}$alkylCONR$_5$R$_6$ wherein R$_4$, R$_5$ and R$_6$ are independently selected from hydrogen, $C_1$-$C_{11}$alkyl, aryl$C_0$-$C_{11}$alkyl, or R$_5$ and R$_6$ are taken together with the nitrogen to which they are attached forming a cyclic system containing 3 to 8 carbon atoms with or without one $C_{1-16}$alkyl, aryl$C_0$-$C_{16}$alkyl, or $C_0$-Cl$_{16}$alkylaryl substituent. Aryl includes but is not limited to pyrazolyl and triazolyl.

For brevity, the term "aryl" when used in combination with other terms (e.g., aryloxy, arylthioxy, arylalkyl) includes both aryl and heteroaryl rings as defined above. Thus, the terms "arylalkyl," "aralkyl" and the like are meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like), or a sulfur atom. Accordingly, the terms "arylalkyl" and the like (e.g. (4-hydroxyphenyl)ethyl, (2-aminonaphthyl)hexyl, pyridylcyclopentyl) represents an aryl group as defined above attached through an alkyl group as defined above having the indicated number of carbon atoms.

Each of the above terms (e.g., "alkyl," "heteroalkyl," "aryl," and "heteroaryl") includes both substituted and unsubstituted forms of the indicated radical. Preferred substituents for each type of radical are provided herein.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C (O)NR"R'", —NR"C(O)$_2$R', —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", and R'" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound disclosed herein includes more than one R group, for example, each of the R groups is independently selected as are each R', R", and R'" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R") =NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", and R'" groups when more than one of these groups is present.

Two or more substituents can optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring can optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring can optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed can optionally be replaced with a double bond. Alternatively, two of the substituents on adjacent atoms of the aryl or heteroaryl ring can optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

The term "alkyloxy" (e.g. methoxy, ethoxy, propyloxy, allyloxy, cyclohexyloxy) represents an alkyl group as defined above having the indicated number of carbon atoms attached through an oxygen bridge (—O—).

The term "alkylthio" (e.g. methylthio, ethylthio, propylthio, cyclohexylthio and the like) represents an alkyl group as defined above having the indicated number of carbon atoms attached through a sulfur bridge (—S—).

The term "alkylamino" represents one or two alkyl groups as defined above having the indicated number of carbon atoms attached through an amine bridge. The two alkyl groups can be taken together with the nitrogen to which they are attached forming a cyclic system containing 3 to 8 carbon atoms with or without one C$_1$-C$_{16}$alkyl, arylC$_0$-C$_{16}$alkyl, or C$_0$-C$_{16}$alkylaryl substituent.

The term "alkylaminoalkyl" represents an alkylamino group attached through an alkyl group as defined above having the indicated number of carbon atoms.

The term "alkyloxy(alkyl)amino" (e.g. methoxy(methyl)amine, ethoxy(propyl)amine) represents an alkyloxy group as defined above attached through an amino group, the amino group itself having an alkyl substituent.

The term "alkylcarbonyl" (e.g. cyclooctylcarbonyl, pentylcarbonyl, 3-hexylcarbonyl) represents an alkyl group as defined above having the indicated number of carbon atoms attached through a carbonyl group.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen.

The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonylaminomethyl, methylcarbonylaminophenyl) represents an alkylcarbonyl group as defined above wherein the carbonyl is in turn attached through the nitrogen atom of an amino group.

The nitrogen group can itself be substituted with an alkyl or aryl group.

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' can have a specified number of carbons (e.g., "C$_1$-C$_4$ alkylsulfonyl").

The term "carbonyloxy" represents a carbonyl group attached through an oxygen bridge.

In the above definitions, the terms "alkyl" and "alkenyl" can be used interchangeably in so far as a stable chemical entity is formed, as would be apparent to those skilled in the art.

The term "linker" refers to attachment groups interposed between substituents, e.g., $R^1$, $R^2$, $R^3$ or $R^4$ described herein, e.g., Formula (Ia) and generically referred to as R″, and the group which is substituted, e.g., "ring A" group of e.g., Formula (Ia). In some embodiments, the linker includes amido (—CONH—R″ or —NHCO—R″), thioamido (—CSNH—R″ or —NHCS—R″), carboxyl (—CO$_2$—R″ or —OCOR″), carbonyl (—CO—R″), urea (—NHCONH—R″), thiourea (—NHCSNH—R″), sulfonamido (—NHSO$_2$—R″ or —SO$_2$NH—R″), ether (—O—R″), sulfonyl (—SO$_2$—R″), sulfoxyl (—SO—R″), carbamoyl (—NHCO$_2$—R″ or —OCONH—R″), or amino (—NHR″) linking moieties.

A "substituent group," as used herein, means a group selected from the following moieties:

(A) —OH, —NH$_2$, —SH, —CN, —CF$_3$, —NO$_2$, oxo, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2-20-membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4-8-membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2-8-membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5-7-membered heterocycloalkyl.

The term "about" used in the context of a numeric value indicates a range of +/−10% of the numeric value, unless expressly indicated otherwise.

II. Compounds

In one aspect, there is provided a compound with structure of Formula (Ia):

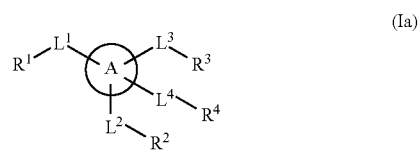

(Ia)

or pharmaceutically acceptable salt, ester, solvate, or prodrug thereof. Ring A is substituted or unsubstituted pyrazolyl. $L^1$, $L^2$ and $L^4$ are independently a bond, substituted or unsubstituted alkylene, substituted or unsubstituted heteroalkylene, —S—, —SO—, —SO$_2$—, —O—, —NHSO$_2$—, or —NR$^5$—. $L^3$ is a bond, substituted or unsubstituted alkylene, or substituted or unsubstituted heteroalkylene. $R^1$, $R^2$, and $R^4$ are independently hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted heteroaryl, or substituted or unsubstituted fused ring aryl. $R^3$ is substituted or unsubstituted heteroalkyl, substituted or unsubstituted cycloalkyl, substituted or unsubstituted cycloalkenyl, substituted or unsubstituted heterocycloalkyl, or substituted or unsubstituted heterocycloalkenyl. $R^5$ is hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted cycloalkenyl, substituted or unsubstituted heterocycloalkenyl, substituted or unsubstituted heterocycloalkyl, substituted or unsubstituted aryl, substituted or unsubstituted fused ring aryl, or substituted or unsubstituted heteroaryl.

In some embodiments, the compound is a pharmaceutically acceptable salt, ester, solvate, or prodrug of a compound of Formula (Ia). In some embodiments, the compound is not an ester, not a solvate, and not a prodrug.

In some embodiments, $L^4$ and $R^4$ are absent, providing a compound with structure of Formula (Ib) following.

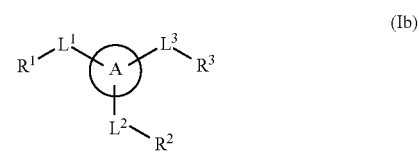

(Ib)

In some embodiments, there is provided a compound according to Formula (Ib) with structure of Formula (II) following.

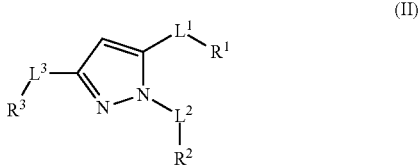

(II)

In some embodiments, the compound has the structure of Formula (II), wherein $L^3$ is a bond or substituted or unsubstituted alkylene, and $R^3$ is substituted or unsubstituted heteroalkyl, substituted or unsubstituted cycloalkyl, substituted or unsubstituted cycloalkenyl, or substituted or unsubstituted heterocycloalkyl. In some embodiments, $R^3$ is substituted or unsubstituted heteroalkyl. In some embodiments, $R^3$ is substituted or unsubstituted cycloalkyl. In some embodiments, $R^3$ is substituted or unsubstituted cyclohexyl, substituted or unsubstituted cyclopentyl, substituted or unsubstituted cycloheptyl. In some embodiments, $R^3$ is substituted or unsubstituted cycloalkenyl. In some embodiments, $R^3$ is substituted or unsubstituted cyclohexenyl. In some embodiments, $R^3$ is substituted or unsubstituted heterocycloalkyl. In some embodiments, $R^3$ is substituted or unsubstituted piperidinyl. In some embodiments, $R^3$ is substituted or unsubstituted pyrrolidinyl. In some embodiments, $R^3$ is substituted or unsubstituted pyrrolidinyl. In some embodiments, $R^3$ is substituted or unsubstituted azetidinyl. In some embodiments, $R^3$ is substituted or unsubstituted oxetanyl. In some embodiments, $R^3$ is substituted or unsubstituted oxolanyl. In some embodiments, $R^3$ is substituted or unsubstituted oxanyl.

Further to any embodiment above wherein the compound has the structure of Formula (II), in some embodiments L is —S—, —O—, —NR$^5$—, substituted or unsubstituted alkylene, or substituted or unsubstituted heteroalkylene, where $R^5$ is as described in formula Ia, and $R^1$ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, $R^1$ is substituted or unsubstituted phenyl. In some embodiments is an $R^1$ is unsubstituted phenyl. In some embodiments, $R^1$ is a substituted or unsubstituted pyridyl. In some embodiments, $R^1$ is a substituted or unsubsituted pyridazinyl. In some embodiments, $R^1$ is a substituted or unsubsituted pyrimidinyl. In some embodiments, $R^1$ is a substituted or unsubsituted thienyl. In some embodiments, $R^1$ is a substituted or unsubsituted furyl. In some embodiments, $R^1$ is an unsubsituted pyridyl. In some embodiments, $R^1$ is an unsubsituted pyridazinyl. In some embodiments, $R^1$ is an unsubsituted pyrimidinyl. In some embodiments, $R^1$ is an unsubsituted thienyl. In some embodiments, $R^1$ is a chloro-substituted thienyl. In some embodiments, $R^1$ is an unsubsituted furyl. In some embodiments, $R^1$ is a substituted or unsubsituted morpholinyl. In some embodiments, $R^1$ is a substituted or unsubsituted oxanyl. In some embodiments, $R^1$ is a substituted or unsubsituted oxetanyl. In some embodiments, $R^1$ is an unsubsituted morpholinyl. In some embodiments, $R^1$ is an unsubsituted oxanyl. In some embodiments, $R^1$ is an unsubsituted oxetanyl. In some embodiments, $R^1$ is substituted or unsubstituted benzodioxinyl. In some embodiments, $R^1$ is substituted or unsubstituted naphthyl. In some embodiments, $R^1$ is unsubstituted benzodioxinyl. In some embodiments, $R^1$ is unsubstituted naphthyl. In some embodiments, $L^2$ and $R^2$ are absent. In some embodiments, $L^2$ is a bond. In some embodiments, $L^2$ is a bond and $R^2$ is hydrogen.

Further to any embodiment above wherein the compound has the structure of Formula (II), $R^2$ is hydrogen, substituted or unsubstituted alkyl, substituted or unsubstituted heteroalkyl, substituted or unsubstituted cycloalkyl, substituted or unsubstituted cycloalkenyl, or substituted or unsubstituted heterocycloalkyl, substituted or unsubstituted aryl, substituted or unsubstituted fused ring aryl, or substituted or unsubstituted heteroaryl. In some embodiments, $R^2$ is substituted or unsubstituted phenyl. In some embodiments is an $R^2$ is unsubstituted phenyl. In some embodiments, $R^2$ is a substituted or unsubstituted pyridyl. In some embodiments, $R^2$ is a substituted or unsubsituted pyridazinyl. In some embodiments, $R^2$ is a substituted or unsubsituted pyrimidinyl. In some embodiments, $R^2$ is a substituted or unsubsituted thienyl. In some embodiments, $R^2$ is a substituted or unsubsituted furyl. In some embodiments, $R^2$ is an unsubsituted pyridyl. In some embodiments, $R^2$ is an unsubsituted pyridazinyl. In some embodiments, $R^2$ is an unsubsituted pyrimidinyl. In some embodiments, $R^2$ is an unsubsituted thienyl. In some embodiments, $R^2$ is a chloro-substituted thienyl. In some embodiments, $R^2$ is an unsubsituted furyl. In some embodiments, $R^2$ is a substituted or unsubsituted morpholinyl. In some embodiments, $R^2$ is a substituted or unsubsituted oxanyl. In some embodiments, $R^2$ is a substituted or unsubsituted oxetanyl. In some embodiments, $R^2$ is an unsubsituted morpholinyl. In some embodiments, $R^2$ is an unsubsituted oxanyl. In some embodiments, $R^2$ is an unsubsituted oxetanyl. In some embodiments, $R^2$ is substituted or unsubstituted benzodioxinyl. In some embodiments, $R^2$ is substituted or unsubstituted naphthyl. In some embodiments, $R^2$ is unsubstituted benzodioxinyl. In some embodiments, $R^2$ is unsubstituted naphthyl.

In some embodiments, there is provided a compound according to Formula (Ia) with structure of Formula (III) following.

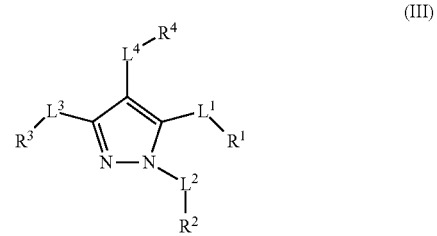

(III)

In some embodiments, there is provided a compound according to Formula (III) wherein $L^4$ is a bond; and $R^4$ is hydrogen, halogen, substituted or unsubstituted alkyl, or substituted or unsubstituted heteroalkyl, substituted or unsubstituted aryl, or substituted or unsubstituted heteroaryl. In some embodiments, $R^4$ is halogen. In some embodiments, $R^4$ is unsubstituted alkyl. Further to any embodiment wherein the compound has the structure of Formula (III), in some embodiments $L^3$ is a bond or substituted or unsubstituted alkylene, and $R^3$ is substituted or unsubstituted heteroalkyl, substituted or unsubstituted cycloalkyl, substituted or unsubstituted cycloalkenyl, or substituted or unsubstituted heterocycloalkyl. In some embodiments, $R^3$ is substituted or unsubstituted heteroalkyl. In some embodiments, $R^3$ is substituted or unsubstituted cycloalkyl. In some embodiments, $R^3$ is substituted or unsubstituted cyclohexyl, substituted or unsubstituted cyclopentyl, substituted or unsubstituted cycloheptyl. In some embodiments, $R^3$ is substituted or unsubstituted cycloalkenyl. In some embodiments, $R^3$ is substituted or unsubstituted cyclohexenyl. In some embodiments, R³ is substituted or unsubstituted heterocycloalkyl. In some embodiments, R³ is substituted or unsubstituted piperidinyl. In some embodiments, R³ is substituted or unsubstituted pyrrolidinyl. In some embodiments, R³ is substituted or unsubstituted pyrrolidinyl. In some embodiments, R³ is substituted or unsubstituted azetidinyl. In some embodiments, R³ is substituted or unsubstituted oxetanyl. In some embodiments, R³ is substituted or unsubstituted oxolanyl. In some embodiments, R³ is substituted or unsubstituted oxanyl.

Further to any embodiment above wherein the compound has the structure of Formula (III), in some embodiments L¹ is —S—, —O—, —NR⁵—, substituted or unsubstituted alkylene, or substituted or unsubstituted heteroalkylene, where R⁵ is as described in formula Ia, and R¹ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, R¹ is substituted or unsubstituted phenyl. In some embodiments is an R¹ is unsubstituted phenyl. In some embodiments, R¹ is a substituted or unsubstituted pyridyl. In some embodiments, R¹ is a substituted or unsubsituted pyridazinyl. In some embodiments, R¹ is a substituted or unsubsituted pyrimidinyl. In some embodiments, R¹ is a substituted or unsubsituted thienyl. In some embodiments, R¹ is a substituted or unsubstituted furyl. In some embodiments, R¹ is an unsubsituted pyridyl. In some embodiments, R¹ is an unsubsituted pyridazinyl. In some embodiments, R¹ is an unsubstituted pyrimidinyl. In some embodiments, R¹ is an unsubstituted thienyl. In some embodiments, R¹ is a chloro-substituted thienyl. In some embodiments, R¹ is an unsubstituted furyl. In some embodiments, R¹ is a substituted or unsubstituted morpholinyl. In some embodiments, R¹ is a substituted or unsubsituted oxanyl. In some embodiments, R¹ is a substituted or unsubsituted oxetanyl. In some embodiments, R¹ is an unsubsituted morpholinyl. In some embodiments, R¹ is an unsubstituted oxanyl. In some embodiments, R¹ is an unsubsituted oxetanyl. In some embodiments, R¹ is substituted or unsubstituted benzodioxinyl. In some embodiments, R¹ is substituted or unsubstituted naphthyl. In some embodiments, R¹ is unsubstituted benzodioxinyl. In some embodiments, R¹ is unsubstituted naphthyl. In some embodiments, L² and R² are absent. In some embodiments, L² is a bond. In some embodiments, L² is a bond and R² is hydrogen.

Further to any embodiment above wherein the compound has the structure of Formula (III), R² is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted aryl, substituted or unsubstituted fused ring aryl, or substituted or unsubstituted heteroaryl. In some embodiments, R² is substituted or unsubstituted phenyl. In some embodiments is an R² is unsubstituted phenyl. In some embodiments, R² is a substituted or unsubstituted pyridyl. In some embodiments, R² is a substituted or unsubsituted pyridazinyl. In some embodiments, R² is a substituted or unsubsituted pyrimidinyl. In some embodiments, R² is a substituted or unsubsituted thienyl. In some embodiments, R² is a substituted or unsubstituted furyl. In some embodiments, R² is an unsubsituted pyridyl. In some embodiments, R² is an unsubsituted pyridazinyl. In some embodiments, R² is an unsubstituted pyrimidinyl. In some embodiments, R² is an unsubstituted thienyl. In some embodiments, R² is a chloro-substituted thienyl. In some embodiments, R² is an unsubstituted furyl. In some embodiments, R² is a substituted or unsubstituted morpholinyl. In some embodiments, R² is a substituted or unsubsituted oxanyl. In some embodiments, R² is a substituted or unsubstituted oxetanyl. In some embodiments, R² is an unsubsituted morpholinyl. In some embodiments, R² is an unsubstituted oxanyl. In some embodiments, R² is an unsubsituted oxetanyl. In some embodiments, R² is substituted or unsubstituted benzodioxinyl. In some embodiments, R² is substituted or unsubstituted naphthyl. In some embodiments, R² is unsubstituted benzodioxinyl. In some embodiments, R² is unsubstituted naphthyl.

In some embodiments, there is provided a compound according to Formula (III) wherein L³ is a bond, R³ is substituted or unsubstituted heterocycloalkyl, or substituted or unsubstituted heterocycloalkenyl, with structure of Formula (IV) following.

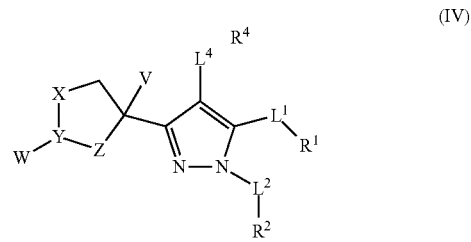

wherein: L¹, L², and L⁴ are independently a bond, substituted or unsubstituted alkylene, substituted or unsubstituted heteroalkylene, —C(O)—, —S—, —SO—, —SO₂—, —O—, —NHSO₂—, —NHC(O)—, or —NR⁵—; R¹, R², and R⁴ are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted fused ring aryl, or substituted or unsubstituted heteroaryl; R⁵ is hydrogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted fused ring aryl, or substituted or unsubstituted heteroaryl; V is hydrogen or substituted or unsubstituted alkyl; W is absent, hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted heteroaryl, —C(O)R⁶, —C(O)OR⁶, —C(O)NR⁶R⁷, —SR⁶, —SOR⁶, —SO₂R⁶, —SO₂NR⁶R⁷, —OR⁶, —NHSO₂R⁶, or —NR⁶R⁷, where R⁶ and R⁷ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, or substituted or unsubstituted heteroaryl, wherein $R^6$ and $R^7$ can be combined if both are present to form a substituted or unsubstituted alkylene, or substituted or unsubstituted heteroalkylene; X is a bond, substituted or unsubstituted alkylene, —O—, or —NR$^8$—; Y is a bond, substituted or unsubstituted alkylene, —O—, or —N—, provided that when Y is —O—, W is absent; and Z is a bond, —C(O)—, substituted or unsubstituted alkylene, —O—, or —NR$^9$—; wherein $R^8$ and $R^9$ are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted heteroaryl, —C(O)R$^6$, —C(O)OR$^6$, —C(O)NR$^6$R$^7$, —SR$^6$, —SOR$^6$, —SO$_2$R$^6$, —SO$_2$NR$^6$R$^7$, —OR$^6$, —NHSO$_2$R$^6$, or —NR$^6$R$^7$, wherein $R^6$ and $R^7$ are as defined above; and provided that either at least one of X is —O— or —NR$^8$—, Y is —O— or —N—, or Z is —O— or —NR$^9$—. In some embodiments, the compound is a pharmaceutically acceptable salt, ester, solvate, or prodrug of a compound of Formula (IV). In some embodiments, the compound is not an ester, not a solvate, and not a prodrug.

In some embodiments, X is a bond or substituted or unsubstituted alkylene. In some embodiments, Z is a bond or substituted or unsubstituted alkylene. In some embodiments, X is a bond or substituted or unsubstituted alkylene, and Z is a bond or substituted or unsubstituted alkylene.

In some embodiments, wherein X is a bond or substituted or unsubstituted alkylene and Z is a bond or substituted or unsubstituted alkylene, Y is —N—, and W is hydrogen, substituted or unsubstituted alkyl, substituted or unsubstituted heteroalkyl, substituted or unsubstituted aryl, —C(O)R$^6$, —C(O)OR$^6$, —C(O)NR$^6$R$^7$, —SO$_2$R$^6$, or SO$_2$NR$^6$R$^7$, wherein $R^6$ and $R^7$ are independently substituted or unsubstituted alkyl, substituted or unsubstituted cycloalkyl, or substituted or unsubstituted heterocycloalkyl, or $R^6$ and $R^7$ can be combined if both are present to form a substituted or unsubstituted alkylene, or substituted or unsubstituted heteroalkylene.

In some embodiments, X is selected from the group consisting of substituted or unsubstituted methylene, substituted or unsubstituted ethylene, substituted or unsubstituted propylene, substituted or unsubstituted butylene, and substituted or unsubstituted pentylene, and Z is a bond. In some embodiments, X is a bond, and Z is selected from the group consisting of substituted or unsubstituted methylene, substituted or unsubstituted ethylene, substituted or unsubstituted propylene, substituted or unsubstituted butylene, and substituted or unsubstituted pentylene. In some embodiments, X is selected from the group consisting of substituted or unsubstituted methylene, substituted or unsubstituted ethylene, substituted or unsubstituted propylene, substituted or unsubstituted butylene, and substituted or unsubstituted pentylene, and wherein Z is selected from the group consisting of substituted or unsubstituted methylene, substituted or unsubstituted ethylene, substituted or unsubstituted propylene, substituted or unsubstituted butylene, and substituted or unsubstituted pentylene. In some embodiments, X and Z are both branched alkylene and X and Z are covalently attached. In some embodiments, Z is can be substituted methylene, substituted ethylene, substituted propylene, substituted butylene, or substituted pentylene, having one or more substituent groups selected from the group consisting of —OH, —NH$_2$, —SH, —CN, —CF$_3$, —NO$_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, X is selected from the group consisting of substituted or unsubstituted methylene, substituted or unsubstituted ethylene, substituted or unsubstituted propylene, substituted or unsubstituted butylene, and substituted or unsubstituted pentylene, and wherein Z is —C(O)—. In some embodiments, W is hydrogen. In some embodiments, W is selected from the group consisting of substituted or unsubstituted alkyl, substituted or unsubstituted heteroalkyl, substituted or unsubstituted alkenyl, substituted or unsubstituted heteroalkenyl, substituted or unsubstituted cycloalkyl, substituted or unsubstituted heterocycloalkyl, —C(O)R$^6$, —C(O)OR$^6$, —C(O)NR$^6$R$^{7'}$ —SR$^6$, —SOR$^6$, —SO$_2$R$^6$, and —SO$_2$NR$^6$. In some embodiments, W is substituted alkyl, substituted heteroalkyl, substituted alkenyl, substituted heteroalkenyl, substituted cycloalkyl, or substituted heterocycloalkyl, having one or more substituent groups selected from the group consisting of —OH, —NH$_2$, —SH, —CN, —CF$_3$, —NO$_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, W is —COR$^6$, —C(O)OR$^6$, —C(O)NR$^6$R$^7$, —SO$_2$R$^6$ or —SO$_2$NR$^6$R$^7$, and wherein $R^6$ and $R^7$ are selected from the group consisting of substituted or unsubstituted alkyl, substituted or unsubstituted heteroalkyl, substituted or unsubstituted aryl, and substituted or unsubstituted heteroaryl, or $R^6$ and $R^7$ combine to form a substituted or unsubstituted alkylene.

In some embodiments, W is absent, X is —NR$^8$—, Y is a bond or substituted or unsubstituted alkylene, and Z is —NR$^9$—. In some embodiments wherein W is absent, X is —NR$^8$—, Y is a bond or substituted or unsubstituted alkylene, and Z is —NR$^9$—, Y is selected from the group consisting of substituted or unsubstituted methylene, substituted or unsubstituted ethylene, substituted or unsubstituted propylene, substituted or unsubstituted butylene, and substituted or unsubstituted pentylene. In some embodiments, $R^8$ is selected from the group consisting of substituted or unsubstituted alkyl, substituted or unsubstituted heteroalkyl, substituted or unsubstituted alkenyl, substituted or unsubstituted heteroalkenyl, —COR$^6$, —C(O)OR$^6$, —C(O)NR$^6$R$^7$, —SR$^6$, —SOR$^6$, —SO$_2$R$^6$, and —SO$_2$NR$^6$R$^7$, and wherein $R^9$ is selected from the group consisting of substituted or unsubstituted alkyl, substituted or unsubstituted heteroalkyl, substituted or unsubstituted alkenyl, substituted or unsubstituted heteroalkenyl, —COR$^6$, —C(O)OR$^6$, —C(O)NR$^6$R$^7$, —SR$^6$, —SOR$^6$, —SO$_2$R$^6$, and —SO$_2$NR$^6$R$^7$.

In some embodiments, Y is —O—, and W is absent. In some embodiments wherein Y is —O—, and W is absent, X is selected from the group consisting of substituted or unsubstituted methylene, substituted or unsubstituted ethylene, substituted or unsubstituted propylene, substituted or unsubstituted butylene, and substituted or unsubstituted pentylene, and Z is a bond. In some embodiments, X is a bond, and Z is selected from the group consisting of substituted or unsubstituted methylene, substituted or unsubstituted ethylene, substituted or unsubstituted propylene, substituted or unsubstituted butylene, and substituted or unsubstituted pentylene. In some embodiments, X is selected from the group consisting of substituted or unsubstituted methylene, substituted or unsubstituted ethylene, substituted or unsubstituted propylene, substituted or unsubstituted butylene, and substituted or unsubstituted pentylene, and wherein Z is selected from the group consisting of substituted or unsubstituted methylene, substituted or unsubstituted ethylene, substituted or unsubstituted propylene, substituted or unsubstituted butylene, and substituted or unsubstituted pentylene.

In some embodiments, V is hydrogen or substituted or unsubstituted methyl.

Further to any embodiment above wherein the compound has the structure of Formula (IV), in some embodiments, L is —S—, —O—, —NR$^5$—, substituted or unsubstituted alkylene, or substituted or unsubstituted heteroalkylene; R$^1$ is substituted or unsubstituted alkyl, substituted or unsubstituted aryl, substituted or unsubstituted fused ring aryl, substituted or unsubstituted heteroaryl, or substituted or unsubstituted heterocycloalkyl; and R$^5$ is hydrogen, substituted or unsubstituted alkyl, or substituted or unsubstituted heterocycloalkyl. In some embodiments, L$^1$ is —NR$^5$— or substituted or unsubstituted heteroalkyl, and R$^1$ is substituted or unsubstituted alkyl or substituted or unsubstituted heteroaryl. In some embodiments, L$^1$ is —NR$^5$—, and R$^1$ is substituted alkyl having one or more substituent groups selected from the group consisting of substituted or unsubstituted heteroaryl and substituted or unsubstituted heterocycloalkyl. In some embodiments, R$^1$ is substituted alkyl substituted by chloro-substituted thiophenyl. In some embodiments, L$^1$ is substituted or unsubstituted heteroalkyl, and R$^1$ is substituted or unsubstituted heteroaryl. In some embodiments, L$^1$ and R$^1$ can be any specific group as set forth above for any of Formulae (Ia), (Ib), (II), or (III).

Further to any embodiment above wherein the compound has the structure of Formula (IV), in some embodiments, L$^2$ is bond, substituted or unsubstituted alkylene, —C(O)—, or —SO$_2$—, and R$^2$ is hydrogen, substituted or unsubstituted alkyl, substituted or unsubstituted heteroalkyl, substituted or unsubstituted cycloalkyl, substituted or unsubstituted aryl, substituted or unsubstituted fused ring aryl, substituted or unsubstituted heteroaryl, or substituted or unsubstituted heterocycloalkyl. In some embodiments, L$^2$ is bond, and R$^2$ is hydrogen. In some embodiments, L$^2$ is-C(O)—, and R$^2$ is substituted or unsubstituted alkyl, substituted or unsubstituted heteroalkyl, substituted or unsubstituted cycloalkyl, substituted or unsubstituted aryl, substituted or unsubstituted fused ring aryl, substituted or unsubstituted heteroaryl, or substituted or unsubstituted heterocycloalkyl. In some embodiments, L$^2$ and R$^2$ can be any specific group as set forth above for any of Formulae (Ia), (Ib), (II), or (III).

Further to any embodiment above wherein the compound has the structure of Formula (IV), in some embodiments, L$^4$ is a bond, and R$^4$ is hydrogen, halogen, substituted or unsubstituted alkyl, substituted or unsubstituted heteroalkyl, substituted or unsubstituted aryl, or substituted or unsubstituted heteroaryl. In some embodiments, L$^4$ and R$^4$ can be any specific group as set forth above for any of Formulae (Ia), (Ib), (II), or (III).

In some embodiments, there is provided a compound according to Formula (IV) and its listed embodiments, wherein L$^2$ is a bond, and R$^2$ is hydrogen, providing a compound with structure of Formula (V) following.

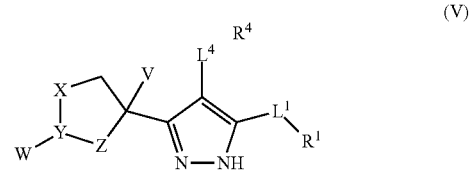

In some embodiments, the compound is a pharmaceutically acceptable salt, ester, solvate, or prodrug of a compound of Formula (V). In some embodiments, the compound is not an ester, not a solvate, and not a prodrug.

Exemplary compounds, e.g., multisubstituted aromatic compounds, in accordance with the present disclosure are provided herein. In Table A and B following, entry number, chemical name (i.e., International Union of Pure and Applied Chemistry [IUPAC] name), calculated molecular weight (MW) and biological activity (i.e., inhibition activity in thrombin and KLKB1 assays) are disclosed. In Table C following, chemical names are disclosed.

For Table A following, the disclosed compounds were assayed for inhibition of the protease activity of thrombin as described herein. In Table A, the level of inhibition in the thrombin assay is indicated as follows: a IC$_{50}$≤0.1 µM; b: 0.1 µM<IC$_{50}$<1 µM; c: 1 µM<IC$_{50}$<10 µM; d: 10 µM<IC$_{50}$<100 µM; e: IC$_{50}$≥100 µM. Accordingly, in some embodiments, there is provided a compound as expressly set forth in Table A following.

TABLE A

| Entry | IUPAC name | MW | Thrombin Activity |
|---|---|---|---|
| 1 | 1,4-bis(prop-2-en-1-yl) 2-(5-[(5-chlorothiophen-2-yl)methyl]amino-1-(2,2-dimethylpropanoyl)-1H-pyrazol-3-yl)piperazine-1,4-dicarboxylate | 550 | e |
| 2 | 1,4-bis(prop-2-en-1-yl) 2-(5-[(5-chlorothiophen-2-yl)methyl]amino-1H-pyrazol-3-yl)piperazine-1,4-dicarboxylate | 466 | e |
| 3 | 1-(3-8-azabicyclo[3.2.1]octan-3-yl-5-[(5-chlorothiophen-2-yl)methyl]amino-1H-pyrazol-1-yl)-2,2-dimethylpropan-1-one | 407 | a |
| 4 | 1-(5-[(5-chlorothiophen-2-yl)methyl]amino-3-(1-methanesulfonylazepan-4-yl)-1H-pyrazol-1-yl)-2,2-dimethylpropan-1-one | 473 | b |
| 5 | 1-(5-[(5-chlorothiophen-2-yl)methyl]amino-3-(1-methanesulfonylazetidin-3-yl)-1H-pyrazol-1-yl)-2,2-dimethylpropan-1-one | 431 | b |
| 6 | 1-(5-[(5-chlorothiophen-2-yl)methyl]amino-3-(1-methanesulfonylpiperidin-4-yl)-1H-pyrazol-1-yl)-2,2-dimethylpropan-1-one | 459 | b |

TABLE A-continued

| Entry | IUPAC name | MW | Thrombin Activity |
|---|---|---|---|
| 7 | 1-(5-[(5-chlorothiophen-2-yl)methyl]amino-3-(1-methanesulfonylpiperidin-4-yl)-1H-pyrazol-1-yl)-3-hydroxy-2,2-dimethylpropan-1-one | 475 | b |
| 8 | 1-(5-[(5-chlorothiophen-2-yl)methyl]amino-3-(1-methanesulfonylpyrrolidin-2-yl)-1H-pyrazol-1-yl)-2,2-dimethylpropan-1-one | 445 | a |
| 9 | 1-(5-[(5-chlorothiophen-2-yl)methyl]amino-3-(1-methanesulfonylpyrrolidin-3-yl)-1H-pyrazol-1-yl)-2,2-dimethylpropan-1-one | 445 | a |
| 10 | 1-(5-[(5-chlorothiophen-2-yl)methyl]amino-3-(1-[6-(trifluoromethyl)pyridin-2-yl]methylpiperidin-4-yl)-1H-pyrazol-1-yl)-2,2-dimethylpropan-1-one | 540 | b |
| 11 | 1-(5-[(5-chlorothiophen-2-yl)methyl]amino-3-(2-methylpyrrolidin-2-yl)-1H-pyrazol-1-yl)-3-hydroxy-2,2-dimethylpropan-1-one; formic acid | 397 | b |
| 12 | 1-(5-[(5-chlorothiophen-2-yl)methyl]amino-3-(3-methylpiperidin-3-yl)-1H-pyrazol-1-yl)-3-hydroxy-2,2-dimethylpropan-1-one; formic acid | 411 | c |
| 13 | 1-(5-[(5-chlorothiophen-2-yl)methyl]amino-3-(3-methylpiperidin-3-yl)-1H-pyrazol-1-yl)-3-methoxy-2,2-dimethylpropan-1-one | 425 | c |
| 14 | 1-(5-[(5-chlorothiophen-2-yl)methyl]amino-3-(4-methanesulfonylpiperazin-2-yl)-1H-pyrazol-1-yl)-2,2-dimethylpropan-1-one | 460 | a |
| 15 | 1-(5-[(5-chlorothiophen-2-yl)methyl]amino-3-(4-methylpiperidin-4-yl)-1H-pyrazol-1-yl)-2,2-dimethylpropan-1-one; formic acid | 395 | b |
| 16 | 1-(5-[(5-chlorothiophen-2-yl)methyl]amino-3-(4-methylpiperidin-4-yl)-1H-pyrazol-1-yl)-3-hydroxy-2,2-dimethylpropan-1-one | 411 | c |
| 17 | 1-(5-[(5-chlorothiophen-2-yl)methyl]amino-3-(4-methylpiperidin-4-yl)-1H-pyrazol-1-yl)-3-methoxy-2,2-dimethylpropan-1-one | 425 | e |
| 18 | 1-(5-[(5-chlorothiophen-2-yl)methyl]amino-3-(oxan-4-yl)-1H-pyrazol-1-yl)-2,2-dimethylpropan-1-one | 382 | b |
| 19 | 1-(5-[(5-chlorothiophen-2-yl)methyl]amino-3-(oxolan-2-yl)-1H-pyrazol-1-yl)-2,2-dimethylpropan-1-one | 368 | a |
| 20 | 1-(5-[(5-chlorothiophen-2-yl)methyl]amino-3-(piperazin-2-yl)-1H-pyrazol-1-yl)-2,2-dimethylpropan-1-one | 382 | b |
| 21 | 1-(5-[(5-chlorothiophen-2-yl)methyl]amino-3-(piperidin-3-yl)-1H-pyrazol-1-yl)-2,2-dimethylpropan-1-one; formic acid | 381 | a |
| 22 | 1-(5-[(5-chlorothiophen-2-yl)methyl]amino-3-(piperidin-3-yl)-1H-pyrazol-1-yl)-3-hydroxy-2,2-dimethylpropan-1-one; formic acid | 397 | b |
| 23 | 1-(5-[(5-chlorothiophen-2-yl)methyl]amino-3-(piperidin-3-yl)-1H-pyrazol-1-yl)-3-methoxy-2,2-dimethylpropan-1-one | 411 | b |
| 24 | 1-(5-[(5-chlorothiophen-2-yl)methyl]amino-3-(piperidin-4-yl)-1H-pyrazol-1-yl)-2,2-dimethylpropan-1-one | 381 | b |
| 25 | 1-(5-[(5-chlorothiophen-2-yl)methyl]amino-3-(piperidin-4-yl)-1H-pyrazol-1-yl)-3-hydroxy-2,2-dimethylpropan-1-one | 397 | b |
| 26 | 1-(5-[(5-chlorothiophen-2-yl)methyl]amino-3-(piperidin-4-yl)-1H-pyrazol-1-yl)-3-methoxy-2,2-dimethylpropan-1-one | 411 | c |
| 27 | 1-(5-[(5-chlorothiophen-2-yl)methyl]amino-3-(pyrrolidin-2-yl)-1H-pyrazol-1-yl)-2,2-dimethylpropan-1-one | 367 | a |
| 28 | 1-(5-[(5-chlorothiophen-2-yl)methyl]amino-3-(pyrrolidin-2-yl)-1H-pyrazol-1-yl)-3-hydroxy-2,2-dimethylpropan-1-one | 383 | a |
| 29 | 1-(5-[(5-chlorothiophen-2-yl)methyl]amino-3-(pyrrolidin-2-yl)-1H-pyrazol-1-yl)-3-methoxy-2,2-dimethylpropan-1-one | 397 | a |
| 30 | 1-(5-[(5-chlorothiophen-2-yl)methyl]amino-3-(pyrrolidin-3-yl)-1H-pyrazol-1-yl)-2,2-dimethylpropan-1-one | 367 | a |
| 31 | 1-(5-[(5-chlorothiophen-2-yl)methyl]amino-3-[1-(1,2,4-oxadiazol-3-ylmethyl)piperidin-4-yl]-1H-pyrazol-1-yl)-2,2-dimethylpropan-1-one | 463 | a |
| 32 | 1-(5-[(5-chlorothiophen-2-yl)methyl]amino-3-[1-(1,3-oxazol-4-ylmethyl)piperidin-4-yl]-1H-pyrazol-1-yl)-2,2-dimethylpropan-1-one | 462 | a |
| 33 | 1-(5-[(5-chlorothiophen-2-yl)methyl]amino-3-[1-(1,3-oxazol-5-ylmethyl)piperidin-4-yl]-1H-pyrazol-1-yl)-2,2-dimethylpropan-1-one | 462 | b |

TABLE A-continued

| Entry | IUPAC name | MW | Thrombin Activity |
|---|---|---|---|
| 34 | 1-(5-[(5-chlorothiophen-2-yl)methyl]amino-3-[1-(1H-1,2,3,4-tetrazol-5-ylmethyl)piperidin-4-yl]-1H-pyrazol-1-yl)-2,2-dimethylpropan-1-one | 463 | c |
| 35 | 1-(5-[(5-chlorothiophen-2-yl)methyl]amino-3-[1-(1H-1,2,3-triazol-5-ylmethyl)piperidin-4-yl]-1H-pyrazol-1-yl)-2,2-dimethylpropan-1-one | 462 | b |
| 36 | 1-(5-[(5-chlorothiophen-2-yl)methyl]amino-3-[1-(1H-imidazol-4-ylmethyl)piperidin-4-yl]-1H-pyrazol-1-yl)-2,2-dimethylpropan-1-one | 461 | b |
| 37 | 1-(5-[(5-chlorothiophen-2-yl)methyl]amino-3-[1-(2,2,2-trifluoroethyl)piperidin-4-yl]-1H-pyrazol-1-yl)-2,2-dimethylpropan-1-one | 463 | c |
| 38 | 1-(5-[(5-chlorothiophen-2-yl)methyl]amino-3-[1-(2,2,2-trifluoroethyl)piperidin-4-yl]-1H-pyrazol-1-yl)-3-hydroxy-2,2-dimethylpropan-1-one | 479 | a |
| 39 | 1-(5-[(5-chlorothiophen-2-yl)methyl]amino-3-[1-(2,2-dimethylpropanoyl)piperidin-4-yl]-1H-pyrazol-1-yl)-2,2-dimethylpropan-1-one | 465 | a |
| 40 | 1-(5-[(5-chlorothiophen-2-yl)methyl]amino-3-[1-(2-cyclopropoxyethyl)piperidin-4-yl]-1H-pyrazol-1-yl)-2,2-dimethylpropan-1-one | 465 | a |
| 41 | 1-(5-[(5-chlorothiophen-2-yl)methyl]amino-3-[1-(2-cyclopropoxyethyl)piperidin-4-yl]-1H-pyrazol-1-yl)-3-hydroxy-2,2-dimethylpropan-1-one | 481 | a |
| 42 | 1-(5-[(5-chlorothiophen-2-yl)methyl]amino-3-[1-(2-methoxyethyl)piperidin-4-yl]-1H-pyrazol-1-yl)-2,2-dimethylpropan-1-one | 439 | b |
| 43 | 1-(5-[(5-chlorothiophen-2-yl)methyl]amino-3-[1-(2-methoxyethyl)piperidin-4-yl]-1H-pyrazol-1-yl)-3-hydroxy-2,2-dimethylpropan-1-one | 455 | b |
| 44 | 1-(5-[(5-chlorothiophen-2-yl)methyl]amino-3-[1-(cyclopropylmethyl)piperidin-4-yl]-1H-pyrazol-1-yl)-2,2-dimethylpropan-1-one | 435 | b |
| 45 | 1-(5-[(5-chlorothiophen-2-yl)methyl]amino-3-[1-(cyclopropylmethyl)piperidin-4-yl]-1H-pyrazol-1-yl)-3-hydroxy-2,2-dimethylpropan-1-one | 451 | c |
| 46 | 1-(5-[(5-chlorothiophen-2-yl)methyl]amino-3-[1-(morpholine-4-carbonyl)azepan-4-yl]-1H-pyrazol-1-yl)-2,2-dimethylpropan-1-one | 508 | a |
| 47 | 1-(5-[(5-chlorothiophen-2-yl)methyl]amino-3-[1-(morpholine-4-carbonyl)azetidin-3-yl]-1H-pyrazol-1-yl)-2,2-dimethylpropan-1-one | 466 | b |
| 48 | 1-(5-[(5-chlorothiophen-2-yl)methyl]amino-3-[1-(morpholine-4-carbonyl)piperidin-4-yl]-1H-pyrazol-1-yl)-2,2-dimethylpropan-1-one | 494 | a |
| 49 | 1-(5-[(5-chlorothiophen-2-yl)methyl]amino-3-[1-(morpholine-4-carbonyl)piperidin-4-yl]-1H-pyrazol-1-yl)-3-hydroxy-2,2-dimethylpropan-1-one | 510 | a |
| 50 | 1-(5-[(5-chlorothiophen-2-yl)methyl]amino-3-[1-(morpholine-4-carbonyl)pyrrolidin-2-yl]-1H-pyrazol-1-yl)-2,2-dimethylpropan-1-one | 480 | b |
| 51 | 1-(5-[(5-chlorothiophen-2-yl)methyl]amino-3-[1-(morpholine-4-carbonyl)pyrrolidin-3-yl]-1H-pyrazol-1-yl)-2,2-dimethylpropan-1-one | 480 | a |
| 52 | 1-(5-[(5-chlorothiophen-2-yl)methyl]amino-3-[1-(morpholine-4-sulfonyl)piperidin-4-yl]-1H-pyrazol-1-yl)-2,2-dimethylpropan-1-one | 530 | a |
| 53 | 1-(5-[(5-chlorothiophen-2-yl)methyl]amino-3-[1-(morpholine-4-sulfonyl)piperidin-4-yl]-1H-pyrazol-1-yl)-3-hydroxy-2,2-dimethylpropan-1-one | 546 | a |
| 54 | 1-(5-[(5-chlorothiophen-2-yl)methyl]amino-3-[1-(oxetan-3-ylmethyl)piperidin-4-yl]-1H-pyrazol-1-yl)-2,2-dimethylpropan-1-one | 451 | b |
| 55 | 1-(5-[(5-chlorothiophen-2-yl)methyl]amino-3-[1-(oxetan-3-ylmethyl)piperidin-4-yl]-1H-pyrazol-1-yl)-3-hydroxy-2,2-dimethylpropan-1-one | 467 | b |
| 56 | 1-(5-[(5-chlorothiophen-2-yl)methyl]amino-3-[1-(pyridin-2-ylmethyl)piperidin-4-yl]-1H-pyrazol-1-yl)-2,2-dimethylpropan-1-one | 472 | a |
| 57 | 1-(5-[(5-chlorothiophen-2-yl)methyl]amino-3-[1-(pyridin-2-ylmethyl)piperidin-4-yl]-1H-pyrazol-1-yl)-3-hydroxy-2,2-dimethylpropan-1-one | 488 | a |
| 58 | 1-(5-[(5-chlorothiophen-2-yl)methyl]amino-3-[1-(pyridin-3-ylmethyl)piperidin-4-yl]-1H-pyrazol-1-yl)-2,2-dimethylpropan-1-one | 472 | a |

TABLE A-continued

| Entry | IUPAC name | MW | Thrombin Activity |
|---|---|---|---|
| 59 | 1-(5-[(5-chlorothiophen-2-yl)methyl]amino-3-[4-(morpholine-4-carbonyl)piperazin-2-yl]-1H-pyrazol-1-yl)-2,2-dimethylpropan-1-one | 495 | a |
| 60 | 1-(5-[(5-chlorothiophen-2-yl)methyl]amino-3-[8-(morpholine-4-carbonyl)-8-azabicyclo[3.2.1]octan-3-yl]-1H-pyrazol-1-yl)-2,2-dimethylpropan-1-one | 520 | a |
| 61 | 1-(5-[(5-chlorothiophen-2-yl)methyl]amino-3-1-[(1-methylazetidin-3-yl)methyl]piperidin-4-yl-1H-pyrazol-1-yl)-2,2-dimethylpropan-1-one | 464 | b |
| 62 | 1-(5-[(5-chlorothiophen-2-yl)methyl]amino-3-1-[(2-methoxyphenyl)methyl]piperidin-4-yl-1H-pyrazol-1-yl)-2,2-dimethylpropan-1-one | 501 | a |
| 63 | 1-(5-[(5-chlorothiophen-2-yl)methyl]amino-3-1-[(3-methoxyphenyl)methyl]piperidin-4-yl-1H-pyrazol-1-yl)-2,2-dimethylpropan-1-one | 501 | a |
| 64 | 1-(5-[(5-chlorothiophen-2-yl)methyl]amino-3-1-[(4-methoxyphenyl)methyl]piperidin-4-yl-1H-pyrazol-1-yl)-2,2-dimethylpropan-1-one | 501 | c |
| 65 | 1-(5-[(5-chlorothiophen-2-yl)methyl]amino-3-1-[(6-methylpyridin-2-yl)methyl]piperidin-4-yl-1H-pyrazol-1-yl)-2,2-dimethylpropan-1-one; formic acid | 486 | a |
| 66 | 1-(5-[(5-chlorothiophen-2-yl)methyl]amino-3-1-[2,2,2-trifluoro-1-(pyridin-2-yl)ethyl]piperidin-4-yl-1H-pyrazol-1-yl)-2,2-dimethylpropan-1-one | 540 | a |
| 67 | 1-(5-[(5-chlorothiophen-2-yl)methyl]amino-3-1-[2,2,2-trifluoro-1-(pyridin-2-yl)ethyl]piperidin-4-yl-1H-pyrazol-1-yl)-3-hydroxy-2,2-dimethylpropan-1-one | 556 | a |
| 68 | 1-(5-[(5-chlorothiophen-2-yl)methyl]amino-3-1-[2,2-difluoro-2-(pyridin-2-yl)ethyl]piperidin-4-yl-1H-pyrazol-1-yl)-2,2-dimethylpropan-1-one | 522 | a |
| 69 | 1-(5-[(5-chlorothiophen-2-yl)methyl]amino-3-1-[2,2-difluoro-2-(pyridin-2-yl)ethyl]piperidin-4-yl-1H-pyrazol-1-yl)-3-hydroxy-2,2-dimethylpropan-1-one | 538 | a |
| 70 | 1-(5-[(5-chlorothiophen-2-yl)methyl]amino-3-1-[2-(morpholin-4-yl)-2-oxoethyl]piperidin-4-yl-1H-pyrazol-1-yl)-2,2-dimethylpropan-1-one | 508 | a |
| 71 | 1-(5-[(5-chlorothiophen-2-yl)methyl]amino-3-1-[2-(morpholin-4-yl)-2-oxoethyl]piperidin-4-yl-1H-pyrazol-1-yl)-3-hydroxy-2,2-dimethylpropan-1-one | 524 | b |
| 72 | 1-(5-[(5-chlorothiophen-2-yl)methyl]amino-3-1-[2-(morpholin-4-yl)acetyl]piperidin-4-yl-1H-pyrazol-1-yl)-2,2-dimethylpropan-1-one | 508 | a |
| 73 | 1-(5-[(5-chlorothiophen-2-yl)methyl]amino-3-1-[2-(morpholin-4-yl)acetyl]piperidin-4-yl-1H-pyrazol-1-yl)-2-(morpholin-4-yl)ethan-1-one | 551 | e |
| 74 | 1-(5-[(5-chlorothiophen-2-yl)methyl]amino-3-1-[2-(morpholin-4-yl)acetyl]piperidin-4-yl-1H-pyrazol-1-yl)-3-hydroxy-2,2-dimethylpropan-1-one | 524 | a |
| 75 | 1-(5-[(5-chlorothiophen-2-yl)methyl]amino-3-1-[2-(morpholin-4-yl)acetyl]pyrrolidin-2-yl-1H-pyrazol-1-yl)-2,2-dimethylpropan-1-one | 494 | a |
| 76 | 1-(5-[(5-chlorothiophen-2-yl)methyl]amino-3-1-[2-(morpholin-4-yl)acetyl]pyrrolidin-3-yl-1H-pyrazol-1-yl)-2,2-dimethylpropan-1-one | 494 | a |
| 77 | 1-(5-[(5-chlorothiophen-2-yl)methyl]amino-3-1-[2-(morpholin-4-yl)ethyl]piperidin-4-yl-1H-pyrazol-1-yl)-2,2-dimethylpropan-1-one; formic acid | 494 | b |
| 78 | 1-(5-[(5-chlorothiophen-2-yl)methyl]amino-3-1-[2-(morpholin-4-yl)ethyl]piperidin-4-yl-1H-pyrazol-1-yl)-3-hydroxy-2,2-dimethylpropan-1-one; formic acid | 510 | b |
| 79 | 1-(5-[(5-chlorothiophen-2-yl)methyl]amino-3-1-[2-(pyridin-2-yl)ethyl]piperidin-4-yl-1H-pyrazol-1-yl)-2,2-dimethylpropan-1-one | 486 | a |
| 80 | 1-(5-[(5-chlorothiophen-2-yl)methyl]amino-3-1-[2-(pyridin-2-yl)ethyl]piperidin-4-yl-1H-pyrazol-1-yl)-3-hydroxy-2,2-dimethylpropan-1-one | 502 | a |
| 81 | 1-(5-[(5-chlorothiophen-2-yl)methyl]amino-3-8-methanesulfonyl-8-azabicyclo[3.2.1]octan-3-yl-1H-pyrazol-1-yl)-2,2-dimethylpropan-1-one | 485 | a |
| 82 | 1-(5-[(5-chlorothiophen-2-yl)methyl]amino-4-fluoro-3-(oxan-4-yl)-1H-pyrazol-1-yl)-2,2-dimethylpropan-1-one | 400 | a |
| 83 | 1-(5-[(5-chlorothiophen-2-yl)methyl]amino-4-fluoro-3-(oxan-4-yl)-1H-pyrazol-1-yl)-3-hydroxy-2,2-dimethylpropan-1-one | 416 | a |
| 84 | 1-(5-[(5-chlorothiophen-2-yl)methyl]amino-4-fluoro-3-(oxan-4-yl)-1H-pyrazol-1-yl)-3-methoxy-2,2-dimethylpropan-1-one | 430 | a |

TABLE A-continued

| Entry | IUPAC name | MW | Thrombin Activity |
|---|---|---|---|
| 85 | 1-(5-[(5-chlorothiophen-2-yl)methyl]amino-4-fluoro-3-(piperidin-4-yl)-1H-pyrazol-1-yl)-2,2-dimethylpropan-1-one | 399 | a |
| 86 | 1-(5-[(5-chlorothiophen-2-yl)methyl]amino-4-fluoro-3-(piperidin-4-yl)-1H-pyrazol-1-yl)-2-methoxy-2-methylpropan-1-one | 415 | b |
| 87 | 1-(5-[(5-chlorothiophen-2-yl)methyl]amino-4-fluoro-3-(piperidin-4-yl)-1H-pyrazol-1-yl)-3-hydroxy-2,2-dimethylpropan-1-one | 415 | a |
| 88 | 1-(5-[(5-chlorothiophen-2-yl)methyl]amino-4-fluoro-3-(piperidin-4-yl)-1H-pyrazol-1-yl)-3-methoxy-2,2-dimethylpropan-1-one | 429 | a |
| 89 | 1-(5-[(5-chlorothiophen-2-yl)methyl]amino-4-methyl-3-(piperidin-4-yl)-1H-pyrazol-1-yl)-2,2-dimethylpropan-1-one; formic acid | 395 | c |
| 90 | 1-[2-(5-[(5-chlorothiophen-2-yl)methyl]amino-1-(2-methoxybenzoyl)-1H-pyrazol-3-yl)pyrrolidin-1-yl]-2,2-dimethylpropan-1-one | 501 | b |
| 91 | 1-[2-(5-[(5-chlorothiophen-2-yl)methyl]amino-1-(2-methoxybenzoyl)-1H-pyrazol-3-yl)pyrrolidin-1-yl]-2-methylpropan-1-one | 487 | b |
| 92 | 1-[2-(5-[(5-chlorothiophen-2-yl)methyl]amino-1-(2-methoxybenzoyl)-1H-pyrazol-3-yl)pyrrolidin-1-yl]ethan-1-one | 459 | c |
| 93 | 1-[2-(5-[(5-chlorothiophen-2-yl)methyl]amino-1H-pyrazol-3-yl)pyrrolidin-1-yl]-2-(morpholin-4-yl)ethan-1-one | 410 | e |
| 94 | 1-[3-(1-acetylpiperidin-4-yl)-5-[(5-chlorothiophen-2-yl)methyl]amino-1H-pyrazol-1-yl]-2,2-dimethylpropan-1-one | 423 | a |
| 95 | 1-[3-(1-benzylpiperidin-4-yl)-5-[(5-chlorothiophen-2-yl)methyl]amino-1H-pyrazol-1-yl]-2,2-dimethylpropan-1-one | 471 | a |
| 96 | 1-[3-(5-[(5-chlorothiophen-2-yl)methyl]amino-1-(2,2-dimethylpropanoyl)-1H-pyrazol-3-yl)azetidin-1-yl]-2,2-dimethylpropan-1-one | 437 | b |
| 97 | 1-[3-(5-[(5-chlorothiophen-2-yl)methyl]amino-1H-pyrazol-3-yl)azetidin-1-yl]-2,2-dimethylpropan-1-one | 353 | e |
| 98 | 1-[3-(5-[(5-chlorothiophen-2-yl)methyl]amino-1H-pyrazol-3-yl)pyrrolidin-1-yl]-2-(morpholin-4-yl)ethan-1-one | 410 | e |
| 99 | 1-[4-(5-[(5-chlorothiophen-2-yl)methyl]amino-1-(2-methoxybenzoyl)-1H-pyrazol-3-yl)piperidin-1-yl]-2,2-dimethylpropan-1-one | 515 | a |
| 100 | 1-[4-(5-[(5-chlorothiophen-2-yl)methyl]amino-1-(2-methoxybenzoyl)-1H-pyrazol-3-yl)piperidin-1-yl]ethan-1-one | 473 | b |
| 101 | 1-[4-(5-[(5-chlorothiophen-2-yl)methyl]amino-1-(thiophene-3-carbonyl)-1H-pyrazol-3-yl)piperidin-1-yl]-2,2-dimethylpropan-1-one | 491 | a |
| 102 | 1-[4-(5-[(5-chlorothiophen-2-yl)methyl]amino-1-(thiophene-3-carbonyl)-1H-pyrazol-3-yl)piperidin-1-yl]ethan-1-one | 449 | b |
| 103 | 1-[4-(5-[(5-chlorothiophen-2-yl)methyl]amino-1H-pyrazol-3-yl)piperidin-1-yl]-2-(morpholin-4-yl)ethan-1-one | 424 | e |
| 104 | 1-[4-(5-[(5-chlorothiophen-2-yl)methyl]amino-4-fluoro-1H-pyrazol-3-yl)piperidine-1-carbonyl]cyclopropan-1-ol | 399 | d |
| 105 | 1-benzoyl-N-[(5-chlorothiophen-2-yl)methyl]-3-(piperidin-4-yl)-1H-pyrazol-5-amine hydrochloride | 401 | b |
| 106 | 1-benzoyl-N-[(5-chlorothiophen-2-yl)methyl]-4-fluoro-3-(oxan-4-yl)-1H-pyrazol-5-amine | 420 | a |
| 107 | 1-3-[1-(benzenesulfonyl)piperidin-4-yl]-5-[(5-chlorothiophen-2-yl)methyl]amino-1H-pyrazol-1-yl-2,2-dimethylpropan-1-one | 521 | b |
| 108 | 1-3-[1-(benzenesulfonyl)piperidin-4-yl]-5-[(5-chlorothiophen-2-yl)methyl]amino-1H-pyrazol-1-yl-3-hydroxy-2,2-dimethylpropan-1-one | 537 | a |
| 109 | 2-[4-(5-[(5-chlorothiophen-2-yl)methyl]amino-1-(2,2-dimethylpropanoyl)-1H-pyrazol-3-yl)piperidin-1-yl]acetic acid | 439 | b |
| 110 | 2-[4-(5-[(5-chlorothiophen-2-yl)methyl]amino-1-(3-hydroxy-2,2-dimethylpropanoyl)-1H-pyrazol-3-yl)piperidin-1-yl]acetic acid | 455 | b |
| 111 | 2-[4-(5-[(5-chlorothiophen-2-yl)methyl]amino-1H-pyrazol-3-yl)piperidin-1-yl]-1-(morpholin-4-yl)ethan-1-one | 424 | e |

TABLE A-continued

| Entry | IUPAC name | MW | Thrombin Activity |
|---|---|---|---|
| 112 | 2-[4-(5-[(5-chlorothiophen-2-yl)methyl]amino-1H-pyrazol-3-yl)piperidin-1-yl]acetic acid | 355 | e |
| 113 | 3-(1-benzylpiperidin-4-yl)-N-[(5-chlorothiophen-2-yl)methyl]-1H-pyrazol-5-amine | 387 | e |
| 114 | 3-(1-benzylpyrrolidin-3-yl)-N-[(5-chlorothiophen-2-yl)methyl]-1-(furan-3-carbonyl)-1H-pyrazol-5-amine | 467 | c |
| 115 | 3-(5-[(5-chlorothiophen-2-yl)methyl]amino-1-(2,2-dimethylpropanoyl)-1H-pyrazol-3-yl)-3-methylpiperidin-2-one | 409 | b |
| 116 | 3-(5-[(5-chlorothiophen-2-yl)methyl]amino-1-(2,2-dimethylpropanoyl)-1H-pyrazol-3-yl)-3-methylpyrrolidin-2-one | 395 | a |
| 117 | 3-(5-[(5-chlorothiophen-2-yl)methyl]amino-1-(2-methoxybenzoyl)-1H-pyrazol-3-yl)-3-methylpiperidin-2-one | 459 | b |
| 118 | 3-(5-[(5-chlorothiophen-2-yl)methyl]amino-1-(2-methoxybenzoyl)-1H-pyrazol-3-yl)-3-methylpyrrolidin-2-one | 445 | b |
| 119 | 3-(5-[(5-chlorothiophen-2-yl)methyl]amino-1-(3-hydroxy-2,2-dimethylpropanoyl)-1H-pyrazol-3-yl)-3-methylpiperidin-2-one | 425 | b |
| 120 | 3-(5-[(5-chlorothiophen-2-yl)methyl]amino-1-(3-methoxy-2,2-dimethylpropanoyl)-1H-pyrazol-3-yl)-3-methylpiperidin-2-one | 439 | c |
| 121 | 3-(5-[(5-chlorothiophen-2-yl)methyl]amino-1-(4-methyloxane-4-carbonyl)-1H-pyrazol-3-yl)-3-methylpiperidin-2-one | 451 | c |
| 122 | 3-(5-[(5-chlorothiophen-2-yl)methyl]amino-1-(4-methyloxane-4-carbonyl)-1H-pyrazol-3-yl)-3-methylpyrrolidin-2-one | 437 | b |
| 123 | 3-(5-[(5-chlorothiophen-2-yl)methyl]amino-1-(thiophene-3-carbonyl)-1H-pyrazol-3-yl)-3-methylpiperidin-2-one | 435 | b |
| 124 | 3-(5-[(5-chlorothiophen-2-yl)methyl]amino-1-(thiophene-3-carbonyl)-1H-pyrazol-3-yl)-3-methylpyrrolidin-2-one | 421 | b |
| 125 | 3-(azepan-4-yl)-N-[(5-chlorothiophen-2-yl)methyl]-1H-pyrazol-5-amine | 311 | e |
| 126 | 3-(azetidin-3-yl)-N-[(5-chlorothiophen-2-yl)methyl]-1-(2,3-dihydro-1,4-benzodioxine-5-carbonyl)-1H-pyrazol-5-amine; trifluoroacetic acid | 431 | c |
| 127 | 3-(azetidin-3-yl)-N-[(5-chlorothiophen-2-yl)methyl]-1-(2-methoxybenzoyl)-1H-pyrazol-5-amine hydrochloride | 403 | d |
| 128 | 3-(azetidin-3-yl)-N-[(5-chlorothiophen-2-yl)methyl]-1-(furan-3-carbonyl)-1H-pyrazol-5-amine; trifluoroacetic acid | 363 | c |
| 129 | 3-(azetidin-3-yl)-N-[(5-chlorothiophen-2-yl)methyl]-1-(thiophene-3-carbonyl)-1H-pyrazol-5-amine; trifluoroacetic acid | 379 | c |
| 130 | 3-[1-(benzenesulfonyl)piperidin-4-yl]-N-[(5-chlorothiophen-2-yl)methyl]-1H-pyrazol-5-amine | 437 | c |
| 131 | 3-8-azabicyclo[3.2.1]octan-3-yl-N-[(5-chlorothiophen-2-yl)methyl]-1H-pyrazol-5-amine | 323 | e |
| 132 | 4-(5-[(5-chlorothiophen-2-yl)methyl]amino-1-(2,2-dimethylpropanoyl)-1H-pyrazol-3-yl)-N,N-dimethylpiperidine-1-carboxamide | 452 | a |
| 133 | 4-(5-[(5-chlorothiophen-2-yl)methyl]amino-1-(2,2-dimethylpropanoyl)-1H-pyrazol-3-yl)-N,N-dimethylpiperidine-1-sulfonamide | 488 | b |
| 134 | 4-(5-[(5-chlorothiophen-2-yl)methyl]amino-1-(3-hydroxy-2,2-dimethylpropanoyl)-1H-pyrazol-3-yl)-N,N-dimethylpiperidine-1-carboxamide | 468 | a |
| 135 | 4-(5-[(5-chlorothiophen-2-yl)methyl]amino-1-(3-hydroxy-2,2-dimethylpropanoyl)-1H-pyrazol-3-yl)-N,N-dimethylpiperidine-1-sulfonamide | 504 | a |
| 136 | 4-(5-[(5-chlorothiophen-2-yl)methyl]amino-1-(dimethylcarbamoyl)-1H-pyrazol-3-yl)-N,N-dimethylpiperidine-1-carboxamide | 439 | e |
| 137 | 4-(5-[(5-chlorothiophen-2-yl)methyl]amino-1H-pyrazol-3-yl)-N,N-dimethylpiperidine-1-carboxamide | 368 | e |
| 138 | 4-(5-[(5-chlorothiophen-2-yl)methyl]amino-1H-pyrazol-3-yl)-N,N-dimethylpiperidine-1-sulfonamide | 404 | e |
| 139 | 4-(5-[(5-chlorothiophen-2-yl)methyl]amino-3-[1-(morpholine-4-carbonyl)piperidin-4-yl]-1H-pyrazole-1-carbonyl)-4-methylcyclohexan-1-ol | 550 | a |

TABLE A-continued

| Entry | IUPAC name | MW | Thrombin Activity |
|---|---|---|---|
| 140 | 5-[(5-chlorothiophen-2-yl)methyl]amino-1-(2,2-dimethylpropanoyl)-3-[1-(morpholine-4-carbonyl)piperidin-4-yl]-1H-pyrazole-4-carbonitrile | 519 | a |
| 141 | 5-[(5-chlorothiophen-2-yl)methyl]amino-3-[1-(morpholine-4-carbonyl)piperidin-4-yl]-1H-pyrazole-4-carbonitrile | 435 | e |
| 142 | N-[(5-chlorothiophen-2-yl)methyl]-1-(1,4-dimethylpiperidine-4-carbonyl)-3-[1-(morpholine-4-carbonyl)piperidin-4-yl]-1H-pyrazol-5-amine; formic acid | 549 | b |
| 143 | N-[(5-chlorothiophen-2-yl)methyl]-1-(2,3-dihydro-1,4-benzodioxine-5-carbonyl)-3-(piperidin-4-yl)-1H-pyrazol-5-amine hydrochloride | 459 | c |
| 144 | N-[(5-chlorothiophen-2-yl)methyl]-1-(2,3-dihydro-1,4-benzodioxine-5-carbonyl)-3-(pyrrolidin-2-yl)-1H-pyrazol-5-amine hydrochloride | 445 | a |
| 145 | N-[(5-chlorothiophen-2-yl)methyl]-1-(2,3-dihydro-1,4-benzodioxine-5-carbonyl)-4-fluoro-3-(oxan-4-yl)-1H-pyrazol-5-amine | 478 | a |
| 146 | N-[(5-chlorothiophen-2-yl)methyl]-1-(2,3-dihydro-1,4-benzodioxine-5-carbonyl)-4-fluoro-3-(piperidin-4-yl)-1H-pyrazol-5-amine | 477 | a |
| 147 | N-[(5-chlorothiophen-2-yl)methyl]-1-(2,4-dimethoxybenzoyl)-3-(piperidin-4-yl)-1H-pyrazol-5-amine | 461 | c |
| 148 | N-[(5-chlorothiophen-2-yl)methyl]-1-(2,4-dimethoxybenzoyl)-3-(pyrrolidin-2-yl)-1H-pyrazol-5-amine | 447 | a |
| 149 | N-[(5-chlorothiophen-2-yl)methyl]-1-(2,4-dimethoxybenzoyl)-4-fluoro-3-(oxan-4-yl)-1H-pyrazol-5-amine | 480 | a |
| 150 | N-[(5-chlorothiophen-2-yl)methyl]-1-(2,4-dimethoxybenzoyl)-4-fluoro-3-(piperidin-4-yl)-1H-pyrazol-5-amine | 479 | a |
| 151 | N-[(5-chlorothiophen-2-yl)methyl]-1-(2,6-dimethylcyclohexanecarbonyl)-3-(piperidin-4-yl)-1H-pyrazol-5-amine hydrochloride | 435 | c |
| 152 | N-[(5-chlorothiophen-2-yl)methyl]-1-(2-methoxybenzoyl)-3-(2-methylpyrrolidin-2-yl)-1H-pyrazol-5-amine; formic acid | 431 | b |
| 153 | N-[(5-chlorothiophen-2-yl)methyl]-1-(2-methoxybenzoyl)-3-(3-methylpiperidin-3-yl)-1H-pyrazol-5-amine | 445 | c |
| 154 | N-[(5-chlorothiophen-2-yl)methyl]-1-(2-methoxybenzoyl)-3-(4-methylpiperidin-4-yl)-1H-pyrazol-5-amine | 445 | c |
| 155 | N-[(5-chlorothiophen-2-yl)methyl]-1-(2-methoxybenzoyl)-3-(oxan-4-yl)-1H-pyrazol-5-amine | 432 | c |
| 156 | N-[(5-chlorothiophen-2-yl)methyl]-1-(2-methoxybenzoyl)-3-(oxolan-2-yl)-1H-pyrazol-5-amine | 418 | a |
| 157 | N-[(5-chlorothiophen-2-yl)methyl]-1-(2-methoxybenzoyl)-3-(piperidin-3-yl)-1H-pyrazol-5-amine | 431 | b |
| 158 | N-[(5-chlorothiophen-2-yl)methyl]-1-(2-methoxybenzoyl)-3-(piperidin-4-yl)-1H-pyrazol-5-amine hydrochloride | 431 | c |
| 159 | N-[(5-chlorothiophen-2-yl)methyl]-1-(2-methoxybenzoyl)-3-(pyrrolidin-2-yl)-1H-pyrazol-5-amine | 417 | b |
| 160 | N-[(5-chlorothiophen-2-yl)methyl]-1-(2-methoxybenzoyl)-3-[1-(2,2,2-trifluoroethyl)piperidin-4-yl]-1H-pyrazol-5-amine | 513 | c |
| 161 | N-[(5-chlorothiophen-2-yl)methyl]-1-(4-methyloxane-4-carbonyl)-3-(2-methylpyrrolidin-2-yl)-1H-pyrazol-5-amine | 423 | b |
| 162 | N-[(5-chlorothiophen-2-yl)methyl]-1-(4-methyloxane-4-carbonyl)-3-(3-methylpiperidin-3-yl)-1H-pyrazol-5-amine | 437 | c |
| 163 | N-[(5-chlorothiophen-2-yl)methyl]-1-(4-methyloxane-4-carbonyl)-3-(4-methylpiperidin-4-yl)-1H-pyrazol-5-amine | 437 | c |
| 164 | N-[(5-chlorothiophen-2-yl)methyl]-1-(4-methyloxane-4-carbonyl)-3-(piperidin-3-yl)-1H-pyrazol-5-amine | 423 | b |
| 165 | N-[(5-chlorothiophen-2-yl)methyl]-1-(4-methyloxane-4-carbonyl)-3-(pyrrolidin-2-yl)-1H-pyrazol-5-amine | 409 | a |
| 166 | N-[(5-chlorothiophen-2-yl)methyl]-1-(furan-3-carbonyl)-3-(piperidin-4-yl)-1H-pyrazol-5-amine hydrochloride | 391 | b |

TABLE A-continued

| Entry | IUPAC name | MW | Thrombin Activity |
|---|---|---|---|
| 167 | N-[(5-chlorothiophen-2-yl)methyl]-1-(furan-3-carbonyl)-3-(pyrrolidin-2-yl)-1H-pyrazol-5-amine | 377 | a |
| 168 | N-[(5-chlorothiophen-2-yl)methyl]-1-(morpholine-4-carbonyl)-3-[1-(morpholine-4-carbonyl)piperidin-4-yl]-1H-pyrazol-5-amine | 523 | c |
| 169 | N-[(5-chlorothiophen-2-yl)methyl]-1-cyclohexanecarbonyl-3-(piperidin-4-yl)-1H-pyrazol-5-amine hydrochloride | 407 | e |
| 170 | N-[(5-chlorothiophen-2-yl)methyl]-1-cyclopentanecarbonyl-3-(piperidin-4-yl)-1H-pyrazol-5-amine hydrochloride | 393 | e |
| 171 | N-[(5-chlorothiophen-2-yl)methyl]-3-(1-methanesulfonylazepan-4-yl)-1H-pyrazol-5-amine | 389 | e |
| 172 | N-[(5-chlorothiophen-2-yl)methyl]-3-(1-methanesulfonylazetidin-3-yl)-1H-pyrazol-5-amine | 347 | e |
| 173 | N-[(5-chlorothiophen-2-yl)methyl]-3-(1-methanesulfonylpiperidin-4-yl)-1H-pyrazol-5-amine | 375 | e |
| 174 | N-[(5-chlorothiophen-2-yl)methyl]-3-(1-methanesulfonylpyrrolidin-2-yl)-1H-pyrazol-5-amine | 361 | e |
| 175 | N-[(5-chlorothiophen-2-yl)methyl]-3-(1-methanesulfonylpyrrolidin-3-yl)-1H-pyrazol-5-amine | 361 | e |
| 176 | N-[(5-chlorothiophen-2-yl)methyl]-3-(1-[6-(trifluoromethyl)pyridin-2-yl]methylpiperidin-4-yl)-1H-pyrazol-5-amine | 456 | e |
| 177 | N-[(5-chlorothiophen-2-yl)methyl]-3-(2-methylpyrrolidin-2-yl)-1-(thiophene-3-carbonyl)-1H-pyrazol-5-amine; formic acid | 407 | a |
| 178 | N-[(5-chlorothiophen-2-yl)methyl]-3-(3-methylpiperidin-3-yl)-1-(thiophene-3-carbonyl)-1H-pyrazol-5-amine | 421 | b |
| 179 | N-[(5-chlorothiophen-2-yl)methyl]-3-(4-methanesulfonylpiperazin-2-yl)-1H-pyrazol-5-amine | 376 | e |
| 180 | N-[(5-chlorothiophen-2-yl)methyl]-3-(4-methylpiperidin-4-yl)-1-(thiophene-3-carbonyl)-1H-pyrazol-5-amine | 421 | c |
| 181 | N-[(5-chlorothiophen-2-yl)methyl]-3-(oxan-4-yl)-1-(thiophene-3-carbonyl)-1H-pyrazol-5-amine | 408 | b |
| 182 | N-[(5-chlorothiophen-2-yl)methyl]-3-(oxan-4-yl)-1H-pyrazol-5-amine | 298 | e |
| 183 | N-[(5-chlorothiophen-2-yl)methyl]-3-(oxolan-2-yl)-1-(thiophene-3-carbonyl)-1H-pyrazol-5-amine | 394 | a |
| 184 | N-[(5-chlorothiophen-2-yl)methyl]-3-(oxolan-2-yl)-1H-pyrazol-5-amine | 284 | e |
| 185 | N-[(5-chlorothiophen-2-yl)methyl]-3-(piperidin-3-yl)-1-(thiophene-3-carbonyl)-1H-pyrazol-5-amine | 407 | b |
| 186 | N-[(5-chlorothiophen-2-yl)methyl]-3-(piperidin-3-yl)-1H-pyrazol-5-amine | 297 | c |
| 187 | N-[(5-chlorothiophen-2-yl)methyl]-3-(piperidin-4-yl)-1-(thiophene-3-carbonyl)-1H-pyrazol-5-amine hydrochloride | 407 | b |
| 188 | N-[(5-chlorothiophen-2-yl)methyl]-3-(piperidin-4-yl)-1H-pyrazol-5-amine | 297 | e |
| 189 | N-[(5-chlorothiophen-2-yl)methyl]-3-(pyrrolidin-2-yl)-1H-pyrazol-5-amine | 283 | e |
| 190 | N-[(5-chlorothiophen-2-yl)methyl]-3-(pyrrolidin-3-yl)-1H-pyrazol-5-amine | 283 | c |
| 191 | N-[(5-chlorothiophen-2-yl)methyl]-3-[1-(1,2,4-oxadiazol-3-ylmethyl)piperidin-4-yl]-1H-pyrazol-5-amine | 379 | e |
| 192 | N-[(5-chlorothiophen-2-yl)methyl]-3-[1-(1,2,4-oxadiazol-5-ylmethyl)piperidin-4-yl]-1H-pyrazol-5-amine | 379 | e |
| 193 | N-[(5-chlorothiophen-2-yl)methyl]-3-[1-(1,3-oxazol-2-ylmethyl)piperidin-4-yl]-1H-pyrazol-5-amine | 378 | e |
| 194 | N-[(5-chlorothiophen-2-yl)methyl]-3-[1-(1,3-oxazol-5-ylmethyl)piperidin-4-yl]-1H-pyrazol-5-amine | 378 | e |
| 195 | N-[(5-chlorothiophen-2-yl)methyl]-3-[1-(1H-1,2,3,4-tetrazol-5-ylmethyl)piperidin-4-yl]-1H-pyrazol-5-amine | 379 | c |
| 196 | N-[(5-chlorothiophen-2-yl)methyl]-3-[1-(1H-1,2,3-triazol-5-ylmethyl)piperidin-4-yl]-1H-pyrazol-5-amine | 378 | e |
| 197 | N-[(5-chlorothiophen-2-yl)methyl]-3-[1-(1H-imidazol-4-ylmethyl)piperidin-4-yl]-1H-pyrazol-5-amine | 377 | c |
| 198 | N-[(5-chlorothiophen-2-yl)methyl]-3-[1-(2,2,2-trifluoroethyl)piperidin-4-yl]-1H-pyrazol-5-amine | 379 | e |
| 199 | N-[(5-chlorothiophen-2-yl)methyl]-3-[1-(2-cyclopropoxyethyl)piperidin-4-yl]-1H-pyrazol-5-amine; formic acid | 381 | e |
| 200 | N-[(5-chlorothiophen-2-yl)methyl]-3-[1-(2-methoxyethyl)piperidin-4-yl]-1H-pyrazol-5-amine | 355 | e |

TABLE A-continued

| Entry | IUPAC name | MW | Thrombin Activity |
|---|---|---|---|
| 201 | N-[(5-chlorothiophen-2-yl)methyl]-3-[1-(cyclopropylmethyl)piperidin-4-yl]-1H-pyrazol-5-amine | 351 | e |
| 202 | N-[(5-chlorothiophen-2-yl)methyl]-3-[1-(morpholine-4-carbonyl)azepan-4-yl]-1H-pyrazol-5-amine | 424 | e |
| 203 | N-[(5-chlorothiophen-2-yl)methyl]-3-[1-(morpholine-4-carbonyl)piperidin-4-yl]-1H-pyrazol-5-amine | 410 | e |
| 204 | N-[(5-chlorothiophen-2-yl)methyl]-3-[1-(morpholine-4-carbonyl)pyrrolidin-2-yl]-1H-pyrazol-5-amine | 396 | e |
| 205 | N-[(5-chlorothiophen-2-yl)methyl]-3-[1-(morpholine-4-carbonyl)pyrrolidin-3-yl]-1-(1,3-thiazole-4-carbonyl)-1H-pyrazol-5-amine | 507 | a |
| 206 | N-[(5-chlorothiophen-2-yl)methyl]-3-[1-(morpholine-4-carbonyl)pyrrolidin-3-yl]-1H-pyrazol-5-amine | 396 | e |
| 207 | N-[(5-chlorothiophen-2-yl)methyl]-3-[1-(morpholine-4-sulfonyl)piperidin-4-yl]-1H-pyrazol-5-amine | 446 | e |
| 208 | N-[(5-chlorothiophen-2-yl)methyl]-3-[1-(oxan-4-yl)piperidin-4-yl]-1H-pyrazol-5-amine | 381 | e |
| 209 | N-[(5-chlorothiophen-2-yl)methyl]-3-[1-(oxetan-3-ylmethyl)piperidin-4-yl]-1H-pyrazol-5-amine; formic acid | 367 | e |
| 210 | N-[(5-chlorothiophen-2-yl)methyl]-3-[1-(pyridin-2-ylmethyl)piperidin-4-yl]-1H-pyrazol-5-amine | 388 | c |
| 211 | N-[(5-chlorothiophen-2-yl)methyl]-3-[1-(pyridin-3-ylmethyl)piperidin-4-yl]-1H-pyrazol-5-amine | 388 | e |
| 212 | N-[(5-chlorothiophen-2-yl)methyl]-3-[4-(morpholine-4-carbonyl)piperazin-2-yl]-1H-pyrazol-5-amine hydrochloride | 411 | e |
| 213 | N-[(5-chlorothiophen-2-yl)methyl]-3-[8-(morpholine-4-carbonyl)-8-azabicyclo[3.2.1]octan-3-yl]-1-(1,3-thiazole-4-carbonyl)-1H-pyrazol-5-amine | 547 | a |
| 214 | N-[(5-chlorothiophen-2-yl)methyl]-3-[8-(morpholine-4-carbonyl)-8-azabicyclo[3.2.1]octan-3-yl]-1H-pyrazol-5-amine | 436 | e |
| 215 | N-[(5-chlorothiophen-2-yl)methyl]-3-1-[(1-methylazetidin-3-yl)methyl]piperidin-4-yl-1H-pyrazol-5-amine | 380 | e |
| 216 | N-[(5-chlorothiophen-2-yl)methyl]-3-1-[(2-methoxyphenyl)methyl]piperidin-4-yl-1H-pyrazol-5-amine | 417 | e |
| 217 | N-[(5-chlorothiophen-2-yl)methyl]-3-1-[(3-methoxyphenyl)methyl]piperidin-4-yl-1H-pyrazol-5-amine | 417 | c |
| 218 | N-[(5-chlorothiophen-2-yl)methyl]-3-1-[(4-methoxyphenyl)methyl]piperidin-4-yl-1-(thiophene-3-carbonyl)-1H-pyrazol-5-amine | 527 | c |
| 219 | N-[(5-chlorothiophen-2-yl)methyl]-3-1-[(4-methoxyphenyl)methyl]piperidin-4-yl-1H-pyrazol-5-amine | 417 | e |
| 220 | N-[(5-chlorothiophen-2-yl)methyl]-3-1-[(6-methylpyridin-2-yl)methyl]piperidin-4-yl-1H-pyrazol-5-amine | 402 | e |
| 221 | N-[(5-chlorothiophen-2-yl)methyl]-3-1-[2,2,2-trifluoro-1-(pyridin-2-yl)ethyl]piperidin-4-yl-1H-pyrazol-5-amine | 456 | e |
| 222 | N-[(5-chlorothiophen-2-yl)methyl]-3-1-[2,2-difluoro-2-(pyridin-2-yl)ethyl]piperidin-4-yl-1H-pyrazol-5-amine | 438 | e |
| 223 | N-[(5-chlorothiophen-2-yl)methyl]-3-1-[2-(morpholin-4-yl)ethyl]piperidin-4-yl-1H-pyrazol-5-amine | 410 | c |
| 224 | N-[(5-chlorothiophen-2-yl)methyl]-3-1-[2-(pyridin-2-yl)ethyl]piperidin-4-yl-1H-pyrazol-5-amine | 402 | e |
| 225 | N-[(5-chlorothiophen-2-yl)methyl]-3-8-methanesulfonyl-8-azabicyclo[3.2.1]octan-3-yl-1-(1,3-thiazole-4-carbonyl)-1H-pyrazol-5-amine | 512 | a |
| 226 | N-[(5-chlorothiophen-2-yl)methyl]-3-8-methanesulfonyl-8-azabicyclo[3.2.1]octan-3-yl-1H-pyrazol-5-amine | 401 | e |
| 227 | N-[(5-chlorothiophen-2-yl)methyl]-4-fluoro-1-(2-methoxybenzoyl)-3-(oxan-4-yl)-1H-pyrazol-5-amine | 450 | a |
| 228 | N-[(5-chlorothiophen-2-yl)methyl]-4-fluoro-1-(2-methoxybenzoyl)-3-(piperidin-4-yl)-1H-pyrazol-5-amine | 449 | a |
| 229 | N-[(5-chlorothiophen-2-yl)methyl]-4-fluoro-1-(4-methyloxane-4-carbonyl)-3-(oxan-4-yl)-1H-pyrazol-5-amine | 442 | a |
| 230 | N-[(5-chlorothiophen-2-yl)methyl]-4-fluoro-1-(furan-3-carbonyl)-3-(oxan-4-yl)-1H-pyrazol-5-amine | 410 | a |
| 231 | N-[(5-chlorothiophen-2-yl)methyl]-4-fluoro-1-(furan-3-carbonyl)-3-(piperidin-4-yl)-1H-pyrazol-5-amine | 409 | a |

TABLE A-continued

| Entry | IUPAC name | MW | Thrombin Activity |
|---|---|---|---|
| 232 | N-[(5-chlorothiophen-2-yl)methyl]-4-fluoro-1-[4-(2-methoxyethoxy)benzoyl]-3-(oxan-4-yl)-1H-pyrazol-5-amine | 494 | a |
| 233 | N-[(5-chlorothiophen-2-yl)methyl]-4-fluoro-1-[4-(morpholin-4-yl)benzoyl]-3-(oxan-4-yl)-1H-pyrazol-5-amine | 505 | a |
| 234 | N-[(5-chlorothiophen-2-yl)methyl]-4-fluoro-3-(oxan-4-yl)-1-(thiophene-3-carbonyl)-1H-pyrazol-5-amine | 426 | a |
| 236 | N-[(5-chlorothiophen-2-yl)methyl]-4-methyl-3-[1-(1,3-thiazole-4-carbonyl)piperidin-4-yl]-1H-pyrazol-5-amine | 422 | e |
| 237 | N-[(5-chlorothiophen-2-yl)methyl]-4-methyl-3-[1-(morpholine-4-carbonyl)piperidin-4-yl]-1H-pyrazol-5-amine | 424 | d |
| 238 | N-[(5-chlorothiophen-2-yl)methyl]-N-3-[1-(morpholine-4-sulfonyl)piperidin-4-yl]-1H-pyrazol-5-ylmorpholine-4-sulfonamide | 595 | c |
| 239 | [1-(5-[(5-chlorothiophen-2-yl)methyl]amino-4-fluoro-3-(oxan-4-yl)-1H-pyrazole-1-carbonyl)cyclopropyl]methanol | 414 | a |
| 240 | prop-2-en-1-yl 2-(5-[(5-chlorothiophen-2-yl)methyl]amino-1-(1,3-thiazole-4-carbonyl)-1H-pyrazol-3-yl)-4-(morpholine-4-carbonyl)piperazine-1-carboxylate | 606 | b |
| 241 | prop-2-en-1-yl 2-(5-[(5-chlorothiophen-2-yl)methyl]amino-1-(1,3-thiazole-4-carbonyl)-1H-pyrazol-3-yl)-4-[2-(morpholin-4-yl)acetyl]piperazine-1-carboxylate | 620 | b |
| 242 | prop-2-en-1-yl 2-(5-[(5-chlorothiophen-2-yl)methyl]amino-1-(1,3-thiazole-4-carbonyl)-1H-pyrazol-3-yl)-4-methanesulfonylpiperazine-1-carboxylate | 571 | b |
| 243 | prop-2-en-1-yl 2-(5-[(5-chlorothiophen-2-yl)methyl]amino-1-(1,3-thiazole-4-carbonyl)-1H-pyrazol-3-yl)pyrrolidine-1-carboxylate | 478 | a |
| 244 | prop-2-en-1-yl 2-(5-[(5-chlorothiophen-2-yl)methyl]amino-1-(2,2-dimethylpropanoyl)-1H-pyrazol-3-yl)-4-(morpholine-4-carbonyl)piperazine-1-carboxylate | 579 | c |
| 245 | prop-2-en-1-yl 2-(5-[(5-chlorothiophen-2-yl)methyl]amino-1-(2,2-dimethylpropanoyl)-1H-pyrazol-3-yl)-4-[2-(morpholin-4-yl)acetyl]piperazine-1-carboxylate | 593 | c |
| 246 | prop-2-en-1-yl 2-(5-[(5-chlorothiophen-2-yl)methyl]amino-1-(2,2-dimethylpropanoyl)-1H-pyrazol-3-yl)-4-methanesulfonylpiperazine-1-carboxylate | 544 | e |
| 247 | prop-2-en-1-yl 2-(5-[(5-chlorothiophen-2-yl)methyl]amino-1-(2,2-dimethylpropanoyl)-1H-pyrazol-3-yl)pyrrolidine-1-carboxylate | 451 | a |
| 248 | prop-2-en-1-yl 2-(5-[(5-chlorothiophen-2-yl)methyl]amino-1H-pyrazol-3-yl)-4-(2,2,2-trifluoroethyl)piperazine-1-carboxylate | 464 | e |
| 249 | prop-2-en-1-yl 2-(5-[(5-chlorothiophen-2-yl)methyl]amino-1H-pyrazol-3-yl)-4-(morpholine-4-carbonyl)piperazine-1-carboxylate | 495 | e |
| 250 | prop-2-en-1-yl 2-(5-[(5-chlorothiophen-2-yl)methyl]amino-1H-pyrazol-3-yl)-4-(morpholine-4-sulfonyl)piperazine-1-carboxylate | 531 | e |
| 251 | prop-2-en-1-yl 2-(5-[(5-chlorothiophen-2-yl)methyl]amino-1H-pyrazol-3-yl)-4-[2-(morpholin-4-yl)acetyl]piperazine-1-carboxylate | 509 | e |
| 252 | prop-2-en-1-yl 2-(5-[(5-chlorothiophen-2-yl)methyl]amino-1H-pyrazol-3-yl)-4-methanesulfonylpiperazine-1-carboxylate | 460 | e |
| 253 | prop-2-en-1-yl 2-(5-[(5-chlorothiophen-2-yl)methyl]amino-1H-pyrazol-3-yl)pyrrolidine-1-carboxylate | 367 | e |
| 254 | prop-2-en-1-yl 3-(5-[(5-chlorothiophen-2-yl)methyl]amino-1-(2,2-dimethylpropanoyl)-1H-pyrazol-3-yl)-8-azabicyclo[3.2.1]octane-8-carboxylate | 491 | a |
| 255 | prop-2-en-1-yl 3-(5-[(5-chlorothiophen-2-yl)methyl]amino-1-(2,2-dimethylpropanoyl)-1H-pyrazol-3-yl)azetidine-1-carboxylate | 437 | a |
| 256 | prop-2-en-1-yl 3-(5-[(5-chlorothiophen-2-yl)methyl]amino-1-(2,2-dimethylpropanoyl)-1H-pyrazol-3-yl)pyrrolidine-1-carboxylate | 451 | a |
| 257 | prop-2-en-1-yl 3-(5-[(5-chlorothiophen-2-yl)methyl]amino-1H-pyrazol-3-yl)-8-azabicyclo[3.2.1]octane-8-carboxylate | 407 | d |

TABLE A-continued

| Entry | IUPAC name | MW | Thrombin Activity |
|---|---|---|---|
| 258 | prop-2-en-1-yl 3-(5-[(5-chlorothiophen-2-yl)methyl]amino-1H-pyrazol-3-yl)azetidine-1-carboxylate | 353 | d |
| 259 | prop-2-en-1-yl 3-(5-[(5-chlorothiophen-2-yl)methyl]amino-1H-pyrazol-3-yl)pyrrolidine-1-carboxylate | 367 | e |
| 260 | prop-2-en-1-yl 4-(5-[(5-chlorothiophen-2-yl)methyl]amino-1-(1,3-thiazole-4-carbonyl)-1H-pyrazol-3-yl)azepane-1-carboxylate | 506 | a |
| 261 | prop-2-en-1-yl 4-(5-[(5-chlorothiophen-2-yl)methyl]amino-1-(2,2-dimethylpropanoyl)-1H-pyrazol-3-yl)azepane-1-carboxylate | 479 | a |
| 262 | prop-2-en-1-yl 4-(5-[(5-chlorothiophen-2-yl)methyl]amino-1-(2,2-dimethylpropanoyl)-1H-pyrazol-3-yl)piperidine-1-carboxylate | 465 | a |
| 263 | prop-2-en-1-yl 4-(5-[(5-chlorothiophen-2-yl)methyl]amino-1-(2,2-dimethylpropanoyl)-4-fluoro-1H-pyrazol-3-yl)piperidine-1-carboxylate | 483 | a |
| 264 | prop-2-en-1-yl 4-(5-[(5-chlorothiophen-2-yl)methyl]amino-1-(2,2-dimethylpropanoyl)-4-methyl-1H-pyrazol-3-yl)piperidine-1-carboxylate | 479 | a |
| 265 | prop-2-en-1-yl 4-(5-[(5-chlorothiophen-2-yl)methyl]amino-1H-pyrazol-3-yl)azepane-1-carboxylate | 395 | e |
| 266 | prop-2-en-1-yl 4-(5-[(5-chlorothiophen-2-yl)methyl]amino-1H-pyrazol-3-yl)piperidine-1-carboxylate | 381 | e |
| 267 | prop-2-en-1-yl 4-(5-[(5-chlorothiophen-2-yl)methyl]amino-4-cyano-1-(2,2-dimethylpropanoyl)-1H-pyrazol-3-yl)piperidine-1-carboxylate | 490 | a |
| 268 | prop-2-en-1-yl 4-(5-[(5-chlorothiophen-2-yl)methyl]amino-4-cyano-1H-pyrazol-3-yl)piperidine-1-carboxylate | 406 | c |
| 269 | prop-2-en-1-yl 4-(5-[(5-chlorothiophen-2-yl)methyl]amino-4-fluoro-1H-pyrazol-3-yl)piperidine-1-carboxylate | 399 | e |
| 270 | prop-2-en-1-yl 4-(5-[(5-chlorothiophen-2-yl)methyl]amino-4-methyl-1-(1,3-thiazole-4-carbonyl)-1H-pyrazol-3-yl)piperidine-1-carboxylate | 506 | a |
| 271 | prop-2-en-1-yl 4-(5-[(5-chlorothiophen-2-yl)methyl]amino-4-methyl-1H-pyrazol-3-yl)piperidine-1-carboxylate | 395 | e |
| 272 | tert-butyl 2-(5-[(5-chlorothiophen-2-yl)methyl]amino-1-(2-methoxybenzoyl)-1H-pyrazol-3-yl)-2-methylpyrrolidine-1-carboxylate | 531 | c |
| 273 | tert-butyl 2-(5-[(5-chlorothiophen-2-yl)methyl]amino-1-(2-methoxybenzoyl)-1H-pyrazol-3-yl)pyrrolidine-1-carboxylate | 517 | c |
| 274 | tert-butyl 2-(5-[(5-chlorothiophen-2-yl)methyl]amino-1-(3-hydroxy-2,2-dimethylpropanoyl)-1H-pyrazol-3-yl)-2-methylpyrrolidine-1-carboxylate | 497 | b |
| 275 | tert-butyl 2-(5-[(5-chlorothiophen-2-yl)methyl]amino-1-(4-methyloxane-4-carbonyl)-1H-pyrazol-3-yl)-2-methylpyrrolidine-1-carboxylate | 523 | c |
| 276 | tert-butyl 2-(5-[(5-chlorothiophen-2-yl)methyl]amino-1-(thiophene-3-carbonyl)-1H-pyrazol-3-yl)-2-methylpyrrolidine-1-carboxylate | 507 | e |
| 277 | tert-butyl 2-(5-[(5-chlorothiophen-2-yl)methyl]amino-1H-pyrazol-3-yl)pyrrolidine-1-carboxylate | 383 | e |
| 278 | tert-butyl 3-(5-[(5-chlorothiophen-2-yl)methyl]amino-1-(2,2-dimethylpropanoyl)-1H-pyrazol-3-yl)-3-methylpiperidine-1-carboxylate | 495 | a |
| 279 | tert-butyl 3-(5-[(5-chlorothiophen-2-yl)methyl]amino-1-(2,2-dimethylpropanoyl)-1H-pyrazol-3-yl)piperidine-1-carboxylate | 481 | a |
| 280 | tert-butyl 3-(5-[(5-chlorothiophen-2-yl)methyl]amino-1-(2-methoxybenzoyl)-1H-pyrazol-3-yl)-3-methylpiperidine-1-carboxylate | 545 | a |
| 281 | tert-butyl 3-(5-[(5-chlorothiophen-2-yl)methyl]amino-1-(2-methoxybenzoyl)-1H-pyrazol-3-yl)piperidine-1-carboxylate | 531 | a |
| 282 | tert-butyl 3-(5-[(5-chlorothiophen-2-yl)methyl]amino-1-(3-hydroxy-2,2-dimethylpropanoyl)-1H-pyrazol-3-yl)-3-methylpiperidine-1-carboxylate | 511 | a |
| 283 | tert-butyl 3-(5-[(5-chlorothiophen-2-yl)methyl]amino-1-(3-hydroxy-2,2-dimethylpropanoyl)-1H-pyrazol-3-yl)piperidine-1-carboxylate | 497 | a |

TABLE A-continued

| Entry | IUPAC name | MW | Thrombin Activity |
|---|---|---|---|
| 284 | tert-butyl 3-(5-[(5-chlorothiophen-2-yl)methyl]amino-1-(3-methoxy-2,2-dimethylpropanoyl)-1H-pyrazol-3-yl)-3-methylpiperidine-1-carboxylate | 525 | b |
| 285 | tert-butyl 3-(5-[(5-chlorothiophen-2-yl)methyl]amino-1-(3-methoxy-2,2-dimethylpropanoyl)-1H-pyrazol-3-yl)piperidine-1-carboxylate | 511 | a |
| 286 | tert-butyl 3-(5-[(5-chlorothiophen-2-yl)methyl]amino-1-(4-methyloxane-4-carbonyl)-1H-pyrazol-3-yl)-3-methylpiperidine-1-carboxylate | 537 | b |
| 287 | tert-butyl 3-(5-[(5-chlorothiophen-2-yl)methyl]amino-1-(4-methyloxane-4-carbonyl)-1H-pyrazol-3-yl)piperidine-1-carboxylate | 523 | a |
| 288 | tert-butyl 3-(5-[(5-chlorothiophen-2-yl)methyl]amino-1-(thiophene-3-carbonyl)-1H-pyrazol-3-yl)-3-methylpiperidine-1-carboxylate | 521 | a |
| 289 | tert-butyl 3-(5-[(5-chlorothiophen-2-yl)methyl]amino-1-(thiophene-3-carbonyl)-1H-pyrazol-3-yl)piperidine-1-carboxylate | 507 | a |
| 290 | tert-butyl 3-(5-[(5-chlorothiophen-2-yl)methyl]amino-1H-pyrazol-3-yl)piperidine-1-carboxylate | 397 | e |
| 291 | tert-butyl 4-(5-[(5-chlorothiophen-2-yl)methyl]amino-1-(2,2-dimethylpropanoyl)-1H-pyrazol-3-yl)-4-methylpiperidine-1-carboxylate | 495 | a |
| 292 | tert-butyl 4-(5-[(5-chlorothiophen-2-yl)methyl]amino-1-(2,2-dimethylpropanoyl)-1H-pyrazol-3-yl)piperidine-1-carboxylate | 481 | a |
| 293 | tert-butyl 4-(5-[(5-chlorothiophen-2-yl)methyl]amino-1-(2,2-dimethylpropanoyl)-4-methyl-1H-pyrazol-3-yl)piperidine-1-carboxylate | 495 | b |
| 294 | tert-butyl 4-(5-[(5-chlorothiophen-2-yl)methyl]amino-1-(2-methoxybenzoyl)-1H-pyrazol-3-yl)-4-methylpiperidine-1-carboxylate | 545 | a |
| 295 | tert-butyl 4-(5-[(5-chlorothiophen-2-yl)methyl]amino-1-(2-methoxybenzoyl)-1H-pyrazol-3-yl)piperidine-1-carboxylate | 531 | a |
| 296 | tert-butyl 4-(5-[(5-chlorothiophen-2-yl)methyl]amino-1-(3-hydroxy-2,2-dimethylpropanoyl)-1H-pyrazol-3-yl)-4-methylpiperidine-1-carboxylate | 511 | a |
| 297 | tert-butyl 4-(5-[(5-chlorothiophen-2-yl)methyl]amino-1-(3-hydroxy-2,2-dimethylpropanoyl)-1H-pyrazol-3-yl)piperidine-1-carboxylate | 497 | a |
| 298 | tert-butyl 4-(5-[(5-chlorothiophen-2-yl)methyl]amino-1-(3-methoxy-2,2-dimethylpropanoyl)-1H-pyrazol-3-yl)-4-methylpiperidine-1-carboxylate | 525 | a |
| 299 | tert-butyl 4-(5-[(5-chlorothiophen-2-yl)methyl]amino-1-(4-methyloxane-4-carbonyl)-1H-pyrazol-3-yl)-4-methylpiperidine-1-carboxylate | 537 | a |
| 300 | tert-butyl 4-(5-[(5-chlorothiophen-2-yl)methyl]amino-1-(thiophene-3-carbonyl)-1H-pyrazol-3-yl)-4-methylpiperidine-1-carboxylate | 521 | a |
| 301 | tert-butyl 4-(5-[(5-chlorothiophen-2-yl)methyl]amino-1-(thiophene-3-carbonyl)-1H-pyrazol-3-yl)piperidine-1-carboxylate | 507 | a |
| 302 | tert-butyl 4-(5-[(5-chlorothiophen-2-yl)methyl]amino-1H-pyrazol-3-yl)piperidine-1-carboxylate | 397 | e |
| 303 | tert-butyl 4-(5-[(5-chlorothiophen-2-yl)methyl]amino-4-methyl-1H-pyrazol-3-yl)piperidine-1-carboxylate | 411 | e |

For Table B following, the disclosed compounds were assayed for inhibition of the protease activity of KLKB1 as described herein. In Table B following, the level of inhibition in the KLKB1 assay is indicated as follows: a: $IC_{50} \leq 1$ µM; b: 1 µM<$IC_{50}$<10 µM; c: $IC_{50} \geq 10$ µM. Accordingly, in some embodiments, there is provided a compound as expressly set forth in Table B following.

TABLE B

| Entry | IUPAC name | MW | KLKB1 Activity |
|---|---|---|---|
| 1 | 1,4-bis(prop-2-en-1-yl) 2-(5-[(5-chlorothiophen-2-yl)methyl]amino-1-(1,3-thiazole-4-carbonyl)-1H-pyrazol-3-yl)piperazine-1,4-dicarboxylate | 577 | c |
| 2 | 1-(5-[(5-chlorothiophen-2-yl)methyl]amino-3-(piperazin-2-yl)-1H-pyrazol-1-yl)-2,2-dimethylpropan-1-one | 382 | c |

TABLE B-continued

| Entry | IUPAC name | MW | KLKB1 Activity |
|---|---|---|---|
| 3 | 1-(5-[(5-chlorothiophen-2-yl)methyl]amino-3-(piperidin-3-yl)-1H-pyrazol-1-yl)-2,2-dimethylpropan-1-one; formic acid | 381 | c |
| 4 | 1-(5-[(5-chlorothiophen-2-yl)methyl]amino-3-(piperidin-4-yl)-1H-pyrazol-1-yl)-2,2-dimethylpropan-1-one | 381 | c |
| 5 | 1-(5-[(5-chlorothiophen-2-yl)methyl]amino-3-(pyrrolidin-3-yl)-1H-pyrazol-1-yl)-2,2-dimethylpropan-1-one | 367 | c |
| 6 | 1-(5-[(5-chlorothiophen-2-yl)methyl]amino-3-[1-(1,3-oxazol-4-ylmethyl)piperidin-4-yl]-1H-pyrazol-1-yl)-2,2-dimethylpropan-1-one | 462 | c |
| 7 | 1-(5-[(5-chlorothiophen-2-yl)methyl]amino-3-[1-(1H-1,2,3,4-tetrazol-5-ylmethyl)piperidin-4-yl]-1H-pyrazol-1-yl)-2,2-dimethylpropan-1-one | 463 | c |
| 8 | 1-(5-[(5-chlorothiophen-2-yl)methyl]amino-3-[1-(1H-1,2,3-triazol-5-ylmethyl)piperidin-4-yl]-1H-pyrazol-1-yl)-2,2-dimethylpropan-1-one | 462 | c |
| 9 | 1-(5-[(5-chlorothiophen-2-yl)methyl]amino-3-[1-(1H-imidazol-4-ylmethyl)piperidin-4-yl]-1H-pyrazol-1-yl)-2,2-dimethylpropan-1-one | 461 | c |
| 10 | 1-(5-[(5-chlorothiophen-2-yl)methyl]amino-3-[1-(2-cyclopropoxyethyl)piperidin-4-yl]-1H-pyrazol-1-yl)-2,2-dimethylpropan-1-one | 465 | c |
| 11 | 1-(5-[(5-chlorothiophen-2-yl)methyl]amino-3-[1-(2-cyclopropoxyethyl)piperidin-4-yl]-1H-pyrazol-1-yl)-3-hydroxy-2,2-dimethylpropan-1-one | 481 | c |
| 12 | 1-(5-[(5-chlorothiophen-2-yl)methyl]amino-3-[1-(2-methoxyethyl)piperidin-4-yl]-1H-pyrazol-1-yl)-2,2-dimethylpropan-1-one | 439 | c |
| 13 | 1-(5-[(5-chlorothiophen-2-yl)methyl]amino-3-[1-(cyclopropylmethyl)piperidin-4-yl]-1H-pyrazol-1-yl)-2,2-dimethylpropan-1-one | 435 | c |
| 14 | 1-(5-[(5-chlorothiophen-2-yl)methyl]amino-3-[1-(morpholine-4-carbonyl)azetidin-3-yl]-1H-pyrazol-1-yl)-2,2-dimethylpropan-1-one | 466 | c |
| 15 | 1-(5-[(5-chlorothiophen-2-yl)methyl]amino-3-[1-(oxetan-3-ylmethyl)piperidin-4-yl]-1H-pyrazol-1-yl)-2,2-dimethylpropan-1-one | 451 | c |
| 16 | 1-(5-[(5-chlorothiophen-2-yl)methyl]amino-3-[1-(pyridin-2-ylmethyl)piperidin-4-yl]-1H-pyrazol-1-yl)-2,2-dimethylpropan-1-one | 472 | c |
| 17 | 1-(5-[(5-chlorothiophen-2-yl)methyl]amino-3-[1-(pyridin-3-ylmethyl)piperidin-4-yl]-1H-pyrazol-1-yl)-2,2-dimethylpropan-1-one | 472 | c |
| 18 | 1-(5-[(5-chlorothiophen-2-yl)methyl]amino-3-1-[(4-methoxyphenyl)methyl]piperidin-4-yl-1H-pyrazol-1-yl)-2,2-dimethylpropan-1-one | 501 | c |
| 19 | 1-(5-[(5-chlorothiophen-2-yl)methyl]amino-3-1-[2-(morpholin-4-yl)ethyl]piperidin-4-yl-1H-pyrazol-1-yl)-2,2-dimethylpropan-1-one; formic acid | 494 | c |
| 20 | 1-(5-[(5-chlorothiophen-2-yl)methyl]amino-3-1-[2-(pyridin-2-yl)ethyl]piperidin-4-yl-1H-pyrazol-1-yl)-2,2-dimethylpropan-1-one | 486 | c |
| 21 | 1-(5-[(5-chlorothiophen-2-yl)methyl]amino-4-fluoro-3-(piperidin-4-yl)-1H-pyrazol-1-yl)-2,2-dimethylpropan-1-one | 399 | b |
| 22 | 1-(5-[(5-chlorothiophen-2-yl)methyl]amino-4-fluoro-3-(piperidin-4-yl)-1H-pyrazol-1-yl)-3-hydroxy-2,2-dimethylpropan-1-one | 415 | c |
| 23 | 1-[3-(1-benzylpiperidin-4-yl)-5-[(5-chlorothiophen-2-yl)methyl]amino-1H-pyrazol-1-yl]-2,2-dimethylpropan-1-one | 471 | c |
| 24 | 1-[4-(5-[(5-chlorothiophen-2-yl)methyl]amino-1-(thiophene-3-carbonyl)-1H-pyrazol-3-yl)piperidin-1-yl]ethan-1-one | 449 | c |
| 25 | 1-benzoyl-N-[(5-chlorothiophen-2-yl)methyl]-3-(piperidin-4-yl)-1H-pyrazol-5-amine hydrochloride | 401 | b |
| 26 | 3-(5-[(5-chlorothiophen-2-yl)methyl]amino-1-(thiophene-3-carbonyl)-1H-pyrazol-3-yl)-3-methylpiperidin-2-one | 435 | c |
| 27 | 3-(5-[(5-chlorothiophen-2-yl)methyl]amino-1-(thiophene-3-carbonyl)-1H-pyrazol-3-yl)-3-methylpyrrolidin-2-one | 421 | c |
| 28 | 5-[(5-chlorothiophen-2-yl)methyl]amino-1-(2,2-dimethylpropanoyl)-3-[1-(morpholine-4-carbonyl)piperidin-4-yl]-1H-pyrazole-4-carbonitrile | 519 | b |
| 29 | N-[(5-chlorothiophen-2-yl)methyl]-1-(2,3-dihydro-1,4-benzodioxine-5-carbonyl)-3-(piperidin-4-yl)-1H-pyrazol-5-amine hydrochloride | 459 | c |

TABLE B-continued

| Entry | IUPAC name | MW | KLKB1 Activity |
|---|---|---|---|
| 30 | N-[(5-chlorothiophen-2-yl)methyl]-1-(2-methoxybenzoyl)-3-(piperidin-3-yl)-1H-pyrazol-5-amine | 431 | c |
| 31 | N-[(5-chlorothiophen-2-yl)methyl]-1-(2-methoxybenzoyl)-3-(piperidin-4-yl)-1H-pyrazol-5-amine hydrochloride | 431 | c |
| 32 | N-[(5-chlorothiophen-2-yl)methyl]-1-(4-methyloxane-4-carbonyl)-3-(piperidin-3-yl)-1H-pyrazol-5-amine | 423 | c |
| 33 | N-[(5-chlorothiophen-2-yl)methyl]-1-(furan-3-carbonyl)-3-(piperidin-4-yl)-1H-pyrazol-5-amine hydrochloride | 391 | c |
| 34 | N-[(5-chlorothiophen-2-yl)methyl]-3-(1-methanesulfonylazepan-4-yl)-1-(1,3-thiazole-4-carbonyl)-1H-pyrazol-5-amine | 500 | b |
| 35 | N-[(5-chlorothiophen-2-yl)methyl]-3-(1-methanesulfonylazetidin-3-yl)-1-(1,3-thiazole-4-carbonyl)-1H-pyrazol-5-amine | 458 | b |
| 36 | N-[(5-chlorothiophen-2-yl)methyl]-3-(1-methanesulfonylpyrrolidin-2-yl)-1-(1,3-thiazole-4-carbonyl)-1H-pyrazol-5-amine | 472 | b |
| 37 | N-[(5-chlorothiophen-2-yl)methyl]-3-(1-methanesulfonylpyrrolidin-3-yl)-1-(1,3-thiazole-4-carbonyl)-1H-pyrazol-5-amine | 472 | b |
| 38 | N-[(5-chlorothiophen-2-yl)methyl]-3-(2-methylpyrrolidin-2-yl)-1-(thiophene-3-carbonyl)-1H-pyrazol-5-amine; formic acid | 407 | c |
| 39 | N-[(5-chlorothiophen-2-yl)methyl]-3-(3-methylpiperidin-3-yl)-1-(thiophene-3-carbonyl)-1H-pyrazol-5-amine | 421 | c |
| 40 | N-[(5-chlorothiophen-2-yl)methyl]-3-(4-methylpiperidin-4-yl)-1-(thiophene-3-carbonyl)-1H-pyrazol-5-amine | 421 | c |
| 41 | N-[(5-chlorothiophen-2-yl)methyl]-3-(oxan-4-yl)-1-(thiophene-3-carbonyl)-1H-pyrazol-5-amine | 408 | c |
| 42 | N-[(5-chlorothiophen-2-yl)methyl]-3-(oxolan-2-yl)-1-(thiophene-3-carbonyl)-1H-pyrazol-5-amine | 394 | c |
| 43 | N-[(5-chlorothiophen-2-yl)methyl]-3-(piperidin-3-yl)-1-(thiophene-3-carbonyl)-1H-pyrazol-5-amine | 407 | b |
| 44 | N-[(5-chlorothiophen-2-yl)methyl]-3-(piperidin-4-yl)-1-(thiophene-3-carbonyl)-1H-pyrazol-5-amine hydrochloride | 407 | b |
| 45 | N-[(5-chlorothiophen-2-yl)methyl]-3-[1-(morpholine-4-carbonyl)azepan-4-yl]-1-(1,3-thiazole-4-carbonyl)-1H-pyrazol-5-amine | 535 | b |
| 46 | N-[(5-chlorothiophen-2-yl)methyl]-3-[1-(morpholine-4-carbonyl)azetidin-3-yl]-1-(1,3-thiazole-4-carbonyl)-1H-pyrazol-5-amine | 493 | b |
| 47 | N-[(5-chlorothiophen-2-yl)methyl]-3-[1-(morpholine-4-carbonyl)pyrrolidin-2-yl]-1-(1,3-thiazole-4-carbonyl)-1H-pyrazol-5-amine | 507 | b |
| 48 | N-[(5-chlorothiophen-2-yl)methyl]-3-[1-(morpholine-4-carbonyl)pyrrolidin-3-yl]-1-(1,3-thiazole-4-carbonyl)-1H-pyrazol-5-amine | 507 | b |
| 49 | N-[(5-chlorothiophen-2-yl)methyl]-3-[8-(morpholine-4-carbonyl)-8-azabicyclo[3.2.1]octan-3-yl]-1-(1,3-thiazole-4-carbonyl)-1H-pyrazol-5-amine | 547 | b |
| 50 | N-[(5-chlorothiophen-2-yl)methyl]-3-1-[(4-methoxyphenyl)methyl]piperidin-4-yl-1-(thiophene-3-carbonyl)-1H-pyrazol-5-amine | 527 | b |
| 51 | N-[(5-chlorothiophen-2-yl)methyl]-3-8-methanesulfonyl-8-azabicyclo[3.2.1]octan-3-yl-1-(1,3-thiazole-4-carbonyl)-1H-pyrazol-5-amine | 512 | c |
| 52 | N-[(5-chlorothiophen-2-yl)methyl]-4-fluoro-1-(furan-3-carbonyl)-3-(oxan-4-yl)-1H-pyrazol-5-amine | 410 | c |
| 53 | [1-(5-[(5-chlorothiophen-2-yl)methyl]amino-4-fluoro-3-(oxan-4-yl)-1H-pyrazole-1-carbonyl)cyclopropyl]methanol | 414 | c |
| 54 | prop-2-en-1-yl 2-(5-[(5-chlorothiophen-2-yl)methyl]amino-1-(1,3-thiazole-4-carbonyl)-1H-pyrazol-3-yl)-4-(morpholine-4-carbonyl)piperazine-1-carboxylate | 606 | d |
| 55 | prop-2-en-1-yl 2-(5-[(5-chlorothiophen-2-yl)methyl]amino-1-(1,3-thiazole-4-carbonyl)-1H-pyrazol-3-yl)-4-[2-(morpholin-4-yl)acetyl]piperazine-1-carboxylate | 620 | c |
| 56 | prop-2-en-1-yl 2-(5-[(5-chlorothiophen-2-yl)methyl]amino-1-(1,3-thiazole-4-carbonyl)-1H-pyrazol-3-yl)-4-methanesulfonylpiperazine-1-carboxylate | 571 | b |
| 57 | prop-2-en-1-yl 2-(5-[(5-chlorothiophen-2-yl)methyl]amino-1-(1,3-thiazole-4-carbonyl)-1H-pyrazol-3-yl)pyrrolidine-1-carboxylate | 478 | c |
| 58 | prop-2-en-1-yl 3-(5-[(5-chlorothiophen-2-yl)methyl]amino-1-(1,3-thiazole-4-carbonyl)-1H-pyrazol-3-yl)-8-azabicyclo[3.2.1]octane-8-carboxylate | 518 | c |

TABLE B-continued

| Entry | IUPAC name | MW | KLKB1 Activity |
|---|---|---|---|
| 59 | prop-2-en-1-yl 3-(5-[(5-chlorothiophen-2-yl)methyl]amino-1-(1,3-thiazole-4-carbonyl)-1H-pyrazol-3-yl)azetidine-1-carboxylate | 464 | b |
| 60 | prop-2-en-1-yl 3-(5-[(5-chlorothiophen-2-yl)methyl]amino-1-(1,3-thiazole-4-carbonyl)-1H-pyrazol-3-yl)pyrrolidine-1-carboxylate | 478 | b |
| 61 | prop-2-en-1-yl 4-(5-[(5-chlorothiophen-2-yl)methyl]amino-1-(1,3-thiazole-4-carbonyl)-1H-pyrazol-3-yl)azepane-1-carboxylate | 506 | b |
| 62 | prop-2-en-1-yl 4-(5-[(5-chlorothiophen-2-yl)methyl]amino-4-methyl-1-(1,3-thiazole-4-carbonyl)-1H-pyrazol-3-yl)piperidine-1-carboxylate | 506 | c |

In some embodiments, there is provided a compound as expressly set forth in Table C following.

TABLE C 1-(2,2-dimethylpropanoyl)-3-[1-(2,2-dimethylpropanoyl)-4-fluoro-5-{[(4-fluorophenyl)methyl]amino}-1H-pyrazol-3-yl]piperidine-2-carboxylic acid
1-(2,2-dimethylpropanoyl)-4-(5-{[(4-fluorophenyl)methyl](methyl)amino}-4-methoxy-1-(1,3-thiazole-4-carbonyl)-1H-pyrazol-3-yl)-3-(trifluoromethyl)piperidin-2-one
1-(2-chlorobenzoyl)-5-[(5-chlorothiophen-2-yl)methoxy]-3-[1-methanesulfonyl-4-(trifluoromethyl)pyrrolidin-3-yl]-1H-pyrazole
1-(2-chlorobenzoyl)-5-{[(4-fluorophenyl)methyl](methyl)amino}-3-{1-[(3-hydroxypyrrolidin-1-yl)sulfonyl]-6-oxo-4-(trifluoromethyl)piperidin-3-yl}-1H-pyrazole-4-carbonitrile
1-(2-chlorobenzoyl)-5-{[(4-fluorophenyl)methyl]sulfanyl}-3-{4-[2-(morpholin-4-yl)-2-oxoethyl]-3-(trifluoromethyl)piperazin-2-yl}-1H-pyrazole-4-carbonitrile
1-(2-chlorobenzoyl)-5-{[(5-chlorothiophen-2-yl)methyl]sulfanyl}-4-fluoro-3-[3-(trifluoromethyl)azetidin-2-yl]-1H-pyrazole
1-(2-chlorobenzoyl)-N-[(4-fluorophenyl)methyl]-N-methyl-3-[1-(morpholine-4-carbonyl)-3-(trifluoromethyl)piperazin-2-yl]-1H-pyrazol-5-amine
1-(2-fluorobenzoyl)-N-[(4-fluorophenyl)methyl]-3-[3-(trifluoromethyl)azetidin-2-yl]-1H-pyrazol-5-amine
1-(2-{5-[(5-chlorothiophen-2-yl)methoxy]-1-(furan-2-carbonyl)-4-methoxy-1H-pyrazol-3-yl}-3-methylpiperazin-1-yl)-2,2-dimethylpropan-1-one
1-(3-{5-[(4-fluorophenyl)methoxy]-4-methyl-1-(4-methylfuran-3-carbonyl)-1H-pyrazol-3-yl}-2-(trifluoromethyl)azetidin-1-yl)-2-(morpholin-4-yl)ethan-1-one
1-(3-{5-[(5-chlorothiophen-2-yl)methoxy]-1-(2-methoxybenzoyl)-4-methyl-1H-pyrazol-3-yl}-2-(trifluoromethyl)piperazin-1-yl)-2-(morpholin-4-yl)ethan-1-one
1-(3-{5-[(5-chlorothiophen-2-yl)methoxy]-4-fluoro-1-(1,3-thiazole-4-carbonyl)-1H-pyrazol-3-yl}-2-(trifluoromethyl)piperidin-1-yl)-2,2-dimethylpropan-1-one
1-(3-{5-[(5-chlorothiophen-2-yl)methoxy]-4-methoxy-1H-pyrazol-3-yl}piperazin-1-yl)-2,2-dimethylpropan-1-one
1-(5-{[(4-fluorophenyl)methyl]amino}-3-[4-(morpholine-4-carbonyl)piperazin-2-yl]-1H-pyrazol-1-yl)-2,2-dimethylpropan-1-one
1-(5-{[(4-fluorophenyl)methyl]sulfanyl}-3-(1-methanesulfonyl-4-methylpiperidin-3-yl)-1H-pyrazol-1-yl)-3-methoxy-2,2-dimethylpropan-1-one
1-(5-{[(4-fluorophenyl)methyl]sulfanyl}-3-[5-hydroxy-2-methyl-1-(pyrrolidine-1-sulfonyl)pyrrolidin-3-yl]-4-methyl-1H-pyrazol-1-yl)-3-methoxy-2,2-dimethylpropan-1-one
1-(5-{[(4-fluorophenyl)methyl]sulfanyl}-4-methoxy-3-{4-methyl-1-[2-(morpholin-4-yl)-2-oxoethyl]piperidin-3-yl}-1H-pyrazol-1-yl)-3-methoxy-2,2-dimethylpropan-1-one
1-(5-{[(5-chlorothiophen-2-yl)methyl](methyl)amino}-3-[5-hydroxy-1-(pyrrolidine-1-carbonyl)pyrrolidin-3-yl]-1H-pyrazol-1-yl)-2,2-dimethylpropan-1-one
1-(5-{[(5-chlorothiophen-2-yl)methyl](methyl)amino}-3-{5-hydroxy-2-methyl-1-[2-(morpholin-4-yl)-2-oxoethyl]pyrrolidin-3-yl}-4-methoxy-1H-pyrazol-1-yl)-3-hydroxy-2,2-dimethylpropan-1-one
1-(5-{[(5-chlorothiophen-2-yl)methyl](methyl)amino}-4-methoxy-3-(morpholin-3-yl)-1H-pyrazol-1-yl)-2,2-dimethylpropan-1-one
1-(5-{[(5-chlorothiophen-2-yl)methyl]amino}-3-[1-(morpholine-4-carbonyl)pyrrolidin-3-yl]-1H-pyrazol-1-yl)-2,2-dimethylpropan-1-one
1-(5-{[(5-chlorothiophen-2-yl)methyl]amino}-{1-[(3-hydroxypyrrolidin-1-yl)sulfonyl]-4-methylpyrrolidin-3-yl}-4-methyl-1H-pyrazol-1-yl)-3-hydroxy-2,2-dimethylpropan-1-one
1-(5-{[(5-chlorothiophen-2-yl)methyl]sulfanyl}-3-[1-(3-hydroxypyrrolidine-1-carbonyl)-2-methylpiperidin-3-yl]-1H-pyrazol-1-yl)-3-methoxy-2,2-dimethylpropan-1-one
1-(5-{[4-(aminomethyl)phenyl]methoxy}-3-{3-methyl-1-[2-(morpholin-4-yl)-2-oxoethyl]piperidin-4-yl}-1H-pyrazol-1-yl)-3-methoxy-2,2-dimethylpropan-1-one
1-(5-{[4-(aminomethyl)phenyl]methoxy}-4-fluoro-3-[1-(3-hydroxypyrrolidine-1-carbonyl)-3-methylpiperidin-4-yl]-1H-pyrazol-1-yl)-3-methoxy-2,2-dimethylpropan-1-one

TABLE C-continued 1-(dimethylcarbamoyl)-3-(5-{[(4-fluorophenyl)methyl]amino}-1-(thiophene-3-carbonyl)-1H-pyrazol-3-yl)-4-methylpiperidine-2-carboxylic acid
1-(dimethylsulfamoyl)-3-(5-{[(4-fluorophenyl)methyl](methyl)amino}-1-(furan-3-carbonyl)-1H-pyrazol-3-yl)-4-methylpyrrolidine-2-carboxylic acid
1-(dimethylsulfamoyl)-3-{4-fluoro-5-[(4-fluorophenyl)methoxy]-1-(3-hydroxy-2,2-dimethylpropanoyl)-1H-pyrazol-3-yl}-4-methylpyrrolidine-2-carboxylic acid
1-({3-[5-({[4-(aminomethyl)phenyl]methyl}(methyl)amino)-1-benzoyl-4-fluoro-1H-pyrazol-3-yl]-2-methylpiperidin-1-yl}sulfonyl)pyrrolidin-3-ol
1-({3-[5-({[4-(aminomethyl)phenyl]methyl}amino)-1-(2-fluorobenzoyl)-4-methoxy-1H-pyrazol-3-yl]-2-(trifluoromethyl)piperazin-1-yl}sulfonyl)pyrrolidin-3-ol
1-[(2-{4-fluoro-5-[(4-fluorophenyl)methoxy]-1-(2-methylfuran-3-carbonyl)-1H-pyrazol-3-yl}-3-(trifluoromethyl)piperazin-1-yl)sulfonyl]pyrrolidin-3-ol
1-[(3-{5-[(5-chlorothiophen-2-yl)methoxy]-4-fluoro-1-(furan-3-carbonyl)-1H-pyrazol-3-yl}-4-methylpyrrolidin-1-yl)sulfonyl]pyrrolidin-3-ol
1-[2-(5-{[(4-fluorophenyl)methyl](methyl)amino}-1-(1,3-thiazole-4-carbonyl)-1H-pyrazol-3-yl]-3-(trifluoromethyl)piperazin-1-yl]-2-(morpholin-4-yl)ethan-1-one
1-[2-(5-{[(5-chlorothiophen-2-yl)methyl]amino}-1-(4-methylfuran-3-carbonyl)-1H-pyrazol-3-yl]-3-(trifluoromethyl)azetidin-1-yl]-2,2-dimethylpropan-1-one
1-[2-(5-{[(5-chlorothiophen-2-yl)methyl]amino}-1-(thiophene-3-carbonyl)-1H-pyrazol-3-yl]-3-methylpiperazin-1-yl]-2,2-dimethylpropan-1-one
1-[3-(1-benzoyl-5-{[(4-fluorophenyl)methyl]amino}-4-methoxy-1H-pyrazol-3-yl)-2-methylpiperidine-1-carbonyl]pyrrolidin-3-ol
1-[3-(4-fluoro-5-{[(4-fluorophenyl)methyl](methyl)amino}-1-(1,3-thiazole-4-carbonyl)-1H-pyrazol-3-yl]-2-(trifluoromethyl)azetidin-1-yl]-2-(morpholin-4-yl)ethan-1-one
1-[3-(5-{[(4-fluorophenyl)methyl](methyl)amino}-1-(furan-2-carbonyl)-1H-pyrazol-3-yl)-4-methylpyrrolidine-1-carbonyl]pyrrolidin-3-ol
1-[3-(5-{[(4-fluorophenyl)methyl](methyl)amino}-1-(furan-2-carbonyl)-4-methyl-1H-pyrazol-3-yl]-4-methylpiperidin-1-yl]-2-(morpholin-4-yl)ethan-1-one
1-[3-(5-{[(4-fluorophenyl)methyl] amino}-1-(4-methylfuran-3-carbonyl)-1H-pyrazol-3-yl)-4-(trifluoromethyl)piperidine-1-carbonyl]pyrrolidin-3-ol
1-[3-(5-{[(4-fluorophenyl)methyl]sulfanyl}-1-(furan-3-carbonyl)-4-methoxy-1H-pyrazol-3-yl)-2-methylpiperazine-1-carbonyl]pyrrolidin-3-ol
1-[3-(5-{[(5-chlorothiophen-2-yl)methyl](methyl)amino}-1-(4-methylfuran-3-carbonyl)-1H-pyrazol-3-yl)-2-(trifluoromethyl)piperidin-1-yl]-2,2-dimethylpropan-1-one
1-[3-(5-{[(5-chlorothiophen-2-yl)methyl](methyl)amino}-4-fluoro-1-(2-methylfuran-3-carbonyl)-1H-pyrazol-3-yl]-2-(trifluoromethyl)piperazin-1-yl]-2-(morpholin-4-yl)ethan-1-one
1-[3-(5-{[(5-chlorothiophen-2-yl)methyl]amino}-1-(5-methylfuran-3-carbonyl)-1H-pyrazol-3-yl)piperazin-1-yl]-2,2-dimethylpropan-1-one
1-[3-(5-{[(5-chlorothiophen-2-yl)methyl]amino}-4-fluoro-1-(thiophene-3-carbonyl)-1H-pyrazol-3-yl]-2-methylazetidine-1-carbonyl]pyrrolidin-3-ol
1-[3-(5-{[(5-chlorothiophen-2-yl)methyl]amino}-4-methyl-1-(5-methylfuran-3-carbonyl)-1H-pyrazol-3-yl)pyrrolidin-1-yl]-2,2-dimethylpropan-1-one
1-[3-(5-{[(5-chlorothiophen-2-yl)methyl]sulfanyl}-4-methoxy-1-(2-methoxybenzoyl)-1H-pyrazol-3-yl)-2-(trifluoromethyl)pyrrolidin-1-yl]-2-(morpholin-4-yl)ethan-1-one
1-[3-(5-{[4-(aminomethyl)phenyl]methoxy}-4-methoxy-1-(1,3-thiazole-4-carbonyl)-1H-pyrazol-3-yl)-4-(trifluoromethyl)piperidine-1-carbonyl]pyrrolidin-3-ol
1-[4-(1-benzoyl-5-{[(4-fluorophenyl)methyl]amino}-4-methyl-1H-pyrazol-3-yl)-3-methylpiperidine-1-carbonyl]pyrrolidin-3-ol
1-[5-({[4-(aminomethyl)phenyl]methyl}(methyl)amino)-3-(1-methanesulfonylazetidin-2-yl)-1H-pyrazol-1-yl]-2,2-dimethylpropan-1-one
1-[5-({[4-(aminomethyl)phenyl]methyl}(methyl)amino)-4-fluoro-3-{1-[2-(morpholin-4-yl)-2-oxoethyl]piperazin-2-yl}-1H-pyrazol-1-yl]-2,2-dimethylpropan-1-one
1-[5-({[4-(aminomethyl)phenyl]methyl}(methyl)amino)-4-methoxy-3-{4-methyl-1-[2-(morpholin-4-yl)acetyl]pyrrolidin-3-yl}-1H-pyrazol-1-yl]-3-hydroxy-2,2-dimethylpropan-1-one
1-[5-({[4-(aminomethyl)phenyl]methyl}amino)-3-[1-(pyrrolidine-1-sulfonyl)piperidin-4-yl]-1H-pyrazol-1-yl]-2,2-dimethylpropan-1-one
1-[5-({[4-(aminomethyl)phenyl]methyl}amino)-4-fluoro-3-[5-hydroxy-1-(3-hydroxypyrrolidine-1-carbonyl)-2-methylpyrrolidin-3-yl]-1H-pyrazol-1-yl]-3-hydroxy-2,2-dimethylpropan-1-one
1-[5-({[4-(aminomethyl)phenyl]methyl}sulfanyl)-3-(5-hydroxy-1-methanesulfonyl-2-methylpyrrolidin-3-yl)-4-methyl-1H-pyrazol-1-yl]-3-methoxy-2,2-dimethylpropan-1-one
1-benzoyl-5-{[(4-fluorophenyl)methyl]amino}-3-(4-methyl-2-oxopyrrolidin-3-yl)-1H-pyrazole-4-carbonitrile
1-benzoyl-5-{[(5-chlorothiophen-2-yl)methyl](methyl)amino}-3-[1-(2,2-dimethylpropanoyl)-2-methylpyrrolidin-3-yl]-1H-pyrazole-4-carbonitrile
1-benzoyl-5-{[(5-chlorothiophen-2-yl)methyl]amino}-3-(4-methyloxolan-3-yl)-1H-pyrazole-4-carbonitrile
1-benzoyl-N-[(5-chlorothiophen-2-yl)methyl]-4-fluoro-3-(1-methanesulfonyl-4-methylpiperidin-3-yl)-N-methyl-1H-pyrazol-5-amine
1-{2-[1-(2-fluorobenzoyl)-5-{[(4-fluorophenyl)methyl]amino}-4-methoxy-1H-pyrazol-3-yl]-3-(trifluoromethyl)piperazine-1-carbonyl}pyrrolidin-3-ol
1-{2-[5-({[4-(aminomethyl)phenyl]methyl}amino)-4-methyl-1-(5-methylfuran-3-carbonyl)-1H-pyrazol-3-yl]azetidin-1-yl}-2-(morpholin-4-yl)ethan-1-one
1-(2-[5-({[4-(aminomethyl)phenyl]methyl}sulfanyl)-1-(furan-3-carbonyl)-4-methoxy-1H-pyrazol-3-yl]-3-methylazetidine-1-carbonyl}pyrrolidin-3-ol
1-{3-[1-(2,2-dimethylpropanoyl)-5-[(4-fluorophenyl)methoxy]-4-methyl-1H-pyrazol-3-yl]azetidin-1-yl}-2,2-dimethylpropan-1-one TABLE C-continued 1-{3-[1-(2-chlorobenzoyl)-5-[(5-chlorothiophen-2-yl)methoxy]-4-methoxy-1H-pyrazol-3-yl]-5-hydroxy-2-(trifluoromethyl)pyrrolidin-1-yl}-2-(morpholin-4-yl)ethan-1-one
1-{3-[5-({[4-(aminomethyl)phenyl]methyl}sulfanyl)-1-(2-methoxybenzoyl)-4-methyl-1H-pyrazol-3-yl]-4-(trifluoromethyl)piperidin-1-yl}-2,2-dimethylpropan-1-one
1-{4-[5-({[4-(aminomethyl)phenyl]methyl}(methyl)amino)-4-methyl-1-(2-methylfuran-3-carbonyl)-1H-pyrazol-3-yl]-3-(trifluoromethyl)piperidin-1-yl}-2,2-dimethylpropan-1-one
1-(4-[5-({[4-(aminomethyl)phenyl]methyl}sulfanyl)-4-fluoro-1-(1,3-thiazole-4-carbonyl)-1H-pyrazol-3-yl]-3-(trifluoromethyl)piperidin-1-yl}-2-(morpholin-4-yl)ethan-1-one
1-{5-[(4-fluorophenyl)methoxy]-3-(1-methanesulfonyl-2-methylazetidin-3-yl)-4-methoxy-1H-pyrazol-1-yl}-3-hydroxy-2,2-dimethylpropan-1-one
1-{5-[(5-chlorothiophen-2-yl)methoxy]-3-[1-(2,2-dimethylpropanoyl)-2-methylpyrrolidin-3-yl]-4-methoxy-1H-pyrazol-1-yl}-3-methoxy-2,2-dimethylpropan-1-one
1-{[2-(5-{[(4-fluorophenyl)methyl]sulfanyl}-1-(2-methoxybenzoyl)-4-methyl-1H-pyrazol-3-yl)-3-(trifluoromethyl)piperazin-1-yl]sulfonyl}pyrrolidin-3-ol
1-{[3-(5-{[4-(aminomethyl)phenyl]methoxy}-1-(thiophene-2-carbonyl)-1H-pyrazol-3-yl)pyrrolidin-1-yl]sulfonyl}pyrrolidin-3-ol
1-{[4-(5-{[(5-chlorothiophen-2-yl)methyl]sulfanyl}-4-methoxy-1-(1,3-thiazole-4-carbonyl)-1H-pyrazol-3-yl)-3-(trifluoromethyl)piperidin-1-yl]sulfonyl}pyrrolidin-3-ol
2-(3-{5-[(4-fluorophenyl)methoxy]-1-(thiophene-3-carbonyl)-1H-pyrazol-3-yl}-2-methylazetidin-1-yl)-1-(morpholin-4-yl)ethan-1-one
2-(3-{5-[(5-chlorothiophen-2-yl)methoxy]-1-(furan-3-carbonyl)-1H-pyrazol-3-yl}-5-hydroxy-2-methylpyrrolidin-1-yl)-1-(morpholin-4-yl)ethan-1-one
2-(4-fluoro-5-{[(4-fluorophenyl)methyl]amino}-1-(3-hydroxy-2,2-dimethylpropanoyl)-1H-pyrazol-3-yl)-N,N,3-trimethylazetidine-1-sulfonamide
2-(5-{[(4-carbamimidoylphenyl)methyl]sulfanyl}-4-methoxy-1-(thiophene-2-carbonyl)-1H-pyrazol-3-yl)-N,N-dimethyl-4-oxoazetidine-1-carboxamide
2-(5-{[(4-fluorophenyl)methyl](methyl)amino}-4-methyl-1-(thiophene-2-carbonyl)-1H-pyrazol-3-yl)-N,N-dimethylpiperazine-1-carboxamide
2-(5-{[(4-fluorophenyl)methyl]sulfanyl}-1-(furan-2-carbonyl)-4-methyl-1H-pyrazol-3-yl)-N,N,3-trimethylazetidine-1-carboxamide
2-(5-{[(5-chlorothiophen-2-yl)methyl](methyl)amino}-4-cyano-1-(thiophene-3-carbonyl)-1H-pyrazol-3-yl)-N,N,3-trimethylazetidine-1-carboxamide
2-(5-{[(5-chlorothiophen-2-yl)methyl]sulfanyl}-1-(furan-3-carbonyl)-4-methyl-1H-pyrazol-3-yl)-N,N,3-trimethylazetidine-1-sulfonamide
2-[2-(4-fluoro-5-{[(4-fluorophenyl)methyl](methyl)amino}-1-(furan-2-carbonyl)-1H-pyrazol-3-yl)-3-methylazetidin-1-yl]-1-(morpholin-4-yl)ethan-1-one
2-[3-(1-benzoyl-5-{[(5-chlorothiophen-2-yl)methyl](methyl)amino}-1H-pyrazol-3-yl)-4-methylpiperidin-1-yl]-1-(morpholin-4-yl)ethan-1-one
2-[3-(4-fluoro-5-{[(4-fluorophenyl)methyl]sulfanyl}-1-(furan-2-carbonyl)-1H-pyrazol-3-yl)-2-methylazetidin-1-yl]-1-(morpholin-4-yl)ethan-1-one
2-[3-(5-{[(5-chlorothiophen-2-yl)methyl]sulfanyl}-1-(thiophene-2-carbonyl)-1H-pyrazol-3-yl)pyrrolidin-1-yl]-1-(morpholin-4-yl)ethan-1-one
2-[4-cyano-1-(2,2-dimethylpropanoyl)-5-[(4-fluorophenyl)methoxy]-1H-pyrazol-3-yl]-N,N-dimethylpiperazine-1-sulfonamide
2-[5-({[4-(aminomethyl)phenyl]methyl}amino)-1-(2-fluorobenzoyl)-1H-pyrazol-3-yl]-N,N-dimethyl-4-oxo-3-(trifluoromethyl)azetidine-1-sulfonamide
2-chloro-3-(5-{[(4-fluorophenyl)methyl](methyl)amino}-3-{1-[(3-hydroxypyrrolidin-1-yl)sulfonyl]-5-oxopyrrolidin-3-yl}-4-methoxy-1H-pyrazole-1-carbonyl)benzoic acid
2-chloro-3-(5-{[(4-fluorophenyl)methyl]sulfanyl}-3-(2-oxoazetidin-3-yl)-1H-pyrazole-1-carbonyl)benzoic acid
2-chloro-3-(5-{[(4-fluorophenyl)methyl]sulfanyl}-4-methyl-3-[1-(morpholine-4-carbonyl)-6-oxopiperidin-3-yl]-1H-pyrazole-1-carbonyl)benzoic acid
2-chloro-3-(5-{[(5-chlorothiophen-2-yl)methyl]sulfanyl}-4-cyano-3-[1-(morpholine-4-carbonyl)-2-oxopyrrolidin-3-yl]-1H-pyrazole-1-carbonyl)benzoic acid
2-chloro-3-(5-{[(5-chlorothiophen-2-yl)methyl]sulfanyl}-4-methoxy-3-[4-(pyrrolidine-1-carbonyl)piperazin-2-yl]-1H-pyrazole-1-carbonyl)benzoic acid
2-chloro-3-{3-[1-(2,2-dimethylpropanoyl)-2-oxoazetidin-3-yl]-5-{[(4-fluorophenyl)methyl](methyl)amino}-1H-pyrazole-1-carbonyl}benzoic acid
2-chloro-3-{3-[1-(2,2-dimethylpropanoyl)azetidin-3-yl]-4-fluoro-5-{[(4-fluorophenyl)methyl](methyl)amino}-1H-pyrazole-1-carbonyl}benzoic acid
2-chloro-3-{5-[(5-chlorothiophen-2-yl)methoxy]-3-(morpholin-3-yl)-1H-pyrazole-1-carbonyl}benzoic acid
2-chloro-3-{5-[(5-chlorothiophen-2-yl)methoxy]-4-fluoro-3-[5-hydroxy-1-(pyrrolidine-1-carbonyl)pyrrolidin-3-yl]-1H-pyrazole-1-carbonyl}benzoic acid
2-{3-[1-(2-fluorobenzoyl)-5-[(4-fluorophenyl)methoxy]-4-methyl-1H-pyrazol-3-yl]-2-(trifluoromethyl)piperazin-1-yl}-1-(morpholin-4-yl)ethan-1-one
2-{4-[5-({[4-(aminomethyl)phenyl]methyl}(methyl)amino)-1-benzoyl-4-methoxy-1H-pyrazol-3-yl]-3-methylpiperidin-1-yl}-1-(morpholin-4-yl)ethan-1-one
3-(1-benzoyl-5-{[(4-carbamimidoylphenyl)methyl](methyl)amino}-4-methoxy-1H-pyrazol-3-yl)-4-methyl-1-(morpholine-4-carbonyl)piperidine-2-carboxylic acid
3-(1-benzoyl-5-{[(4-carbamimidoylphenyl)methyl]amino}-4-fluoro-1H-pyrazol-3-yl)-N,N,2-trimethyl-4-oxopyrrolidine-1-carboxamide
3-(1-benzoyl-5-{[(4-carbamimidoylphenyl)methyl]amino}-4-methoxy-1H-pyrazol-3-yl)-N,N,4-trimethylpiperidine-1-carboxamide
3-(1-benzoyl-5-{[(5-chlorothiophen-2-yl)methyl]amino}-4-methyl-1H-pyrazol-3-yl)-1-(dimethylcarbamoyl)-4-methylpyrrolidine-2-carboxylic acid TABLE C-continued 3-(4-cyano-5-{[(4-fluorophenyl)methyl]amino}-3-{1-[2-(morpholin-4-yl)acetyl]-5-oxopyrrolidin-3-yl}-1H-pyrazole-1-carbonyl)benzoic acid
3-(4-cyano-5-{[(4-fluorophenyl)methyl]sulfanyl}-1-(3-methoxy-2,2-dimethylpropanoyl)-1H-pyrazol-3-yl)-N,N,2-trimethylpyrrolidine-1-carboxamide
3-(4-cyano-5-{[(4-fluorophenyl)methyl]sulfanyl}-1-(furan-2-carbonyl)-1H-pyrazol-3-yl)-N,N,2-trimethylpiperidine-1-sulfonamide
3-(4-fluoro-5-{[(4-fluorophenyl)methyl]amino}-1-(2-methylfuran-3-carbonyl)-1H-pyrazol-3-yl)-1-(3-hydroxypyrrolidine-1-carbonyl)-4-(trifluoromethyl)pyrrolidin-2-one
3-(4-fluoro-5-{[(4-fluorophenyl)methyl]amino}-1-(4-methylfuran-3-carbonyl)-1H-pyrazol-3-yl)-N,N-dimethyl-2-oxo-4-(trifluoromethyl)pyrrolidine-1-sulfonamide
3-(5-{[(4-carbamimidoylphenyl)methyl](methyl)amino}-1-(2-fluorobenzoyl)-4-methoxy-1H-pyrazol-3-yl)-N,N-dimethyl-2-(trifluoromethyl)piperidine-1-carboxamide
3-(5-{[(4-carbamimidoylphenyl)methyl](methyl)amino}-1-(3-hydroxy-2,2-dimethylpropanoyl)-1H-pyrazol-3-yl)-5-hydroxy-N,N,2-trimethylpyrrolidine-1-carboxamide
3-(5-{[(4-carbamimidoylphenyl)methyl](methyl)amino}-3-[1-(3-hydroxypyrrolidine-1-carbonyl)-4-oxopyrrolidin-3-yl]-4-methoxy-1H-pyrazole-1-carbonyl)benzoic acid
3-(5-{[(4-carbamimidoylphenyl)methyl](methyl)amino}-3-[1-(dimethylsulfamoyl)piperidin-4-yl]-4-fluoro-1H-pyrazole-1-carbonyl)benzoic acid
3-(5-{[(4-carbamimidoylphenyl)methyl](methyl)amino}-3-[1-(pyrrolidine-1-carbonyl)pyrrolidin-3-yl]-1H-pyrazole-1-carbonyl)benzoic acid
3-(5-{[(4-carbamimidoylphenyl)methyl](methyl)amino}-4-cyano-1-(5-methylfuran-3-carbonyl)-1H-pyrazol-3-yl)-1-(pyrrolidine-1-carbonyl)piperidine-2-carboxylic acid
3-(5-{[(4-carbamimidoylphenyl)methyl](methyl)amino}-4-cyano-3-[1-(pyrrolidine-1-carbonyl)pyrrolidin-3-yl]-1H-pyrazole-1-carbonyl)benzoic acid
3-(5-{[(4-carbamimidoylphenyl)methyl](methyl)amino}-4-methoxy-1-(2-methylfuran-3-carbonyl)-1H-pyrazol-3-yl)-1-[2-(morpholin-4-yl)acetyl]-4-(trifluoromethyl)piperidine-2-carboxylic acid
3-(5-{[(4-carbamimidoylphenyl)methyl](methyl)amino}-4-methyl-1-(5-methylfuran-3-carbonyl)-1H-pyrazol-3-yl)-1-(pyrrolidine-1-sulfonyl)piperidine-2-carboxylic acid
3-(5-{[(4-carbamimidoylphenyl)methyl](methyl)amino}-4-methyl-1-(thiophene-3-carbonyl)-1H-pyrazol-3-yl)-N,N,4-trimethyl-2-oxopyrrolidine-1-carboxamide
3-(5-{[(4-carbamimidoylphenyl)methyl]amino}-1-(2,2-dimethylpropanoyl)-4-fluoro-1H-pyrazol-3-yl)-1-methanesulfonylpyrrolidine-2-carboxylic acid
3-(5-{[(4-carbamimidoylphenyl)methyl]amino}-1-(3-carboxybenzoyl)-1H-pyrazol-3-yl)-1-[2-(morpholin-4-yl)-2-oxoethyl]pyrrolidine-2-carboxylic acid
3-(5-{[(4-carbamimidoylphenyl)methyl]amino}-3-[1-(dimethylcarbamoyl)piperazin-2-yl]-4-fluoro-1H-pyrazole-1-carbonyl)benzoic acid
3-(5-{[(4-carbamimidoylphenyl)methyl]amino}-3-[1-(dimethylsulfamoyl)-5-hydroxypyrrolidin-3-yl]-4-methyl-1H-pyrazole-1-carbonyl)benzoic acid
3-(5-{[(4-carbamimidoylphenyl)methyl]amino}-3-{1-[(3-hydroxypyrrolidin-1-yl)sulfonyl]-4-oxopyrrolidin-3-yl}-4-methoxy-1H-pyrazole-1-carbonyl)benzoic acid
3-(5-{[(4-carbamimidoylphenyl)methyl]amino}-4-fluoro-1-(3-hydroxy-2,2-dimethylpropanoyl)-1H-pyrazol-3-yl)-N,N,2-trimethylpiperazine-1-carboxamide
3-(5-{[(4-carbamimidoylphenyl)methyl]amino}-4-methyl-1-(thiophene-3-carbonyl)-1H-pyrazol-3-yl)-N,N,2-trimethyl-4-oxoazetidine-1-carboxamide
3-(5-{[(4-carbamimidoylphenyl)methyl]sulfanyl}-4-cyano-3-(1-methanesulfonyl-4-oxoazetidin-2-yl)-1H-pyrazole-1-carbonyl)-2-chlorobenzoic acid
3-(5-{[(4-carbamimidoylphenyl)methyl]sulfanyl}-4-fluoro-3-[1-(morpholine-4-carbonyl)pyrrolidin-3-yl]-1H-pyrazole-1-carbonyl)-2-chlorobenzoic acid
3-(5-{[(4-carbamimidoylphenyl)methyl]sulfanyl}-4-methoxy-1-(1,3-thiazole-4-carbonyl)-1H-pyrazol-3-yl)-N,N-dimethyl-2-(trifluoromethyl)azetidine-1-carboxamide
3-(5-{[(4-carbamimidoylphenyl)methyl]sulfanyl}-4-methoxy-1H-pyrazol-3-yl)-1-[(3-hydroxypyrrolidin-1-yl)sulfonyl]piperidine-2-carboxylic acid
3-(5-{[(4-carbamimidoylphenyl)methyl]sulfanyl}-4-methyl-3-{1-[2-(morpholin-4-yl)acetyl]-2-oxoazetidin-3-yl}-1H-pyrazole-1-carbonyl)-2-chlorobenzoic acid
3-(5-{[(4-fluorophenyl)methyl](methyl)amino}-1-(2-methoxybenzoyl)-4-methyl-1H-pyrazol-3-yl)-1-[(3-hydroxypyrrolidin-1-yl)sulfonyl]-4-(trifluoromethyl)piperidin-2-one
3-(5-{[(4-fluorophenyl)methyl](methyl)amino}-1-(3-methoxy-2,2-dimethylpropanoyl)-4-methyl-1H-pyrazol-3-yl)-N,N,2-trimethyl-4-oxopyrrolidine-1-carboxamide
3-(5-{[(4-fluorophenyl)methyl](methyl)amino}-4-methoxy-1-(2-methoxybenzoyl)-1H-pyrazol-3-yl)-1-[2-(morpholin-4-yl)-2-oxoethyl]-4-(trifluoromethyl)azetidin-2-one
3-(5-{[(4-fluorophenyl)methyl]amino}-1-(3-hydroxy-2,2-dimethylpropanoyl)-4-methoxy-1H-pyrazol-3-yl)-1-methanesulfonyl-4-methylpyrrolidin-2-one
3-(5-{[(4-fluorophenyl)methyl]amino}-4-methoxy-1-(2-methylfuran-3-carbonyl)-1H-pyrazol-3-yl)-1-(pyrrolidine-1-sulfonyl)-4-(trifluoromethyl)pyrrolidin-2-one
3-(5-{[(4-fluorophenyl)methyl]amino}-4-methoxy-3-{1-[2-(morpholin-4-yl)-2-oxoethyl]pyrrolidin-3-yl}-1H-pyrazole-1-carbonyl)benzoic acid
3-(5-{[(4-fluorophenyl)methyl]amino}-4-methyl-1-(4-methylfuran-3-carbonyl)-1H-pyrazol-3-yl)-1-(3-hydroxypyrrolidine-1-carbonyl)-4-(trifluoromethyl)azetidin-2-one
3-(5-{[(4-fluorophenyl)methyl]amino}-4-methyl-1-(thiophene-3-carbonyl)-1H-pyrazol-3-yl)-4-methyl-1-(morpholine-4-carbonyl)pyrrolidine-2-carboxylic acid
3-(5-{[(4-fluorophenyl)methyl]sulfanyl}-1-(thiophene-2-carbonyl)-1H-pyrazol-3-yl)-1-(3-hydroxypyrrolidine-1-carbonyl)piperidin-2-one
3-(5-{[(4-fluorophenyl)methyl]sulfanyl}-4-methyl-1H-pyrazol-3-yl)-1-[2-(morpholin-4-yl)-2-oxoethyl]pyrrolidin-2-one
3-(5-{[(5-chlorothiophen-2-yl)methyl](methyl)amino}-1-(2,2-dimethylpropanoyl)-4-methyl-1H-pyrazol-3-yl)pyrrolidine-2-carboxylic acid
3-(5-{[(5-chlorothiophen-2-yl)methyl](methyl)amino}-1-(thiophene-3-carbonyl)-1H-pyrazol-3-yl)-4-methyl-1-(pyrrolidine-1-sulfonyl)azetidin-2-one

TABLE C-continued 3-(5-{[(5-chlorothiophen-2-yl)methyl](methyl)amino}-3-[1-(3-hydroxypyrrolidine-1-carbonyl)-5-oxopyrrolidin-3-yl]-4-methyl-1H-pyrazole-1-carbonyl)benzoic acid
3-(5-{[(5-chlorothiophen-2-yl)methyl](methyl)amino}-4-cyano-3-(3-oxopiperidin-4-yl)-1H-pyrazole-1-carbonyl)benzoic acid
3-(5-{[(5-chlorothiophen-2-yl)methyl](methyl)amino}-4-fluoro-1-(2-fluorobenzoyl)-1H-pyrazol-3-yl)-1-[(3-hydroxypyrrolidin-1-yl)sulfonyl]-4-(trifluoromethyl)pyrrolidin-2-one
3-(5-{[(5-chlorothiophen-2-yl)methyl](methyl)amino}-4-fluoro-3-[1-(3-hydroxypyrrolidine-1-carbonyl)-2-oxopiperidin-3-yl]-1H-pyrazole-1-carbonyl)benzoic acid
3-(5-{[(5-chlorothiophen-2-yl)methyl](methyl)amino}-4-methoxy-1-(thiophene-3-carbonyl)-1H-pyrazol-3-yl)-N,N,2-trimethylpiperidine-1-sulfonamide
3-(5-{[(5-chlorothiophen-2-yl)methyl](methyl)amino}-4-methyl-1-(2-methylfuran-3-carbonyl)-1H-pyrazol-3-yl)-4-(trifluoromethyl)piperidine-2-carboxylic acid
3-(5-{[(5-chlorothiophen-2-yl)methyl]amino}-1-(2,2-dimethylpropanoyl)-4-methoxy-1H-pyrazol-3-yl)-1-[(3-hydroxypyrrolidin-1-yl)sulfonyl]pyrrolidine-2-carboxylic acid
3-(5-{[(5-chlorothiophen-2-yl)methyl]amino}-1-(2-methylfuran-3-carbonyl)-1H-pyrazol-3-yl)-1-methanesulfonyl-4-(trifluoromethyl)piperidine-2-carboxylic acid
3-(5-{[(5-chlorothiophen-2-yl)methyl]amino}-3-{1-[(3-hydroxypyrrolidin-1-yl)sulfonyl]azetidin-3-yl}-4-methoxy-1H-pyrazole-1-carbonyl)benzoic acid
3-(5-{[(5-chlorothiophen-2-yl)methyl]amino}-4-cyano-1-(2,2-dimethylpropanoyl)-1H-pyrazol-3-yl)-1-(2,2-dimethylpropanoyl)pyrrolidine-2-carboxylic acid
3-(5-{[(5-chlorothiophen-2-yl)methyl]amino}-4-cyano-1-(4-methylfuran-3-carbonyl)-1H-pyrazol-3-yl)-N,N-dimethyl-4-(trifluoromethyl)piperidine-1-sulfonamide
3-(5-{[(5-chlorothiophen-2-yl)methyl]amino}-4-cyano-3-[1-(dimethylcarbamoyl)-4-oxoazetidin-2-yl]-1H-pyrazole-1-carbonyl)benzoic acid
3-(5-{[(5-chlorothiophen-2-yl)methyl]amino}-4-fluoro-1-(2-methylfuran-3-carbonyl)-1H-pyrazol-3-yl)-1-(morpholine-4-carbonyl)-4-(trifluoromethyl)piperidin-2-one
3-(5-{[(5-chlorothiophen-2-yl)methyl]amino}-4-fluoro-1-(4-methylfuran-3-carbonyl)-1H-pyrazol-3-yl)-1-(2,2-dimethylpropanoyl)-4-(trifluoromethyl)piperidin-2-one
3-(5-{[(5-chlorothiophen-2-yl)methyl]amino}-4-methoxy-1-(4-methylfuran-3-carbonyl)-1H-pyrazol-3-yl)-1-(pyrrolidine-1-carbonyl)-4-(trifluoromethyl)azetidin-2-one
3-(5-{[(5-chlorothiophen-2-yl)methyl]amino}-4-methyl-3-[1-(pyrrolidine-1-sulfonyl)pyrrolidin-3-yl]-1H-pyrazole-1-carbonyl)benzoic acid
3-(5-{[(5-chlorothiophen-2-yl)methyl]sulfanyl}-1-(2-methoxybenzoyl)-1H-pyrazol-3-yl)-1-(pyrrolidine-1-sulfonyl)-4-(trifluoromethyl)pyrrolidin-2-one
3-(5-{[(5-chlorothiophen-2-yl)methyl]sulfanyl}-1-(3-methoxy-2,2-dimethylpropanoyl)-4-methyl-1H-pyrazol-3-yl)-1-[(3-hydroxypyrrolidin-1-yl)sulfonyl]-4-methylazetidin-2-one
3-(5-{[(5-chlorothiophen-2-yl)methyl]sulfanyl}-1-(furan-3-carbonyl)-4-methoxy-1H-pyrazol-3-yl)-5-hydroxy-N,N,2-trimethylpyrrolidine-1-carboxamide
3-(5-{[(5-chlorothiophen-2-yl)methyl]sulfanyl}-4-cyano-1-(furan-2-carbonyl)-1H-pyrazol-3-yl)-4-methyl-1-(morpholine-4-carbonyl)pyrrolidine-2-carboxylic acid
3-(5-{[(5-chlorothiophen-2-yl)methyl]sulfanyl}-4-fluoro-1-(furan-2-carbonyl)-1H-pyrazol-3-yl)-N,N,4-trimethyl-2-oxopyrrolidine-1-carboxamide
3-(5-{[(5-chlorothiophen-2-yl)methyl]sulfanyl}-4-fluoro-1H-pyrazol-3-yl)-1-(pyrrolidine-1-sulfonyl)piperidine-2-carboxylic acid
3-(5-{[4-(aminomethyl)phenyl]methoxy}-1-(2-chlorobenzoyl)-1H-pyrazol-3-yl)-1-(3-hydroxypyrrolidine-1-carbonyl)-4-(trifluoromethyl)piperidine-2-carboxylic acid
3-(5-{[4-(aminomethyl)phenyl]methoxy}-1-(2-chlorobenzoyl)-4-methyl-1H-pyrazol-3-yl)-N,N-dimethyl-2-(trifluoromethyl)piperazine-1-sulfonamide
3-(5-{[4-(aminomethyl)phenyl]methoxy}-1-(2-methoxybenzoyl)-1H-pyrazol-3-yl)-1-(3-hydroxypyrrolidine-1-carbonyl)-4-(trifluoromethyl)pyrrolidin-2-one
3-(5-{[4-(aminomethyl)phenyl]methoxy}-1-(3-carboxy-2-chlorobenzoyl)-4-cyano-1H-pyrazol-3-yl)-1-[2-(morpholin-4-yl)acetyl]pyrrolidine-2-carboxylic acid
3-(5-{[4-(aminomethyl)phenyl]methoxy}-1-(3-methoxy-2,2-dimethylpropanoyl)-4-methyl-1H-pyrazol-3-yl)-4-methylpyrrolidin-2-one
3-(5-{[4-(aminomethyl)phenyl]methoxy}-1-(furan-2-carbonyl)-4-methoxy-1H-pyrazol-3-yl)-1-(dimethylcarbamoyl)-4-methylpiperidine-2-carboxylic acid
3-(5-{[4-(aminomethyl)phenyl]methoxy}-4-fluoro-3-(1-methanesulfonylazetidin-2-yl)-1H-pyrazole-1-carbonyl)-2-chlorobenzoic acid
3-(5-{[4-(aminomethyl)phenyl]methoxy}-4-methoxy-1-(2-methoxybenzoyl)-1H-pyrazol-3-yl)-N,N-dimethyl-4-(trifluoromethyl)pyrrolidine-1-carboxamide
3-(5-{[4-(aminomethyl)phenyl]methoxy}-4-methoxy-1-(3-methoxy-2,2-dimethylpropanoyl)-1H-pyrazol-3-yl)-4-methyl-1-[2-(morpholin-4-yl)acetyl]pyrrolidin-2-one
3-(5-{[4-(aminomethyl)phenyl]methoxy}-4-methoxy-1H-pyrazol-3-yl)-1-(pyrrolidine-1-sulfonyl)piperidin-2-one
3-(5-{[4-(aminomethyl)phenyl]methoxy}-4-methoxy-3-[4-(morpholine-4-carbonyl)piperazin-2-yl]-1H-pyrazole-1-carbonyl)-2-chlorobenzoic acid
3-(5-{[4-(aminomethyl)phenyl]methoxy}-4-methyl-1-(1,3-thiazole-4-carbonyl)-1H-pyrazol-3-yl)-1-methanesulfonyl-4-(trifluoromethyl)azetidin-2-one
3-(5-{[4-(aminomethyl)phenyl]methoxy}-4-methyl-3-{1-[2-(morpholin-4-yl)-2-oxoethyl]piperazin-2-yl}-1H-pyrazole-1-carbonyl)-2-chlorobenzoic acid
3-[1-(2,2-dimethylpropanoyl)-5-[(4-fluorophenyl)methoxy]-4-methoxy-1H-pyrazol-3-yl]azetidin-2-one
3-[1-(2,2-dimethylpropanoyl)-5-{[(4-fluorophenyl)methyl]amino}-4-methoxy-1H-pyrazol-3-yl]-1-[2-(morpholin-4-yl)acetyl]pyrrolidine-2-carboxylic acid TABLE C-continued 3-[1-(2,2-dimethylpropanoyl)-5-{[(4-fluorophenyl)methyl]amino}-4-methyl-1H-pyrazol-3-yl]-1-(morpholine-4-carbonyl)pyrrolidin-2-one
3-[1-(2-chlorobenzoyl)-4-fluoro-5-{[(4-fluorophenyl)methyl]sulfanyl}-1H-pyrazol-3-yl]-1-(pyrrolidine-1-sulfonyl)-2-(trifluoromethyl)piperidine
3-[1-(2-chlorobenzoyl)-5-{[(4-fluorophenyl)methyl](methyl)amino}-4-methoxy-1H-pyrazol-3-yl]-N,N-dimethyl-2-(trifluoromethyl)azetidine-1-sulfonamide
3-[1-(2-chlorobenzoyl)-5-{[(4-fluorophenyl)methyl]sulfanyl}-1H-pyrazol-3-yl]-1-[(3-hydroxypyrrolidin-1-yl)sulfonyl]-4-(trifluoromethyl)pyrrolidin-2-one
3-[1-(2-chlorobenzoyl)-5-{[(4-fluorophenyl)methyl]sulfanyl}-4-methoxy-1H-pyrazol-3-yl]-N,N-dimethyl-2-(trifluoromethyl)pyrrolidine-1-sulfonamide
3-[1-(2-chlorobenzoyl)-5-{[(5-chlorothiophen-2-yl)methyl]sulfanyl}-4-cyano-1H-pyrazol-3-yl]-N,N-dimethyl-2-(trifluoromethyl)piperidine-1-carboxamide
3-[1-(2-chlorobenzoyl)-5-{[(5-chlorothiophen-2-yl)methyl]sulfanyl}-4-methyl-1H-pyrazol-3-yl]-1-(pyrrolidine-1-carbonyl)-4-(trifluoromethyl)pyrrolidin-2-one
3-[1-(3-carboxy-2-chlorobenzoyl)-4-fluoro-5-{[(4-fluorophenyl)methyl]sulfanyl}-1H-pyrazol-3-yl]pyrrolidine-2-carboxylic acid
3-[1-(3-carboxy-2-chlorobenzoyl)-5-[(5-chlorothiophen-2-yl)methoxy]-4-cyano-1H-pyrazol-3-yl]-1-[(3-hydroxypyrrolidin-1-yl)sulfonyl]pyrrolidine-2-carboxylic acid
3-[1-(3-carboxy-2-chlorobenzoyl)-5-[(5-chlorothiophen-2-yl)methoxy]-4-methyl-1H-pyrazol-3-yl]-1-(2,2-dimethylpropanoyl)pyrrolidine-2-carboxylic acid
3-[1-(3-carboxy-2-chlorobenzoyl)-5-{[(5-chlorothiophen-2-yl)methyl]sulfanyl}-4-methyl-1H-pyrazol-3-yl]-1-(2,2-dimethylpropanoyl)piperidine-2-carboxylic acid
3-[1-(3-carboxybenzoyl)-5-{[(5-chlorothiophen-2-yl)methyl]amino}-4-fluoro-1H-pyrazol-3-yl]-1-(pyrrolidine-1-sulfonyl)pyrrolidine-2-carboxylic acid
3-[4-cyano-1-(2-fluorobenzoyl)-5-[(4-fluorophenyl)methoxy]-1H-pyrazol-3-yl]-N,N-dimethyl-2-(trifluoromethyl)pyrrolidine-1-sulfonamide
3-[4-cyano-1-(2-fluorobenzoyl)-5-{[(4-fluorophenyl)methyl]amino}-1H-pyrazol-3-yl]-N,N-dimethyl-2-(trifluoromethyl)piperazine-1-sulfonamide
3-[4-fluoro-1-(2-fluorobenzoyl)-5-{[(4-fluorophenyl)methyl]amino}-1H-pyrazol-3-yl]-1-(pyrrolidine-1-carbonyl)-4-(trifluoromethyl)pyrrolidin-2-one
3-[5-({[4-(aminomethyl)phenyl]methyl}(methyl)amino)-1-(2-fluorobenzoyl)-4-methoxy-1H-pyrazol-3-yl]-1-(3-hydroxypyrrolidine-1-carbonyl)-4-(trifluoromethyl)piperidine-2-carboxylic acid
3-[5-({[4-(aminomethyl)phenyl]methyl}(methyl)amino)-1-(4-methylfuran-3-carbonyl)-1H-pyrazol-3-yl]-N,N-dimethyl-2-(trifluoromethyl)azetidine-1-carboxamide
3-[5-({[4-(aminomethyl)phenyl]methyl}(methyl)amino)-1-(5-methylfuran-3-carbonyl)-1H-pyrazol-3-yl]-1-[(3-hydroxypyrrolidin-1-yl)sulfonyl]piperidine-2-carboxylic acid
3-[5-({[4-(aminomethyl)phenyl]methyl}(methyl)amino)-3-[1-(2,2-dimethylpropanoyl)-5-hydroxypyrrolidin-3-yl]-4-methyl-1H-pyrazole-1-carbonyl]benzoic acid
3-[5-({[4-(aminomethyl)phenyl]methyl}(methyl)amino)-3-{1-[(3-hydroxypyrrolidin-1-yl)sulfonyl]pyrrolidin-3-yl}-4-methoxy-1H-pyrazole-1-carbonyl]benzoic acid
3-[5-({[4-(aminomethyl)phenyl]methyl}(methyl)amino)-4-cyano-1-(2-methylfuran-3-carbonyl)-1H-pyrazol-3-yl]-N,N-dimethyl-4-(trifluoromethyl)pyrrolidine-1-carboxamide
3-[5-({[4-(aminomethyl)phenyl]methyl}(methyl)amino)-4-cyano-3-[1-(dimethylsulfamoyl)-4-oxopyrrolidin-3-yl]-1H-pyrazole-1-carbonyl]benzoic acid
3-[5-({[4-(aminomethyl)phenyl]methyl}(methyl)amino)-4-fluoro-1-(4-methylfuran-3-carbonyl)-1H-pyrazol-3-yl]-1-methanesulfonyl-4-(trifluoromethyl)azetidin-2-one
3-[5-({[4-(aminomethyl)phenyl]methyl}(methyl)amino)-4-methoxy-1-(4-methylfuran-3-carbonyl)-1H-pyrazol-3-yl]-1-methanesulfonyl-4-(trifluoromethyl)piperidin-2-one
3-[5-({[4-(aminomethyl)phenyl]methyl}(methyl)amino)-4-methyl-1-(thiophene-3-carbonyl)-1H-pyrazol-3-yl]-4-methyl-1-(morpholine-4-carbonyl)azetidin-2-one
3-[5-({[4-(aminomethyl)phenyl]methyl}amino)-1-(2,2-dimethylpropanoyl)-4-fluoro-1H-pyrazol-3-yl]-N,N-dimethylpyrrolidine-1-sulfonamide
3-[5-({[4-(aminomethyl)phenyl]methyl}amino)-1-(2-methylfuran-3-carbonyl)-1H-pyrazol-3-yl]-1-(dimethylsulfamoyl)-4-(trifluoromethyl)piperidine-2-carboxylic acid
3-[5-({[4-(aminomethyl)phenyl]methyl}amino)-1-(3-carboxybenzoyl)-4-methoxy-1H-pyrazol-3-yl]-1-[2-(morpholin-4-yl)-2-oxoethyl]piperidine-2-carboxylic acid
3-[5-({[4-(aminomethyl)phenyl]methyl}amino)-1-(3-hydroxy-2,2-dimethylpropanoyl)-4-methyl-1H-pyrazol-3-yl]-N,N,4-trimethyl-2-oxopiperidine-1-sulfonamide
3-[5-({[4-(aminomethyl)phenyl]methyl}amino)-1-(5-methylfuran-3-carbonyl)-1H-pyrazol-3-yl]-N,N-dimethyl-2-oxopiperidine-1-carboxamide
3-[5-({[4-(aminomethyl)phenyl]methyl}amino)-1-benzoyl-1H-pyrazol-3-yl]-1-(3-hydroxypyrrolidine-1-carbonyl)-4-methylpyrrolidine-2-carboxylic acid
3-[5-({[4-(aminomethyl)phenyl]methyl}amino)-3-[1-(dimethylsulfamoyl)-3-oxopiperidin-4-yl]-1H-pyrazole-1-carbonyl]benzoic acid
3-[5-({[4-(aminomethyl)phenyl]methyl}amino)-4-fluoro-3-[1-(morpholine-4-carbonyl)-3-oxopiperidin-4-yl]-1H-pyrazole-1-carbonyl]benzoic acid
3-[5-({[4-(aminomethyl)phenyl]methyl}amino)-4-methyl-1-(thiophene-3-carbonyl)-1H-pyrazol-3-yl]-4-methylpiperidin-2-one
3-[5-({[4-(aminomethyl)phenyl]methyl}sulfanyl)-1-(1,3-thiazole-4-carbonyl)-1H-pyrazol-3-yl]-N,N-dimethyl-2-oxo-4-(trifluoromethyl)azetidine-1-sulfonamide
3-[5-({[4-(aminomethyl)phenyl]methyl}sulfanyl)-1-(3-carboxy-2-chlorobenzoyl)-1H-pyrazol-3-yl]-1-methanesulfonylpyrrolidine-2-carboxylic acid
3-[5-({[4-(aminomethyl)phenyl]methyl}sulfanyl)-1-(furan-2-carbonyl)-4-methoxy-1H-pyrazol-3-yl]-4-methyl-1-[2-(morpholin-4-yl)-2-oxoethyl]piperidin-2-one
3-[5-({[4-(aminomethyl)phenyl]methyl}sulfanyl)-1-(furan-3-carbonyl)-1H-pyrazol-3-yl]-N,N,2-trimethylpiperazine-1-carboxamide
3-[5-({[4-(aminomethyl)phenyl]methyl}sulfanyl)-4-cyano-1-(3-methoxy-2,2-dimethylpropanoyl)-1H-pyrazol-3-yl]-N,N,4-trimethylpiperidine-1-carboxamide

TABLE C-continued

3-[5-({[4-(aminomethyl)phenyl]methyl}sulfanyl)-4-cyano-1-(furan-3-carbonyl)-1H-pyrazol-3-yl]-N,N,4-trimethyl-2-oxopiperidine-1-sulfonamide
3-[5-({[4-(aminomethyl)phenyl]methyl}sulfanyl)-4-cyano-3-[5-oxo-1-(pyrrolidine-1-sulfonyl)pyrrolidin-3-yl]-1H-pyrazole-1-carbonyl]-2-chlorobenzoic acid
3-[5-({[4-(aminomethyl)phenyl]methyl}sulfanyl)-4-fluoro-1-(2-methoxybenzoyl)-1H-pyrazol-3-yl]-1-(dimethylsulfamoyl)-4-(trifluoromethyl)piperidine-2-carboxylic acid
3-[5-({[4-(aminomethyl)phenyl]methyl}sulfanyl)-4-fluoro-1-(3-methoxy-2,2-dimethylpropanoyl)-1H-pyrazol-3-yl]-1-(3-hydroxypyrrolidine-1-carbonyl)-4-methylpyrrolidine-2-carboxylic acid
3-[5-({[4-(aminomethyl)phenyl]methyl}sulfanyl)-4-fluoro-1-(furan-2-carbonyl)-1H-pyrazol-3-yl]-N,N,2-trimethyl-4-oxoazetidine-1-carboxamide
3-[5-({[4-(aminomethyl)phenyl]methyl}sulfanyl)-4-fluoro-1H-pyrazol-3-yl]-N,N-dimethyl-2-oxopiperidine-1-carboxamide
3-[5-({[4-(aminomethyl)phenyl]methyl}sulfanyl)-4-fluoro-3-{1-[2-(morpholin-4-yl)acetyl]-3-oxopiperidin-4-yl}-1H-pyrazole-1-carbonyl]-2-chlorobenzoic acid
3-[5-({[4-(aminomethyl)phenyl]methyl}sulfanyl)-4-methoxy-1-(thiophene-2-carbonyl)-1H-pyrazol-3-yl]-1-[2-(morpholin-4-yl)-2-oxoethyl]pyrrolidine-2-carboxylic acid
3-[5-({[4-(aminomethyl)phenyl]methyl}sulfanyl)-4-methoxy-3-{1-[2-(morpholin-4-yl)acetyl]piperidin-3-yl}-1H-pyrazole-1-carbonyl]-2-chlorobenzoic acid
3-{1-benzoyl-5-[(4-fluorophenyl)methoxy]-4-methyl-1H-pyrazol-3-yl}-N,N,2-trimethylpyrrolidine-1-carboxamide
3-{3-[1-(dimethylcarbamoyl)piperidin-4-yl]-5-{[(4-fluorophenyl)methyl]amino}-1H-pyrazole-1-carbonyl}benzoic acid
3-{3-[1-(dimethylsulfamoyl)-5-oxopyrrolidin-3-yl]-5-[(4-fluorophenyl)methoxy]-1H-pyrazole-1-carbonyl}benzoic acid
3-{3-[1-(dimethylsulfamoyl)-6-oxopiperidin-3-yl]-5-[(4-fluorophenyl)methoxy]-4-methyl-1H-pyrazole-1-carbonyl}benzoic acid
3-{4-fluoro-5-[(4-fluorophenyl)methoxy]-1-(5-methylfuran-3-carbonyl)-1H-pyrazol-3-yl}-1-[2-(morpholin-4-yl)-2-oxoethyl]pyrrolidin-2-one
3-{4-fluoro-5-[(4-fluorophenyl)methoxy]-3-(pyrrolidin-3-yl)-1H-pyrazole-1-carbonyl}benzoic acid
3-{5-[(4-carbamimidoylphenyl)methoxy]-1-(2-methoxybenzoyl)-1H-pyrazol-3-yl}-1-[2-(morpholin-4-yl)acetyl]-4-(trifluoromethyl)piperidine-2-carboxylic acid
3-{5-[(4-carbamimidoylphenyl)methoxy]-1-(3-methoxy-2,2-dimethylpropanoyl)-1H-pyrazol-3-yl}-4-methyl-1-(morpholine-4-carbonyl)piperidine-2-carboxylic acid
3-{5-[(4-carbamimidoylphenyl)methoxy]-3-[1-(dimethylsulfamoyl)pyrrolidin-3-yl]-1H-pyrazole-1-carbonyl}-2-chlorobenzoic acid
3-{5-[(4-carbamimidoylphenyl)methoxy]-4-cyano-1-(thiophene-2-carbonyl)-1H-pyrazol-3-yl}-1-[2-(morpholin-4-yl)-2-oxoethyl]piperidine-2-carboxylic acid
3-{5-[(4-carbamimidoylphenyl)methoxy]-4-cyano-3-[2-oxo-1-(pyrrolidine-1-carbonyl)piperidin-3-yl]-1H-pyrazole-1-carbonyl}-2-chlorobenzoic acid
3-{5-[(4-carbamimidoylphenyl)methoxy]-4-methoxy-1H-pyrazol-3-yl}-1-(pyrrolidine-1-carbonyl)piperidine-2-carboxylic acid
3-{5-[(4-carbamimidoylphenyl)methoxy]-4-methoxy-3-[1-(pyrrolidine-1-sulfonyl)piperidin-4-yl]-1H-pyrazole-1-carbonyl}-2-chlorobenzoic acid
3-{5-[(4-fluorophenyl)methoxy]-1-(2-methylfuran-3-carbonyl)-1H-pyrazol-3-yl}-1-[2-(morpholin-4-yl)-2-oxoethyl]-4-(trifluoromethyl)azetidin-2-one
3-{5-[(5-chlorothiophen-2-yl)methoxy]-1-(2-methoxybenzoyl)-1H-pyrazol-3-yl}-1-(morpholine-4-carbonyl)-4-(trifluoromethyl)piperidin-2-one
3-{5-[(5-chlorothiophen-2-yl)methoxy]-1-(furan-2-carbonyl)-4-methyl-1H-pyrazol-3-yl}-1-methanesulfonyl-2-methylpiperazine
3-{5-[(5-chlorothiophen-2-yl)methoxy]-1-(furan-3-carbonyl)-4-methyl-1H-pyrazol-3-yl}-2-methyl-1-(pyrrolidine-1-carbonyl)piperidine
3-{5-[(5-chlorothiophen-2-yl)methoxy]-1-(thiophene-2-carbonyl)-1H-pyrazol-3-yl}-1-(pyrrolidine-1-sulfonyl)pyrrolidine-2-carboxylic acid
3-{5-[(5-chlorothiophen-2-yl)methoxy]-4-cyano-1-(2-methoxybenzoyl)-1H-pyrazol-3-yl}-4-(trifluoromethyl)piperidine-2-carboxylic acid
3-{5-[(5-chlorothiophen-2-yl)methoxy]-4-cyano-1H-pyrazol-3-yl}-1-(pyrrolidine-1-carbonyl)pyrrolidine-2-carboxylic acid
3-{5-[(5-chlorothiophen-2-yl)methoxy]-4-fluoro-1-(furan-2-carbonyl)-1H-pyrazol-3-yl}-4-methyl-1-(pyrrolidine-1-sulfonyl)azetidin-2-one
3-{5-[(5-chlorothiophen-2-yl)methoxy]-4-methoxy-1-(2-methoxybenzoyl)-1H-pyrazol-3-yl}-1-methanesulfonyl-4-(trifluoromethyl)piperidine-2-carboxylic acid
3-{5-[(5-chlorothiophen-2-yl)methoxy]-4-methyl-1-(1,3-thiazole-4-carbonyl)-1H-pyrazol-3-yl}-N,N-dimethyl-4-(trifluoromethyl)piperidine-1-sulfonamide
4-(1-benzoyl-5-{[(5-chlorothiophen-2-yl)methyl]amino}-4-fluoro-1H-pyrazol-3-yl)-1-[(3-hydroxypyrrolidin-1-yl)sulfonyl]-3-methylpiperidin-2-one
4-(4-cyano-5-{[(4-fluorophenyl)methyl](methyl)amino}-1-(thiophene-2-carbonyl)-1H-pyrazol-3-yl)-2-hydroxy-N,N-dimethylpyrrolidine-1-sulfonamide
4-(4-fluoro-5-{[(4-fluorophenyl)methyl](methyl)amino}-1-(furan-3-carbonyl)-1H-pyrazol-3-yl)-1-methanesulfonyl-5-methylpiperidin-3-one
4-(4-fluoro-5-{[(4-fluorophenyl)methyl](methyl)amino}-1H-pyrazol-3-yl)-1-(pyrrolidine-1-sulfonyl)piperidin-2-one
4-(4-fluoro-5-{[(4-fluorophenyl)methyl]amino}-1-(5-methylfuran-3-carbonyl)-1H-pyrazol-3-yl)-1-(pyrrolidine-1-carbonyl)piperidin-3-one
4-(4-fluoro-5-{[(4-fluorophenyl)methyl]sulfanyl}-1-(1,3-thiazole-4-carbonyl)-1H-pyrazol-3-yl)-1-(3-hydroxypyrrolidine-1-carbonyl)-3-(trifluoromethyl)azetidin-2-one
4-(4-fluoro-5-{[(4-fluorophenyl)methyl]sulfanyl}-1-(furan-3-carbonyl)-1H-pyrazol-3-yl)-3-methylpyrrolidin-2-one TABLE C-continued 4-(4-fluoro-5-{[(4-fluorophenyl)methyl]sulfanyl}-1H-pyrazol-3-yl)-1-methanesulfonylpyrrolidin-3-one
4-(5-{[(4-carbamimidoylphenyl)methyl]sulfanyl}-4-cyano-1-(2-methoxybenzoyl)-1H-pyrazol-3-yl)-N,N-dimethyl-2-oxo-3-(trifluoromethyl)pyrrolidine-1-carboxamide
4-(5-{[(4-fluorophenyl)methyl](methyl)amino}-1-(furan-3-carbonyl)-4-methoxy-1H-pyrazol-3-yl)-3-methyl-1-[2-(morpholin-4-yl)-2-oxoethyl]azetidin-2-one
4-(5-{[(4-fluorophenyl)methyl](methyl)amino}-4-methoxy-1-(3-methoxy-2,2-dimethylpropanoyl)-1H-pyrazol-3-yl)-3-methylpiperidin-2-one
4-(5-{[(4-fluorophenyl)methyl](methyl)amino}-4-methoxy-1-(thiophene-2-carbonyl)-1H-pyrazol-3-yl)-N,N-dimethyl-2-oxopyrrolidine-1-sulfonamide
4-(5-{[(4-fluorophenyl)methyl](methyl)amino}-4-methyl-1H-pyrazol-3-yl)-1-[2-(morpholin-4-yl)acetyl]azetidin-2-one
4-(5-{[(4-fluorophenyl)methyl]amino}-1-(3-hydroxy-2,2-dimethylpropanoyl)-1H-pyrazol-3-yl)-1-[(3-hydroxypyrrolidin-1-yl)sulfonyl]-5-methylpiperidin-3-one
4-(5-{[(4-fluorophenyl)methyl]sulfanyl}-1-(1,3-thiazole-4-carbonyl)-1H-pyrazol-3-yl)-1-[2-(morpholin-4-yl)-2-oxoethyl]-3-(trifluoromethyl)pyrrolidin-2-one
4-(5-{[(4-fluorophenyl)methyl]sulfanyl}-4-methoxy-1H-pyrazol-3-yl)-1-(3-hydroxypyrrolidine-1-carbonyl)piperidin-2-one
4-(5-{[(4-fluorophenyl)methyl]sulfanyl}-4-methyl-1-(1,3-thiazole-4-carbonyl)-1H-pyrazol-3-yl)-3-(trifluoromethyl)azetidin-2-one
4-(5-{[(5-chlorothiophen-2-yl)methyl](methyl)amino}-1-(3-hydroxy-2,2-dimethylpropanoyl)-4-methyl-1H-pyrazol-3-yl)-3-methylpyrrolidin-2-one
4-(5-{[(5-chlorothiophen-2-yl)methyl](methyl)amino}-1-(5-methylfuran-3-carbonyl)-1H-pyrazol-3-yl)-1-(3-hydroxypyrrolidine-1-carbonyl)piperidin-2-one
4-(5-{[(5-chlorothiophen-2-yl)methyl](methyl)amino}-4-methoxy-1-(4-methylfuran-3-carbonyl)-1H-pyrazol-3-yl)-1-[2-(morpholin-4-yl)acetyl]-5-(trifluoromethyl)pyrrolidin-3-one
4-(5-{[(5-chlorothiophen-2-yl)methyl](methyl)amino}-4-methoxy-1-(5-methylfuran-3-carbonyl)-1H-pyrazol-3-yl)-1-[2-(morpholin-4-yl)-2-oxoethyl]pyrrolidin-3-one
4-(5-{[(5-chlorothiophen-2-yl)methyl]amino}-1-(3-hydroxy-2,2-dimethylpropanoyl)-1H-pyrazol-3-yl)-3-methyl-1-(pyrrolidine-1-sulfonyl)azetidin-2-one
4-(5-{[(5-chlorothiophen-2-yl)methyl]amino}-1-(3-hydroxy-2,2-dimethylpropanoyl)-4-methoxy-1H-pyrazol-3-yl)-3-methyl-1-(morpholine-4-carbonyl)pyrrolidin-2-one
4-(5-{[(5-chlorothiophen-2-yl)methyl]amino}-4-fluoro-1-(5-methylfuran-3-carbonyl)-1H-pyrazol-3-yl)-1-[(3-hydroxypyrrolidin-1-yl)sulfonyl]azetidin-2-one
4-(5-{[(5-chlorothiophen-2-yl)methyl]amino}-4-methyl-1-(2-methylfuran-3-carbonyl)-1H-pyrazol-3-yl)-N,N-dimethyl-2-oxo-3-(trifluoromethyl)pyrrolidine-1-carboxamide
4-(5-{[(5-chlorothiophen-2-yl)methyl]sulfanyl}-1-(2-methoxybenzoyl)-4-methyl-1H-pyrazol-3-yl)-1-[2-(morpholin-4-yl)acetyl]-3-(trifluoromethyl)piperidin-2-one
4-(5-{[(5-chlorothiophen-2-yl)methyl]sulfanyl}-1-(furan-2-carbonyl)-1H-pyrazol-3-yl)-5-methyl-1-(pyrrolidine-1-carbonyl)pyrrolidin-3-one
4-(5-{[(5-chlorothiophen-2-yl)methyl]sulfanyl}-1-(furan-2-carbonyl)-4-methoxy-1H-pyrazol-3-yl)-5-methylpyrrolidin-3-one
4-(5-{[(5-chlorothiophen-2-yl)methyl]sulfanyl}-1H-pyrazol-3-yl)-1-(pyrrolidine-1-sulfonyl)piperidin-3-one
4-(5-{[(5-chlorothiophen-2-yl)methyl]sulfanyl}-3-[1-(pyrrolidine-1-carbonyl)-3-(trifluoromethyl)azetidin-2-yl]-1H-pyrazole-1-carbonyl)-1,3-thiazole
4-(5-{[(5-chlorothiophen-2-yl)methyl]sulfanyl}-4-fluoro-1-(3-methoxy-2,2-dimethylpropanoyl)-1H-pyrazol-3-yl)-1-methanesulfonyl-3-methylpiperidin-2-one
4-(5-{[(5-chlorothiophen-2-yl)methyl]sulfanyl}-4-fluoro-1-(furan-3-carbonyl)-1H-pyrazol-3-yl)-1-[(3-hydroxypyrrolidin-1-yl)sulfonyl]-5-methylpiperidin-3-one
4-(5-{[(5-chlorothiophen-2-yl)methyl]sulfanyl}-4-fluoro-1-(thiophene-2-carbonyl)-1H-pyrazol-3-yl)-N,N-dimethylpiperidine-1-carboxamide
4-(5-{[(5-chlorothiophen-2-yl)methyl]sulfanyl}-4-methoxy-1H-pyrazol-3-yl)-1-(pyrrolidine-1-carbonyl)pyrrolidin-2-one
4-(5-{[4-(aminomethyl)phenyl]methoxy}-1-(furan-2-carbonyl)-4-methyl-1H-pyrazol-3-yl)-N,N,3-trimethyl-5-oxopiperidine-1-carboxamide
4-(5-{[4-(aminomethyl)phenyl]methoxy}-1H-pyrazol-3-yl)-1-(pyrrolidine-1-carbonyl)piperidin-3-one
4-(5-{[4-(aminomethyl)phenyl]methoxy}-4-cyano-1-(1,3-thiazole-4-carbonyl)-1H-pyrazol-3-yl)-N,N-dimethyl-2-oxo-3-(trifluoromethyl)piperidine-1-carboxamide
4-(5-{[4-(aminomethyl)phenyl]methoxy}-4-fluoro-1-(furan-3-carbonyl)-1H-pyrazol-3-yl)-3-methyl-1-[2-(morpholin-4-yl)-2-oxoethyl]piperidin-2-one
4-(5-{[4-(aminomethyl)phenyl]methoxy}-4-methyl-1-(thiophene-2-carbonyl)-1H-pyrazol-3-yl)-1-[2-(morpholin-4-yl)acetyl]pyrrolidin-2-one
4-({[1-(2,2-dimethylpropanoyl)-3-[1-(2,2-dimethylpropanoyl)-2-oxoazetidin-3-yl]-4-methoxy-1H-pyrazol-5-yl]amino}methyl)benzene-1-carboximidamide
4-({[1-(2,2-dimethylpropanoyl)-3-[4-(pyrrolidine-1-carbonyl)piperazin-2-yl]-1H-pyrazol-5-yl](methyl)amino}methyl)benzene-1-carboximidamide
4-({[1-(2,2-dimethylpropanoyl)-4-fluoro-3-[1-(morpholine-4-carbonyl)-4-oxopyrrolidin-3-yl]-1H-pyrazol-5-yl](methyl)amino}methyl)benzene-1-carboximidamide
4-({[1-(2,2-dimethylpropanoyl)-4-methyl-3-[2-oxo-1-(pyrrolidine-1-carbonyl)piperidin-3-yl]-1H-pyrazol-5-yl](methyl)amino}methyl)benzene-1-carboximidamide
4-({[1-(2,2-dimethylpropanoyl)-4-methyl-3-{1-[2-(morpholin-4-yl)acetyl]-3-oxopiperidin-4-yl}-1H-pyrazol-5-yl]amino}methyl)benzene-1-carboximidamide
4-({[1-(2-chlorobenzoyl)-3-[1-(dimethylsulfamoyl)-4-oxo-3-(trifluoromethyl)azetidin-2-yl]-4-methoxy-1H-pyrazol-5-yl]oxy}methyl)benzene-1-carboximidamide
4-({[1-(2-chlorobenzoyl)-3-[1-(pyrrolidine-1-sulfonyl)-4-(trifluoromethyl)piperidin-3-yl]-1H-pyrazol-5-yl]sulfanyl}methyl)benzene-1-carboximidamide
4-({[1-(2-chlorobenzoyl)-3-{1-[(3-hydroxypyrrolidin-1-yl)sulfonyl]-3-

TABLE C-continued (trifluoromethyl)azetidin-2-yl}-4-methyl-1H-pyrazol-5-yl]oxy}methyl)benzene-1-carboximidamide
4-({[1-(2-chlorobenzoyl)-4-cyano-3-{4-[(3-hydroxypyrrolidin-1-yl)sulfonyl]-3-(trifluoromethyl)piperazin-2-yl}-1H-pyrazol-5-yl]oxy}methyl)benzene-1-carboximidamide
4-({[1-(2-chlorobenzoyl)-4-fluoro-3-[3-(trifluoromethyl)piperazin-2-yl]-1H-pyrazol-5-yl]sulfanyl}methyl)benzene-1-carboximidamide
4-({[1-(2-chlorobenzoyl)-4-methyl-3-[1-(pyrrolidine-1-sulfonyl)-3-(trifluoromethyl)piperazin-2-yl]-1H-pyrazol-5-yl]sulfanyl}methyl)benzene-1-carboximidamide
4-({[1-(2-fluorobenzoyl)-3-[4-(trifluoromethyl)oxan-3-yl]-1H-pyrazol-5-yl]amino}methyl)benzene-1-carboximidamide
4-({[1-(2-fluorobenzoyl)-3-{1-[(3-hydroxypyrrolidin-1-yl)sulfonyl]-6-oxo-4-(trifluoromethyl)piperidin-3-yl}-4-methyl-1H-pyrazol-5-yl]amino}methyl)benzene-1-carboximidamide
4-({[1-(2-fluorobenzoyl)-3-{1-[2-(morpholin-4-yl)-2-oxoethyl]-2-(trifluoromethyl)piperidin-3-yl}-1H-pyrazol-5-yl](methyl)amino}methyl)benzene-1-carboximidamide
4-({[1-(2-methoxybenzoyl)-3-[6-oxo-4-(trifluoromethyl)piperidin-3-yl]-1H-pyrazol-5-yl]sulfanyl}methyl)benzene-1-carboximidamide
4-({[1-(2-methylfuran-3-carbonyl)-3-[1-(pyrrolidine-1-sulfonyl)-2-(trifluoromethyl)pyrrolidin-3-yl]-1H-pyrazol-5-yl]amino}methyl)benzene-1-carboximidamide
4-({[1-(3-hydroxy-2,2-dimethylpropanoyl)-3-(1-methanesulfonyl-4-methyl-5-oxopyrrolidin-3-yl)-4-methyl-1H-pyrazol-5-yl]amino}methyl)benzene-1-carboximidamide
4-({[1-(3-hydroxy-2,2-dimethylpropanoyl)-3-[1-(3-hydroxypyrrolidine-1-carbonyl)-2-methylpyrrolidin-3-yl]-4-methyl-1H-pyrazol-5-yl](methyl)amino}methyl)benzene-1-carboximidamide
4-({[1-(3-hydroxy-2,2-dimethylpropanoyl)-4-methoxy-3-[3-methyl-4-oxo-1-(pyrrolidine-1-carbonyl)azetidin-2-yl]-1H-pyrazol-5-yl](methyl)amino}methyl)benzene-1-carboximidamide
4-({[1-(5-methylfuran-3-carbonyl)-3-[2-oxo-1-(pyrrolidine-1-sulfonyl)piperidin-4-yl]-1H-pyrazol-5-yl]amino}methyl)benzene-1-carboximidamide
4-({[1-(furan-2-carbonyl)-3-[1-(3-hydroxypyrrolidine-1-carbonyl)-2-methylazetidin-3-yl]-4-methyl-1H-pyrazol-5-yl]sulfanyl}methyl)benzene-1-carboximidamide
4-({[1-(furan-2-carbonyl)-3-[3-methyl-1-(pyrrolidine-1-carbonyl)piperazin-2-yl]-1H-pyrazol-5-yl]oxy}methyl)benzene-1-carboximidamide
4-({[1-(furan-2-carbonyl)-4-methoxy-3-[2-methyl-1-(morpholine-4-carbonyl)pyrrolidin-3-yl]-1H-pyrazol-5-yl]oxy}methyl)benzene-1-carboximidamide
4-({[1-(furan-3-carbonyl)-3-[1-(3-hydroxypyrrolidine-1-carbonyl)-3-methyl-5-oxopiperidin-4-yl]-4-methyl-1H-pyrazol-5-yl]oxy}methyl)benzene-1-carboximidamide
4-({[1-(furan-3-carbonyl)-3-[4-methyl-1-(morpholine-4-carbonyl)-5-oxopyrrolidin-3-yl]-1H-pyrazol-5-yl]sulfanyl}methyl)benzene-1-carboximidamide
4-({[1-(furan-3-carbonyl)-3-[5-hydroxy-1-(3-hydroxypyrrolidine-1-carbonyl)-2-methylpyrrolidin-3-yl]-1H-pyrazol-5-yl]oxy}methyl)benzene-1-carboximidamide
4-({[3-(1-methanesulfonyl-3-methylpiperidin-4-yl)-1-(3-methoxy-2,2-dimethylpropanoyl)-4-methyl-1H-pyrazol-5-yl]oxy}methyl)benzene-1-carboximidamide
4-({[3-(oxan-4-yl)-1H-pyrazol-5-yl]sulfanyl}methyl)benzene-1-carboximidamide
4-({[4-cyano-1-(2,2-dimethylpropanoyl)-3-{1-[(3-hydroxypyrrolidin-1-yl)sulfonyl]-5-oxopyrrolidin-3-yl}-1H-pyrazol-5-yl]amino}methyl)benzene-1-carboximidamide
4-({[4-cyano-1-(2-methylfuran-3-carbonyl)-3-{1-[2-(morpholin-4-yl)acetyl]-2-oxo-3-(trifluoromethyl)piperidin-4-yl}-1H-pyrazol-5-yl](methyl)amino}methyl)benzene-1-carboximidamide
4-({[4-cyano-1-(3-hydroxy-2,2-dimethylpropanoyl)-3-{3-methyl-1-[2-(morpholin-4-yl)-2-oxoethyl]-4-oxoazetidin-2-yl}-1H-pyrazol-5-yl]amino}methyl)benzene-1-carboximidamide
4-({[4-cyano-1-(3-methoxy-2,2-dimethylpropanoyl)-3-(2-methylazetidin-3-yl)-1H-pyrazol-5-yl]oxy}methyl)benzene-1-carboximidamide
4-({[4-cyano-1-(4-methylfuran-3-carbonyl)-3-[2-(trifluoromethyl)oxolan-3-yl]-1H-pyrazol-5-yl](methyl)amino}methyl)benzene-1-carboximidamide
4-({[4-cyano-1-(furan-2-carbonyl)-3-[2-methyl-1-(pyrrolidine-1-sulfonyl)azetidin-3-yl]-1H-pyrazol-5-yl]sulfanyl}methyl)benzene-1-carboximidamide
4-({[4-cyano-1-(furan-3-carbonyl)-3-[1-(3-hydroxypyrrolidine-1-carbonyl)-2-methylpyrrolidin-3-yl]-1H-pyrazol-5-yl]oxy}methyl)benzene-1-carboximidamide
4-({[4-cyano-1-(furan-3-carbonyl)-3-{4-methyl-1-[2-(morpholin-4-yl)acetyl]pyrrolidin-3-yl}-1H-pyrazol-5-yl]sulfanyl}methyl)benzene-1-carboximidamide
4-({[4-cyano-3-(3-methylpiperazin-2-yl)-1-(thiophene-3-carbonyl)-1H-pyrazol-5-yl]amino}methyl)benzene-1-carboximidamide
4-({[4-fluoro-1-(2-fluorobenzoyl)-3-[4-(trifluoromethyl)piperidin-3-yl]-1H-pyrazol-5-yl]amino}methyl)benzene-1-carboximidamide
4-({[4-fluoro-1-(2-fluorobenzoyl)-3-{1-[(3-hydroxypyrrolidin-1-yl)sulfonyl]-3-(trifluoromethyl)azetidin-2-yl}-1H-pyrazol-5-yl](methyl)amino}methyl)benzene-1-carboximidamide
4-({[4-fluoro-1-(2-methoxybenzoyl)-3-{1-[2-(morpholin-4-yl)-2-oxoethyl]-3-oxo-5-(trifluoromethyl)piperidin-4-yl}-1H-pyrazol-5-yl]oxy}methyl)benzene-1-carboximidamide
4-({[4-fluoro-1-(3-hydroxy-2,2-dimethylpropanoyl)-3-[1-(3-hydroxypyrrolidine-1-carbonyl)-3-methyl-5-oxopiperidin-4-yl]-1H-pyrazol-5-

TABLE C-continued yl](methyl)amino}methyl)benzene-1-carboximidamide
4-({[4-fluoro-1-(3-methoxy-2,2-dimethylpropanoyl)-3-[3-methyl-1-(morpholine-4-carbonyl)-2-oxopiperidin-4-yl]-1H-pyrazol-5-yl]sulfanyl}methyl)benzene-1-carboximidamide
4-({[4-fluoro-1-(4-methylfuran-3-carbonyl)-3-[1-(pyrrolidine-1-carbonyl)-3-(trifluoromethyl)azetidin-2-yl]-1H-pyrazol-5-yl](methyl)amino}methyl)benzene-1-carboximidamide
4-({[4-fluoro-1-(5-methylfuran-3-carbonyl)-3-[3-oxo-1-(pyrrolidine-1-sulfonyl)piperidin-4-yl]-1H-pyrazol-5-yl](methyl)amino}methyl)benzene-1-carboximidamide
4-({[4-fluoro-1-(furan-2-carbonyl)-3-(4-methyl-2-oxopiperidin-3-yl)-1H-pyrazol-5-yl]oxy}methyl)benzene-1-carboximidamide
4-({[4-fluoro-1-(furan-3-carbonyl)-3-[3-methyl-4-oxo-1-(pyrrolidine-1-sulfonyl)azetidin-2-yl]-1H-pyrazol-5-yl]sulfanyl}methyl)benzene-1-carboximidamide
4-({[4-methoxy-1-(1,3-thiazole-4-carbonyl)-3-[2-(trifluoromethyl)oxolan-3-yl]-1H-pyrazol-5-yl]oxy}methyl)benzene-1-carboximidamide
4-({[4-methoxy-1-(2-methoxybenzoyl)-3-{1-[2-(morpholin-4-yl)-2-oxoethyl]-4-(trifluoromethyl)pyrrolidin-3-yl}-1H-pyrazol-5-yl]sulfanyl}methyl)benzene-1-carboximidamide
4-({[4-methoxy-1-(2-methylfuran-3-carbonyl)-3-[2-(trifluoromethyl)oxetan-3-yl]-1H-pyrazol-5-yl]amino}methyl)benzene-1-carboximidamide
4-({[4-methoxy-1-(3-methoxy-2,2-dimethylpropanoyl)-3-(4-methyloxolan-3-yl)-1H-pyrazol-5-yl]sulfanyl}methyl)benzene-1-carboximidamide
4-({[4-methoxy-1-(4-methylfuran-3-carbonyl)-3-{1-[2-(morpholin-4-yl)acetyl]-3-(trifluoromethyl)piperazin-2-yl}-1H-pyrazol-5-yl]amino}methyl)benzene-1-carboximidamide
4-({[4-methoxy-1-(5-methylfuran-3-carbonyl)-3-(piperidin-3-yl)-1H-pyrazol-5-yl]amino}methyl)benzene-1-carboximidamide
4-({[4-methoxy-1-(5-methylfuran-3-carbonyl)-3-{1-[2-(morpholin-4-yl)-2-oxoethyl]-6-oxopiperidin-3-yl}-1H-pyrazol-5-yl](methyl)amino}methyl)benzene-1-carboximidamide
4-({[4-methyl-1-(4-methylfuran-3-carbonyl)-3-{1-[2-(morpholin-4-yl)acetyl]-3-(trifluoromethyl)piperidin-4-yl}-1H-pyrazol-5-yl]amino}methyl)benzene-1-carboximidamide
4-({methyl[1-(2-methylfuran-3-carbonyl)-3-{1-[2-(morpholin-4-yl)-2-oxoethyl]-3-oxo-5-(trifluoromethyl)piperidin-4-yl}-1H-pyrazol-5-yl]amino}methyl)benzene-1-carboximidamide
4-({methyl[4-methyl-1-(2-methylfuran-3-carbonyl)-3-[1-(morpholine-4-carbonyl)-2-(trifluoromethyl)piperidin-3-yl]-1H-pyrazol-5-yl]amino}methyl)benzene-1-carboximidamide
4-({methyl[4-methyl-1-(4-methylfuran-3-carbonyl)-3-[2-oxo-1-(pyrrolidine-1-carbonyl)-3-(trifluoromethyl)piperidin-4-yl]-1H-pyrazol-5-yl]amino}methyl)benzene-1-carboximidamide
4-[({1-benzoyl-3-[2-methyl-4-oxo-1-(pyrrolidine-1-sulfonyl)pyrrolidin-3-yl]-1H-pyrazol-5-yl}amino)methyl]benzene-1-carboximidamide
4-[({3-[1-(2,2-dimethylpropanoyl)-2-oxo-4-(trifluoromethyl)piperidin-3-yl]-4-methyl-1-(1,3-thiazole-4-carbonyl)-1H-pyrazol-5-yl}sulfanyl)methyl]benzene-1-carboximidamide
4- [({3-[1-(2,2-dimethylpropanoyl)-3-(trifluoromethyl)azetidin-2-yl]-4-fluoro-1-(1,3-thiazole-4-carbonyl)-1H-pyrazol-5-yl}sulfanyl)methyl]benzene-1-carboximidamide
4-[({3-[1-(2,2-dimethylpropanoyl)-3-oxo-5-(trifluoromethyl)piperidin-4-yl]-1-(2-methoxybenzoyl)-4-methyl-1H-pyrazol-5-yl}oxy)methyl]benzene-1-carboximidamide
4-[({3-[1-(2,2-dimethylpropanoyl)-4-methyl-2-oxopyrrolidin-3-yl]-1-(furan-3-carbonyl)-4-methyl-1H-pyrazol-5-yl}sulfanyl)methyl]benzene-1-carboximidamide
4-[({3-[1-(2,2-dimethylpropanoyl)-4-methyl-6-oxopiperidin-3-yl]-1-(furan-3-carbonyl)-4-methoxy-1H-pyrazol-5-yl}oxy)methyl]benzene-1-carboximidamide
4-[({3-[1-(2,2-dimethylpropanoyl)-5-hydroxypyrrolidin-3-yl]-4-fluoro-1-(thiophene-2-carbonyl)-1H-pyrazol-5-yl}sulfanyl)methyl]benzene-1-carboximidamide
4-[({3-[1-(3-hydroxypyrrolidine-1-carbonyl)-4-methylpyrrolidin-3-yl]-4-methoxy-1-(thiophene-3-carbonyl)-1H-pyrazol-5-yl}amino)methyl]benzene-1-carboximidamide
4-[({3-[1-(dimethylsulfamoyl)-3-methyl-2-oxopiperidin-4-yl]-1-(furan-2-carbonyl)-4-methoxy-1H-pyrazol-5-yl}sulfanyl)methyl]benzene-1-carboximidamide
4-[({3-[1-(dimethylsulfamoyl)-4-oxopyrrolidin-3-yl]-4-methyl-1-(thiophene-2-carbonyl)-1H-pyrazol-5-yl}sulfanyl)methyl]benzene-1-carboximidamide
4-[({3-[1-(dimethylsulfamoyl)piperidin-4-yl]-4-methyl-1-(thiophene-2-carbonyl)-1H-pyrazol-5-yl}oxy)methyl]benzene-1-carboximidamide
4-[({3-[1-(morpholine-4-carbonyl)-4-oxo-3-(trifluoromethyl)azetidin-2-yl]-1-(1,3-thiazole-4-carbonyl)-1H-pyrazol-5-yl}oxy)methyl]benzene-1-carboximidamide
4-[({4-cyano-3-[1-(2,2-dimethylpropanoyl)-2-oxo-3-(trifluoromethyl)piperidin-4-yl]-1-(4-methylfuran-3-carbonyl)-1H-pyrazol-5-yl}amino)methyl]benzene-1-carboximidamide
4-[({4-cyano-3-[1-(2,2-dimethylpropanoyl)-4-(trifluoromethyl)piperidin-3-yl]-1-(2-methylfuran-3-carbonyl)-1H-pyrazol-5-yl}amino)methyl]benzene-1-carboximidamide
4-[({4-cyano-3-[1-(2,2-dimethylpropanoyl)-4-oxoazetidin-2-yl]-1-(5-methylfuran-3-carbonyl)-1H-pyrazol-5-yl}amino)methyl]benzene-1-carboximidamide
4-[({4-cyano-3-[1-(2,2-dimethylpropanoyl]pyrrolidin-3-yl]-1H-pyrazol-5-yl}sulfanyl)methyl]benzene-1-carboximidamide
4-[({4-cyano-3-[1-methanesulfonyl-2-oxo-4-(trifluoromethyl)piperidin-3-yl]-1-(1,3-thiazole-4-carbonyl)-1H-pyrazol-5-yl}sulfanyl)methyl]benzene-1-carboximidamide
4-[({4-cyano-3-[2-methyl-1-(morpholine-4-carbonyl)pyrrolidin-3-yl]-1-(thiophene-3-carbonyl)-1H-pyrazol-5-yl}(methyl)amino)methyl]benzene-1-carboximidamide

TABLE C-continued

4-[({4-cyano-3-[2-oxo-1-(pyrrolidine-1-carbonyl)-3-(trifluoromethyl)piperidin-4-yl]-1-(1,3-thiazole-4-carbonyl)-1H-pyrazol-5-yl}oxy)methyl]benzene-1-carboximidamide
4-[({4-fluoro-3-[1-(pyrrolidine-1-carbonyl)pyrrolidin-3-yl]-1-(thiophene-2-carbonyl)-1H-pyrazol-5-yl}oxy)methyl]benzene-1-carboximidamide
4-[({4-fluoro-3-[2-methyl-4-oxo-1-(pyrrolidine-1-carbonyl)pyrrolidin-3-yl]-1-(thiophene-3-carbonyl)-1H-pyrazol-5-yl}(methyl)amino)methyl]benzene-1-carboximidamide
4-[({4-fluoro-3-[4-(pyrrolidine-1-sulfonyl)-3-(trifluoromethyl)piperazin-2-yl]-1-(1,3-thiazole-4-carbonyl)-1H-pyrazol-5-yl}oxy)methyl]benzene-1-carboximidamide
4-[3-(5-{[(5-chlorothiophen-2-yl)methyl]sulfanyl}-4-fluoro-1-(2-methoxybenzoyl)-1H-pyrazol-3-yl)-2-(trifluoromethyl)piperidine-1-carbonyl]morpholine
4-[5-({[4-(aminomethyl)phenyl]methyl}(methyl)amino)-1-(2,2-dimethylpropanoyl)-4-methoxy-1H-pyrazol-3-yl]-1-methanesulfonylazetidin-2-one
4-[5-({[4-(aminomethyl)phenyl]methyl}(methyl)amino)-1-(3-hydroxy-2,2-dimethylpropanoyl)-1H-pyrazol-3-yl]-3-methyl-1-[2-(morpholin-4-yl)-2-oxoethyl]piperidin-2-one
4-[5-({[4-(aminomethyl)phenyl]methyl}(methyl)amino)-1-(thiophene-3-carbonyl)-1H-pyrazol-3-yl]-N,N,3-trimethyl-2-oxopiperidine-1-sulfonamide
4-[5-({[4-(aminomethyl)phenyl]methyl}(methyl)amino)-1-benzoyl-4-methyl-1H-pyrazol-3-yl]-3-methyl-1-(morpholine-4-carbonyl)piperidin-2-one
4-[5-({[4-(aminomethyl)phenyl]methyl}(methyl)amino)-4-fluoro-1-(thiophene-3-carbonyl)-1H-pyrazol-3-yl]-N,N,3-trimethyl-5-oxopiperidine-1-carboxamide
4-[5-({[4-(aminomethyl)phenyl]methyl}(methyl)amino)-4-methyl-1-(4-methylfuran-3-carbonyl)-1H-pyrazol-3-yl]-N,N-dimethyl-2-oxo-3-(trifluoromethyl)piperidine-1-carboxamide
4-[5-({[4-(aminomethyl)phenyl]methyl}(methyl)amino)-4-methyl-1-(5-methylfuran-3-carbonyl)-1H-pyrazol-3-yl]pyrrolidin-2-ol
4-[5-({[4-(aminomethyl)phenyl]methyl}amino)-1-(2,2-dimethylpropanoyl)-4-methyl-1H-pyrazol-3-yl]-1-(pyrrolidine-1-sulfonyl)pyrrolidin-2-one
4-[5-({[4-(aminomethyl)phenyl]methyl}amino)-1-benzoyl-4-fluoro-1H-pyrazol-3-yl]-1-methanesulfonyl-5-methylpyrrolidin-2-ol
4-[5-({[4-(aminomethyl)phenyl]methyl}amino)-4-fluoro-1-(2-fluorobenzoyl)-1H-pyrazol-3-yl]-1-(2,2-dimethylpropanoyl)-3-(trifluoromethyl)pyrrolidin-2-one
4-[5-({[4-(aminomethyl)phenyl]methyl}amino)-4-fluoro-1-(4-methylfuran-3-carbonyl)-1H-pyrazol-3-yl]-1-(morpholine-4-carbonyl)-3-(trifluoromethyl)azetidin-2-one
4-[5-({[4-(aminomethyl)phenyl]methyl}amino)-4-methoxy-1-(5-methylfuran-3-carbonyl)-1H-pyrazol-3-yl]-1-(2,2-dimethylpropanoyl)pyrrolidin-3-one
4-[5-({[4-(aminomethyl)phenyl]methyl}amino)-4-methoxy-1-(thiophene-3-carbonyl)-1H-pyrazol-3-yl]-1-[(3-hydroxypyrrolidin-1-yl)sulfonyl]-5-methylpyrrolidin-2-ol
4-[5-({[4-(aminomethyl)phenyl]methyl}sulfanyl)-1-(2-chlorobenzoyl)-4-methyl-1H-pyrazol-3-yl]-1-(2,2-dimethylpropanoyl)-3-(trifluoromethyl)pyrrolidin-2-one
4-[5-({[4-(aminomethyl)phenyl]methyl}sulfanyl)-1-(furan-2-carbonyl)-1H-pyrazol-3-yl]-1-[(3-hydroxypyrrolidin-1-yl)sulfonyl]-5-methylpyrrolidin-2-ol
4-[5-({[4-(aminomethyl)phenyl]methyl}sulfanyl)-1H-pyrazol-3-yl]-1-(2,2-dimethylpropanoyl)pyrrolidin-3-one
4-[5-({[4-(aminomethyl)phenyl]methyl}sulfanyl)-4-methoxy-1-(3-methoxy-2,2-dimethylpropanoyl)-1H-pyrazol-3-yl]-5-methyl-1-(pyrrolidine-1-sulfonyl)pyrrolidin-3-one
4-[5-({[4-(aminomethyl)phenyl]methyl}sulfanyl)-4-methyl-1-(thiophene-2-carbonyl)-1H-pyrazol-3-yl]-1-(morpholine-4-carbonyl)piperidin-3-one
4-[5-({[4-(aminomethyl)phenyl]methyl}sulfanyl)-4-methyl-1H-pyrazol-3-yl]-1-(2,2-dimethylpropanoyl)azetidin-2-one
4-fluoro-N-[(4-fluorophenyl)methyl]-1-(2-methoxybenzoyl)-N-methyl-3-[1-(pyrrolidine-1-sulfonyl)-2-(trifluoromethyl)pyrrolidin-3-yl]-1H-pyrazol-5-amine
4-{1-benzoyl-4-fluoro-5-[(4-fluorophenyl)methoxy]-1H-pyrazol-3-yl}-5-methyl-1-(pyrrolidine-1-sulfonyl)pyrrolidin-2-ol
4-{1-benzoyl-5-[(4-fluorophenyl)methoxy]-1H-pyrazol-3-yl}-3-methylpiperidin-2-one
4-{2-[4-fluoro-1-(2-fluorobenzoyl)-5-[(4-fluorophenyl)methoxy]-1H-pyrazol-3-yl]-3-(trifluoromethyl)piperazine-1-carbonyl}morpholine
4-{3-[1-(2-chlorobenzoyl)-5-[(5-chlorothiophen-2-yl)methoxy]-4-fluoro-1H-pyrazol-3-yl]-4-(trifluoromethyl)piperidine-1-carbonyl}morpholine
4-{5-[(4-fluorophenyl)methoxy]-1-(3-hydroxy-2,2-dimethylpropanoyl)-4-methyl-1H-pyrazol-3-yl}-1-methanesulfonyl-5-methylpiperidin-3-one
4-{5-[(4-fluorophenyl)methoxy]-1-(4-methylfuran-3-carbonyl)-1H-pyrazol-3-yl}-1-(3-hydroxypyrrolidine-1-carbonyl)-3-(trifluoromethyl)azetidin-2-one
4-{5-[(4-fluorophenyl)methoxy]-1-(5-methylfuran-3-carbonyl)-1H-pyrazol-3-yl}-1-methanesulfonylpyrrolidin-3-one
4-{5-[(4-fluorophenyl)methoxy]-4-methoxy-1-(4-methylfuran-3-carbonyl)-1H-pyrazol-3-yl}-1-[2-(morpholin-4-yl)-2-oxoethyl]-3-(trifluoromethyl)pyrrolidin-2-one
4-{5-[(4-fluorophenyl)methoxy]-4-methoxy-1-(5-methylfuran-3-carbonyl)-1H-pyrazol-3-yl}piperidine
4-{5-[(5-chlorothiophen-2-yl)methoxy]-1-(3-methoxy-2,2-dimethylpropanoyl)-1H-pyrazol-3-yl}-1-[(3-hydroxypyrrolidin-1-yl)sulfonyl]-3-methylpiperidin-2-one
4-{5-[(5-chlorothiophen-2-yl)methoxy]-4-methoxy-1-(thiophene-2-carbonyl)-1H-pyrazol-3-yl}piperidin-3-one
4-{[(1-benzoyl-3-{1-[(3-hydroxypyrrolidin-1-yl)sulfonyl]-4-methylpiperidin-3-yl}-1H-pyrazol-5-yl)(methyl)amino]methyl}benzene-1-carboximidamide
4-{[(1-benzoyl-4-cyano-3-{1-[(3-hydroxypyrrolidin-1-yl)sulfonyl]-2-methyl-4-oxoazetidin-3-yl}-1H-pyrazol-5-yl)(methyl)amino]methyl}benzene-1-carboximidamide
4-{[(3-{1-[(3-hydroxypyrrolidin-1-yl)sulfonyl]-2-methylpiperidin-3-yl}-1-(3-methoxy-

TABLE C-continued 2,2-dimethylpropanoyl)-1H-pyrazol-5-yl)sulfanyl]methyl}benzene-1-carboximidamide
4-{[(3-{1-[(3-hydroxypyrrolidin-1-yl)sulfonyl]-3-(trifluoromethyl)piperidin-4-yl}-1-(4-methylfuran-3-carbonyl)-1H-pyrazol-5-yl)(methyl)amino]methyl}benzene-1-carboximidamide
4-{[(3-{1-[(3-hydroxypyrrolidin-1-yl)sulfonyl]-4-oxoazetidin-2-yl}-4-methyl-1H-pyrazol-5-yl)sulfanyl]methyl}benzene-1-carboximidamide
4-{[(3-{1-[(3-hydroxypyrrolidin-1-yl)sulfonyl]azetidin-3-yl}-1-(thiophene-2-carbonyl)-1H-pyrazol-5-yl)sulfanyl]methyl}benzene-1-carboximidamide
4-{[(3-{1-[2-(morpholin-4-yl)-2-oxoethyl]-6-oxopiperidin-3-yl}-1H-pyrazol-5-yl)oxy]methyl}benzene-1-carboximidamide
4-{[(3-{3-methyl-1-[2-(morpholin-4-yl)-2-oxoethyl]azetidin-2-yl}-1-(thiophene-3-carbonyl)-1H-pyrazol-5-yl)amino]methyl}benzene-1-carboximidamide
4-{[(4-fluoro-3-{1-[(3-hydroxypyrrolidin-1-yl)sulfonyl]-2-oxo-4-(trifluoromethyl)piperidin-3-yl}-1-(2-methylfuran-3-carbonyl)-1H-pyrazol-5-yl)amino]methyl}benzene-1-carboximidamide
4-{[(4-fluoro-3-{1-[(3-hydroxypyrrolidin-1-yl)sulfonyl]-4-methylpiperidin-3-yl}-1-(3-methoxy-2,2-dimethylpropanoyl)-1H-pyrazol-5-yl)oxy]methyl}benzene-1-carboximidamide
4-{[(4-fluoro-3-{1-[2-(morpholin-4-yl)acetyl]azetidin-2-yl}-1H-pyrazol-5-yl)oxy]methyl}benzene-1-carboximidamide
4-{[(4-methyl-3-{1-[2-(morpholin-4-yl)acetyl]-2-oxopiperidin-3-yl}-1H-pyrazol-5-yl)oxy]methyl}benzene-1-carboximidamide
5-(1-benzoyl-5-{[(5-chlorothiophen-2-yl)methyl](methyl)amino}-4-methyl-1H-pyrazol-3-yl)-4-methyl-1-(pyrrolidine-1-carbonyl)piperidin-2-one
5-(4-cyano-5-{[(4-fluorophenyl)methyl]sulfanyl}-1-(thiophene-2-carbonyl)-1H-pyrazol-3-yl)-N,N-dimethyl-2-oxopiperidine-1-sulfonamide
5-(4-fluoro-5-{[(4-fluorophenyl)methyl]amino}-1-(thiophene-3-carbonyl)-1H-pyrazol-3-yl)-1-methanesulfonyl-4-methylpiperidin-2-one
5-(5-{[(4-fluorophenyl)methyl]sulfanyl}-4-methoxy-1-(thiophene-2-carbonyl)-1H-pyrazol-3-yl)-1-(pyrrolidine-1-sulfonyl)piperidin-2-one
5-(5-{[(5-chlorothiophen-2-yl)methyl](methyl)amino}-4-cyano-1-(3-hydroxy-2,2-dimethylpropanoyl)-1H-pyrazol-3-yl)-N,N,4-trimethyl-2-oxopiperidine-1-carboxamide
5-(5-{[4-(aminomethyl)phenyl]methoxy}-1-(furan-2-carbonyl)-1H-pyrazol-3-yl)-1-methanesulfonyl-4-methylpiperidin-2-one
5-({[4-(aminomethyl)phenyl]methyl}(methyl)amino)-1-(2-fluorobenzoyl)-3-[1-(pyrrolidine-1-sulfonyl)-3-(trifluoromethyl)piperazin-2-yl]-1H-pyrazole-4-carbonitrile
5-({[4-(aminomethyl)phenyl]methyl}(methyl)amino)-1-(5-methylfuran-3-carbonyl)-3-[2-oxo-1-(pyrrolidine-1-sulfonyl)piperidin-3-yl]-1H-pyrazole-4-carbonitrile
5-({[4-(aminomethyl)phenyl]methyl}(methyl)amino)-1-benzoyl-3-{4-methyl-1-[2-(morpholin-4-yl)acetyl]-2-oxopyrrolidin-3-yl}-1H-pyrazole-4-carbonitrile
5-({[4-(aminomethyl)phenyl]methyl}(methyl)amino)-3-[1-(2,2-dimethylpropanoyl)-4-methyl-2-oxopyrrolidin-3-yl]-1-(3-hydroxy-2,2-dimethylpropanoyl)-1H-pyrazole-4-carbonitrile
5-({[4-(aminomethyl)phenyl]methyl}amino)-1-(2,2-dimethylpropanoyl)-3-{1-[2-(morpholin-4-yl)acetyl]piperidin-3-yl}-1H-pyrazole-4-carbonitrile
5-({[4-(aminomethyl)phenyl]methyl}amino)-1-(4-methylfuran-3-carbonyl)-3-[1-(morpholine-4-carbonyl)-3-(trifluoromethyl)piperidin-4-yl]-1H-pyrazole-4-carbonitrile
5-({[4-(aminomethyl)phenyl]methyl}amino)-1-(5-methylfuran-3-carbonyl)-3-{1-[2-(morpholin-4-yl)acetyl]-2-oxopiperidin-3-yl}-1H-pyrazole-4-carbonitrile
5-({[4-(aminomethyl)phenyl]methyl}amino)-1-benzoyl-3-(1-methanesulfonyl-3-methylpiperidin-4-yl)-1H-pyrazole-4-carbonitrile
5-({[4-(aminomethyl)phenyl]methyl}amino)-3-[1-(2,2-dimethylpropanoyl)-3-oxo-5-(trifluoromethyl)piperidin-4-yl]-1-(2-methylfuran-3-carbonyl)-1H-pyrazole-4-carbonitrile
5-({[4-(aminomethyl)phenyl]methyl}amino)-3-{4-methyl-1-[2-(morpholin-4-yl)-2-oxoethyl]-2-oxopiperidin-3-yl}-1-(thiophene-3-carbonyl)-1H-pyrazole-4-carbonitrile
5-({[4-(aminomethyl)phenyl]methyl}sulfanyl)-1-(2-chlorobenzoyl)-3-[1-(pyrrolidine-1-carbonyl)-3-(trifluoromethyl)piperidin-4-yl]-1H-pyrazole-4-carbonitrile
5-({[4-(aminomethyl)phenyl]methyl}sulfanyl)-1-(2-methoxybenzoyl)-3-[2-(trifluoromethyl)oxetan-3-yl]-1H-pyrazole-4-carbonitrile
5-({[4-(aminomethyl)phenyl]methyl}sulfanyl)-3-{1-[(3-hydroxypyrrolidin-1-yl)sulfonyl]-4-oxopyrrolidin-3-yl}-1-(thiophene-2-carbonyl)-1H-pyrazole-4-carbonitrile
5-[(4-fluorophenyl)methoxy]-1-(3-hydroxy-2,2-dimethylpropanoyl)-3-[4-(3-hydroxypyrrolidine-1-carbonyl)-3-methylpiperazin-2-yl]-1H-pyrazole-4-carbonitrile
5-[(4-fluorophenyl)methoxy]-1-(4-methylfuran-3-carbonyl)-3-[1-(morpholine-4-carbonyl)-3-(trifluoromethyl)azetidin-2-yl]-1H-pyrazole-4-carbonitrile
5-[(4-fluorophenyl)methoxy]-1-(5-methylfuran-3-carbonyl)-3-{1-[2-(morpholin-4-yl)acetyl]-4-oxoazetidin-2-yl}-1H-pyrazole-4-carbonitrile
5-[(4-fluorophenyl)methoxy]-3-{4-methyl-1-[2-(morpholin-4-yl)acetyl]piperidin-3-yl}-1-(thiophene-3-carbonyl)-1H-pyrazole-4-carbonitrile
5-[(4-fluorophenyl)methoxy]-4-methoxy-1-(2-methylfuran-3-carbonyl)-3-[2-(trifluoromethyl)oxan-3-yl]-1H-pyrazole
5-[(4-fluorophenyl)methoxy]-4-methoxy-3-[3-methyl-1-(pyrrolidine-1-sulfonyl)azetidin-2-yl]-1-(thiophene-3-carbonyl)-1H-pyrazole
5-[(5-chlorothiophen-2-yl)methoxy]-1-(3-methoxy-2,2-dimethylpropanoyl)-3-[4-methyl-6-oxo-1-(pyrrolidine-1-carbonyl)piperidin-3-yl]-1H-pyrazole-4-carbonitrile
5-[(5-chlorothiophen-2-yl)methoxy]-1-(furan-2-carbonyl)-3-[4-methyl-1-(pyrrolidine-1-carbonyl)piperidin-3-yl]-1H-pyrazole-4-carbonitrile
5-[(5-chlorothiophen-2-yl)methoxy]-3-[1-(3-hydroxypyrrolidine-1-carbonyl)-5-oxopyrrolidin-3-yl]-1-(thiophene-2-carbonyl)-1H-pyrazole-4-carbonitrile TABLE C-continued 5-[(5-chlorothiophen-2-yl)methoxy]-3-[2-oxo-1-(pyrrolidine-1-carbonyl)-4-(trifluoromethyl)azetidin-3-yl]-1-(1,3-thiazole-4-carbonyl)-1H-pyrazole-4-carbonitrile
5-[(5-chlorothiophen-2-yl)methoxy]-4-fluoro-3-[1-(pyrrolidine-1-sulfonyl)pyrrolidin-3-yl]-1-(thiophene-2-carbonyl)-1H-pyrazole
5-[(5-chlorothiophen-2-yl)methoxy]-4-methyl-3-(pyrrolidin-3-yl)-1H-pyrazole
5-[5-({[4-(aminomethyl)phenyl]methyl}(methyl)amino)-4-fluoro-1-(2-methylfuran-3-carbonyl)-1H-pyrazol-3-yl]-4-(trifluoromethyl)piperidin-2-one
5-[5-({[4-(aminomethyl)phenyl]methyl}amino)-1-(3-hydroxy-2,2-dimethylpropanoyl)-1H-pyrazol-3-yl]-1-(2,2-dimethylpropanoyl)-4-methylpiperidin-2-one
5-{1-benzoyl-5-[(4-fluorophenyl)methoxy]-4-methoxy-1H-pyrazol-3-yl}-1-(3-hydroxypyrrolidine-1-carbonyl)-4-methylpiperidin-2-one
5-{[(4-fluorophenyl)methyl](methyl)amino}-1-(2-methoxybenzoyl)-3-[2-(trifluoromethyl)oxan-3-yl]-1H-pyrazole-4-carbonitrile
5-{[(4-fluorophenyl)methyl](methyl)amino}-1-(furan-3-carbonyl)-3-(1-methanesulfonyl-4-methyl-5-oxopyrrolidin-3-yl)-1H-pyrazole-4-carbonitrile
5-{[(4-fluorophenyl)methyl](methyl)amino}-3-(piperidin-4-yl)-1H-pyrazole-4-carbonitrile
5-{[(4-fluorophenyl)methyl](methyl)amino}-3-[1-(3-hydroxypyrrolidine-1-carbonyl)-4-methyl-6-oxopiperidin-3-yl]-1-(3-methoxy-2,2-dimethylpropanoyl)-1H-pyrazole-4-carbonitrile
5-{[(4-fluorophenyl)methyl]amino}-1-(2-methylfuran-3-carbonyl)-3-{1-[2-(morpholin-4-yl)acetyl]-2-(trifluoromethyl)pyrrolidin-3-yl}-1H-pyrazole-4-carbonitrile
5-{[(4-fluorophenyl)methyl]amino}-1-(5-methylfuran-3-carbonyl)-3-[5-oxo-1-(pyrrolidine-1-carbonyl)pyrrolidin-3-yl]-1H-pyrazole-4-carbonitrile
5-{[(4-fluorophenyl)methyl]amino}-3-(2-methyl-4-oxopyrrolidin-3-yl)-1-(thiophene-3-carbonyl)-1H-pyrazole-4-carbonitrile
5-{[(4-fluorophenyl)methyl]sulfanyl}-1-(2-methoxybenzoyl)-3-{1-[2-(morpholin-4-yl)acetyl]-6-oxo-4-(trifluoromethyl)piperidin-3-yl}-1H-pyrazole-4-carbonitrile
5-{[(4-fluorophenyl)methyl]sulfanyl}-1-(furan-3-carbonyl)-3-(1-methanesulfonyl-2-methylazetidin-3-yl)-1H-pyrazole
5-{[(4-fluorophenyl)methyl]sulfanyl}-3-{1-[2-(morpholin-4-yl)-2-oxoethyl]-4-oxopyrrolidin-3-yl}-1H-pyrazole-4-carbonitrile
5-{[(4-fluorophenyl)methyl]sulfanyl}-3-{1-[2-(morpholin-4-yl)acetyl]-4-oxo-2-(trifluoromethyl)pyrrolidin-3-yl}-1-(1,3-thiazole-4-carbonyl)-1H-pyrazole-4-carbonitrile
5-{[(4-fluorophenyl)methyl]sulfanyl}-4-methoxy-1-(2-methoxybenzoyl)-3-[3-(trifluoromethyl)oxetan-2-yl]-1H-pyrazole
5-{[(5-chlorothiophen-2-yl)methyl](methyl)amino}-1-(2,2-dimethylpropanoyl)-3-[1-(morpholine-4-carbonyl)-6-oxopiperidin-3-yl]-1H-pyrazole-4-carbonitrile
5-{[(5-chlorothiophen-2-yl)methyl](methyl)amino}-1-(2-fluorobenzoyl)-3-{5-hydroxy-1-[2-(morpholin-4-yl)acetyl]-2-(trifluoromethyl)pyrrolidin-3-yl}-1H-pyrazole-4-carbonitrile
5-{[(5-chlorothiophen-2-yl)methyl](methyl)amino}-1-(4-methylfuran-3-carbonyl)-3-[4-oxo-3-(trifluoromethyl)azetidin-2-yl]-1H-pyrazole-4-carbonitrile
5-{[(5-chlorothiophen-2-yl)methyl]amino}-1-(2-fluorobenzoyl)-3-[5-hydroxy-1-(morpholine-4-carbonyl)-2-(trifluoromethyl)pyrrolidin-3-yl]-1H-pyrazole-4-carbonitrile
5-{[(5-chlorothiophen-2-yl)methyl]amino}-1-(2-methylfuran-3-carbonyl)-3-{1-[2-(morpholin-4-yl)-2-oxoethyl]-4-(trifluoromethyl)pyrrolidin-3-yl}-1H-pyrazole-4-carbonitrile
5-{[(5-chlorothiophen-2-yl)methyl]amino}-1-(3-hydroxy-2,2-dimethylpropanoyl)-3-[2-methyl-1-(pyrrolidine-1-carbonyl)piperidin-3-yl]-1H-pyrazole-4-carbonitrile
5-{[(5-chlorothiophen-2-yl)methyl]sulfanyl}-1-(furan-3-carbonyl)-3-[3-methyl-4-oxo-1-(pyrrolidine-1-carbonyl)azetidin-2-yl]-1H-pyrazole-4-carbonitrile
5-{[(5-chlorothiophen-2-yl)methyl]sulfanyl}-3-[1-(3-hydroxypyrrolidine-1-carbonyl)-2-oxo-4-(trifluoromethyl)azetidin-3-yl]-1-(1,3-thiazole-4-carbonyl)-1H-pyrazole-4-carbonitrile
5-{[(5-chlorothiophen-2-yl)methyl]sulfanyl}-3-[1-(3-hydroxypyrrolidine-1-carbonyl)-4-oxopyrrolidin-3-yl]-1-(thiophene-2-carbonyl)-1H-pyrazole-4-carbonitrile
5-{[(5-chlorothiophen-2-yl)methyl]sulfanyl}-4-methyl-3-[1-(pyrrolidine-1-carbonyl)pyrrolidin-3-yl]-1-(thiophene-2-carbonyl)-1H-pyrazole
5-{[4-(aminomethyl)phenyl]methoxy}-1-(2-chlorobenzoyl)-3-[1-(3-hydroxypyrrolidine-1-carbonyl)-3-(trifluoromethyl)piperazin-2-yl]-1H-pyrazole-4-carbonitrile
5-{[4-(aminomethyl)phenyl]methoxy}-1-(furan-2-carbonyl)-3-[2-methyl-1-(morpholine-4-carbonyl)-4-oxoazetidin-3-yl]-1H-pyrazole-4-carbonitrile
5-{[4-(aminomethyl)phenyl]methoxy}-1-(furan-3-carbonyl)-3-(1-methanesulfonyl-4-methyl-2-oxopyrrolidin-3-yl)-1H-pyrazole-4-carbonitrile
5-{[4-(aminomethyl)phenyl]methoxy}-3-(5-hydroxypyrrolidin-3-yl)-1H-pyrazole-4-carbonitrile
N-[(4-fluorophenyl)methyl]-3-[1-methanesulfonyl-2-(trifluoromethyl)piperidin-3-yl]-4-methyl-1-(2-methylfuran-3-carbonyl)-1H-pyrazol-5-amine
N-[(4-fluorophenyl)methyl]-4-methyl-1-(5-methylfuran-3-carbonyl)-3-(morpholin-2-yl)-1H-pyrazol-5-amine
N-[(4-fluorophenyl)methyl]-N,4-dimethyl-3-[1-(morpholine-4-carbonyl)-3-(trifluoromethyl)azetidin-2-yl]-1-(1,3-thiazole-4-carbonyl)-1H-pyrazol-5-amine
N-[(4-fluorophenyl)methyl]-N-methyl-3-(pyrrolidin-3-yl)-1-(thiophene-2-carbonyl)-1H-pyrazol-5-amine
N-[(5-chlorothiophen-2-yl)methyl]-1-(2-fluorobenzoyl)-3-[1-methanesulfonyl-4-(trifluoromethyl)pyrrolidin-3-yl]-4-methoxy-N-methyl-1H-pyrazol-5-amine
N-[(5-chlorothiophen-2-yl)methyl]-1-(2-fluorobenzoyl)-4-methoxy-3-[1-(pyrrolidine-1-sulfonyl)-4-(trifluoromethyl)piperidin-3-yl]-1H-pyrazol-5-amine

TABLE C-continued

N-[(5-chlorothiophen-2-yl)methyl]-1-(2-fluorobenzoyl)-4-methyl-3-[1-(morpholine-4-carbonyl)-4-(trifluoromethyl)piperidin-3-yl]-1H-pyrazol-5-amine
N-[(5-chlorothiophen-2-yl)methyl]-1-(2-fluorobenzoyl)-N,4-dimethyl-3-[1-(pyrrolidine-1-sulfonyl)-2-(trifluoromethyl)piperidin-3-yl]-1H-pyrazol-5-amine
N-[(5-chlorothiophen-2-yl)methyl]-4-fluoro-3-(4-methanesulfonyl-3-methylpiperazin-2-yl)-N-methyl-1-(thiophene-3-carbonyl)-1H-pyrazol-5-amine
N-[(5-chlorothiophen-2-yl)methyl]-4-fluoro-N-methyl-1-(5-methylfuran-3-carbonyl)-3-(pyrrolidin-3-yl)-1H-pyrazol-5-amine
N-[(5-chlorothiophen-2-yl)methyl]-4-methoxy-3-[4-methyl-1-(pyrrolidine-1-carbonyl)piperidin-3-yl]-1-(thiophene-3-carbonyl)-1H-pyrazol-5-amine
N-[(5-chlorothiophen-2-yl)methyl]-4-methyl-3-[2-methyl-1-(pyrrolidine-1-sulfonyl)azetidin-3-yl]-1-(thiophene-3-carbonyl)-1H-pyrazol-5-amine
N-[(5-chlorothiophen-2-yl)methyl]-N-methyl-1-(2-methylfuran-3-carbonyl)-3-[3-(trifluoromethyl)oxetan-2-yl]-1H-pyrazol-5-amine
N-{[4-(aminomethyl)phenyl]methyl}-1-(2-fluorobenzoyl)-3-[1-methanesulfonyl-2-(trifluoromethyl)pyrrolidin-3-yl]-N-methyl-1H-pyrazol-5-amine
N-{[4-(aminomethyl)phenyl]methyl}-1-(2-fluorobenzoyl)-4-methyl-3-[1-(pyrrolidine-1-carbonyl)-3-(trifluoromethyl)piperidin-4-yl]-1H-pyrazol-5-amine
N-{[4-(aminomethyl)phenyl]methyl}-1-(2-fluorobenzoyl)-N,4-dimethyl-3-[3-(trifluoromethyl)piperazin-2-yl]-1H-pyrazol-5-amine
N-{[4-(aminomethyl)phenyl]methyl}-1-benzoyl-4-methoxy-3-(2-methylazetidin-3-yl)-1H-pyrazol-5-amine
N-{[4-(aminomethyl)phenyl]methyl}-4-fluoro-N-methyl-1-(5-methylfuran-3-carbonyl)-3-(oxan-4-yl)-1H-pyrazol-5-amine
N-{[4-(aminomethyl)phenyl]methyl}-4-methoxy-1-(2-methylfuran-3-carbonyl)-3-[1-(morpholine-4-carbonyl)-2-(trifluoromethyl)azetidin-3-yl]-1H-pyrazol-5-amine
N-{[4-(aminomethyl)phenyl]methyl}-4-methyl-1-(4-methylfuran-3-carbonyl)-3-[4-(pyrrolidine-1-sulfonyl)-3-(trifluoromethyl)piperazin-2-yl]-1H-pyrazol-5-amine
[4-({[1-(2-chlorobenzoyl)-3-[4-(trifluoromethyl)piperidin-3-yl]-1H-pyrazol-5-yl]sulfanyl}methyl)phenyl]methanamine
[4-({[1-(2-chlorobenzoyl)-4-fluoro-3-[1-methanesulfonyl-2-(trifluoromethyl)pyrrolidin-3-yl]-1H-pyrazol-5-yl]oxy}methyl)phenyl]methanamine
[4-({[1-(2-chlorobenzoyl)-4-methoxy-3-[4-(trifluoromethyl)oxan-3-yl]-1H-pyrazol-5-yl]sulfanyl}methyl)phenyl]methanamine
[4-({[1-(2-methoxybenzoyl)-3-[1-(morpholine-4-carbonyl)-2-(trifluoromethyl)azetidin-3-yl]-1H-pyrazol-5-yl]sulfanyl}methyl)phenyl]methanamine
[4-({[1-(furan-2-carbonyl)-4-methyl-3-(3-methylpiperazin-2-yl)-1H-pyrazol-5-yl]sulfanyl}methyl)phenyl]methanamine
[4-({[1-(furan-3-carbonyl)-4-methyl-3-[2-methyl-1-(pyrrolidine-1-carbonyl)azetidin-3-yl]-1H-pyrazol-5-yl]oxy}methyl)phenyl]methanamine
[4-({[4-fluoro-3-(1-methanesulfonylpiperazin-2-yl)-1-(thiophene-2-carbonyl)-1H-pyrazol-5-yl]oxy}methyl)phenyl]methanamine
[4-({[4-fluoro-3-(morpholin-2-yl)-1H-pyrazol-5-yl]oxy}methyl)phenyl]methanamine
{4-[({4-fluoro-3-[1-methanesulfonyl-2-(trifluoromethyl)piperidin-3-yl]-1-(2-methoxybenzoyl)-1H-pyrazol-5-yl}oxy)methyl]phenyl}methanamine
{4-[({4-methoxy-3-[1-(morpholine-4-carbonyl)-3-(trifluoromethyl)piperidin-4-yl]-1-(1,3-thiazole-4-carbonyl)-1H-pyrazol-5-yl]sulfanyl)methyl]phenyl}methanamine
N-[(5-chlorothiophen-2-yl)methyl]-3-(piperazin-2-yl)-1H-pyrazol-5-amine
1-(5-{[(5-chlorothiophen-2-yl)methyl]amino}-3-{4-[2-(morpholin-4-yl)acetyl]piperazin-2-yl}-1H-pyrazol-1-yl)-2,2-dimethylpropan-1-one
1-[3-(5-{[(5-chlorothiophen-2-yl)methyl]amino}-1H-pyrazol-3-yl)piperazin-1-yl]-2-(morpholin-4-yl)ethan-1-one
1-(5-{[(5-chlorothiophen-2-yl)methyl]amino}-3-[4-(morpholine-4-sulfonyl)piperazin-2-yl]-1H-pyrazol-1-yl)-2,2-dimethylpropan-1-one
1-(5-{[(5-chlorothiophen-2-yl)methyl]amino}-3-[4-(2,2,2-trifluoroethyl)piperazin-2-yl]-1H-pyrazol-1-yl)-2,2-dimethylpropan-1-one
N-[(5-chlorothiophen-2-yl)methyl]-3-(pyrrolidin-2-yl)-1-(1,3-thiazole-4-carbonyl)-1H-pyrazol-5-amine
1-[2-(5-{[(5-chlorothiophen-2-yl)methyl]amino}-1-(1,3-thiazole-4-carbonyl)-1H-pyrazol-3-yl)pyrrolidin-1-yl]-2-(morpholin-4-yl)ethan-1-one
N-[(5-chlorothiophen-2-yl)methyl]-3-(pyrrolidin-3-yl)-1-(1,3-thiazole-4-carbonyl)-1H-pyrazol-5-amine
1-[3-(5-{[(5-chlorothiophen-2-yl)methyl]amino}-1-(1,3-thiazole-4-carbonyl)-1H-pyrazol-3-yl)pyrrolidin-1-yl]-2-(morpholin-4-yl)ethan-1-one
N-[(5-chlorothiophen-2-yl)methyl]-3-(piperazin-2-yl)-1-(1,3-thiazole-4-carbonyl)-1H-pyrazol-5-amine
1-[3-(5-{[(5-chlorothiophen-2-yl)methyl]amino}-1-(1,3-thiazole-4-carbonyl)-1H-pyrazol-3-yl)piperazin-1-yl]-2-(morpholin-4-yl)ethan-1-one
N-[(5-chlorothiophen-2-yl)methyl]-3-(4-methanesulfonylpiperazin-2-yl)-1-(1,3-thiazole-4-carbonyl)-1H-pyrazol-5-amine
N-[(5-chlorothiophen-2-yl)methyl]-3-[4-(morpholine-4-carbonyl)piperazin-2-yl]-1-(1,3-thiazole-4-carbonyl)-1H-pyrazol-5-amine
1-[3-(azepan-4-yl)-5-{[(5-chlorothiophen-2-yl)methyl]amino}-1H-pyrazol-1-yl]-2,2-dimethylpropan-1-one
3-(azepan-4-yl)-N-[(5-chlorothiophen-2-yl)methyl]-1-(1,3-thiazole-4-carbonyl)-1H-pyrazol-5-amine
1-[3-(azetidin-3-yl)-5-{[(5-chlorothiophen-2-yl)methyl]amino}-1H-pyrazol-1-yl]-2,2-dimethylpropan-1-one
N-[(5-chlorothiophen-2-yl)methyl]-3-[1-(morpholine-4-carbonyl)azetidin-3-yl]-1H-pyrazol-5-amine

TABLE C-continued 3-(azetidin-3-yl)-N-[(5-chlorothiophen-2-yl)methyl]-1-(1,3-thiazole-4-carbonyl)-1H-pyrazol-5-amine
3-[1-(2-chlorobenzoyl)-5-{[(5-chlorothiophen-2-yl)methyl]amino}-1H-pyrazol-3-yl]-N,N-dimethylpyrrolidine-1-sulfonamide
1-(2-chlorobenzoyl)-N-[(5-chlorothiophen-2-yl)methyl]-3-[1-(pyrrolidine-1-sulfonyl)pyrrolidin-3-yl]-1H-pyrazol-5-amine
1-(2-chlorobenzoyl)-N-[(5-chlorothiophen-2-yl)methyl]-3-[1-(piperazine-1-sulfonyl)pyrrolidin-3-yl]-1H-pyrazol-5-amine
1-(2-chlorobenzoyl)-N-[(5-chlorothiophen-2-yl)methyl]-3-[1-(piperazine-1-carbonyl)pyrrolidin-3-yl]-1H-pyrazol-5-amine
3-[1-(2-chlorobenzoyl)-5-{[(5-chlorothiophen-2-yl)methyl]amino}-1H-pyrazol-3-yl]-N,N-dimethylazetidine-1-sulfonamide
1-(2-chlorobenzoyl)-N-[(5-chlorothiophen-2-yl)methyl]-3-[1-(pyrrolidine-1-sulfonyl)azetidin-3-yl]-1H-pyrazol-5-amine
1-(2-chlorobenzoyl)-N-[(5-chlorothiophen-2-yl)methyl]-3-[1-(piperazine-1-sulfonyl)azetidin-3-yl]-1H-pyrazol-5-amine
1-(2-chlorobenzoyl)-N-[(5-chlorothiophen-2-yl)methyl]-3-[1-(piperazine-1-carbonyl)azetidin-3-yl]-1H-pyrazol-5-amine
1-(5-{[(5-chlorothiophen-2-yl)methyl]amino}-3-[4-(2-cyclopropoxyethyl)piperazin-2-yl]-1H-pyrazol-1-yl)-2,2-dimethylpropan-1-one
4-[3-(5-{[(5-chlorothiophen-2-yl)methyl]amino}-1-(2,2-dimethylpropanoyl)-1H-pyrazol-3-yl)piperazine-1-carbonyl]morpholine-3-carboxylic acid
1-(5-{[(5-chlorothiophen-2-yl)methyl]amino}-3-[4-(3-methylmorpholine-4-carbonyl)piperazin-2-yl]-1H-pyrazol-1-yl)-2,2-dimethylpropan-1-one
1-(5-{[(5-chlorothiophen-2-yl)methyl]amino}-3-[4-(3,5-dimethylmorpholine-4-carbonyl)piperazin-2-yl]-1H-pyrazol-1-yl)-2,2-dimethylpropan-1-one
1-(5-{[(5-chlorothiophen-2-yl)methyl]amino}-3-{4-[2-(morpholin-4-yl)-2-oxoethyl]piperazin-2-yl}-1H-pyrazol-1-yl)-2,2-dimethylpropan-1-one
1-(5-{[(5-chlorothiophen-2-yl)methyl]amino}-3-{4-[2-(morpholin-4-yl)ethyl]piperazin-2-yl}-1H-pyrazol-1-yl)-2,2-dimethylpropan-1-one
4-{2-[3-(5-{[(5-chlorothiophen-2-yl)methyl]amino}-1-(2,2-dimethylpropanoyl)-1H-pyrazol-3-yl)piperazin-1-yl]ethyl}morpholine-3-carboxylic acid
1-(5-{[(5-chlorothiophen-2-yl)methyl]amino}-3-{4-[4-(hydroxymethyl)-1,3-oxazol-2-yl]piperazin-2-yl}-1H-pyrazol-1-yl)-2,2-dimethylpropan-1-one
1-(5-{[(5-chlorothiophen-2-yl)methyl]amino}-3-(4-{[4-(hydroxymethyl)-1,3-oxazol-2-yl]methyl}piperazin-2-yl)-1H-pyrazol-1-yl)-2,2-dimethylpropan-1-one
2-[3-(5-{[(5-chlorothiophen-2-yl)methyl]amino}-1-(2,2-dimethylpropanoyl)-1H-pyrazol-3-yl)piperazin-1-yl]acetic acid For Table D following, the disclosed compounds were assayed for inhibition of the protease activity of chymotrypsin and Factor XIa as described herein. In Table D, the level of inhibition in the assay is indicated as follows: a $IC_{50}<0.1$ μM; b: $0.1$ μM$<IC_{50}<1$ μM; c: $1$ μM$<IC_{50}<10$ μM; d: $10$ μM$<IC_{50}<100$ μM; e: $IC_{50}\geq 100$ μM. Accordingly, in some embodiments, there is provided a compound as expressly set forth in Table D following.

TABLE D

| Table, Entry or IUPAC name | Chymotrypsin Inhibition | Factor XIa Inhibition |
|---|---|---|
| A, 24 | d | d |
| A, 25 | c | d |
| A, 26 | e | d |
| A, 37 | e | e |
| A, 56 | e | (no data) |
| A, 57 | d | (no data) |
| A, 291 | d | e |
| A, 292 | e | e |
| N-[(5-chlorothiophen-2-yl)methyl]-1-(2-methoxybenzoyl)-3-phenyl-1H-1,2,4-triazol-5-amine | a | c |
| N-[(5-chlorothiophen-2-yl)methyl]-1-(2-methoxybenzoyl)-3-(pyridin-2-yl)-1H-pyrazol-5-amine | b | c |

Compounds disclosed herein also include racemic mixtures, stereoisomers and mixtures of the compounds, including isotopically-labeled and radio-labeled compounds. See e.g., Goding, 1986, MONOCLONAL ANTIBODIES PRINCIPLES AND PRACTICE; Academic Press, p. 104. Such isomers can be isolated by standard resolution techniques, including e.g., fractional crystallization, chiral chromatography, and the like. See e.g., Eliel, E. L. & Wilen S. H., 1993, STEREOCHEMISTRY IN ORGANIC COMPOUNDS; John Wiley & Sons, New York.

In some embodiments, compounds disclosed herein have asymmetric centers and can occur as racemates, racemic mixtures, and as individual enantiomers or diastereoisomers, with all isomeric forms as well as mixtures thereof being contemplated for use in the compounds and methods described herein. The compounds contemplated for use in the compounds and methods described herein do not include those that are known in the art to be too unstable to synthesize and/or isolate.

The compounds disclosed herein can also contain unnatural proportions of atomic isotopes at one or more of the atoms that constitute such compounds. For example, the compounds can be radiolabeled with radioactive isotopes, such as for example tritium ($^3H$), iodine-125 ($^{125}I$), or carbon-14 ($^{14}C$). All isotopic variations of the compounds disclosed herein, whether radioactive or not, are encompassed within the contemplated scope.

In some embodiments, metabolites of the compounds disclosed herein are useful for the methods disclosed herein.

In some embodiments, compounds contemplated herein are provided in the form of a prodrug. The term "prodrug" refers to a compound that can be converted into a compound (e.g., a biologically active compound) described herein in vivo. Prodrugs can be useful for a variety of reason known in the art, including e.g., ease of administration due e.g., to enhanced bioavailability in oral administration, and the like. The prodrug can also have improved solubility in pharmaceutical compositions over the biologically active compounds. An example, without limitation, of a prodrug is a compound which is administered as an ester (i.e., the "prodrug") to facilitate transmittal across a cell membrane where water solubility is detrimental to mobility but which then is metabolically hydrolyzed to the carboxylic acid, the active entity, once inside the cell where water solubility is beneficial. Conventional procedures for the selection and preparation of suitable prodrug derivatives are described, for example, in DESIGN OF PRODRUGS, (ed. H. Bundgaard, Elsevier, 1985), which is hereby incorporated herein by reference for the limited purpose describing procedures and preparation of suitable prodrug derivatives.

Accordingly, in some embodiments, compounds contemplated herein are provided in the form of a prodrug ester. The term "prodrug ester" refers to derivatives of the compounds disclosed herein formed by the addition of any of a variety of ester-forming groups, e.g., groups known in the art, that are hydrolyzed under physiological conditions. Examples of prodrug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in, for example, T. Higuchi and V. Stella, in "Pro-drugs as Novel Delivery Systems", Vol. 14, A.C.S. Symposium Series, American Chemical Society (1975); and BIOREVERSIBLE CARRIERS IN DRUG DESIGN: THEORY AND APPLICATION, edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

In some embodiments, prodrugs can be slowly converted to the compounds described herein useful for the methods described herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope of contemplated compounds. Certain compounds of the present invention can exist in multiple crystalline or amorphous forms. In general, all physical forms are equivalent for the compounds and methods contemplated herein and are intended to be within the scope disclosed herein.

III. Biological Activities

In some embodiments, compounds described herein exhibit inhibitory activity against thrombin with activities ≥1 µM, e.g., about 1, 2, 3, 4, 5, 6, 7, 8, 9, 10, 11, 12, 13, 14, 16, 18, 20, 22, 24, 26, 28, 30, 32, 34, 36, 38, 40, 45, 50, 55, 60, 65, 70, 75, 80, 85, 90, 95, 100 µM, or even greater. In some embodiments, the compounds exhibit inhibitory activity against thrombin with activities between 0.1 µM and 1 µM, e.g., about 0.1, 0.2, 0.3, 0.4, 0.5, 0.6, 0.7, 0.8, 0.9 or 1.0 µM. In some embodiments, compounds described herein exhibit inhibitory activity against thrombin with activities ≤0.1 µM, e.g., about 1, 2, 5, 10, 15, 20, 30, 40, 50, 60, 70, 80, 90, or 100 nM. Ranges of values using a combination of any of the values recited herein as upper and/or lower limits are also contemplated, for example, but not limited to, 1-10 nM, 10-100 nM, 0.1-1 µM, 1-10 µM, 10-100 µM, 100-200 µM, 200-500 µM, or even 500-1000 µM. In some embodiments, the inhibitory activity is in the range of about 1-10 nM, 10-100 nM, 0.1-1 µM, 1-10 µM, 10-100 µM, 100-200 µM, 200-500 µM, or even 500-1000 µM. It is understood that for purposes of quantification, the terms "activity," "inhibitory activity," "biological activity," "thrombin activity and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

Inhibitory activity against thrombin in turn inhibits the blood coagulation process. Accordingly, compounds disclosed herein are indicated in the treatment or management of thrombotic disorders. In some embodiments, a dose or a therapeutically effective dose of a compound disclosed herein will be that which is sufficient to achieve a plasma concentration of the compound or its active metabolite(s) within a range set forth herein, e.g., about 1-10 nM, 10-100 nM, 0.1-1 µM, 1-10 µM, 10-100 µM, 100-200 µM, 200-500 µM, or even 500-1000 µM, preferably about 1-10 nM, 10-100 nM, or 0.1-1 µM. Without wishing to be bound by any theory, it is believe that such compounds are indicated in the treatment or management of thrombotic disorders.

In some embodiments, compounds described herein exhibit inhibitory activity against KLKB1 with activities between 1 µM and 10 µM, e.g., about 1, 2, 3, 4, 5, 6, 7, 8, 9 or 10 µM. In some embodiments, compounds described herein exhibit inhibitory activity against KLKB1 with activities ≥10 µM, e.g., about 10, 20, 50, 100, 150, 200, 300, 400, 500, 600, 700, 800, 900, 1000 µM or even greater. In some embodiments, compounds described herein exhibit inhibitory activity against KLKB1 with activities ≤1 µM, e.g., about 900, 800, 700, 600, 500, 400, 300, 200, 100, 50 nM or even lower. Ranges of values using a combination of any of the values recited herein as upper and/or lower limits are also contemplated, for example, but not limited to, 1-10 nM, 10-100 nM, 0.1-1 µM, 1-10 µM, 10-100 µM, 100-200 µM, 200-500 µM, or even 500-1000 µM. In some embodiments, the inhibitory activity is in the range of about 1-10 nM, 10-100 nM, 0.1-1 µM, 1-10 µM, 10-100 µM, 100-200 µM, 200-500 µM, or even 500-1000 µM. It is understood that for purposes of quantification, the terms "activity," "inhibitory activity," "biological activity," "KLKB1 activity" and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

Inhibitory activity against KLKB1 has an effect on the coagulation cascade and the inflammatory response. Thus, it has been proposed that KLKB1 inhibitors can be useful in the treatment of thrombotic and fibrinolytic diseases and disease conditions.

Accordingly, compounds disclosed herein are indicated in the treatment or management of a variety of diseases or disorders. In some embodiments, a dose or a therapeutically effective dose of a compound disclosed herein will be that which is sufficient to achieve a plasma concentration of the compound or its active metabolite(s) within a range set forth herein, e.g., about 1-10 nM, 10-100 nM, 0.1-1 µM, 1-10 µM, 10-100 µM, 100-200 µM, 200-500 µM, or even 500-1000 µM, preferably about 1-10 nM, 10-100 nM, or 0.1-1 µM. Without wishing to be bound by any theory, it is believe that such compounds are indicated in the treatment or management of diseases associated with thrombin or kallikrein.

In some embodiments, the compounds selectively inhibit thrombin and/or plasma kallikrein over related serine proteases such as trypsin, chymotrypsin, factor XIIa, factor XIa, factor Xa, and factor VIIa. In some embodiments, the compounds inhibit chymotrypsin with an $IC_{50}$ greater than 1 uM. In some embodiments, the compounds inhibit chymotrypsin with an $IC_{50}$ greater than 10 uM. In some embodiments, the compounds inhibit chymotrypsin with an $IC_{50}$ greater than 100 uM. In some embodiments, the compounds inhibit Factor XIa with an $IC_{50}$ greater than 1 uM. In some embodiments, the compounds inhibit Factor XIa with an $IC_{50}$ greater than 10 uM. In some embodiments, the compounds inhibit Factor XIa with an $IC_{50}$ greater than 100 uM.

In some embodiments, the compounds persist in the blood plasma after intravenous infusion. In some embodiments, greater than 50% of the initial compound concentration persists in the blood plasma of mice 1 hour after intravenous injection. In some embodiments, greater than 50% of the initial compound concentration persists in the blood plasma of mice 3 hours or longer after intravenous injection.

IV. Methods of Treating and Preventing Disease

Thrombin-Related Diseases and Conditions (e.g. Thrombosis).

Thrombotic diseases are the primary indications for thrombin inhibition, because of thrombin's location in the coagulation cascade and, in turn, the importance of the coagulation cascade in the progression of blood clotting processes. However, without wishing to be bound by any theory, it is believed the coagulation cascade in general, and thrombin in particular, is important in a variety other disease states.

It has been discovered that compounds described herein, e.g., multisubstituted aromatic compounds, exhibit inhibitory action against thrombin (activated blood-coagulation factor II; EC 3.4.21.5). This, in turn inhibits the blood coagulation process.

This inhibitory action is useful in the treatment of a variety of thrombotic disorders, such as, but not limited to, acute vascular diseases such as acute coronary syndromes; venous-, arterial- and cardiogenic thromboembolisms; the prevention of other states such as disseminated intravascular coagulation, or other conditions that involve the presence or the potential formation of a blood clot thrombus. Other indications for methods described herein include the following.

It has long been recognized that cancer progression is accompanied by venous thrombosis, but it has not been understood how each disease is related. From several clinical trials studying the treatment of VTE, meta-analyses have shown that low molecular weight heparins (LMWHs) improve overall survival in subgroups of cancer patients. See e.g., Zacharski, L. R. & Lee, A. Y., 2008, *Expert Opin Investig Drugs*, 17:1029-1037; Falanga, A. & Piccioli, A., 2005, *Current Opinion in Pulmonary Medicine*, 11:403-407; Smorenburg, S. M., et al., 1999, *Thromb Haemost*, 82:1600-1604; Hettiarachchi, R. J., et al., 1999, *Thromb Haemost*, 82:947-952. This finding was substantiated in later clinical trials that measured specifically the survival of cancer patients. See e.g., Lee, A. Y. et al., 2005, *J Clin Oncol*, 23:2123-2129; Klerk, C. P. et al., *J Clin Oncol* 2005, 23:2130-2135; Kakkar, A. K., et al., 2004, *J Clin Oncol*, 22:1944-1948; Altinbas, M., et al., 2004, *J Thromb Haemost*, 2:1266-1271.

More recently, researchers have focused on the specific anticancer effect of DTIs. For example, it was shown that heparin significantly prolonged the survival of patients with limited small cell lung cancer. See e.g., Akl, E. A., et al., 2008, *J Exp Clin Cancer Res*, 27:4. Other investigators found that systemic use of argatroban reduced tumor mass and prolonged survival time in rat glioma models leading to the conclusion that argatroban should be considered as a novel therapeutic for glioma, a notoriously difficult to treat cancer type. See e.g., Hua, Y., et al., 2005, *Acta Neurochir*, Suppl 2005, 95:403-406; Hua, Y., et al., 2005, *J Thromb Haemost*, 3:1917-1923. Very recently, it was demonstrated that dabigatran etexilate, a DTI recently FDA-approved (see e.g., Hughes, B., 2010, *Nat Rev Drug Discov*, 9:903-906) for DVT indications, inhibited both the invasion and metastasis of malignant breast tumors. See e.g., DeFeo, K. et al., 2010, *Thrombosis Research*, 125 (Supplement 2): S188-S188; Defeo, K., et al., 2010, *Cancer Biol Ther*, 10:1001-1008. Thus, dabigatran etexilate treatment led to a 50% reduction in tumor volume at 4 weeks with no weight loss in treated mice. Dabigatran etexilate also reduced tumor cells in the blood and liver micrometastases by 50-60%. These investigators concluded that dabigatran etexilate can be beneficial in not only preventing thrombotic events in cancer patients, but also as adjunct therapy to treat malignant tumors.

Further, hirudin and the LMWH nadroparin dramatically reduced the number of lung metastases when administered prior to cancer cell inoculation. See e.g., Hu, L., et al., 2004, *Blood*, 104:2746-51.

The de novo thrombin inhibitor d-Arg-Oic-Pro-d-Ala-Phe (p-Me) has been found to block thrombin-stimulated invasion of prostate cancer cell line PC-3 in a concentration dependent manner. See e.g., Nieman, M. T., et al., 2008, *J Thromb Haemost*, 6:837-845. A reduced rate of tumor growth was observed in mice dosed with the pentapeptide through their drinking water. The mice also showed reduced fold rate in tumor size and reduced overall tumor weight compared to untreated mice. Microscopic examination of treated tumors showed reduced number of large blood vessels thus concluding that the pentapeptide interfered with tumor angiogenesis. Nieman, M. T., et al., *Thromb Haemost*, 104:1044-8.

In view of these and related studies, it is suggested that anticoagulants affect tumor metastasis; that is, angiogenesis, cancer cell adhesion, migration and invasion processes. See e.g., Van Noorden, C. J., et al., 2010, *Thromb Res*, 125 Suppl 2:S77-79.

Alzheimer's Disease.

Very recent experiments confirm higher thrombin levels in brain endothelial cells of patients with Alzheimer's disease. While 'normal' thrombin levels are connected to regulatory CNS functions, thrombin accumulation in the brain is toxic. It has also been found that the neural thrombin inhibitor Protease Nexin 1 (PN-1) is significantly reduced in the Alzheimer's disease brain, despite the fact that PN-1 mRNA levels are unchanged. These observations have led some investigators to suggest that reduction of CNS-resident thrombin will prove useful in Alzheimer's Disease (AD) treatment. See e.g., Vaughan, P. J., et al., 1994, *Brain Res*, 668:160-170; Yin, X., et al., 2010, *Am J Pathol*, 176:1600-1606; Akiyama, H., et al., 1992, *Neurosci Lett*, 146:152-154.

Multiple Sclerosis.

Investigators found that hirudin treatment in an animal model of Multiple Sclerosis (MS) showed a dramatic improvement in disease severity. See e.g., Han, M. H., et al., 2008, *Nature*, 451:1076-1081. Similar results were obtained following treatment with heparin (a DTI) and dermatan sulfate, another coagulation inhibitor. See e.g., Chelmicka-Szorc, E. & Arnason, B. G., 1972, *Arch Neurol*, 27:153-158; Inaba, Y., et al., 1999, *Cell Immunol*, 198:96-102. Other evidence shows that naturally occurring antithrombin III has anti-inflammatory effects in diseases such as endotoxemia and other sepsis-related conditions. See e.g., Wiedermann, C. J. & Romisch, J., 2002, *Acta Med Austriaca*, 29:89-92. Naturally occurring thrombin inhibitors are presumably synthesized in situ and have protective roles in CNS inflammation. Therefore, therapeutic thrombin inhibition has been proposed as a potential MS treatment. See e.g., Luo, W., et al., 2009, In: THROMBIN, Maragoudakis, M. E.; Tsopanoglou, N. E., Eds. Springer New York: 2009; pp 133-159.

Pain.

In a rat pain model with partial lesion of the sciatic nerve, intrathecal hirudin prevented the development of neuropathic pain and curbed pain responses for 7 days. The investigators found that following injury, neuropathic pain was mediated by thrombin generation, which in turn activated PAR-1 receptor in the spinal cord. Hirudin inhibited thrombin generation and ultimately led to pain relief. See e.g., Garcia, P. S., et al., 2010, *Thromb Haemost*, 103:1145-1151; Narita, M., et al., 2005, *J Neurosci*, 25:10000-10009. Researchers hypothesize that thrombin and the PARs are involved not just as part of the coagulation cascade, but in inflammation, nociception and neurodevelopment. Development of a DTI to intersect an unexploited pharmacology will lead to pain therapeutics distinct from opioids and NSAIDs, whose shortcomings are well documented. See e.g., Garcia 2010, Id. Known thrombin inhibitors have been reported to be useful in preventing stroke in individuals with atrial fibrillation. The selective thrombin inhibitor ximelagatran was studied in two phase III clinical trials ((SPORTIF III and SPORTIF V), which compared ximelagatran to warfarin for the prevention of cardioembolic events in patients with non-valvular atrial fibrillation. The investigators for the SPORTIF III clinical trial that ximelagatran, administered in a fixed dose without coagulation monitoring, protects high-risk patients with atrial fibrillation against thromboembolism at least as effectively as well-controlled warfarin, and is associated with less bleeding. When the results of SPORTIF III and V were combined, ximelagatran was associated with a 16% relative risk reduction in the composite outcome measure of all strokes (ischemic or hemorrhagic), systemic embolic events, major bleeding, and death. (Olsson, S. B. *Lancet* 2003, 362 (9397), 1691-1698; Hirsh, J. et al. *Blood* 2005, 105 (2), 453-463; Clemens, A. et al. WIPO Patent Application WO/2008/009638). Without further wishing to be bound by any theory, it is reasonable to believe that thrombin inhibition in general can be useful in preventing stroke in individuals with atrial fibrillation.

Known thrombin inhibitors have been reported to be useful in the treatment and prevention of acute coronary syndrome (Clemens, A. et al. WIPO Patent Application WO/2008/009638). ACS is a group of symptoms that are caused by myocardial ischemia. The drug could be used as a prophylaxis for myocardial infarction, or a certain time after the event (e.g. after myocardial infarction, post-MI; i.e. chronic therapy, secondary prevention). Without further wishing to be bound by any theory, it is reasonable to believe that thrombin inhibition in general can be useful in treating and preventing acute coronary syndrome.

Known thrombin inhibitors have been reported to be useful in the prevention of recurrent cardiac events after myocardial infarction. The selective thrombin inhibitor ximelagatran was studied in a phase II clinical trial entitled ESTEEM, measuring the efficacy and safety of the oral direct thrombin inhibitor ximelagatran in patients with recent myocardial damage. The result of the ESTEEM trial supports the notion that long-term treatment with an oral direct thrombin inhibitor reduces arterial thrombotic events. Oral ximelagatran in combination with acetylsalicylic acid was more effective than acetylsalicylic acid alone in reducing the frequency of major cardiovascular events during 6 months of treatment in patients with a recent myocardial infarction. (Hirsh, J. et al. *Blood* 2005, 105 (2), 453-463.). Without further wishing to be bound by any theory, it is reasonable to believe that thrombin inhibition in general can be useful in preventing recurrent cardiac events after myocardial infarction.

Known thrombin inhibitors have been reported to be useful in post-operative prophylaxis of deep vein thrombosis. The selective thrombin inhibitor ximelagatran was found to be efficacious for the prevention of venous thromboembolism following a medical procedure like total hip or knee replacement (Francis, C. W. et al. *Ann Intern Med* 2002; 137:648-55; Heit, J. A. et al. *Arch Intern Med* 2001; 161: 2215-21; Eriksson B I et al. *Thromb Haemost* 2003; 89: 288-96). Without further wishing to be bound by any theory, it is reasonable to believe that thrombin inhibition in general can be useful in post-operative prophylaxis of deep vein thrombosis.

Known thrombin inhibitors like dabigatran have been reported to be useful in long-term treatment of pulmonary embolism. (Robertson L, Kesteven P, McCaslin J E. *Cochrane Database Syst Rev.* 2015 Dec. 4; 12). Without further wishing to be bound by any theory, it is reasonable to believe that thrombin inhibition in general can be useful in treating pulmonary embolism.

Known thrombin inhibitors have been reported to be useful for the prevention of coagulation in patients undergoing percutaneous coronary intervention. Percutaneous coronary intervention (PCI) requires aggressive anticoagulation therapy, and was historically achieved with unfractionated heparin. However, in many patients heparin is contraindicated, especially in patients with heparin-induced thrombocytopenia (HIT). In such instances, the endovascular disruption and the hypercoagulable state that characterized HIT means patients are put at risk of thrombosis during PCI. (Lewis, B. E. et al. *Catheterization and cardiovascular interventions* 2002, 57 (2), 177-184; Kokolis, S et al. *Progress in cardiovascular diseases* 2004, 46 (6), 506-523.) Dabigatran, which had already been claimed as a thrombin inhibitor and a useful anticoagulant in the clinical setting, was also published as a secondary medication in percutaneous interventional cardiac catherization. (Reilly et al. WIPO Patent Application WO/2010/020602). Without further wishing to be bound by any theory, it is reasonable to believe that thrombin inhibition in general can be useful in preventing coagulation in patients undergoing percutaneous coronary intervention.

Known thrombin inhibitors have been reported to be useful for the treatment of pulmonary-arterial hypertension. Dabigatran, a selective thrombin inhibitor, has been published as a useful drug for the treatment of pulmonary-arterial hypertension (PAH). Furthermore, dabigatran had found use as a treatment of: (i); pulmonary hypertension caused by left heart disorders, (ii); pulmonary hypertension associated with lung diseases such as pulmonary fibroses, particularly idiopathic pulmonary fibrosis, and/or hypoxia, (iii); pulmonary hypertension caused by chronic thromboembolic diseases. (Feuring, M. WIPO Patent Application WO/2010/020600). Without further wishing to be bound by any theory, it is reasonable to believe that thrombin inhibition in general can be useful for the treatment of pulmonary-arterial hypertension.

Known thrombin inhibitors have been reported to be useful for the treatment of pulmonary-arterial hypertension caused by left heart disorders (Feuring, M. WIPO Patent Application WO/2010/020600). Without further wishing to be bound by any theory, it is reasonable to believe that thrombin inhibition in general can be useful for the treatment of pulmonary-arterial hypertension caused by left heart disorders.

Known thrombin inhibitors have been reported to be useful for the treatment of pulmonary-arterial hypertension associated with lung diseases such as pulmonary fibroses, particularly idiopathic pulmonary fibrosis, and/or hypoxia (Feuring, M. WIPO Patent Application WO/2010/020600). Without further wishing to be bound by any theory, it is reasonable to believe that thrombin inhibition in general can be useful for the treatment of pulmonary-arterial hypertension associated with lung diseases.

Known thrombin inhibitors have been reported to be useful for the treatment of pulmonary hypertension caused by chronic thromboembolic diseases (Feuring, M. WIPO Patent Application WO/2010/020600). Without further wishing to be bound by any theory, it is reasonable to believe that thrombin inhibition in general can be useful for the treatment of pulmonary hypertension caused by chronic thromboembolic diseases.

Non-valvular atrial fibrillation is a sustained cardiac disturbance often associated with heart disease. Known thrombin inhbitors like ximelagatran have been reported to be useful for stroke prevention in patients with non-valvular atrial fibrillation (Diener H.-C. *Cerebrovasc Dis* 2006; 21:279-293). Without further wishing to be bound by any theory, it is reasonable to believe that thrombin inhibition in general can be useful for stroke prevention in patients with non-valvular atrial fibrillation.

A Transient Ischemic Attack (TIA) is an acute episode of temporary neurologic dysfunction that typically lasts less than an hour; results from focal cerebral, spinal cord, or retinal ischemia; and is not associated with acute tissue infarction. In people who have a TIA, the incidence of subsequent stroke is as high as 11% over the next 7 days and 24-29% over the following 5 years. In view of the high short-term risk of stroke after TIA, many physicians believe antithrombotic therapy should be initiated as soon as intracranial hemorrhage has been ruled out. Stroke prevention medication typically recommended for cardioembolic TIA is as follows: For patients with atrial fibrillation after TIA, long-term anticoagulation with warfarin (aspirin 325 mg/day for those unable to take oral anticoagulants); In acute myocardial infarction (MI) with left ventricular thrombus, oral anticoagulation with warfarin; concurrent aspirin up to 162 mg/day for ischemic coronary artery disease [CAD]); In dilated cardiomyopathy, oral anticoagulation with warfarin or antiplatelet therapy; In rheumatic mitral valve disease, oral anticoagulation with warfarin. For patients with TIA and ischaemic stroke of cardiac origin due to atrial fibrillation, vitamin K antagonists (VKAs) are highly effective in preventing recurrent ischaemic stroke but have important limitations and are thus underused. Antiplatelet therapy is much less effective than VKAs. The direct thrombin inhibitor, dabigatran etexilate, has shown efficacy over warfarin in a recent trial. Other new anticoagulants, including the oral factor Xa inhibitors, rivaroxaban, apixaban, and edoxaban, the parenteral factor Xa inhibitor, idrabiotaparinux, and the novel VKA, tecarfarin, were being assessed in 2010. (Hankey, G. J.; Eikelboom, J. W. 'Antithrombotic Drugs for Patients with Ischaemic Stroke and Transient Ischaemic Attack to Prevent Recurrent Major Vascular Events.' The Lancet Neurology 2010, 9 (3), 273-284.)

Known thrombin inhibitors have been reported to be useful for the treatment of venous thromboembolism due to formation of a thrombus within a vein (venous thrombosis) associated with acquired (prolonged bedrest, surgery, injury, malignancy, pregnancy and postpartum states) or inherited (deficiency of natural coagulation inhibitors) risk factors (Marsic, L. P. et al. WIPO Patent Application WO/2003/048155). Without further wishing to be bound by any theory, it is reasonable to believe that thrombin inhibition in general can be useful for the treatment of venous thromboembolism due to formation of a thrombus within a vein associated with acquired or inherited risk factors and/or embolism of peripheral veins caused by a detached thrombus. An example of an acquired risk factor would be a previous venous thromboembolism and/or embolism of peripheral veins caused by a detached thrombus. An example of an acquired risk factor would be a previous venous thromboembolism.

Known thrombin inhibitors have been reported to be useful for the treatment of cardiogenic thromboembolism due to formation of a thrombus in the heart associated with cardiac arrhythmia, heart valve defect, prosthetic heart valves or heart disease, embolism of peripheral arteries caused by a detached thrombus, most commonly in the brain (ischemic stroke). See Marsic, L. P. et al. WIPO Patent Application WO/2003/048155. Without further wishing to be bound by any theory, it is reasonable to believe that thrombin inhibition in general can be useful for the treatment of cardiogenic thromboembolism.

Known thrombin inhibitors have been reported to be useful for the treatment of arterial thrombosis due to underlying atherosclerotic processes in the arteries which obstructs or occludes an artery and causes myocardial ischemia (angina pectoris, acute coronary syndrome) or myocardial infarction, obstructs or occludes a peripheral artery (ischemic peripheral artery disease) and obstructs or occludes the artery after the procedure on the blood vessel (reocclusion or restenosis after transluminal coronary angioplasty, reocclusion or restenosis after percutaneous transluminal angioplasty of peripheral arteries). See Marsic, L. P. et al. WIPO Patent Application WO/2003/048155. Without further wishing to be bound by any theory, it is reasonable to believe that thrombin inhibition in general can be useful for the treatment of arterial thrombosis.

Known thrombin inhibitors have been reported to be useful for the treatment of disseminated intravascular coagulation in a number of states (e.g., in complications in pregnancy, in metastasing malignant diseases, after extensive injuries, in bacterial sepsis) when thrombogenic activation causes dysfunctional coagulation with widespread formation of thrombi within the vascular system. See Marsic, L. P. et al. WIPO Patent Application WO/2003/048155. Without further wishing to be bound by any theory, it is reasonable to believe that thrombin inhibition in general can be useful for the treatment of disseminated intravascular coagulation.

Known thrombin inhibitors have been reported to be useful as an adjunct therapy in conjunction with thrombolytic therapy in recent myocardial infarction, in combination with aspirin in patients with unstable angina pectoris designed to undergo percutaneous transluminal angioplasty and in the treatment of patients with thrombosis and with heparin-induced thrombocytopenia (Marsic, L. P. et al. WIPO Patent Application WO/2003/048155). Without further wishing to be bound by any theory, it is reasonable to believe that thrombin inhibition in general can be useful as an adjunct therapy with other antithrombotic therapies.

Known thrombin inhibitors have been reported to be useful for the treatment of inflammation (Kirk, I. WIPO Patent Application WO/2000/041716), type I diabetes mellitus (Korsgren, O.; Nillson, B. WIPO Patent Application WO/2003/061682), cancer (Kakkar, A. K. et al. *J Clin Oncol* 2004, 22, (10), 1944-8; Hua, Y. et al. *Acta Neurochir* Suppl 2005, 95, 403-6; Nieman, M. T. et al. *J Thromb Haemost*, 6 (2008), 837-845; Van Ryn, J.; Clemens, A. WIPO Patent Application WO/2010/020601), fibrosis (Duplantier, J. G. et al. *Gut*, 2004, 53:1682-1687; Seijo, S. et al. *J Hepatol*, 2007, 46:286-294; Assy, N. et al. *Dig Dis Sci*, 2007, 52:1187-1193; Bogatkevich, G. S. et al. *Arthritis Rheum*, 2009, 60:3455-3464), and pain (Garcia, P. S. et al. *Thromb Haemost*, 103:1145-1151; Narita, M. et al. *J Neurosci*, 2005, 25:10000-10009). Metaanalyses of clinical trials that studied the use of anticoagulants in oncology patients showed that low molecular weight heparins (LMWHs), selective thrombin inhibitors, improve overall survival in subgroups of cancer patients. This finding was substantiated in later clinical trials, in particular the FAMOUS clinical trials, that measured specifically the survival of cancer patients.

Without further wishing to be bound by any theory, it is reasonable to believe that thrombin inhibition in general can be useful for the treatment of thrombotic diseases or disorders and/or diseases or disorders which involve a blood clot thrombus or the potential formation of a blood clot thrombus and/or further involves stroke and/or one or more transient ischemic attacks (TIA) and/or pulmonary hypertension. Such conditions include, for example, acute coronary syndrome, thromboembolism, thrombosis, inflammation, diabetes mellitus, cancer, fibrosis, Alzheimer's Disease, multiple sclerosis, pain, recurrent cardiac events after myocardial infarction, or the like.

Kallikrein-Related Diseases and Conditions.

Kallikrein-related diseases or disorders are biological conditions associated with or moderated by kallikrein. They include, but are not limited by, those conditions associated with biological pathways that are moderated by plasma kallikrein. An example of such a pathway is the kallikrein-kinin system (Moreau, M. E. 2005, *Journal of Pharmacological Sciences*, 99, 6). Kallikrein-related diseases or disorders include, but are not limited to, fibrosis, inflammation, thrombosis, hereditary angioedema, skin disorders, cancer, and ophthalmic diseases. Ophthalmic diseases include, but are not limited to, diabetic macular edema, diabetic retinopathy, and age-related macular degeneration.

Diabetic Macular Edema.

In rodent models, it has been shown that activation of KLKB1 in the eye increases retinal vascular permeability; whereas inhibition of the kallikrein-kinin system reduces retinal leakage induced by diabetes and hypertension. These findings suggest that intraocular activation of the KLKB1 pathway can contribute to excessive retinal vascular permeability that can lead to diabetic macular edema. Thus, evidence suggests that KLKB1 inhibitors can provide a new therapeutic opportunity to reduce retinal vascular permeability (Feener, E. P. 2010, *Curr Diab Rep* 10, 270).

Hereditary Angioedema.

Ecallantide (Kalbitor) is a 60-amino acid recombinant protein that acts as a potent reversible inhibitor of KLKB1 (Schneider L, et al. 2007, *J Allergy Clin Immunol*, 120, 416) and has been approved by the FDA for the treatment of acute attacks of hereditary angioedema (HAE). Thus plasma kallikrein inhibition can be a useful treatment for HAE, and there is strong interest in the development of plasma kallikrein inhibitors as a therapy for HAE.

Hyperglycemic and diabetic individuals have an elevated risk of hemorrhage during thrombolytic therapy. In rodent models of intracerebral hemorrhage (ICH), it has been shown that KLKB1 inhibition or knockout reduces this effect. While the mechanism is not fully understood, this evidence suggests that plasma kallikrein inhibitors can be useful in the treatment of cerebral hemorrhage (Feener, E. P. *Curr Diab Rep* 2010, 10, 270).

Plasma kallikrein and Factor XIIa inhibitors have been shown to be neuroprotective in animal models of acute ischemic stroke and traumatic brain injury, reducing edema formation, inflammation, and thrombosis (Albert-Weißenberger C, Sirén A L, Kleinschnitz C. *Prog Neurobiol*. 2013, 101-102, 65-82.). Thus, evidence suggests that plasma kallikrein inhibitors can be useful in the treatment of acute ischemic stroke and traumatic brain injury.

Plasma kallikrein can also cleave glucagon-like peptide 1 (GLP-1) and neuropeptide Y (NPY), both substrates for dipeptidyl peptidase-4 (DPP-4), a validated diabetes drug target. In the case of GLP-1, cleavage by KLKB1 reduces both its potency as well as plasma stability. In the case of NPY, cleavage by KLKB1 reduces its affinity to the Y2 and Y5 receptors. Thus, evidence suggests that plasma kallikrein inhibitors can be useful in the modulation of energy homeostasis and in the treatment of diabetes. (Feener, E. P. *Curr Diab Rep* 2010, 10, Feener, E. P. et al., *Biol. Chem.* 2013, 394, 319).

The Kallikrein-kinin system is involved in the regulation of vascular endothelial growth factor (VEGF), endothelial NO synthase, and fibroblast growth factor 2, all of which are involved in angiogenesis (Bader M. 2009, *Arteriosclerosis, Thrombosis, and Vascular Biology*, 29: 617). Tissue kallikrein (KLK1) has been linked to blood vessel growth (Miura S., 2003, *Hypertension*, 41, 1118). Therapies that moderate angiogenesis have been proposed for the treatment of both diabetic macular edema (DME) and age-related macular degeneration (AMD) (Syed, B. A.; Evans, J. B.; Bielory, L., 2012, *Nature Reviews Drug Discovery*, 11, 827). Without further wishing to be bound by any theory, it is therefore reasonable to conclude that KLK1 inhibitors can be useful in the treatment of diabetic retinopathy, DME, and AMD.

Studies have shown that inflammation plays an important role in the origin and development of AMD, and treatment often includes anti-inflammatories such as corticosteroid (Telander, D., 2011, *Seminars in Ophthalmology*, 26(3), 192). The connection between the kallikrein-kinin system and inflammation is also well established (Duchene, 2011, "Kallikrein-kinin kystem in inflammatory diseases". *Kinins*. De Gruyter. 261). Without further wishing to be bound by any theory, it is reasonable to conclude that the anti-inflammatory nature of kallikrein (e.g. KLK1 and KLKB1) inhibitors can be useful in the treatment of AMD.

PF-04886847 is an inhibitor of plasma kallikrein and has shown to be effective at reducing 6-keto-PGF$_{1\alpha}$ plasma levels in lipopolysaccharide (LPS) treated rats (Kolte, D et al. *Cardiovascular & Hematological Agents in Medicinal Chemistry*, 2012, 10, 154-166). Without further wishing to be bound by any theory, it is reasonable to believe that plasma kallikrein inhibitors can be useful in the treatment of hypotensive shock during sepsis.

Daiichi Seiyaku Co Ltd received approval in Japan to market cetraxate for gastritis and peptic ulcers. Cetraxate is reported as a plasma kallikrein inhibitor (WIPO Patent Application WO/2006/108643). Without further wishing to be bound by any theory, it is reasonable to believe that plasma kallikrein inhibition in general can be useful in the treatment of gastritis and peptic ulcers.

Fibrosis.

Kallikreins are a subgroup of serine proteases, divided into plasma kallikrein (KLKB1) and tissue kallikreins. KLKB1 liberates kinins (bradykinin and kallidin) from the kininogens, peptides responsible for the regulation of blood pressure and activation of inflammation. In the Contact Activation Pathway of the coagulation cascade, KLKB1 assists in the conversion of factor XII to factor XIIa (Keel, M.; Trentz, O. *Injury* 2005, 36, 691-709). Factor XIIa converts FXI into FXIa, which in turn activates FIX, which with its co-factor FVIIIa forms the tenase complex, which finally activates FX to FXa. In the fibrinolysis part of the coagulation cascade, KLKB1 serves to convert plasminogen to plasmin. Thus, it has been proposed that KLKB1 inhibitors can be useful in the treatment of thrombotic and fibrinolytic diseases and disease conditions (U.S. Pat. No. 7,625,944; Bird et al. *Thrombosis and Hemostasis* 2012, 107, 1141).

Several studies have shown the utility of anticoagulant therapy in fibrotic disorders. For example, in a rat model of $CCl_4$-induced chronic liver injury, the DTI SSR182289 decreased liver fibrogenesis significantly after 7 weeks of administration. Similar observations were made in other studies using the LMWHs nadroparin, tinzaparin, enoxaparin, and dalteparin sodium. See e.g., Duplantier, J. G., et al., 2004, *Gut,* 53:1682-1687; Abdel-Salam, O. M., et al., 2005, *Pharmacol Res,* 51:59-67; Assy, N., et al., 2007, *Dig Dis Sci,* 52:1187-1193; Abe, W., et al., 2007, *J Hepatol,* 46:286-294. Thus a thrombin inhibitor as an anticoagulant can be useful in the treatment of fibrinolytic diseases.

In another example, the DTI melagatran greatly reduced ischemia reperfusion injury in a kidney transplant model in the large white pig. This led to a drastically improved kidney graft survival at 3 months. See e.g., Favreau, F., et al., 2010, *Am J Transplant,* 10:30-39.

Recent studies have shown that in a bleomycin-induced mouse model of pulmonary fibrosis, dabigatran etexilate treatment reduced important profibrotic events in lung fibroblasts, including the production of collagen and connective tissue growth factor. See e.g., Silver, R. M., et al., 2010, *Am. J. Respir. Crit. Care Med.,* 181:A6780; Bogatkevich, G. S., et al., 2009, *Arthritis Rheum,* 60:3455-3464.

The above experimental evidence points to a close relationship between thrombin and fibrosis and suggests novel therapeutic opportunities for fibrosis using thrombin inhibitors. See e.g., Calvaruso, V., et al., 2008, *Gut,* 57:1722-1727; Chambers, R. C., 2008, *Br J Pharmacol,* 153 Suppl 1:S367-378; Chambers, R. C. & Laurent, G. J., 2002, *Biochem Soc Trans,* 30:194-200; Howell, D. C., et al., 2001, *Am J Pathol,* 159:1383-1395.

Inflammation.

Kallikrein has long been implicated in inflammation (Clements, J. A. *The Molecular Biology of the Kallikreins and Their Roles in Inflammation,* Academic Press: San Diego, Calif., 1997; Vol. 5). There is experimental evidence that KLKB1 is associated with sepsis and inflammatory arthritis (Colman, R. W., 1998, *Clinical Reviews in Allergy and Immunology,* 16: 365). Thus a KLKB1 inhibitor can be useful in the treatment of inflammatory conditions associated with the kallikrein-kinin system, such as systemic inflammatory response syndrome, sepsis, rheumatoid arthritis, and inflammatory bowel disease.

Without further wishing to be bound by any theory, it is reasonable to believe that kallikrein inhibition in general can be useful for the treatment of kallikrein-related diseases or disorders and/or diseases or disorders. Such conditions include, for example, thrombotic diseases, fibrinolytic diseases, fibrotic disorders, cancer, inflammatory conditions, dermatological conditions, or the like.

Accordingly, in a further aspect, there is provided a method for treating a disease or disorder in a subject in need thereof. The method includes administering a compound of any of Formulae (Ia), (Ib), (II), (III), (IV), or (V) as disclosed herein, a compound as set forth in Table A, Table B, Table C, or Table D, pharmaceutically acceptable salt, ester, solvate, or prodrug thereof, or pharmaceutical composition thereof, to a subject in need thereof in an amount effective to treat the disease or disorder. The terms "therapeutically effective amount," "amount effective to treat," "amount effective to prevent" and the like refer to that amount of drug or pharmaceutical agent (e.g., compound or pharmaceutical composition disclosed herein) that will elicit the biological or medical response of a tissue, system, animal, or human that is being sought by a researcher, veterinarian, medical doctor or other clinician.

Compounds useful for methods disclosed herein include the compounds set forth for Formulae (Ia), (Ib), (II), (III), (IV), or (V) and for the compounds set forth in Table A, Table B, Table C, or Table D above.

In some embodiments of the methods described herein, the disease or disorder to be treated can include one or more thrombotic diseases or disorders and/or can involve a blood clot thrombus or the potential formation of a blood clot thrombus. In some embodiments, the thrombotic disease or disorder can be acute coronary syndrome, thromboembolism, and/or thrombosis. In some embodiments, the thromboembolism can be venous thromboembolism, arterial thromboembolism, and/or cardiogenic thromboembolism. In some embodiments, the venous thromboembolism can include deep vein thrombosis and/or pulmonary embolism. In some embodiments, the deep vein thrombosis and/or pulmonary embolism can occur following a medical procedure. In some embodiments, the thrombotic disease or disorder can involve dysfunctional coagulation or disseminated intravascular coagulation. In some embodiments, the subject with dysfunctional coagulation can be undergoing percutaneous coronary intervention (PCI). In some embodiments, the thrombotic disease or disorder can involve a blood clot thrombus or the potential formation of a blood clot thrombus and further can involve stroke and/or one or more transient ischemic attacks (TIA). In some embodiments, the thrombotic disease or disorder involving a blood clot thrombus or the potential formation of a blood clot thrombus can further involve stroke, wherein the subject can have non-valvular atrial fibrillation. In some embodiments, the thrombotic disease or disorder can involve a blood clot thrombus or the potential formation of a blood clot thrombus and further can involve pulmonary hypertension. In some embodiments, the pulmonary hypertension can be caused by one or more left heart disorder and/or chronic thromboembolic disease. In some embodiments, the pulmonary hypertension can be associated with one or more lung disease, including pulmonary fibrosis (idiopathic or otherwise), and/or hypoxia.

In some embodiments, the venous thromboembolism can be associated with formation of a thrombus within a vein associated with one or more acquired or inherited risk factors and/or embolism of peripheral veins caused by a detached thrombus. In some embodiments, the one or more risk factors can include a previous venous thromboembolism. In some embodiments, the cardiogenic thromboembolism can be due to formation of a thrombus in the heart associated with cardiac arrhythmia, heart valve defect, prosthetic heart valves or heart disease, and/or embolism of peripheral arteries caused by a detached thrombus. In some embodiments, the detached thrombus can be in the brain (ischemic stroke). In some embodiments, the detached thrombus can cause a transient ischemic attack (TIA). In some embodiments, the cardiogenic thromboembolism can be due to non-valvular atrial fibrillation. In some embodiments, the thrombosis can be arterial thrombosis. In some embodiments, the arterial thrombosis can be due to one or more underlying atherosclerotic processes in the arteries. In some embodiments, the one or more underlying atherosclerotic processes in the arteries can obstruct or occlude an artery, cause myocardial ischemia (angina pectoris, acute coronary syndrome), cause myocardial infarction, obstruct or occlude a peripheral artery (ischemic peripheral artery disease), and/or obstruct or occlude the artery after a procedure on a blood vessel (reocclusion or restenosis after transluminal coronary angioplasty, reocclusion or restenosis after percutaneous transluminal angioplasty of peripheral arteries).

In some embodiments, the disease or disorder can include fibrosis, Alzheimer's Disease, multiple sclerosis, pain, cancer, inflammation, and/or Type I diabetes mellitus. In some embodiments, the disease or disorder can involve recurrent cardiac events after myocardial infarction.

In some embodiments, the treatment or prevention can include an adjunct therapy. In some embodiments, the subject can have myocardial infarction, and the adjunct therapy can be in conjunction with thrombolytic therapy. In some embodiments, the subject can have unstable angina pectoris, thrombosis, and/or heparin-induced thrombocytopenia, and the adjunct therapy can be in combination with antiplatelet therapy. In some embodiments, the subject can have non-valvular atrial fibrillation, and the adjunct therapy can be in conjunction with one or more other therapies.

In some embodiments of the methods described herein, the disease or disorder can be a kallikrein-related disorder. In some embodiments, the kallikrein-related disorder can be a thrombotic disease, a fibrinolytic disease, a fibrotic disorder, a type of cancer, an inflammatory condition, or a dermatological condition.

In some embodiments, the kallikrein-related disorder can be an ophthalmic disease. In some embodiments, the compound or pharmaceutical composition can be administered in the form of an ophthalmic composition applied topically to the eye. In some embodiments, the ophthalmic composition can be in the form of eye drops. In some embodiments, the compound or pharmaceutical composition can be administered in the form of an ophthalmic composition via intravitreal injection. In some embodiments, the ophthalmic disease can be diabetic macular edema, hereditary angioedema, age-related macular degeneration, or diabetic retinopathy.

In some embodiments wherein the disease or disorder can be a type of cancer, said type of cancer can be cervical-, testicular-, or non-small-cell lung adenocarcinoma. In some embodiments, the cancer can be limited small cell lung cancer. In some embodiments, the cancer can be a glioma. In some embodiments, the cancer can be malignant breast cancer. In some embodiments, the cancer can be a micrometastasis. In some embodiments, the micrometastasis can be of the blood or liver. In some embodiments, the cancer can be a lung metastasis. In some embodiments, the cancer can be prostatic cancer.

In some embodiments wherein the disease or disorder can be an inflammatory condition, said inflammatory condition can be sepsis, inflammatory bowel disease, systemic inflammatory response syndrome, inflammatory arthritis, or rheumatoid arthritis.

In some embodiments wherein the disease or disorder can be a dermatological condition, said dermatological condition can be atopic dermatitis, psoriasis, or Netherton Syndrome.

In another aspect, there is provided a method for preventing a disease or disorder in a subject. The method includes administering a compound of any of Formulae (Ia), (Ib), (II), (III), (IV), or (V) as disclosed herein, compound as set forth in any of Table A, Table B, Table C, or Table D herein, pharmaceutically acceptable salt, ester, solvate, or prodrug thereof, or pharmaceutical composition thereof, to a subject in need thereof in an amount effective to prevent the disease or disorder.

V. Assays

Compounds described herein can be assayed, by a variety of methods known in the art and described herein, for inhibition of biological activity, e.g., protease activity, of a variety of proteins, e.g., thrombin and KLKB1.

The thrombin activity reported herein (e.g., Table A) was obtained as follows. Human thrombin was obtained from Haematologic Technologies Inc. The chromogenic substrate S-2238 was obtained from DiaPharma. Thrombin was assayed in buffer containing 0.05 M Tris (pH 7.4), 0.015 M NaCl and 0.01% PEG-8000. The final concentration of enzyme used was 3 nM thrombin. The final concentration of substrate used was 125 µM S-2238 for thrombin. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor $IC_{50}$ values were determined by adding test compound as ten point, three-fold serial dilutions in buffer solution, as known in the art. The plate was read at 10 minutes after substrate addition. The $IC_{50}$ was calculated by plotting the percent (%) inhibition against compound concentration and fitting the data to a constrained four parameter sigmoidal curve, as known in the art.

The KLKB1 kallikrein activity reported herein (e.g., Table B) was obtained as follows. Human KLKB1 protein was obtained from Enzyme Research Labs. The chromogenic substrate S-2302 was obtained from DiaPharma. KLKB1 was assayed in buffer containing 0.05 M Tris (pH 7.4), 0.01 M NaCl and 0.2% w/v PEG-8000. The final concentration of enzyme used was 3 nM KLKB1. The final concentration of substrate used was 250 µM S-2302 for KLKB1. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor $IC_{50}$ values were determined by adding test compound as ten point, three-fold serial dilutions in buffer solution, as known in the art. The plate was read at 10 minutes after substrate addition. The $IC_{50}$ was calculated by plotting the percent (%) inhibition against compound concentration and fitting the data to a constrained four parameter sigmoidal curve, as known in the art.

The chymotrypsin activity reported herein (e.g., Table D) was obtained as follows. Human pancreas a-chymotrypsin was obtained from Sigma. The chromogenic substrate S-7388 was obtained from Sigma. The final concentration of substrate used was 250 uM for chymotrypsin. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor $IC_{50}$ values were determined by adding test compound as ten point, three-fold serial dilutions in buffer solution, as known in the art. The plate was read at 5 minutes after substrate addition. The $IC_{50}$ was calculated by plotting the percent (%) inhibition against compound concentration and fitting the data to a constrained four parameter sigmoidal curve, as known in the art.

The Factor XIa activity reported herein (e.g., Table D) was obtained as follows. Human Factor XIa was obtained from Enzyme Research. The chromogenic substrate S-2366 was obtained from DiaPharma. The final concentration of substrate used was 10 mM for Factor XIa. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor $IC_{50}$ values were determined by adding test compound as ten point, three-fold serial dilutions in buffer solution, as known in the art. The plate was read at 10 minutes after substrate addition. The $IC_{50}$ was calculated by plotting the percent (%) inhibition against compound concentration and fitting the data to a constrained four parameter sigmoidal curve, as known in the art.

VI. Pharmaceutical Compositions

In another aspect, there is provided a pharmaceutical composition comprising a compound disclosed herein and a pharmaceutically acceptable excipient. The compound is a compound of any of Formulae (Ia), (Ib), (II), (III), (IV), or (V) as disclosed herein, a compound as set forth in Table A, Table B, Table C, or Table D herein, or pharmaceutically acceptable salt, ester, solvate, or prodrug thereof. In some embodiments, the compound is set forth in Table A, Table B, Table C, or Table D herein.

The term "pharmaceutically acceptable salts" is meant to include salts of the active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galacturonic acids and the like (see, for example, Berge et al., "Pharmaceutical Salts", *Journal of Pharmaceutical Science*, 1977, 66, 1-19). Certain specific compounds disclosed herein contain both basic and acidic functionalities that allow the compounds to be converted into either base or acid addition salts.

Compounds disclosed herein can exist as salts, such as with pharmaceutically acceptable acids. Accordingly, the compounds contemplated herein include such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts can be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Pharmaceutically acceptable salts of the compounds above, where a basic or acidic group is present in the structure, are also included within the scope of compounds contemplated herein. When an acidic substituent is present, such as —$NHSO_3H$, —COOH and —$P(O)(OH)_2$, there can be formed the ammonium, sodium, potassium, calcium salt, and the like, for use as the dosage form. Basic groups, such as amino or basic heteroaryl radicals, or pyridyl and acidic salts, such as hydrochloride, hydrobromide, acetate, maleate, palmoate, methanesulfonate, p-toluenesulfonate, and the like, can be used as the dosage form.

Also, in the embodiments in which R—COOH is present, pharmaceutically acceptable esters can be employed, e. g., methyl, ethyl, tert-butyl, pivaloyloxymethyl, and the like, and those esters known in the art for modifying solubility or hydrolysis characteristics for use as sustained release or prodrug formulations.

A. Formulations

The compounds disclosed herein can be prepared and administered in a wide variety of ophthalmic, oral, parenteral, and topical dosage forms. The compounds described herein can be administered by eye drop. Also, compounds described herein can be administered by injection (e.g. intravenously, intramuscularly, intravitreally, intracutaneously, subcutaneously, intraduodenally, or intraperitoneally). As such, compounds described herein can also be administered by intravitreal injection. Also, the compounds described herein can be administered by inhalation, for example, intranasally. Additionally, the compounds disclosed herein can be administered transdermally. It is also envisioned that multiple routes of administration (e.g., intramuscular, oral, ocular) can be used to administer the compounds disclosed herein.

In some embodiments, the compounds disclosed herein can be prepared in liquid pharmaceutical compositions for ocular administration. The composition for ocular use can contain one or more agents selected from the group of buffering agents, solubilizing agents, coloring agents, viscosity enhancing agents, and preservation agents in order to produce pharmaceutically elegant and convenient preparations.

In some embodiments, the composition for ocular use can contain preservatives for protection against microbiological contamination, including but not limited to benzalkonium chloride and/or EDTA. Other possible preservatives include but are not limited to benzyl alcohol, methyl parabens, propyl parabens, and chlorobutanol. Preferably, a preservative, or combination of preservatives, will be employed to impart microbiological protection in addition to protection against oxidation of components.

In some embodiments, the compounds disclosed herein can be administered orally as tablets, aqueous or oily suspensions, lozenges, troches, powders, granules, emulsions, capsules, syrups or elixirs. The composition for oral use can contain one or more agents selected from the group of sweetening agents, flavoring agents, coloring agents and preserving agents in order to produce pharmaceutically elegant and palatable preparations. Accordingly, there are also provided pharmaceutical compositions comprising a pharmaceutically acceptable carrier or excipient and one or more compounds disclosed herein.

In some embodiments, tablets contain the acting ingredient in admixture with non-toxic pharmaceutically acceptable excipients that are suitable for the manufacture of tablets. These excipients can be, for example, (1) inert diluents, such as calcium carbonate, lactose, calcium phosphate, carboxymethylcellulose, or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets can be uncoated or coated by known techniques to delay disintegration and absorption in the gastrointestinal tract and thereby provide a sustained action over a longer period. For example, a time delay material such as glyceryl monostearate or glyceryl distearate can be employed.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substance that can also act as diluents, flavoring agents, binders, preservatives, tablet disintegrating agents, or an encapsulating material.

A compound disclosed herein, in the form of a free compound or a pharmaceutically-acceptable pro-drug, metabolite, analogue, derivative, solvate or salt, can be administered, for in vivo application, parenterally by injection or by gradual perfusion over time. Administration can be intravenously, intraperitoneally, intramuscularly, subcutaneously, intracavity, or transdermally. For in vitro studies the compounds can be added or dissolved in an appropriate biologically acceptable buffer and added to a cell or tissue.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds disclosed herein can also be incorporated into liposomes or administered via transdermal pumps or patches. Pharmaceutical admixtures suitable for use in the pharmaceuticals compositions and methods disclosed herein include those described, for example, in PHARMACEUTICAL SCIENCES (17th Ed., Mack Pub. Co., Easton, Pa.) and WO 96/05309, the teachings of both of which are hereby incorporated by reference.

In some embodiments, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, growth factors and inert gases and the like.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation can be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds can have limited solubility in water and therefore can require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions can be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions disclosed herein can additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

By the present, there are provided methods for ameliorating wound healing and for mediating tissue repair (including but not limited to treatment of peripheral and coronary vascular disease). According to these methods, a subject having a wound or in need of tissue repair, is treated at the site of the wound or damaged tissue or treated systemically, with a compound disclosed herein in the form of a free compound or a pharmaceutically-acceptable prodrug, metabolite, analogue, derivative, solvate or salt.

Generally, the terms "treating", "treatment" and the like are used herein to mean affecting a subject, tissue or cell to obtain a desired pharmacologic and/or physiologic effect. The effect can be prophylactic in terms of completely or partially preventing a disease or disorder or sign or symptom thereof, and/or can be therapeutic in terms of a partial or complete cure for a disorder and/or adverse effect attributable to it, e.g. pulmonary embolism following a medical procedure. "Treating" as used herein covers any treatment of, or prevention of a disease or disorder in a vertebrate, a mammal, particularly a human, and includes: (a) preventing the disease or disorder from occurring in a subject that can be predisposed to the disease or disorder, but has not yet been diagnosed as having it; (b) inhibiting the disease or disorder, i.e., arresting its development; or (c) relieving or ameliorating the disease or disorder, i.e., cause regression of the disease or disorder.

There are provided various pharmaceutical compositions useful for ameliorating certain diseases and disorders. The pharmaceutical compositions according to one embodiment are prepared by formulating a compound disclosed herein in the form of a free compound or a pharmaceutically-acceptable pro-drug, metabolite, analogue, derivative, solvate or salt, either alone or together with other pharmaceutical agents, suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See e.g., Goodman and Gilman (eds.), 1990, THE PHARMACOLOGICAL BASIS FOR THERAPEUTICS (7th ed.).

The pharmaceutical compositions are preferably prepared and administered in dose units. Solid dose units are tablets, capsules and suppositories. For treatment of a subject, depending on activity of the compound, manner of administration, nature and severity of the disease or disorder, age and body weight of the subject, different daily doses can be used.

Under certain circumstances, however, higher or lower daily doses can be appropriate. The administration of the daily dose can be carried out both by single administration in the form of an individual dose unit or else several smaller dose units and also by multiple administrations of subdivided doses at specific intervals.

The pharmaceutical compositions contemplated herein can be administered locally or systemically in a therapeutically effective dose. Amounts effective for this use will, of course, depend on the severity of the disease or disorder and the weight and general state of the subject. Typically, dosages used in vitro can provide useful guidance in the amounts useful for in situ administration of the pharmaceutical composition, and animal models can be used to determine effective dosages for treatment of particular disorders.

Various considerations are described, e. g., in Langer, 1990, Science, 249: 1527; Goodman and Gilman's (eds.), 1990, Id., each of which is herein incorporated by reference and for all purposes. Dosages for parenteral administration of active pharmaceutical agents can be converted into corresponding dosages for oral administration by multiplying parenteral dosages by appropriate conversion factors. As to general applications, the parenteral dosage in mg/mL times 1.8=the corresponding oral dosage in milligrams ("mg"). As to oncology applications, the parenteral dosage in mg/mL times 1.6=the corresponding oral dosage in mg. An average adult weighs about 70 kg. See e.g., Miller-Keane, 1992, ENCYCLOPEDIA & DICTIONARY OF MEDICINE, NURSING & ALLIED HEALTH, 5th Ed., (W.B. Saunders Co.), pp. 1708 and 1651.

The method by which the compound disclosed herein can be administered for oral use would be, for example, in a hard gelatin capsule wherein the active ingredient is mixed with an inert solid diluent, or soft gelatin capsule, wherein the active ingredient is mixed with a co-solvent mixture, such as PEG 400 containing Tween-20. A compound disclosed herein can also be administered in the form of a sterile injectable aqueous or oleaginous solution or suspension. The compound can generally be administered intravenously or as an oral dose of 0.1 µg to 20 mg/kg given, for example, every 3-24 hours.

Formulations for oral use can be in the form of hard gelatin capsules wherein the active ingredient is mixed with an inert solid diluent, for example, calcium carbonate, calcium phosphate or kaolin. They can also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients can be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which can be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions can be in the form of a sterile injectable aqueous or oleagenous suspension. This suspension can be formulated according to known methods using those suitable dispersing or wetting agents and suspending agents that have been mentioned above. The sterile injectable preparation can also a sterile injectable solution or suspension in a non-toxic parenterally-acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

A compound disclosed herein can also be administered in the form of ophthalmic compositions applied topically to the eye, preferably in the form of eye drops. A compound disclosed herein can also be administered in the form of intravitreal injection.

A compound disclosed herein can also be administered in the form of suppositories for rectal administration of the drug. These compositions can be prepared by mixing the drug with a suitable non-irritating excipient that is solid at ordinary temperature but liquid at the rectal temperature and will therefore melt in the rectum to release the drug. Such materials include cocoa butter and polyethylene glycols.

The compounds disclosed herein as used in the methods disclosed herein can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds disclosed herein, are employed.

In addition, some of the compounds disclosed herein can form solvates with water or common organic solvents. Such solvates are encompassed within the scope of the methods contemplated herein.

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to inhibition of thrombin, and/or KLKB1); presence of other diseases or other health-related problems; kind of concurrent treatment; and complications from any disease or treatment regimen. Other therapeutic regimens or agents can be used in conjunction with the methods and compounds disclosed herein.

For any compound described herein, the therapeutically effective amount can be initially determined from a variety of techniques known in the art, e.g., biochemical characterization of inhibition of enzyme (thrombin or KLKB1), cell culture assays, and the like. Target concentrations will be those concentrations of active compound(s) that are capable of decreasing enzymatic activity as measured, for example, using the methods described.

Therapeutically effective amounts for use in humans can be determined from animal models. For example, a dose for humans can be formulated to achieve a concentration that has been found to be effective in animals. The dosage in humans can be adjusted by monitoring enzymatic inhibition and adjusting the dosage upwards or downwards, as described above.

Dosages can be varied depending upon the requirements of the patient and the compound being employed. The dose administered to a patient, in the context of the methods disclosed herein, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments of a method disclosed herein, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Accordingly, in some embodiments, dosage levels of the compounds disclosed herein as used in the present methods are of the order of e.g., about 0.1 mg to about 1 mg, about 1 mg to about 10 mg, about 0.5 mg to about 20 mg per kilogram body weight, an average adult weighing 70 kilograms, with a preferred dosage range between about 0.1 mg to about 20 mg per kilogram body weight per day (from about 7.0 mg to about 1.4 gm per patient per day). The amount of the compound disclosed herein that can be combined with the carrier materials to produce a single dosage will vary depending upon the host treated and the particular mode of administration. For example, a formulation intended for oral administration to humans can contain about µg to 1 g of a compound disclosed herein with an appropriate and convenient amount of carrier material that can vary from about 5 to 95 percent of the total composition. Dosage unit forms will generally contain between from about 0.1 mg to 500 mg of a compound disclosed herein.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from in vitro assays, cell culture assays and/or animal studies can be used in formulating a range of dosages for use in humans. The dosage of such compounds preferably lies within a range of plasma concentrations that include the $ED_{50}$ with little or no toxicity. The dosage can vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual practitioner in view of the patient's condition and the particular method in which the compound is used. For in vitro formulations, the exact formulation and dosage can be chosen by the individual practitioner in view of the patient's condition and the particular method in which the compound is used.

VII. Examples

The examples below are meant to illustrate certain embodiments of the invention and not to limit the scope of the invention. Abbreviations used herein have their conventional meaning in the art, unless indicated otherwise. Specific abbreviations include the following: Å=Ångstrom; Ac₂O=acetic anhydride; AcOH=acetic acid; aq=aqueous; Bt=benzotriazole; BOC=N-tert-butoxycarbonyl; br=broad; t-BuOH=tert-butanol; ° C.=degree Celsius; d=doublet; DABCO=1,4-diazabicyclo[2.2.2]octane; DCE=1,2-dichloroethane; DCM=dichloromethane; dd=doublet of doublets; DIEA=diethylisopropylamine; DMAP=4-dimethylaminopyridine; DMF=N,N-dimethylformamide; DMSO=dimethylsulfoxide; δ=chemical shift (given in ppm, unless otherwise indicated); EDCI=1-ethyl-3-(3-dimethylaminopropyl)carbodiimide; eq=equivalent; Et₂O=diethyl ether; Et₃N=triethylamine; EtOAc=ethyl acetate; EtOH=ethanol; g=gram; h (or hr)=hour; HOBt=hydroxybenzotriazole; HPLC=high performance liquid chromatography; Hz=Hertz; $IC_{50}$=inhibitory concentration at 50% inhibition; J=coupling constant (given in Hz, unless otherwise indicated); LC=liquid chromatography; LHMDS=lithium hexamethyldisilazide; m=multiplet; M=molar; [M+H]⁺=parent mass spectrum peak plus H⁺; MS=mass spectrum; ms=molecular sieves; MP=melting point; Me₂NH= dimethylamine; MeOH=methanol; mg=milligram; mL=milliliter; mM=millimolar; mmol=millimole; min=minute; L=microliter; M=micromolar; ng=nanogram; nM=nanomolar; NMR=nuclear magnetic resonance; ppm=parts per million; q=quartet; $R_f$=retention factor; RT=room temperature; s=singlet; t=triplet; TFA=trifluoroacetic acid; THF= tetrahydrofuran; TLC=thin layer chromatography.

List of General Procedures

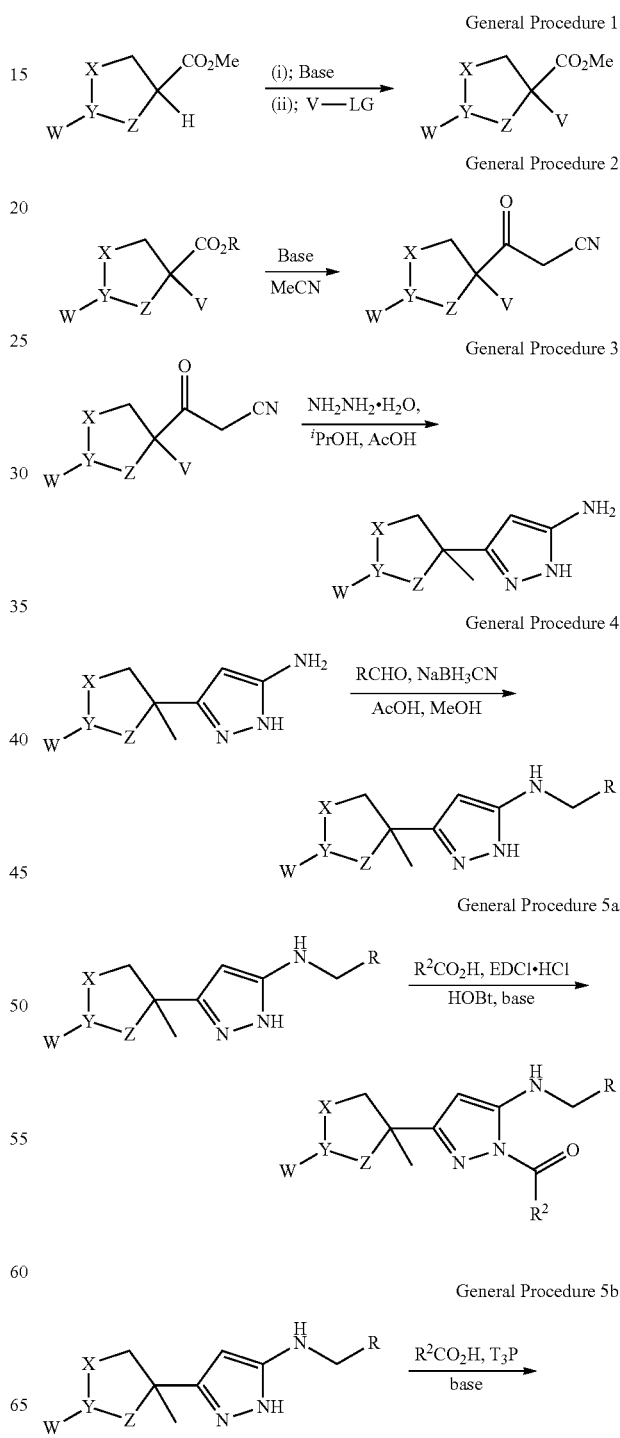

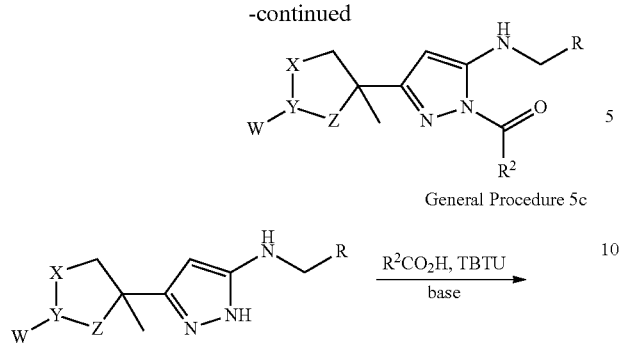
General Procedure 5c
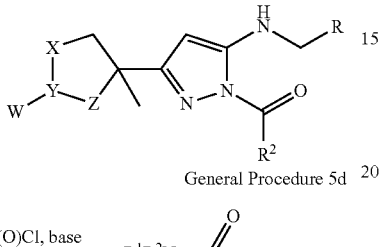
General Procedure 5d
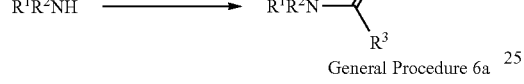
General Procedure 6a
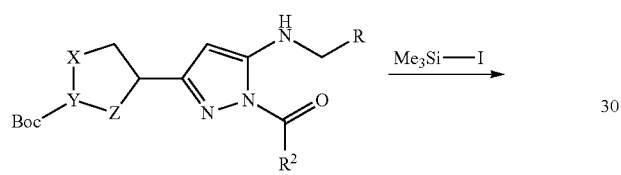
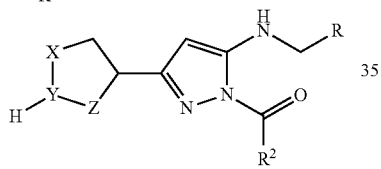
General Procedure 6b
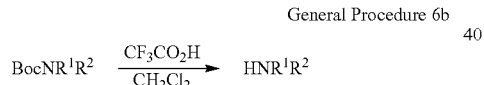
General Procedure 6c
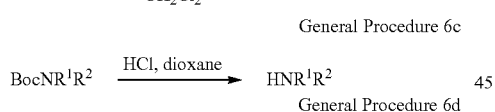
General Procedure 6d
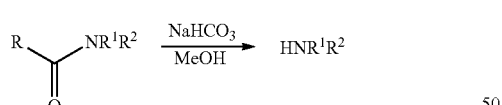
General Procedure 7
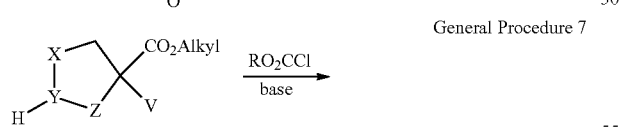
General Procedure 8a

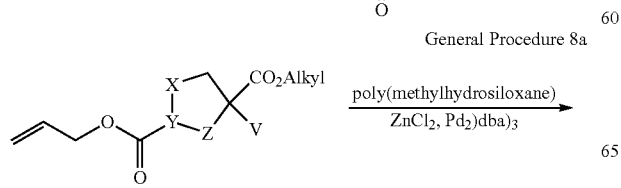
General Procedure 8b
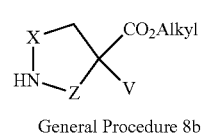
General Procedure 9
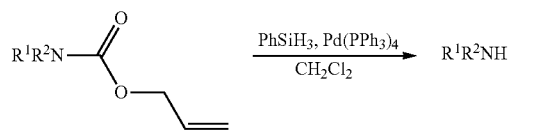
General Procedure 10
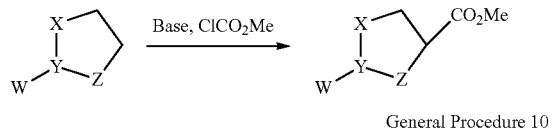
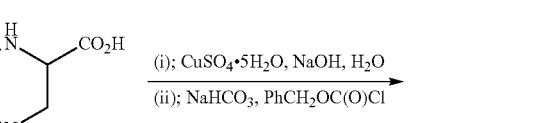
General Procedure 11
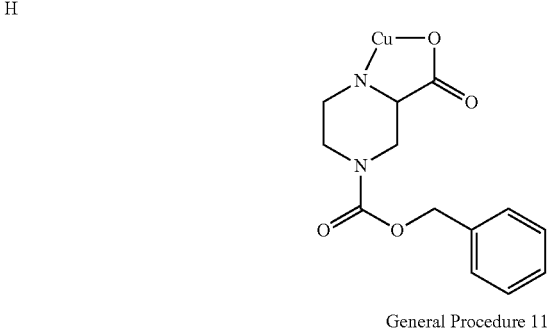
General Procedure 12
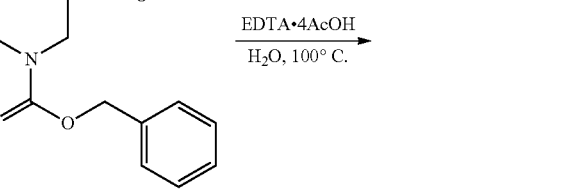

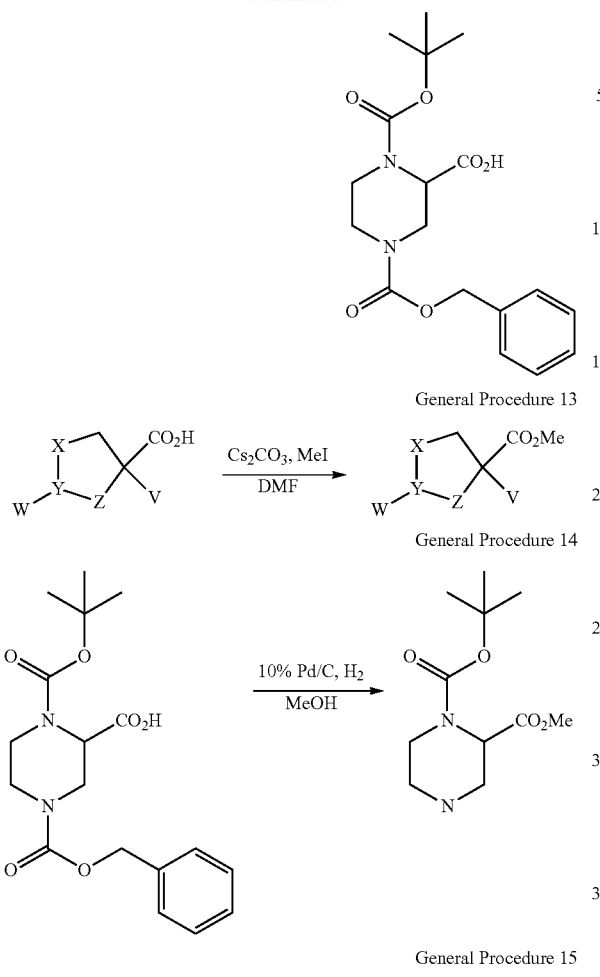
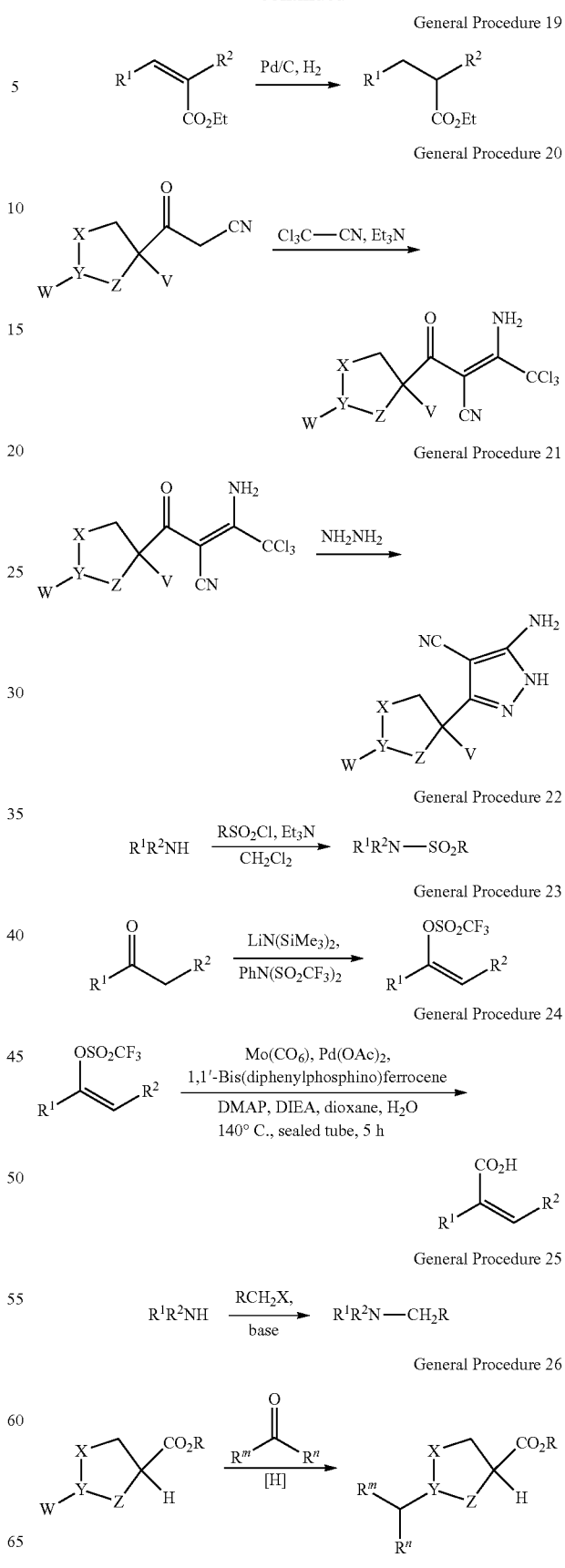
General Procedure 13
General Procedure 14
General Procedure 15
General Procedure 16
General Procedure 17
General Procedure 18
General Procedure 19
General Procedure 20
General Procedure 21
General Procedure 22
General Procedure 23
General Procedure 24
General Procedure 25
General Procedure 26

SYNTHETIC EXAMPLES

Example 1—Preparation of Intermediate 1

The synthesis of Intermediate 1 followed General Procedure 1 following.

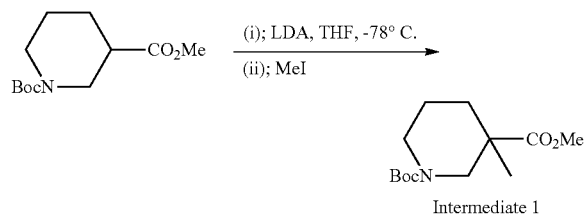

Intermediate 1

To a solution of diisopropylamine (6.55 g, 64.7 mmol, 2.1 eq) in cold THF (−78° C., 80 mL) was added n-butyllithium (4.04 g, 63.1 mmol, 2.05 eq), and then stirred for 1 hour at 0° C. The reaction mixture was then cooled to −78° C. and to it was then added 1-(tert-butyl)-3-methylpiperidine-1,3-dicarboxylate (7.5 g, 30.8 mmol, 1 eq). The mixture was stirred for 1 hour, and to it was added methyl iodide (13.12 g, 97.4 mmol, 3.0 eq). The reaction mixture was warmed to room temperature overnight. It was monitored by TLC and LC-MS. After completion, the reaction mixture was quenched with ammonium chloride and extracted with ethyl acetate (2×150 mL). The combined organic phases were washed with water and brine, then dried over sodium sulfate and concentrated under reduced pressure. The residue was purified by flash chromatography using silica gel (60-120 mesh size), eluting with 5-10% ethyl acetate in n-hexane to give product (Intermediate 1, 4.8 g, yield: 60.5%) m/z 202 [M−56]+ $^1$H NMR (400 MHz, CDCl$_3$) δ 3.87 (d, J=13.3 Hz, 1H), 3.70 (s, 3H), 3.46 (s, 1H), 3.27 (d, J=5.9 Hz, 1H), 3.15 (d, J=13.3 Hz, 1H), 2.04 (dd, J=12.7, 6.2 Hz, 1H), 1.58 (s, 1H), 1.49 (m, 11H), 1.18 (s, 3H) ppm.

Example 2—Preparation of Intermediate 2

The synthesis of Intermediate 2 followed the procedure of General Procedure 2 following.

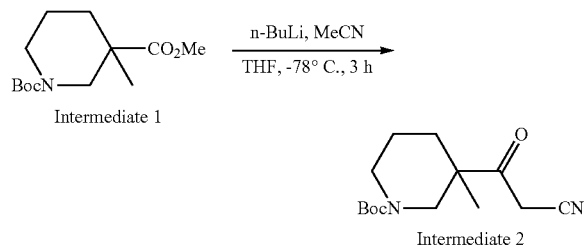

To a cold solution (−78° C.) of acetonitrile (1.67 g, 40.8 mmol, 1.5 eq) in tetrahydrofuran (70 mL) was added n-BuLi (23% in hexane, 2.61 g, 40.8 mmol, 1.5 eq) under inert N$_2$ atmosphere over a period of 20 minutes. After completion of addition, the reaction was stirred for another 60 minutes. To the cold (−78° C.) mixture was then added Intermediate 1 (7.0 g, 27.2 mmol, 1.0 eq) in portions, and the reaction mixture was stirred for 3 hours. The reaction mixture was quenched with saturated ammonium chloride solution and the product was extracted with ethyl acetate. The organic phase was dried with sodium sulfate and concentrated under reduced pressure. The residue was purified by column chromatography using silica gel (60-120 mesh size) eluting with 10-40% ethyl acetate in n-hexane, yielding product tert-butyl 3-(2-cyanoacetyl)-3-methylpiperidine-1-carboxylate (Intermediate 2; 4.775 g, yield: 65.9%) m/z 211.0 [M−56]+ $^1$H NMR (400 MHz, DMSO) δ 4.26 (q, J=20.1 Hz, 2H), 3.74 (d, J=12.6 Hz, 1H), 3.38-3.32 (m, 1H), 3.21-3.06 (m, 2H), 1.94-1.77 (m, 1H), 1.56-1.31 (m, 12H), 1.06 (s, 3H) ppm.

Example 3—Preparation of Compound 1

The synthesis of Compound 1 followed the procedure of General Procedure 3 following.

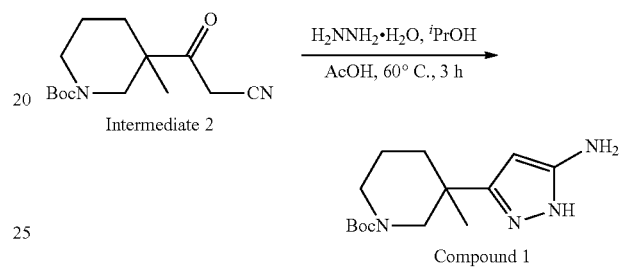

To a solution of tert-butyl 3-(2-cyanoacetyl)-3-methylpiperidine-1-carboxylate (Intermediate 2, 9.5 g, 35 mmol, 1.0 eq) in acetic acid (0.2 mL) and isopropanol (80 mL) was added hydrazine monohydrate (2.67 g, 53 mmol, 1.5 eq) dropwise. The reaction mixture was stirred at 60° C. for 3 hours. The reaction mixture was monitored by LC-MS, and on completion was concentrated under reduced pressure. The residue was purified by column chromatography using silica gel (60-120 mesh), eluting with 5-10% methanol in dichloromethane to yield tert-butyl 3-(5-amino-1H-pyrazol-3-yl)-3-methylpiperidine-1-carboxylate (Compound 1; 9.005 g, yield: 90.0%) m/z 225.05 [M−56]+ 1H NMR (400 MHz, DMSO) δ 11.26 (s, 1H), 4.62 (s, 2H), 3.38 (d, J=22.7 Hz, 2H), 3.32 (d, J=12.2 Hz, 1H), 3.16 (d, J=12.5 Hz, 1H), 1.58-1.43 (m, 2H), 1.38 (d, J=9.7 Hz, 11H), 1.09 (d, J=8.6 Hz, 3H) ppm.

Example 4—Preparation of Compound 2

The synthesis of Compound 2 followed the procedure of General Procedure 4 following.

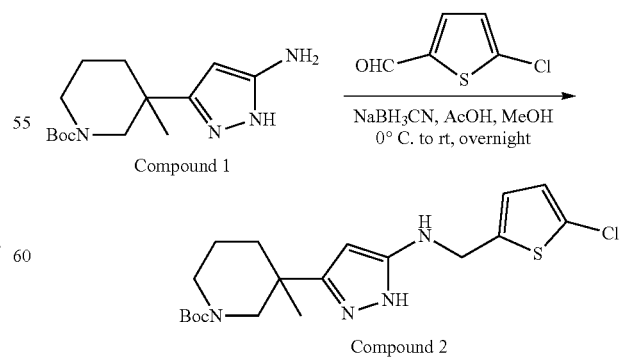

To a cold solution (0° C.) of tert-butyl 3-(5-amino-1H-pyrazol-3-yl)-3-methylpiperidine-1-carboxylate (Compound 1, 9.0 g, 32.1 mmol, 1.0 eq) and 5-chlorothiophene-2-carbaldehyde (5.64 g, 38.5 mmol, 1.2 eq) in methanol (100 mL) was added acetic acid (1.92 g, 32.1 mmol, 1.0 eq). After stirring for 3 hours, sodium cyanoborohydride (4.03 g, 64.2 mmol, 2.0 eq) was added. The reaction mixture was warmed to room temperature overnight and monitored by TLC. The reaction mixture was poured into water (200 mL) and extracted with ethyl acetate (2×150 mL). The combined organic phases were washed with water, brine, dried over sodium sulfate, filtered and concentrated under reduced pressure. The residue was purified by flash chromatography using silica gel (60-120 mesh size), eluting with 10-40% ethyl acetate in n-hexane yielding tert-butyl 3-(5-(((5-chlorothiophen-2-yl)methyl)amino)-1H-pyrazol-3-yl)-3-methylpiperidine-1-carboxylate (Compound 2, 7.0 g, yield: 53.0%) m/z 411.40 [M+1]+ 1H NMR (400 MHz, DMSO) δ 6.92 (d, J=3.7 Hz, 1H), 6.84 (s, 1H), 5.67 (s, 1H), 5.35 (s, 1H), 4.28 (d, J=5.5 Hz, 2H), 3.44-3.34 (m, 2H), 3.29-3.26 (m, 2H), 1.90 (s, 1H), 1.54-1.43 (m, 3H), 1.39 (s, 9H), 1.12 (s, 3H) ppm.

Example 5—Preparation of Compound 3

The synthesis of Compound 3 followed the procedure of General Procedure 5a following.

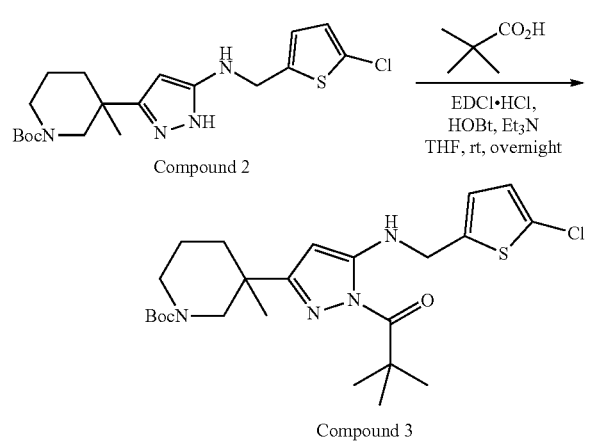

To a solution of pivalic acid (0.373 g, 3.65 mmol, 1.5 eq) in cold (0° C.) THF (15 mL) under a nitrogen atmosphere was added 1-(3-dimethylaminopropyl)-3-ethylcarbodiimide hydrochloride (EDCI.HCl, 0.701 g, 3.65 mmol, 1.5 eq) and triethylamine (0.74 g, 7.31 mmol, 3.0 eq). The reaction mixture was stirred for 30 minutes, and to it was added hydroxybenzotriazole (HOBt, 0.065 g, 0.48 mmol, 0.2 eq), followed by tert-butyl 3-(5-(((5-chlorothiophen-2-yl)methyl)amino)-1H-pyrazol-3-yl)-3-methylpiperidine-1-carboxylate (Compound 2, 1.0 g, 3.43 mmol, 1.0 eq). The mixture was stirred overnight at room temperature. The reaction was monitored by LC-MS, and after completion was poured into water (20 mL), extracted with ethyl acetate (2×20 mL), washed with water, brine, dried over sodium sulfate, filtered and evaporated under reduced pressure. The residue was purified by flash chromatography using silica gel (60-120 mesh size), eluting with 0-20% ethyl acetate in n-hexane, yielding tert-butyl 3-(5-(((5-chlorothiophen-2-yl)methyl)amino)-1-pivaloyl-1H-pyrazol-3-yl)-3-methylpiperidine-1-carboxylate (Compound 3, 0.500 g, yield: 41.4%) m/z 494.88 [M+1]+ 1H NMR (400 MHz, DMSO) δ 7.63 (d, J=5.6 Hz, 1H), 6.97 (s, 2H), 5.47 (s, 1H), 4.41 (s, 2H), 3.44 (d, J=45.8 Hz, 2H), 3.24 (s, 2H), 1.94 (s, 1H), 1.50 (d, J=47.4 Hz, 3H), 1.40 (s, 9H), 1.34 (s, 9H), 1.12 (s, 3H) ppm.

Example 6—Preparation of Compound 4

The synthesis of Compound 4 followed the procedure of General Procedure 5b following.

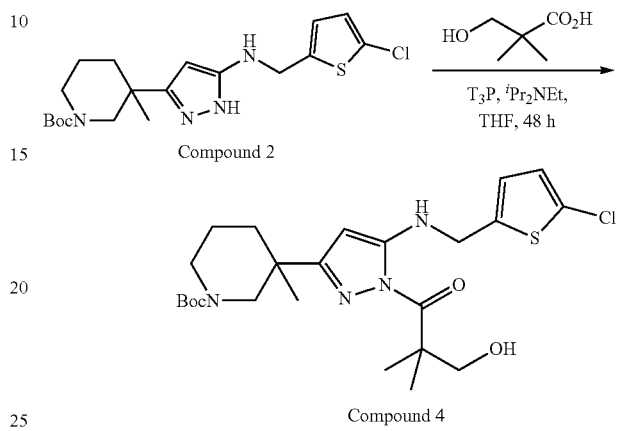

To a cold solution (0° C.) of 3-hydroxy-2,2-dimethylpropanoic acid (0.576 g, 4.85 mmol, 2.0 eq) in THF (25 mL) was added 1-propanephosphonic anhydride (T3P, 1.551 g, 4.85 mmol, 2.0 eq), followed by diisopropylethylamine (DIPEA, 0.986 g, 9.75 mmol, 4.0 eq) under nitrogen. The reaction mixture was stirred for 1 hour, and to it was added tert-butyl 3-(5-(((5-chlorothiophen-2-yl)methyl)amino)-1H-pyrazol-3-yl)-3-methylpiperidine-1-carboxylate (Compound 2, 1.0 g, 3.43 mmol, 1.0 eq). The reaction was stirred for 48 hours and monitored by TLC. After reaction completion, the mixture was poured into water (50 mL), extracted with ethyl acetate (2×20 mL), washed with water and then brine, then dried over sodium sulfate, filtered and evaporated under reduced pressure. The residue was purified by flash chromatography using silica gel (60-120 mesh size) eluting with 10-20% ethyl acetate in n-hexane, yielding tert-butyl 3-(5-(((5-chlorothiophen-2-yl)methyl)amino)-1-(3-hydroxy-2,2-dimethylpropanoyl)-1H-pyrazol-3-yl)-3-methylpiperidine-1-carboxylate (Compound 4, 0.410 g, yield: 32.9%) m/z 511.8 [M+1]+ 1H NMR (400 MHz, DMSO) δ 7.63 (s, 1H), 6.92 (d, J=37.7 Hz, 2H), 5.46 (s, 1H), 4.83 (t, J=5.3 Hz, 1H), 4.41 (s, 2H), 3.87 (s, 2H), 3.42 (s, 2H), 3.19 (d, J=5.2 Hz, 2H), 1.91 (s, 1H), 1.55 (s, 2H), 1.36 (s, 3H), 1.30 (s, 6H), 1.12 (s, 3H) ppm.

Example 7—Preparation of Compound 5

The synthesis of Compound 5 followed the procedure of General Procedure 6a following.

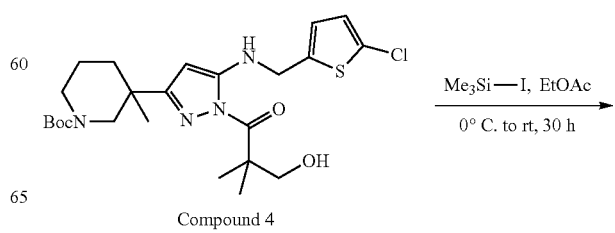

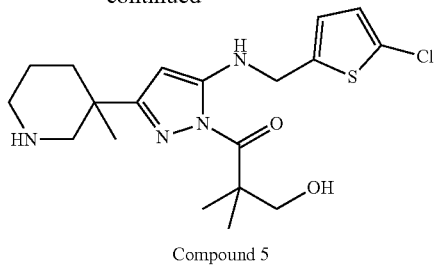

Compound 5

To a cold (0° C.) solution of tert-butyl 3-(5-(((5-chlorothiophen-2-yl)methyl)amino)-1-(3-hydroxy-2,2-dimethylpropanoyl)-1H-pyrazol-3-yl)-3-methylpiperidine-1-carboxylate (Compound 4, 0.4 g, 0.78 mmol, 1.0 eq) in ethyl acetate (600 mL) was added iodotrimethylsilane (0.5 mL) dropwise. The reaction mixture was allowed to room temperature and stirred for 30 hours. The reaction was monitored by LC-MS and TLC. After completion, the reaction mixture was washed with sodium bicarbonate solution (20%, 150 mL), water (150 mL), followed by brine (150 mL). The organic layer was dried over sodium sulfate and concentrated under reduced pressure. The residue was purified by preparative HPLC using ammonia-water as mobile phase, yielding 1-(5-(((5-chlorothiophen-2-yl)methyl)amino)-3-(3-methylpiperidin-3-yl)-1H-pyrazol-1-yl)-3-hydroxy-2,2-dimethylpropan-1-one (Compound 5, 0.030 g, yield: 9.3%) m/z 410.90 [M+1]+ 1H NMR (400 MHz, DMSO) δ 7.71 (s, 1H), 7.00 (s, 2H), 5.57 (s, 1H), 4.89-4.75 (m, 1H), 4.44 (s, 2H), 3.85 (s, 2H), 2.89 (s, 4H), 2.02-1.99 (m, 1H), 1.62 (s, 3H), 1.32 (s, 6H), 1.19 (s, 3H) ppm.

Example 8—Preparation of Compound 6

The synthesis of Compound 6 followed the procedure of General Procedure 5a following.

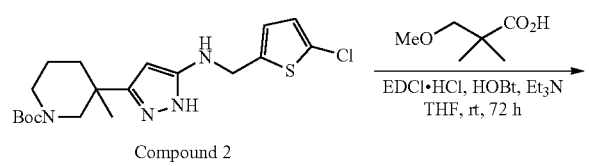

Compound 2

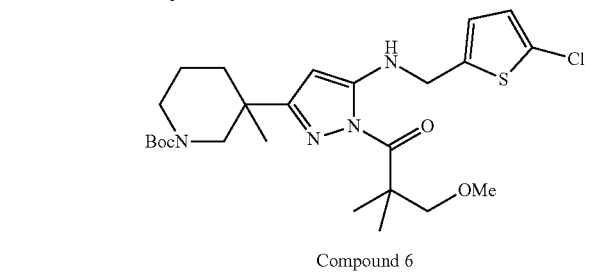

Compound 6

To a cold solution (0° C.) of 3-methoxy-2,2-dimethylpropanoic acid (0.483 g, 3.65 mmol, 1.5 eq) in THF (15 mL) was added 1-(3-dimethylaminopropyl)-3-ethylcarbodiimide hydrochloride (EDCI.HCl, (0.701 g, 3.65 mmol, 1.5 eq) and then triethylamine (TEA, 0.74 g, 7.31 mmol, 3.0 eq) under nitrogen. After stirring for 30 minutes, to the mixture was then added hydroxybenzotriazole (HOBt, 0.065 g, 0.48 mmol, 0.2 eq), followed by tert-butyl 3-(5-(((5-chlorothiophen-2-yl)methyl)amino)-1H-pyrazol-3-yl)-3-methylpiperidine-1-carboxylate (Compound 2, 1.0 g, 3.43 mmol, 1.0 eq).

The reaction mixture was monitored by LC-MS, and stirred for 72 hours at room temperature. After completion the reaction mixture was poured into water (20 mL) and extracted with ethyl acetate (2×20 mL). The combined organic phases were washed with water, brine, then dried over sodium sulfate, filtered and evaporated under reduced pressure. The residue was purified by flash chromatography using silica gel (60-120 mesh size), eluting with 0-20% ethyl acetate in n-hexane, to yield tert-butyl 3-(5-(((5-chlorothiophen-2-yl)methyl)amino)-1-(3-methoxy-2,2-dimethylpropanoyl)-1H-pyrazol-3-yl)-3-methylpiperidine-1-carboxylate (Compound 6, 0.625 g, yield: 48.9%) m/z 524.93 [M+1]+ 1H NMR (400 MHz, DMSO) δ 7.60 (t, J=5.6 Hz, 1H), 6.97 (s, 2H), 5.47 (s, 1H), 4.41 (s, 2H), 3.84 (s, 2H), 3.52 (d, J=13.0 Hz, 1H), 3.24 (s, 3H), 3.13 (s, 3H), 1.95 (s, 1H), 1.57 (s, 3H), 1.35 (d, J=4.6 Hz, 6H), 1.33 (s, 9H), 1.13 (s, 3H) ppm.

Example 9—Preparation of Compound 7

The synthesis of Compound 7 followed the procedure of General Procedure 6b following.

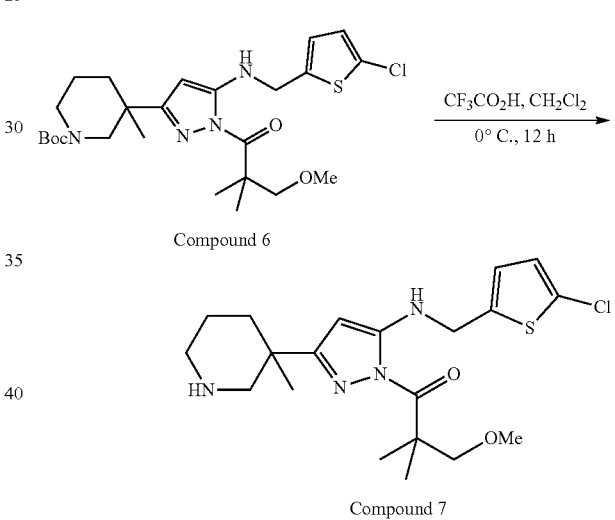

Compound 6

Compound 7

To a cold solution (0° C.) of tert-butyl 3-(5-(((5-chlorothiophen-2-yl)methyl)amino)-1-(3-methoxy-2,2-dimethylpropanoyl)-1H-pyrazol-3-yl)-3-methylpiperidine-1-carboxylate (Compound 6, 0.4 g (0.76 mmol, 1.0 eq) in dichloromethane (300 mL) was added a solution of trifluoroacetic acid (TFA, 2.5 mL) in dichloromethane (6 mL). The reaction was monitored by LC-MS and TLC, and after completion (12 hours) the reaction mixture was washed with 20% sodium bicarbonate (200 mL), water (200 mL) and brine (200 mL). The organic layer was dried over sodium sulfate and concentrated under reduced pressure. The residue was purified by preparative HPLC using ammonia-water as mobile phase to yield 1-(5-(((5-chlorothiophen-2-yl)methyl)amino)-3-(3-methylpiperidin-3-yl)-1H-pyrazol-1-yl)-3-methoxy-2,2-dimethylpropan-1-one (Compound 7, 0.22 g, yield: 83.4%) m/z 425.36 [M+1]+ 1H NMR (400 MHz, DMSO) δ 8.27 (s, 1H), 7.63 (d, J=6.2 Hz, 1H), 6.98 (q, J=3.8 Hz, 2H), 5.52 (s, 1H), 4.42 (d, J=6.3 Hz, 2H), 3.82 (dd, J=20.7, 8.4 Hz, 4H), 3.14 (s, 4H), 2.86-2.61 (m, 3H), 1.98 (s, 2H), 1.41 (t, J=44.2 Hz, 6H), 1.16 (s, 3H) ppm.

Example 10—Preparation of Compound 8

The synthesis of Compound 8 followed the procedure of General Procedure 5a following.

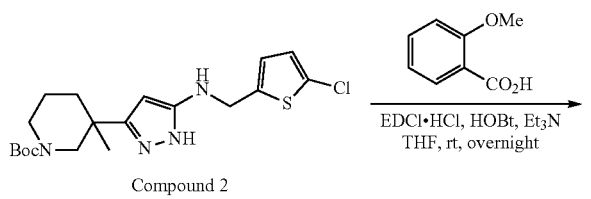

Compound 2

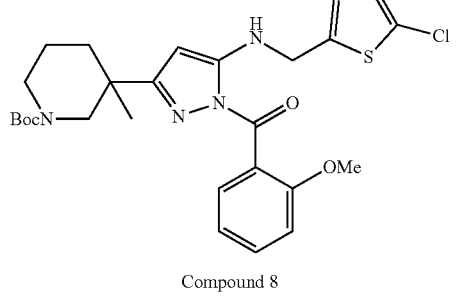

Compound 8

To a cooled solution (0° C.) of 2-methoxybenzoic acid (0.278 g, 1.82 mmol, 1.5 eq) in THF (12 mL) was added 1-(3-dimethylaminopropyl)-3-ethylcarbodiimide hydrochloride (EDCI.HCl, 0.351 g, 1.82 mmol, 1.5 eq) and then triethylamine (TEA, 0.369 g, 3.65 mmol, 3.0 eq) under nitrogen. After stirring for 30 minutes, hydroxybenzotriazole (HOBt, 0.032 g, 0.24 mmol, 0.2 eq) and then tert-butyl 3-(5-(((5-chlorothiophen-2-yl)methyl)amino)-1H-pyrazol-3-yl)-3-methylpiperidine-1-carboxylate (Compound 2, 0.5 g, 1.21 mmol, 1.0 eq) were added. The reaction was monitored by LC-MS, and after stirring overnight the reaction mixture was poured into water (20 mL) and extracted with ethyl acetate (2×20 mL). The combined organic phases were washed with water, brine, dried over sodium sulfate, filtered and evaporated under reduced pressure. The residue was purified by flash chromatography using silica gel (60-120 mesh size), eluting with 0-20% ethyl acetate in n-hexane, to yield tert-butyl 3-(5-(((5-chlorothiophen-2-yl)methyl)amino)-1-(2-methoxybenzoyl)-1H-pyrazol-3-yl)-3-methylpiperidine-1-carboxylate (Compound 8, 0.25 g, yield: 46%) m/z 545.49 [M+1] 1H NMR (400 MHz, DMSO) δ 7.60 (t, J=6.2 Hz, 1H), 7.47 (dt, J=35.7, 14.2 Hz, 1H), 7.38 (dd, J=7.5, 1.6 Hz, 1H), 7.13 (d, J=8.4 Hz, 1H), 7.05-6.98 (m, 3H), 6.50-6.50 (m, 1H), 5.55 (s, 2H), 4.43 (d, J=38.0 Hz, 2H), 3.73 (s, 3H), 3.48-3.11 (m, 4H), 1.73 (s, 1H), 1.60-1.06 (m, 13H), 1.03 (s, 3H) ppm.

Example 11—Preparation of Compound 9

The synthesis of Compound 9 followed the procedure of General Procedure 6b following:

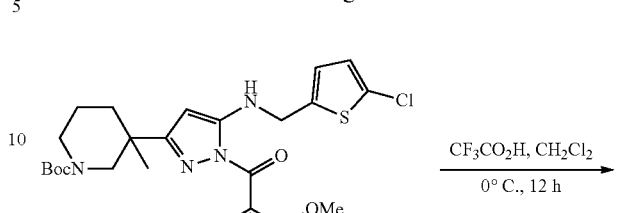

Compound 8

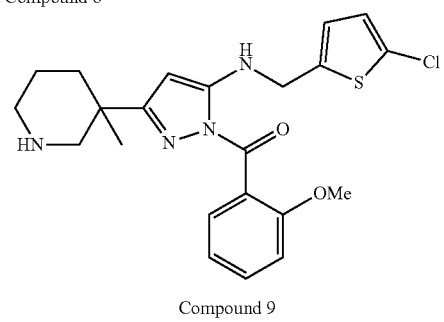

Compound 9

To a cooled solution (0° C.) of tert-butyl 3-(5-(((5-chlorothiophen-2-yl)methyl)amino)-1-(2-methoxybenzoyl)-1H-pyrazol-3-yl)-3-methylpiperidine-1-carboxylate (Compound 8, 0.4 g, 0.73 mmol, 1.0 eq) in dichloromethane (250 mL) was added a solution of TFA (2.5 mL) in DCM (10 mL) dropwise. The reaction was monitored by LC-MS and TLC, and after stirring at 0° C. for 12 hours, the mixture was washed with 20% sodium bicarbonate (200 mL), water (200 mL) and then brine (200 mL). The organic layer was dried over sodium sulfate, filtered and evaporated under reduced pressure. The residue was purified by preparative HPLC eluting with ammonia-water as mobile phase, yielding product (5-(((5-chlorothiophen-2-yl)methyl)amino)-3-(3-methylpiperidin-3-yl)-1H-pyrazol-1-yl)(2-methoxyphenyl)methanone (Compound 9, 0.08 g, yield: 24%) m/z 444.81 [M+1]+ 1H NMR (400 MHz, DMSO) δ 7.71 (t, J=6.4 Hz, 1H), 7.50 (dd, J=11.4, 4.4 Hz, 1H), 7.44 (dd, J=7.5, 1.6 Hz, 1H), 7.14 (d, J=8.2 Hz, 1H), 7.02 (dd, J=12.5, 4.5 Hz, 3H), 5.64 (s, 1H), 4.49 (d, J=6.3 Hz, 2H), 3.07 (d, J=13.1 Hz, 1H), 2.81 (s, 1H), 2.69 (d, J=12.1 Hz, 2H), 1.85 (s, 1H), 1.49 (d, J=11.6 Hz, 3H), 1.09 (s, 3H) ppm.

Example 12—Preparation of Compound 10

The synthesis of Compound 10 followed the procedure of General Procedure 5a following.

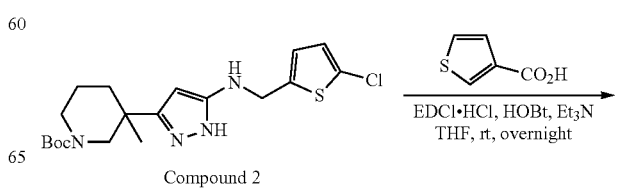

Compound 2

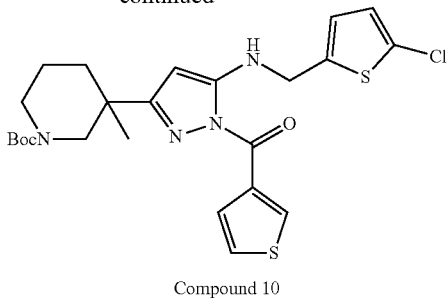

Compound 10

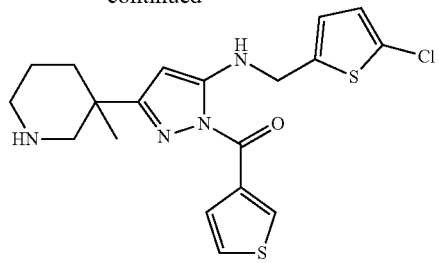

Compound 11

To a cooled solution (0° C.) of thiophene-3-carboxylic acid (0.374 g, 2.9 mmol, 1.5 eq) in THF (20 mL) was added 1-(3-dimethylaminopropyl)-3-ethylcarbodiimide hydrochloride (EDCI.HCl, 0.561 g, 2.9 mmol, 1.5 eq) and triethylamine (0.591 g, 5.8 mmol, 3.0 eq) under nitrogen. The reaction mixture was stirred for 30 minutes, and to it was added hydroxybenzotriazole (HOBt, 0.052 g, 0.39 mmol, 0.2 eq) followed by tert-butyl 3-(5-(((5-chlorothiophen-2-yl)methyl)amino)-1H-pyrazol-3-yl)-3-methylpiperidine-1-carboxylate (compound 2, 0.8 g, 1.9 mmol, 1.0 eq). The reaction was monitored by LC-MS, and after stirring overnight at room temperature the reaction mixture was poured into water (20 mL) and extracted with ethyl acetate (2×20 mL). The combined organic phases were washed with water and then brine, dried over sodium sulfate, filtered and evaporated under reduced pressure. The residue was purified by flash chromatography using silica gel (60-120 mesh size) eluting with 0-20% ethyl acetate in n-hexane, yielding product tert-butyl 3-(5-(((5-chlorothiophen-2-yl)methyl) amino)-1-(thiophene-3-carbonyl)-1H-pyrazol-3-yl)-3-methylpiperidine-1-carboxylate (compound 10, 0.4 g, yield: 49%) m/z 521.77 [M+1]+ $^1$H NMR (400 MHz, DMSO) δ 8.95 (d, J=58.3 Hz, 1H), 7.78 (dd, J=12.2, 5.9 Hz, 2H), 7.66 (d, J=3.0 Hz, 1H), 6.99 (dd, J=11.6, 3.7 Hz, 2H), 5.61 (s, 1H), 4.49 (s, 2H), 3.70-3.53 (m, 1H), 3.29-3.15 (m, 3H), 1.98 (s, 1H), 1.59 (d, J=14.8 Hz, 3H), 1.33 (s, 9H), 1.16 (s, 3H) ppm.

Example 13—Preparation of Compound 11

The synthesis of Compound 11 followed the procedure of General Procedure 6b following:

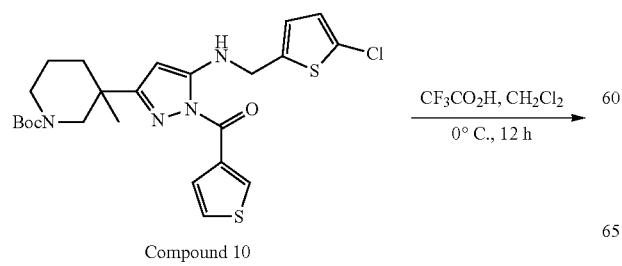

To a cooled solution (0° C.) of tert-butyl 3-(5-(((5-chlorothiophen-2-yl)methyl)amino)-1-(thiophene-3-carbonyl)-1H-pyrazol-3-yl)-3-methylpiperidine-1-carboxylate (Compound 10, 0.4 g, 0.76 mmol, 1.0 eq) in dichloromethane (250 mL) was added a solution of TFA (2.5 mL) in DCM (10 mL) dropwise. The reaction was monitored by LC-MS and TLC, and after stirring at 12 hours at 0° C. the solution was washed with sodium bicarbonate (20%, 200 mL), water (200 mL) and brine (200 mL). The organic layer was dried over sodium sulfate, filtered and evaporated under reduced pressure. The residue was concentrated and purified by preparative HPLC, eluting with ammonia-water as the mobile phase, yielding desired product (5-(((5-chlorothiophen-2-yl) methyl)amino)-3-(3-methylpiperidin-3-yl)-1H-pyrazol-1-yl)(thiophen-3-yl)methanone (Compound 11, 0.075 g, yield: 23%) m/z 420.80 [M+1]+ $^1$H NMR (400 MHz, DMSO) δ 8.90 (d, J=1.8 Hz, 1H), 8.31 (s, 1H), 7.85-7.77 (m, 2H), 7.66 (dd, J=5.1, 3.0 Hz, 1H), 7.01 (t, J=7.5 Hz, 1H), 6.98 (d, J=3.7 Hz, 1H), 5.68 (s, 1H), 4.50 (d, J=6.2 Hz, 2H), 3.34 (d, J=12.3 Hz, 1H), 2.81 (d, J=12.0 Hz, 3H), 2.00 (s, 1H), 1.60 (d, J=8.9 Hz, 2H), 1.48 (s, 1H), 1.19 (d, J=12.7 Hz, 3H) ppm.

Example 14—Preparation of Compound 12

The synthesis of Compound 12 followed the procedure of General Procedure 5a following.

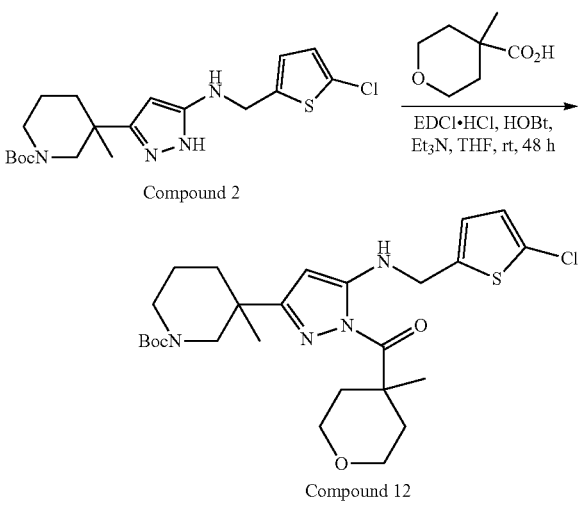

To a cooled solution (0° C.) of 4-methyltetrahydro-2H-pyran-4-carboxylic acid (0.527 g, 3.6 mmol, 1.5 eq) in THF (20 mL) was added 1-(3-dimethylaminopropyl)-3-ethylcarbodiimide hydrochloride (EDCI.HCl, 0.701 g, 3.6 mmol, 1.5 eq) and triethylamine (0.74 g, 7.3 mmol, 3.0 eq) under nitrogen. After stirring for 30 minutes at 0° C., to the reaction mixture was added hydroxybenzotriazole (HOBt, 0.065 g, 4.8 mmol, 0.2 eq) followed by tert-butyl 3-(5-(((5-chlorothiophen-2-yl)methyl)amino)-1H-pyrazol-3-yl)-3-methylpiperidine-1-carboxylate (Compound 2, 1.0 g, 2.4 mmol, 1.0 eq). The reaction mixture was stirred for 48 hours at room temperature, and monitored by LC-MS. The solution was poured into water (20 mL) and extracted with ethyl acetate (2×20 mL). The combined organic phases were washed with water, brine, and then dried over sodium sulfate, filtered and evaporated under reduced pressure. The residue was purified by flash chromatography using silica gel (60-120 mesh size), eluting with 0-20% ethyl acetate in n-hexane, yielding tert-butyl 3-(5-(((5-chlorothiophen-2-yl)methyl)amino)-1-(4-methyltetrahydro-2H-pyran-4-carbonyl)-1H-pyrazol-3-yl)-3-methylpiperidine-1-carboxylate (Compound 12, 0.610 g, yield: 47%) m/z 536.89 [M+1]+ $^1$H NMR (400 MHz, DMSO) δ 7.67 (s, 1H), 6.97 (s, 2H), 5.48 (s, 1H), 4.42 (s, 2H), 3.67 (s, 2H), 3.47 (s, 3H), 3.22 (s, 1H), 2.34 (s, 2H), 1.91 (s, 1H), 1.71 (s, 2H), 1.51 (s, 5H), 1.33 (s, 9H), 1.11 (s, 3H) ppm.

Example 15—Preparation of Compound 13

The synthesis of Compound 13 followed the procedure of General Procedure 6b following.

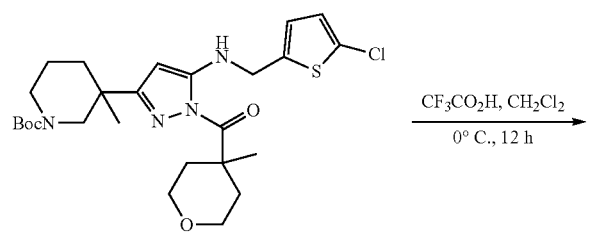

To a cooled solution (0° C.) of tert-butyl 3-(5-(((5-chlorothiophen-2-yl)methyl)amino)-1-(4-methyltetrahydro-2H-pyran-4-carbonyl)-1H-pyrazol-3-yl)-3-methylpiperidine-1-carboxylate (Compound 12, 0.4 g, 0.74 mmol, 1.0 eq) in dichloromethane (300 mL) was added a solution of TFA (2.5 mL) in dichloromethane (6 mL) dropwise. The reaction was monitored by LC-MS and TLC, and after stirring at 0° C. for 12 hours the reaction mixture was washed with sodium bicarbonate (20%, 200 mL), water (200 mL) and brine (200 mL). The organic layer was dried over sodium sulfate, filtered and evaporated under reduced pressure. The residue was purified by preparative HPLC using ammonia-water as mobile phase, yielding (5-(((5-chlorothiophen-2-yl)methyl)amino)-3-(3-methylpiperidin-3-yl)-1H-pyrazol-1-yl)(4-methyltetrahydro-2H-pyran-4-yl)methanone (Compound 13, 0.09 g, yield: 28%) m/z 436.81 [M+1]+ $^1$H NMR (400 MHz, DMSO) δ 8.29 (s, 1H), 7.67 (s, 1H), 6.99 (d, J=5.4 Hz, 2H), 5.53 (s, 1H), 4.44 (d, J=6.2 Hz, 2H), 3.69 (s, 2H), 3.48 (s, 2H), 3.10 (s, 1H), 2.72 (s, 2H), 2.34 (s, 2H), 1.94 (s, 1H), 1.70 (s, 2H), 1.52 (s, 5H), 1.14 (s, 3H) ppm.

Example 16—Preparation of Intermediate 3

The synthesis of Intermediate 3 followed the procedure of General Procedure 2 following:

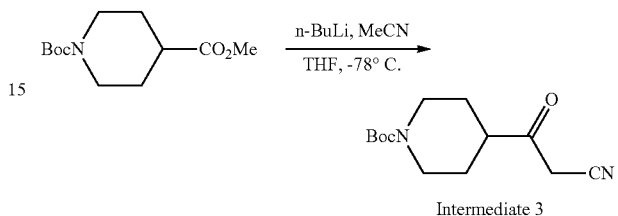

To a cooled solution (−78° C.) of acetonitrile (3.86 mL, 69.8 mmol, 1.7 eq) in tetrahydrofuran (150 mL) was added n-BuLi (2.5M in hexane, 27.9 mL, 69.8 mmol, 1.7 eq) dropwise over a period of 30 minutes, followed by stirring at −78° C. for a further 30 minutes. To this was then added 1-(tert-butyl) 4-methyl piperidine-1,4-dicarboxylate (10.0 g, 41.1 mmol, 1.0 eq) portionwise, and the mixture stirred at −78° C. for a further 3 hours. The reaction mixture was quenched with saturated aqueous ammonium chloride, then extracted with ethyl acetate. The organic phase were dried (sodium sulfate), filtered and evaporated to an oil, used without further purification (Intermediate 3, 9.28 g, yield: 89%) m/z 252.15.

Example 17—Preparation of Compound 14

The synthesis of Compound 14 followed the procedure of General Procedure 3 following:

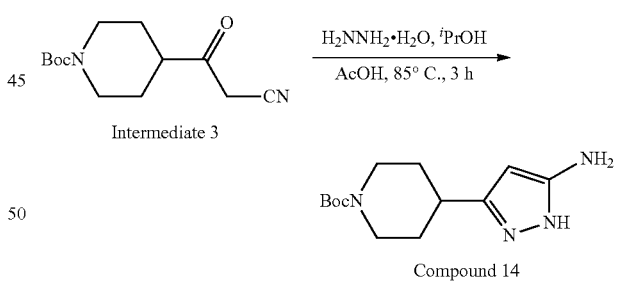

To a solution of tert-butyl 4-(2-cyanoacetyl)piperidine-1-carboxylate) (Intermediate 3, 7.0 g, 27.6 mmol, 1.0 eq) in isopropanol (210 mL) was added hydrazine monohydrate (1.65 mL, 33.2 mmol, 1.2 eq) dropwise, followed by the addition of acetic acid (1.65 mL, 27.6 mmol, 1.0 eq). The reaction mixture was stirred at 85° C. for 4-5 hours. After completion, the reaction mixture was evaporated under reduced pressure. The residue was purified by column chromatography using silica gel (60-120 mesh), eluting with 10-15% methanol in dichloromethane to yield tert-butyl 4-(5-amino-1H-pyrazol-3-yl)piperidine-1-carboxylate (Compound 14, 6.2 g, yield: 84%) m/z 266.17. $^1$H NMR (DMSO-d$_6$, 400 MHz) δ 5.182 (1H, s), 3.935-3.965 (2H, d), 3.172 (2H, s), 2.791 (1H, m), 1.747-1.802 (2H, d), 1.424 (9H, s), 1.361-1.402 (2H, d), 1.341-1.351 (1H, d) ppm.

Example 18—Preparation of Compound 15

The synthesis of Compound 15 followed the procedure of General Procedure 4 following:

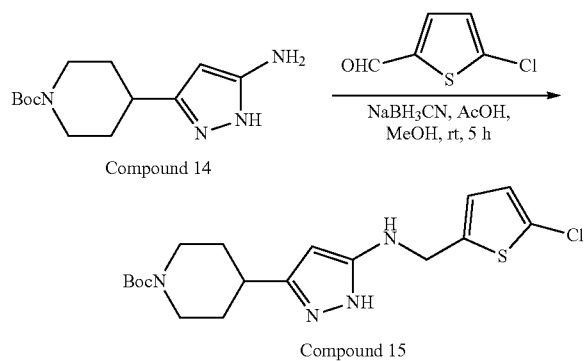

Compound 14

Compound 15

To a solution of tert-butyl 4-(5-amino-1H-pyrazol-3-yl)piperidine-1-carboxylate (Compound 14, 3.0 g, 11.3 mmol, 1.0 eq) in methanol (30 mL) was added acetic acid (0.67 mL, 11.3 mmol, 1.0 eq), followed by 5-chlorothiophene-2-carbaldehyde (1.81 g, 12.4 mmol, 1.1 eq) portionwise. The reaction was stirred for 2 hours at room temperature. To the reaction mixture was then added sodium cyanoborohydride (1.42 g, 22.6 mmol, 1.5 eq) portionwise over a period of 45 minutes. The reaction mixture was stirred for a further 3 hours. After reaction completion, the reaction mixture was concentrated under reduced pressure, and the residue was poured into stirred ice cold water and extracted with ethyl acetate. The organic layer was dried over sodium sulfate, filtered and evaporated under reduced pressure. The residue was purified by column chromatography using neutral silica gel, eluting with 5-10% methanol in dichloromethane, yielding tert-butyl 4-(5-(((5-chlorothiophen-2-yl)methyl)amino)-1H-pyrazol-3-yl)piperidine-1-carboxylate (Compound 15, 3.0 g, yield: 68%) m/z[M+H]+ 396.14 $^1$H NMR (DMSO-d$_6$, 400 MHz) δ 11.34 (1H, s), 6.87-6.94 (1H, q), 6.834-6.843 (1H, q), 5.68 (1H, s), 4.275-4.288 (1H, s), 3.945-3.975 (2H, d), 2.786-2.796 (2H, d), 2.623-2.681 (1H, d), 1.725-1.995 (2H, d), 1.402-1.559 (12H, m) ppm.

Example 19—Preparation of Compound 16

The synthesis of Compound 16 followed the procedure of General Procedure 5a following:

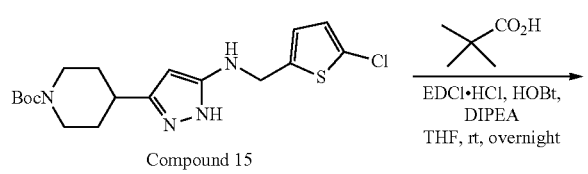

Compound 15

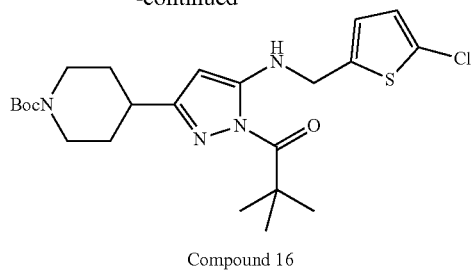

Compound 16

To a cooled solution (0° C.) of pivalic acid (0.19 g, 1.9 mmol, 1.5 eq) in THF (10 mL) was added diisopropylethylamine (DIPEA, 0.24 mL, 1.4 mmol, 1.5 eq) and then 1-(3-dimethylaminopropyl)-3-ethylcarbodiimide hydrochloride (EDCI.HCl, 0.365 g, 1.9 mmol, 1.5 eq). After stirring for a further 20 minutes, to the reaction mixture was added tert-butyl 4-(5-(((5-chlorothiophen-2-yl)methyl)amino)-1H-pyrazol-3-yl)piperidine-1-carboxylate (Compound 15, 0.5 g, 1.3 mmol, 1.0 eq), followed by hydroxybenzotriazole (HOBt, 0.035 g, 0.25 mmol, 0.2 eq). The reaction was stirred for 16 hours at room temperature. After completion, the reaction mixture was diluted with stirred ice cold water, and the product was extracted with ethyl acetate. The organic layer was dried over sodium sulfate, filtered and evaporated under reduced pressure. The residue was purified by column chromatography using silica gel (60-120 mesh, pre-rinsed with triethylamine) eluting with 20-40% ethyl acetate in hexane to yield tert-butyl 4-(5-(((5-chlorothiophen-2-yl)methyl)amino)-1-pivaloyl-1H-pyrazol-3-yl)piperidine-1-carboxylate (Compound 16, 0.5 g, yield: 83%) m/z[M+H]+ 480.20 1H NMR (DMSO-d6, 400 MHz) δ 7.691-7.66 (1H, t), 6.957-6.984 (2H, t), 5.415 (1H, s), 4.4-4.416 (2H, d), 3.916-3.948 (2H, d), 2.867 (2H, s), 2.624-2.681 (2H, m), 1.818-1.852 (2H, d), 1.402-1.484 (16H, s) ppm.

Example 20—Preparation of Compound 17

The synthesis of Compound 17 followed the procedure of General Procedure 6a following:

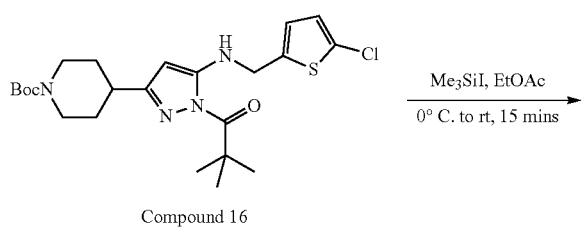

Compound 16

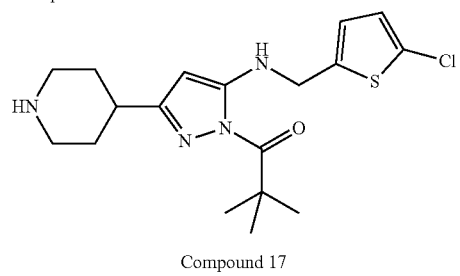

Compound 17

To a cooled solution (0° C.) of tert-butyl 4-(5-(((5-chlorothiophen-2-yl)methyl)amino)-1-pivaloyl-1H-pyrazol-3-yl)

piperidine-1-carboxylate (Compound 16, 0.5 g, 1.0 mmol, 1.0 eq) in ethyl acetate was added iodotrimethylsilane (0.148 g, 1.0 mmol, 1.0 eq) diluted in ethyl acetate dropwise. The reaction was stirred for 15 minutes with the temperature below 10° C. After reaction completion, the mixture was diluted with sodium bicarbonate solution under stirring and extracted with ethyl acetate. The organic layer was dried over sodium sulfate, filtered and concentrated under reduced pressure. The residue was purified by preparative HPLC method to yield 1-(5-(((5-chlorothiophen-2-yl)methyl)amino)-3-(piperidin-4-yl)-1H-pyrazol-1-yl)ethan-1-one (Compound 17, 0.042 g, yield: 10%) m/z[M+H]+ 380.14 1H NMR (DMSO-d6, 400 MHz) δ 8.473 (1H, s), 8.189 (1H, s), 7.733-7.764 (1H, t), 6.945-6.971 (2H, s), 5.39 (1H, d), 4.421-4.436 (2H, d), 3.289-3.344 (2H, d), 2.985-3.035 (2H, d), 2.896-2.736 (1H, m), 2.029-2.057 (2H, d), 1.715-1.782 (2H, d), 1.366-1.413 (9H, s) 1.247-1.127 (1H, m) ppm.

Example 21—Preparation of Intermediate 4

The synthesis of Intermediate 4 followed the procedure of General Procedure 7 following:

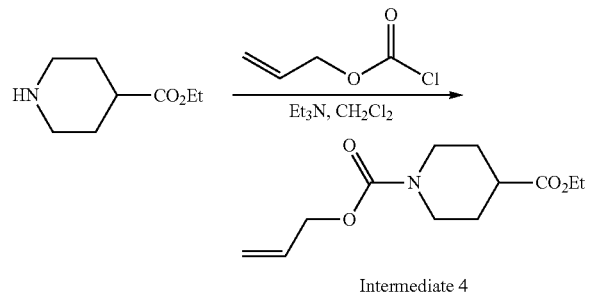

Intermediate 4

To a cooled solution (0° C.) of ethyl piperidine-4-carboxylate (10.0 g, 64.1 mmol, 1.0 eq) and triethylamine (6.4 g, 64.1 mmol, 1.0 eq) in dichloromethane (300 mL) was added allyl chloroformate (7.7 g, 64.1 mmol, 1.0 eq) dropwise. The reaction was stirred at room temperature for 16 hours. After completion, the mixture was diluted with ice cold water under stirring and extracted with dichloromethane (3×100 ml). The combined organic layers were dried over sodium sulfate, filtered and concentrated under reduced pressure. The residue was purified by column chromatography using silica gel (60-120 mesh) to furnish 1-allyl 4-ethyl piperidine-1,4-dicarboxylate (10.0 g, yield: 89%) m/z 241.13 1H NMR (400 MHz, CDCl3) δ 5.96-5.81 (m, 1H), 5.32-5.10 (m, 2H), 4.53 (dt, J=5.5, 1.4 Hz, 2H), 4.16-4.05 (m, 2H), 4.06-3.93 (m, 2H), 2.88 (s, 2H), 2.42 (tt, J=10.9, 3.9 Hz, 1H), 1.82 (dd, J=24.3, 8.9 Hz, 2H), 1.60 (dtd, J=13.6, 11.2, 4.3 Hz, 2H), 1.21 (t, J=7.1 Hz, 3H) ppm.

Example 22—Preparation of Intermediate 5

The synthesis of Intermediate 5 followed the procedure of General Procedure 2 following:

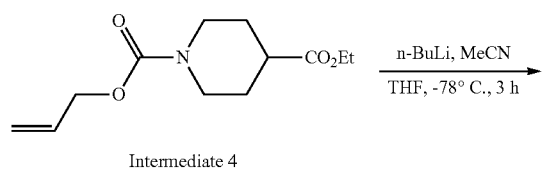

Intermediate 4

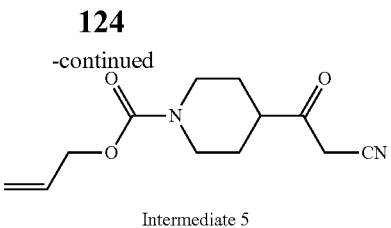

Intermediate 5

To a cooled solution (−78° C.) of acetonitrile (3.9 mL, 70.5 mmol, 1.7 eq) in tetrahydrofuran (150 mL) was added n-BuLi (2.5 M in hexane, 28.2 mL, 70.5 mmol, 1.7 eq) dropwise over a period of 30 minutes, followed by another period of stirring for 30 minutes. To this mixture, 1-allyl 4-ethyl piperidine-1,4-dicarboxylate (Intermediate 4, 10.0 g, 41.5 mmol, 1.0 eq) was added portionwise, and the reaction mixture maintained at −78° C. for 3 hours. The reaction was quenched with the addition of saturated aqueous ammonium chloride, and the product was extracted with ethyl acetate. After drying (sodium sulfate), the product was stirred in ethyl acetate/hexane mixture and then dried in vacuum to yield allyl 4-(2-cyanoacetyl)piperidine-1-carboxylate (Intermediate 5, 9.8 g, yield: 99%) m/z 236.12 1H NMR (400 MHz, CDCl3) δ 5.95 (ddd, J=22.7, 10.8, 5.6 Hz, 1H), 5.27 (ddd, J=13.8, 11.7, 1.4 Hz, 2H), 4.60 (d, J=5.5 Hz, 2H), 4.22 (s, 2H), 3.56 (s, 2H), 2.92 (s, 2H), 2.77 (tt, J=11.3, 3.7 Hz, 1H), 1.92 (d, J=11.4 Hz, 2H), 1.68-1.54 (m, 2H) ppm.

Example 23—Preparation of Compound 18

The synthesis of Compound 18 followed the procedure of General Procedure 3 following:

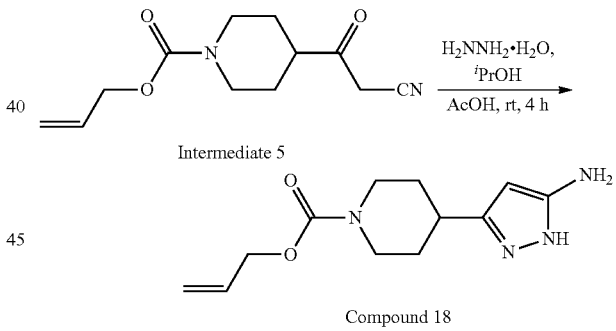

To a solution of allyl 4-(2-cyanoacetyl) piperidine-1-carboxylate (Intermediate 5, 9.5 g, 40.1 mmol, 1.0 eq) in isopropanol (285 mL) was added hydrazine monohydrate (2.0 mL, 40.1 mmol, 1.0 eq) dropwise, followed by acetic acid (2.88 mL, 48.1 mmol, 1.2 eq). The reaction was stirred at room temperature for 3-4 hours. After completion, the reaction mixture was concentrated under reduced pressure, and the residue was purified by column chromatography using silica gel (60-120 mesh), eluting with 10-15% methanol in dichloromethane to yield allyl 4-(5-amino-1H-pyrazol-3-yl)piperidine-1-carboxylate (Compound 18, 7.0 g, yield: 70%) m/z 250.14. 1H NMR (400 MHz, DMSO) δ 11.84-10.78 (m, 1H), 5.94 (ddd, J=22.4, 10.5, 5.2 Hz, 1H), 5.28 (d, J=17.3 Hz, 1H), 5.19 (d, J=6.0 Hz, 2H), 4.53 (d, J=5.1 Hz, 2H), 4.01 (d, J=13.1 Hz, 2H), 3.17 (s, 2H), 2.89 (s, 2H), 2.62 (dd, J=34.1, 22.6 Hz, 1H), 1.82 (d, J=12.7 Hz, 2H), 1.52-1.21 (m, 2H) ppm.

Example 24—Preparation of Compound 19

The synthesis of Compound 19 followed the procedure of General Procedure 4 following:

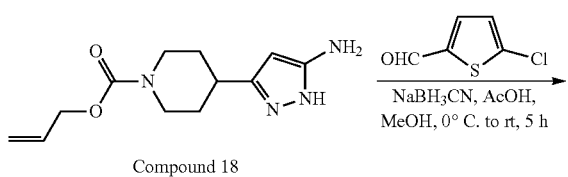

To a cooled solution (0° C.) of allyl 4-(5-amino-1H-pyrazol-3-yl)piperidine-1-carboxylate (Compound 18, 7.0 g, 28 mmol, 1.0 eq) in MeOH (140 mL) was added acetic acid (2.52 mL, 42 mmol, 1.5 eq), followed by 5-chlorothiophene-2-carbaldehyde (4.9 g, 33.6 mmol, 1.2 eq) portionwise. The reaction was stirred for 4-5 hours at room temperature. To this was then added sodium cyanoborohydride (3.5 g, 56 mmol, 2.0 eq) portionwise over a period of 45 minutes, and the reaction mixture was stirred for a further 4-5 hours. After completion of reaction, the reaction mixture was concentrated under reduced pressure, and the residual mass was poured into ice cold water under stirring. The produce was then extracted with ethyl acetate, and the organic layer was dried over sodium sulfate, filtered and concentrated under reduced pressure. The residue was purified by column chromatography using neutral silica gel, eluting with 2-4% methanol in dichloromethane to give pure allyl 4-(5-(((5-chlorothiophen-2-yl)methyl)amino)-1H-pyrazol-3-yl)piperidine-1-carboxylate (Compound 19, 4.5 g, yield: 45%) m/z[M+H]+ 380.11 1H NMR (400 MHz, DMSO) δ 11.41 (s, 1H), 6.88 (dd, J=30.0, 3.7 Hz, 2H), 5.94 (ddd, J=22.4, 10.5, 5.2 Hz, 1H), 5.68 (d, J=6.2 Hz, 1H), 5.28 (dd, J=16.4, 2.5 Hz, 2H), 5.19 (dd, J=10.5, 1.5 Hz, 1H), 4.60-4.46 (m, 2H), 4.28 (d, J=6.1 Hz, 2H), 4.12 (d, J=4.8 Hz, 1H), 4.02 (d, J=13.2 Hz, 2H), 3.17 (d, J=4.0 Hz, 2H), 2.90 (s, 2H), 2.69 (t, J=11.6 Hz, 1H) ppm.

Example 25—Preparation of Compound 20

5 [0260] The synthesis of Compound 20 followed the procedure of General Procedure 5a following:

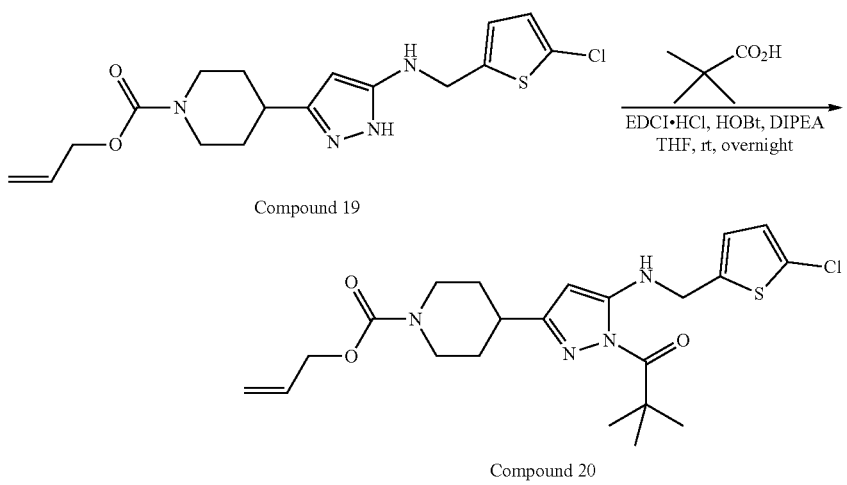

To a cooled solution (0° C.) of pivalic acid (0.644 g, 6.3 mmol, 1.2 eq) in THF (10 mL) was added diisopropylethylamine (DIEA, 1.38 mL, 7.9 mmol, 1.5 eq) and then 1-(3-dimethylaminopropyl)-3-ethylcarbodiimide hydrochloride (EDCI.HCl, 1.52 g, 7.9 mmol, 1.5 eq). After stirring for 20 minutes, allyl 4-(5-(((5-chlorothiophen-2-yl)methyl)amino)-1H-pyrazol-3-yl)piperidine-1-carboxylate (Compound 19, 2.0 g, 5.3 mmol, 1.0 eq) was added, followed by hydroxybenzotriazole (HOBt, 0.142 g, 1.05 mmol, 0.2 eq). The reaction was stirred for 16 hours at room temperature. After completion, the reaction mixture was diluted with stirred ice cold water, and then extracted with ethyl acetate. The organic layer was dried over sodium sulfate, filtered and evaporated under reduced pressure. The residue was purified by column chromatography using silica gel (60-120 mesh) pre-washed with triethylamine, and the product was eluted with 2-5% ethyl acetate in hexane to give allyl 4-(5-(((5-chlorothiophen-2-yl) methyl)amino)-1-pivaloyl-1H-pyrazol-3-yl)piperidine-1-carboxylate (Compound 20, 1.5 g, yield: 61%) m/z[M+H]+ 464.16 1H NMR (400 MHz, DMSO) δ 7.69 (t, J=6.2 Hz, 1H), 6.97 (dd, J=8.1, 3.7 Hz, 2H), 5.94 (ddd, J=22.4, 10.4, 5.2 Hz, 1H), 5.42 (s, 1H), 5.28 (dd, J=17.2, 1.5 Hz, 1H), 5.19 (d, J=10.5 Hz, 1H), 4.53 (d, J=5.1 Hz, 2H), 4.41 (d, J=6.1 Hz, 2H), 3.99 (d, J=13.2 Hz, 2H), 2.96 (s, 2H), 2.69 (t, J=11.0 Hz, 1H), 1.86 (d, J=11.1 Hz, 2H), 1.56-1.44 (m, 2H), 1.40 (s, 9H) ppm.

-continued

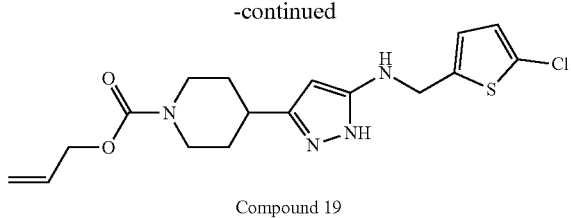

Example 26—Preparation of Compound 21

The synthesis of Compound 21 followed the procedure of General Procedure 8a following:

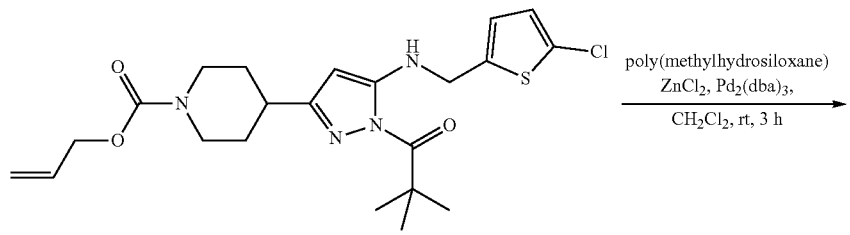

Compound 20

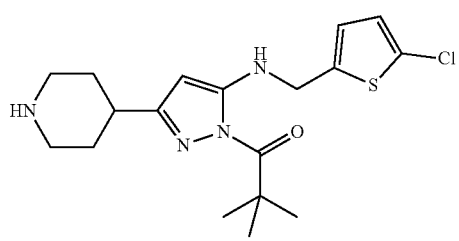

Compound 21

A solution of allyl 4-(5-(((5-chlorothiophen-2-yl)methyl)amino)-1-pivaloyl-1H-pyrazol-3-yl)piperidine-1-carboxylate (Compound 20, 0.1 g, 0.22 mmol, 1.0 eq) and zinc chloride (0.003 g, 21.6 mmol, 0.1 eq) in dichloromethane (10 mL) was degassed with a nitrogen stream for 15 minutes. To the mixture was then added tris(dibenzylideneacetone)dipalladium(0) (Pd$_2$(dba)$_3$, 0.0098 g, 0.011 mmol, 0.05 eq), and then solution again degassed with a nitrogen stream for 15 minutes. Poly(methylhydrosiloxane) (PMHS, 0.818 g, 0.43 mmol, 2.0 eq) was then added dropwise at room temperature, and the reaction mixture was stirred for 3-4 hours at room temperature. After completion, the reaction mixture was filtered through Celite®, and the solvent then evaporated solvent under reduced pressure. To the residue was added hexane and then acetonitrile, and the mixture then stirred for 10 minutes. The black particles were filtered, and the acetonitrile and hexane layers were separated. The acetonitrile layer was washed with hexane 3 times and the solvent evaporated. The residue was purified by preparative HPLC to yield 1-(5-(((5-chlorothiophen-2-yl)methyl)amino)-3-(piperidin-4-yl)-1H-pyrazol-1-yl)-2,2-dimethylpropan-1-one (Compound 21, 0.0375 g, yield: 32%) m/z[M+H]+ 380.14 1H NMR (400 MHz, DMSO) δ 8.36 (s, 1H), 7.72 (t, J=6.2 Hz, 1H), 6.97 (s, 2H), 5.38 (s, 1H), 4.42 (d, J=6.1 Hz, 2H), 3.21 (d, J=12.6 Hz, 2H), 2.88 (dd, J=12.2, 9.6 Hz, 2H), 2.75 (dd, J=12.9, 9.4 Hz, 1H), 1.98 (d, J=11.2 Hz, 2H), 1.76-1.61 (m, 2H), 1.41 (s, 9H) ppm.

Example 27—Preparation of Intermediate 6

The synthesis of Intermediate 6 followed the procedure of General Procedure 9 following:

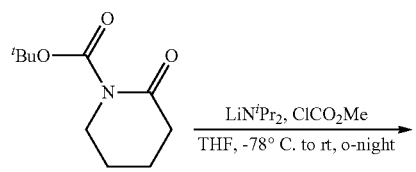

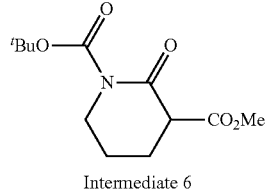

Intermediate 6

To a cooled solution (−78° C.) of diisopropylamine (8.74 g, 86.4 mmol, 1.6 eq) in THF (200 mL) was added n-BuLi (34.5 mL, 86.4 mmol, 1.6 eq), and the mixture stirred for 1 hour at 0° C. The mixture was cooled to −78° C. and to it was added tert-butyl 2-oxopiperidine-1-carboxylate (10.0 g, 54.0 mmol, 1.0 eq). The mixture was stirred for 1 hour and methyl chloroformate (6.12 g, 64.8 mmol, 1.2 eq) was added. The reaction mixture was allowed to warm to room temperature overnight, and was monitored by TLC and LC-MS. After completion, the reaction mixture was quenched with ammonium chloride and evaporated under reduced pressure. The residue was extracted with ethyl acetate (2×150 mL), and the combined organic phases were washed with water, brine, dried over anhydrous sodium sulfate, filtered and evaporated under reduced pressure. The residue was purified by flash chromatography using silica gel (60-120 mesh) eluting with 40% ethyl acetate in n-hexane to yield 1-(tert-butyl)-3-methyl-2-oxopiperidine-1,3-dicarboxylate (Intermediate 6, 9.2 g, yield: 70%) m/z 202.13 [M−56]+; 1H NMR (400 MHz, DMSO) δ 3.70 (s, 1H), 3.62-3.50 (m, 3H), 2.10-1.89 (m, 2H), 1.88-1.72 (m, 2H), 1.42 (s, 9H) ppm.

Example 28—Preparation of Intermediate 7

The synthesis of Intermediate 7 followed the procedure of General Procedure 1 following:

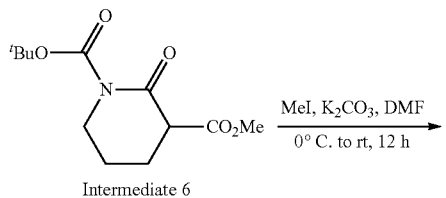

Intermediate 6

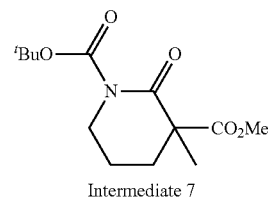

Intermediate 7

To a cooled solution (0° C.) of 1-(tert-butyl)-3-methyl-2-oxopiperidine-1,3-dicarboxylate (Intermediate 6, 10.0 g, 38.9 mmol, 1.0 eq) in DMF (100 mL) was added potassium carbonate (27.0 g. 194 mmol, 5.0 eq), and the reaction mixture stirred for 1 hour. To the mixture was added methyl iodide (6.62 g, 46.7 mmol, 1.2 eq). The reaction mixture was allowed to come at room temperature and stirred overnight. After completion, the reaction mixture was poured into ice-cold water and filtered to yield product 1-(tert-butyl)-3-methyl-3-methyl-2-oxopiperidine-1,3-dicarboxylate (Intermediate 7, 7.91 g, yield: 75%) m/z 272.2 [M+1]$^+$; $^1$H NMR (400 MHz, DMSO) δ 3.72-3.61 (m, 4H), 3.56-3.45 (m, 1H), 2.17 (d, J=8.0 Hz, 1H), 1.78 (dd, J=17.4, 12.4 Hz, 3H), 1.45 (s, 9H), 1.36 (s, 3H) ppm.

Example 29—Preparation of Intermediate 8

The synthesis of Intermediate 8 followed the procedure of General Procedure 6b following:

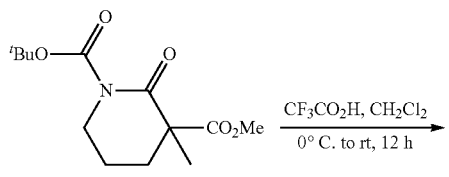

Intermediate 7

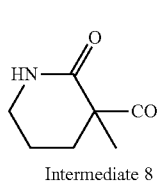

Intermediate 8

To a cooled solution (0° C.) of 1-(tert-butyl)-3-methyl-3-methyl-2-oxopiperidine-1,3-dicarboxylate (Intermediate 7, 5.0 g, 18.4 mmol, 1.0 eq) in dichloromethane (50 mL) was added trifluoroacetic acid (2.5 mL), and the reaction mixture stirred for 1 hour at 0° C. The reaction mixture was allowed to warm to room temperature overnight. After reaction completion, the reaction mixture was treated with saturated NaHCO$_3$ and extracted with dichloromethane (2×50 mL). The combined organic layers were washed with brine, dried over anhydrous sodium sulfate and evaporated under reduced pressure to yield methyl 3-methyl-2-oxopiperidine-3-carboxylate (Intermediate 8, 2.8 g yield: 89%); m/z 173.16 [M+2]$^+$; $^1$H NMR (400 MHz, DMSO) δ 7.94 (s, 1H), 3.63 (s, 3H), 3.32-3.14 (m, 2H), 2.58-2.37 (m, 2H), 2.04-1.99 (m, 2H), 1.26 (s, 3H) ppm.

Example 30—Preparation of Intermediate 9

The synthesis of Intermediate 9 followed the procedure of General Procedure 2 following:

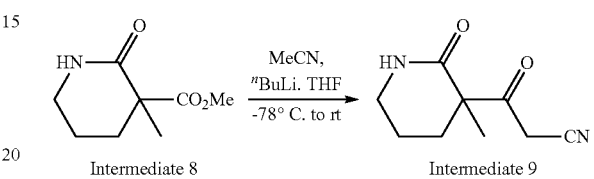

To a cooled (−78° C.) solution of acetonitrile (1.0 g, 24.3 mmol, 1.6 eq) in tetrahydrofuran (30 mL) was added n-BuLi (2.5M in hexane, 9.73 mL, 24.3 mmol, 1.6 eq) dropwise over a period of 20 minutes. The reaction was stirred for another 60 minutes at −78° C. To the mixture was added methyl 3-methyl-2-oxopiperidine-3-carboxylate (Intermediate 8, 2.6 g, 15.2 mmol, 1.0 eq) portionwise, and the solution stirred at −78° C. for 3 hours. The mixture was quenched with saturated ammonium chloride solution and extracted with ethyl acetate. The organic layer was dried over anhydrous sodium sulfate, filtered and concentrated under reduced pressure. The residue was purified by column chromatography using silica gel (60-120 mesh size), eluting with 70% ethyl acetate in n-hexane, to give 3-(3-methyl-2-oxopiperidin-3-yl)-3-oxopropanenitrile (Intermediate 9, 2.41 g, yield: 88%) m/z 181.11 [M+1]$^+$; $^1$H NMR (400 MHz, DMSO) δ 7.89 (s, 1H), 4.39-4.05 (m, 2H), 3.27-3.06 (m, 2H), 2.14 (ddd, J=19.7, 10.0, 5.2 Hz, 1H), 1.80-1.60 (m, 2H), 1.60-1.43 (m, 1H), 1.32 (s, 3H) ppm.

Example 31—Preparation of Compound 22

The synthesis of Compound 22 followed the procedure of General Procedure 3 following:

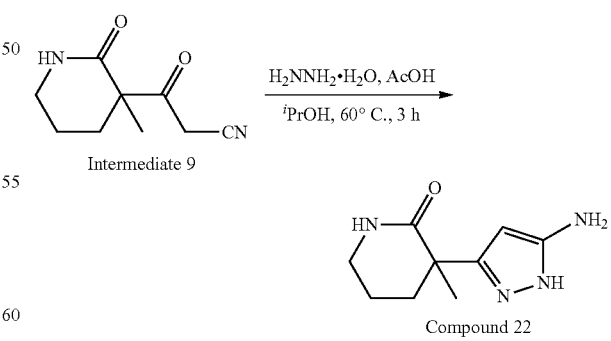

To a solution of 3-(3-methyl-2-oxopiperidin-3-yl)-3-oxopropanenitrile (Intermediate 9, 2.0 g, 11.0 mmol, 1.0 eq) in isopropanol (10 mL) and acetic acid (2.0 mL) was added hydrazine monohydrate (0.825 g, 16.5 mmol, 1.5 eq) dropwise, and the reaction then stirred at 60° C. for 3 hours. The reaction mixture was monitored by TLC and LC-MS, and after completion concentrated under reduced pressure. The residue was purified by column chromatography using silica gel (60-120 mesh), eluting with 0-5% methanol in dichloromethane to give 3-(5-amino-1H-pyrazol-3-yl)-3-methylpiperidin-2-one (Compound 22, 1.16 g, yield: 54%); m/z 195.19 [M+1]$^+$.

Example 32—Preparation of Compound 23

The synthesis of Compound 23 followed the procedure of General Procedure 4 following:

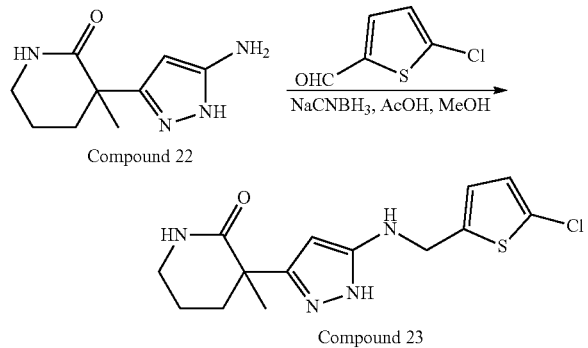

To a cooled solution (0° C.) of 3-(5-amino-1H-pyrazol-3-yl)-3-methylpiperidin-2-one (Compound 22, 1.0 g, 5.15 mmol, 1.0 eq) in methanol (20 mL) was added acetic acid (0.3 g, 5.15 mmol, 1.0 eq) dropwise. To the mixture was added 5-chlorothiophene-2-carbaldehyde (0.91 g, 6.18 mmol, 1.2 eq) dropwise and the mixture was warmed to room temperature over 45 minutes. Sodium cyanoborohydride (0.644 g, 10.3 mmol, 2.0 eq) was added portionwise over a period of 15 minutes, and the reaction mixture was stirred at room temperature for 12 hours. After completion of reaction, the mixture was concentrated under reduced pressure. The residue was purified by column chromatography using silica gel (60-100 mesh), eluting with 0-5% methanol in dichloromethane to give 3-(5-(((5-chlorothiophen-2-yl)methyl)amino)-1H-pyrazol-3-yl)-3-methylpiperidin-2-one (Compound 23, 0.686 g, yield: 41%); m/z 325.25; $^1$H NMR (400 MHz, DMSO) δ 11.26 (s, 1H), 7.50 (s, 1H), 6.88 (dd, J=31.3, 3.6 Hz, 2H), 5.66 (s, 1H), 5.30 (s, 1H), 4.29 (d, J=6.2 Hz, 2H), 3.14 (s, 2H), 2.10 (s, 1H), 1.65 (s, 3H), 1.37 (s, 3H) ppm.

Example 33—Preparation of Compound 24

The synthesis of Compound 24 followed the procedure of General Procedure 5a following:

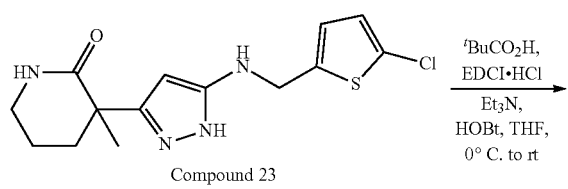

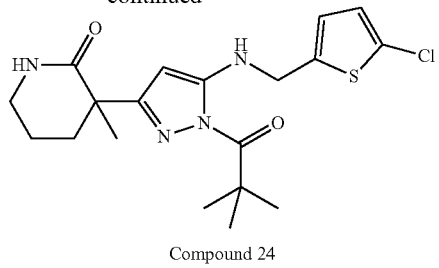

To a cooled solution (0° C.) of pivalic acid (0.188 g, 1.84 mmol, 1.5 eq) in THF (15 mL) under nitrogen was added 1-(3-dimethylaminopropyl)-3-ethylcarbodiimide hydrochloride (EDCI.HCl, 0.352 g, 1.84 mmol, 1.5 eq), followed by triethylamine (TEA, 0.373 g, 3.69 mmol, 3.0 eq). The reaction mixture was stirred for 30 minutes, then to the mixture was added hydroxybenzotriazole (HOBt, 0.033 g, 0.24 mmol, 0.2 eq), followed by 3-(5-(((5-chlorothiophen-2-yl)methyl)amino)-1H-pyrazol-3-yl)-3-methylpiperidin-2-one (Compound 23, 0.4 g, 1.23 mmol, 1.0 eq). The reaction was monitored by LC-MS, and after completion the reaction mixture was poured into water (50 mL) and extracted with ethyl acetate (3×25 mL). The combined organic phases were washed with water, brine, dried over anhydrous sodium sulfate, filtered and evaporated under reduced pressure. The residue was purified by preparative HPLC using acetonitrile-water as mobile phase to give product 3-(5-(((5-chlorothiophen-2-yl)methyl)amino)-1-pivaloyl-1H-pyrazol-3-yl)-3-methylpiperidin-2-one (Compound 24, 0.21 g, yield: 42%) m/z 408.95 [M+1]$^+$; $^1$H NMR (400 MHz, DMSO) δ 7.62 (t, J=6.2 Hz, 1H), 7.53 (s, 1H), 6.96 (dd, J=12.1, 3.7 Hz, 2H), 5.42 (s, 1H), 4.41 (d, J=6.1 Hz, 2H), 3.25-3.06 (m, 2H), 2.29-2.17 (m, 1H), 1.73 (ddd, J=21.5, 11.1, 7.2 Hz, 3H), 1.41 (s, 9H), 1.37 (s, 3H) ppm.

Example 34—Preparation of Compound 25

The synthesis of Compound 25 followed the procedure of General Procedure 5c following:

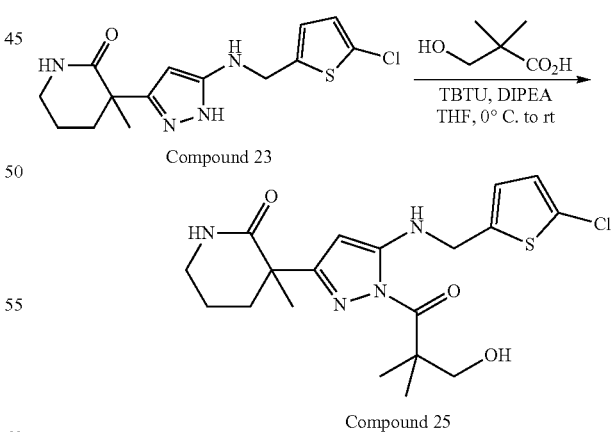

To a cooled solution (0° C.) of 3-hydroxy-2,2-dimethylpropanoic acid (0.130 g, 1.1 mmol, 1.2 eq) in THF (10 mL) under nitrogen was added N,N,N',N'-tetramethyl-O-(benzotriazol-1-yl)uronium tetrafluoroborate (TBTU, 0.320 g, 1.0 mmol, 1.1 eq) and diisopropylethylamine (DIEA, 0.280 g, 2.9 mmol, 3.0 eq). The reaction mixture was stirred for 30 minutes, and to it was added 3-(5-(((5-chlorothiophen-2-yl)methyl)amino)-1H-pyrazol-3-yl)-3-methylpiperidin-2-one (Compound 23, 0.3 g, 0.9 mmol, 1.0 eq). The reaction was monitored by LC-MS, and after completion the mixture was poured into water (40 mL) and extracted with ethyl acetate (3×25 mL). The combined organic phases were washed with water, brine, dried over anhydrous sodium sulfate, filtered and evaporated under reduced pressure. The residue was purified by preparative HPLC using acetonitrile-water as mobile phase to give desired product 3-(5-(((5-chlorothiophen-2-yl)methyl)amino)-1-(3-hydroxy-2,2-dimethylpropanoyl)-1H-pyrazol-3-yl)-3-methylpiperidin-2-one (Compound 25, 0.0129 g, yield: 3%) m/z 425.30 [M+1]$^+$; $^1$H NMR (400 MHz, CD$_3$CN) δ 7.48 (s, 1H), 6.88 (q, J=3.8 Hz, 2H), 6.10 (s, 1H), 5.44 (s, 1H), 4.45 (d, J=6.2 Hz, 2H), 3.89 (d, J=6.2 Hz, 2H), 3.43 (t, J=6.2 Hz, 1H), 3.27 (d, J=6.6 Hz, 2H), 2.34-2.23 (m, 1H), 1.91-1.70 (m, 3H), 1.49-1.34 (m, 3H), 1.30 (s, 6H) ppm.

Example 35—Preparation of Compound 26

The synthesis of Compound 26 followed the procedure of General Procedure 5c following:

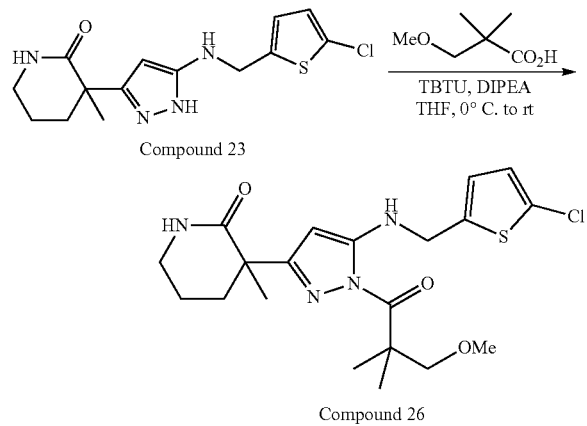

To a cooled solution (0° C.) of 3-methoxy-2,2-dimethylpropanoic acid (0.134 g, 1.0 mmol, 1.1 eq) in THF (12 mL) under nitrogen was added N,N,N',N'-tetramethyl-O-(benzotriazol-1-yl)uronium tetrafluoroborate (TBTU, 0.326 g, 1.0 mmol, 1.1 eq) and diisopropylethylamine (DIPEA, 0.280 g, 2.8 mmol, 3.0 eq). The reaction mixture was stirred for 30 minutes, and to it was added 3-(5-(((5-chlorothiophen-2-yl)methyl)amino)-1H-pyrazol-3-yl)-3-methylpiperidin-2-one (Compound 23, 0.3 g, 0.92 mmol, 1.0 eq). The reaction was monitored by LC-MS, and after completion the mixture was poured into water (30 mL) and extracted with ethyl acetate (3×25 mL). The combined organic phases were washed with water, brine, dried over anhydrous sodium sulfate, filtered and evaporated under reduced pressure. The residue was purified by preparative HPLC using acetonitrile-water as mobile phase to give 3-(5-(((5-chlorothiophen-2-yl)methyl)amino)-1-(3-methoxy-2,2-dimethylpropanoyl)-1H-pyrazol-3-yl)-3-methylpiperidin-2-one (Compound 26, 0.061 g, yield: 15%); m/z 439.21 [M+1]$^+$; $^1$H NMR (400 MHz, DMSO) δ 7.59 (s, 1H), 7.54 (s, 1H), 6.96 (t, J=6.9 Hz, 2H), 5.42 (s, 1H), 4.41 (d, J=6.0 Hz, 2H), 3.83 (d, J=5.1 Hz, 2H), 3.13 (s, 3H), 2.22 (s, 1H), 1.70 (s, 3H), 1.40-1.29 (m, 6H) ppm.

Example 36—Preparation of Compound 27

The synthesis of Compound 27 followed the procedure of General Procedure 5a following:

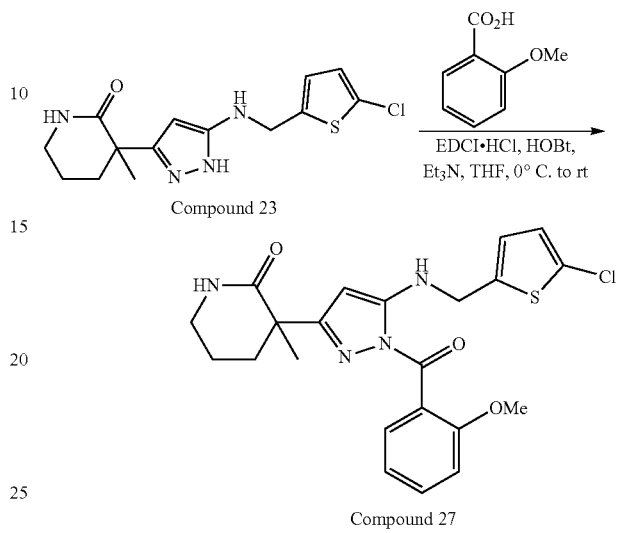

To a cooled solution (0° C.) of 2-methoxybenzoic acid (0.351 g, 2.3 mmol, 1.5 eq) in THF (15 mL) under nitrogen was added 1-(3-dimethylaminopropyl)-3-ethylcarbodiimide hydrochloride (EDCI.HCl, 0.441 g, 2.3 mmol, 1.5 eq) and then triethylamine (TEA, 0.467 g, 4.6 mmol, 3.0 eq). The reaction mixture was stirred for 30 minutes, and to it was added hydroxybenzotriazole (HOBt, 0.041 g, 0.3 mmol, 0.2 eq) followed by 3-(5-(((5-chlorothiophen-2-yl)methyl)amino)-1H-pyrazol-3-yl)-3-methylpiperidin-2-one (Compound 23, 0.5 g, 1.53 mmol, 1.0 eq). The reaction was monitored by LC-MS, and after completion the reaction mixture was poured into water (5 mL) and extracted with ethyl acetate (3×25 mL). The combined organic phases were washed with water, brine, dried over anhydrous sodium sulfate, filtered and evaporated under reduced pressure. The residue was purified by preparative HPLC using ammonia-water as mobile phase to give desired product 3-(5-(((5-chlorothiophen-2-yl)methyl)amino)-1-(2-methoxybenzoyl)-1H-pyrazol-3-yl)-3-methylpiperidin-2-one (Compound 27, 0.23 g, yield: −32%); m/z 458.91 [M+1]$^+$; $^1$H NMR (400 MHz, DMSO) δ 7.59 (t, J=6.0 Hz, 1H), 7.55-7.34 (m, 3H), 7.12 (d, J=8.3 Hz, 1H), 7.01 (dd, J=13.4, 5.8 Hz, 2H), 5.48 (s, 1H), 4.48 (d, J=6.0 Hz, 2H), 3.73 (s, 3H), 3.07 (s, 2H), 2.15-1.94 (m, 2H), 1.73-1.45 (m, 3H), 1.25 (s, 3H) ppm.

Example 37—Preparation of Compound 28

The synthesis of Compound 28 followed the procedure of General Procedure 5a following:

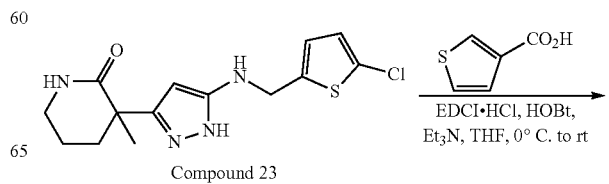

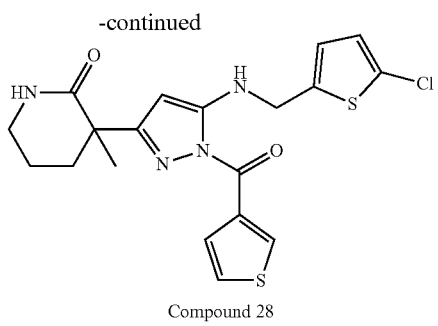

Compound 28

To a cooled solution (0° C.) of 3-thiophene carboxylic acid (0.177 g, 1.38 mmol, 1.5 eq) in THF (15 mL) under nitrogen was added 1-(3-dimethylaminopropyl)-3-ethylcarbodiimide hydrochloride (EDCI.HCl, 0.264 g, 1.38 mmol, 1.5 eq) and then triethylamine (TEA, 0.28 g, 2.77 mmol, 3.0 eq). The reaction mixture was stirred for 30 minutes, and to it was added hydroxybenzotriazole (HOBt, 0.024 g, 0.18 mmol, 0.2 eq) followed by 3-(5-(((5-chlorothiophen-2-yl)methyl)amino)-1H-pyrazol-3-yl)-3-methylpiperidin-2-one (Compound 23, 0.3 g, 0.92 mmol, 1.0 eq). The reaction was monitored by LC-MS, and after completion the reaction mixture was poured into water (30 mL) and extracted with ethyl acetate (3×25 mL). The combined organic phases were washed with water, brine, dried over anhydrous sodium sulfate, filtered and evaporated under reduced pressure. The residue was purified by preparative HPLC using ammonia-water as mobile phase to yield desired product 3-(5-(((5-chlorothiophen-2-yl)methyl)amino)-1-(thiophene-3-carbonyl)-1H-pyrazol-3-yl)-3-methylpiperidin-2-one (Compound 28, 0.12 g, yield: 30%) m/z 436.06 [M+1]$^+$; $^1$H NMR (400 MHz, DMSO) δ 8.90 (d, J=2.4 Hz, 1H), 7.90-7.49 (m, 4H), 6.98 (s, 2H), 5.55 (s, 1H), 4.49 (d, J=6.2 Hz, 2H), 3.18 (s, 2H), 2.23 (d, J=10.4 Hz, 1H), 1.75 (d, J=10.8 Hz, 3H), 1.42 (s, 3H) ppm.

Example 38—Preparation of Compound 29

The synthesis of Compound 29 followed the procedure of General Procedure 5a following:

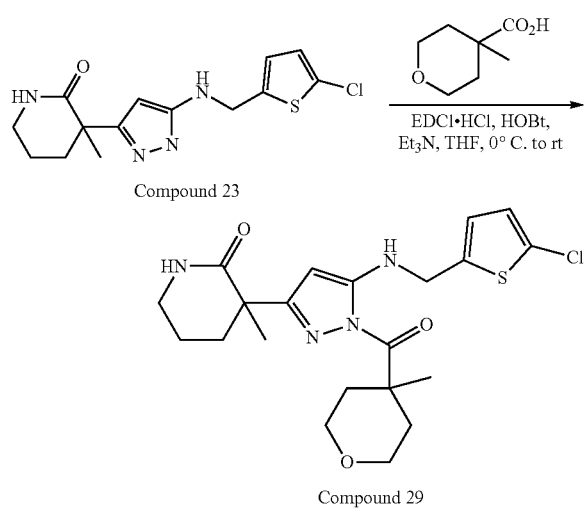

To a cooled solution (0° C.) of 4-methyltetrahydro-2H-pyran-4-carboxylic acid (0.2 g, 1.4 mmol, 1.5 eq) in THF (15 mL) under nitrogen was added 1-(3-dimethylaminopropyl)-3-ethylcarbodiimide hydrochloride (EDCI.HCl, 0.265 g, 1.4 mmol, 1.5 eq) and then triethylamine (TEA, 0.283 g, 2.8 mmol, 3.0 eq). The reaction mixture was stirred for 30 minutes, and to it was added hydroxybenzotriazole (HOBt, 0.025 g, 0.19 mmol, 0.2 eq) and 3-(5-(((5-chlorothiophen-2-yl)methyl)amino)-1H-pyrazol-3-yl)-3-methylpiperidin-2-one (Compound 23, 0.3 g, 0.92 mmol, 1.0 eq). The reaction was stirred for 2 days and monitored by LC-MS. After completion reaction the mixture was poured into water (40 mL) and extracted with ethyl acetate (3×25 mL). The combined organic phases were washed with water, brine, dried over anhydrous sodium sulfate, filtered and evaporated under reduced pressure. The residue was purified by preparative HPLC using acetonitrile-water as mobile phase to give desired product 3-(5-(((5-chlorothiophen-2-yl)methyl)amino)-1-(1-methylcyclohexane-1-carbonyl)-1H-pyrazol-3-yl)-3-methylpiperidin-2-one (Compound 29, 0.052 g, yield: 13%) m/z 450.96 [M+2]$^+$; $^1$H NMR (400 MHz, DMSO) δ 7.65 (t, J=6.3 Hz, 1H), 7.53 (s, 1H), 6.96 (dd, J=11.0, 3.7 Hz, 2H), 5.43 (s, 1H), 4.42 (d, J=6.1 Hz, 2H), 3.81-3.60 (m, 2H), 3.45 (dd, J=11.8, 8.8 Hz, 2H), 3.14 (s, 2H), 2.34 (s, 2H), 2.18 (d, J=9.3 Hz, 1H), 1.70 (d, J=8.5 Hz, 5H), 1.51 (s, 3H), 1.36 (s, 3H) ppm.

Example 39—Preparation of Intermediate 10

The synthesis of Intermediate 10 followed the procedure of General Procedure 9 following:

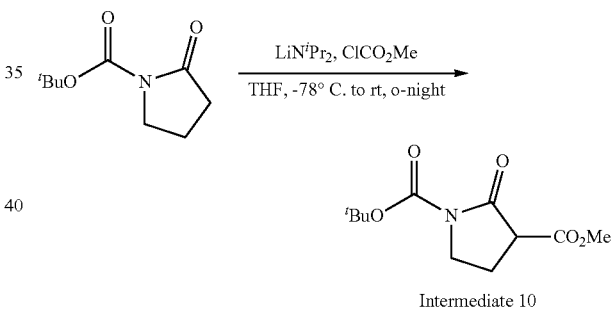

Intermediate 10

To a cooled solution (−78° C.) of diisopropylamine (8.74 g, 86.4 mmol, 1.6 eq) in anhydrous THF (200 mL) was added n-BuLi (34.5 mL, 86.4 mmol, 1.6 eq), followed by stirring at 0° C. for 1 hour. The mixture was re-cooled to −78° C. and to it was added tert-butyl-2-oxopyrrolidine-1-carboxylate (10.0 g, 54 mmol, 1.0 eq) portionwise, stirred for 1 hour and to it added methyl chloroformate (6.12 g, 64.8 mmol, 1.2 eq). The reaction mixture was allowed to come at room temperature and stirred overnight. It was monitored by TLC and LC-MS. After completion, the reaction mixture was quenched with ammonium chloride and evaporated to a residue, which was extracted with ethyl acetate (2×150 mL). The combined organic phases were washed with water, brine, dried over anhydrous sodium sulfate, filtered and evaporated under reduced pressure. The residue was purified by flash chromatography using silica gel (60-120 mesh) eluting with 40% ethyl acetate in n-hexane to give 1-(tert-butyl) 3-methyl 2-oxopyrrolidine-1,3-dicarboxylate (Intermediate 10, 9.46 g, yield: 45%) m/z 188.17 [M−56]+; 1H NMR (400 MHz, CDCl3) δ 3.90 (ddd, J=10.8, 8.5, 5.4 Hz, 1H), 3.81 (s, 3H), 3.73 (ddd, J=10.8, 8.1, 6.6 Hz, 1H), 3.62-3.52 (m, 1H), 2.50-2.34 (m, 1H), 2.25 (dddd, J=13.3, 9.1, 8.1, 5.4 Hz, 1H), 1.55 (s, 9H) ppm.

Example 40—Preparation of Intermediate 11

The synthesis of Intermediate 11 followed the procedure of General Procedure 1 following:

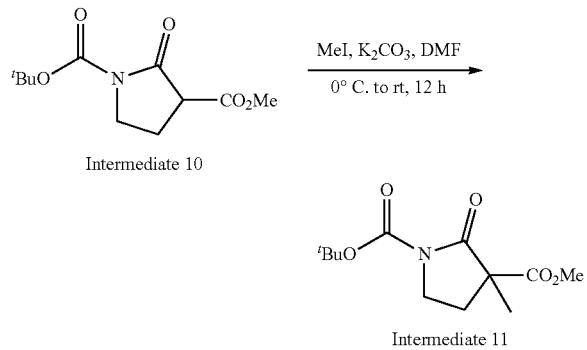

To a cooled solution (0° C.) of 1-(tert-butyl)-3-methyl-2-oxopyrrolidine-1,3-dicarboxylate (Intermediate 10, 10.0 g, 41.1 mmol, 1.0 eq) in DMF (100 mL) was added potassium carbonate (28.4 g, 205.5 mmol, 5.0 eq). After stirring for 1 hour at 0° C., methyl iodide (7.02 g, 49.3 mmol, 1.2 eq) was added. The reaction mixture was allowed to come at room temperature and stirred overnight. It was monitored by TLC and LC-MS. After completion, the reaction mixture was poured into ice-cooled water and filtered to yield 1-(tert-butyl)-3-methyl 3-methyl-2-oxopyrrolidine-1,3-dicarboxylate (Intermediate 11, 7.3 g, yield: 69%) m/z 202.13 [M−56]+ $^1$H NMR (400 MHz, CDCl3) δ $^1$H NMR (400 MHz, CDCl$_3$) δ 3.78 (d, J=6.0 Hz, 5H), 2.54 (ddd, J=13.0, 7.4, 4.3 Hz, 1H), 1.91 (dt, J=13.1, 8.2 Hz, 1H), 1.54 (d, J=11.7 Hz, 9H), 1.49 (d, J=11.6 Hz, 3H) ppm.

Example 41—Preparation of Intermediate 12

The synthesis of Intermediate 12 followed the procedure of General Procedure 6b following:

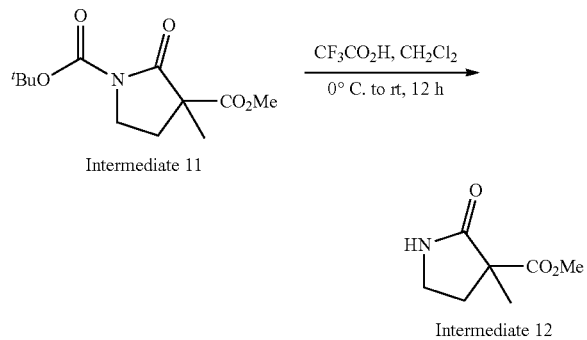

To a cooled solution (0° C.) of 1-(tert-butyl)-3-methyl-3-methyl-2-oxopiperidine-1,3-dicarboxylate (Intermediate 11, 5.0 g, 19.4 mmol, 1.0 eq.) in dichloromethane (50 mL) was added trifluoroacetic acid (2.5 mL). After stirring for 1 hour, the mixture was allowed to come to room temperature overnight. It was monitored by TLC and LC-MS. After completion, the reaction mixture was treated with saturated solution of NaHCO$_3$ and extracted with dichloromethane (2×50 mL). The combined organic layers were washed with brine, dried over anhydrous sodium sulfate, filtered and concentrated to give methyl 3-methyl-2-oxopyrrolidine-3-carboxylate (Intermediate 12, 2.26 g, yield: 74%) m/z 158.04 [M+1]+ $^1$H NMR (400 MHz, DMSO) δ $^1$H NMR (400 MHz, DMSO) δ 7.94 (s, 1H), 3.63 (s, 3H), 3.32-3.14 (m, 2H), 2.58-2.37 (m, 1H), 2.04-1.86 (m, 1H), 1.26 (s, 3H) ppm.

Example 42—Preparation of Intermediate 13

The synthesis of Intermediate 13 followed the procedure of General Procedure 2 following:

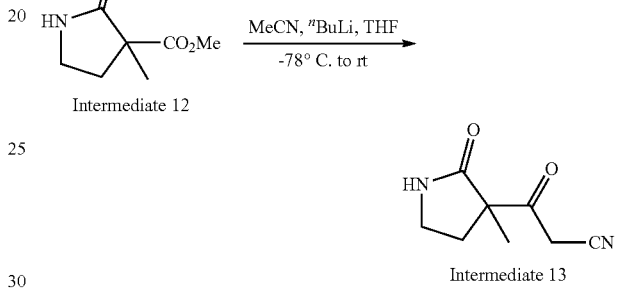

To a cooled solution (−78° C.) of acetonitrile (1.2 g, 26.5 mmol, 1.6 eq) in anhydrous tetrahydrofuran (30 mL) was added n-BuLi (2.5M in hexane, 10.6 mL, 26.5 mmol, 1.6 eq) dropwise over a period of 20 minutes. After stirring for 1 hour, methyl-3-methyl-2-oxopyrrolidine-3-carboxylate (Intermediate 12, 2.6 g, 16.5 mmol, 1.0 eq) was added portionwise, and the reaction mixture stirred at −78° C. for 3 hours. The reaction was quenched with saturated ammonium chloride solution and product was extracted with ethyl acetate. The organic layer was dried over anhydrous sodium sulfate, filtered and concentrated under reduced pressure. The residue was purified by column chromatography using silica gel (60-120 mesh size), eluting with 70% ethyl acetate in n-hexane to give desired product 3-(3-methyl-2-oxopyrrolidin-3-yl)-3-oxopropanenitrile (Intermediate 13, 2.17 g, yield: 79%) m/z 167.1 [M+1]+; $^1$H NMR (400 MHz, DMSO) δ 8.09 (s, 1H), 4.27 (q, J=20.3 Hz, 2H), 3.35 (s, 3H), 3.20 (dd, J=13.0, 5.6 Hz, 2H), 1.81 (ddd, J=13.1, 7.7, 5.6 Hz, 1H), 1.35-1.20 (m, 1H) ppm.

Example 43—Preparation of Compound 30

The synthesis of Compound 30 followed the procedure of General Procedure 3 following:

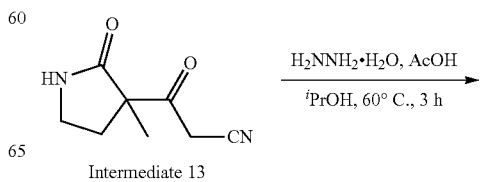

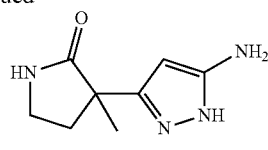

Compound 30

To a solution of 3-(3-methyl-2-oxopyrrolidin-3-yl)-3-oxo-propanenitrile (Intermediate 13, 0.5 g, 3.0 mmol, 1.0 eq) in isopropanol (10 mL) and acetic acid (2.0 mL) was added hydrazine monohydrate (0.25 g, 4.5 mmol, 1.5 eq) dropwise. The reaction was stirred at 60° C. for 3 hours and monitored by TLC and LC-MS. After completion the reaction mixture was concentrated under reduced pressure to obtain a residue, which was purified by column chromatography using silica gel (60-120 mesh). Product was eluted with 0-5% methanol in dichloromethane to give 3-(5-amino-1H-pyrazol-3-yl)-3-methylpyrrolidin-2-one (Compound 30, 0.435 g, yield: 80%) m/z 181.19 [M+1]$^+$.

Example 44—Preparation of Compound 31

The synthesis of Compound 31 followed the procedure of General Procedure 4 following:

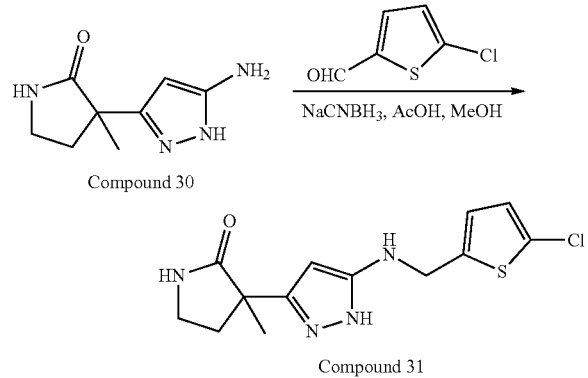

To a cooled solution (0° C.) of 3-(5-amino-1H-pyrazol-3-yl)-3-methylpyrrolidin-2-one (Compound 30, 1.0 g, 5.5 mmol, 1.0 eq) in methanol (20 mL) was added acetic acid (0.3 g, 5.5 mmol, 1.0 eq) dropwise, followed by 5-chloro-thiophene-2-carbaldehyde (0.92 g, 6.6 mmol, 1.2 eq). The reaction was stirred for 30-45 minutes at room temperature. Sodium cyanoborohydride (0.65 g, 11.0 mmol, 2.0 eq) was then added portionwise over a period of 15 minutes. The reaction was stirred at room temperature for 12 hours. After completion of reaction, the reaction mixture was concentrated under reduced pressure. The residue was purified by column chromatography using silica gel (60-100 mesh, eluting with 0-5% methanol in dichloromethane to give 3-(5-(((5-chlorothiophen-2-yl)methyl)amino)-1H-pyrazol-3-yl)-3-methylpyrrolidin-2-one (Compound 31, 0.21 g, yield: 12%) m/z 311.3 [M+1]$^+$; $^1$H NMR (400 MHz, DMSO) δ 11.43 (s, 1H), 7.70 (s, 1H), 6.89 (dd, J=29.1, 3.5 Hz, 2H), 5.77 (s, 1H), 5.35 (s, 1H), 4.29 (s, 2H), 3.20 (t, J=6.5 Hz, 2H), 2.33 (s, 1H), 2.01 (d, J=11.9 Hz, 1H), 1.32 (s, 3H) ppm.

Example 45—Preparation of Compound 32

The synthesis of Compound 32 followed the procedure of General Procedure 5a following:

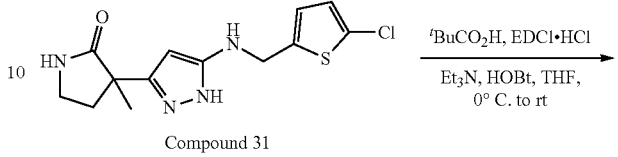

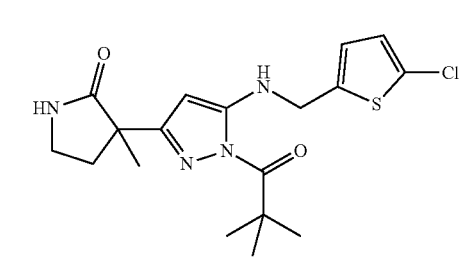

Compound 32

To a cooled solution (0° C.) of pivalic acid (0.147 g, 1.45 mmol, 1.5 eq) in THF (15 mL) was added 1-(3-dimethylaminopropyl)-3-ethylcarbodiimide hydrochloride (EDCI·HCl, 0.276 g, 1.45 mmol, 1.5 eq) followed by triethylamine (TEA, 0.4 mL, 2.89 mmol, 3.0 eq). After stirring for 30 minutes, hydroxybenzotriazole (HOBt, 0.026 g, 0.2 mmol, 0.2 eq) and 3-(5-(((5-chlorothiophen-2-yl) methyl)amino)-1H-pyrazol-3-yl)-3-methylpyrrolidin-2-one (Compound 31, 0.3 g, 0.96 mmol, 1.0 eq) were then added. The reaction was monitored by LC-MS, and after completion the reaction mixture was poured into water (50 mL) and extracted with ethyl acetate (3×25 mL). The combined organic phases were washed with water, brine, dried over anhydrous sodium sulfate, filtered and evaporated under reduced pressure. The residue was purified by preparative HPLC using acetonitrile-water as mobile phase to give 3-(5-(((5-chlorothiophen-2-yl)methyl)amino)-1-pivaloyl-1H-pyrazol-3-yl)-3-methyl-pyrrolidin-2-one (Compound 32, 0.05 g, yield: 13%) m/z 395.7 [M+1]$^+$; $^1$H NMR (400 MHz, DMSO) δ 7.74 (s, 1H), 7.66 (t, J=6.2 Hz, 1H), 6.97 (s, 2H), 5.43 (s, 1H), 4.43 (d, J=6.2 Hz, 2H), 3.30-3.18 (m, 2H), 2.54 (s, 1H), 2.00 (dt, J=12.6, 7.7 Hz, 1H), 1.41 (s, 9H), 1.34 (s, 3H) ppm.

Example 46—Preparation of Compound 33

The synthesis of Compound 33 followed the procedure of General Procedure 5a following:

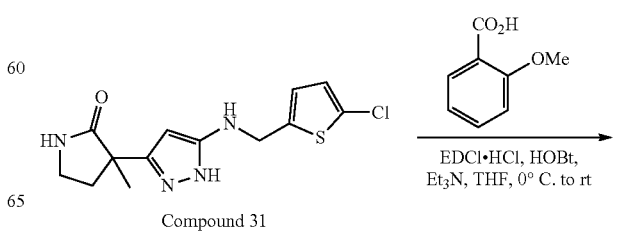

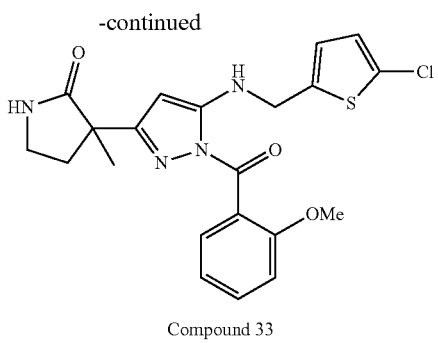

Compound 33

To a cooled solution (0° C.) of 2-methoxybenzoic acid (0.219 g, 1.45 mmol, 1.5 eq) in THF (15 mL) was added 1-(3-dimethylaminopropyl)-3-ethylcarbodiimide hydrochloride (EDCI.HCl, 0.276 g, 1.45 mmol, 1.5 eq) followed by triethylamine (TEA, 0.4 mL, 2.89 mmol, 3.0 eq). After stirring for 30 minutes, hydroxybenzotriazole (HOBt, 0.026 g, 0.19 mmol, 0.2 eq) and 3-(5-(((5-chlorothiophen-2-yl)methyl)amino)-1H-pyrazol-3-yl)-3-methylpyrrolidin-2-one (Compound 31, 0.3 g, 0.96 mmol, 1.0 eq) were added. The reaction was monitored by LC-MS, and after completion the mixture was poured into water (40 mL) and extracted with ethyl acetate (3×25 mL). The combined organic phases were washed with water, brine, dried over anhydrous sodium sulfate, filtered and evaporated under reduced pressure. The residue was purified by preparative HPLC using acetonitrile-water as mobile phase to give 3-(5-(((5-chlorothiophen-2-yl)methyl)amino)-1-(2-methoxybenzoyl)-1H-pyrazol-3-yl)-3-methylpyrrolidin-2-one (Compound 33, 0.05 g, yield: 12%) m/z 447.18; $^1$H NMR (400 MHz, DMSO) δ 7.70-7.58 (m, 2H), 7.55-7.44 (m, 1H), 7.38 (dd, J=7.5, 1.7 Hz, 1H), 7.13 (d, J=8.2 Hz, 1H), 7.09-6.95 (m, 3H), 5.51 (s, 1H), 4.49 (d, J=6.2 Hz, 2H), 3.74 (s, 3H), 3.18-3.00 (m, 2H), 2.35 (ddd, J=12.0, 7.1, 4.7 Hz, 1H), 1.84 (dt, J=12.5, 7.5 Hz, 1H), 1.27-1.18 (m, 3H) ppm.

Example 47—Preparation of Compound 34

The synthesis of Compound 34 followed the procedure of General Procedure 5a following:

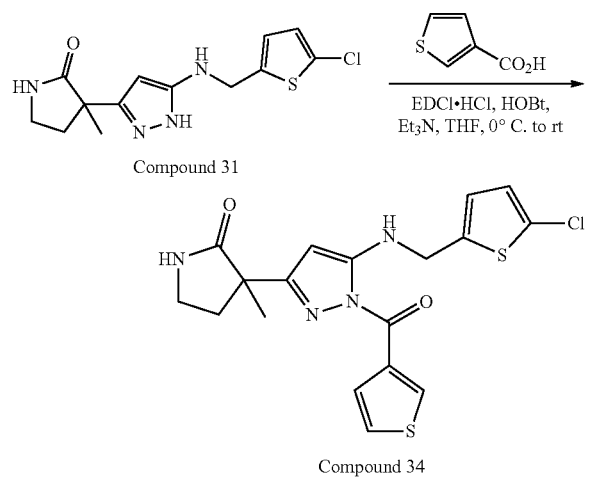

Compound 34

To a cold solution (0° C.) of thiophene-3-carboxylic acid (0.123 g, 0.96 mmol, 1.5 eq) in THF (12 mL) was added 1-(3-dimethylaminopropyl)-3-ethylcarbodiimide hydrochloride (EDCI.HCl, 0.187 g, 0.96 mmol, 1.5 eq) and then triethylamine (TEA, 0.26 mL, 1.93 mmol, 3.0 eq) under nitrogen. After stirring for 30 minutes, hydroxybenzotriazole (HOBt, 0.0173 g, 0.138 mmol, 0.2 eq) and then 3-(5-(((5-chlorothiophen-2-yl)methyl)amino)-1H-pyrazol-3-yl)-3-methylpyrrolidin-2-one (Compound 31, 0.2 g, 0.643 mmol, 1.0 eq) were added. The reaction was stirred for 2 days and monitored by LC-MS. After completion the reaction mixture was poured into water (40 mL) and extracted with ethyl acetate (3×25 mL). The combined organic phases were washed with water, brine, dried over anhydrous sodium sulfate, filtered and evaporated under reduced pressure. The residue was purified by preparative HPLC using acetonitrile-water as mobile phase to give 3-(5-(((5-chlorothiophen-2-yl)methyl)amino)-1-(thiophene-3-carbonyl)-1H-pyrazol-3-yl)-3-methylpyrrolidin-2-one (Compound 34, 0.05 g, yield-19%) m/z 421.01 [M+1]$^+$; $^1$H NMR (400 MHz, DMSO) δ 8.90 (dd, J=3.0, 1.1 Hz, 1H), 7.86-7.73 (m, 3H), 7.66 (dd, J=5.1, 3.0 Hz, 1H), 6.98 (q, J=3.8 Hz, 2H), 5.57 (s, 1H), 4.50 (d, J=6.2 Hz, 2H), 3.32-3.17 (m, 2H), 2.54-2.60 (m, 1H), 2.12-1.96 (m, 2H), 1.38 (s, 3H) ppm.

Example 48—Preparation of Compound 35

The synthesis of Compound 35 followed the procedure of General Procedure 5a following:

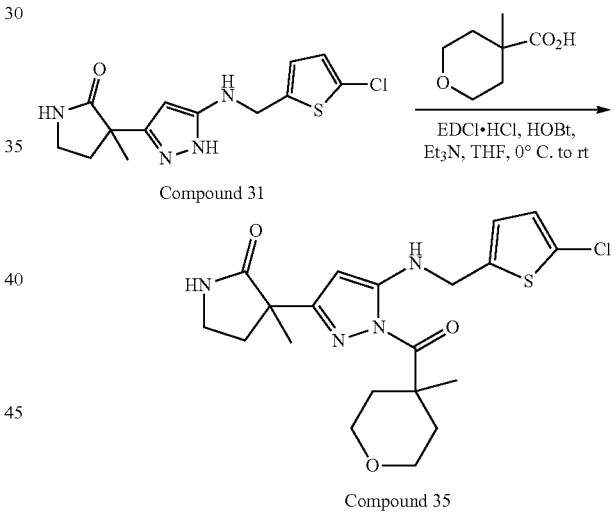

Compound 35

To a cold solution (0° C.) of 4-methyltetrahydro-2H-pyran-4-carboxylic acid (0.184 g, 1.45 mmol, 1.5 eq) in THF (15 mL) was added 1-(3-dimethylaminopropyl)-3-ethylcarbodiimide hydrochloride (EDCI.HCl, 0.276 g, 1.45 mmol, 1.5 eq), followed by triethylamine (TEA, 0.3 g, 2.9 mmol, 3.0 eq) under nitrogen. After stirring for 30 minutes, hydroxybenzotriazole (HOBt, 0.026 g, 0.19 mmol, 0.2 eq) was added, followed by 3-(5-(((5-chlorothiophen-2-yl) methyl) amino)-1H-pyrazol-3-yl)-3-methylpyrrolidin-2-one (Compound 31, 0.3 g, 0.96 mmol, 1.0 eq). The reaction was stirred for 2 days and monitored by LC-MS, and after completion the reaction mixture was poured into water (40 mL) and extracted with ethyl acetate (3×25 mL). The combined organic phases were washed with water, brine, dried over anhydrous sodium sulfate, filtered and evaporated under reduced pressure. The residue was purified by preparative HPLC using acetonitrile-water as mobile phase to give 3-(5-(((5-chlorothiophen-2-yl)methyl)amino)-1-(4-methyl-tetrahydro-2H-pyran-4-carbonyl)-1H-pyrazol-3-yl)-3-methylpyrrolidin-2-one (Compound 35, 0.05 g, yield: 12%) m/z 437.39 [M+1]⁺; ¹H NMR (400 MHz, DMSO) δ 7.71 (dd, J=15.0, 8.8 Hz, 2H), 6.96 (d, J=4.3 Hz, 2H), 5.44 (s, 1H), 4.44 (d, J=6.2 Hz, 2H), 3.69 (d, J=11.6 Hz, 2H), 3.48 (t, J=8.6 Hz, 2H), 3.24 (dd, J=9.2, 5.0 Hz, 2H), 2.35 (d, J=6.8 Hz, 3H), 1.99 (dt, J=12.5, 7.5 Hz, 1H), 1.69 (s, 2H), 1.52 (s, 3H), 1.33 (s, 3H) ppm.

Example 49—Preparation of Intermediate 14

The synthesis of Intermediate 14 followed the procedure of General Procedure 10 following:

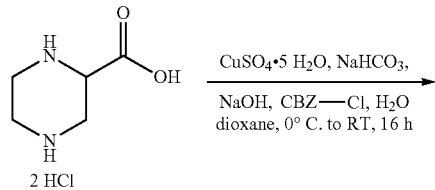

To a stirred solution of (+/−)-piperazine-2-carboxylic acid dihydrochloride (25 g, 123.2 mmol) in water (200 mL) at room temperature was added aqueous sodium hydroxide (2.5M, 200 mL) followed by copper sulfate pentahydrate (CuSO₄.5H₂O solution, 15.88 g, 61.5 mmol in 100 mL H₂O) dropwise. The mixture was cooled to 0° C., and to it was added solid sodium bicarbonate (12.5 g, 148.8 mmol). After stirring at 0° C. for 15 minutes, a solution of CBZ-Cl in 1,4-dioxane was added. The reaction mixture was stirred at room temperature for 16 hours. (NOTE: The pH was maintained >7 throughout the reaction). The volatiles were evaporated under reduced pressure to afford 4-(benzyloxycarbonyl)piperazine-2-carboxylic acid (Intermediate 14, 45 g, crude) as a blue color copper complex solid. It was considered for the next step without any purification; TLC: 5% MeOH in dichloromethane, R$_f$: 0.4.

Example 50—Preparation of Intermediate 15

The synthesis of Intermediate 15 followed the procedure of General Procedure 11 following:

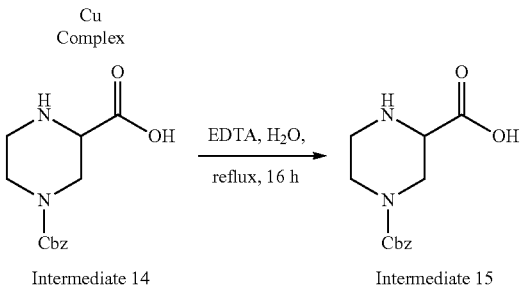 [SMILES: O=C(O)C1CN(C(=O)OCc2ccccc2)CCN1 ; O=C(O)C1CN(C(=O)OCc2ccccc2)CCN1]

To a stirred solution of 4-(benzyloxycarbonyl)piperazine-2-carboxylic acid-copper complex (Intermediate 15, 40 g, 122.6 mmol) in water (200 mL) was added ethylenediamine tetraacetic acid (EDTA, 20 g, 61.4 mmol in 200 mL water), and the mixture was heated to 100° C. for 16 hours. The reaction mixture was concentrated under reduced pressure to afford the crude 4-(benzyloxycarbonyl)piperazine-2-carboxylic acid (Intermediate 15, 30 g) as blue color solid which was taken forward to the next step without further purification; TLC System: 5% MeOH in dichloromethane R$_f$: 0.2.

Example 51—Preparation of Intermediate 16

The synthesis of Intermediate 16 followed the procedure of General Procedure 12 following:

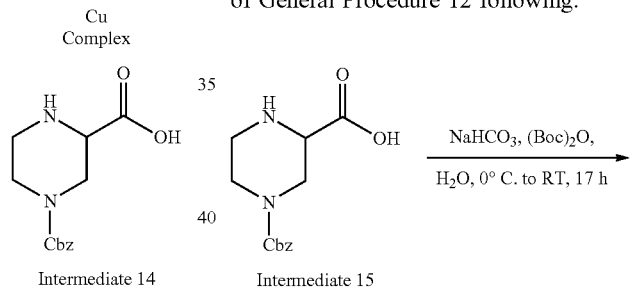

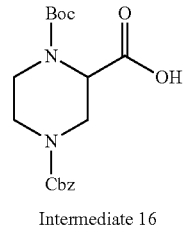

Intermediate 16

To a cooled solution (0° C.) of 4-(benzyloxycarbonyl) piperazine-2-carboxylic acid (Intermediate 15, 48 g, 181.8 mmol) in water (10 volumes, 480 mL) was added solid NaHCO₃ (45.8 g, 545.4 mmol) followed by di-tert-butyl dicarbonate ((Boc)₂O, 109 mL, 490.9 mmol). The reaction mixture was stirred at room temperature for 17 hours. After cooling to room temperature it was extracted into EtOAc (4×100 mL). The combined organic layers were dried over sodium sulfate, filtered and concentrated under reduced pressure. The residue was purified by silica gel column chromatography (100-200 mesh), eluting with 50% EtOAc/n-hexane, to afford 4-(benzyloxycarbonyl)-1-(tert-butoxycarbonyl)piperazine-2-carboxylic acid (Intermediate 16, 25 g, yield: 55%) as an off-white solid; TLC: 5% Methanol-dichloromethane, R$_f$: 0.3.

Example 52—Preparation of Intermediate 17

The synthesis of Intermediate 17 followed the procedure of General Procedure 13 following:

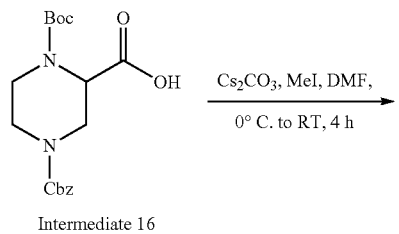

Intermediate 16

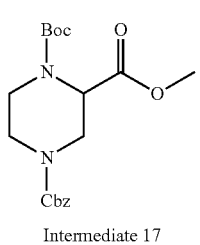

Intermediate 17

To a cooled solution (0° C.) of 4-(benzyloxycarbonyl)-1-(tert-butoxycarbonyl)piperazine-2-carboxylic acid (Intermediate 16, 20 g, 54.9 mmol) in dry DMF (200 mL) was added cesium carbonate ($Cs_2CO_3$, 35.8 g, 109.9 mmol) followed by methyl iodide (10.26 mL, 164.83 mmol). The reaction mixture was stirred at room temperature for 4 hours. After cooling to 0° C. the mixture was quenched with ice-cold water (90 mL), and extracted with EtOAc (2×100 mL). The combined organic layers were dried over sodium sulfate, filtered and concentrated under reduced pressure. The residue was purified by silica gel column chromatography (100-200 mesh), eluting with 20% EtOAc/n-hexane, to afford 4-benzyl 1-tert-butyl 2-methyl piperazine-1,2,4-tricarboxylate (Intermediate 17, 25 g, yield-55%) as an off-white solid. TLC: 30% ethyl acetate in hexane. $R_f$: 0.5.

Example 53—Preparation of Intermediate 18

The synthesis of Intermediate 18 followed the procedure of General Procedure 14 following:

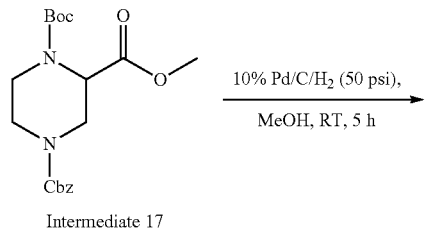

Intermediate 17

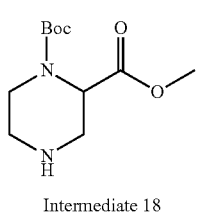

Intermediate 18

To a stirred solution of 4-benzyl 1-tert-butyl 2-methyl piperazine-1,2,4-tricarboxylate (Intermediate 17, 10 g, 26.5 mmol) in MeOH (100 mL) in a steel vessel was added 10% Pd/C (30% w/w, 3.0 g), and the mixture stirred under 50 psi hydrogen pressure at room temperature for 5 hours. The reaction mixture was filtered through a Celite pad and the volatiles were concentrated under reduced pressure to afford 1-tert-butyl 2-methyl piperazine-1,2-dicarboxylate (Intermediate 18, 5.6 g, yield: 88%) as a light yellow liquid; TLC: 5% Methanol-dichloromethane. $R_f$-0.3.

Example 54—Preparation of Intermediate 19

The synthesis of Intermediate 19 followed the procedure of General Procedure 15 following:

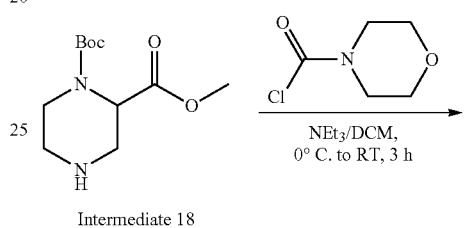

Intermediate 18

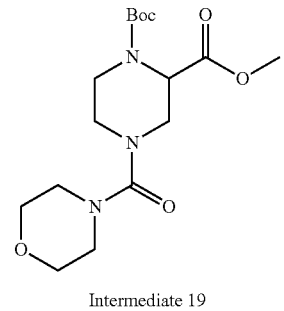

Intermediate 19

To a cooled solution (0° C.) of 1-tert-butyl 2-methyl piperazine-1,2-dicarboxylate (Intermediate 18, 3.5 g, 14.3 mmol) in dry dichloromethane (70 mL) was added triethylamine (TEA, 5 mL, 35.9 mmol) followed by morpholine-4-carbonyl chloride (3.35 mL, 28.7 mmol). The reaction mixture was stirred at room temperature for 3 hours. To the mixture was added ice-cold water (20 mL), then it was extracted into EtOAc (2×50 mL). The combined organic layers were dried over sodium sulfate, filtered and concentrated under reduced pressure. The crude residue was purified by flash chromatography using 30% EtOAc/n-hexane to afford 1-tert-butyl 2-methyl 4-(morpholine-4-carbonyl)piperazine-1,2-dicarboxylate (Intermediate 19, 3.6 g, yield: 72%) as an off white solid; TLC: 50% ethyl acetate in hexane. $R_f$-0.5.

Example 55—Preparation of Intermediate 20

The synthesis of Intermediate 20 followed the procedure of General Procedure 6c following:

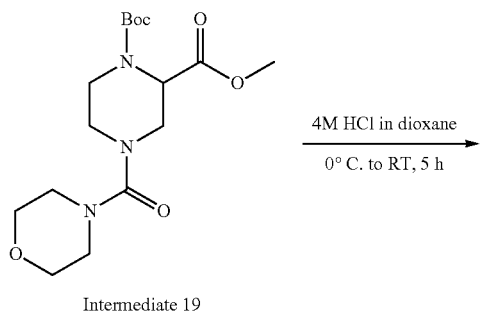

Intermediate 19

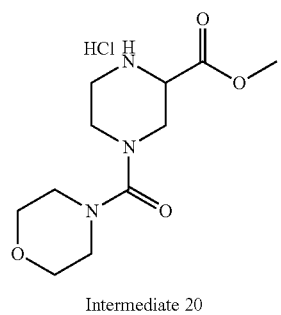

Intermediate 20

To a cooled solution (0° C.) of 1-tert-butyl-2-methyl-4-(morpholine-4-carbonyl)piperazine-1,2-dicarboxylate (Intermediate 19, 1.0 g, 2.8 mmol) in 1,4-dioxane (10 mL) was added HCl (4M in dioxane, 10 mL), and the mixture was then stirred at room temperature for 5 hours. The reaction mixture was concentrated and triturated with diethyl ether to afford methyl 4-(morpholine-4-carbonyl)piperazine-2-carboxylate hydrochloride salt (Intermediate 20, 800 mg, yield: 86%) as an off white solid; TLC: 5% Methanol-dichloromethane. $R_f$-0.3.

Example 56—Preparation of Intermediate 21

The synthesis of Intermediate 21 followed the procedure of General Procedure 7 following:

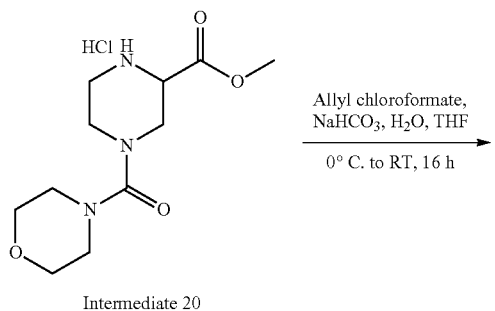

Intermediate 20

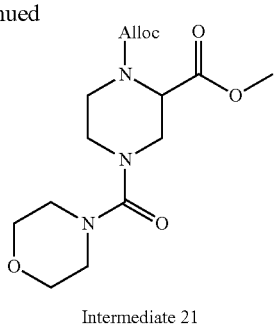

Intermediate 21

To a cooled (0° C.) stirred solution of methyl 4-(morpholine-4-carbonyl)piperazine-2-carboxylate (Intermediate 20, 8.2 g, 28.0 mmol) in H$_2$O (300 mL) at 0° C. was added solid NaHCO$_3$ (7.05 g, 83.2 mmol), followed by allyl chloroformate (8 mL, 30.8 mmol) in THF (50 mL). After stirring at room temperature for 16 hours, ice-cold water (100 mL) was added to the reaction mixture and extracted into EtOAc (2×100 mL). The combined organic layers were dried over sodium sulfate, filtered and concentrated under reduced pressure. The residue was purified by silica gel column chromatography (100-200 mesh), eluting with 40-50% EtOAc/n-hexane to afford 1-allyl 2-methyl 4-(morpholine-4-carbonyl)piperazine-1,2-dicarboxylate (Intermediate 21, 7.2 g, yield: 84%) as a pale yellow color liquid; TLC System: 5% Methanol-dichloromethane R$_f$-0.6.

Example 57—Preparation of Intermediate 22

The synthesis of Intermediate 22 followed the procedure of General Procedure 2 following:

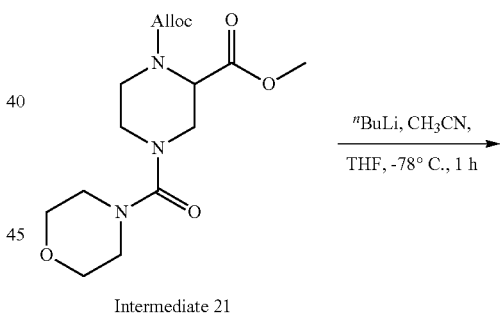

Intermediate 21

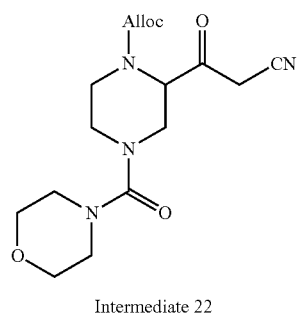

Intermediate 22

To a cooled solution (−78° C.) of acetonitrile (4.04 mL, 77 mmol) in dry THF (120 mL) was added n-BuLi (2.5M in hexane, 26 mL, 65 mmol). After stirring at −78° C. for 30 minutes, to the mixture was added a solution of 1-allyl-2-methyl-4-(morpholine-4-carbonyl)piperazine-1,2-dicarboxylate (Intermediate 21, 7.5 g, 22 mmol) in dry THF (30 mL). The mixture was stirred at −78° C. for a further 30 minutes. The reaction mixture was quenched with saturated NH₄Cl solution (80 mL) and extracted into EtOAc (2×120 mL). The combined organic layers were dried over sodium sulfate, filtered and concentrated under reduced pressure. The residue was purified by silica gel column chromatography (100-200 mesh), eluting with 50% EtOAc/n-hexane, to afford allyl-2-(2-cyanoacetyl)-4-(morpholine-4-carbonyl) piperazine-1-carboxylate (Intermediate 22, 6.5 g, yield-85%) as a light yellow liquid; TLC System: 5% Methanol-dichloromethane R$_f$-0.5.

Example 58—Preparation of Compound 36

The synthesis of Compound 36 followed the procedure of General Procedure 3 following:

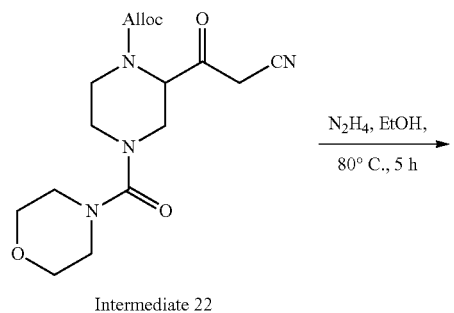

Intermediate 22

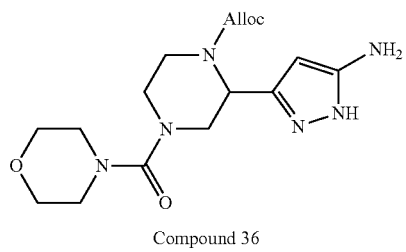

Compound 36

To a solution of allyl 2-(2-cyanoacetyl)-4-(morpholine-4-carbonyl)piperazine-1-carboxylate (Intermediate 22, 6.5 g, 18.6 mmol) in ethanol (65 mL) was added N₂H₄ (1.1 mL, 22.3 mmol) and the reaction mixture was heated to 80° C. for 5 hours. The reaction mixture was cooled to room temperature, the volatiles were evaporated and the resultant residue was purified by silica gel column chromatography (100-200 mesh), eluting with 3% methanol-dichloromethane, to afford allyl-2-(5-amino-1H-pyrazol-3-yl)-4-(morpholine-4-carbonyl)piperazine-1-carboxylate (Compound 36, 4.5 g, yield: 67%) as a pale yellow color semi solid; TLC System: 5% Methanol-dichloromethane R$_f$-0.3; m/z 365.28 [M+1]+ ¹H NMR (400 MHz, DMSO) δ 11.2 (s, 1H), 5.9 (m, 1H), 5.0-5.3 (m, 4H), 4.8 (br s, 2H), 4.6 (br s, 2H), 3.85 (m, 2H), 3.4-3.6 (m, 4H), 3.0-3.2 (m, 6H), 2.8 (m, 1H) ppm.

Example 59—Preparation of Compound 37

The synthesis of Compound 37 followed the procedure of General Procedure 4 following:

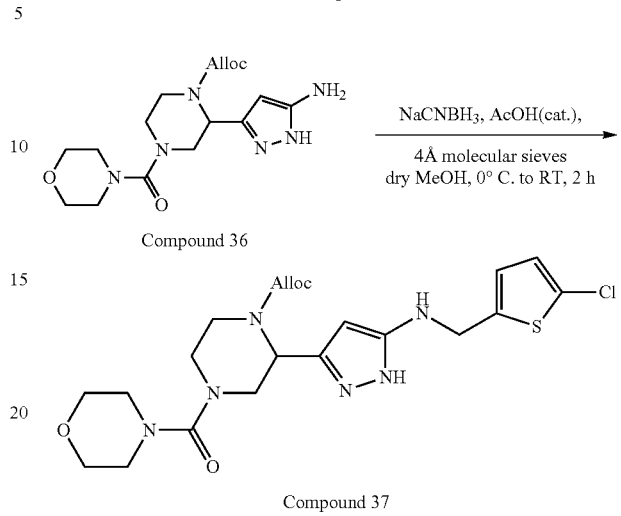

To a cooled solution (0° C.) of allyl 2-(5-amino-1H-pyrazol-3-yl)-4-(morpholine-4-carbonyl)piperazine-1-carboxylate (Compound 36, 3.5 g, 9.6 mmol) in dry MeOH (70 mL) was added 5-chlorothiophene-2-carbaldehyde (2.1 mL, 19.2 mmol), AcOH (0.2 mL) and 4 Å powdered molecular sieves. The reaction mixture was stirred at room temperature for 1 hour. (Formation of imine was observed as a less polar spot by TLC). To the reaction mixture was added sodium cyanoborohydride (NaCNBH₃ 0.73 g, 11.5 mmol) portionwise, and the mixture stirred at room temperature for 1 hour. To the mixture was then added ice-cold water (50 mL), then filtered through a Celite pad and the filtrate was extracted into EtOAc (4×100 mL). The combined organic layers were dried over sodium sulfate, filtered and concentrated under reduced pressure. The residue was purified by silica gel column chromatography (100-200 mesh), eluting with 3% MeOH-DCM, to afford the desired product (1.95 g, yield: 41%) as a light yellow liquid which was used in the next step. A sample (120 mg) was further purified by preparative HPLC to afford allyl 2-(5-((5-chlorothiophen-2-yl)methyl-amino)-1H-pyrazol-3-yl)-4-(morpholine-4-carbonyl)piperazine-1-carboxylate (Compound 37; 55 mg) as a gummy liquid. ¹H NMR (400 MHz, DMSO-d₆) δ=11.55-11.41 (br s, 1H), 6.96-6.77 (m, 2H), 6.15-5.71 (m, 2H), 5.41-4.97 (m, 4H), 4.56 (br s, 2H), 4.27 (br s, 2H), 3.83 (br t, J=12.5 Hz, 2H), 3.67-3.32 (m, 5H), 3.25-2.85 (m, 6H), 2.81-2.64 (m, 1H); TLC System: 5% Methanol-dichloromethane R$_f$-0.5.

Example 60—Preparation of Compound 38

The synthesis of Compound 38 followed the procedure of General Procedure 5d following:

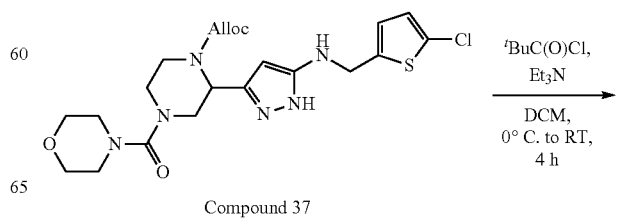

Compound 37

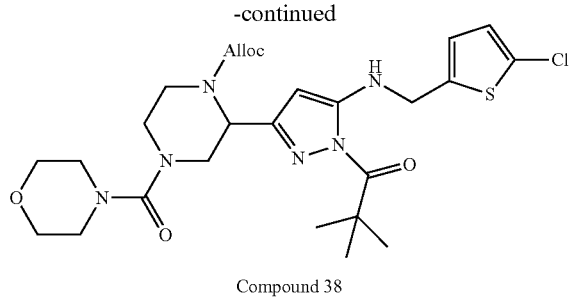

Compound 38

To a cooled solution (0° C.) of allyl 2-(5-((5-chlorothiophen-2-yl)methylamino)-1H-pyrazol-3-yl)-4-(morpholine-4-carbonyl)piperazine-1-carboxylate (Compound 37, 1.0 g, 2.0 mmol) in dry dichloromethane (20 mL) was added triethylamine (TEA, 0.4 mL, 3.0 mmol), followed by trimethylacetyl chloride (0.23 mL, 1.8 mmol). The mixture was stirred at room temperature for 4 hours, and then quenched with water (25 mL). This was extracted into dichloromethane (3×40 mL). The combined organic layers were dried over sodium sulfate, filtered and concentrated under reduced pressure. The residue was purified by silica gel column chromatography (100-200 mesh), eluting with 20% EtOAc/n-hexane, to afford allyl 2-(5-((5-chlorothiophen-2-yl)methylamino)-1-pivaloyl-1H-pyrazol-3-yl)-4-(morpholine-4-carbonyl)piperazine-1-carboxylate (Compound 38, 600 mg, yield: 69%) as a pale yellow solid. $^1$H NMR (400 MHz, DMSO-$d_6$) δ=7.71 (t, J=6.1 Hz, 1H), 6.97-6.91 (m, 2H), 5.87 (br s, 1H), 5.37 (s, 1H), 5.14 (br s, 1H), 5.05 (br d, J=2.0 Hz, 1H), 4.53 (br s, 2H), 4.40 (d, J=6.4 Hz, 2H), 3.94-3.79 (m, 2H), 3.60-3.36 (m, 6H), 3.22-3.15 (m, 1H), 3.19 (br dd, J=4.4, 13.2 Hz, 2H), 2.93-2.78 (m, 3H), 1.35 (s, 9H) ppm; TLC System: 30% ethyl acetate in hexane $R_f$ 0.5.

Example 61—Preparation of Compound 39

The synthesis of Compound 39 followed the procedure of General Procedure 8b following:

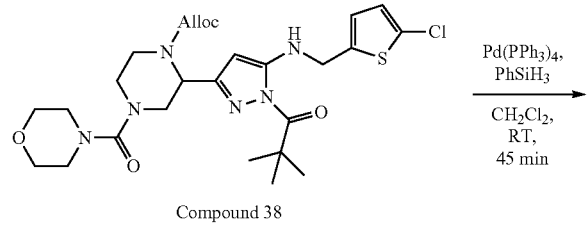

Compound 38

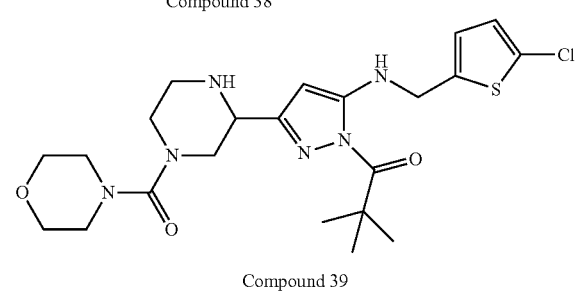

Compound 39

A stirred solution of allyl 2-(5-((5-chlorothiophen-2-yl)methylamino)-1-pivaloyl-1H-pyrazol-3-yl)-4-(morpholine-4-carbonyl)piperazine-1-carboxylate (Compound 38, 500 mg, 0.86 mmol) in dichloromethane (10 mL) was degassed with a stream of argon for 15 minutes, then to the solution was added tetrakis(triphenylphosphine)palladium(0) (Pd(PPh$_3$)$_4$, 100 mg, 0.087 mmol) followed by phenylsilane (PhSiH$_3$, 0.64 mL, 5.2 mmol). The reaction mixture was stirred at room temperature for 45 minutes, then filtered through a pad of Celite pad and evaporated. The crude residue was purified by CombiFlash® chromatography eluting with 4% MeOH-dichloromethane to afford 1-(5-((5-chlorothiophen-2-yl)methylamino)-3-(4-(morpholine-4-carbonyl)piperazin-2-yl)-1H-pyrazol-1-yl)-2,2-dimethyl- propan-1-one (Compound 39, 130 mg, yield: 31%) as an off-white solid. $^1$H NMR (400 MHz, DMSO-$d_6$) δ=7.72 (t, J=6.4 Hz, 1H), 6.98-6.94 (m, 2H), 5.47 (s, 1H), 4.42 (d, J=6.4 Hz, 2H), 3.67 (br d, J=12.7 Hz, 1H), 3.61-3.53 (m, 5H), 3.43 (br d, J=11.7 Hz, 1H), 3.11 (dd, J=3.7, 5.1 Hz, 4H), 2.92-2.63 (m, 5H), 1.41 (s, 9H) ppm; TLC System: 5% Methanol-dichloromethane $R_f$ 0.5.

Example 62—Preparation of Compound 40

The synthesis of Compound 40 followed the procedure of General Procedure 6c following:

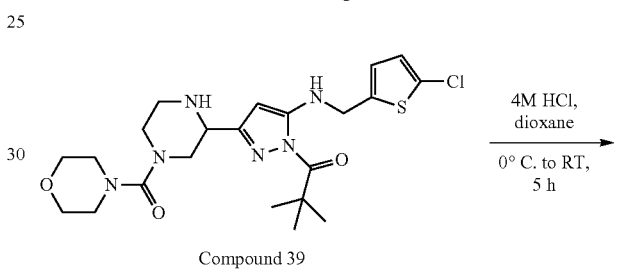

Compound 39

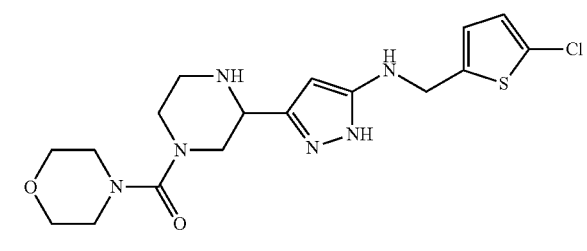

Compound 40

To a cooled (0° C.) solution of 1-(5-((5-chlorothiophen-2-yl)methylamino)-3-(4-(morpholine-4-carbonyl)piperazin-2-yl)-1H-pyrazol-1-yl)-2,2-dimethylpropan-1-one (Compound 39, 100 mg, 0.2 mmol) in 1,4-dioxane (10 mL) was added HCl (10 mL in dioxane), and the reaction was then stirred at room temperature for 5 hours. The reaction mixture was concentrated under reduced pressure and triturated with diethyl ether to afford 100 mg of a semi-pure sample. This was purified by preparative HPLC to afford (3-(5-((5-chlorothiophen-2-yl)methylamino)-1H-pyrazol-3-yl)piperazin-1-yl)(morpholino)methanone hydrochloride (Compound 40, 28 mg, yield: 34%) as an off-white solid $^1$H NMR (400 MHz, DMSO-$d_6$) δ=12.02 (br s, 1H), 11.61 (br s, 1H), 9.06 (s, 2H), 6.92 (br d, J=13.7 Hz, 2H), 6.39 (br s, 1H), 5.81 (br s, 1H), 5.53 (br s, 1H), 4.32 (br d, J=5.9 Hz, 2H), 4.17 (br s, 1H), 3.95-3.40 (m, 6H), 3.27-2.57 (m, 8H) ppm; TLC System: 10% Methanol-dichloromethane $R_f$ 0.5.

Example 63—Preparation of Compound 41

The synthesis of Compound 41 followed the procedure of General Procedure 5d following:

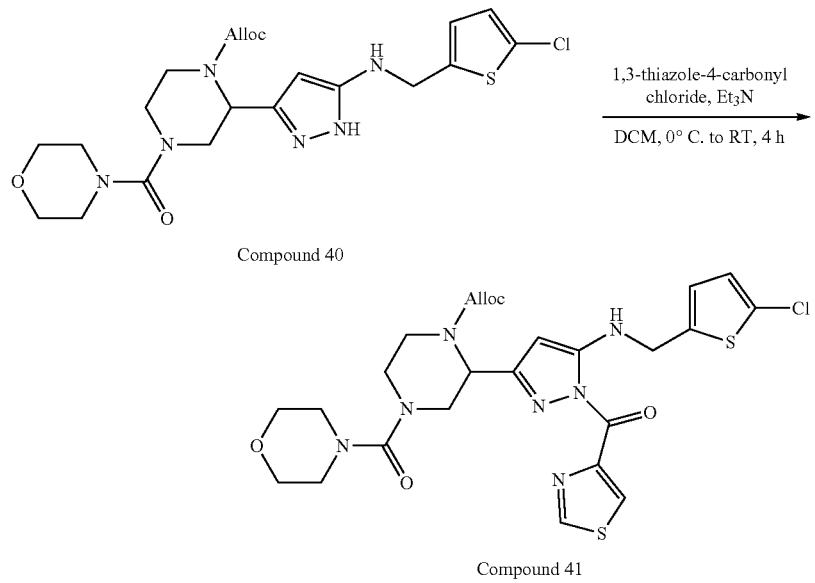

Example 64—Preparation of Intermediate 23

The synthesis of Intermediate 23 followed the procedure of General Procedure 16 following:

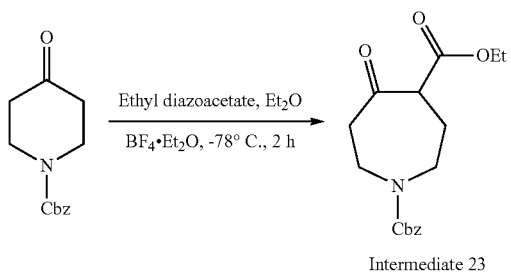 [SMILES: O=C1CCN(C(=O)OCc2ccccc2)CC1 ; CCOC(=O)C1CCN(C(=O)OCc2ccccc2)CCC1=O]

To a cooled solution (0° C.) of allyl 2-(5-(((5-chlorothiophen-2-yl)methylamino)-1H-pyrazol-3-yl)-4-(morpholine-4-carbonyl)piperazine-1-carboxylate (Compound 40, 2.0 g, 4 mmol) in dry dichloromethane (20 mL) was added triethylamine (TEA, 1.1 mL, 8.1 mmol) followed by 1,3-thiazole-4-carbonyl chloride (896 mg, 1.8 mmol). After stirring at room temperature for 4 hours, the reaction mixture was combined with water (25 mL) and extracted into dichloromethane (3×40 mL). The combined organic layers were dried over sodium sulfate, filtered and concentrated under reduced pressure. The residue was purified by silica gel column chromatography (100-200 mesh), eluting with 20% EtOAc/n-hexane, to afford allyl 2-(5-(((5-chlorothiophen-2-yl)methylamino)-1-(thiazole-4-carbonyl)-1H-pyrazol-3-yl)-4-(morpholine-4-carbonyl)piperazine-1-carboxylate (Compound 41, 600 mg, yield: 69%) as a light yellow liquid. 300 mg of this sample was further purified by preparative HPLC to give pure compound as a light yellow solid. $^1$H NMR (400 MHz, DMSO-$d_6$) δ=9.22 (d, J=2.0 Hz, 1H), 8.98 (d, J=2.0 Hz, 1H), 7.87 (br t, J=6.1 Hz, 1H), 6.96 (s, 2H), 5.88 (br s, 1H), 5.48 (s, 1H), 5.12 (br d, J=2.4 Hz, 3H), 4.59-4.48 (m, 4H), 4.02 (br d, J=13.7 Hz, 1H), 3.84 (br d, J=12.7 Hz, 1H), 3.56 (br d, J=13.2 Hz, 1H), 3.39 (br d, J=2.9 Hz, 2H), 3.33 (br s, 2H), 3.23-3.18 (m, 2H), 3.06-2.99 (m, 2H), 2.90-2.81 (m, 3H) ppm; TLC System: 10% Methanol-dichloromethane $R_f$-0.5.

To a cold solution (−78° C.) of benzyl 4-oxopiperidine-1-carboxylate (20 g, 8.6 mmol) in diethyl ether (Et$_2$O, 250 mL) was added ethyl diazoacetate (11.6 mL, 11.1 mmol), followed by boron trifluoride diethyl etherate (BF$_3$OEt$_2$, 10.7 mL, 8.6 mmol). The reaction mixture was allowed to stir at −78° C. for 1 h, then stirred at room temperature for 1 hour, then was quenched with saturated K$_2$CO$_3$. The solution was stirred until nitrogen evolution ceased, then extracted with EtOAc (300 mL). The combined organic layer was dried over sodium sulfate, filtered and concentrated under reduced pressure to obtain 1-benzyl 4-ethyl 5-oxoazepane-1,4-dicarboxylate (Intermediate 23, 26 g) as a yellow liquid. The crude compound was taken forward to the next step without further purification. MS (ESI): m/z 320.1 [M+H]$^+$; TLC System: 20% ethyl acetate in hexane. $R_f$-0.3.

Example 65—Preparation of Intermediate 24

The synthesis of Intermediate 24 followed the procedure of General Procedure 17 following:

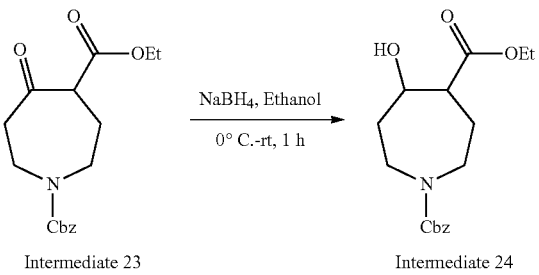 [SMILES: CCOC(=O)C1CCN(C(=O)OCc2ccccc2)CCC1=O ; CCOC(=O)C1CCN(C(=O)OCc2ccccc2)CCC1O]

To a cold solution (0° C.) of 1-benzyl 4-ethyl 5-oxoazepane-1,4-dicarboxylate (Intermediate 23, 26 g, 81.5 mmol) in EtOH (250 ml) was added sodium borohydride (NaBH$_4$, 3 g, 81.5 mmol) portionwise. After 10 minutes the reaction was raised to room temperature and stirred for a further 30 minutes. The reaction was concentrated and was diluted with EtOAc (350 mL) and washed with water (2×150 ml), dried over Na$_2$SO$_4$, filtered and concentrated at reduced pressure. The residue was purified by silica gel (100-200 mesh) eluting with 20% EtOAc in hexane to give 1-benzyl 4-ethyl 5-hydroxyazepane-1,4-dicarboxylate (Intermediate 24, 12 g, 46%) as a colorless oil MS (ESI): m/z 321.96 ([M+H]$^+$); TLC System: 50% ethyl acetate in hexane. R$_f$-0.3.

Example 66—Preparation of Intermediate 25

The synthesis of Intermediate 25 followed the procedure of General Procedure 18 following:
General Procedure 18

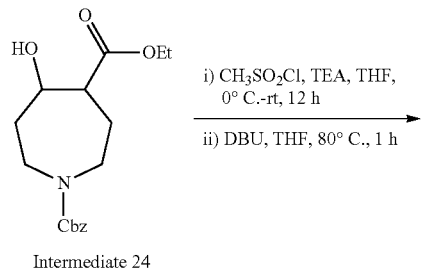

To a stirred solution of 1-benzyl 4-ethyl-5-hydroxyazepane-1,4-dicarboxylate (Intermediate 24, 12 g, 37.3 mmol) in THF (270 mL) was added methanesulfonyl chloride (MsCl, 7.1 mL, 93.4 mmol) and triethylamine (TEA, 15.5 mL, 112.1 mmol) in two portions, and the mixture stirred for 12 hours. The mixture was then concentrated under reduced pressure, diluted with EtOAc (300 mL) washed with saturated aqueous NaHCO$_3$ (2×100 mL), dried (Na$_2$SO$_4$), filtered and concentrated under reduced pressure. The residue was dissolved in THF (270 mL), and to it was added 1,8-diazabicycloundec-7-ene (DBU, 8.4 mL, 56.3 mmol), and the resulting mixture was heated at 80° C. for 1 hour. The reaction was then concentrated, diluted with EtOAc (300 mL), washed with saturated aqueous NaHCO$_3$ (3×80 mL) and water (200 mL), dried (Na$_2$SO$_4$), filtered and concentrated under reduced pressure. The residue was purified by silica gel chromatography (100-200 mesh) eluting with 20% EtOAc in hexane to give 1-benzyl 4-ethyl 2,3-dihydro-1H-azepine-1,4(6H,7H)-dicarboxylate (Intermediate 25, 10.5 g, 92%) as a colorless oil; MS (ESI): m/z 304 ([M+H]$^+$); TLC System: 20% ethyl acetate in hexane. R$_f$-0.9.

Example 67—Preparation of Intermediate 26

The synthesis of Intermediate 26 followed the procedure of General Procedure 19 following:

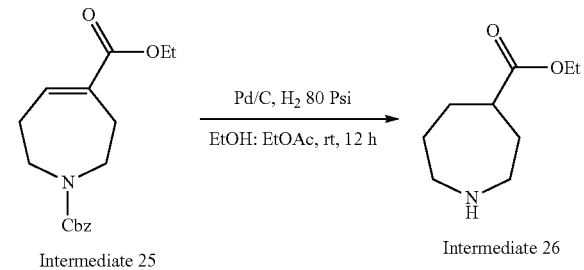 [SMILES: CCOC(=O)C1=CCCN(C(=O)OCc2ccccc2)CC1 ; CCOC(=O)C1CCCNCC1]

A suspension of 1-benzyl 4-ethyl 2,3-dihydro-1H-azepine-1,4(6H,7H)-dicarboxylate (Intermediate 25, 10.5 g, 34.6 mmol) and 20% Pd/C (2.1 g) in ethanol and ethyl acetate (1:1, 200 mL) was stirred under 80 psi hydrogen atmosphere for 12 hours. The mixture was then filtered on a pad of Celite and the Celite bed was washed with methanol (2×50 mL). The combined organic layers were concentrated to give crude ethyl azepane-4-carboxylate (Intermediate 26, 5.6 g, 94%) as a yellow oil; TLC System: 10% MeOH in dichloromethane. R$_f$-0.1.

Example 68—Preparation of Intermediate 27

The synthesis of Intermediate 27 followed the procedure of General Procedure 7 following:

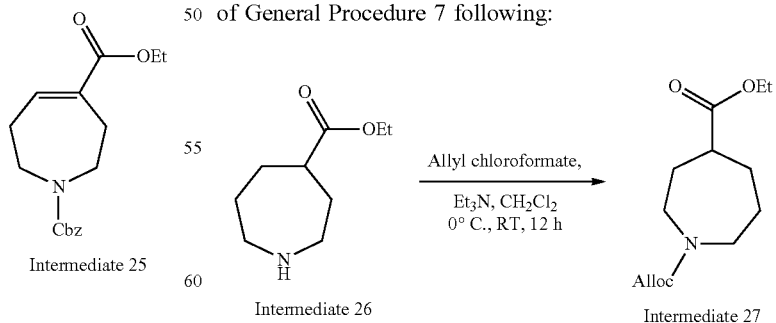

To a cooled solution (0° C.) of ethyl azepane-4-carboxylate (Intermediate 26, 5.6 g, 32.9 mmol) in dichloromethane (100 mL) was added triethylamine (TEA, 13.7 mL, 98.8 mmol) followed by allyl chloroformate (7 mL, 65.8 mmol), and the mixture was then stirred at room temperature for 12 hours. The reaction mixture was quenched with water (100 mL) and extracted into dichloromethane (2×200 mL). The combined organic layers were dried over sodium sulfate, filtered and concentrated under reduced pressure. The residue was purified by silica gel column chromatography (100-200 mesh), eluting with 20% EtOAc/n-hexane, to afford 1-allyl 4-ethyl azepane-1,4-dicarboxylate (Intermediate 27, 6.5 g, 77%) as a colorless liquid; MS (ESI): m/z 256.59 [M+H]$^+$; TLC System: 20% ethyl acetate in hexane. $R_f$ 0.7.

Example 69—Preparation of Intermediate 28

The synthesis of Intermediate 28 followed the procedure of General Procedure 2 following:

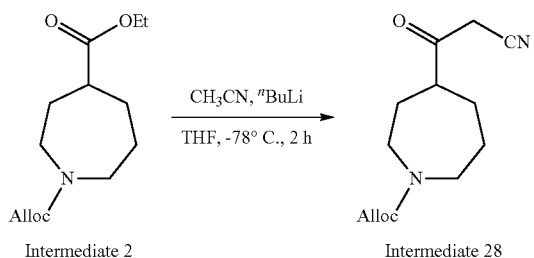

Intermediate 2                Intermediate 28

To a cooled solution (−78° C.) of acetonitrile (1.2 mL, 23.5 mmol) in dry THF (30 mL) was added n-BuLi in THF (2.5M, 9.4 mL, 23.5 mmol). After stirring for 30 minutes, a solution of 1-allyl 4-ethyl azepane-1,4-dicarboxylate (Intermediate 27, 5 g, 19.6 mmol) in dry THF (10 mL) was added. The reaction mixture was stirred at −78° C. for 1 hour, then quenched with saturated NH$_4$Cl solution (10 mL) and extracted into EtOAc (2×120 mL). The combined organic layer was dried over sodium sulfate, filtered and concentrated under reduced pressure. The residue was purified by silica gel column chromatography (100-200 mesh), eluting with 50% EtOAc/n-hexane, to afford allyl 4-(2-cyanoacetyl)azepane-1-carboxylate (Intermediate 28, 3.1 g, 63%) as a light yellow liquid. MS (ESI): m/z 251.55 [M+H]$^+$; TLC System: 50% ethyl acetate in hexane $R_f$ 0.5.

Example 70—Preparation of Compound 42

The synthesis of Compound 42 followed the procedure of General Procedure 3 following:

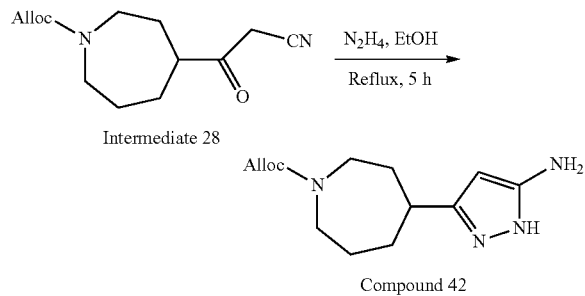

To a stirred solution of allyl 4-(2-cyanoacetyl)azepane-1-carboxylate (Intermediate 28, 3.1 g, 12.4 mmol) in ethanol (30 mL) was added hydrazine hydrate (N$_2$H$_4$.H$_2$O, 0.74 mL, 14.8 mmol), and the reaction mixture was then heated to 80° C. for 5 hours. The reaction mixture was cooled to room temperature and the volatiles were evaporated. The residue was purified by silica gel column chromatography (100-200 mesh), eluting with 5% MeOH-dichloromethane, to afford allyl 4-(5-amino-1H-pyrazol-3-yl)azepane-1-carboxylate (Compound 42, 2.8 g, 87%) as an orange liquid. MS (ESI): m/z 265.13 [M+H]$^+$; TLC System: 10% Methanol-dichloromethane. $R_f$ 0.3.

Example 71—Preparation of Compound 43

The synthesis of Compound 43 followed the procedure of General Procedure 4 following:

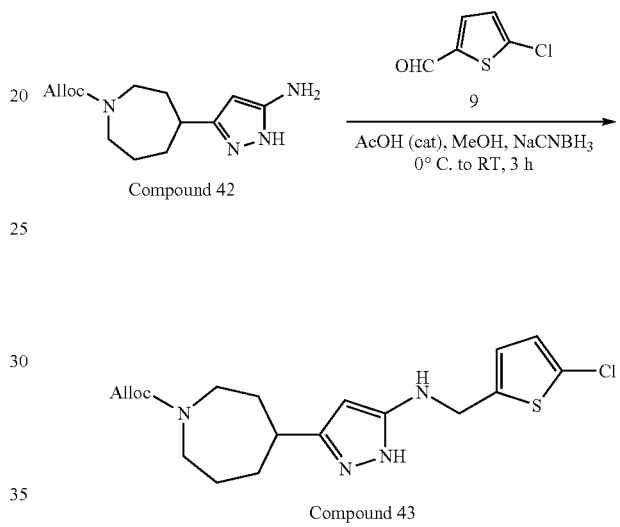

To a cold solution (0° C.) of allyl 4-(5-amino-1H-pyrazol-3-yl)azepane-1-carboxylate (Compound 42, 2.8 g, 10.6 mmol) in dry MeOH (28 mL) was added 5-chlorothiophene-2-carbaldehyde (1.2 mL, 12.6 mmol), AcOH (0.6 mL) and then 4 Å powdered molecular sieves (1.6 g). The reaction mixture was stirred at room temperature for 1 hour. (The formation of imine was observed as a less polar spot on TLC). To this was then added sodium cyanoborohydride (NaCNBH$_3$, 0.8 g, 12.6 mmol) portionwise at 0° C., and stirring was continued at room temperature for 2 hours. The reaction mixture was quenched with ice-cold water (50 mL), filtered through a Celite pad and the filtrate was extracted into EtOAc (4×100 mL). The combined organic layers were dried over sodium sulfate, filtered and concentrated under reduced pressure. The residue was purified by silica gel column chromatography (100-200 mesh), eluting with 60% EtOAc/n-hexane, to afford desired product (2.5 g, 60%) as a light yellow liquid. A portion (200 mg) of semi-pure sample was further purified by preparative HPLC to afford allyl 4-(5-((5-chlorothiophen-2-yl)methylamino)-1H-pyrazol-3-yl)azepane-1-carboxylate (Compound 43, 110 mg) as a gum. MS (ESI): m/z 395.05 [M+H]$^+$. $^1$H NMR (300 MHz, DMSO-d6): δ 11.23 (s, 1H), 6.89-6.91 (d, J=6.0 Hz, 1H), 6.83 (d, J=3.0 Hz, 1H), 5.89-5.91 (m, 1H), 5.62 (brs, 1H), 5.16-5.29 (m, 3H), 4.54 (d, J=6.0 Hz, 2H), 4.27 (d, J=6.1 Hz, 2H), 3.23-3.61 (m, 4H), 2.63 (t, J=9.0 Hz, 1H), 1.83-1.97 (m, 4H), 1.70-1.97 (m, 2H) ppm; TLC System: Ethyl acetate. $R_f$ 0.5.

Example 72—Preparation of Compound 44

The synthesis of Compound 44 followed the procedure of General Procedure 5d following:

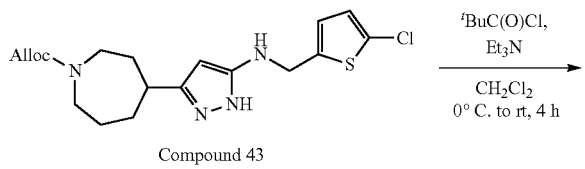

Compound 43

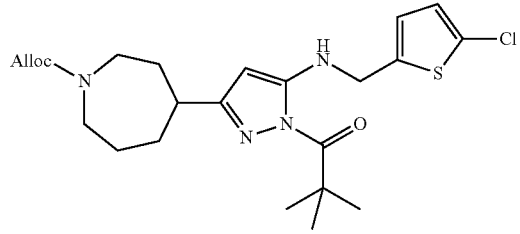

Compound 44

To a cooled solution (0° C.) of allyl 4-(5-((5-chlorothiophen-2-yl)methylamino)-1H-pyrazol-3-yl)azepane-1-carboxylate (Compound 43, 2.5 g, 6.3 mmol) in dry dichloromethane (100 mL) was added triethylamine (TEA, 1.3 mL, 9.5 mmol) followed by trimethylacetyl chloride (0.7 mL, 5.7 mmol). After stirring at room temperature for 4 hours, the reaction mixture was diluted with water (25 mL) and extracted into dichloromethane (3×40 mL). The combined organic layers were dried over sodium sulfate, filtered and concentrated under reduced pressure. The residue was purified by silica gel column chromatography (100-200 mesh), eluting with 10% EtOAc/n-hexane, to afford desired product allyl 4-(5-((5-chlorothiophen-2-yl)methylamino)-1-pivaloyl-1H-pyrazol-3-yl)azepane-1-carboxylate (Compound 44, 1.8 g, 60%) as a colorless liquid. MS (ESI): m/z 479.26 [M+H]$^+$. $^1$H NMR (400 MHz, DMSO-d6): δ 7.63 (t, J=6.0 Hz, 1H), 6.95 (s, 2H), 5.88-5.96 (m, 1H), 5.37 (d, J=3.2 Hz, 1H), 5.14-5.28 (m, 2H), 4.53 (d, J=5.2 Hz, 2H), 4.40 (d, J=6.0 Hz, 2H), 3.28-3.61 (m, 4H), 2.64-2.61 (m, 1H), 1.84-1.88 (m, 4H), 1.54-1.72 (m, 2H), 1.39 (s, 9H).

TLC System: 20% ethyl acetate in hexane. $R_f$-0.5.

Example 73—Preparation of Compound 45

The synthesis of Compound 45 followed the procedure of General Procedure 8b following:

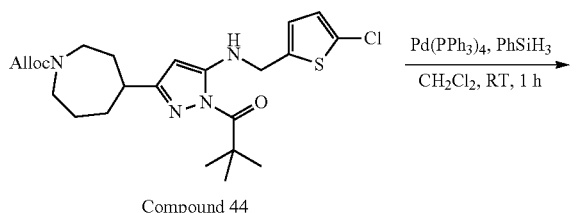

Compound 44

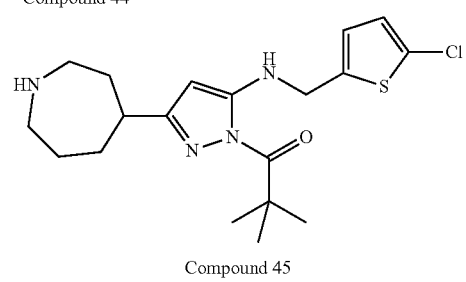

Compound 45

A stirred solution of allyl 4-(5-((5-chlorothiophen-2-yl)methylamino)-1-pivaloyl-1H-pyrazol-3-yl)azepane-1-carboxylate (Compound 44, 400 mg, 0.8 mmol) in dichloromethane (30 mL) was degassed with stream of argon for 15 minutes, then to it was added phenylsilane (PhSiH$_3$, 0.6 mL, 4.8 mmol) followed by tetrakis(triphenylphosphine) palladium(0) (Pd(PPh$_3$)$_4$, 93 mg, 0.08 mmol). The reaction mixture was stirred at room temperature for 45 minutes, then the mixture was filtered through a Celite pad and then evaporated. The crude residue was purified by flash chromatography using 30% MeOH-DCM to afford the semi-pure 1-(3-(azepan-4-yl)-5-((5-chlorothiophen-2-yl)methylamino)-1H-pyrazol-1-yl)-2,2-dimethylpropan-1-one (Compound 45, 200 mg; 94% by LCMS). MS (ESI) m/z 395.19 [M+H]$^+$, $^1$H NMR (300 MHz, DMSO-d$_6$) δ 7.62 (t, J=6.0 Hz, 1H), 6.96 (s, 2H), 5.34 (s, 1H), 4.40 (d, J=5.7 Hz, 2H), 3.18-2.68 (m, 6H), 2.05-1.62 (m, 6H), 1.38 (s, 9H) ppm; TLC System: 20% MeOH-dichloromethane, $R_f$-0.2.

Example 74—Preparation of Compound 46

The synthesis of Compound 46 followed the procedure of General Procedure 15 following:

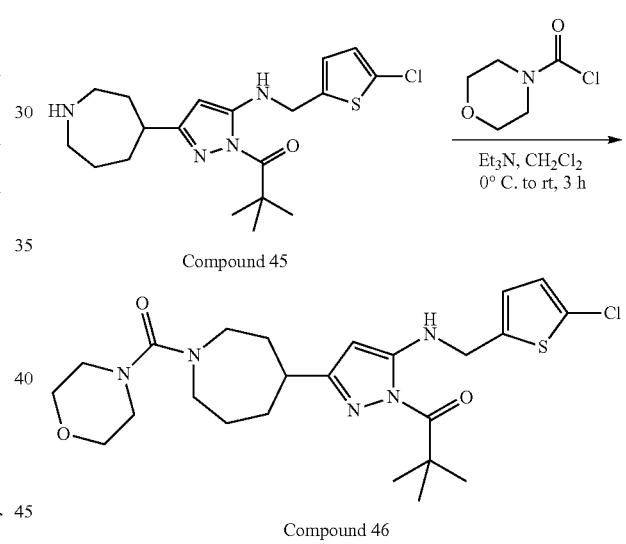

To a cold solution (0° C.) of 1-(3-(azepan-4-yl)-5-((5-chlorothiophen-2-yl)methylamino)-1H-pyrazol-1-yl)-2,2-dimethylpropan-1-one (Compound 45, 317 mg, 0.8 mmol) in dry dichloromethane (50 mL) was added triethylamine (TEA, 0.28 mL, 2 mmol) followed by morpholine carbamyl chloride (0.14 mL, 1.2 mmol). The mixture was stirred at room temperature for 3 hours. The reaction mixture was diluted with water (20 mL) and extracted into dichloromethane (2×20 mL). The combined organic layers were dried over sodium sulfate, filtered and concentrated under reduced pressure. The residue was purified by CombiFlash, eluting with 30% EtOAc/n-hexane, to afford 1-(5-((5-chlorothiophen-2-yl)methylamino)-3-(1-(morpholine-4-carbonyl)azepan-4-yl)-1H-pyrazol-1-yl)-2,2-dimethylpropan-1-one (Compound 46, 140 mg, 34%) as an off-white semi-solid; MS (ESI): m/z 508.28 [M+H]$^+$. $^1$H NMR (400 MHz, DMSO-d6): δ 7.63 (t, J=6.4 Hz, 1H), 6.95 (s, 2H), 5.36 (s, 1H), 4.40 (d, J=6.0 Hz, 2H), 3.57-3.55 (m, 4H), 3.51-3.41 (m, 2H), 3.31-3.21 (m, 2H), 3.06-2.98 (m, 4H), 2.64-2.62

(m, 1H), 2.00-1.83 (m, 5H), 1.81-1.51 (m, 1H), 1.39 (s, 9H) ppm; TLC System: 50% ethyl acetate in hexane. $R_f$-0.5.

Example 75—Preparation of Compound 47

The synthesis of Compound 47 followed the procedure of General Procedure 6d following:

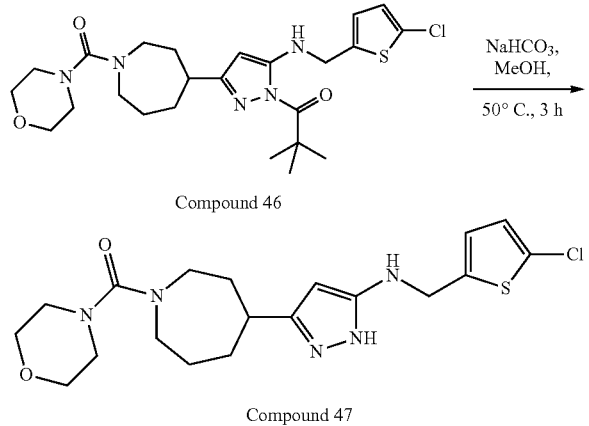

Compound 46

Compound 47

To a stirred solution of 1-(5-((5-chlorothiophen-2-yl)methylamino)-3-(1-(morpholine-4-carbonyl)azepan-4-yl)-1H-pyrazol-1-yl)-2,2-dimethylpropan-1-one (Compound 46, 200 mg, 0.39 mmol) in methanol (5 mL) was added sodium bicarbonate (NaHCO₃, 100 mg, 1.1 mmol). The reaction mixture was stirred at 50° C. for 3 hours. The reaction mixture was cooled to room temperature and the volatiles were evaporated and the resultant residue was diluted with EtOAc (20 mL) and washed with water (2×10 mL). The organic layer was dried over sodium sulfate, filtered and concentrated under reduced pressure. The resulting solid was triturated with diethyl ether and pentane and dried under high vacuum for 1 hour affording (4-(5-((5-chlorothiophen-2-yl)methylamino)-1H-pyrazol-3-yl)azepan-1-yl)(morpholino)methanone (Compound 47, 150 mg, 90%) as an off-white solid. LCMS: m/z 424.24 [M+H]⁺; ¹H-NMR (400 MHz, DMSO-d₆) δ 11.21 (s, 1H), 6.90-6.82 (dd, J=10.0, 3.2 Hz, 2H), 5.58 (brs, 1H), 5.25 (s, 1H), 4.27 (d, J=5.6 Hz, 2H), 3.57-3.53 (m, 4H), 3.50-3.42 (m, 2H), 3.27-3.17 (m, 2H), 3.08-2.98 (m, 4H), 2.66-2.62 (m, 1H), 1.69-1.92 (m, 5H), 1.46-1.49 (m, 1H) ppm; TLC System: 50% ethyl acetate in hexane. $R_f$-0.2.

Example 76—Preparation of Compound 48

The synthesis of Compound 48 followed the procedure of General Procedure 5d following:

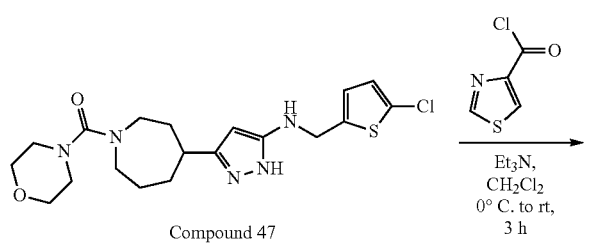

Compound 47

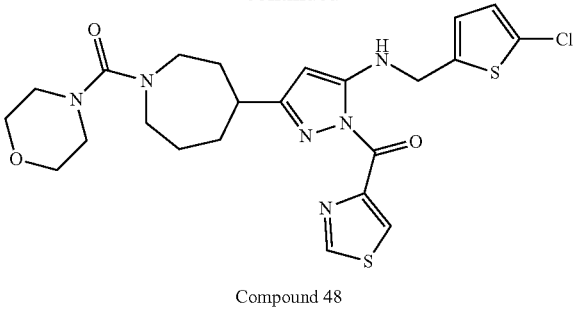

Compound 48

To a cooled solution (0° C.) of (4-(5-((5-chlorothiophen-2-yl)methylamino)-1H-pyrazol-3-yl)azepan-1-yl)(morpholino)methanone (Compound 47, 187 mg, 0.44 mmol) in dry dichloromethane (10 mL) was added triethylamine (TEA, 1.84 mL, 1.32 mmol) followed by thiazole-4-carbonyl chloride (78 mg, 0.53 mmol). The mixture was stirred at room temperature for 3 hours. The reaction mixture was diluted with water (15 mL) and extracted into dichloromethane (3×40 mL). The combined organic layers were dried over sodium sulfate, filtered and concentrated under reduced pressure. The residue was purified by CombiFlash, eluting with 60% EtOAc/n-hexane, to afford (4-(5-((5-chlorothiophen-2-yl)methylamino)-1-(thiazole-4-carbonyl)-1H-pyrazol-3-yl)azepan-1-yl)(morpholino)methanone (Compound 48, 60 mg, 25%) as a yellow solid. MS (ESI): m/z 535.21 [M+H]⁺; ¹H NMR (400 MHz, DMSO-d6) δ 9.19 (d, J=1.2 Hz, 1H), 9.03 (d, J=1.2 Hz, 1H), 7.77 (t, J=6.4 Hz, 1H), 6.98 (dd, J=9.2, 3.2 Hz, 2H), 5.52 (s, 1H), 4.50 (d, J=6.4 Hz, 2H), 3.56-3.42 (m, 6H), 3.31-3.21 (m, 2H), 3.06-2.96 (m, 4H), 2.68-2.64 (m, 1H), 2.04-1.85 (m, 4H), 1.72-1.67 (m, 1H), 1.60-1.59 (m, 1H) ppm; TLC System: 80% ethyl acetate in hexane. $R_f$-0.7.

Example 77—Preparation of Intermediate 29

The synthesis of Intermediate 29 followed the procedure of General Procedure 20 following:

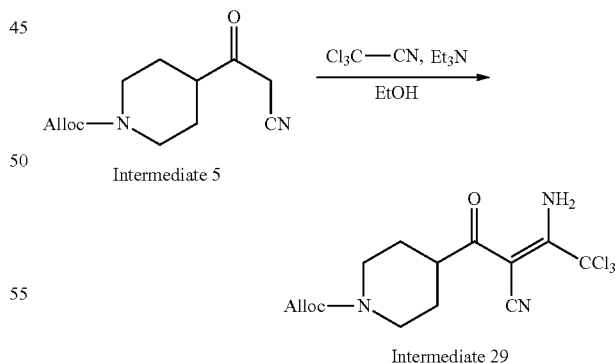

Intermediate 5

Intermediate 29

To a stirred solution of allyl 4-(3-amino-cyanoacetyl)piperidine-1-carboxylate (Intermediate 5, 2.5 g, 10.6 mmol) in ethanol (30 mL) was added trichloroacetonitrile (2.1 mL, 21.2 mmol) and triethylamine (TEA, 0.2 mL). The reaction mixture was stirred at room temperature for 2 hours. The volatiles were evaporated and the resultant residue was purified by silica gel column chromatography (100-200 mesh), eluting with 50% EtOAc/n-hexane, to afford the desired product (Z)-allyl 4-(3-amino-4,4,4-trichloro-2-cyanobut-2-enoyl)piperidine-1-carboxylate (Intermediate 29, 3.2 g, 80%) as a brown liquid. MS (ESI): m/z 380.13 [M+H]$^+$; TLC System: 30% Ethyl acetate in hexane R$_f$-0.5.

Example 78—Preparation of Compound 49

The synthesis of Compound 49 followed the procedure of General Procedure 21 following:

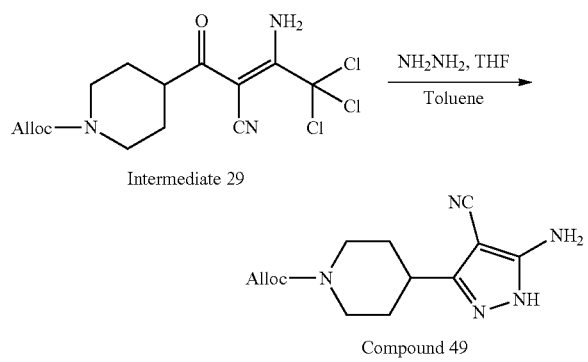

To a stirred solution of (Z)-allyl 4-(3-amino-4,4,4-trichloro-2-cyanobut-2-enoyl)piperidine-1-carboxylate (Intermediate 29, 3.2 g, 8.4 mmol) in toluene (30 mL) was added N$_2$H$_4$ (1M in THF) (16.8 mL, 16.8 mmol) and the reaction mixture was heated to 100° C. for 15 hours. The reaction mixture was cooled to room temperature, the volatiles were evaporated and the resultant residue was purified by silica gel column chromatography (100-200 mesh), eluting with 5% MeOH-dichloromethane, to afford the desired product allyl 4-(5-amino-4-cyano-1H-pyrazol-3-yl)piperidine-1-carboxylate (Compound 49, 1.4 g, 61%) as an off-white solid. MS (ESI): m/z 275.13 [M+H]$^+$. TLC System: 10% Methanol-dichloromethane. R$_f$-0.3.

Example 79—Preparation of Compound 50

The synthesis of Compound 50 followed the procedure of General Procedure 4 following:

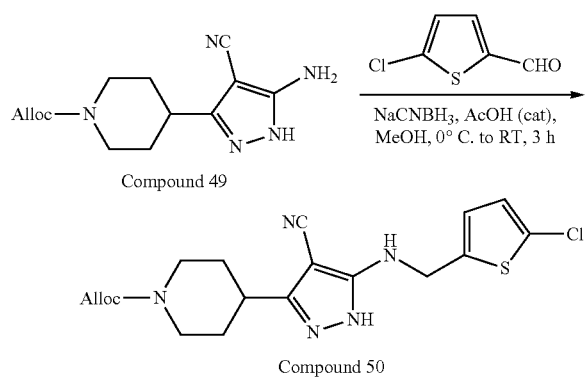

To a cold solution (0° C.) of allyl 4-(5-amino-4-cyano-1H-pyrazol-3-yl)piperidine-1-carboxylate (Compound 49, 3.2 g, 11.6 mmol) in dry MeOH (30 mL) was added 5-chlorothiophene-2-carbaldehyde (1.8 mL, 14 mmol), AcOH (2 mL) and powdered 4 Å molecular sieves (1.6 g). The reaction mixture was stirred at room temperature for 1 hour. Formation of imine was observed as a less polar spot on TLC. To the mixture was then added sodium cyanoborohydride (NaCNBH$_3$, 1.08 g, 17.5 mmol) portionwise at 0° C. and the reaction was stirred at room temperature for 2 hours. The reaction mixture was quenched with ice-cold water (50 mL), filtered through a Celite pad and the Celite bed was rinsed several times with EtOAc. The two layers were separated and the aqueous layer was extracted into EtOAc (4×100 mL). The combined organic layers were dried over sodium sulfate, filtered and concentrated under reduced pressure. The residue was purified by silica gel column chromatography (100-200 mesh), eluting with 60% EtOAc/n-hexane, to afford desired product (2.5 g, 60%) as a light yellow liquid. A portion of the sample (200 mg) was further purified by preparative HPLC to afford allyl 4-(5-((5-chlorothiophen-2-yl)methylamino)-4-cyano-1H-pyrazol-3-yl)piperidine-1-carboxylate (Compound 50, 110 mg) as a gummy liquid. MS (ESI): m/z 405.05 [M+H]$^+$; $^1$H NMR (300 MHz, CDCl$_3$) δ 6.81-6.74 (m, 2H), 5.98-5.89 (m, 1H), 5.32-5.21 (m, 2H), 4.60 (d, J 8.0 Hz, 2H), 4.52 (s, 2H), 4.48-4.42 (br s, 1H), 4.40-4.24 (m, 2H), 3.00-2.84 (m, 3H), 2.04-1.96 (m, 2H), 1.76-1.67 (m, 2H) ppm; TLC System: 80% Ethyl acetate in hexane R$_f$-0.4.

Example 80—Preparation of Compound 51

The synthesis of Compound 51 followed the procedure of General Procedure 5d following:

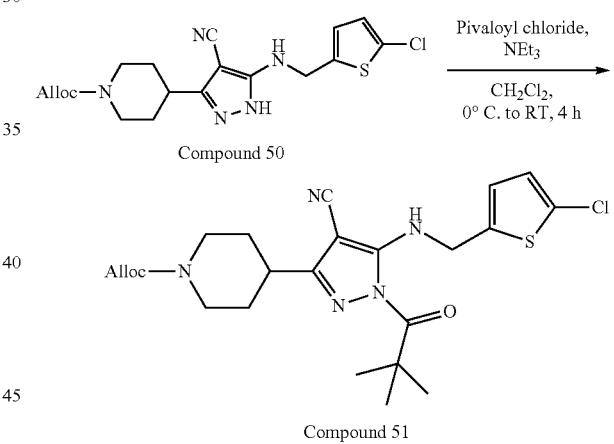

To a cooled solution (0° C.) of compound 50 (2.1 g, 5.2 mmol) in dry dichloromethane (100 mL) was added triethylamine (2.2 mL, 15.5 mmol) followed by pivaloyl chloride 5 (0.66 mL, 6.2 mmol), and the mixture was stirred at room temperature for 4 hours. The reaction mixture was diluted with water (25 mL) and extracted into dichloromethane (3×40 mL). The combined organic layers were dried over sodium sulfate, filtered and concentrated under reduced pressure. The residue was purified by silica gel column chromatography (100-200 mesh), eluting with 10% EtOAc/n-hexane, to afford desired product (1.8 g, 72%) as a colorless liquid. A 200 mg portion of sample was further purified by preparative HPLC to afford allyl 4-(5-((5-chlorothiophen-2-yl)methylamino)-4-cyano-1-pivaloyl-1H-pyrazol-3-yl)piperidine-1-carboxylate (Compound 51, 104 mg/99%) as a gummy liquid. MS (ESI): m/z 479.26 [M+H]$^+$. $^1$H NMR (400 MHz, CDCl$_3$) δ 8.44 (t, J 5.6 Hz, 1H), 6.90 (d, J 4.0 Hz, 1H), 6.80 (d, J 4.0 Hz, 1H), 6.00-5.91 (m, 1H), 5.33-5.20 (m, 2H), 4.85 (d, J 4.0 Hz, 2H), 4.61 (d, J 4.0 Hz, 2H), 4.30-4.14 (m, 2H), 3.04-2.90 (m, 2H), 2.89-2.81 (m, 1H), 2.01 (d, J 10.8 Hz, 2H), 1.73 (d, J 10.8 Hz, 2H), 1.42 (s, 9H); TLC System: 20% ethyl acetate in hexane. $R_f$-0.5.

Example 81—Preparation of Compound 52

The synthesis of Compound 52 followed the procedure of General Procedure 8b following:

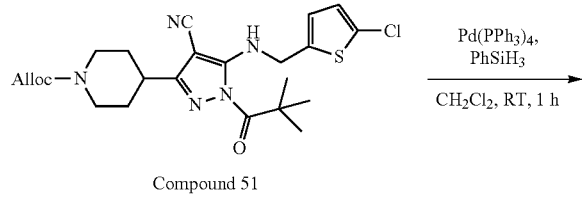

A stirred solution of Compound 51 (250 mg, 0.51 mmol) in dichloromethane (10 mL) was degassed with a stream of argon for 15 minutes, then to it was added phenylsilane (PhSiH$_3$, 0.19 mL, 1.53 mmol) followed by tetrakis(triphenylphosphine)palladium(0) (Pd(PPh$_3$)$_4$, 58 mg, 0.05 mmol). The reaction mixture was stirred at room temperature for 45 minutes, then filtered through a Celite pad and the filtrate was evaporated. The residue was purified by flash chromatography using 30% MeOH-dichloromethane to afford the semi-pure desired product 1-(3-(piperdine-4-yl)-5-((5-chlorothiophen-2-yl)methylamino)-4-cyano-1H-pyrazol-1-yl)-2,2-dimethylpropan-1-one (Compound 52, 280 mg/74% by LCMS), used directly for the next reaction without further purification; TLC System: 20% MeOH-dichloromethane, $R_f$-0.2.

Example 82—Preparation of Compound 53

The synthesis of Compound 53 followed the procedure of General Procedure 15 following:

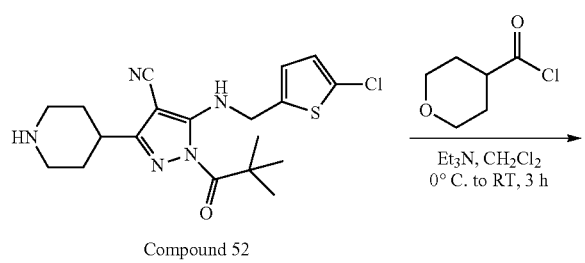

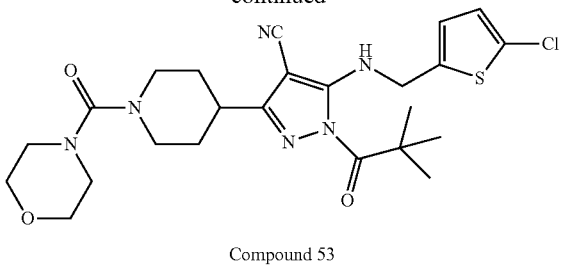

To a cooled solution (0° C.) of 1-(3-(piperdine-4-yl)-5-((5-chlorothiophen-2-yl)methylamino)-4-cyano-1H-pyrazol-1-yl)-2,2-dimethylpropan-1-one (Compound 52, 280 mg, 0.69 mmol) in dry dichloromethane (50 mL) was added triethylamine (TEA, 0.28 mL, 2.1 mmol), followed by morpholine carbamyl chloride (0.12 mg, 0.83 mmol). The mixture was stirred at room temperature for 3 hours. The reaction mixture was diluted with water (20 mL) and extracted into dichloromethane (2×20 mL). The combined organic layers were dried over sodium sulfate, filtered and concentrated under reduced pressure. The residue was purified by CombiFlash, eluting with 30% EtOAc/n-hexane followed by preparative HPLC to afford desired product 1-(5-((5-chlorothiophen-2-yl)methylamino)-3-(1-(morpholine-4-carbonyl)piperdine-4-yl)-4-cyano-1H-pyrazol-1-yl)-2,2-dimethylpropan-1-one (Compound 53, 140 mg, 34%) as an off-white semi-solid. MS (ESI): m/z 508.28 [M+H]$^+$. $^1$H NMR (400 MHz, CDCl3) δ 8.45 (t, J=6.0 Hz, 1H), 6.90 (d, J=4.0 Hz, 1H), 6.80 (d, J=4.0 Hz, 1H), 4.85 (d, J=6.0 Hz, 2H), 3.80 (d, J=13.2 Hz, 2H), 3.71-3.68 (m, 4H), 3.28-3.25 (m, 4H), 2.97-2.90 (m, 2H), 2.87-2.81 (m, 1H), 2.04-2.00 (m, 2H), 1.80-1.71 (m, 2H), 1.42 (s, 9H) ppm; TLC System: 50% ethyl acetate in hexane. $R_f$-0.5.

Example 83—Preparation of Intermediate 31

The synthesis of Intermediate 31 followed the procedure of General Procedure 2 following:

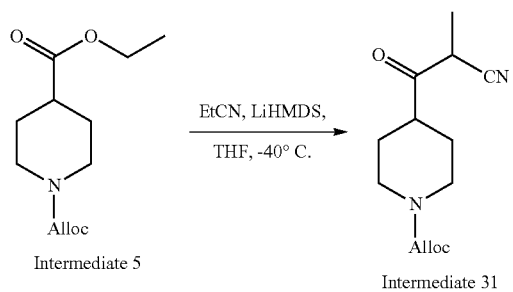

To a cooled solution (−40° C.) of propionitrile (5.8 mL, 74.7 mmol) in dry THF (120 mL) was added lithium hexamethylsilazide (LHMDS, 1M in THF, 99 mL, 99.6 mmol). After stirring at −40° C. for 15 minutes, a solution of 1-allyl-4-ethyl piperidine-1,4-dicarboxylate (Intermediate 5, 12 g, 49.8 mmol) in dry THF (30 mL) was added and the reaction mixture was stirred at the same temperature for 30 minutes. The reaction mixture was quenched with saturated NH$_4$Cl solution (80 mL) and extracted with EtOAc (2×120 mL). The combined organic layers were dried over sodium sulfate, filtered and concentrated under reduced pressure. The residue was purified by silica gel column chromatography (100-200 mesh), eluting with 50% EtOAc/n-hexane, to afford allyl 4-(2-cyanopropanoyl)piperidine-1-carboxylate (Intermediate 31, 9 g, yield: 72%) as a light yellow liquid. m/z 250.87 [M+H]+; TLC System: 30% ethyl acetate in hexane R$_f$-0.5.

Example 84—Preparation of Compound 54

The synthesis of Compound 54 followed the procedure of General Procedure 3 following:

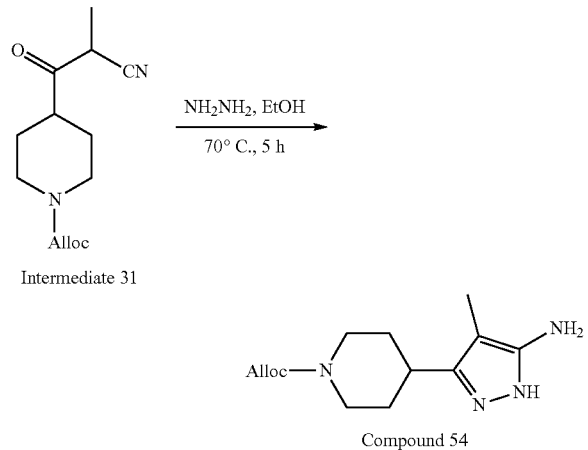

To a stirred solution of allyl 4-(2-cyanopropanoyl)piperidine-1-carboxylate (Intermediate 31, 9 g, 36 mmol) in ethanol (90 mL) was added N$_2$H$_4$ (1.6 mL, 32.4 mmol) and the reaction mixture was heated to 70° C. for 5 hours. The reaction mixture was cooled to room temperature, the volatiles were evaporated and the resultant residue was purified by silica gel column chromatography (100-200 mesh), eluting with 3% MeOH-dichloromethane, to afford allyl 4-(5-amino-4-methyl-1H-pyrazol-3-yl)piperidine-1-carboxylate (Compound 54, 8 g, yield: 84%) colorless liquid. m/z 265.13 [M+H]+; TLC System: 5% Methanol-dichloromethane. R$_f$-0.5.

Example 85—Preparation of Compound 55

The synthesis of Compound 55 followed the procedure of General Procedure 4 following:

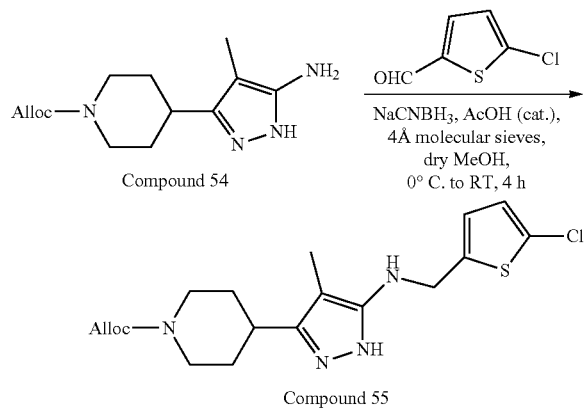

To a cooled solution (0° C.) of allyl 4-(5-amino-4-methyl-1H-pyrazol-3-yl)piperidine-1-carboxylate (Compound 54, 5 g, 18.9 mmol) in dry MeOH (50 mL) was added 5-chlorothiophene-2-carbaldehyde (4.2 mL, 37.8 mmol), AcOH (0.2 mL), and then powdered 4 Å molecular sieves. The reaction mixture was stirred at room temperature for 1 hour. The formation of imine was observed as a less polar spot by TLC. To the reaction mixture was then added sodium cyanoborohydride (NaCNBH$_3$, 1.4 g, 22.7 mmol) portionwise, and the mixture stirred at room temperature for 2 hours. To the mixture was added ice-cold water (50 mL), then filtered through a Celite pad and the filtrate was extracted with EtOAc (4×100 mL). The combined organic layers were dried over sodium sulfate, filtered and concentrated under reduced pressure. The residue was purified by silica gel column chromatography (100-200 mesh), eluting with 50% EtOAc/n-hexane, to afford desired product (3.5 g, yield: 46%) as a light yellow liquid. A portion (300 mg) of semi-pure sample was further purified by preparative HPLC to afford allyl 4-(5-((5-chlorothiophen-2-yl)methylamino)-4-methyl-1H-pyrazol-3-yl)piperidine-1-carboxylate (Compound 55, 110 mg) as a gummy liquid. m/z 395.16 [M+H]+. $^1$H NMR (400 MHz, CDCl$_3$) δ 11.08 (br s, 1H), 6.89 (d, J=3.9 Hz, 1H), 6.82 (d, J=3.4 Hz, 1H), 5.94 (tdd, J=5.2, 10.5, 17.2 Hz, 1H), 5.38-5.26 (m, 2H), 5.19 (dd, J=1.5, 10.3 Hz, 1H), 4.56-4.50 (m, 2H), 4.33 (d, J=6.4 Hz, 2H), 4.08 (br d, J=13.2 Hz, 2H), 2.86 (br s, 2H), 2.73 (tt, J=3.5, 12.2 Hz, 1H), 1.79-1.71 (m, 3H), 1.70-1.63 (m, 2H), 1.59-1.48 (m, 2H) ppm; TLC System: 50% ethyl acetate in hexane. R$_f$-0.5.

Example 86—Preparation of Compound 56

The synthesis of Compound 56 followed the procedure of General Procedure 5d following:

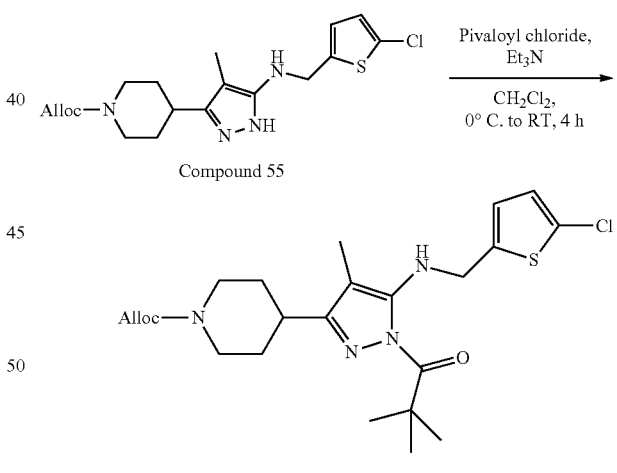

To a cooled solution (0° C.) of allyl 4-(5-((5-chlorothiophen-2-yl)methylamino)-4-methyl-1H-pyrazol-3-yl)piperidine-1-carboxylate (Compound 55, 1.9 g, 4.8 mmol) in dry dichloromethane (20 mL) was added trimethylacetyl chloride (0.57 mL, 4.3 mmol), followed by triethylamine (TEA, 1 mL, 7.2 mmol), and the mixture was stirred at room temperature for 4 hours. The reaction mixture was combined with water (25 mL) and extracted with dichloromethane (3×40 mL). The combined organic layers were dried over sodium sulfate, filtered and concentrated under reduced pressure. The residue was purified by silica gel column chromatography (100-200 mesh), eluting with 20% EtOAc/n-hexane, to afford desired product (1.3 g, yield-69%) as a light yellow liquid. A portion (300 mg) of semi-pure sample was further purified by preparative HPLC to afford allyl 4-(5-((5-chlorothiophen-2-yl)methylamino)-4-methyl-1-pivaloyl-1H-pyrazol-3-yl)piperidine-1-carboxylate (Compound 56, 70 mg) as a light yellow liquid. m/z 479.23 [M+H]+ 1H NMR (400 MHz, CDCl$_3$) δ=7.26 (s, 1H), 6.74 (d, J=3.9 Hz, 1H), 6.69 (d, J=3.4 Hz, 1H), 6.02-5.91 (m, 1H), 5.32 (dd, J=1.5, 17.1 Hz, 1H), 5.22 (dd, J=1.2, 10.5 Hz, 1H), 4.61 (br d, J=5.4 Hz, 2H), 4.51 (br d, J=5.4 Hz, 2H), 4.20 (br d, J=10.8 Hz, 2H), 2.98 (br t, J=10.8 Hz, 2H), 2.68 (tt, J=3.7, 10.8 Hz, 1H), 2.01-1.97 (m, 3H), 1.86 (br d, J=11.2 Hz, 2H), 1.78-1.69 (m, 2H), 1.43 (s, 9H) ppm; TLC System: 50% ethyl acetate in hexane. R$_f$-0.5.

Example 87—Preparation of Compound 57

5 [0322] The synthesis of Compound 57 followed the procedure of General Procedure 8b following:

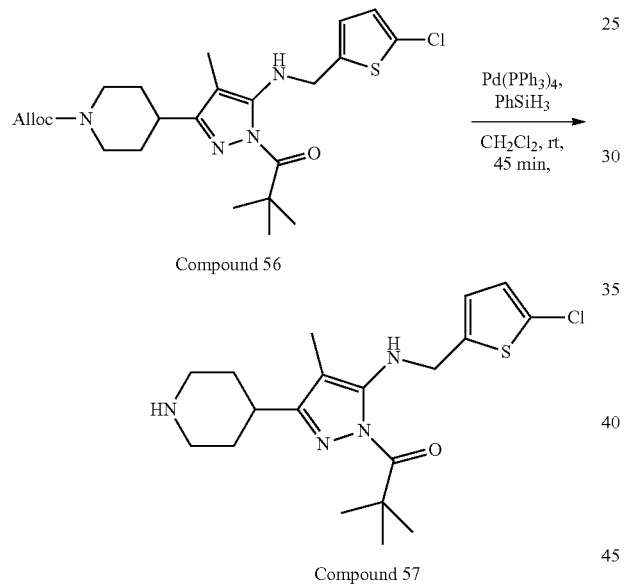

Compound 56

Compound 57

A stirred solution of allyl 4-(5-((5-chlorothiophen-2-yl)methylamino)-4-methyl-1-pivaloyl-1H-pyrazol-3-yl)piperidine-1-carboxylate (Compound 56, 1 g, 2.1 mmol) in dichloromethane (10 mL) was degassed with a stream of argon for 15 minutes, then to the solution was added tetrakis(triphenylphosphine)palladium(0) (Pd(PPh$_3$)$_4$, 240 mg, 0.21 mmol), followed by phenylsilane (PhSiH$_3$, 1.6 mL, 12.5 mmol). The reaction mixture was stirred at room temperature for 45 minutes, then filtered through a Celite pad and the filtrate was evaporated. The crude residue was purified by flash chromatography eluting with 4% MeOH-dichloromethane to afford the semi-pure desired product (600 mg (91% by LCMS), yield: 72%). A portion (130 mg) of the semi-pure sample was purified by preparative HPLC to afford 1-(5-((5-chlorothiophen-2-yl)methylamino)-4-methyl-3-(piperidin-4-yl)-1H-pyrazol-1-yl)-2,2-dimethylpropan-1-one (Compound 57, 40 mg) as an off-white solid. m/z 395.19 [M+H]$^+$, $^1$H NMR (400 MHz, DMSO-d$_6$) δ=8.37 (br s, 1H), 7.26 (br t, J=7.1 Hz, 1H), 6.96 (d, J=3.9 Hz, 1H), 6.82 (d, J=3.9 Hz, 1H), 4.55 (d, J=6.8 Hz, 2H), 3.16 (br d, J=12.2 Hz, 2H), 2.86-2.72 (m, 3H), 1.92 (s, 3H), 1.83 (br d, J=12.7 Hz, 2H), 1.67 (q, J=10.9 Hz, 2H), 1.38 (s, 9H) ppm; TLC System: 10% MeOH-dichloromethane, R$_f$-0.5.

Example 88—Preparation of Compound 58

The synthesis of Compound 58 followed the procedure of General Procedure 6d following:

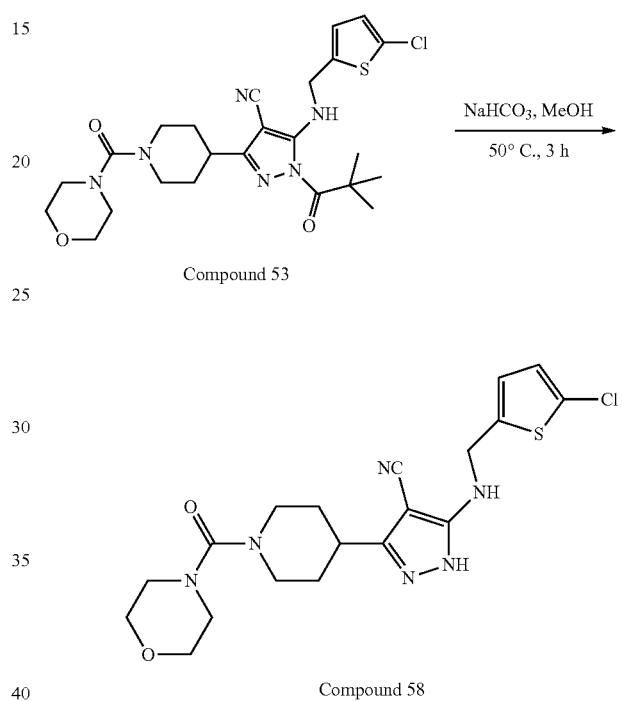

Compound 53

Compound 58

To a solution of 1-(5-((5-chlorothiophen-2-yl)methylamino)-3-(1-(morpholine-4-carbonyl)piperdine-4-yl)-4-cyano-1H-pyrazol-1-yl)-2,2-dimethylpropan-1-one (Compound 53, 350 mg, 0.67 mmol) in methanol (15 mL) was added sodium bicarbonate (NaHCO$_3$, 113 mg, 1.3 mmol). The reaction mixture was stirred at 50° C. for 3 hours. The reaction mixture was cooled to room temperature, the volatiles were evaporated and the resultant residue was diluted with EtOAc (20 mL) and washed with water (2×10 mL). The organic layer was dried over sodium sulfate, filtered and concentrated under reduced pressure. The solid obtained was triturated with diethyl ether and pentane and dried under high vacuum for 1 h to afford 5-((5-chlorothiophen-2-yl)methylamino)-3-(1-(morpholine-4-carbonyl)piperidin-4-yl)-1H-pyrazole-4-carbonitrile (Compound 58, 250 mg, 90%) as an off-white solid. m/z 424.24 [M+H]+; 1H-NMR (400 MHz, DMSO-d6, mixture of rotamers) δ 12.30 (s, 0.7H), 12.12 (s, 0.3H), 7.45 (br s, 0.3H), 7.00-6.80 (m, 2H), 6.60 (t, J=5.2 Hz, 0.7H), 4.48-4.32 (m, 2H), 3.74-3.62 (m, 2H), 3.56 (br s, 4H), 3.11 (br s, 4H), 2.93-2.66 (3H), 1.86-1.78 (m, 2H), 1.70-1.52 (m, 2H) ppm; TLC System: 50% ethyl acetate in hexane. Rf-0.2.

Example 89—Preparation of Intermediate 32

The synthesis of Intermediate 32 followed the procedure of General Procedure 6c following:

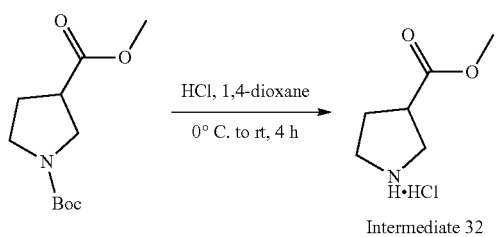

Intermediate 32

To a cooled solution (0° C.) of dl-1-tert-butyl-3-methylpyrrolidine-1,3-dicarboxylate (12 g, 52.4 mmol) in 1,4-dioxane (30 mL) was added 4M HCl in dioxane (24 mL). The solution was allowed to warm to room temperature for 4 hours. The reaction mixture was concentrated under reduced pressure to obtain dl-methyl pyrrolidine-3-carboxylate hydrochloride (8.6 g, yield: 100%). It was used 'as is' for the next step without any purification.

Example 90—Preparation of Intermediate 33

The synthesis of Intermediate 33 followed the procedure of General Procedure 7 following:

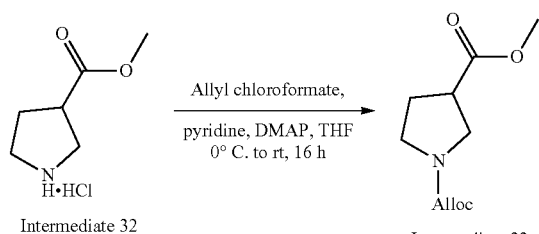

Intermediate 32 → Intermediate 33

To a cooled solution (0° C.) of dl-methylpyrrolidine-3-carboxylate hydrochloride (Intermediate 32, 14.4 g, 87.3 mmol) in THF (150 mL) was added pyridine (28.1 mL, 349.3 mmol) and 4-(dimethylamino)pyridine (DMAP, 1.07 g, 8.7 mmol), followed by allyl chloroformate (18.5 mL, 174.7 mmol). After warming to room temperature for 16 hours, to the reaction mixture was added water (100 mL) and then extracted into dichloromethane (2×100 mL). The combined organic layers were dried over sodium sulfate, filtered and concentrated under reduced pressure. The residue was purified by silica gel column chromatography (100-200 mesh), eluted with 20-25% EtOAc/n-hexanes, to obtain dl-1-allyl-3-methylpyrrolidine-1,3-dicarboxylate (Intermediate 33, 15 g, yield: 80%) as a colorless liquid. m/z 214.07 [M+H]$^+$; TLC System: 50% ethyl acetate in hexane $R_f$-0.5.

Example 91—Preparation of Intermediate 34

The synthesis of Intermediate 34 followed the procedure of General Procedure 2 following:

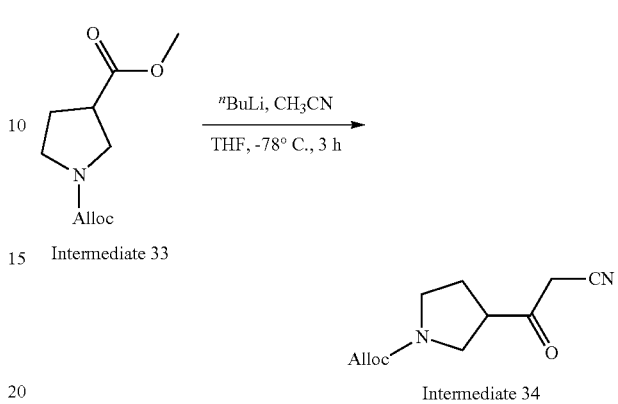

Intermediate 33 → Intermediate 34

To a cooled solution (−78° C.) of acetonitrile (5.5 mL, 105.6 mmol) in dry THF (25 mL) was added n-butyllithium (2.5 M in n-hexane, 42.2 mL, 105.6 mmol). After stirring for 45 minutes, a solution of dl-1-allyl-3-methylpyrrolidine-1,3-dicarboxylate (Intermediate 33, 15 g, 70.4 mmol) in dry THF (30 mL) was added and stirred at −78° C. for 30 minutes. The reaction mixture was quenched with saturated NH$_4$Cl solution (50 mL) and extracted into EtOAc (2×100 mL). The combined organic layers were dried over sodium sulfate, filtered and concentrated under reduced pressure. The residue was purified by silica gel column chromatography (100-200 mesh), eluting with 30-35% EtOAc/n-hexane, to afford dl-allyl-3-(2-cyanoacetyl)pyrrolidine-1-carboxylate (Intermediate 34, 11 g, yield: 70%) as a light yellow liquid; TLC System: 50% ethyl acetate in hexane $R_f$-0.2.

Example 92—Preparation of Compound 59

The synthesis of Compound 59 followed the procedure of General Procedure 3 following:

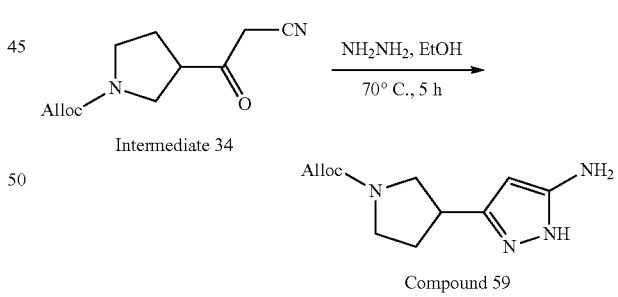

Intermediate 34 → Compound 59

To a stirred solution of dl-allyl-3-(2-cyanoacetyl)pyrrolidine-1-carboxylate (Intermediate 34, 15 g, 67.6 mmol) in ethanol (150 mL) was added hydrazine monohydrate (2.9 mL, 60.8 mmol), and then the reaction mixture was heated to 70° C. for 5 hours. The mixture was cooled to room temperature, the volatiles were evaporated and the resultant residue was purified by silica gel column chromatography (100-200 mesh), eluting with 3% methanol-dichloromethane, to afford dl-allyl-3-(5-amino-1H-pyrazol-3-yl)pyrrolidine-1-carboxylate (Compound 59, 12 g, yield: 75%) as a colorless liquid. m/z 237.54 [M+H]$^+$; TLC System: 5% methanol in dichloromethane $R_f$-0.3.

Example 93—Preparation of Compound 60

The synthesis of Compound 60 followed the procedure of General Procedure 4 following:

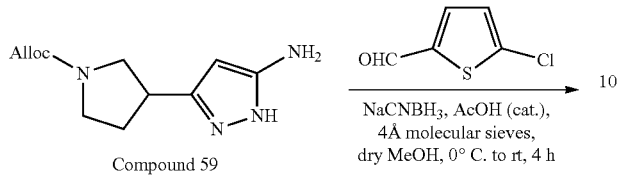

Compound 59

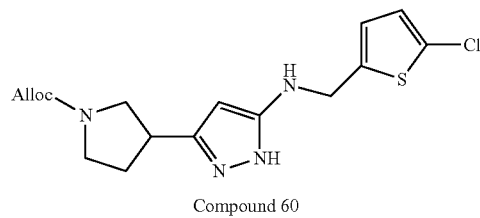

Compound 60

To a cooled solution (0° C.) of dl-allyl-3-(5-amino-1H-pyrazol-3-yl)pyrrolidine-1-carboxylate (Compound 59, 3 g, 12.7 mmol) in dry MeOH (30 mL) was added 5-chlorothiophene-2-carbaldehyde (2.7 mL, 25.4 mmol), AcOH (0.1 mL) and powdered 4 Å molecular sieves. The reaction mixture was stirred at room temperature for 1 hour (formation of imine was observed as a less polar spot on TLC). Sodium cyanoborohydride (NaCNBH₃, 1.18 g, 19.1 mmol) was added portionwise. After the reaction mixture was stirred at room temperature for 2 hours, ice-cold water (30 mL) was added, the mixture filtered through a Celite pad and the filtrate was extracted into EtOAc (3×50 mL). The combined organic layers were dried over sodium sulfate, filtered and concentrated under reduced pressure. The residue was purified by Reveleris C-18 reverse phase column using 35%-40% acetonitrile in aqueous formic acid (0.1%) to obtain dl-allyl-3-(5-((5-chlorothiophen-2-yl)methylamino)-1H-pyrazol-3-yl)pyrrolidine-1-carboxylate (Compound 60, 1.6 g, yield: 34%) as an off-white solid. m/z 367.10 [M+H]$^+$; $^1$H NMR (400 MHz, DMSO-d$_6$) δ 11.43 (br s, 1H), 6.91 (d, J=3.9 Hz, 1H), 6.84 (br s, 1H), 5.98-5.88 (m, 1H), 5.67 (br s, 1H, exchangeable), 5.37-5.24 (m, 2H), 5.18 (br d, J=10.3 Hz, 1H), 4.52 (td, J=1.5, 3.3 Hz, 2H), 4.28 (d, J=6.4 Hz, 2H), 3.67 (br s, 1H), 3.49-3.35 (m, 2H), 3.30-3.21 (m, 2H), 2.16 (br s, 1H), 1.99-1.85 (m, 1H) ppm; TLC System: 10% methanol in dichloromethane R$_f$-0.4.

Example 94—Preparation of Compound 61

The synthesis of Compound 61 followed the procedure of General Procedure 5d following:

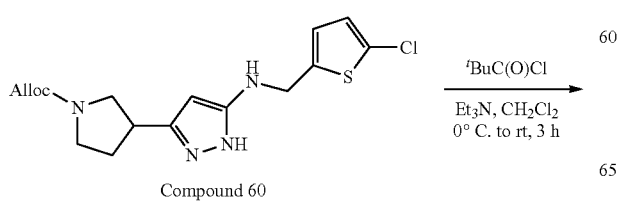

Compound 60

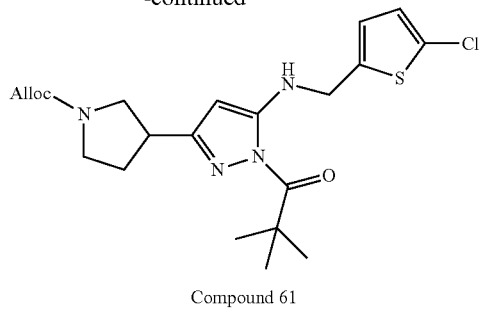

Compound 61

To a cooled solution (0° C.) of dl-allyl 3-(5-((5-chlorothiophen-2-yl)methylamino)-1H-pyrazol-3-yl)pyrrolidine-1-carboxylate (Compound 60, 900 mg, 2.45 mmol) in dry dichloromethane (10 mL) was added trimethylacetyl chloride (0.27 mL, 2.2 mmol) followed by triethylamine (TEA, 0.51 mL, 3.7 mmol). After stirring at room 5 temperature for 3 hours, the reaction mixture was diluted with water (25 mL) and extracted into dichloromethane (3×40 mL). The combined organic layers were dried over sodium sulfate, filtered and concentrated under reduced pressure. The residue was purified by silica gel column chromatography (100-200 mesh), eluting with 10% EtOAc/n-hexane, yielding dl-allyl 3-(5-((5-chlorothiophen-2-yl)methylamino)-1-pivaloyl-1H-pyrazol-3-yl)pyrrolidine-1-carboxylate (Compound 61, 450 mg, yield: 40%) as a colorless gummy liquid. m/z 451.47 [M+H]$^+$. $^1$H NMR (400 MHz, DMSO-d$_6$) δ 7.69 (t, J=6.4 Hz, 1H), 6.98-6.94 (m, 2H), 5.97-5.86 (m, 1H), 5.44 (s, 1H), 5.27 (dd, J=1.5, 17.1 Hz, 1H), 5.17 (dd, J=1.7, 10.5 Hz, 1H), 4.51 (br d, J=5.4 Hz, 2H), 4.41 (d, J=6.4 Hz, 2H), 3.65-3.55 (m, 1H), 3.53-3.37 (m, 3H), 3.36-3.33 (m, 1H), 2.24-2.12 (m, 1H), 2.03-1.94 (m, 1H), 1.39 (s, 9H) ppm; TLC System: 50% ethyl acetate in hexane R$_f$-0.7.

Example 95—Preparation of Compound 62

The synthesis of Compound 62 followed the procedure of General Procedure 5d following:

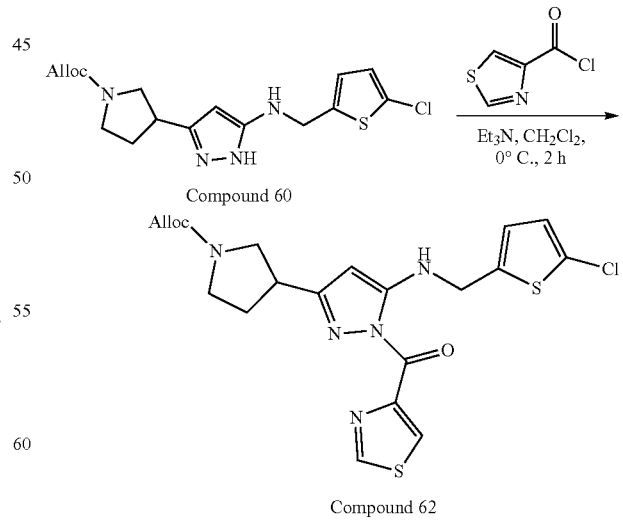

To an ice-cold solution of dl-allyl-3-(5-((5-chlorothiophen-2-yl)methylamino)-1H-pyrazol-3-yl)pyrrolidine-1-carboxylate (Compound 60, 300 mg, 0.8 mmol) in dry dichloromethane (10 mL) was added 1,3-thiazole-4-carbonyl chloride (158 mg, 1.1 mmol) followed by triethylamine (TEA, 0.28 mL, 2.0 mmol). After stirring at 0° C. for 2 hours, ice-cold water (15 mL) was added and extracted into dichloromethane (3×20 mL). The combined organic layers were dried over sodium sulfate, filtered and concentrated under reduced pressure. The residue was purified by flash silica gel column chromatography (100-200 mesh), eluting using 2-4% MeOH-dichloromethane, to obtain semi-pure product (270 mg, yield: 69%). It was further purified by preparative HPLC to give dl-allyl 3-(5-((5-chlorothiophen-2-yl)methylamino)-1-(thiazole-4-carbonyl)-1H-pyrazol-3-yl)pyrrolidine-1-carboxylate (Compound 62, 62 mg) as a pale yellow solid. m/z 478.17 [M+H]+. $^1$H NMR (400 MHz, CDCl$_3$) δ 9.12 (d, J=8.8 Hz, 1H), 8.88 (s, 1H), 7.70 (t, J=5.6 Hz, 1H), 6.82-6.76 (m, 2H), 6.00-5.90 (m, 1H), 5.35-5.26 (m, 2H), 5.21 (dd, J=1.2, 10.5 Hz, 1H), 4.62 (d, J=5.4 Hz, 2H), 4.47 (d, J=5.9 Hz, 2H), 3.86-3.76 (m, 1H), 3.68-3.50 (m, 3H), 3.36 (td, J=7.0, 13.5 Hz, 1H), 2.28 (br s, 1H), 2.10 (dt, J=4.2, 8.2 Hz, 1H) ppm; TLC System: 5% Methanol-dichloromethane. R$_f$-0.6.

Example 96—Preparation of Compound 63

The synthesis of Compound 63 followed the procedure of General Procedure 8b following:

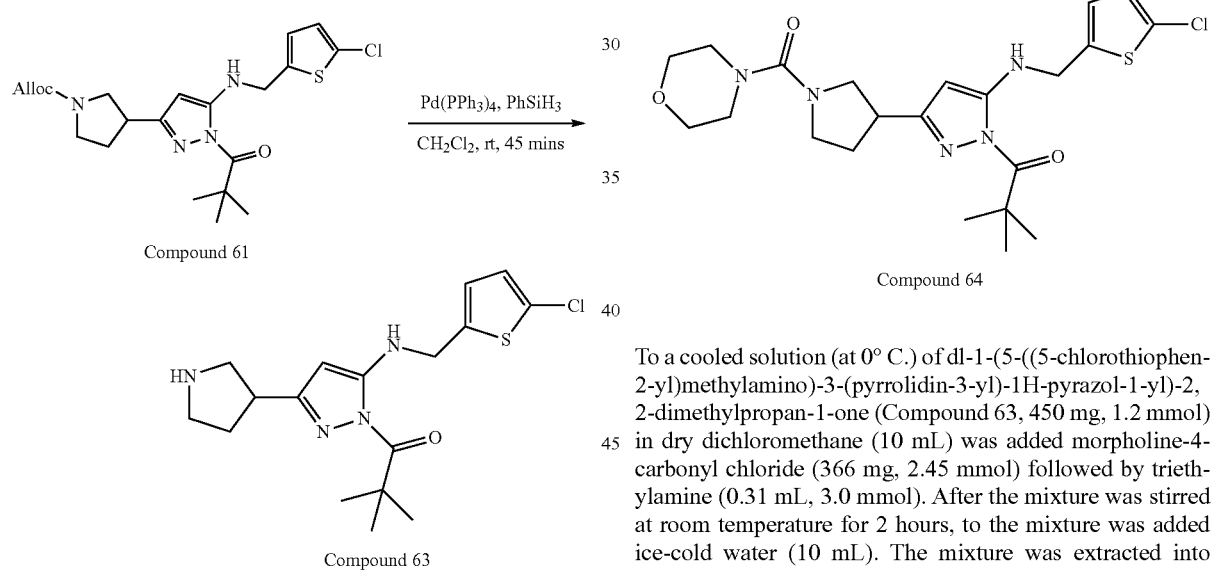

Compound 61

Compound 63

A stirred solution of allyl-3-(5-((5-chlorothiophen-2-yl) methylamino)-1-pivaloyl-1H-pyrazol-3-yl)pyrrolidine-1-carboxylate (Compound 61, 1.5 g, 3.3 mmol) in dry dichloromethane (30 mL) was degassed with a stream of argon for 15 minutes., then to it was added tetrakis(triphenylphosphine)palladium(0) (Pd(PPh$_3$)$_4$, 385 mg, 0.33 mmol) followed by phenylsilane (PhSiH$_3$, 1.2 mL, 10 mmol). The reaction mixture was stirred at room temperature for 45 minutes. The reaction mixture was filtered through a Celite pad and the filtrate was evaporated. The crude residue was purified by combi-flash silica chromatography using 4% MeOH-dichloromethane afforded 1-(5-((5-chlorothiophen-2-yl)methylamino)-3-(pyrrolidin-3-yl)-1H-pyrazol-1-yl)-2,2-dimethylpropan-1-one (Compound 63, 1.1 g, yield: 91%) as an off-white solid. m/z 367.26 [M+H]+, $^1$H NMR (400 MHz, DMSO-d$_6$) δ=9.11 (br s, 2H, exchangeable), 7.78 (br t, J=6.1 Hz, 1H, exchangeable), 7.02-6.95 (m, 2H), 5.50 (s, 1H), 4.42 (br d, J=5.9 Hz, 2H), 3.57-3.34 (m, 2H), 3.32-3.16 (m, 3H), 2.34-2.20 (m, 1H), 2.05-1.90 (m, 1H), 1.41 (s, 9H) ppm; TLC System: 10% methanol in dichloromethane R$_f$-0.1.

Example 97—Preparation of Compound 64

The synthesis of Compound 64 followed the procedure of General Procedure 15 following:

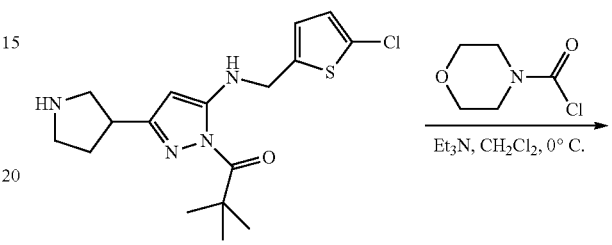

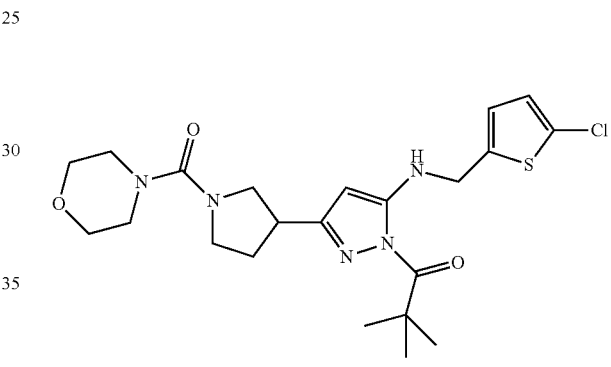

Compound 64

To a cooled solution (at 0° C.) of dl-1-(5-((5-chlorothiophen-2-yl)methylamino)-3-(pyrrolidin-3-yl)-1H-pyrazol-1-yl)-2,2-dimethylpropan-1-one (Compound 63, 450 mg, 1.2 mmol) in dry dichloromethane (10 mL) was added morpholine-4-carbonyl chloride (366 mg, 2.45 mmol) followed by triethylamine (0.31 mL, 3.0 mmol). After the mixture was stirred at room temperature for 2 hours, to the mixture was added ice-cold water (10 mL). The mixture was extracted into dichloromethane (2×15 mL), and the combined organic layers were dried over sodium sulfate, filtered and concentrated under reduced pressure. The residue was purified by silica gel column chromatography (100-200 mesh), eluting with 50% EtOAc-hexanes, to afford the desired product (370 mg, yield: 62%) as a light yellow semi solid. A portion (160 mg) of semi-pure material (85% by LCMS) was further purified by preparative HPLC to obtain dl-1-(5-((5-chlorothiophen-2-yl)methylamino)-3-(1-(morpholine-4-carbonyl) pyrrolidin-3-yl)-1H-pyrazol-1-yl)-2,2-dimethylpropan-1-one (Compound 64, 60 mg) as an off-white solid. m/z 480.16 [M+H]+. $^1$H NMR (400 MHz, DMSO-d$_6$) δ 7.70 (t, J=6.1 Hz, 1H, exchangeable), 6.96 (s, 2H), 5.42 (s, 1H), 4.41 (d, J=6.4 Hz, 2H), 3.58-3.47 (m, 6H), 3.36 (d, J=3.9 Hz, 2H), 3.24-3.19 (m, 1H), 3.15-3.10 (m, 4H), 2.11 (dd, J=6.1, 12.5 Hz, 1H), 1.97-1.89 (m, 1H), 1.39 (s, 9H) ppm; TLC System: 70% ethyl acetate in n-hexane—R$_f$-0.6.

Example 98—Preparation of Compound 65

The synthesis of Compound 65 followed the procedure of General Procedure 6d following:

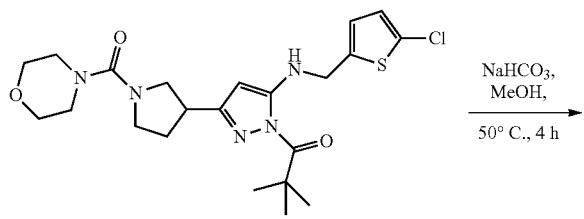

Compound 64

To a solution of dl-1-(5-((5-chlorothiophen-2-yl)methylamino)-3-(1-(morpholine-4-carbonyl)pyrrolidin-3-yl)-1H-pyrazol-1-yl)-2,2-dimethylpropan-1-one (Compound 64, 500 mg, 1.0 mmol) in methanol (10 mL) was added sodium bicarbonate (438 mg, 5.2 mmol) at room temperature. The mixture was then stirred at 50° C. for 4 hours. The reaction mixture was cooled back to room temperature, water (20 mL) was added and then extracted into dichloromethane (3×20 mL). The combined organic layers were dried over sodium sulfate, filtered and concentrated under reduced pressure. The residue was partially purified by silica gel column chromatography (100-200 mesh), eluting with 5-7% methanol in dichloromethane, to obtain desired product (300 mg, yield: 72%) as a light yellow semi solid. A portion (150 mg, 72% by LCMS) of semi-pure material was further purified by preparative HPLC purification to yield dl-(3-(5-((5-chlorothiophen-2-yl)methylamino)-1H-pyrazol-3-yl)pyrrolidin-1-yl)(morpholino)methanone (Compound 65, 62 mg) as an off-white solid. m/z 396.21 [M+H]+. $^1$H NMR (400 MHz, DMSO-$d_6$) δ 11.42 (br s, 1H, exchangeable), 6.91 (d, J=3.4 Hz, 1H), 6.83 (br s, 1H), 5.67 (br s, 1H, exchangeable), 5.35 (br s, 1H), 4.28 (d, J=5.9 Hz, 2H), 3.56 (td, J=3.8, 5.6 Hz, 5H), 3.37 (td, J=3.7, 7.7 Hz, 2H), 3.21-3.07 (m, 6H), 2.12 (br s, 1H), 1.84 (dd, J=8.6, 12.0 Hz, 1H) ppm; TLC System: 10% methanol in dichloromethane—$R_f$-0.3.

Example 99—Preparation of Compound 66

The synthesis of Compound 66 followed the procedure of General Procedure 5d following:

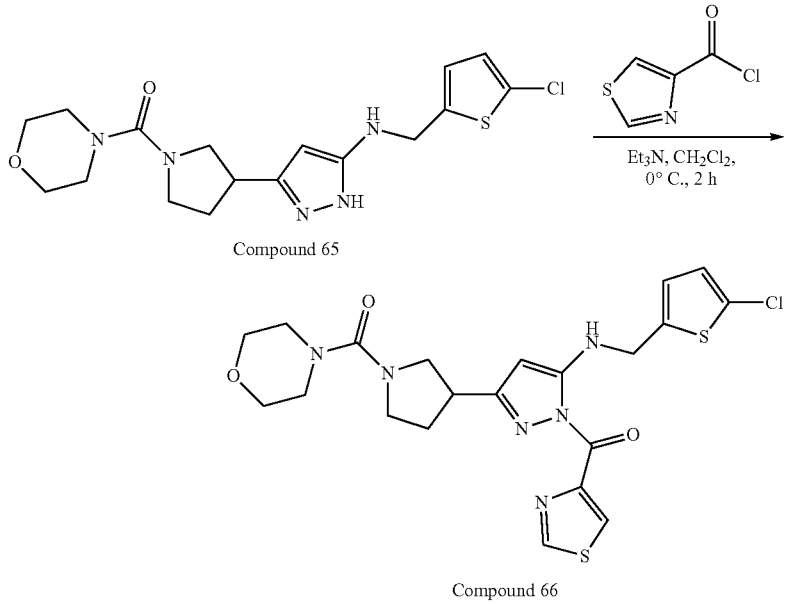

To a cooled solution (0° C.) of dl-(3-(5-((5-chlorothiophen-2-yl)methylamino)-1H-pyrazol-3-yl)pyrrolidin-1-yl)(morpholino)methanone (Compound 65, 150 mg, 0.37 mmol) in dry dichloromethane (10 mL) was added 1,3-thiazole-4-carbonyl chloride (73 mg, 0.5 mmol), followed by triethylamine (TEA, 0.13 mL, 0.9 mmol) and the mixture was stirred at 0° C. for 2 hours. Ice-cold water (10 mL) was added to the reaction mixture, and then extracted into dichloromethane (2×15 mL). The combined organic layers were dried over sodium sulfate, filtered and concentrated under reduced pressure. The crude residue was initially purified by flash chromatography using 4-5% MeOH—dichloromethane to give the desired product (146 mg, yield: 76%) as a light yellow semi solid. It was further purified by preparative HPLC to afford dl-(3-(5-((5-chlorothiophen-2-yl)methylamino)-1-(thiazole-4-carbonyl)-1H-pyrazol-3-yl)pyrrolidin-1-yl)(morpholino)methanone (Compound 66, 55 mg) as a pale yellow solid. m/z: 507.22 [M+H]+. $^1$H NMR (400 MHz, CDCl$_3$) δ 9.13 (d, J=2.4 Hz, 1H), 8.88 (d, J=2.0 Hz, 1H), 7.70 (t, J=5.9 Hz, 1H, exchangeable), 6.82-6.77 (m, 2H), 5.28 (s, 1H), 4.47 (d, J=5.4 Hz, 2H), 3.73-3.67 (m, 5H), -continued

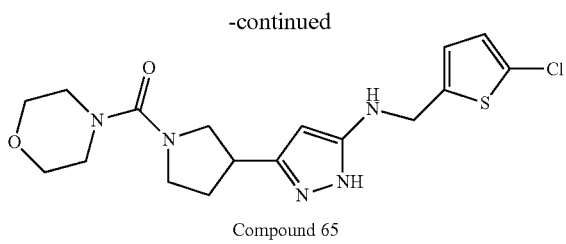

Compound 65

3.62-3.53 (m, 3H), 3.36-3.28 (m, 5H), 2.27-2.22 (m, 1H), 2.10-2.03 (m, 1H) ppm; TLC System: 10% Methanol-dichloromethane. $R_f$-0.6.

Example 100—Preparation of Compound 67

The synthesis of Compound 67 followed the procedure of General Procedure 22 following:

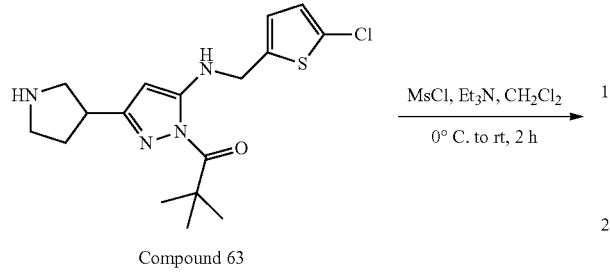

Compound 63

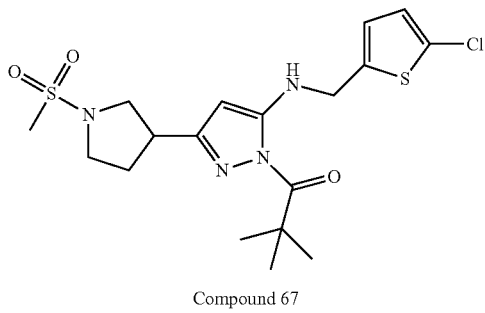

Compound 67

To a cold solution (0° C.) of dl-1-(5-((5-chlorothiophen-2-yl)methylamino)-3-(pyrrolidin-3-yl)-1H-pyrazol-1-yl)-2,2-dimethylpropan-1-one (Compound 63, 650 mg, 1.77 mmol) in dry dichloromethane (20 mL) was added methanesulfonyl chloride (304.4 mg, 2.65 mmol) followed by triethylamine (TEA, 0.62 mL, 4.42 mmol). The mixture was stirred at room temperature for 2 hours. The reaction mixture was quenched with NaHCO$_3$ solution (10 mL) and extracted into dichloromethane (3×20 mL). The residue was purified by silica gel column chromatography (100-200 mesh), eluting with 20-25% ethyl acetate in n-hexane, to obtain the desired product (550 mg, yield: 69%). A portion of the sample (170 mg) was further purified by preparative HPLC to afford dl-1-(5-((5-chlorothiophen-2-yl)methylamino)-3-(1-(methyl sulfonyl)pyrrolidin-3-yl)-1H-pyrazol-1-yl)-2,2-dimethyl-propan-1-one (Compound 67, 60 mg) as a pale yellow liquid. m/z 445.20 [M+H]$^+$. $^1$H NMR (400 MHz, CDCl$_3$) δ 7.50 (t, J=5.4 Hz, 1H, exchangeable), 6.89-6.62 (m, 2H), 5.16 (s, 1H), 4.36 (d, J=5.9 Hz, 2H), 3.73 (dd, J=7.3, 9.8 Hz, 1H), 3.61-3.42 (m, 3H), 3.40-3.28 (m, 1H), 2.80 (s, 3H), 2.39-2.10 (m, 2H), 1.45 (s, 9H) ppm; TLC System: 30% ethyl acetate in n-hexane—$R_f$-0.6.

Example 101—Preparation of Compound 68

The synthesis of Compound 68 followed the procedure of General Procedure 6d following:

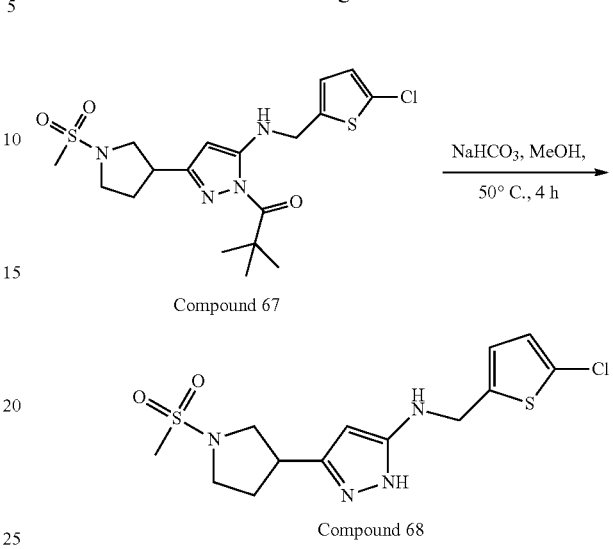

To a cooled solution (0° C.) of dl-1-(5-((5-chlorothiophen-2-yl)methylamino)-3-(1-(methyl sulfonyl)pyrrolidin-3-yl)-1H-pyrazol-1-yl)-2,2-dimethylpropan-1-one (Compound 67, 380 mg, 0.86 mmol) in dry methanol (10 mL) was added sodium bicarbonate (431.2 mg, 5.13 mmol) and the mixture was stirred at 70° C. for 4 hours. The reaction mixture was cooled to room temperature, then added water (20 mL) and extracted into dichloromethane (3×20 mL). The residue was purified by silica gel column chromatography (100-200 mesh), eluting with 5-7% methanol in dichloromethane, to obtain the desired compound (300 mg, yield: 72%) as a light yellow semi-solid. Preparative HPLC purification of a portion of this material (130 mg; 89% of LCMS purity) yielded dl-N-((5-chlorothiophen-2-yl)methyl)-3-(1-(methylsulfonyl)pyrrolidin-3-yl)-1H-pyrazol-5-amine (Compound 68, 30 mg) as a white solid. m/z 360.8 [M+H]$^+$. $^1$H NMR (400 MHz, DMSO-d$_6$) δ 11.44 (br s, 1H, exchangeable), 6.94-6.82 (m, 2H), 5.69 (br s, 1H, exchangeable), 5.41 (br s, 1H), 4.29 (d, J=6.4 Hz, 2H), 3.59 (br d, J=4.4 Hz, 1H), 3.36 (br d, J=6.8 Hz, 2H), 3.28 (br s, 1H), 3.15 (br s, 1H), 2.88 (br s, 3H), 2.20 (br s, 1H), 2.01-1.89 (m, 1H) ppm; TLC System: 5% methanol in dichloromethane—$R_f$-0.3.

Example 102—Preparation of Compound 69

The synthesis of Compound 69 followed the procedure of General Procedure 5d following:

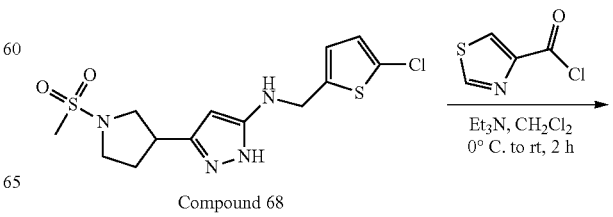

Compound 68

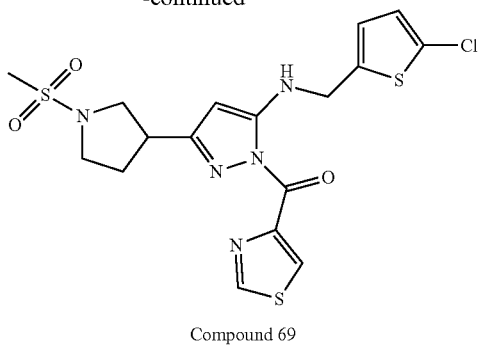

Compound 69

To a cooled solution (0° C.) of dl-N-((5-chlorothiophen-2-yl)methyl)-3-(1-(methylsulfonyl)pyrrolidin-3-yl)-1H-pyrazol-5-amine (Compound 68, 170 mg, 0.47 mmol) in dry dichloromethane (10 mL) was added 1,3-thiazole-4-carbonyl chloride (83.4 mg, 0.56 mmol) followed by triethylamine (TEA, 0.13 mL, 0.94 mmol). After stirring the mixture at room temperature for 2 hours, the reaction mixture was quenched with NaHCO₃ solution (10 mL) and extracted into dichloromethane (3×20 mL). The combined organic extracts were dried over sodium sulfate, filtered and concentrated under reduced pressure to afford the crude product (200 mg, yield-89%) as a light yellow semi-solid. Preparative HPLC purification of a portion of the material (200 mg, 87% LCMS purity) yielded dl-(5-((5-chlorothiophen-2-yl)methylamino)-3-(1-(methylsulfonyl)pyrrolidin-3-yl)-1H-pyrazol-1-yl)(thiazol-4-yl)methanone (Compound 69, 65 mg) as a pale yellow solid. m/z 472.10 [M+H]⁺. ¹H NMR (400 MHz, DMSO-d₆) δ 9.20 (d, J=1.5 Hz, 1H), 9.04 (d, J=1.5 Hz, 1H), 7.85 (t, J=6.4 Hz, 1H, exchangeable), 7.03-7.00 (d, 1H), 6.97 (d, J=3.9 Hz, 1H), 5.64 (s, 1H), 4.51 (d, J=5.9 Hz, 2H), 3.66-3.59 (m, 1H), 3.42-3.33 (m, 4H), 2.87 (s, 3H), 2.29-2.20 (m, 1H), 2.12-2.02 (m, 1H) ppm; TLC System: 5% methanol in dichloromethane—R$_f$-0.6.

Example 103—Preparation of Compound 70

The synthesis of Compound 70 followed the procedure of General Procedure 6d following:

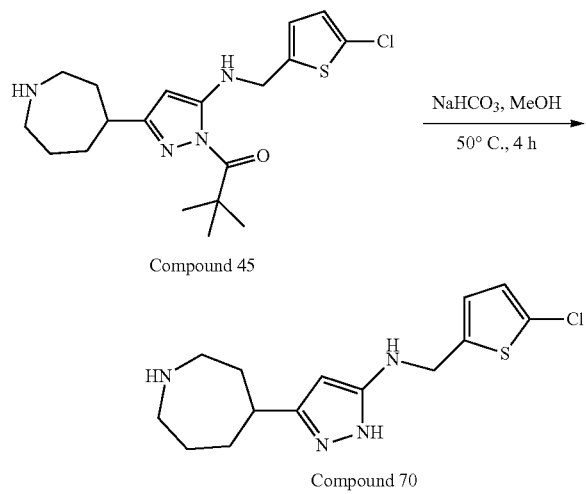

To a solution of 1-(3-(azepan-4-yl)-5-((5-chlorothiophen-2-yl)methylamino)-1H-pyrazol-1-yl)-2,2-dimethylpropan-1-one (Compound 45, 100 mg, 0.25 mmol) in methanol (5 mL) was added NaHCO₃ (63 mg, 0.76 mmol). The reaction mixture was stirred at 50° C. for 3 hours. The reaction mixture was cooled to room temperature, the volatiles were evaporated under reduced pressure and the resultant residue was diluted with 30% ⁱPrOH—CHCl₃ (20 mL) and washed with water (2×10 mL). The organic layer was dried over sodium sulfate, filtered and concentrated under reduced pressure. The resulting residue (70 mg) was purified by preparative HPLC to afford 3-(azepan-4-yl)-N-((5-chlorothiophen-2-yl)methyl)-1H-pyrazol-5-amine (Compound 70, 15 mg, yield: 19%) as a brown solid. MS: m/z 311.15 [M+H]⁺. ¹H NMR (400 MHz, DMSO-d6): δ 11.24 (s, 1H), 6.90 (d, J 3.6 Hz, 1H), 6.83 (d, J 4.0 Hz, 1H), 5.60-5.57 (m, 1H), 5.24 (s, 1H), 4.27 (d, J 6.0 Hz, 2H), 3.97-3.18 (m, 2H), 2.86-2.64 (m, 4H), 1.90-1.80 (m, 2H), 1.71-1.47 (m, 4H) ppm; TLC System: 10% ethyl acetate in hexane. R$_f$-0.1.

Example 104—Preparation of Compound 71

The synthesis of Compound 71 followed the procedure of General Procedure 22 following:

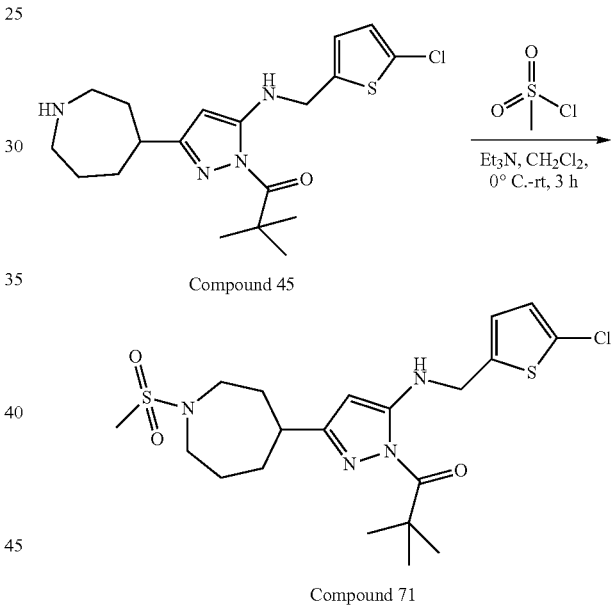

To a cooled solution (0° C.) of 1-(3-(azepan-4-yl)-5-((5-chlorothiophen-2-yl)methylamino)-1H-pyrazol-1-yl)-2,2-dimethylpropan-1-one (Compound 45, 280 mg, 0.71 mmol) in dry dichloromethane (10 mL) was added triethylamine (TEA, 0.25 mL, 1.77 mmol), followed by methanesulfonyl chloride (MsCl, 0.082 mL, 1.06 mmol). After the reaction was stirred at room temperature for 2 hours, the mixture was diluted with water (10 mL) and extracted into dichloromethane (2×20 mL). The combined organic layer was dried over sodium sulfate, filtered and concentrated under reduced pressure. The residue was purified by CombiFlash, eluting with 10% EtOAc/n-hexane, to afford desired product 1-(5-((5-chlorothiophen-2-yl)methylamino)-3-(1-(methylsulfonyl)azepan-4-yl)-1H-pyrazol-1-yl)-2,2-dimethylpropan-1-one (Compound 71, 100 mg, yield: 40%) as an off-white solid. MS (ESI): m/z 473.08 [M+H]⁺. ¹H NMR (300 MHz, DMSO-d6) δ 7.65 (t, J 6.3 Hz, 1H), 6.96 (s, 2H), 5.39 (s, 1H), 4.41 (d, J 6.0 Hz, 2H), 3.49-3.34 (m, 2H), 3.32-3.17 (m, 2H), 2.97 (s, 3H), 2.72-2.50 (m, 1H), 2.07-1.60 (m, 6H), 1.40 (s, 9H) ppm; TLC System: 50% ethyl acetate in hexane. $R_f$-0.7.

Example 105—Preparation of Compound 72

The synthesis of Compound 72 followed the procedure of General Procedure 6d following:

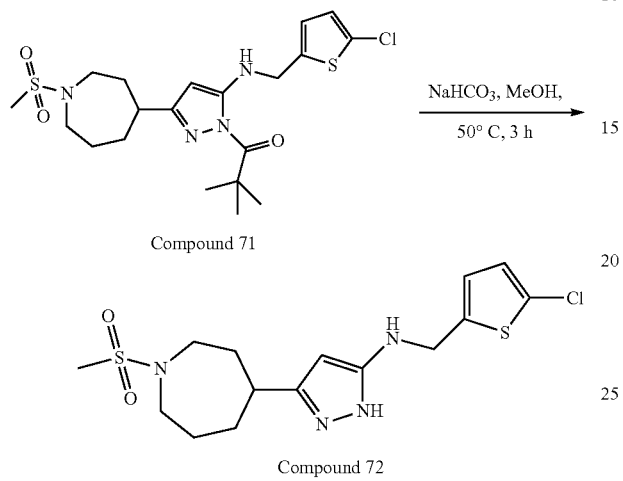

Compound 71

Compound 72

To a stirred solution of 1-(5-(((5-chlorothiophen-2-yl)methylamino)-3-(1-(methyl sulfonyl)azepan-4-yl)-1H-pyrazol-1-yl)-2,2-dimethylpropan-1-one (Compound 71, 80 mg, 0.17 mmol) in methanol (5 mL) was added NaHCO$_3$ (37 mg, 0.51 mmol). The reaction mixture was stirred at 50° C. for 3 hours. The reaction mixture was cooled to room temperature, the volatiles were evaporated and the resultant residue was diluted with EtOAc (20 mL) and washed with water (2×10 mL). The organic layer was dried over sodium sulfate, filtered and concentrated under reduced pressure. The resulting solid was triturated with diethyl ether and pentane and dried under reduced pressure for 1 hour to afford N-((5-chlorothiophen-2-yl)methyl)-3-(1-(methylsulfonyl)azepan-4-yl)-1H-pyrazol-5-amine (Compound 72, 55 mg, yield: 84%) as an off-white solid. MS (ESI): m/z 389.15 [M+H]$^+$. $^1$H NMR (400 MHz, DMSO-d6) δ 11.24 (s, 1H), 6.90-6.83 (m, 2H), 5.60 (br s, 1H), 5.28 (s, 1H), 4.28 (s, 2H), 3.42-3.31 (m, 2H), 3.26-3.14 (m, 2H), 2.87 (s, 3H), 2.80-2.70 (m, 1H), 2.04-1.60 (m, 3H), 1.72-1.62 (m, 3H) ppm; TLC System: 70% ethyl acetate in hexane. $R_f$-0.2.

Example 106—Preparation of Compound 73

The synthesis of Compound 73 followed the procedure of General Procedure 5d following:

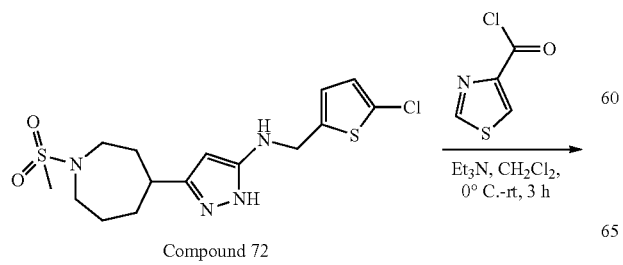

Compound 72

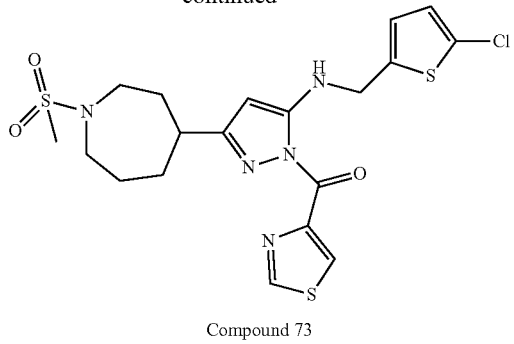

Compound 73

To a cooled solution (0° C.) of N-((5-chlorothiophen-2-yl)methyl)-3-(1-(methylsulfonyl)azepan-4-yl)-1H-pyrazol-5-amine (Compound 72, 110 mg, 0.28 mmol) in dry dichloromethane (10 mL) was added triethylamine (TEA, 0.12 mL, 0.85 mmol) followed by thiazole-4-carbonyl chloride (54 mg, 0.36 mmol). After the mixture was stirred at room temperature for 3 hours, the reaction mixture was diluted with water (10 mL) and extracted into dichloromethane (3×10 mL). The combined organic layers were dried over sodium sulfate, filtered and concentrated under reduced pressure. The residue was purified by CombiFlash, eluting with 50% EtOAc/n-hexane, to afford (5-((5-chlorothiophen-2-yl)methylamino)-3-(1-(methylsulfonyl)azepan-4-yl)-1H-pyrazol-1-yl)(thiazol-4-yl)methanone (Compound 73, 60 mg, yield: 41%) as an off-white solid. MS (ESI): m/z 500.13 [M+H]$^+$. $^1$H NMR (400 MHz, DMSO-d6) δ 9.18 (s, 1H), 9.03 (s, 1H), 7.78 (br s, 1H), 6.98 (d, J=12.8 Hz, 2H), 5.55 (s, 1H), 4.50 (d, J=5.2 Hz, 2H), 3.47-3.39 (m, 2H), 3.24-3.22 (m, 2H), 2.88 (s, 3H), 2.75 (br s, 1H), 2.07-1.67 (m, 6H) ppm; TLC System: 80% ethyl acetate in hexane. $R_f$-0.7.

Example 107—Preparation of Compound 74

The synthesis of Compound 74 followed the procedure of General Procedure 5d following:

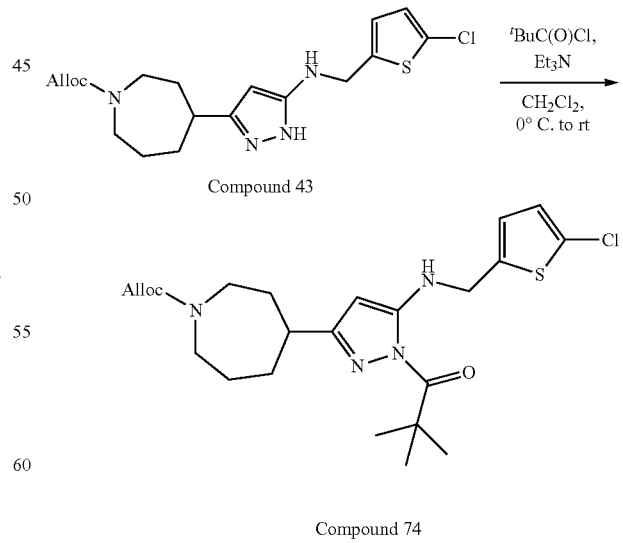

Compound 43

Compound 74

To a cooled solution (0° C.) of allyl 4-(5-((5-chlorothiophen-2-yl)methylamino)-1H-pyrazol-3-yl)azepane-1-carboxylate (Compound 43, 250 mg, 0.634 mmol) in dry dichloromethane (10 mL) was added triethylamine (TEA, 0.26 mL, 1.9 mmol) followed by thiazole-4-carbonyl chloride (112 mg, 0.76 mmol). After the mixture was stirred at room temperature for 3 hours, the reaction mixture was diluted with water (10 mL) and extracted into dichloromethane (3×10 mL). The combined organic layers were dried over sodium sulfate, filtered and concentrated under reduced pressure. The residue was purified by CombiFlash, eluting with 30% EtOAc/n-hexane, then trituration with diethyl ether and pentane, to afford allyl 4-(5-((5-chlorothiophen-2-yl)methylamino)-1-(thiazole-4-carbonyl)-1H-pyrazol-3-yl)azepane-1-carboxylate (Compound 74, 180 mg, yield: 61%) as a yellow solid. m/z 506.13 [M+H]$^+$. $^1$H NMR (400 MHz, DMSO-d6): δ 9.18 (d, J=1.6 Hz, 1H), 9.02-9.01 (m, 1H), 7.77 (t, J=6.0 Hz, 1H), 7.00 (d, J=4.0 Hz, 1H), 6.97 (d, J=3.6 Hz, 1H), 5.93-5.92 (m, 1H), 5.53 (d, J=2.8 Hz, 1H), 5.28-5.23 (m, 1H), 5.18-5.15 (m, 1H), 4.53-4.48 (m, 4H), 3.64-3.58 (m, 1H), 3.48-3.31 (m, 3H), 2.68-2.64 (m, 1H), 2.04-1.86 (m, 3H), 1.76-1.54 (m, 3H) ppm; TLC System: 50% ethyl acetate in hexane. R$_f$-0.8.

Example 108—Preparation of Intermediate 35

The synthesis of Intermediate 35 followed the procedure of General Procedure 23 following:

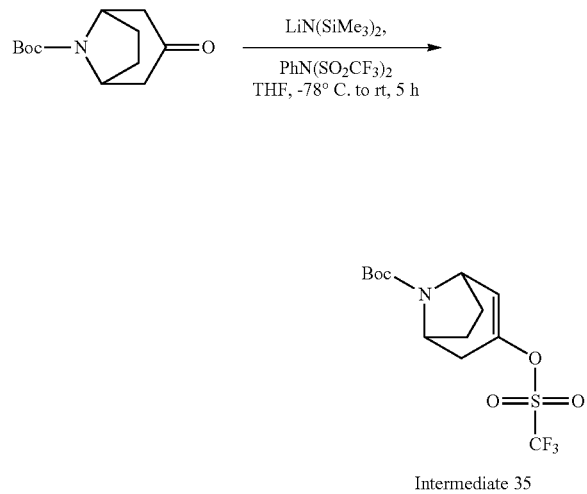

Intermediate 35

To a cooled solution (−78° C.) of tert-butyl-3-oxo-8-azabicyclo[3.2.1]octane-8-carboxylate (30 g, 133.3 mmol) in dry THF (300 mL) was added LiHMDS (lithium hexamethyldisilazide, 1M in THF, 146 mL, 146.7 mmol). After stirring for 30 minutes, a solution of N-phenyl-bis(trifluoromethanesulfonimide) (PhNTf$_2$, 52 g, 146.7 mmol) in dry THF (30 mL) was added and the mixture stirred at room temperature for 5 hours. The reaction mixture was quenched with saturated ammonium chloride solution (80 mL), and extracted with EtOAc (2×300 mL). The combined organic layers were dried over sodium sulfate, filtered and concentrated under reduced pressure. The residue was purified by silica gel column chromatography (100-200 mesh), eluting with 3-5% EtOAc/n-hexane, to afford tert-butyl-3-(trifluoromethylsulfonyloxy)-8-azabicyclo[3.2.1]oct-3-ene-8-carboxylate (Intermediate 35, 40 g, yield: 84%) as a pale yellow liquid; TLC System: 20% ethyl acetate in hexane. R$_f$-0.5.

Example 109—Preparation of Intermediate 36

The synthesis of Intermediate 36 followed the procedure of General Procedure 24 following:

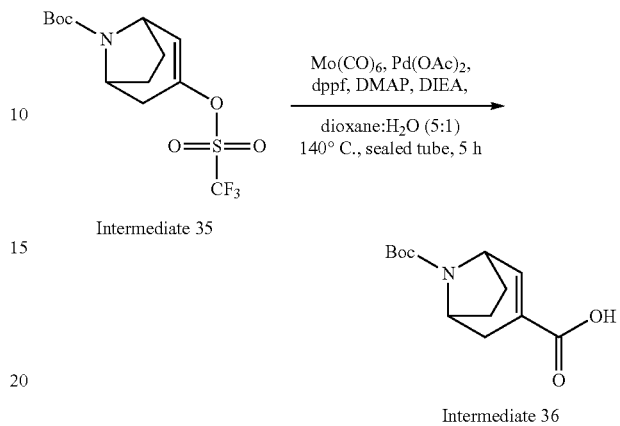

To a stirred solution of tert-butyl-3-(trifluoromethylsulfonyloxy)-8-azabicyclo[3.2.1]oct-3-ene-8-carboxylate (Intermediate 35, 21 g, 58.8 mmol) in 1,4-dioxane:water (5:1, 125 mL) in a sealed tube was added molybdenum hexacarbonyl (Mo(CO)$_6$, 7.7 g, 29.4 mmol), 4-dimethylaminopyridine (DMAP, 14.3 g, 117.6 mmol), and N,N-diisopropylethylamine (DIEA, 25 mL, 141.2 mmol). After degassing with a stream of argon for 15 minutes, palladium acetate (Pd(OAc)$_2$, 1.3 g, 5.9 mmol) was added, followed by 1,1'-bis(diphenylphosphino)ferrocene (dppf, 3.3 g, 5.9 mmol). The reaction mixture was stirred at 120° C. for 5 hours. The reaction mixture was filtered through a Celite pad and poured into aqueous sodium bicarbonate (60 mL) and extracted with EtOAc (200 mL). The aqueous layer was acidified with HCl (2N, to pH=2) and extracted with EtOAc (2×200 mL). The combined organic layers were dried over sodium sulfate, filtered and concentrated under reduced pressure to afford 8-(tert-butoxycarbonyl)-8-azabicyclo[3.2.1]oct-3-ene-3-carboxylic acid (Intermediate 36, 14 g, yield: 94%) as a light brown liquid; TLC System: 50% ethyl acetate in hexane. R$_f$-0.2.

Example 110—Preparation of Intermediate 37

The synthesis of Intermediate 37 followed the procedure of General Procedure 13 following:

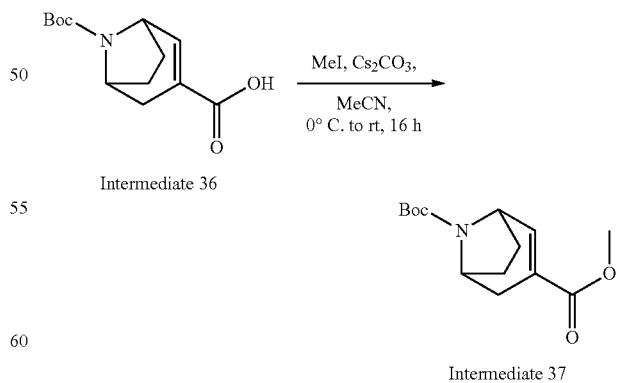

To a cooled solution (0° C.) of 8-(tert-butoxycarbonyl)-8-azabicyclo[3.2.1]oct-3-ene-3-carboxylic acid (Intermediate 36, 14 g, 55.3 mmol) in acetonitrile (105 mL) was added cesium carbonate (36 g, 110.7 mmol). After stirring for 15 minutes, iodomethane (MeI, 14 mL, 221.3 mmol) was added and then stirred at room temperature for 16 hours. After cooling to 0° C. it was quenched with ice cold water (50 mL), and extracted with EtOAc (2×150 mL). The combined organic layers were dried over sodium sulfate, filtered and concentrated under reduced pressure. The residue was purified by silica gel column chromatography (100-200 mesh), eluting with 5-10% EtOAc/n-hexane, to afford 8-tert-butyl-3-methyl 8-azabicyclo[3.2.1]oct-3-ene-3,8-dicarboxylate (Intermediate 37, 11.8 g, yield: 80%) as an off-white solid; TLC System: 50% ethyl acetate in hexane. $R_f$-0.6.

Example 111—Preparation of Intermediate 38

The synthesis of Intermediate 38 followed the procedure of General Procedure 19 following:

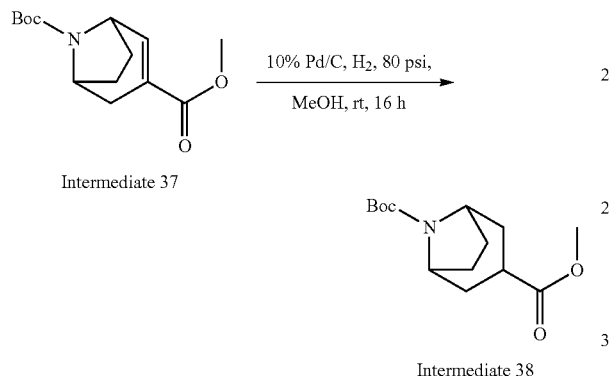

To a solution of 8-tert-butyl-3-methyl-8-azabicyclo[3.2.1]oct-3-ene-3,8-dicarboxylate (Intermediate 37, 11.8 g, 44.2 mmol) in MeOH (120 mL) in a steel vessel was added 10% Pd/C (2.7 g), and stirred under 80 psi hydrogen pressure at room temperature for 16 hours. The reaction mixture was filtered through a Celite pad, and the volatiles were concentrated under reduced pressure to give 8-tert-butyl-3-methyl-8-azabicyclo[3.2.1]octane-3,8-dicarboxylate (Intermediate 38, 11 g, yield: 92%) as a white solid; TLC System: 10% ethyl acetate in hexane. $R_f$-0.5.

Example 112—Preparation of Intermediate 39

The synthesis of Intermediate 39 followed the procedure of General Procedure 6c following:

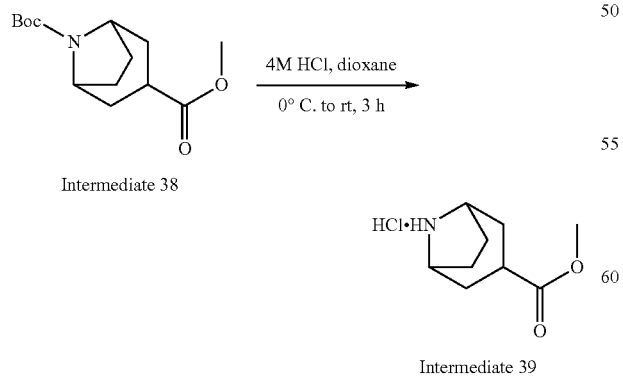

To a cooled solution (0° C.) of 8-tert-butyl-3-methyl-8-azabicyclo[3.2.1]octane-3,8-dicarboxylate (Intermediate 38, 11 g, 40.9 mmol) in 1,4-dioxane (33 mL) was added HCl (4M in 1,4-dioxane, 66 mL) at 0° C. and then warmed to room temperature for 3 hours. The reaction mixture was concentrated and triturated with diethyl ether to afford methyl 8-azabicyclo[3.2.1]octane-3-carboxylate hydrochloride (Intermediate 39, 8 g, yield: 95%) as a white solid; TLC System: 50% ethyl acetate in hexane. $R_f$-0.1.

Example 113—Preparation of Intermediate 40

The synthesis of Intermediate 40 followed the procedure of General Procedure 7 following:

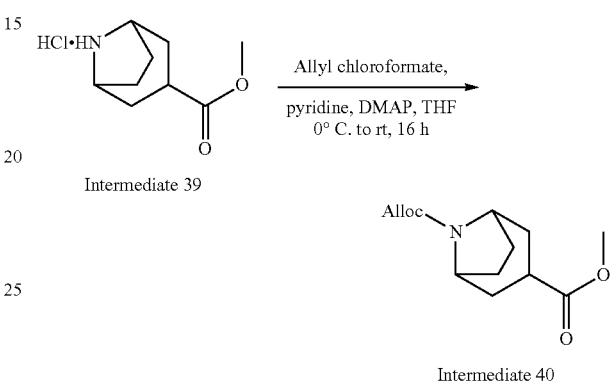

To a cooled (0° C.) solution of 8-azabicyclo[3.2.1]octane-3-carboxylate hydrochloride (Intermediate 39, 10 g, 48.8 mmol) in water (130 mL) was added sodium bicarbonate (12.3 g, 146.3 mmol), followed by a solution of allyl chloroformate (5.7 mL, 53.7 mmol) in THF (60 mL). After stirring at room temperature for 16 hours, ice-cold water (100 mL) was added and then extracted into EtOAc (2×150 mL). The combined organic layers were dried over sodium sulfate, filtered and concentrated under reduced pressure. The residue was purified by silica gel column chromatography (100-200 mesh), eluting with 15% EtOAc/n-hexane, to give 8-allyl-3-methyl-8-azabicyclo[3.2.1]octane-3,8-dicarboxylate (Intermediate 40, 8 g, yield: 64%) as a colorless liquid; TLC System: 5% Methanol-dichloromethane. $R_f$-0.5.

Example 114—Preparation of Intermediate 41

The synthesis of Intermediate 41 followed the procedure of General Procedure 2 following:

Alloc-N... (nBuLi, CH₃CN, THF, -78° C., 3 h) → Intermediate 41

Intermediate 40

To a cooled solution (−78° C.) of acetonitrile (4.1 mL, 79.1 mmol) in dry THF (50 mL) was added n-BuLi (2.5M in hexane, 28 mL, 69.2 mmol). After stirring for 1 hour, a solution of 8-allyl-3-methyl-8-azabicyclo[3.2.1]octane-3,8-dicarboxylate (Intermediate 40, 5 g, 19.8 mmol) in dry THF (10 mL) was added and then stirred at −78° C. for 2 hours. The reaction mixture was quenched with saturated NH$_4$Cl solution (80 mL) and extracted into EtOAc (2×100 mL). The combined organic layers were dried over sodium sulfate, filtered and concentrated under reduced pressure. The residue was purified by silica gel column chromatography (100-200 mesh), eluting with 25% EtOAc/n-hexane, to give allyl 3-(2-cyanoacetyl)-8-azabicyclo[3.2.1]octane-8-carboxylate (Intermediate 41, 2.7 g, yield: 52%) as a light yellow liquid; TLC System: 50% ethyl acetate in hexane. R$_f$-0.3.

Example 115—Preparation of Compound 74

The synthesis of Compound 74 followed the procedure of General Procedure 3 following:

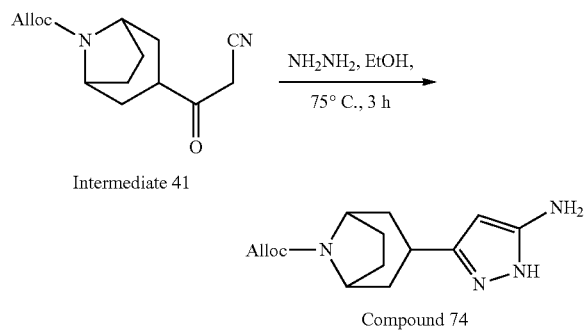

To a stirred solution of allyl-3-(2-cyanoacetyl)-8-azabicyclo[3.2.1]octane-8-carboxylate (Intermediate 41, 6 g, 22.9 mmol) in ethanol (60 mL) was added hydrazine (1 mL, 20.6 mmol), and the reaction mixture was heated to 75° C. for 3 hours. The reaction mixture was cooled to room temperature, the volatiles were evaporated and the resultant residue was purified by silica gel column chromatography (100-200 mesh), eluting with 2-3% MeOH-dichloromethane, to give allyl-3-(5-amino-1H-pyrazol-3-yl)-8-azabicyclo[3.2.1]octane-8-carboxylate (Compound 74, 4 g, yield: 63%) as a pale yellow color semi-solid; TLC System: 5% Methanol-dichloromethane R$_f$-0.2.

Example 116—Preparation of Compound 75

The synthesis of Compound 75 followed the procedure of General Procedure 4 following:

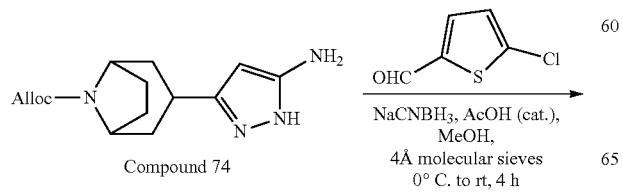

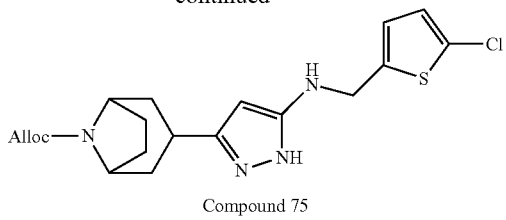

Compound 75

To a cooled solution (0° C.) of allyl-3-(5-amino-1H-pyrazol-3-yl)-8-azabicyclo[3.2.1]octane-8-carboxylate (Compound 74, 3.2 g, 11.6 mmol) in dry MeOH (35 mL) was added 5-chlorothiophene-2-carbaldehyde (2.6 mL, 23.18 mmol), followed by AcOH (0.2 mL), and then powdered 4 Å molecular sieves. The reaction mixture was stirred at room temperature for 1 hour (formation of imine was observed as a less polar spot by TLC). To this was added sodium cyanoborohydride (NaCNBH$_3$, 575 mg, 9.3 mmol) portionwise, and the mixture was stirred at room temperature for 2 hours. To the mixture was added ice-cold water (50 mL), then filtered through a Celite pad, and the filtrate was extracted with EtOAc (4×100 mL). The combined organic layers were dried over sodium sulfate, filtered and concentrated under reduced pressure. The residue was purified by silica gel column chromatography (100-200 mesh), eluting with 2-5% MeOH-dichloromethane, to afford desired product (2.1 g, yield: 44%) as a light yellow solid. A portion (170 mg of semi-pure sample) was further purified by preparative HPLC to afford allyl 3-(5-((5-chlorothiophen-2-yl)methylamino)-1H-pyrazol-3-yl)-8-azabicyclo[3.2.1]octane-8-carboxylate (Compound 75, 50 mg) as an off white solid. m/z 407.27 [M+H]+. $^1$H NMR (300 MHz, DMSO-d$_6$) δ=11.28 (s, 1H, exchangeable), 6.90 (d, J=4.0 Hz, 1H), 6.82 (d, J=3.7 Hz, 1H), 5.93 (tdd, J=5.3, 10.4, 17.2 Hz, 1H), 5.61 (br s, 1H, exchangeable), 5.33-5.14 (m, 3H), 4.54 (br d, J=4.4 Hz, 2H), 4.31-4.15 (m, 4H), 3.11 (br s, 1H), 1.92 (br s, 2H), 1.82-1.57 (m, 6H) ppm; TLC System: 5% Methanol-dichloromethane R$_f$-0.4.

Example 117—Preparation of Compound 76

The synthesis of Compound 76 followed the procedure of General Procedure 5d following:

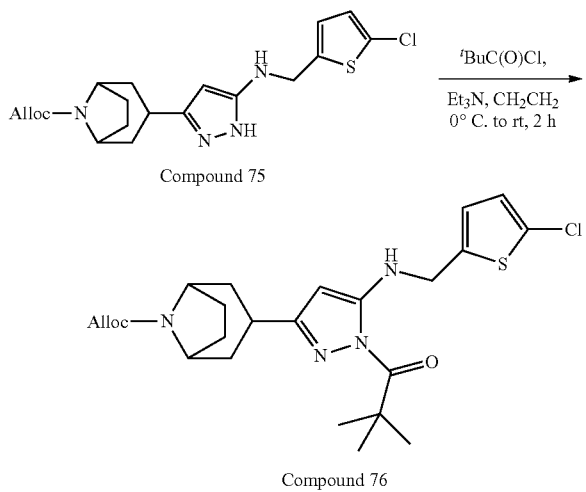

To a cooled solution (0° C.) of allyl 3-(5-((5-chlorothiophen-2-yl)methylamino)-1H-pyrazol-3-yl)-8-azabicyclo[3.2.1]octane-8-carboxylate (Compound 75, 1 g, 2.5 mmol) in dry dichloromethane (15 mL) was added triethylamine (TEA, 0.52 mL, 3.7 mmol) followed by trimethylacetyl chloride (0.27 mL, 2.2 mmol). After stirring at room temperature for 2 hours, the reaction mixture was added to water (25 mL) and extracted into dichloromethane (2×40 mL). The combined organic layers were dried over sodium sulfate, filtered and concentrated under reduced pressure. The residue was purified by silica gel column chromatography (100-200 mesh), eluting with 1-2% MeOH-dichloromethane, to give the desired product (900 mg, yield: 75%) as a light yellow liquid. A portion (250 mg) of semi-pure material was further purified by preparative HPLC to give allyl 3-(5-((5-chlorothiophen-2-yl)methylamino)-1-pivaloyl-1H-pyrazol-3-yl)-8-azabicyclo[3.2.1]octane-8-carboxylate (Compound 76, 60 mg) as a white solid. m/z 491.21 [M+H]+. $^1$H NMR (400 MHz, DMSO-d$_6$) δ=7.65 (t, J=6.4 Hz, 1H, exchangeable), 6.97-6.93 (m, 2H), 5.97-5.86 (m, 1H), 5.33 (s, 1H), 5.26 (dd, J=1.5, 17.1 Hz, 1H), 5.16 (dd, J=1.5, 10.3 Hz, 1H), 4.61-4.47 (m, 2H), 4.40 (d, J=5.9 Hz, 2H), 4.21 (br s, 2H), 3.11-3.01 (m, 1H), 1.93 (br s, 2H), 1.83-1.65 (m, 6H), 1.39 (s, 9H) ppm; TLC System: 5% Methanol-dichloromethane R$_f$-0.7.

Example 118—Preparation of Compound 77

The synthesis of Compound 77 followed the procedure of General Procedure 8b following:

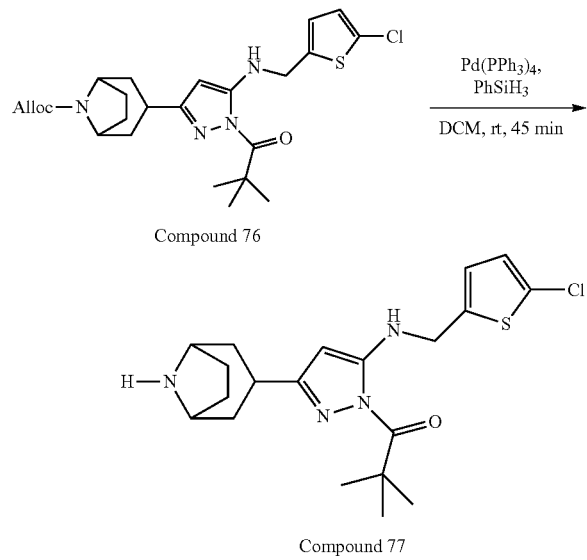

A stirred solution of allyl 3-(5-((5-chlorothiophen-2-yl)methylamino)-1-pivaloyl-1H-pyrazol-3-yl)-8-azabicyclo[3.2.1]octane-8-carboxylate (Compound 76, 500 mg, 1 mmol) in dichloromethane (10 mL) was degassed with a stream of argon for 15 minutes, then to the solution was added tetrakis(triphenylphosphine)palladium(0) (Pd(PPh$_3$)$_4$, 70 mg, 0.06 mmol) followed by phenylsilane (PhSiH$_3$, 0.5 mL, 4.1 mmol). After stirring for 45 minutes, the reaction mixture was filtered through a Celite pad and the filtrate evaporated. The crude residue was purified by silica gel column chromatography eluting with 5-10% MeOH-dichloromethane to give 1-(3-(8-azabicyclo[3.2.1]octan-3-yl)-5-((5-chlorothiophen-2-yl)methylamino)-1H-pyrazol-1-yl)-2,2-dimethylpropan-1-one (60 mg) as an off-white solid. m/z 407.24 [M+H]+. $^1$H NMR (400 MHz, DMSO-d$_6$) δ=8.89 (br s, 2H, exchangeable), 7.72 (t, J=6.1 Hz, 1H), 6.98-6.93 (m, 2H), 5.36 (s, 1H), 4.41 (d, J=6.4 Hz, 2H), 4.00 (br s, 2H), 3.00 (tt, J=5.9, 11.5 Hz, 1H), 2.03-1.86 (m, 8H), 1.41 (s, 9H) ppm; TLC System: 10% Methanol-dichloromethane R$_f$-0.2.

Example 119—Preparation of Compound 78

The synthesis of Compound 78 followed the procedure of General Procedure 8b following:

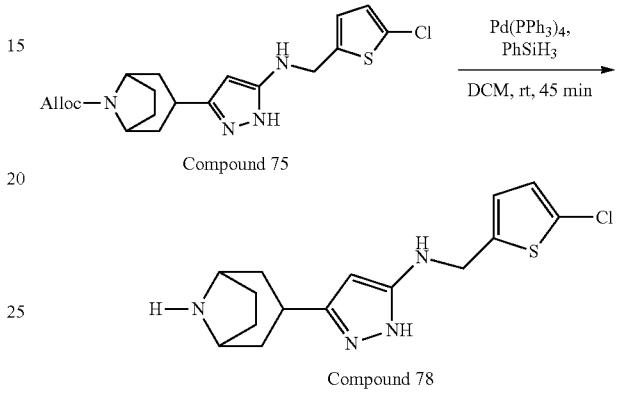

A solution of allyl-3-(5-((5-chlorothiophen-2-yl)methylamino)-1H-pyrazol-3-yl)-8-azabicyclo[3.2.1]octane-8-carboxylate (Compound 75, 250 mg, 0.6 mmol) in dry dichloromethane (10 mL) was degassed with a stream of argon for 15 minutes, then to the solution was added tetrakis(triphenylphosphine)palladium(0) (Pd(PPh$_3$)$_4$, 42 mg, 0.03 mmol) followed by phenylsilane (PhSiH$_3$, 0.3 mL, 2.5 mmol). After stirring at room temperature for 45 minutes, the reaction mixture was filtered through a Celite pad and the filtrate was evaporated. The crude residue was purified by silica gel column chromatography using 10% MeOH-dichloromethane to give the desired product (150 mg, yield: 75%) as a light brown solid. It was further purified by preparative HPLC to give 3-(8-azabicyclo[3.2.1]octan-3-yl)-N-((5-chlorothiophen-2-yl)methyl)-1H-pyrazol-5-amine (25 mg) as a light yellow solid as the formic acid salt; m/z 323.23 [M+H]+. $^1$H NMR (400 MHz, DMSO-d$_6$) δ=12.89-8.82 (m, 3H, exchangeable), 8.40 (br s, 1H), 6.91 (d, J=3.9 Hz, 1H), 6.83 (d, J=3.4 Hz, 1H), 5.71 (br s, 1H), 5.25 (s, 1H), 4.28 (br s, 2H), 3.79 (br s, 2H), 2.97 (ddd, J=5.9, 10.9, 17.0 Hz, 1H), 1.95-1.74 (m, 8H) ppm; TLC System: 10% Methanol-dichloromethane R$_f$-0.1.

Example 120—Preparation of Compound 79

The synthesis of Compound 79 followed the procedure of General Procedure 5d following:

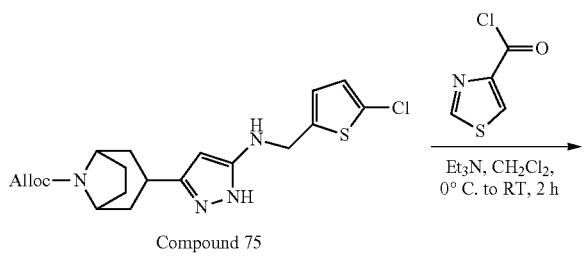

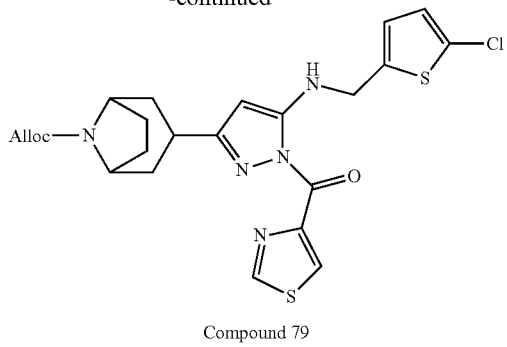

Compound 79

To a cooled solution (0° C.) of allyl-3-(5-((5-chlorothiophen-2-yl)methylamino)-1H-pyrazol-3-yl)-8-azabicyclo[3.2.1]octane-8-carboxylate (Compound 75, 300 mg, 0.73 mmol) in dry dichloromethane (15 mL) was added triethylamine (TEA, 0.26 mL, 1.84 mmol), then 1,3-thiazole-4-carbonyl chloride (218 mg, 1.47 mmol). After stirring at room temperature for 2 hours, this was added to ice-cold water (10 mL) and extracted into dichloromethane (2×20 mL). The combined organic layers were dried over sodium sulfate, filtered and concentrated under reduced pressure. The residue was purified by flash chromatography using 1-2% MeOH-dichloromethane to give the desired product (300 mg, yield: 78%) as a light brown liquid. A portion was further purified by preparative HPLC to give allyl-3-(5-((5-chlorothiophen-2-yl)methylamino)-1-(thiazole-4-carbonyl)-1H-pyrazol-3-yl)-8-azabicyclo[3.2.1]octane-8-carboxylate (Compound 79, 75 mg) as pale yellow solid. m/z 518.18 [M+H]+. $^1$H NMR (400 MHz, DMSO-$d_6$) δ=9.19 (d, J=2.0 Hz, 1H), 9.02 (d, J=2.0 Hz, 1H), 7.79 (t, J=6.4 Hz, 1H), 7.00-6.95 (m, 2H), 5.93 (tdd, J=5.3, 10.4, 17.2 Hz, 1H), 5.50 (s, 1H), 5.27 (dd, J=1.5, 17.1 Hz, 1H), 5.16 (dd, J=1.5, 10.3 Hz, 1H), 4.57-4.47 (m, 4H), 4.23 (br s, 2H), 3.16-3.08 (m, 1H), 1.96-1.66 (m, 8H) ppm; TLC System: 5% Methanol-dichloromethane. $R_f$-0.7.

Example 121—Preparation of Compound 80

The synthesis of Compound 80 followed the procedure of General Procedure 15 following:

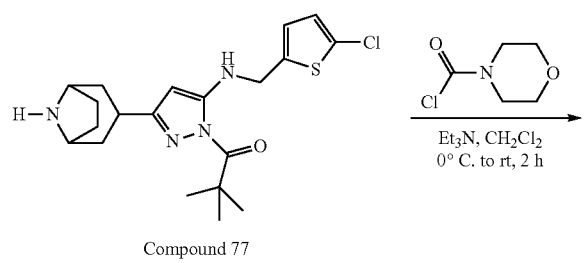

Compound 77

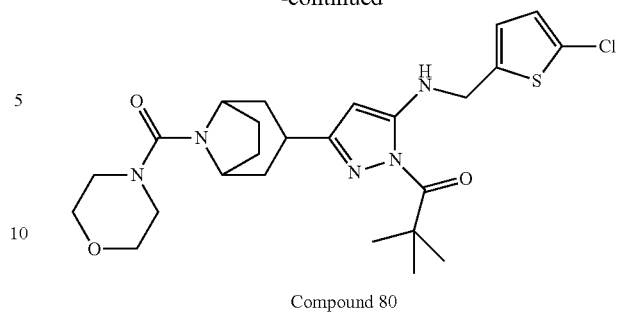

Compound 80

To a cooled solution (0° C.) of 1-(3-(8-azabicyclo[3.2.1]octan-3-yl)-5-((5-chlorothiophen-2-yl)methylamino)-1H-pyrazol-1-yl)-2,2-dimethylpropan-1-one (Compound 77, 350 mg, 0.86 mmol) in dry dichloromethane (10 mL) was added triethylamine (TEA, 0.3 mL, 2.15 mmol) and then morpholine-4-carbonyl chloride (0.2 mL, 1.72 mmol). After stirring at room temperature for 2 hours, ice-cold water (5 mL) was added, and washed with dichloromethane (2×20 mL). The combined organic layers were dried with sodium sulfate, filtered and concentrated under reduced pressure. The residue was purified by flash chromatography using 1-2% MeOH-dichloromethane, to give the desired semi-pure product (320 mg, yield: 71%) as a light brown liquid. A portion (120 mg) was further purified by preparative HPLC to afford 1-(5-((5-chlorothiophen-2-yl)methylamino)-3-(8-(morpholine-4-carbonyl)-8-azabicyclo[3.2.1]octan-3-yl)-1H-pyrazol-1-yl)-2,2-dimethylpropan-1-one (Compound 80, 60 mg) as an off white solid. m/z 520.25 [M+H]+. $^1$H NMR (400 MHz, DMSO-$d_6$) δ=7.65 (t, J=6.1 Hz, 1H, exchangeable), 6.97-6.93 (m, 2H), 5.35 (s, 1H), 4.40 (d, J=6.4 Hz, 2H), 4.03 (br s, 2H), 3.58-3.52 (m, 4H), 3.25-3.18 (m, 4H), 2.93 (tt, J=5.7, 11.7 Hz, 1H), 1.85-1.66 (m, 8H), 1.39 (s, 9H) ppm; TLC System: 5% Methanol-dichloromethane. $R_f$-0.6.

Example 122—Preparation of Compound 81

The synthesis of Compound 81 followed the procedure of General Procedure 6d following:

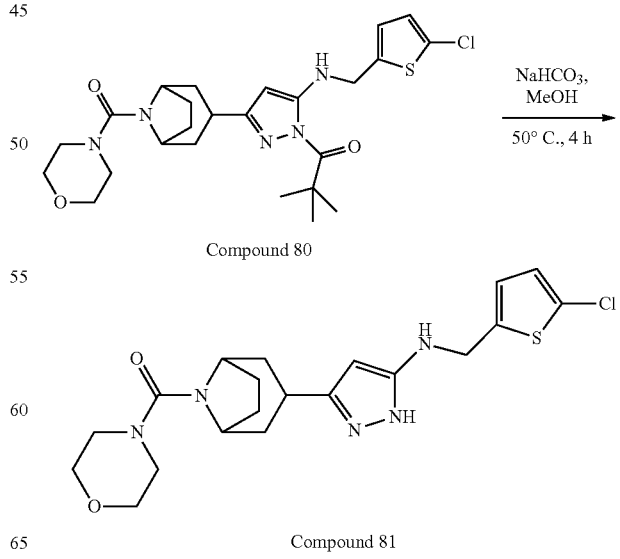

To a solution of 1-(5-((5-chlorothiophen-2-yl)methylamino)-3-(8-(morpholine-4-carbonyl)-8-azabicyclo[3.2.1]octan-3-yl)-1H-pyrazol-1-yl)-2,2-dimethylpropan-1-one (Compound 80, 140 mg, 0.26 mmol) in methanol (5 mL) at room temperature was added sodium bicarbonate (113 mg, 1.34 mmol). After stirring at 50° C. for 4 hours, the reaction mixture was concentrated and washed with dichloromethane (2×15 mL). The combined organic layers were dried with sodium sulfate, filtered and concentrated under reduced pressure. The residue was purified by preparative HPLC to give (3-(5-((5-chlorothiophen-2-yl)methylamino)-1H-pyrazol-3-yl)-8-azabicyclo[3.2.1]octan-8-yl)(morpholino)methanone (Compound 81, 30 mg) as an off-white solid. m/z 436.22 [M+H]+. $^1$H NMR (400 MHz, DMSO-d$_6$) δ=11.25 (s, 1H), 6.90 (d, J=3.4 Hz, 1H), 6.82 (br d, J=2.9 Hz, 1H), 5.59 (br s, 1H, exchangeable), 5.26 (br s, 1H), 4.27 (d, J=6.4 Hz, 2H), 4.01 (br s, 2H), 3.59-3.52 (m, 4H), 3.27-3.19 (m, 4H), 2.99 (br s, 1H), 1.84-1.64 (m, 8H) ppm; TLC System: 5% Methanol-dichloromethane. R$_f$-0.2.

Example 123—Preparation of Compound 82

The synthesis of Compound 82 followed the procedure of General Procedure 5d following:

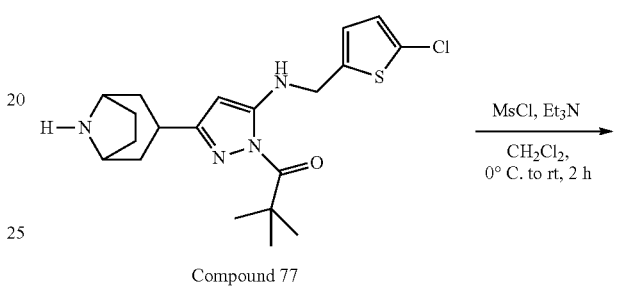

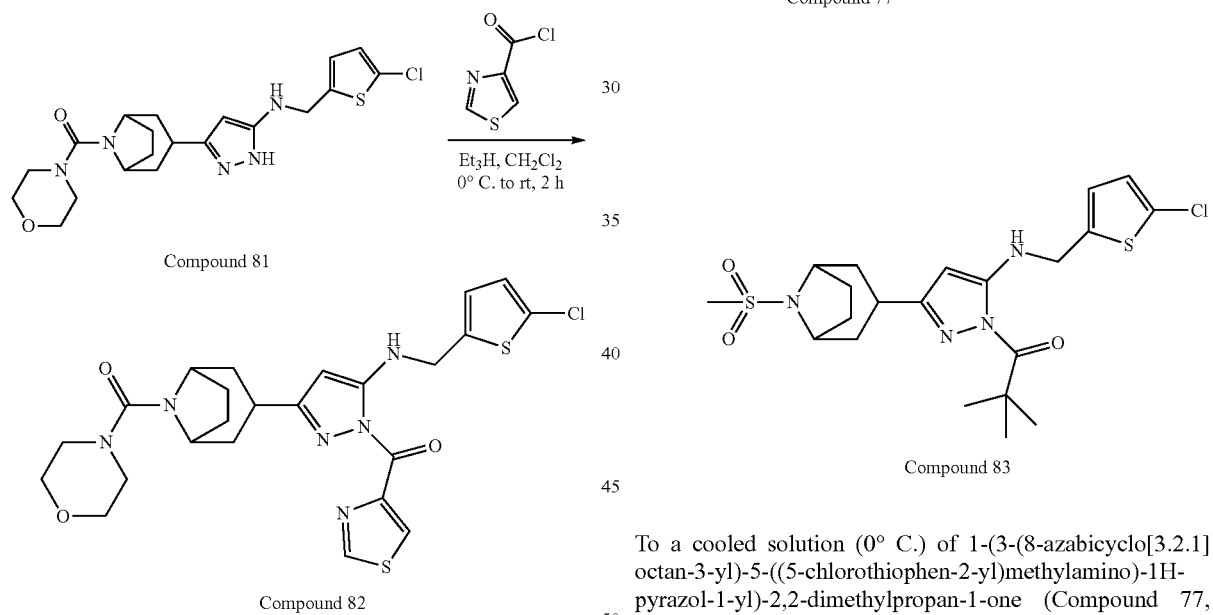

To a cooled solution (0° C.) of (3-(5-((5-chlorothiophen-2-yl)methylamino)-1H-pyrazol-3-yl)-8-azabicyclo[3.2.1]octan-8-yl)(morpholino)methanone (Compound 81, 175 mg, 0.4 mmol) in dry dichloromethane (10 mL) was added triethylamine (TEA, 0.14 mL, 1 mmol), followed by 1,3-thiazole-4-carbonyl chloride (119 mg, 0.8 mmol). After stirring at room temperature for 2 hours, ice-cold water (5 mL) was added, and then washed with dichloromethane (2×15 mL). The combined organic layers were dried over sodium sulfate, filtered and concentrated under reduced pressure. The residue was purified by flash column chromatography, eluting with 1-2% MeOH-dichloromethane, to give the desired product (165 mg, yield: 75%) as a light brown liquid. It was further purified by preparative HPLC to give (3-(5-((5-chlorothiophen-2-yl)methylamino)-1-(thiazole-4-carbonyl)-1H-pyrazol-3-yl)-8-azabicyclo[3.2.1]octan-8-yl)(morpholino)methanone (Compound 82, 55 mg) as an off-white solid. m/z 547.23 [M+H]+. $^1$H NMR (400 MHz, DMSO-d$_6$) δ=9.19 (d, J=2.0 Hz, 1H), 9.04 (d, J=2.0 Hz, 1H), 7.78 (br t, J=6.4 Hz, 1H, exchangeable), 6.98 (q, J=3.9 Hz, 2H), 5.52 (s, 1H), 4.50 (br d, J=5.9 Hz, 2H), 4.04 (br s, 2H), 3.58-3.53 (m, 4H), 3.25-3.21 (m, 4H), 2.98 (br dd, J=5.9, 11.7 Hz, 1H), 1.86-1.69 (m, 8H) ppm; TLC System: 5% Methanol-dichloromethane. R$_f$-0.5.

Example 124—Preparation of Compound 83

The synthesis of Compound 83 followed the procedure of General Procedure 22 following:

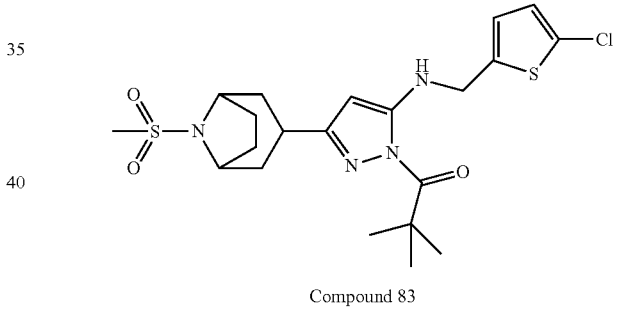

To a cooled solution (0° C.) of 1-(3-(8-azabicyclo[3.2.1]octan-3-yl)-5-((5-chlorothiophen-2-yl)methylamino)-1H-pyrazol-1-yl)-2,2-dimethylpropan-1-one (Compound 77, 350 mg, 0.86 mmol) in dry dichloromethane (10 mL) was added triethylamine (TEA, 0.3 mL, 2.15 mmol) followed by methanesulfonyl chloride (0.1 mL, 1.3 mmol). After stirring at room temperature for 2 hours, ice-cold water (5 mL) was added, and washed with dichloromethane (2×20 mL). The combined organic layers were dried over sodium sulfate, filtered and concentrated under reduced pressure. The residue was purified by flash column chromatography using 1% MeOH— dichloromethane, to give 1-(5-((5-chlorothiophen-2-yl)methylamino)-3-(8-(methylsulfonyl)-8-azabicyclo[3.2.1]octan-3-yl)-1H-pyrazol-1-yl)-2,2-dimethylpropan-1-one (Compound 83, 310 mg, yield: 74%) as an off white solid. m/z 485.15 [M+H]+. $^1$H NMR (400 MHz, DMSO-d$_6$) δ=7.67 (br t, J=6.1 Hz, 1H, exchangeable), 6.96 (s, 2H), 5.36 (s, 1H), 4.41 (d, J=5.9 Hz, 2H), 4.18 (br s, 2H), 3.00-2.90 (m, 4H), 2.05-1.96 (m, 2H), 1.89-1.69 (m, 6H), 1.40 (s, 9H) ppm; TLC System: 5% Methanol-dichloromethane. R$_f$-0.6.

Example 125—Preparation of Compound 84

The synthesis of Compound 84 followed the procedure of General Procedure 6d following:

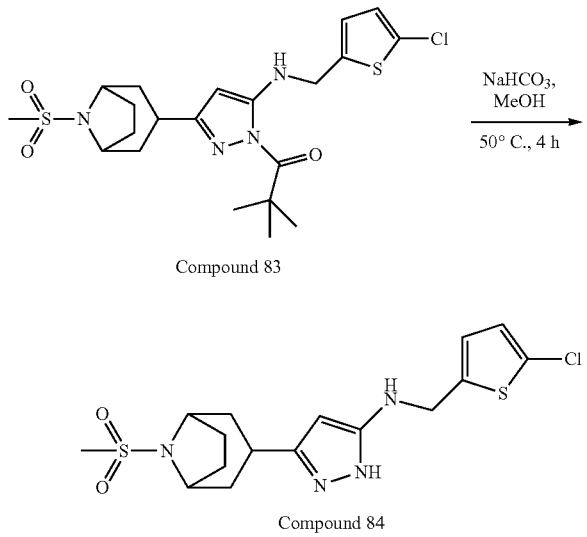 [SMILES: CC(C)(C)C(=O)n1nc(C2CC3CCC(C2)N3S(C)(=O)=O)cc1NCc1ccc(Cl)s1 ; CS(=O)(=O)N1C2CCC1CC(c1cc(NCc3ccc(Cl)s3)[nH]n1)C2]

Compound 83

Compound 84

To a stirred solution of 1-(5-((5-chlorothiophen-2-yl)methylamino)-3-(8-(methylsulfonyl)-8-azabicyclo[3.2.1]octan-3-yl)-1H-pyrazol-1-yl)-2,2-dimethylpropan-1-one (Compound 83, 145 mg, 0.3 mmol) in methanol (5 mL) at room temperature was added sodium bicarbonate (126 mg, 1.5 mmol). After stirring at 50° C. for 4 hours, the reaction mixture was concentrated and extracted into dichloromethane (2×15 mL). The combined organic layers were dried over sodium sulfate, filtered and concentrated under reduced pressure. The residue was purified by preparative HPLC to give N-((5-chlorothiophen-2-yl)methyl)-3-(8-(methylsulfonyl)-8-azabicyclo[3.2.1]octan-3-yl)-1H-pyrazol-5-amine (Compound 84, 25 mg) as an off-white solid. m/z 401.20 [M+H]+. ¹H NMR (400 MHz, DMSO-d₆) δ=11.28 (s, 1H), 6.90 (d, J=3.9 Hz, 1H), 6.83 (br d, J=3.4 Hz, 1H), 5.62 (br s, 1H, exchangeable), 5.27 (br s, 1H), 4.27 (d, J=6.4 Hz, 2H), 4.16 (br s, 2H), 2.94 (s, 4H), 2.05-1.97 (m, 2H), 1.86-1.74 (m, 4H), 1.73-1.64 (m, 2H) ppm; TLC System: 5% Methanol-dichloromethane. R_f-0.2.

Example 126—Preparation of Compound 85

The synthesis of Compound 85 followed the procedure of General Procedure 5d following:

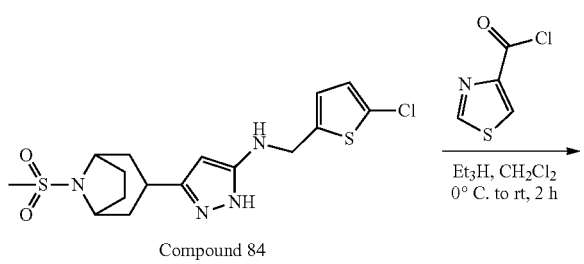

Compound 84

Compound 85

To a cooled solution (0° C.) of N-((5-chlorothiophen-2-yl)methyl)-3-(8-(methylsulfonyl)-8-azabicyclo[3.2.1]octan-3-yl)-1H-pyrazol-5-amine (Compound 84, 170 mg, 0.42 mmol) in dry dichloromethane (10 mL) was added triethylamine (TEA, 0.15 mL, 1.06 mmol) and then 1,3-thiazole-4-carbonyl chloride (125 mg, 0.85 mmol). After stirring at room temperature for 2 hours, ice-cold water (5 mL) was added and then washed with dichloromethane (2×15 mL). The combined organic layers were dried over sodium sulfate, filtered and concentrated under reduced pressure. The residue was purified by flash column chromatography, eluting with 1-2% MeOH-dichloromethane, to give the desired product (170 mg, yield: 78%) as a light brown liquid. It was purified further by preparative HPLC to give the 50 mg of pure (5-((5-chlorothiophen-2-yl)methylamino)-3-(8-(methyl sulfonyl)-8-azabicyclo[3.2.1]octan-3-yl)-1H-pyrazol-1-yl)(thiazol-4-yl)methanone (Compound 85, 50 mg) as a pale yellow solid. m/z 512.14 [M+H]+. ¹H NMR (400 MHz, DMSO-d₆) δ=9.19 (s, 1H), 9.04 (s, 1H), 7.80 (br s, 1H), 7.19 (br s, 1H), 7.05-6.93 (m, 2H), 5.54 (s, 1H), 4.50 (br d, J=5.4 Hz, 2H), 4.19 (br s, 2H), 3.07-2.90 (m, 4H), 2.01 (br s, 2H), 1.92-1.73 (m, 6H) ppm; TLC System: 5% Methanol-dichloromethane. R_f-0.5.

Example 127—Preparation of Intermediate 42

The synthesis of Intermediate 42 followed the procedure of General Procedure 7 following:

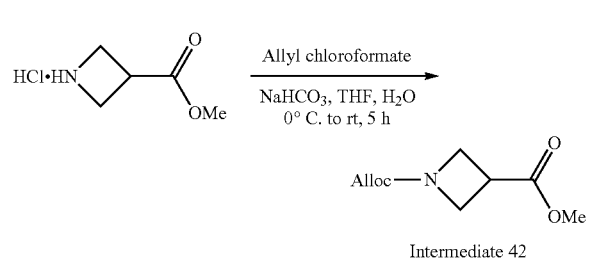

Intermediate 42

To a cooled solution (0° C.) of methyl azetidine-3-carboxylate hydrochloride (10 g, 66 mmol) in THF/H₂O (3:6, 100 mL) was added sodium bicarbonate (16.6 g, 198 mmol) portionwise, followed by allyl chloroformate (7.73 mL, 72.6 mmol). After stirring at room temperature for 5 hours, the mixture was extracted into EtOAc (3×100 mL). The combined organic layers were dried over sodium sulfate, filtered and concentrated under reduced pressure. The residue was purified by silica gel column chromatography (100-200 mesh), eluting with 2% MeOH/dichloromethane, to give 1-allyl 3-methyl azetidine-1,3-dicarboxylate (Intermediate 42, 11 g, yield: 83%) as a colorless syrup. m/z 200.03 [M+H]⁺; TLC System: 5% Methanol-dichloromethane; $R_f$-0.7.

Example 128—Preparation of Intermediate 43

The synthesis of Intermediate 43 followed the procedure of General Procedure 2 following:

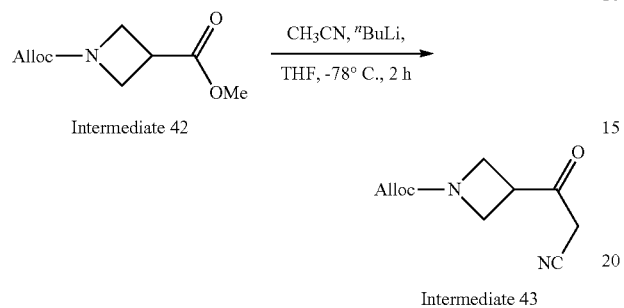

Intermediate 42

Intermediate 43

To a cooled solution (−78° C.) of acetonitrile (3.1 mL, 60.3 mmol) in dry THF (60 mL) was added n-BuLi (2.5M in THF, 24.1 mL, 60.3 mmol) then stirred for 1 hour, and then to it added a solution of 1-allyl-3-methyl azetidine-1,3-dicarboxylate (Intermediate 42, 10 g, 50.3 mmol) in dry THF (20 mL). After stirring at −78° C. for 1 hour, the mixture was quenched with saturated NH₄Cl solution (20 mL) and extracted into EtOAc (2×120 mL). The combined organic layers were dried over sodium sulfate, filtered and concentrated under reduced pressure. The residue was purified by silica gel column chromatography (100-200 mesh), eluting with 50% EtOAc/n-hexane, to afford desired allyl 3-(2-cyanoacetyl)azetidine-1-carboxylate (Intermediate 43, 5.1 g, 49%) as a light yellow liquid; TLC System: 60% ethyl acetate in hexane. $R_f$-0.3.

Example 129—Preparation of Compound 86

The synthesis of Compound 86 followed the procedure of General Procedure 3 following:

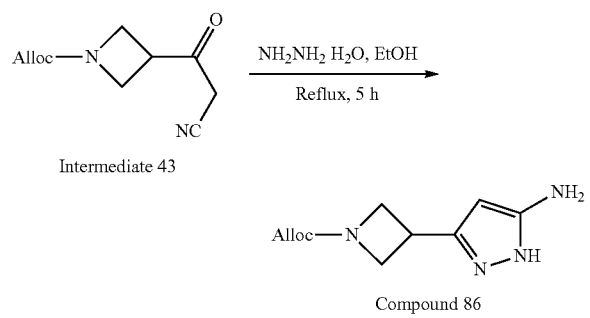

Intermediate 43

Compound 86

To a solution of allyl 3-(2-cyanoacetyl)azetidine-1-carboxylate (Intermediate 43, 5 g, 24 mmol) in ethanol (30 mL) was added hydrazine hydrate (N₂H₄.H₂O, 1.2 mL, 24 mmol) and the reaction mixture was then heated to 80° C. for 5 hours. The reaction mixture was cooled to room temperature and the volatiles were evaporated. The residue was purified by silica gel column chromatography (100-200 mesh), eluting with 4% MeOH-dichloromethane, to afford allyl 3-(5-amino-1H-pyrazol-3-yl)azetidine-1-carboxylate (Compound 86, 3.6 g, 68%) as an orange liquid; m/z 223.11 [M+H]⁺; TLC System: 5% Methanol-dichloromethane. $R_f$-0.3.

Example 130—Preparation of Compound 87

The synthesis of Compound 87 followed the procedure of General Procedure 4 following:

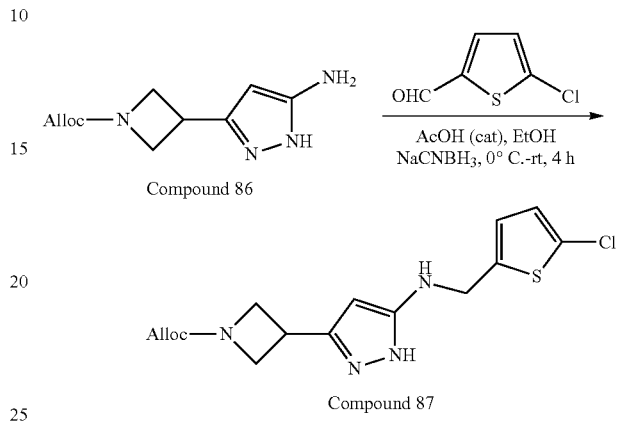

Compound 86

Compound 87

To a cooled solution (0° C.) of allyl 3-(5-amino-1H-pyrazol-3-yl)azetidine-1-carboxylate (Compound 86, 3.5 g, 15.8 mmol) in dry EtOH (40 mL) was added 5-chlorothiophene-2-carbaldehyde (1.9 mL, 18.9 mmol), acetic acid (0.5 mL) and then powdered 4 Å molecular sieves (1 g). The reaction mixture was stirred at room temperature for 1 hour. (Formation of imine was observed as a less polar spot on TLC). To the mixture was then added sodium cyanoborohydride (1.19 g, 18.9 mmol) portionwise and stirring continued at room temperature for 2 hours. The reaction mixture was quenched with ice-cold water (50 mL), filtered through a Celite pad and the filtrate was extracted into EtOAc (3×100 mL). The combined organic layers were dried over sodium sulfate, filtered and concentrated under reduced pressure. The residue was purified by silica gel column chromatography (100-200 mesh), eluting with 5% MeOH/dichloromethane, to afford allyl 3-(5-((5-chlorothiophen-2-yl)methylamino)-1H-pyrazol-3-yl)azetidine-1-carboxylate (Compound 87, 3.2 g, 58%) as a light yellow gummy liquid; m/z 353.17 [M+H]⁺. ¹H NMR (400 MHz, DMSO-d₆) δ 11.54 (br s, 1H), 6.97-6.79 (m, 2H), 5.98-5.84 (m, 1H), 5.73 (br s, 1H), 5.47 (br s, 1H), 5.28 (dd, J=1.5, 17.1 Hz, 1H), 5.19 (dd, J=1.2, 10.5 Hz, 1H), 4.50 (d, J=5.4 Hz, 2H), 4.36-4.10 (m, 4H), 3.97-3.64 (m, 3H) ppm; TLC System: 5% Methanol in dichloromethane $R_f$-0.4.

Example 131—Preparation of Compound 88

The synthesis of Compound 88 followed the procedure of General Procedure 5d following:

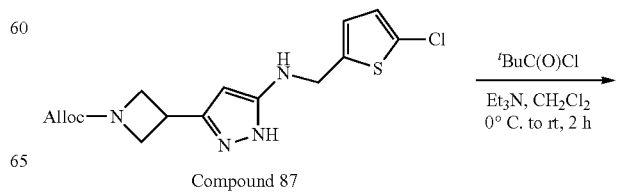

Compound 87

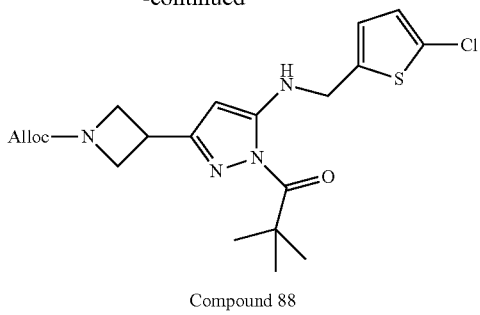

Compound 88

To a cooled solution (0° C.) of allyl 3-(5-((5-chlorothiophen-2-yl)methylamino)-1H-pyrazol-3-yl)azetidine-1-carboxylate (Compound 87, 3 g, 8.5 mmol) in dry dichloromethane (45 mL) was added triethylamine (TEA, 1.84 mL, 12.8 mmol), followed by trimethylacetyl chloride (1.0 mL, 8.5 mmol). After stirring at room temperature for 2 hours, the reaction mixture was diluted with water (50 mL) and extracted into dichloromethane (3×50 mL). The combined organic layers were dried over sodium sulfate, filtered and concentrated under reduced pressure. The residue was purified by silica gel column chromatography (100-200 mesh), eluting with 15% EtOAc/hexanes, to afford allyl 3-(5-((5-chlorothiophen-2-yl)methylamino)-1-pivaloyl-1H-pyrazol-3-yl)azetidine-1-carboxylate (Compound 88, 1.9 g, 51%) as a colorless liquid. MS (ESI): m/z 437.44 [M+H]$^+$. $^1$H NMR (400 MHz, DMSO-$d_6$) δ 7.75 (t, J=6.1 Hz, 1H), 6.96 (q, J=3.4 Hz, 2H), 5.90 (tdd, J=5.3, 10.4, 17.1 Hz, 1H), 5.52 (s, 1H), 5.31-5.23 (m, 1H), 5.18 (dd, J=1.5, 10.8 Hz, 1H), 4.53-4.47 (m, 2H), 4.43 (d, J=5.9 Hz, 2H), 4.24 (br s, 2H), 3.96 (br s, 2H), 3.70 (tt, J=5.9, 8.8 Hz, 1H), 1.41 (s, 9H) ppm; TLC System: 30% Ethyl acetate in hexane. $R_f$-0.6.

Example 132—Preparation of Compound 89

The synthesis of Compound 89 followed the procedure of General Procedures 8b and 15 following:

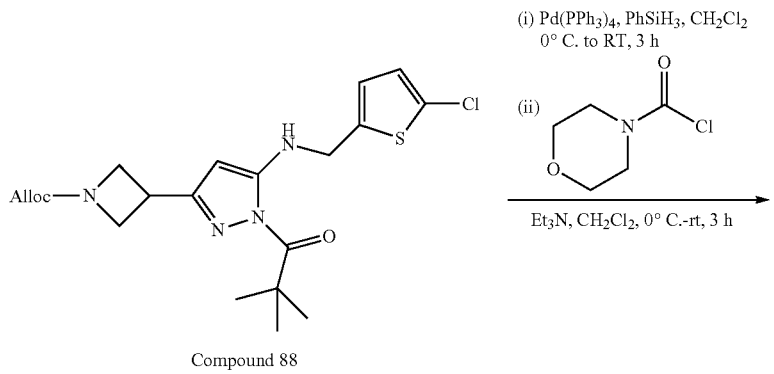

Compound 88

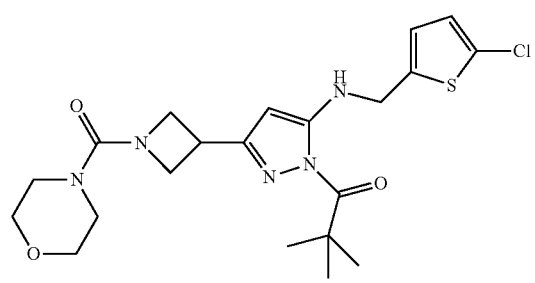

Compound 89

A cooled solution (0° C.) of allyl 3-(5-((5-chlorothiophen-2-yl)methylamino)-1-pivaloyl-1H-pyrazol-3-yl)azetidine-1-carboxylate (Compound 88, 600 mg, 1.4 mmol) in dichloromethane (30 mL) was degassed with a stream of argon for 15 minutes, then to it was added phenylsilane (PhSiH$_3$, 0.5 mL, 4.1 mmol), followed by tetrakis(triphenylphosphine)palladium(0) (Pd(PPh$_3$)$_4$, 79.4 mg, 0.068 mmol). The reaction mixture was stirred at room temperature for 3 hours. After complete consumption of starting material (monitored by TLC), the mixture was re-cooled to 0° C., and to it added triethylamine (TEA, 0.39 mL, 2.75 mmol), followed by morpholine-4-carbamyl chloride (0.16 mL, 1.4 mmol) and the mixture was stirred at room temperature for 3 hours. The reaction mixture was diluted with water (20 mL) and extracted into dichloromethane (2×20 mL). The combined organic layers were dried over sodium sulfate, filtered and concentrated under reduced pressure. The residue was purified by Combi-Flash column chromatography, eluting with 2% MeOH/dichloromethane, to give 1-(5-((5-chlorothiophen-2-yl)methylamino)-3-(1-(morpholine-4-carbonyl)azetidin-3-yl)-1H-pyrazol-1-yl)-2,2-dimethylpropan-1-one (Compound 89, 200 mg, 31% over two steps) as an off-white solid. MS (ESI) m/z 466.49 [M+H]$^+$. $^1$H NMR (400 MHz, DMSO-d$_6$) δ 7.75 (t, J=6.1 Hz, 1H), 6.96 (s, 2H), 5.47 (s, 1H), 4.43 (d, J=5.9 Hz, 2H), 4.20 (t, J=8.3 Hz, 2H), 3.94 (dd, J=6.1, 7.6 Hz, 2H), 3.64 (ddd, J=6.4, 8.7, 14.8 Hz, 1H), 3.57-3.45 (m, 4H), 3.25-3.14 (m, 4H), 1.40 (s, 9H) ppm; TLC System: 5% Methanol in dichloromethane R$_f$-0.6.

Example 133—Preparation of Compound 90

The synthesis of Compound 90 followed the procedure of General Procedure 6d following:

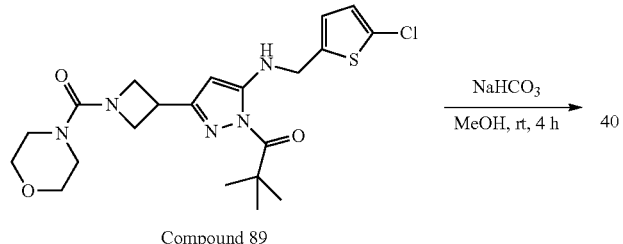

Compound 89

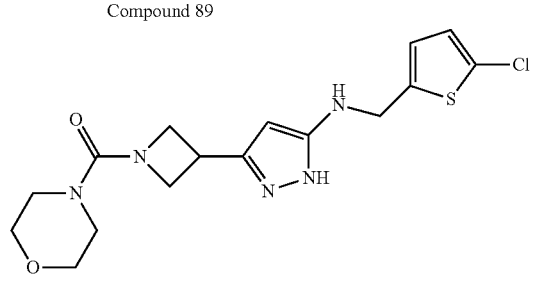

Compound 90

To a solution of 1-(5-((5-chlorothiophen-2-yl)methylamino)-3-(1-(morpholine-4-carbonyl)azetidin-3-yl)-1H-pyrazol-1-yl)-2,2-dimethylpropan-1-one (Compound 89, 200 mg, 0.43 mmol) in methanol (5 mL) was added sodium bicarbonate (NaHCO$_3$, 108 mg, 1.3 mmol). After stirring the reaction mixture at 50° C. for 4 hours, the reaction mixture was cooled to room temperature, the volatiles were evaporated and the resultant residue was diluted with EtOAc (20 mL) and washed with water (2×10 mL). The organic layers were dried over sodium sulfate, filtered and concentrated under reduced pressure. The resulting solid was triturated with diethyl ether and n-pentane and dried under high vacuum for 1 hour to afford (3-(5-((5-chlorothiophen-2-yl)methylamino)-1H-pyrazol-3-yl)azetidin-1-yl)(morpholino)methanone (Compound 90, 150 mg, 92%) as a pale yellow gummy solid; TLC System: 5% Methanol in dichloromethane R$_f$-0.3.

Example 134—Preparation of Compound 91

The synthesis of Compound 91 followed the procedure of General Procedure 5d following:

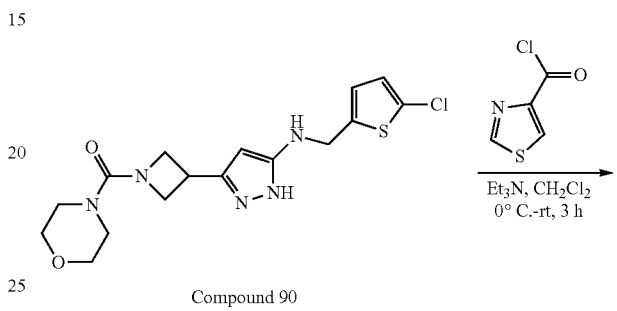

Compound 90

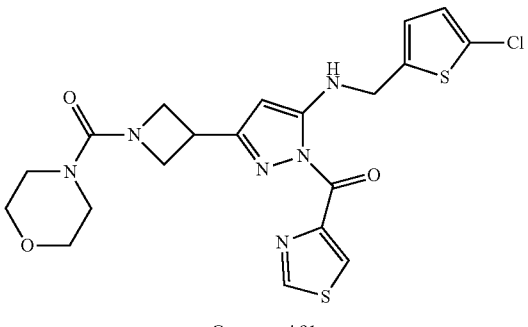

Compound 91

To a cooled solution (0° C.) of (3-(5-((5-chlorothiophen-2-yl)methylamino)-1H-pyrazol-3-yl)azetidin-1-yl)(morpholino)methanone (Compound 90, 120 mg, 0.31 mmol) in dry dichloromethane (5 mL) was added triethylamine (TEA, 0.09 mL, 0.63 mmol), followed by thiazole-4-carbonyl chloride (51 mg, 0.35 mmol). After stirring at room temperature for 3 hours, the reaction mixture was diluted with water (10 mL) and extracted into dichloromethane (3×20 mL). The combined organic layers were dried over sodium sulfate, filtered and concentrated under reduced pressure. The residue was purified by Combi Flash column chromatography, eluting with 20% acetone/dichloromethane, to give (3-(5-((5-chlorothiophen-2-yl)methylamino)-1-(thiazole-4-carbonyl)-1H-pyrazol-3-yl)azetidin-1-yl)(morpholino)methanone (Compound 91, 50 mg, 32%) as a pale yellow solid. m/z 493.16 [M+H]$^+$. $^1$H NMR (400 MHz, DMSO-d$_6$) δ 9.20 (d, J=1.5 Hz, 1H), 9.04 (s, 1H), 7.87 (t, J=6.1 Hz, 1H), 6.99 (dd, J=3.4, 13.2 Hz, 2H), 5.65 (s, 1H), 4.53 (d, J=6.4 Hz, 2H), 4.22 (t, J=8.6 Hz, 2H), 3.98 (t, J=6.8 Hz, 2H), 3.75-3.64 (m, 1H), 3.59-3.49 (m, 4H), 3.26-3.17 (m, 4H) ppm; TLC System: 30% acetone in dichloromethane R$_f$-0.6.

Example 135—Preparation of Compound 92

The synthesis of Compound 92 followed the procedure of General Procedure 8b following:

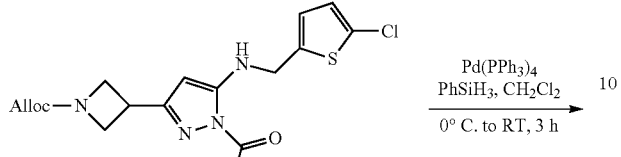

Compound 88

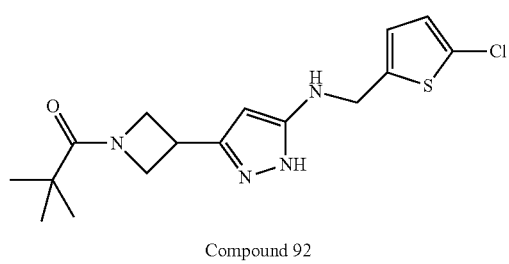

Compound 92

A cooled solution (0° C.) of allyl 3-(5-((5-chlorothiophen-2-yl)methylamino)-1-pivaloyl-1H-pyrazol-3-yl)azetidine-1-carboxylate (Compound 88, 100 mg, 0.23 mmol) in dichloromethane (10 ml) was degassed with a stream of argon for 15 minutes, then to it was added phenylsilane (PhSiH$_3$, 0.075 ml, 0.69 mmol) followed by tetrakis(triphenylphosphine)palladium(0) (Pd(PPh$_3$)$_4$, 13 mg, 0.01 mmol). The reaction mixture was stirred at room temperature for 3 hours, then filtered through a Celite pad and the filtrate was evaporated. The residue was purified by flash chromatography, eluting with 4% MeOH-dichloromethane to give 1-(3-(5-((5-chlorothiophen-2-yl)methylamino)-1H-pyrazol-3-yl)azetidin-1-yl)-2,2-dimethylpropan-1-one (Compound 92, 30 mg, 37%) as a pale yellow gummy liquid. MS (ESI) m/z 353.27 [M+H]$^+$; $^1$H NMR (400 MHz, DMSO-d$_6$) δ 11.54 (s, 1H), 7.01-6.70 (m, 2H), 5.71 (br s, 1H), 5.48 (s, 1H), 4.65 (s, 1H), 4.40-3.97 (m, 4H), 3.71 (s, 2H), 1.30-0.83 (s, 9H) ppm; TLC System: 5% MeOH in dichloromethane, R$_f$-0.4.

Example 136—Preparation of Compound 93

The synthesis of Compound 93 followed the procedures of General Procedures 8b and 5d following:

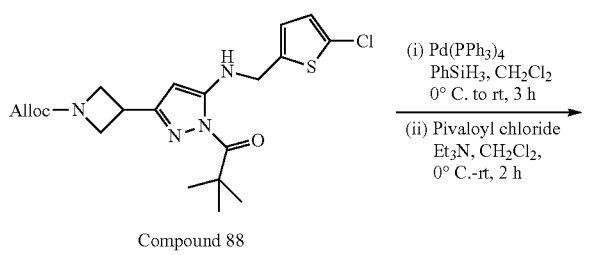

Compound 88

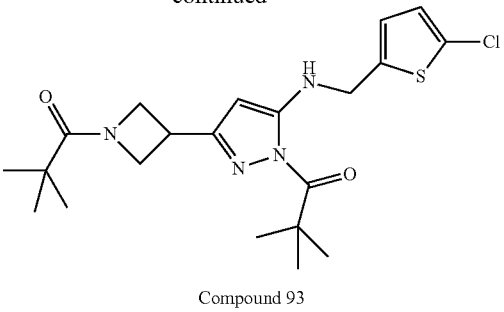

Compound 93

A cooled solution (0° C.) of allyl 3-(5-((5-chlorothiophen-2-yl)methylamino)-1-pivaloyl-1H-pyrazol-3-yl)azetidine-1-carboxylate (Compound 88, 200 mg, 0.46 mmol) in dichloromethane (15 ml) was degassed with a stream of argon for 15 minutes, then to it was added phenylsilane (PhSiH$_3$, 0.16 mL, 1.38 mmol) followed by tetrakis(triphenylphosphine)palladium(0) (Pd(PPh$_3$)$_4$, 26 mg, 0.02 mmol). The reaction mixture was stirred at room temperature for 3 hours. After complete consumption of starting material (monitored by TLC), the mixture was cooled to 0° C. and to it added triethylamine (TEA, 0.16 mL, 1.1 mmol) followed by pivaloyl chloride (0.06 ml, 0.46 mmol). After stirring at room temperature for 2 hours, the reaction mixture was diluted with water (10 mL) and extracted into dichloromethane (3×15 mL). The combined organic layers were dried over sodium sulfate, filtered and concentrated under reduced pressure. The residue was purified by Combi-Flash column chromatography, eluting with 20% EtOAc/hexane, to afford 1-(3-(5-((5-chlorothiophen-2-yl)methylamino)-1-pivaloyl-1H-pyrazol-3-yl)azetidin-1-yl)-2,2-dimethylpropan-1-one (Compound 93, 40 mg, 20%; over two steps) as a pale yellow gummy material. m/z: 437.21 [M+H]$^+$. $^1$H NMR (400 MHz, DMSO-d$_6$) δ 7.72 (t, J=6.4 Hz, 1H), 6.94-6.90 (m, 2H), 5.44 (s, 1H), 4.63 (s, 1H), 4.43-4.28 (m, 3H), 4.10 (s, 1H), 3.79 (s, 1H), 3.63-3.58 (m, 1H), 1.37 (s, 9H), 1.07 (s, 9H) ppm; TLC System: 30% Ethyl acetate in Hexane, R$_f$-0.4.

Example 137—Preparation of Compound 94

The synthesis of Compound 94 followed the procedures of General Procedures 8b and 22 following:

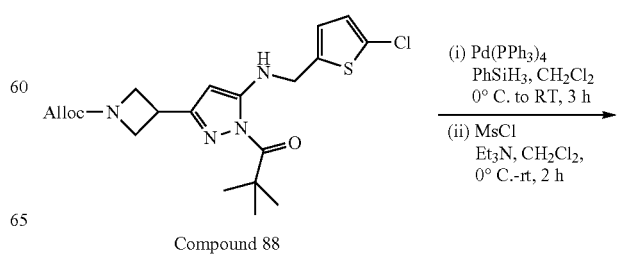

Compound 88

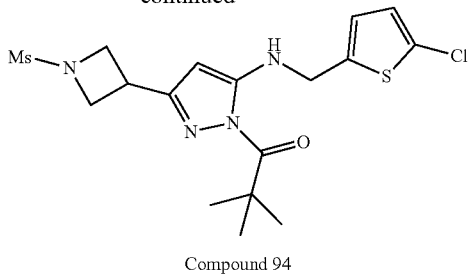

Compound 94

A cooled solution (0° C.) of allyl 3-(5-((5-chlorothiophen-2-yl)methylamino)-1-pivaloyl-1H-pyrazol-3-yl)azetidine-1-carboxylate (Compound 88, 550 mg, 1.3 mmol) in dichloromethane (25 mL) was degassed with a stream of argon for 15 minutes, then to it was added phenylsilane (PhSiH$_3$, 0.46 ml, 3.8 mmol) followed by tetrakis(triphenylphosphine)palladium(0) (Pd(PPh$_3$)$_4$, 72 mg, 0.06 mmol). The reaction mixture was stirred at room temperature for 3 hours. After complete consumption of starting material (monitored by TLC), the mixture was cooled to 0° C. and to it added triethylamine (TEA, 0.35 mL, 2.52 mmol), followed by methanesulfonyl chloride (MsCl, 0.1 mL, 1.3 mmol). The mixture was stirred at room temperature for 2 hours. The reaction mixture was diluted with water (20 mL) and extracted into dichloromethane (3×20 mL). The combined organic layers were dried over sodium sulfate, filtered and concentrated under reduced pressure. The residue was purified by Combi-Flash column chromatography, eluting with 70% dichloromethane/hexane, to afford 1-(5-((5-chlorothiophen-2-yl)methylamino)-3-(1-(methyl sulfonyl)azetidin-3-yl)-1H-pyrazol-1-yl)-2,2-dimethylpropan-1-one (Compound 94, 160 mg, 29% over two steps) as an off-white solid; m/z 431.17 [M+H]$^+$; $^1$H NMR (400 MHz, DMSO-d$_6$) δ 7.78 (t, J=6.1 Hz, 1H), 7.01-6.93 (m, 2H), 5.51 (s, 1H), 4.44 (d, J=6.4 Hz, 2H), 4.18-4.08 (m, 2H), 3.96 (t, J=7.6 Hz, 2H), 3.78-3.65 (m, 1H), 3.02 (s, 3H), 1.42 (s, 9H) ppm; TLC System: dichloromethane R$_f$-0.4.

Example 138—Preparation of Compound 95

The synthesis of Compound 95 followed the procedure 6 of General Procedure 6d following:

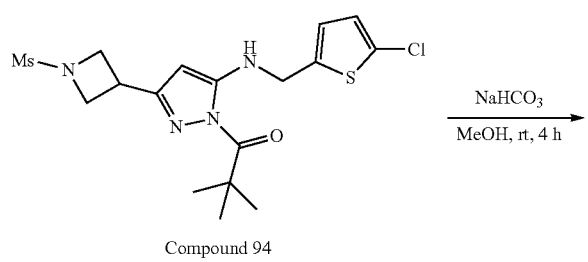

To a solution of 1-(5-((5-chlorothiophen-2-yl)methylamino)-3-(1-(methyl sulfonyl)azetidin-3-yl)-1H-pyrazol-1-yl)-2,2-dimethylpropan-1-one (Compound 94, 140 mg, 0.33 mmol) in methanol (5 mL) was added sodium bicarbonate (NaHCO$_3$, 82 mg, 0.98 mmol) and the reaction mixture was stirred at room temperature for 4 hours. The volatiles were evaporated and the resultant residue was diluted with EtOAc (20 mL) and washed with water (2×10 mL). The organic layer was dried over sodium sulfate, filtered and concentrated under reduced pressure. The residue was triturated with diethyl ether and n-pentane and dried under high vacuum to afford N-((5-chlorothiophen-2-yl)methyl)-3-(1-(methylsulfonyl)azetidin-3-yl)-1H-pyrazol-5-amine (Compound 95, 90 mg, 80%) as a pale yellow solid; m/z 347.19 [M+H]$^+$; $^1$H NMR (400 MHz, DMSO-d$_6$) δ 11.54 (br s, 1H), 6.96-6.78 (m, 2H), 5.85-5.44 (m, 2H), 4.30 (d, J=6.4 Hz, 2H), 4.10 (t, J=7.8 Hz, 2H), 3.87 (t, J=7.3 Hz, 2H), 3.73 (br s, 1H), 3.03 (s, 3H) ppm; TLC System: 5% Methanol in dichloromethane, R$_f$-0.4.

Example 139—Preparation of Compound 96

The synthesis of Compound 96 followed the procedure of General Procedure 5d following:

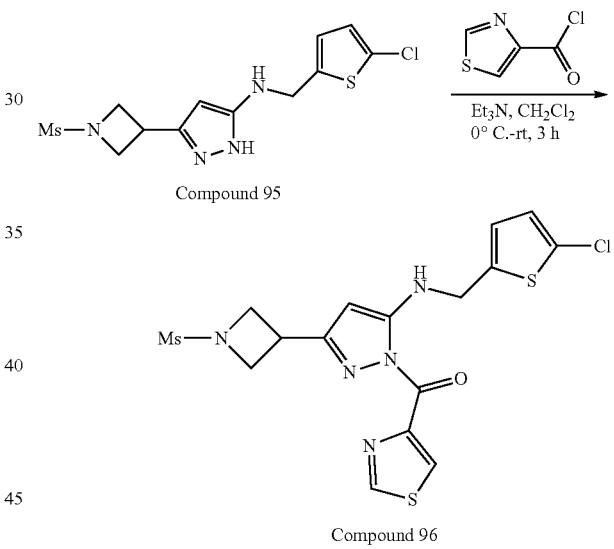

To a cooled solution (0° C.) of N-((5-chlorothiophen-2-yl)methyl)-3-(1-(methylsulfonyl)azetidin-3-yl)-1H-pyrazol-5-amine (Compound 95, 70 mg, 0.202 mmol) in dry dichloromethane (4 mL) was added triethylamine (TEA, 0.07 mL, 0.51 mmol), followed by thiazole-4-carbonyl chloride (32.7 mg, 0.22 mmol). The mixture was then stirred at room temperature for 3 hours. The reaction mixture was diluted with water (10 mL) and extracted into dichloromethane (3×15 mL). The combined organic layers were dried over sodium sulfate, filtered and concentrated under reduced pressure. The resultant residue was purified by Combi-Flash column chromatography, eluting with 5% acetone/dichloromethane, to afford (5-((5-chlorothiophen-2-yl)methylamino)-3-(1-(methylsulfonyl)azetidin-3-yl)-1H-pyrazol-1-yl)(thiazol-4-yl)methanone (Compound 96, 50 mg, 54%) as a pale yellow solid; m/z 458.14 [M+H]$^+$; $^1$H NMR (400 MHz, DMSO-d$_6$) δ 9.20 (d, J=2.0 Hz, 1H), 9.08 (d, J=2.0 Hz, 1H), 7.91 (t, J=6.1 Hz, 1H), 7.07-6.85 (m, 2H), 5.66 (s, 1H), 4.53 (d, J=5.9 Hz, 2H), 4.21-4.11 (m, 2H), 4.02 (t, J=7.3 Hz, 2H), 3.83-3.72 (m, 1H), 3.03 (s, 3H) ppm; TLC System: 10% Acetone in dichloromethane, $R_f$-0.5.

Example 140—Preparation of Compound 97

The synthesis of Compound 97 followed the procedure of General Procedure 5d following:

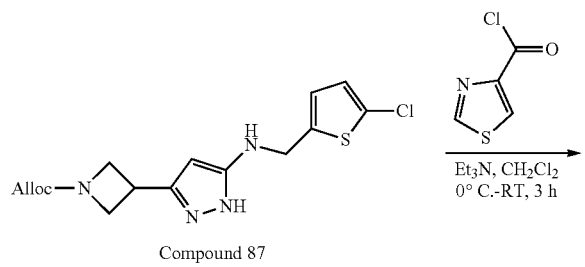

Compound 87

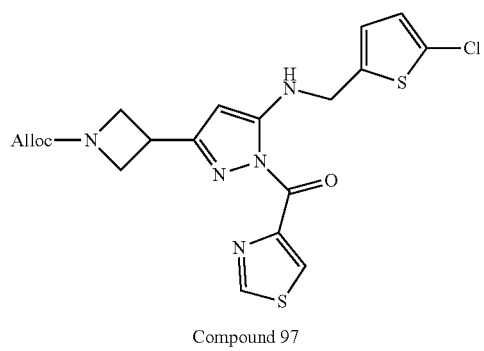

Compound 97

To a cooled solution (0° C.) of allyl 3-(5-((5-chlorothiophen-2-yl)methylamino)-1H-pyrazol-3-yl)azetidine-1-carboxylate (Compound 87, 100 mg, 0.28 mmol) in dry dichloromethane (5 mL) was added triethylamine (TEA, 0.1 mL, 0.71 mmol), followed by thiazole-4-carbonyl chloride (41.8 mg, 0.28 mmol). The mixture was stirred at room temperature for 3 hours. The reaction mixture was diluted with water (10 mL) and extracted into dichloromethane (3×15 mL). The combined organic layers were dried over sodium sulfate, filtered and concentrated under reduced pressure. The residue was purified by Combi-Flash column chromatography, eluting with 2% MeOH/dichloromethane, to afford allyl 3-(5-((5-chlorothiophen-2-yl)methylamino)-1-(thiazole-4-carbonyl)-1H-pyrazol-3-yl)azetidine-1-carboxylate (Compound 97, 60 mg, 45%) as a pale yellow solid; m/z 464.15 [M+H]$^+$. $^1$H NMR (400 MHz, DMSO-d$_6$) δ 9.20 (d, J=1.5 Hz, 1H), 9.03 (d, J=2.0 Hz, 1H), 7.88 (t, J=6.4 Hz, 1H), 7.02 (d, J=3.4 Hz, 1H), 6.97 (d, J=3.9 Hz, 1H), 5.98-5.84 (m, 1H), 5.70 (s, 1H), 5.27 (dd, J=1.7, 17.4 Hz, 1H), 5.18 (dd, J=1.5, 10.3 Hz, 1H), 4.51 (dd, J=5.9, 10.3 Hz, 4H), 4.25 (br s, 2H), 4.00 (br s, 2H), 3.76 (tt, J=6.2, 8.7 Hz, 1H) ppm; TLC System: 5% MeOH in dichloromethane, $R_f$-0.6.

Example 141—Preparation of Intermediate 44

The synthesis of Intermediate 44 followed the procedure of General Procedure 13 following:

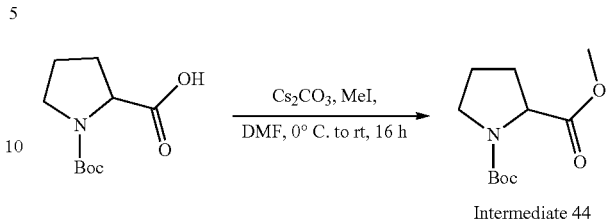

Intermediate 44

To a cooled solution (0° C.) of 1-(tert-butoxycarbonyl) pyrrolidine-2-carboxylic acid (20 g, 92.9 mmol) in dry dimethylformamide (DMF, 100 mL) was added cesium carbonate (Cs$_2$CO$_3$, 103 g, 316 mmol) followed by iodomethane (MeI, 12 mL, 186 mmol). After stirring at room temperature for 16 hours, water (100 mL) was added and extracted into EtOAc (2×100 mL). The combined organic layers were dried over sodium sulfate, filtered and concentrated under reduced pressure. The residue was purified by silica gel column chromatography (100-200 mesh), eluting with 10-15% EtOAc/n-hexanes, to obtain 1-tert-butyl-2-methyl pyrrolidine-1,2-dicarboxylate (Intermediate 44, 19 g, yield: 90%) as a pale yellow liquid; TLC System: 20% ethyl acetate in hexane $R_f$-0.5.

Example 142—Preparation of Intermediate 45

The synthesis of Intermediate 45 followed the procedure of General Procedure 6c following:

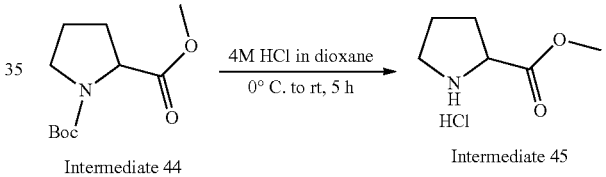

Intermediate 44        Intermediate 45

To a cooled solution (0° C.) of 1-tert-butyl-2-methyl pyrrolidine-1,2-dicarboxylate (Intermediate 44, 19 g, 83 mmol) in 1,4-dioxane (120 mL) was added HCl (4M in 1,4-dioxane, 95 mL) and the reaction was then stirred at room temperature for 5 hours. The reaction mixture was concentrated under reduced pressure and triturated with diethyl ether to afford methyl pyrrolidine-2-carboxylate hydrochloride (Intermediate 45, 12 g, yield-88%) as a white solid.

Example 143—Preparation of Intermediate 46

The synthesis of Intermediate 46 followed the procedure of General Procedure 7 following:

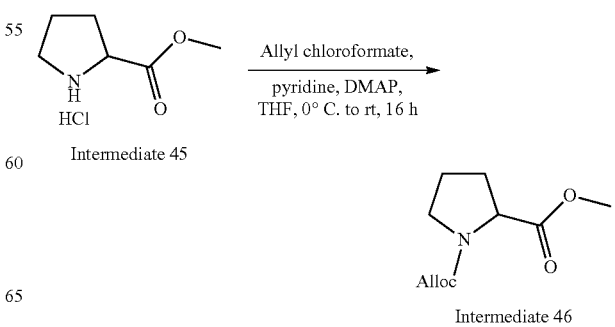

Intermediate 46

To a cooled solution (0° C.) of methylpyrrolidine-2-carboxylate hydrochloride (Intermediate 45, 12 g, 72.7 mmol) in THF (150 mL) was added pyridine (23.5 mL, 290.9 mmol), then 4-(dimethylamino)pyridine (DMAP, 889 mg, 7.3 mmol), followed by allyl chloroformate (15.5 mL, 145.4 mmol). The reaction mixture was stirred at room temperature for 16 hours, then water (100 mL) was added and extracted into dichloromethane (2×100 mL). The combined organic layers were dried over sodium sulfate, filtered and concentrated under reduced pressure. The residue was purified by silica gel column chromatography (100-200 mesh), eluting with 10-15% EtOAc/n-hexanes, to obtain 1-allyl-2-methyl pyrrolidine-1,2-dicarboxylate (Intermediate 46, 13 g, yield: 80%) as a colorless liquid. m/z 236.00 [M+Na]$^+$; TLC System: 20% ethyl acetate in hexane $R_f$-0.5.

Example 144—Preparation of Intermediate 47

The synthesis of Intermediate 47 followed the procedure of General Procedure 2 following:

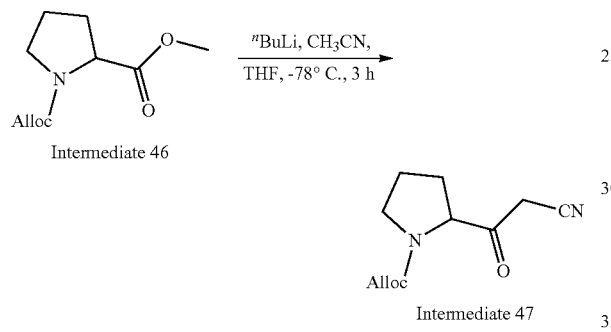

Intermediate 46

Intermediate 47

To a cold solution (−78° C.) of acetonitrile (1.8 mL, 35.2 mmol) in dry THF (50 mL) was added n-butyllithium (2.5M in n-hexane, 14 mL, 35.2 mmol). After stirring at −78° C. for 45 minutes, a solution of 1-allyl-2-methyl pyrrolidine-1,2-dicarboxylate (Intermediate 46, 5 g, 23.5 mmol) in dry THF (10 mL) was added and the reaction stirred at −78° C. for 1 hour. The reaction mixture was quenched with saturated NH$_4$Cl solution (20 mL) and extracted into EtOAc (2×50 mL). The combined organic layers were dried over sodium sulfate, filtered and concentrated under reduced pressure. The residue was purified by silica gel column chromatography (100-200 mesh), eluting with 20-25% EtOAc/n-hexane, to give allyl-2-(2-cyanoacetyl)pyrrolidine-1-carboxylate (Intermediate 47, 4.3 g, yield: 82%) as a brown color liquid: TLC System: 50% ethyl acetate in hexane $R_f$-0.2.

Example 145—Preparation of Compound 98

The synthesis of Compound 98 followed the procedure of General Procedure 3 following:

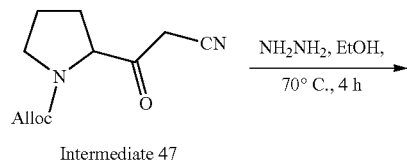

Intermediate 47

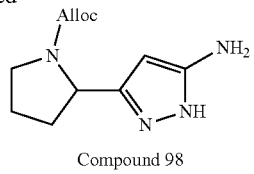

Compound 98

To a stirred solution of allyl-2-(2-cyanoacetyl)pyrrolidine-1-carboxylate (Intermediate 47, 4.3 g, 19.4 mmol) in ethanol (40 mL) was added hydrazine monohydrate (0.85 mL, 17.4 mmol). The reaction mixture was then heated to 70° C. for 5 hours. The reaction mixture was then cooled to room temperature and the volatiles were evaporated. The resultant residue was purified by silica gel column chromatography (100-200 mesh), eluting with 3% MeOH-dichloromethane, to give allyl-2-(5-amino-1H-pyrazol-3-yl)pyrrolidine-1-carboxylate (Compound 98, 4 g, yield: 87%) as a colorless liquid. m/z 237.14 [M+H]+; TLC System: 5% methanol in dichloromethane $R_f$-0.3.

Example 146—Preparation of Compound 99

The synthesis of Compound 99 followed the procedure of General Procedure 4 following:

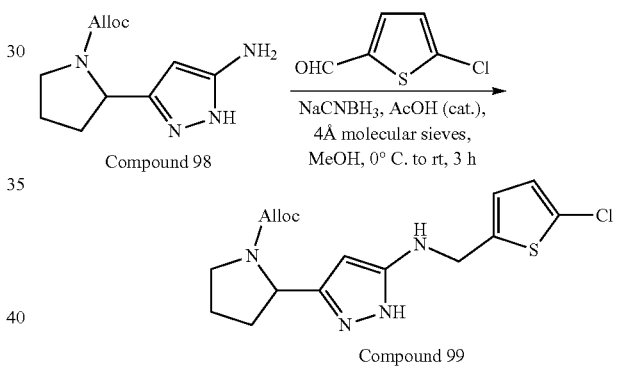

Compound 98

Compound 99

To a cooled solution (0° C.) of allyl-2-(5-amino-1H-pyrazol-3-yl)pyrrolidine-1-carboxylate (Compound 98, 4 g, 16.9 mmol) in dry MeOH (70 mL) was added 5-chlorothiophene-2-carbaldehyde (3.9 mL, 33.9 mmol) and acetic acid (0.1 mL), followed by powdered 4 Å molecular sieves. The reaction mixture was stirred at room temperature for 1 hour (the formation of imine was observed as a less polar spot on TLC). After cooling the reaction mixture back to 0° C., sodium cyanoborohydride (NaCNBH$_3$, 1.52 g, 8.5 mmol) was added portionwise. The mixture was then stirred at room temperature for 2 hours. The reaction mixture was quenched with ice-cold water (30 mL), filtered through a Celite pad and the filtrate was extracted into EtOAc (3×50 mL). The combined organic layers were dried over sodium sulfate, filtered and concentrated under reduced pressure. The residue was purified by preparative HPLC using a Reveleris C-18 reverse phase column, eluting with 35-40% acetonitrile in aqueous formic acid (0.1%), to obtain the required compound (3 g, yield: 45%). A portion (100 mg) of this was further purified by preparative HPLC purification to give allyl-2-(5-((5-chlorothiophen-2-yl)methylamino)-1H-pyrazol-3-yl)pyrrolidine-1-carboxylate (Compound 99, 50 mg) as a pale yellow gummy liquid. m/z 367.07 [M+H]$^+$. $^1$H NMR (300 MHz, DMSO-d$_6$) δ 11.39 (br s, 1H, exchangeable), 7.02-6.92 (m, 1H), 6.83 (br d, J=3.7 Hz, 1H, exchangeable), 6.09-5.47 (m, 2H), 5.38-4.97 (m, 3H), 4.81 (br s, 1H), 4.47 (br d, J=15.0 Hz, 2H), 4.28 (d, J=6.2 Hz, 2H), 3.48 (br s, 2H), 2.08 (br d, J=6.2 Hz, 1H), 1.95-1.58 (m, 3H) ppm; TLC System: 5% methanol in dichloromethane $R_f$-0.4.

Example 147—Preparation of Compound 100

The synthesis of Compound 100 followed the procedure of General Procedure 5d following:

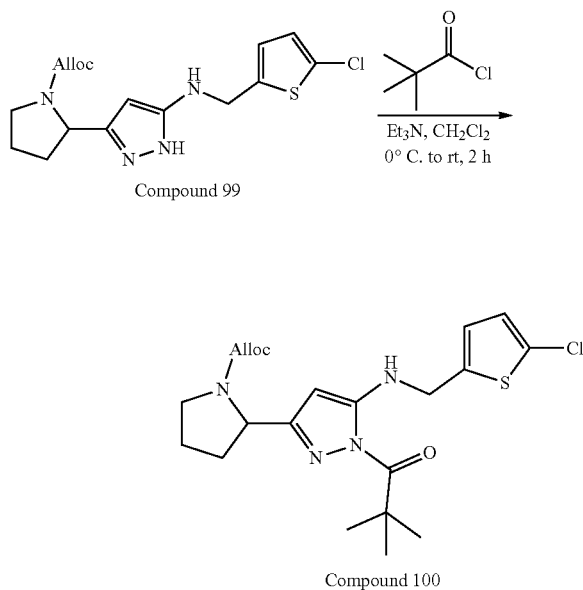

Compound 99

Compound 100

To a cooled solution (0° C.) of allyl-2-(5-((5-chlorothiophen-2-yl)methylamino)-1H-pyrazol-3-yl)pyrrolidine-1-carboxylate (Compound 99, 3.5 g, 9.6 mmol) in dry dichloromethane (50 mL) was added trimethylacetyl chloride (1.1 mL, 8.6 mmol) followed by triethylamine (TEA, 1.9 mL, 14.3 mmol). After stirring at room temperature for 2 hours, water (25 mL) was added and the mixture was extracted into dichloromethane (3×40 mL). The combined organic layers were dried over sodium sulfate, filtered and concentrated under reduced pressure. The residue was purified by silica gel column chromatography (100-200 mesh), eluting with 10% EtOAc/n-hexane, to afford the desired compound (3 g, yield: 69%) as a pale yellow gummy liquid. A portion (120 mg) was further purified by preparative HPLC purification to afford allyl-2-(5-((5-chlorothiophen-2-yl)methylamino)-1-pivaloyl-1H-pyrazol-3-yl)pyrrolidine-1-carboxylate (Compound 100, 50 mg) as a pale yellow gummy liquid; m/z 451.17 [M+H]$^+$. $^1$H NMR (400 MHz, CDCl$_3$) δ 7.49-7.31 (m, 1H), 6.83-6.66 (m, 2H), 6.07-5.74 (m, 1H), 5.38-5.26 (m, 1H), 5.24-5.06 (m, 2H), 4.98-4.77 (m, 1H), 4.64-4.46 (m, 2H), 4.34 (d, J=5.9 Hz, 2H), 3.67-3.41 (m, 2H), 2.27-1.80 (m, 4H), 1.44 (s, 9H) ppm; TLC System: 50% ethyl acetate in hexane $R_f$-0.7.

Example 148—Preparation of Compound 101

The synthesis of Compound 101 followed the procedure of General Procedure 8b following:

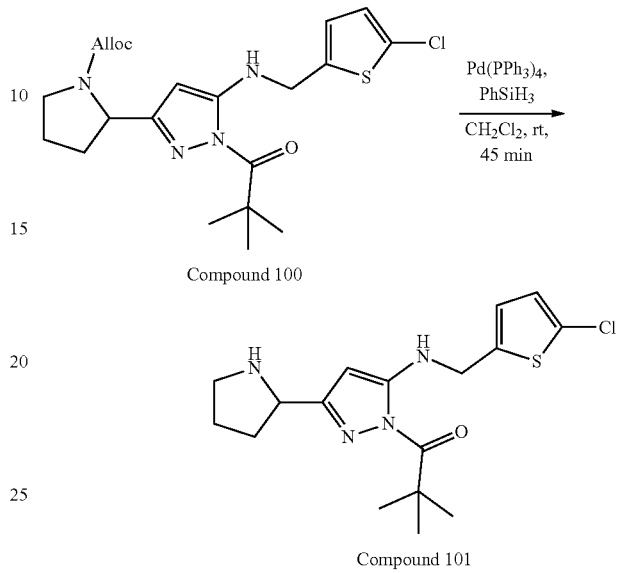

Compound 100

Compound 101

A stirred solution of allyl-2-(5-((5-chlorothiophen-2-yl)methylamino)-1-pivaloyl-1H-pyrazol-3-yl)pyrrolidine-1-carboxylate (Compound 100, 1.5 g, 3.3 mmol) in dichloromethane (30 mL) was degassed with a stream of argon for 15 minutes., then to the mixture was added tetrakis(triphenylphosphine)palladium(0) (Pd(PPh$_3$)$_4$, 193 mg, 0.16 mmol) followed by phenylsilane (PhSiH$_3$, 1.2 mL, 10 mmol). The reaction mixture was stirred at room temperature for 45 minutes, then was filtered through a Celite pad and the filtrate was evaporated. The crude residue was purified by combi-flash silica chromatography eluting with 4% MeOH— dichloromethane to afford 1-(5-((5-chlorothiophen-2-yl)methylamino)-3-(pyrrolidin-3-yl)-1H-pyrazol-1-yl)-2,2-dimethylpropan-1-one (Compound 101, 1 g, yield: 81%) as a pale yellow gummy liquid. m/z 367.26 [M+H]$^+$, $^1$H NMR (300 MHz, DMSO-d$_6$) δ 7.72 (br t, J=6.1 Hz, 1H, exchangeable), 6.96 (s, 2H), 5.44 (s, 1H), 4.42 (br d, J=6.2 Hz, 2H), 4.05 (br t, J=6.6 Hz, 1H), 3.11-2.82 (m, 2H), 2.13-1.95 (m, 1H), 1.87-1.65 (m, 3H), 1.41 (s, 9H) ppm; TLC System: 10% methanol in dichloromethane $R_f$-0.3

Example 149—Preparation of Compound 102

The synthesis of Compound 102 followed the procedure of General Procedure 5d following:

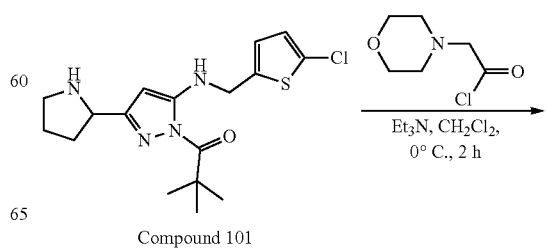

Compound 101

-continued

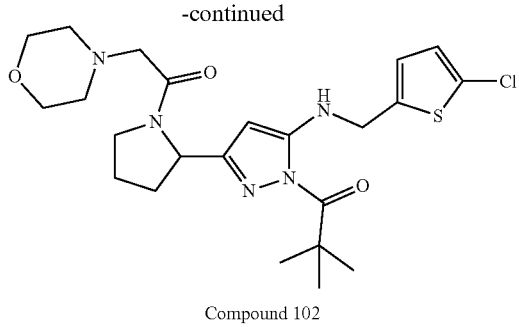

Compound 102

To a cooled solution (0° C.) of 1-(5-((5-chlorothiophen-2-yl)methylamino)-3-(pyrrolidin-2-yl)-1H-pyrazol-1-yl)-2,2-dimethylpropan-1-one (Compound 101, 200 mg, 1.2 mmol) in dry dichloromethane (10 mL) was added 4-morpholineacetic acid chloride (94 mg, 0.66 mmol) followed by triethylamine (TEA, 0.22 mL, 1.6 mmol). After stirring at room temperature for 2 hours, ice-cold water (10 mL) was added, then washed with dichloromethane (2×15 mL). The combined organic layers were dried over sodium sulfate, filtered and concentrated under reduced pressure. The residue was purified by silica gel column chromatography (100-200 mesh), eluting with 50% EtOAc-hexanes, to give the desired product (120 mg, yield: 81%) as a light yellow semi-solid. A portion (160 mg) of this material (85% by LCMS) was purified by preparative HPLC to give 1-(5-((5-chlorothiophen-2-yl)methylamino)-3-(1-(2-morpholinoacetyl)pyrrolidin-2-yl)-1H-pyrazol-1-yl)-2,2-dimethylpropan-1-one (Compound 102, 60 mg) as an off-white gummy semi solid; m/z 494.22 [M+H]+. $^1$H NMR (400 MHz, DMSO-d$_6$) δ 7.49 (br s, 1H), 6.90 (s, 2H), 5.34 (br s, 1H), 5.10 (br s, 2H), 4.42 (br s, 2H), 3.49 (br s, 8H), 2.98 (s, 2H), 2.48 (br s, 3H), 1.94 (br s, 2H), 1.39 (s, 9H) ppm; TLC System: 70% ethyl acetate in n-hexane—R$_f$-0.6.

Example 150—Preparation of Compound 103

The synthesis of Compound 103 followed the procedure of General Procedure 6d following:

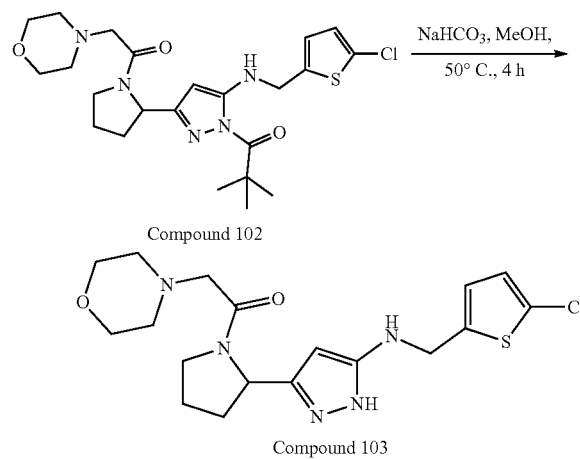

To a room temperature solution of 1-(5-((5-chlorothiophen-2-yl)methylamino)-3-(1-(2-morpholinoacetyl)pyrrolidin-2-yl)-1H-pyrazol-1-yl)-2,2-dimethylpropan-1-one (Compound 102, 230 mg, 0.54 mmol) in methanol (10 mL) was added sodium bicarbonate (NaHCO$_3$, 230 mg, 2.7 mmol). The mixture was stirred at 50° C. for 4 hours, then cooled back to room temperature, water (20 mL) was added and washed with dichloromethane (3×20 mL). The combined organic phases were dried with sodium sulfate, filtered and evaporated under reduced pressure. The residue was purified by silica gel column chromatography (100-200 mesh), eluting with 5-7% methanol in dichloromethane to afford the desired product (130 mg, yield: 67%). A portion (130 mg, 72% by LCMS) of this material was further purified by preparative HPLC to afford 1-(2-(5-((5-chlorothiophen-2-yl)methylamino)-1H-pyrazol-3-yl)pyrrolidin-1-yl)-2-morpholinoethanone (Compound 103, 25 mg) as a pale yellow solid; m/z 410.15 [M+H]+. $^1$H NMR (400 MHz, DMSO-d$_6$) δ 11.84-10.62 (m, 1H, exchangeable), 7.46-5.87 (m, 2H), 5.27 (br s, 2H), 5.04 (br s, 1H), 4.29 (br d, J=6.6 Hz, 2H), 3.53 (br s, 6H), 3.07 (br d, J=6.6 Hz, 1H), 2.97-2.71 (m, 1H), 2.48 (br d, J=1.5 Hz, 4H), 2.07 (br s, 1H), 1.85 (br s, 3H) ppm; TLC System: 10% methanol in dichloromethane—R$_f$-0.3.

Example 151—Preparation of Compound 104

The synthesis of Compound 104 followed the procedure of General Procedure 22 following:

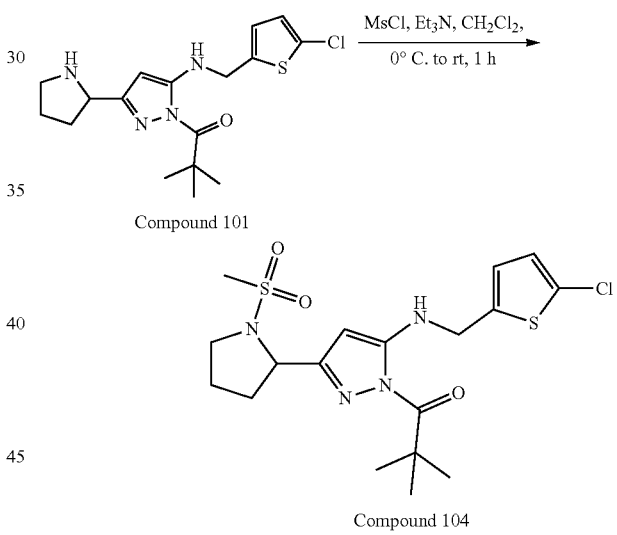

To a cold solution (0° C.) of 1-(5-((5-chlorothiophen-2-yl)methylamino)-3-(pyrrolidin-2-yl)-1H-pyrazol-1-yl)-2,2-dimethylpropan-1-one (Compound 101, 700 mg, 1.9 mmol) in dry dichloromethane (20 mL) was added methanesulfonyl chloride (MsCl, 0.22 mL, 2.8 mmol) followed by triethylamine (TEA, 0.6 mL, 4.4 mmol). After the mixture was stirred at room temperature for 1 hour, ice-cold water (20 mL) was added and extracted into dichloromethane (3×20 mL). The combined organic phases were dried with sodium sulfate, filtered and evaporated under reduced pressure. The residue was purified by silica gel column chromatography (100-200 mesh), eluting with 20-25% ethyl acetate in n-hexane, to give the desired product (550 mg, yield: 64%). A portion (170 mg) was further purified by preparative HPLC chromatography to yield 1-(5-((5-chlorothiophen-2-yl)methylamino)-3-(1-(methyl sulfonyl)pyrrolidin-2-yl)-1H-pyrazol-1-yl)-2,2-dimethylpropan-1-one (Compound 104, 50 mg) as a pale yellow gummy liquid; m/z 445.17

[M+H]⁺; ¹H NMR (400 MHz, CDCl₃) δ 7.52-7.35 (m, 1H, exchangeable), 6.91-6.61 (m, 2H), 5.37 (s, 1H), 4.83 (dd, J=2.7, 7.1 Hz, 1H), 4.37 (d, J=5.9 Hz, 2H), 3.63-3.36 (m, 2H), 2.75 (s, 3H), 2.33-1.89 (m, 4H), 1.45 (s, 9H) ppm; TLC System: 5% methanol in dichloromethane—R_f-0.6.

Example 152—Preparation of Compound 105

The synthesis of Compound 105 followed the procedure of General Procedure 6d following:

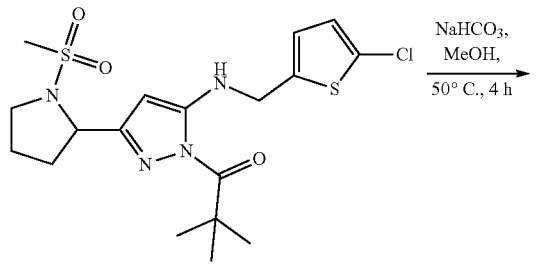

Compound 104

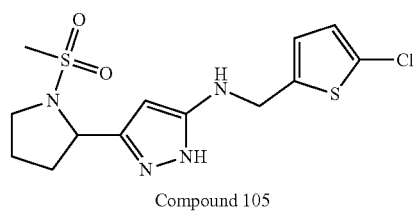

Compound 105

To a cooled solution (0° C.) of 1-(5-((5-chlorothiophen-2-yl)methylamino)-3-(1-(methylsulfonyl)pyrrolidin-2-yl)-1H-pyrazol-1-yl)-2,2-dimethylpropan-1-one (Compound 104, 200 mg, 0.45 mmol) in dry methanol (10 mL) was added sodium bicarbonate (189 mg, 2.25 mmol). After warming the mixture at 50° C. for 4 hours, the reaction mixture was cooled to room temperature, water (15 mL) was added and extracted into dichloromethane (3×20 mL). The combined organic phases were dried with sodium sulfate, filtered and evaporated under reduced pressure. The residue was purified by silica gel column chromatography (100-200 mesh), eluting with 5-7% methanol in dichloromethane, to give the required semi-pure compound (145 mg, yield: 89%) as an off-white solid. A portion (130 mg of 89% of LCMS purity) was further purified by preparative HPLC to yield N-((5-chlorothiophen-2-yl)methyl)-3-(1-(methylsulfonyl)pyrrolidin-2-yl)-1H-pyrazol-5-amine (Compound 105, 50 mg) as a white solid; m/z 361.16 [M+H]⁺; ¹H NMR (400 MHz, DMSO-d₆) δ 11.52-11.30 (m, 1H, exchangeable), 6.99-6.80 (m, 2H), 5.68 (br s, 1H, exchangeable), 5.41 (br s, 1H), 4.74 (br s, 1H), 4.29 (d, J=6.4 Hz, 2H), 3.46-3.24 (m, 2H), 2.84 (br s, 3H), 2.21-2.06 (m, 1H), 1.89 (br d, J=5.4 Hz, 3H) ppm; TLC System: 5% methanol in dichloromethane—R_f-0.3.

Example 153—Preparation of Compound 106

The synthesis of Compound 106 followed the procedure of General Procedure 5d following:

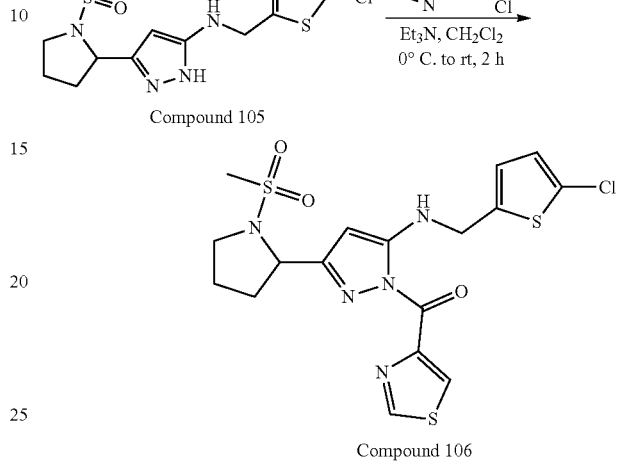

Compound 105

Compound 106

To a cooled solution (0° C.) of N-((5-chlorothiophen-2-yl)methyl)-3-(1-(methylsulfonyl)pyrrolidin-2-yl)-1H-pyrazol-5-amine (Compound 105, 200 mg, 0.56 mmol) in dry dichloromethane (10 mL) was added 1,3-thiazole-4-carbonyl chloride (148 mg, 1.11 mmol) followed by triethylamine (TEA, 0.18 mL, 1.4 mmol). After stirring at room temperature for 2 hours, the reaction mixture was quenched with NaHCO₃ solution (10 mL) and extracted into dichloromethane (3×20 mL). The combined organic phases were dried over sodium sulfate and concentrated under reduced pressure to afford the desired compound (150 mg, yield: 57%) as a light yellow semi-solid. A portion (100 mg with 87% LCMS purity) was further purified by preparative HPLC chromatography to yield (5-((5-chlorothiophen-2-yl)methylamino)-3-(1-(methylsulfonyl)pyrrolidin-2-yl)-1H-pyrazol-1-yl)(thiazol-4-yl)methanone (Compound 106, 40 mg) as an off-white solid. m/z 472.10 [M+H]⁺. ¹H NMR (400 MHz, CDCl₃) δ 9.13 (d, J=2.0 Hz, 1H), 8.88 (d, J=2.0 Hz, 1H), 7.65 (br t, J=5.6 Hz, 1H, exchangeable), 6.89-6.69 (m, 2H), 5.44 (s, 1H), 4.88 (dd, J=3.2, 8.1 Hz, 1H), 4.49 (d, J=5.9 Hz, 2H), 3.66-3.39 (m, 2H), 2.78 (s, 3H), 2.37-2.16 (m, 2H), 2.14-1.95 (m, 2H) ppm; TLC System: 5% methanol in dichloromethane —R_f-0.5.

Example 154—Preparation of Compound 107

The synthesis of Compound 107 followed the procedure of General Procedure 15 following:

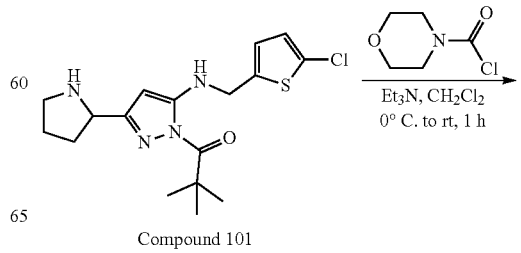

Compound 101

-continued

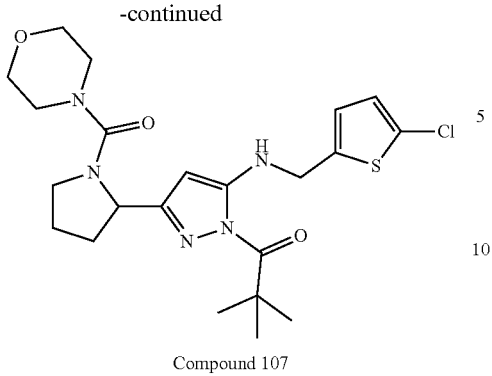

Compound 107

To a cooled solution (0° C.) of 1-(5-((5-chlorothiophen-2-yl)methylamino)-3-(pyrrolidin-2-yl)-1H-pyrazol-1-yl)-2,2-dimethylpropan-1-one (Compound 101, 320 mg, 0.87 mmol) in dry dichloromethane (10 mL) was added morpholine-4-carbonyl chloride (0.2 mL, 1.7 mmol) followed by triethylamine (TEA, 0.29 mL, 2.1 mmol). After stirring at room temperature for 1 hour, ice-cold water (10 mL) was added and then extracted into dichloromethane (2×15 mL). The combined organic layers were dried over sodium sulfate, filtered and concentrated under reduced pressure. The residue was purified by silica gel column chromatography (100-200 mesh), eluting with 50% EtOAc-hexanes, to give the desired product (170 mg, yield: 40%) as a light yellow semi-solid. A portion (160 mg, 85% by LCMS) was purified by preparative HPLC to obtain 1-(5-((5-chlorothiophen-2-yl)methylamino)-3-(1-(morpholine-4-carbonyl)pyrrolidin-2-yl)-1H-pyrazol-1-yl)-2,2-dimethylpropan-1-one (Compound 107, 45 mg) as a pale yellow gummy liquid; m/z 480.25 [M+H]+. $^1$H NMR (400 MHz, CDCl$_3$) δ 7.40 (br t, J=5.6 Hz, 1H, exchangeable), 6.79-6.71 (m, 2H), 5.17 (s, 1H), 5.04 (t, J=6.8 Hz, 1H), 4.34 (d, J=5.4 Hz, 2H), 3.71-3.58 (m, 4H), 3.57-3.41 (m, 2H), 3.36 (ddd, J=3.4, 6.4, 13.2 Hz, 2H), 3.20 (ddd, J=2.9, 6.4, 13.2 Hz, 2H), 2.32-2.19 (m, 1H), 2.06-1.79 (m, 3H), 1.45 (s, 9H) ppm; TLC System: 5% Methanol-dichloromethane. R$_f$-0.5.

Example 155—Preparation of Compound 108

The synthesis of Compound 108 followed the procedure of General Procedure 6d following:

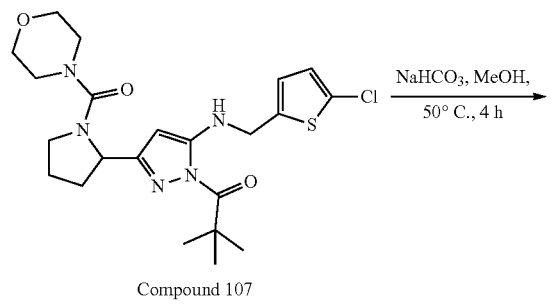

Compound 107

-continued

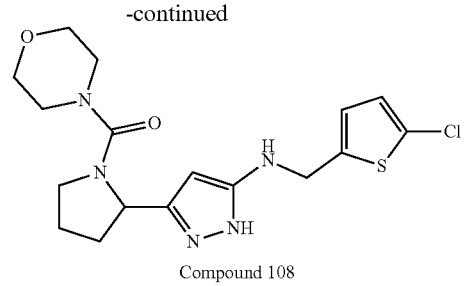

Compound 108

To a room temperature solution of 1-(5-((5-chlorothiophen-2-yl)methylamino)-3-(1-(morpholine-4-carbonyl)pyrrolidin-2-yl)-1H-pyrazol-1-yl)-2,2-dimethylpropan-1-one (Compound 107, 200 mg, 0.42 mmol) in methanol (10 mL) was added sodium bicarbonate (176 mg, 2.1 mmol), followed by heating of the mixture to 50° C. for 4 hours. The reaction mixture was cooled to room temperature, water (20 mL) was added and extracted into dichloromethane (3×20 mL). The residue was purified by silica gel column chromatography (100-200 mesh), eluting with 5-7% methanol in dichloromethane, to give the desired product (100 mg, yield: 65%) as a light yellow semi-solid. A portion (150 mg, 70% by LCMS) of material was further purified by preparative HPLC chromatography to give (2-(5-((5-chlorothiophen-2-yl)methylamino)-1H-pyrazol-3-yl)pyrrolidin-1-yl)(morpholino)methanone (Compound 108, 30 mg) as an off white solid. m/z 396.21 [M+H]+. $^1$H NMR (400 MHz, CDCl$_3$) 10.04 (br s, 1H, exchangeable), 6.83-6.56 (m, 2H), 5.47 (s, 1H), 5.05 (dd, J=6.8, 9.3 Hz, 1H), 4.42 (br d, J=4.9 Hz, 2H), 3.95 (br s, 1H, exchangeable), 3.76-3.51 (m, 4H), 3.50-3.31 (m, 4H), 3.20 (ddd, J=2.9, 6.4, 13.2 Hz, 2H), 2.51-2.15 (m, 1H), 2.10-1.95 (m, 2H), 1.93-1.73 (m, 1H) ppm; TLC System: 5% methanol in dichloromethane—R$_f$-0.3.

Example 156—Preparation of Compound 109

The synthesis of Compound 109 followed the procedure of General Procedure 5d following:

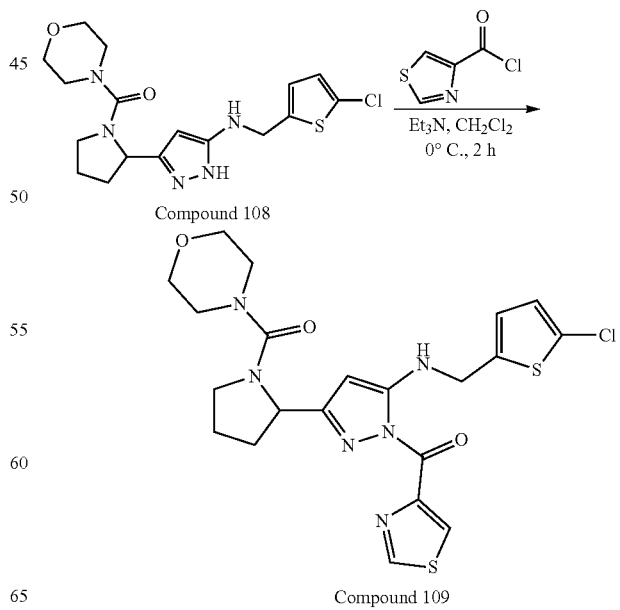

Compound 109

To a cooled (0° C.) solution of (2-(5-((5-chlorothiophen-2-yl)methylamino)-1H-pyrazol-3-yl)pyrrolidin-1-yl)(morpholino)methanone (Compound 108, 260 mg, 0.66 mmol) in dry dichloromethane (15 mL) was added 1,3-thiazole-4-carbonyl chloride (194 mg, 1.3 mmol) followed by triethylamine (TEA, 0.22 mL, 0.94 mmol) and the mixture was stirred at 0° C. for a further 2 hours. To this was then added ice-cold water (15 mL) and the mixture was washed with dichloromethane (2×15 mL). The combined organic layers were dried over sodium sulfate, filtered and concentrated under reduced pressure. The residue was purified by flash chromatography, eluting with 5-10% THF-EtOAc, to yield ((2-(5-((5-chlorothiophen-2-yl)methylamino)-1-(thiazole-4-carbonyl)-1H-pyrazol-3-yl)pyrrolidin-1-yl)(morpholino)methanone (Compound 109, 75 mg) as a pale yellow solid. m/z: 507.22 [M+H]+. 1H NMR (400 MHz, CDCl3) δ=9.18 (d, J=2.0 Hz, 1H), 8.87 (d, J=2.0 Hz, 1H), 7.64 (t, J=6 Hz, 1H, exchangeable), 6.95-6.65 (m, 2H), 5.27 (s, 1H), 5.07 (t, J=7.2 Hz, 1H), 4.46 (d, J=5.9 Hz, 2H), 3.73-3.46 (m, 6H), 3.38 (ddd, J=2.9, 6.4, 13.2 Hz, 2H), 3.20 (ddd, J=2.9, 6.4, 13.2 Hz, 2H), 2.43-2.25 (m, 1H), 2.10-1.79 (m, 3H) ppm; TLC System: 10% THF-EtOAc. $R_f$-0.5.

Example 157—Preparation of Intermediate 48

The synthesis of Intermediate 48 followed the procedure of General Procedure 25 following:

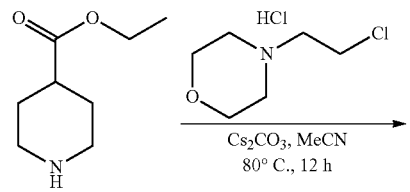

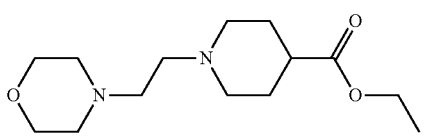

Intermediate 48

Ethyl piperidine-4-carboxylate (1.0 g, 6.4 mmol, 1.0 eq) was dissolved in anhydrous acetonitrile (25.0 mL), followed by the addition of cesium carbonate (4.15 g, 12.7 mmol, 2.0 eq) and the reaction mixture was stirred at room temperature for 30 minutes. Then, the reaction was cooled to 0° C. and 4-(2-chloroethyl)morpholine hydrochloride (1.42 g, 7.6 mmol, 1.2 eq) was added. The mixture was slowly brought to ambient temperature and stirred at 80° C. for 12 hours. After completion of the reaction, as monitored by TLC and LC-MS, the reaction mixture was diluted with cold water (10 mL) and extracted with ethyl acetate (3×20 mL). The organic layer was washed with water and concentrated under reduced pressure to obtain yellow residue, which was purified by column chromatography (silica; 100-200 mesh) eluting with 45% ethyl acetate in hexane to obtain ethyl 1-(2-morpholinoethyl)piperidine-4-carboxylate (Intermediate 48, 1.07 g, yield: 62%).

Example 158—Preparation of Intermediate 49

The synthesis of Intermediate 49 followed the procedure of General Procedure 2 following:

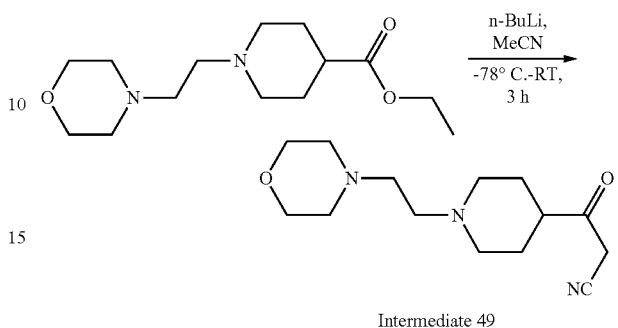

Intermediate 49

In an inert atmosphere with N2 gas flow, acetonitrile (1.14 g, 27.8 mmol, 1.5 eq) was added in tetrahydrofuran (30.0 mL) and cooled to −78° C. To this was added n-BuLi (2.5M in n-hexane, 1.77 mL, 27.8 mmol, 1.5 eq) dropwise over a period of 1 hour and the reaction was stirred for another 60 minutes. Ethyl-1-(2-morpholinoethyl)piperidine-4-carboxylate (Intermediate 48, 5.0 g, 18.5 mmol, 1.0 eq) was added in portions to the reaction mixture and stirred at −78° C. for 3 hours. The reaction was quenched with saturated ammonium chloride solution and product was extracted with ethyl acetate (3×20 mL). The organic layer was dried over anhydrous sodium sulfate and concentrated under reduced pressure to obtain a residue which was washed with ethyl acetate and used 'as is' for the next step ((3-(1-(2-morpholinoethyl)piperidin-4-yl)-3-oxopropanenitrile, Intermediate 49, 4.5 g, yield: 92%) m/z 266.03;

Example 159—Preparation of Compound 110

The synthesis of Compound 110 followed the procedure of General Procedure 3 following:

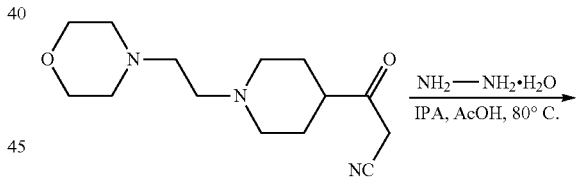

Intermediate 49

Compound 110

To a solution of 3-(1-(2-morpholinoethyl)piperidin-4-yl)-3-oxopropanenitrile (Intermediate 49, 4.5 g, 17.1 mmol, 1.0 eq) in isopropanol (50 mL) and acetic acid (1.02 g) was added hydrazine monohydrate (0.9 g, 18.2 mmol, 1.1 eq) dropwise, and the reaction was stirred at 80° C. for 5 hours. The reaction mixture was monitored by TLC and LC-MS, and after completion the reaction mixture was concentrated under reduced pressure to obtain a residue, which was purified by column chromatography using silica gel (100-200 mesh). The product was eluted with 10% methanol in dichloromethane to give 3-(1-(2-morpholinoethyl)piperidin-4-yl)-1H-pyrazol-5-amine (Compound 110, 4.0 g, yield: 83%) m/z 280.13 [M+1]+.

Example 160—Preparation of Compound 111

The synthesis of Compound 111 followed the procedure of General Procedure 4 following:

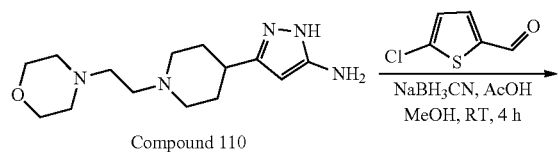

Compound 110

To a cooled solution (0° C.) of 3-(1-(2-morpholinoethyl) piperidin-4-yl)-1H-pyrazol-5-amine (Compound 110, 2.0 g, 7.2 mmol, 1.0 eq.) in MeOH (40.0 mL) and glacial acetic acid (0.431 g) was added 5-chlorothiophene-2-carbaldehyde (1.265 g, 8.6 mmol, 1.2 eq) dropwise. The reaction mixture was slowly brought to ambient temperature and then stirred for one day. After completion, as monitored by TLC and LC-MS, the mixture was cooled back to 0° C. and sodium cyanoborohydride (0.68 g, 10.7 mmol, 1.5 eq.) was added. The mixture was stirred at room temperature for 4 hours. The reaction mixture was concentrated under reduced pressure to obtain a yellow residue which was diluted with cold water (20 mL), extracted with ethyl acetate (3×20 mL) and purified by column chromatography (60-120 mesh) eluting with 6% MeOH in dichloromethane as mobile phase, to give N-((5-chlorothiophen-2-yl)methyl)-3-(1-(2-morpholinoethyl)piperidin-4-yl)-1H-pyrazol-5-amine (Compound 111, 0.60 g, yield: 20%); m/z 412.00 [M+2]+ 1H NMR (400 MHz, DMSO) δ 11.33 (s, 1H), 6.91 (d, J=2.9 Hz, 1H), 6.84 (s, 1H), 5.67 (s, 1H), 5.28 (s, 1H), 4.28 (d, J=5.4 Hz, 2H), 3.56 (s, 5H), 2.98 (s, 2H), 2.42 (d, J=24.9 Hz, 7H), 2.10 (s, 2H), 1.81 (s, 2H), 1.58 (s, 2H) ppm.

Example 161-Preparation of Compound 112

The synthesis of Compound 112 followed the procedure of General Procedure 5a following:

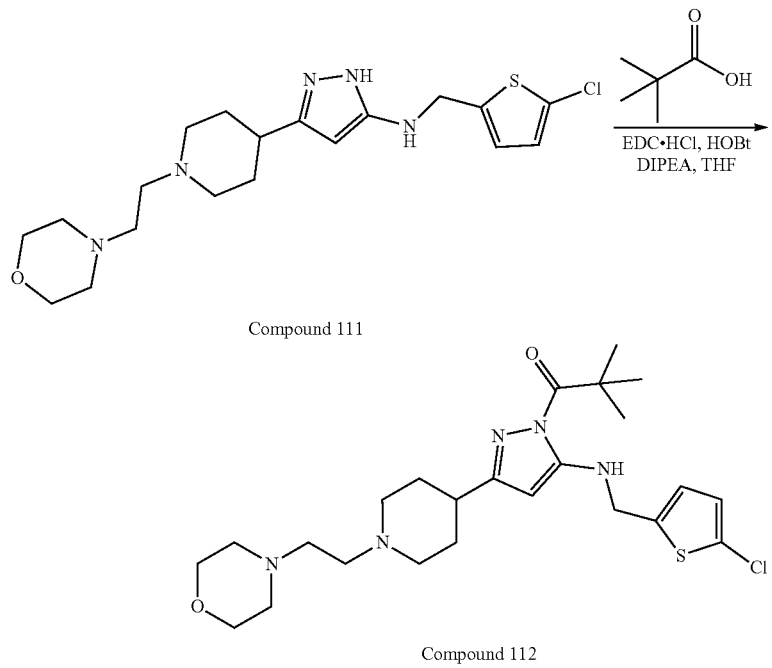

To a solution of pivalic acid (49.0 mg, 0.49 mmol, 1.0 eq) in THF (10.0 mL) was added DIEA (130 mg, 1.0 mmol, 2.0 eq), HOBt (66.0 mg, 0.49 mmol, 1.0 eq.) and EDCI-HCl (143 mg, 0.75 mmol, 1.5 eq.), and the reaction mixture stirred at room temperature for 30 minutes. Then, N-((5-chlorothiophen-2-yl)methyl)-3-(1-(2-morpholinoethyl)piperidin-4-yl)-1H-pyrazol-5-amine (Compound 111, 200 mg, 0.49 mmol, 1.0 eq.) was added to reaction mixture and allowed to stir room temperature for another 12 hours. After completion, the reaction mixture was concentrated, poured in ice-cold water and extracted with ethyl acetate (3×50 mL). The combined organic layers were concentrated under reduced pressure to give a residue which was purified by preparative HPLC using 100% MeCN and 0.1% formic acid in water to give 1-(5-(((5-chlorothiophen-2-yl)methyl) amino)-3-(1-(2-morpholinoethyl) piperidin-4-yl)-1H-pyrazol-1-yl)-2,2-dimethylpropan-1-one (Compound 112, 60.0 mg, yield: 25%) m/z 495.53 [M+1]+; 1H NMR (400 MHz, DMSO) δ 8.20 (s, 1H), 7.67 (t, J=6.2 Hz, 1H), 7.07-6.86 (m, 2H), 5.39 (s, 1H), 4.41 (d, J=6.0 Hz, 2H), 3.62-3.51 (m, 4H), 2.93 (d, J=11.7 Hz, 2H), 2.50-2.31 (m, 9H), 2.10 (dd, J=13.3, 7.1 Hz, 2H), 1.83 (d, J=12.3 Hz, 2H), 1.66-1.53 (m, 2H), 1.40 (s, 9H), 1.35 (s, 1H) ppm.

-continued

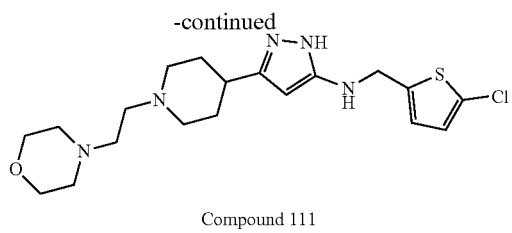

Compound 111

Example 162-Preparation of Compound 113

The synthesis of Compound 113 followed the procedure of General Procedure 5a following:

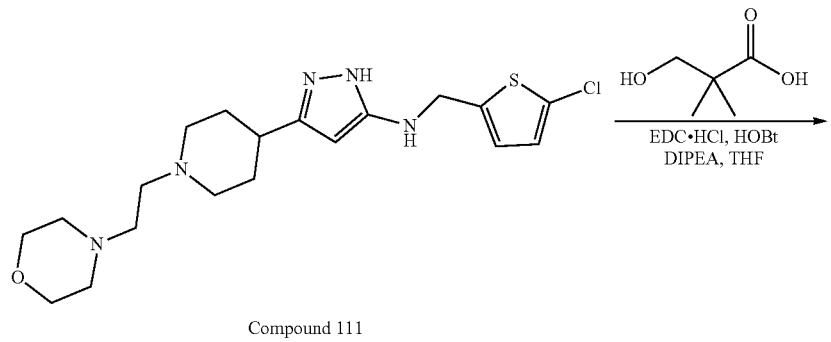

Compound 111

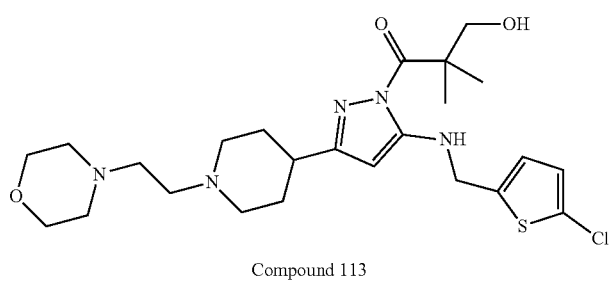

Compound 113

To a solution of hydroxypivalic acid (60.0 mg, 0.49 mmol, 1.0 eq.) in THF (10 mL) was added DIPEA (130.0 mg, 0.98 mmol, 2.0 eq.), HOBt (66.0 mg, 0.49 mmol, 1.0 eq.) and then EDCI-HCl (143.0 mg, 0.75 mmol, 1.5 eq.). The mixture was stirred at room temperature for 30 minutes. To it was added N-((5-chlorothiophen-2-yl)methyl)-3-(1-(2-morpholinoethyl)piperidin-4-yl)-1H-pyrazol-5-amine (Compound 111, 200.0 mg, 0.49 mmol, 1.0 eq.) and the mixture allowed to stir at room temperature for another 12 hours. After completion, the reaction mixture was concentrated and poured on to ice-cold water and extracted with ethyl acetate (3×50 mL). The combined organic layers were concentrated under reduced pressure to give a residue, which was purified by preparative HPLC using 100% MeCN and 0.1% formic acid in water to give 1-(5-(((5-chlorothiophen-2-yl)methyl)amino)-3-(1-(2-morpholinoethyl)piperidin-4-yl)-1H-pyrazol-1-yl)-3-hydroxy-2,2-dimethylpropan-1-one (Compound 113, 55.0 mg, yield: 22%) m/z 510.78 [M+1]+; 1H NMR (400 MHz, DMSO) δ 8.21 (s, 1H), 7.67 (t, J=6.2 Hz, 1H), 6.97 (q, J=3.8 Hz, 2H), 5.38 (s, 1H), 4.40 (d, J=6.2 Hz, 2H), 3.86 (s, 2H), 3.59-3.53 (m, 4H), 2.95 (d, J=11.2 Hz, 2H), 2.43 (d, J=6.7 Hz, 3H), 2.38 (s, 4H), 2.12 (t, J=11.1 Hz, 2H), 1.83 (d, J=11.8 Hz, 2H), 1.67-1.51 (m, 2H), 1.30 (s, 6H), 1.03 (s, 1H) ppm.

Example 163-Preparation of Intermediate 50

The synthesis of Intermediate 50 followed the procedure of General Procedure 5d following:

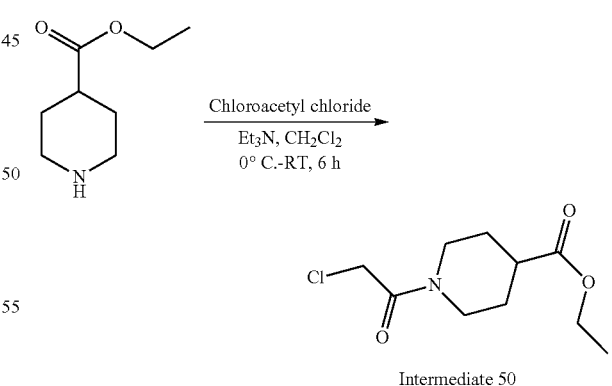

Intermediate 50

To a cooled solution (0° C.) of ethyl piperidine-4-carboxylate (0.2 g, 1.3 mmol, 1.0 eq) in dichloromethane (2.0 mL) was added triethylamine (TEA, 0.34 mL, 2.6 mmol, 2.0 eq.), followed by chloroacetyl chloride (0.13 mL, 1.5 mmol, 1.2 eq.) dropwise. It was then stirred at room temperature for 6 hours. The reaction was monitored by TLC and LCMS, and after completion the reaction mixture was diluted with cold water (10 mL), and product was extracted using dichloromethane (2×10 mL). The organic layers were dried over sodium sulfate and evaporated under vacuum to obtain a residue, was purified by column chromatography, eluting with 3% methanol in dichloromethane, to give ethyl 1-(2-chloroacetyl)piperidine-4-carboxylate (Intermediate 50, 210 mg, yield: 70%) m/z 234.21 [M+H]+ $^1$H NMR (400 MHz, CDCl3) δ 4.39-4.32 (m, 1H), 4.17 (q, J=7.1 Hz, 2H), 4.09 (d, J=1.4 Hz, 2H), 3.85 (d, J=13.6 Hz, 1H), 3.22 (tt, J=16.0, 7.9 Hz, 1H), 2.99-2.86 (m, 1H), 2.58 (tt, J=10.5, 4.0 Hz, 1H), 2.05-1.94 (m, 1H), 1.87-1.76 (m, 1H), 1.69 (dt, J=11.0, 5.3 Hz, 2H), 1.28 (t, J=7.1 Hz, 3H) ppm.

Example 164-Preparation of Intermediate 51

The synthesis of Intermediate 51 followed the procedure of General Procedure 25 following:

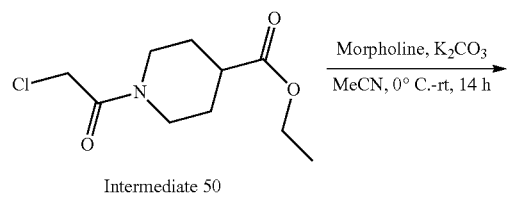

Intermediate 50

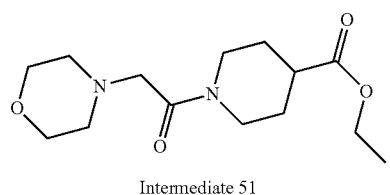

Intermediate 51

To a solution of morpholine (0.08 mL, 1.0 mmol, 1.2 eq.) in acetonitrile (2.0 mL) was added potassium carbonate (0.355 g, 2.4 mmol, 3.0 eq.) and stirred at room temperature for 10-15 minutes. To the mixture was added a solution of ethyl-1-(2-chloroacetyl)piperidine-4-carboxylate (Intermediate 50, 0.2 g, 0.8 mmol, 1.0 eq.) in acetonitrile (2.0 mL) and then stirred at room temperature for 14 hours. After completion of reaction, as monitored on TLC and LCMS, the reaction mixture was diluted with ethyl acetate (20 mL) and washed with water (50 mL). The organic layers were dried over sodium sulfate and evaporated under vacuum to obtain a crude product. This was purified by column chromatography through silica (60-120 Mesh), eluting with 4% methanol in dichloromethane to give ethyl-1-(2-morpholinoacetyl)piperidine-4-carboxylate (Intermediate 51, 0.141 g, yield: 69%) m/z 285.42 [M+H]+ $^1$H NMR (400 MHz, DMSO) δ 4.19 (d, J=13.1 Hz, 1H), 4.11-4.02 (m, 2H), 3.97 (d, J=13.7 Hz, 1H), 3.60-3.50 (m, 4H), 3.21 (d, J=13.3 Hz, 1H), 3.07 (dd, J=21.2, 12.3 Hz, 2H), 2.76-2.65 (m, 1H), 2.59 (tt, J=11.0, 3.9 Hz, 1H), 2.41-2.33 (m, 4H), 1.83 (t, J=12.5 Hz, 2H), 1.54 (ddd, J=24.5, 11.5, 4.0 Hz, 1H), 1.35 (dt, J=11.3, 7.5 Hz, 1H), 1.22-1.15 (m, 3H) ppm.

Example 165-Preparation of Intermediate 52

The synthesis of Intermediate 52 followed the procedure of General Procedure 2 following:

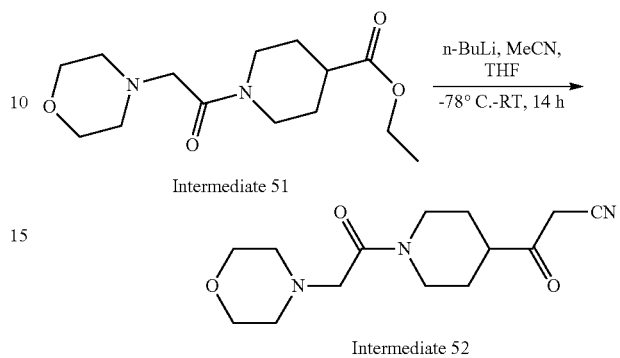

Intermediate 51

Intermediate 52

In an inert atmosphere with N$_2$ gas flow, acetonitrile (0.12 mL, 2.9 mmol, 1.7 eq) was added to THF (7.5 mL) and cooled to −78° C. n-BuLi (2.5M in n-hexane, 1.2 mL, 2.9 mmol, 1.7 eq) was added dropwise over a period of 20 minutes, and the reaction was stirred for another 60 minutes. Ethyl-1-(2-morpholinoacetyl)piperidine-4-carboxylate (Intermediate 51, 0.5 g, 1.7 mmol, 1.0 eq) was added in one portion to the reaction mixture and the temperature maintained at −78° C. for 1 hour, and then stirred at room temperature for 14 hours. The reaction was quenched with saturated ammonium chloride solution, and product was extracted with ethyl acetate (3×20 mL). The organic layer was dried over anhydrous sodium sulfate and concentrated under reduced pressure to obtain a crude product which was washed with ethyl acetate and used for the next step. 3-(1-(2-morpholinoacetyl) piperidin-4-yl)-3-oxopropanenitrile (Intermediate 52, 0.294 g, yield: 60%) m/z 280.44 [M+H]$^+$ 1H NMR (400 MHz, DMSO) δ 4.39-4.25 (m, 1H), 4.07-3.97 (m, 2H), 3.60-3.52 (m, 4H), 3.20-3.12 (m, 1H), 3.02 (d, J=13.4 Hz, 2H), 2.91-2.83 (m, 1H), 2.37 (s, 4H), 1.99 (s, 2H), 1.51 (d, J=15.6 Hz, 1H), 1.45-1.36 (m, 1H), 1.17 (t, J=7.1 Hz, 2H) ppm.

Example 166-Preparation of Compound 114

The synthesis of Compound 114 followed the procedure of General Procedure 3 following:

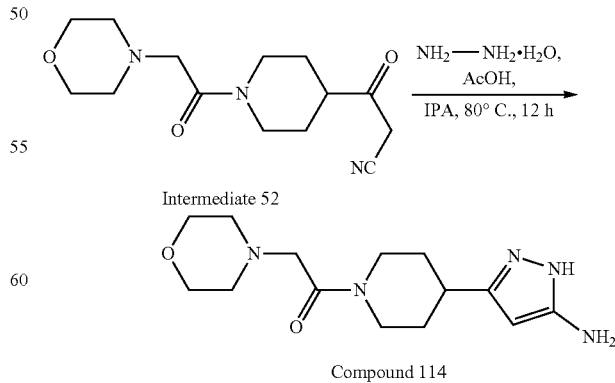

Intermediate 52

Compound 114

To a solution of 3-(1-(2-morpholinoacetyl)piperidin-4-yl)-3-oxopropanenitrile (Intermediate 52, 0.29 g, 1 mmol, 1.0 eq) in isopropanol (9.0 mL) and acetic acid (0.6 mL) was added hydrazine monohydrate (0.5 mL, 1.0 mmol, 1.0 eq) dropwise, and the reaction was stirred at 80° C. for 12 hours. The reaction mixture was monitored by TLC and LC-MS, and after completion the mixture was concentrated under reduced pressure to obtain a crude residue. This was purified by column chromatography using silica gel (100-200 mesh), eluting with 8% methanol in dichloromethane to give 1-(4-(5-amino-1H-pyrazol-3-yl)piperidin-1-yl)-2-morpholinoethan-1-one (Compound 114, 0.164 g, yield: 54%) m/z 294.03 [M+1]$^+$ $^1$H NMR (400 MHz, DMSO) δ 5.17 (s, 1H), 4.34 (d, J=13.1 Hz, 1H), 4.10-4.01 (m, 1H), 3.56 (s, 4H), 3.30-3.22 (m, 1H), 3.05 (t, J=14.3 Hz, 2H), 2.73-2.54 (m, 2H), 2.51 (s, 2H), 2.36 (d, J=19.7 Hz, 3H), 1.89 (d, J=15.2 Hz, 2H), 1.84 (t, J=13.0 Hz, 2H), 1.50 (dd, J=22.8, 10.4 Hz, 1H), 1.37-1.19 (m, 1H) ppm.

Example 167-Preparation of Compound 115

The synthesis of Compound 115 followed the procedure of General Procedure 4 following:

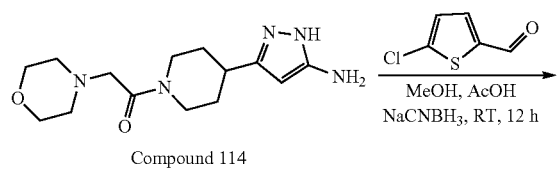

Compound 114

2-carbaldehyde (0.75 g, 5.0 mmol, 1.0 eq) dropwise. The reaction mixture was stirred at room temperature for 16 hours. After completion, as monitored by TLC and LC-MS, the mixture was cooled back to 0° C. and then sodium cyanoborohydride (0.63 g, 10.0 mmol, 2.0 eq) was added and stirred at room temperature for 14 hours. The reaction mixture was slowly concentrated under reduced pressure to obtain a yellow residue, and then diluted with ethyl acetate (100 mL) and then washed with water (25 mL). After drying with sodium sulfate, and filtration, the organic phase was concentrated under reduced pressure to give a residue which was purified by column chromatography (60-120 mesh), eluting with 5% methanol in dichloromethane to give 1-(4-(5-(((5-chlorothiophen-2-yl)methyl)amino)-1H-pyrazol-3-yl)piperidin-1-yl)-2-morpholinoethan-1-one (Compound 115, 0.75 g, yield: 60%); m/z 424.67 [M+1]$^+$ $^1$H NMR (400 MHz, DMSO) δ 11.41 (s, 1H), 6.88 (dd, J=29.5, 3.7 Hz, 2H), 5.69 (t, J=6.1 Hz, 1H), 5.28 (s, 1H), 4.32 (dd, J=27.0, 9.8 Hz, 2H), 4.09 (dd, J=21.6, 9.2 Hz, 1H), 3.65-3.52 (m, 4H), 3.28-3.10 (m, 1H), 3.04 (d, J=13.2 Hz, 2H), 2.76 (d, J=11.6 Hz, 1H), 2.62 (dd, J=25.3, 12.3 Hz, 2H), 2.36 (d, J=22.6 Hz, 4H), 1.87 (dd, J=23.9, 12.8 Hz, 2H), 1.51 (dd, J=21.4, 12.1 Hz, 1H), 1.40-1.24 (m, 1H) ppm.

Example 168-Preparation of Compound 116

The synthesis of Compound 116 followed the procedure of General Procedure 5a following:

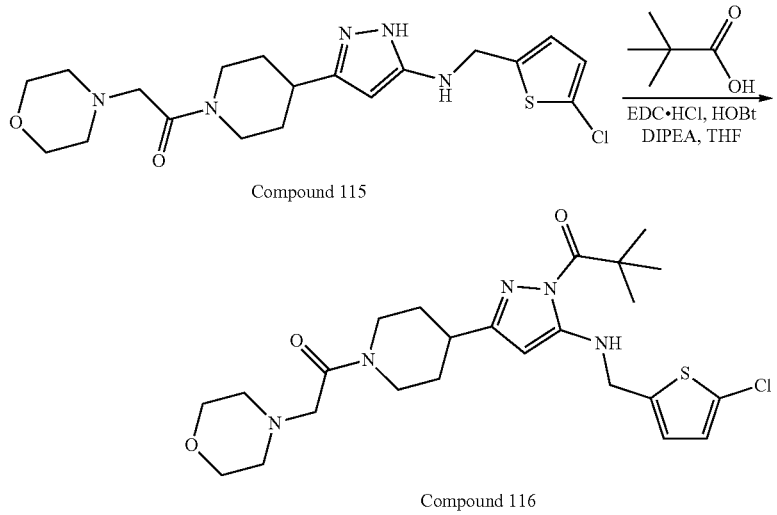

Compound 115

Compound 116

-continued

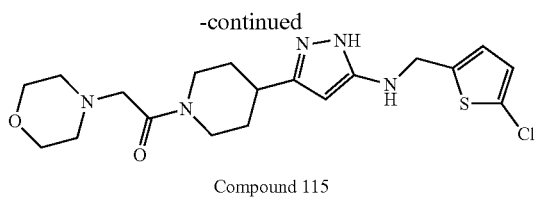

Compound 115

To a cooled solution (0° C.) of 1-(4-(5-amino-1H-pyrazol-3-yl)piperidin-1-yl)-2-morpholinoethan-1-one (Compound 114, 1.5 g, 5.0 mmol, 1.0 eq) in methanol (30 mL) was added glacial acetic acid (0.33 mL) and then 5-chlorothiophene- To a solution of pivalic acid (0.10 g, 1.0 mmol, 1.1 eq.) in THF (2.5 mL) was added DIEA (0.21 mL, 1.2 mmol, 1.5 eq), HOBt (0.021 g, 0.16 mmol, 0.2 eq) and then EDCI.HCl (0.23 g, 1.2 mmol, 1.5 eq), and the mixture stirred at room temperature for 30 minutes. Then, 1-(4-(5-(((5-chlorothiophen-2-yl)methyl)amino)-1H-pyrazol-3-yl)piperidin-1-yl)-2-morpholinoethan-1-one (Compound 115, 0.35 g, 0.8 mmol, 1.0 eq) was added to the mixture and allowed to stir at room temperature for 14 hours. After completion, the reaction mixture was concentrated and poured in to ice-cold water (5.0 mL) and extracted with ethyl acetate (3×10 mL). The combined organic layers were concentrated under reduced pressure to give a residue which was purified by column chromatography (100-200 mesh), eluting with 50% ethyl acetate in hexane, to give 1-(5-(((5-chlorothiophen-2-yl)methyl)amino)-3-(1-(2-morpholinoacetyl)piperidin-4-yl)-1H-pyrazol-1-yl)-2,2-dimethylpropan-1-one (Compound 116, 46 mg, yield: 11%) m/z 509.03 [M+H]$^+$; $^1$H NMR (400 MHz, DMSO) δ 7.69 (t, J=6.2 Hz, 1H), 6.96 (t, J=3.6 Hz, 2H), 5.39 (s, 1H), 4.41 (d, J=6.4 Hz, 2H), 4.29 (d, J=14.3 Hz, 1H), 4.03 (d, J=12.2 Hz, 1H), 3.56 (s, 4H), 3.25 (d, J=13.2 Hz, 1H), 3.10 (d, J=11.6 Hz, 1H), 3.04 (d, J=13.3 Hz, 1H), 2.70 (d, J=22.7 Hz, 3H), 2.39 (s, 3H), 1.88 (s, 2H), 1.61 (s, 2H), 1.40 (s, 9H) ppm.

Example 169-Preparation of Compound 117

The synthesis of Compound 117 followed the procedure of General Procedure 5a following:

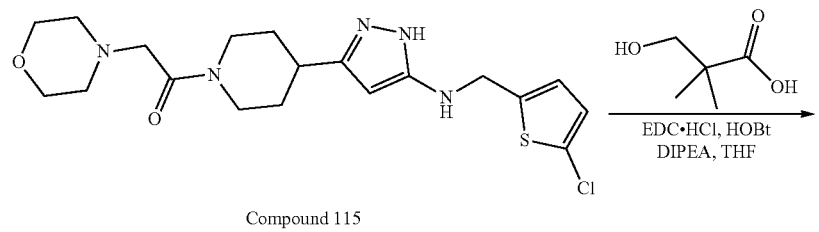

Compound 115

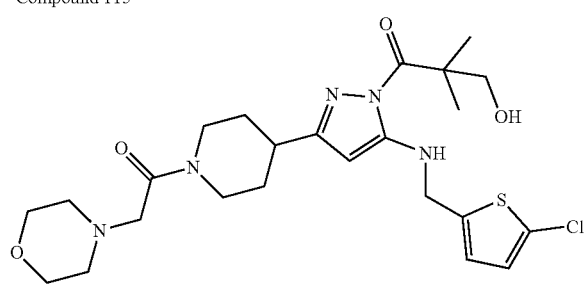

Compound 117

To a solution of hydroxypivalic acid (0.1 g, 0.9 mmol, 1.0 eq) in THF (6.0 mL) was added DIEA (0.18 mL, 1.0 mmol, 1.5 eq), HOBt (0.018 g, 0.14 mmol, 0.2 eq) and then EDCI.HCl (0.13 g, 1.0 mmol, 1.5 eq), and the mixture stirred at room temperature for 30 minutes. To the mixture was then added 1-(4-(5-(((5-chlorothiophen-2-yl)methyl)amino)-1H-pyrazol-3-yl)piperidin-1-yl)-2-morpholinoethan-1-one (Compound 115, 0.30 g, 0.7 mmol, 1.0 eq) and the reaction 5 mixture was stirred at room temperature for 16 hours. After completion, the reaction mixture was concentrated and poured into ice-cold water (5.0 mL) and extracted with ethyl acetate (3×10 mL). The combined organic layers were concentrated under reduced pressure to give a residue, which was purified by preparative HPLC using 100% MeCN and water as mobile phase, to give 1-(5-(((5-chlorothiophen-2-yl)methyl)amino)-3-(1-(2-morpholinoacetyl)piperidin-4-yl)-1H-pyrazol-1-yl)-3-hydroxy-2,2-dimethylpropan-1-one (Compound 117, 38.0 mg, yield: 10%) m/z 524.83 [M+H]+; 1HNMR (400 MHz, DMSO) δ 7.69 (t, J=6.0 Hz, 1H), 6.96 (q, J=3.7 Hz, 2H), 5.39 (s, 1H), 4.83 (t, J=5.4 Hz, 1H), 4.41 (d, J=6.1 Hz, 2H), 4.28 (d, J=12.3 Hz, 1H), 4.03 (d, J=13.0 Hz, 1H), 3.86 (d, J=5.5 Hz, 2H), 3.56 (s, 4H), 3.24 (d, J=13.3 Hz, 1H), 3.18-3.01 (m, 2H), 2.73 (dd, J=23.5, 12.4 Hz, 2H), 2.36 (d, J=22.9 Hz, 4H), 1.87 (s, 2H), 1.60 (d, J=12.5 Hz, 1H), 1.37 (d, J=11.6 Hz, 1H), 1.31 (s, 6H) ppm.

Example 169a—Preparation of Compound 118

The synthesis of Compound 118 followed the procedure of General Procedure 15 following:

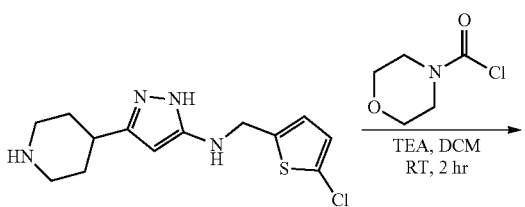

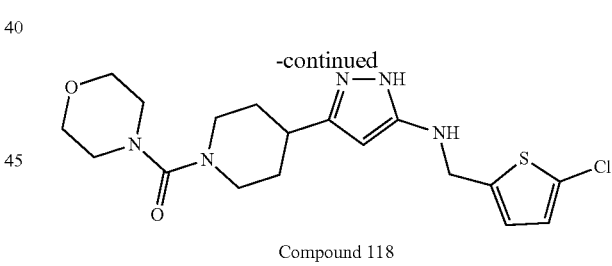

Compound 118

To a cooled solution (0° C.) of N-((5-chlorothiophen-2-yl)methyl)-3-(piperidin-4-yl)-1H-pyrazol-5-amine (0.5 g, 1.7 mmol, 1.0 eq) in dichloromethane (10 mL) was added triethylamine (TEA, 0.26 g, 2.6 mmol, 1.5 eq) and stirred for 10-15 minutes. Then, morpholine-4-carbonyl chloride (0.25 g, 1.7 mmol, 1.0 eq) was added and stirred at room temperature for 2 hours. The reaction was monitored by TLC and LC-MS. After completion, solvent was evaporated to give a residue which was purified by column chromatography using silica gel (60-120 mesh) eluting with 5% methanol in dichloromethane to give (4-(5-(((5-chlorothiophen-2-yl)methyl)amino)-1H-pyrazol-3-yl)piperidin-1-yl)(morpholino)methanone (Compound 118, 0.24 g, yield: 34%); m/z 410.37 [M+1]+ $^1$H NMR (400 MHz, DMSO) δ 11.34 (s, 1H), 6.91 (d, J=3.7 Hz, 1H), 6.84 (d, J=3.3 Hz, 1H), 5.66 (s, 1H), 5.29 (s, 1H), 4.28 (d, J=6.1 Hz, 2H), 3.62 (d, J=13.1 Hz, 2H), 3.57 (dd, J=13.4, 9.1 Hz, 4H), 3.18-3.01 (m, 4H), 2.80 (t, J=11.7 Hz, 2H), 2.66 (s, 1H), 1.81 (d, J=11.0 Hz, 2H), 1.53-1.32 (m, 2H) ppm.

Example 170-Preparation of Compound 119

The synthesis of Compound 119 followed the procedure of General Procedure 5c following:

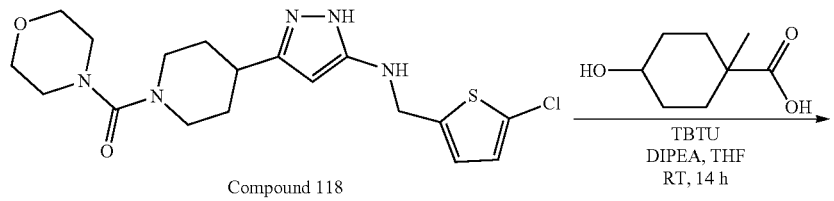

Compound 118

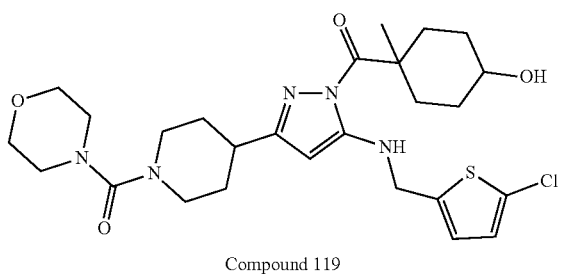

Compound 119

To a cooled solution (0° C.) of 4-hydroxy-1-methylcyclohexane-1-carboxylic acid (0.15 g, 0.95 mmol, 1.3 eq) in THF (5.0 mL) was added TBTU (0.35 g, 1.1 mmol, 1.5 eq) and DIEA (0.38 mL, 2.2 mmol, 3.0 eq) under nitrogen. The reaction mixture was stirred for 30 minutes, and to it was added (4-(5-(((5-chlorothiophen-2-yl)methyl)amino)-1-(4-hydroxy-1-methylcyclohexane-1-carbonyl)-1H-pyrazol-3-yl)piperidin-1-yl)(morpholino)methanone (Compound 118, 0.298 g, 0.73 mmol, 1.0 eq) and then the mixture was stirred at room temperature for 14 hours. The reaction was monitored by LC-MS, and after completion the mixture was concentrated to give a residue, which was purified by preparative HPLC using 0.1% formic acid in water-acetonitrile as mobile phase to give (4-(5-(((5-chlorothiophen-2-yl)methyl)amino)-1-(4-hydroxy-1-methyl cyclohexane-1-carbonyl)-1H-pyrazol-3-yl)piperidin-1-yl)(morpholino) methanone (Compound 119, 0.053 g, yield: 10%); m/z 550.68 [M+1]+ $^1$H NMR (400 MHz, DMSO) δ 7.68 (s, 1H), 6.95 (s, 2H), 5.39 (s, 1H), 4.40 (t, 1H), 4.40 (d, 2H), 3.52 (d, J=29.7 Hz, 6H), 3.11 (m, 4H), 2.84 (m, 2H), 2.58 (m, 1H), 2.53 (m, 3H), 1.98 (d, J=36.1 Hz, 2H), 1.84 (m, 3H), 1.54 (d, J=30.8 Hz, 2H), 1.42 (m, 6H) ppm.

Example 171-Preparation of Compound 120

The synthesis of Compound 120 followed the procedure of General Procedure 25 following:

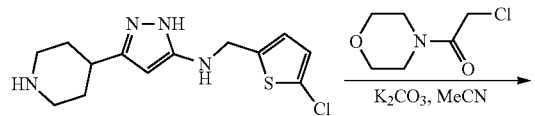

-continued

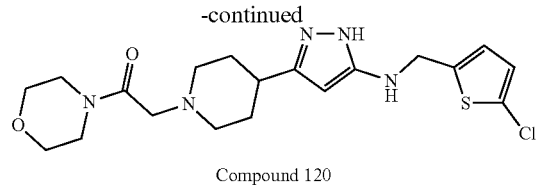

Compound 120

To a cooled solution (0° C.) of N-((5-chlorothiophen-2-yl)methyl)-3-(piperidin-4-yl)-1H-pyrazol-5-amine (0.1 g, 2.4 mmol, 1 eq) in acetonitrile (10 mL) was added 2-chloro-1-morpholinoethan-1-one (1.23 mL, 2.4 mmol, 1.0 eq) and then potassium carbonate (0.102 g, 7.2 mmol, 3.0 eq.). The reaction mixture was stirred at room temperature for 12 hours. The progress of reaction was monitored by TLC. The reaction mixture was diluted with water (10 mL), extracted with dichloromethane (2×10 mL), and the combined organic phases were dried over anhydrous sodium sulfate and concentrated to give crude product. This residue was purified by Combi-flash chromatography, eluting with 6% methanol in dichloromethane, to give 2-(4-(5-(((5-chlorothiophen-2-yl)methyl)amino)-1H-pyrazol-3-yl)piperidine-1-yl)-1-morpholinoethan-1-one (Compound 120, 0.60 g, yield: 57%) m/z 424.42[M+1]+, $^1$H NMR (400 MHz, DMSO) δ 11.29 (s, 1H), 6.91 (d, J=3.7 Hz, 1H), 6.84 (d, J=3.6 Hz, 1H), 5.62 (s, 1H), 5.28 (s, 1H), 4.29 (d, J=6.2 Hz, 2H), 3.50-3.56 (m, 4H), 3.40-3.43 (m, 4H), 3.14 (s, 2H), 2.84 (d, J=11.3 Hz, 2H), 2.44 (s, 1H), 2.07 (t, J=10.7 Hz, 2H), 1.81 (d, J=11.3 Hz, 2H), 1.53 (dd, J=21.3, 11.9 Hz, 2H) ppm;

Example 172-Preparation of Compound 121

The synthesis of Compound 121 followed the procedure of General Procedure 5d following:

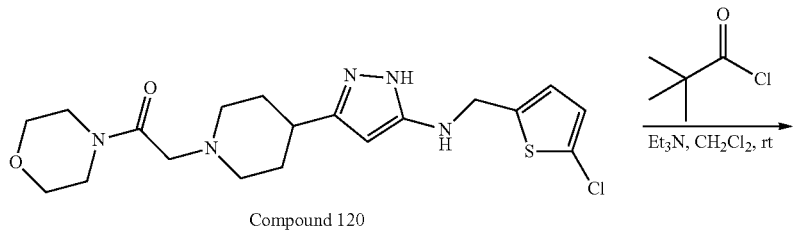

Compound 120

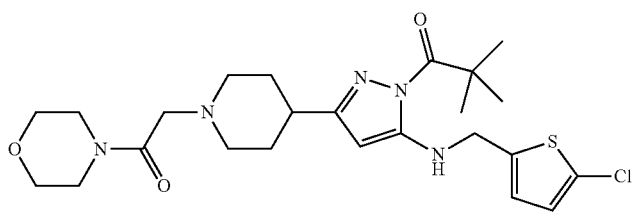

Compound 121

To a cooled solution (0° C.) of 2-(4-(5-(((5-chlorothiophen-2-yl) methyl) amino)-1H-pyrazol-3-yl) piperidin-1-yl)-1-morpholinoethan-1-one (Compound 120, 0.15 g, 3.5 mmol, 1.0 eq) in dichloromethane (10 mL) was added triethylamine (TEA, 0.11 g, 11 mmol, 3 eq) followed by pivaloyl chloride (0.042 g, 3.5 mmol, 1 eq). The reaction mixture was stirred at room temperature for 14 hours. After completion, the mixture was concentrated under reduced pressure to give a crude residue. This was purified by column chromatography, eluting with 60% ethyl acetate in hexane, to give 1-(5-(((5-chlorothiophen-2-yl)methyl)amino)-3-(1-(2-morpholino-2-oxoethyl) piperidin-4-yl)-1H-pyrazol-1-yl)-2,2-dimethyl-propan-1-one (Compound 121, 0.15 g, yield: 83%) m/z 508.48[M+1]+, $^1$H NMR (400 MHz, DMSO) δ 7.68 (d, J=6.3 Hz, 1H), 6.96 (d, J=3.8 Hz, 2H), 5.39 (s, 1H), 4.41 (d, J=5.9 Hz, 2H), 3.50-3.55 (m, 5H), 3.41 (d, J=11.7 Hz, 2H), 3.13 (s, 2H), 2.83 (d, J=10.6 Hz, 2H), 2.38 (d, J=34.4 Hz, 1H), 2.09 (t, J=10.9 Hz, 2H), 1.84 (d, J=11.3 Hz, 2H), 1.56 (d, J=9.2 Hz, 2H), 1.40 (s, 9H), 1.11 (s, 1H) ppm.

Example 173-Preparation of Compound 122

The synthesis of Compound 122 followed the procedure of General Procedure 5c following:

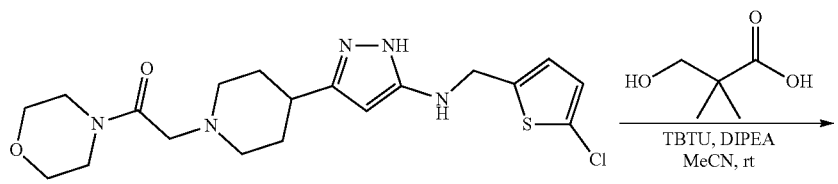

Compound 120

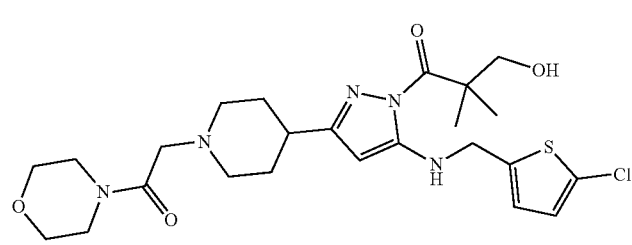

Compound 122

To a solution of hydroxypivalic acid (92 mg, 0.78 mmol, 1.0 eq) in acetonitrile (10 mL) was added DIEA (301 mg, 2.3 mmol, 3.0 eq) and then TBTU (375 mg, 0.78 mmol, 1.0 eq), and then the mixture stirred at room temperature for 30 minutes. To this was added 2-(4-(5-(((5-chlorothiophen-2-yl)methyl)amino)-1H-pyrazol-3-yl)piperidin-1-yl)-1-morpholinoethan-1-one (Compound 120, 0.33 g, 0.78 mmol, 1.0 eq) and the reaction was stirred at room temperature for 12 hours. After completion, the mixture was concentrated under reduced pressure to give a crude product, which was purified by preparative HPLC using 100% MeCN and 0.1% formic acid in water, to give 1-(5-(((5-chlorothiophen-2-yl)methyl)amino)-3-(1-(2-morpholino-2-oxoethyl) piperidin-4-yl)-1H-pyrazol-1-yl)-3-hydroxy-2,2-dimethylpropan-1-one (Compound 122, 50 mg, yield: 12%) m/z 524.63 [M+1]$^+$; $^1$H NMR (400 MHz, DMSO) δ 7.74 (d, J=6.1 Hz, 1H), 6.97 (s, 2H), 5.39 (s, 1H), 4.85 (t, J=5.4 Hz, 1H), 4.42 (d, J=6.2 Hz, 2H), 4.30-4.06 (m, 1H), 3.87 (d, J=5.4 Hz, 2H), 3.66-3.54 (m, 4H), 3.50 (s, 2H), 3.38 (d, J=17.7 Hz, 2H), 3.03 (s, 2H), 2.68 (s, 2H), 2.38-1.74 (m, 6H), 1.32 (s, 6H) ppm.

Example 174-Preparation of Compound 123

The synthesis of Compound 123 followed the procedure of General Procedure 22 following:

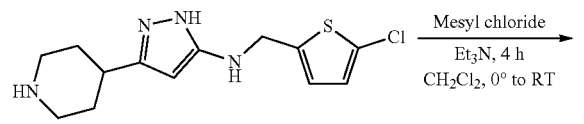

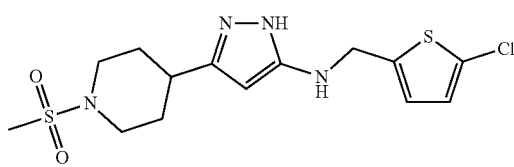

Compound 123

To a cooled solution (0° C.) of N-((5-chlorothiophen-2-yl)methyl)-3-(piperidin-4-yl)-1H-pyrazol-5-amine (0.1 g, 0.24 mmol, 1.0 eq) in dichloromethane (4 mL) was added triethylamine (TEA, 0.1 g, 0.98 mmol, 4.0 eq). After stirring for 15 minutes, methanesulfonyl chloride (MsCl, 0.025 g, 0.22 mmol, 0.9 eq) was added. The reaction mixture was stirred for 4 hours at room temperature and monitored by TLC and LC-MS. After completion of reaction, the reaction mixture was poured into water (10 mL) and extracted with ethyl acetate (2×10 mL). The combined organic phases were washed with water, brine, and dried over sodium sulfate to give a residue, which was purified by preparative HPLC using water-acetonitrile as mobile phase to give N-((5-chlorothiophen-2-yl)methyl)-3-(1-(methylsulfonyl)piperidin-4-yl)-1H-pyrazol-5-amine (Compound 123, 0.05 g, yield: 40%) m/z 375.31 [M+1]+ 1347 $^1$H NMR (400 MHz, DMSO) δ 11.39 (s, 1H), 6.97-6.81 (m, 2H), 5.73 (d, J=32.5 Hz, 1H), 5.32 (s, 1H), 4.29 (d, J=6.0 Hz, 2H), 3.57 (d, J=12.6 Hz, 2H), 2.87 (s, 3H), 2.78 (t, J=11.0 Hz, 2H), 2.61 (s, 1H), 1.93 (d, J=13.0 Hz, 2H), 1.66-1.52 (m, 2H) ppm.

Example 175-Preparation of Compound 124

The synthesis of Compound 124 followed the procedure of General Procedure 5a following:

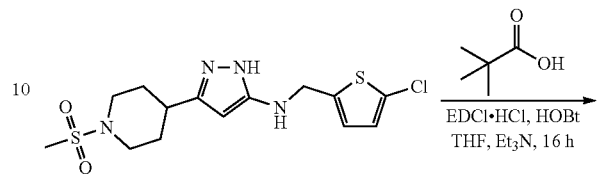

Compound 123

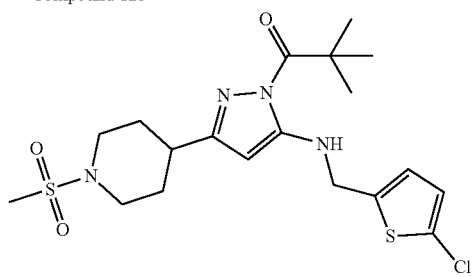

Compound 124

To a cooled solution (0° C.) of pivalic acid (0.098 g, 0.96 mmol, 1.5 eq) in THF (8 mL) was EDCI.HCl (0.18 g, 0.96 mmol, 1.5 eq) and then triethylamine (TEA, 0.194 g, 1.92 mmol, 3.0 eq.). The reaction mixture was stirred for 30 minutes, then to it was added HOBt (0.017 g, 0.13 mmol, 0.2 eq) and N-((5-chlorothiophen-2-yl)methyl)-3-(1-(methylsulfonyl)piperidin-4-yl)-1H-pyrazol-5-amine (Compound 123, 0.24 g, 0.64 mmol, 1 eq). The reaction mixture was stirred at room temperature overnight. After completion (as monitored by LC-MS), the reaction mixture was poured into water (15 mL) and extracted with ethyl acetate (2×15 mL). The combined organic phases were washed with water, brine, and dried over sodium sulfate to give a crude compound. This was purified by preparative HPLC using water-acetonitrile as the mobile phase to give 1-(5-(((5-chlorothiophen-2-yl)methyl)amino)-3-(1-(methylsulfonyl)piperidin-4-yl)-1H-pyrazol-1-yl)-2,2-dimethylpropan-1-one (Compound 124, 0.035 g, yield: 11%) m/z 459.43[M+]+ $^1$H NMR (400 MHz, DMSO) δ 7.70 (t, J=6.2 Hz, 1H), 7.04-6.92 (m, 2H), 5.46 (d, J=13.5 Hz, 1H), 4.42 (d, J=6.1 Hz, 2H), 3.57 (d, J=11.8 Hz, 2H), 2.99-2.73 (m, 5H), 2.60 (dd, J=24.9, 13.6 Hz, 1H), 1.98 (d, J=10.9 Hz, 2H), 1.62 (td, J=15.1, 3.7 Hz, 2H), 1.51-1.35 (m, 9H) ppm.

Example 176-Preparation of Compound 125

The synthesis of Compound 125 followed the procedure of General Procedure 5b following:

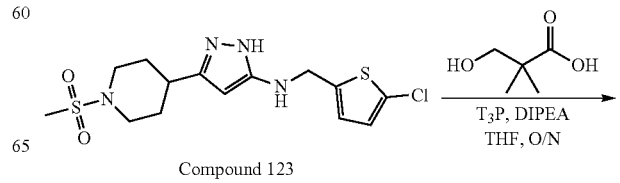

Compound 123

-continued

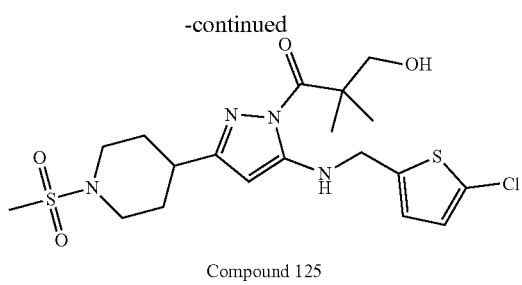

Compound 125

To a solution of hydroxypivalic acid (0.119 g, 1.1 mmol, 1.5 eq.) in THF (8 mL) was added propylphosphonic anhydride (T₃P in 50% solution in ethyl acetate, 0.318 g, 1.0 mmol, 1.5 eq), DIEA (0.20 g, 2 mmol, 3 eq) and then N-((5-chlorothiophen-2-yl)methyl)-3-(1-(methylsulfonyl)piperidin-4-yl)-1H-pyrazol-5-amine (Compound 123, 0.25 g, 0.66 mmol, 1 eq). The reaction mixture was stirred at room temperature overnight. After reaction completion (as monitored by LC-MS), the mixture was poured into water (20 mL) and extracted with ethyl acetate (2×30 mL). The combined organic phases were washed with water, brine, and dried over sodium sulfate to give a residue, which was purified by preparative HPLC using water-acetonitrile as mobile phase, to give 1-(5-(((5-chlorothiophen-2-yl)methyl)amino)-3-(1-(methylsulfonyl)piperidin-4-yl)-1H-pyrazol-1-yl)-3-hydroxy-2,2-dimethylpropan-1-one Compound 125, 0.051 g, yield: 16%) m/z 475.43 [M+]+ ¹H NMR (400 MHz, DMSO) δ 7.70 (d, J=6.0 Hz, 1H), 6.97 (t, J=4.0 Hz, 2H), 5.43 (s, 1H), 4.83 (s, 1H), 4.41 (d, J=6.4 Hz, 2H), 3.87 (d, J=5.1 Hz, 2H), 3.56 (d, J=11.2 Hz, 2H), 3.12-2.74 (m, 5H), 2.64 (d, J=27.0 Hz, 2H), 1.97 (d, J=12.0 Hz, 2H), 1.62 (d, J=9.3 Hz, 2H), 1.27 (d, J=28.3 Hz, 6H) ppm.

Example 177-Preparation of Compound 126

The synthesis of Compound 126 followed the procedure of General Procedure 22 following:

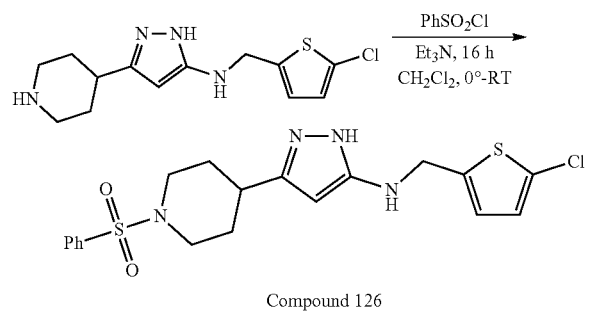

Compound 126

To a cooled solution (0° C.) of N-((5-chlorothiophen-2-yl)methyl)-3-(piperidin-4-yl)-1H-pyrazol-5-amine (0.1 g, 0.24 mmol, 1.0 eq) in dichloromethane (4 mL) was added triethylamine (TEA, 0.1 g, 1.0 mmol, 4.0 eq). After stirring for 15 minutes, benzenesulphonyl chloride (0.039 g, 0.22 mmol, 0.9 eq) was added. The reaction mixture was stirred at room temperature overnight. The reaction was monitored by TLC and LC-MS. After completion of reaction, the reaction mixture was poured into water (10 mL) and extracted with ethyl acetate (2×10 mL). The combined organic phases were washed with water, brine, and dried over sodium sulfate to give a crude compound. This was purified by preparative HPLC using water-acetonitrile as mobile phase to give N-((5-chlorothiophen-2-yl)methyl)-3-(1-(phenylsulfonyl)piperidin-4-yl)-1H-pyrazol-5-amine (Compound 126, 0.045 g, yield: 31%) m/z 437.2 [M+1]+ ¹H NMR (400 MHz, DMSO) δ 11.33 (s, 1H), 8.30-7.26 (m, 5H), 7.08-6.63 (m, 2H), 5.68 (s, 1H), 5.24 (s, 1H), 4.26 (d, J=6.2 Hz, 2H), 3.65 (d, J=11.1 Hz, 2H), 2.32 (t, J=11.2 Hz, 2H), 1.89 (d, J=11.4 Hz, 2H), 1.72-1.38 (m, 2H) ppm.

Example 178-Preparation of Compound 127

The synthesis of Compound 127 followed the procedure of General Procedure 5a following:

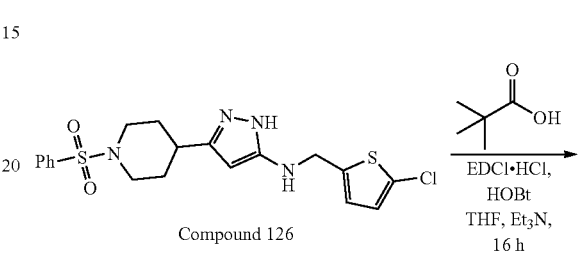

Compound 126

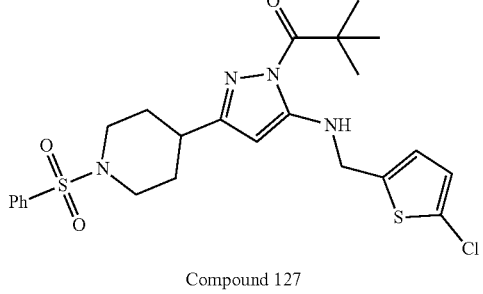

Compound 127

To a cooled solution (0° C.) of pivalic acid (0.080 g, 0.78 mmol, 1.5 eq) in THF (8 mL) was added EDCI.HCl (0.15 g, 0.78 mmol, 1.5 eq) and triethylamine (TEA, 0.16 g, 1.6 mmol, 3.0 eq). The reaction mixture was stirred for 30 minutes, then HOBt (0.014 g, 0.1 mmol, 0.2 eq) and N-((5-chlorothiophen-2-yl)methyl)-3-(1-(phenylsulfonyl)piperidin-4-yl)-1H-pyrazol-5-amine (Compound 126, 0.23 g. 0.5 mmol, 1 eq) were added. The reaction mixture was stirred at room temperature overnight. After completion (as monitored by LC-MS), the reaction mixture was poured into water (15 mL), extracted with ethyl acetate (2×20 mL), and the combined organic phase then washed with water, brine, dried over sodium sulfate, filtered and evaporated under reduced pressure to give a residue. This was purified by preparative HPLC using water-acetonitrile as mobile phase to give 1-(5-(((5-chlorothiophen-2-yl)methyl)amino)-3-(1-(phenylsulfonyl)piperidin-4-yl)-1H-pyrazol-1-yl)-2,2-dimethylpropan-1-one (Compound 127, 0.056 g, yield: 20%) m/z 521.48 [M+]+ ¹H NMR (400 MHz, DMSO) δ 7.83-7.51 (m, 6H), 6.95 (s, 2H), 5.34 (s, 1H), 4.38 (d, J=6.2 Hz, 2H), 3.55 (d, J=12.0 Hz, 2H), 1.91 (d, J=10.6 Hz, 2H), 1.58 (dt, J=34.4, 17.4 Hz, 2H), 1.34 (s, 9H) ppm.

Example 179-Preparation of Compound 128

The synthesis of Compound 128 followed the procedure of General Procedure 5b following:

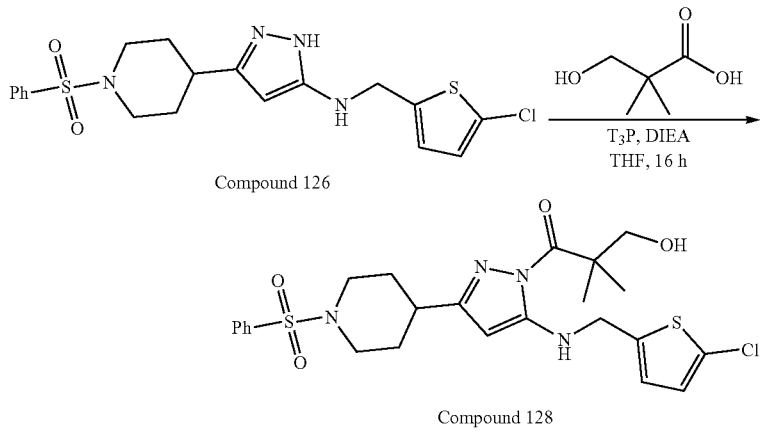

Compound 126

Compound 128

To a solution of hydroxypivalic acid (0.102 g, 0.85 mmol, 1.5 eq) in THF (6 mL) was added propylphosphonic anhydride ($T_3P$ in 50% solution in ethyl acetate, 0.273 g, 0.85 mmol, 1.5 eq), DIEA (0.173 g, 1.7 mmol, 3 eq) followed by N-((5-chlorothiophen-2-yl)methyl)-3-(1-(phenylsulfonyl)piperidin-4-yl)-1H-pyrazol-5-amine (Compound 126, 0.27 g, 0.57 mmol, 1 eq). The reaction mixture was stirred at room temperature overnight. After completion (as monitored by LC-MS), the mixture was poured into water (20 mL) and extracted with ethyl acetate (2×25 mL). The combined organic phases were washed with water, brine, and dried over sodium sulfate, then filtered and evaporated under reduced pressure to give a residue. This was purified by preparative HPLC using water-acetonitrile as mobile phase to give 1-(5-(((5-chlorothiophen-2-yl)methyl)amino)-3-(1-(phenylsulfonyl)piperidin-4-yl)-1H-pyrazol-1-yl)-3-hydroxy-2,2-dimethylpropan-1-one (Compound 128, 0.054 g, yield: 16%) m/z 537.54 [M+]+ $^1$H NMR (400 MHz, DMSO) δ 7.70 (ddd, J=29.6, 11.6, 7.1 Hz, 5H), 6.95 (s, 2H), 5.33 (s, 1H), 4.79 (t, J=5.3 Hz, 1H), 4.38 (d, J=6.2 Hz, 2H), 3.81 (d, J=5.2 Hz, 2H), 3.59 (d, J=11.7 Hz, 2H), 1.91 (d, J=10.8 Hz, 2H), 1.59 (dd, J=21.2, 10.6 Hz, 2H), 1.25 (s, 6H) ppm.

Example 179a—Preparation of Compound 129

The synthesis of Compound 129 followed the procedure of General Procedure 15 following:

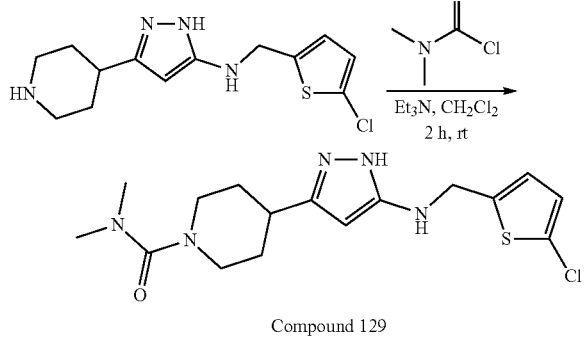

Compound 129

To a cooled solution (0° C.) of N-((5-chlorothiophen-2-yl)methyl)-3-(piperidin-4-yl)-1H-pyrazol-5-amine (0.8 g, 2.7 mmol, 1.0 eq) in dichloromethane (10 mL) was added triethylamine (TEA, 1.36 g, 13.5 mmol, 5.0 eq). After stirring for 10-15 minutes, to the mixture was added N,N-dimethylcarbamoyl chloride (0.22 g, 2.7 mmol, 1.0 eq) and the mixture stirred at room temperature for 2 hours. The reaction was monitored by TLC and LC-MS. After completion, solvent was evaporated to give a residue, which was purified by column chromatography using silica gel (100-200 mesh), eluting with 5% methanol in dichloromethane as mobile phase, to give 4-(5-(((5-chlorothiophen-2-yl)methyl)amino)-1H-pyrazol-3-yl)-N,N-dimethylpiperidine-1-carboxamide, (Compound 129, 0.3 g, yield: 30%); m/z 368.31 [M+1]+; $^1$H NMR (400 MHz, DMSO) δ 11.37 (s, 1H), 6.92 (d, J=3.7 Hz, 1H), 6.84 (d, J=3.6 Hz, 1H), 5.70 (s, 1H), 5.29 (s, 1H), 4.28 (s, 2H), 3.56 (d, J=13.1 Hz, 2H), 3.35 (s, 2H), 3.15-3.02 (m, 1H), 2.80-2.67 (m, 8H), 2.62 (d, J=11.8 Hz, 1H), 1.81 (d, J=11.6 Hz, 2H), 1.48 (dt, J=12.1, 8.9 Hz, 2H), 1.18 (t, J=7.3 Hz, 1H) ppm.

Example 180-Preparation of Compound 130

The synthesis of Compound 130 followed the procedure of General Procedure 5a following:

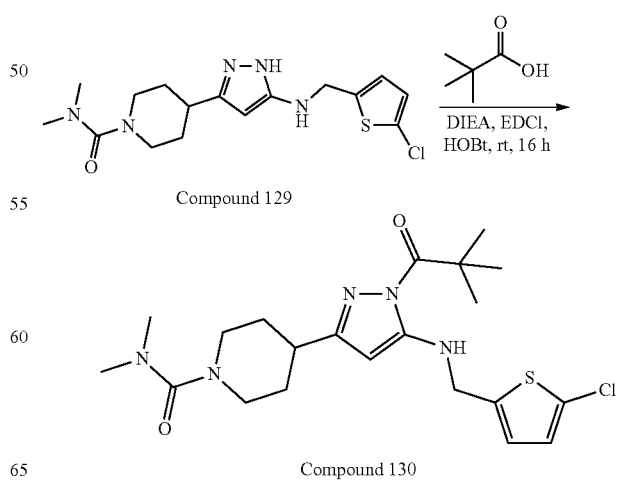

Compound 129

Compound 130

To a solution of pivalic acid (50 mg, 0.49 mmol, 1.0 eq) in THF (10 mL) were added DIEA (100 mg, 0.6 mmol, 1.5 eq), HOBt (11 mg, 0.08 mmol, 0.2 eq) and finally EDCI.HCl (118 mg, 0.6 mmol, 1.5 eq). The solution was stirred at room temperature for 30 minutes. Then was added 4-(5-(((5-chlorothiophen-2-yl)methyl)amino)-1H-pyrazol-3-yl)-N,N-dimethylpiperidine-1-carboxamide (Compound 129, 150 mg, 0.41 mmol, 1.0 eq) and the solution was stirred at room temperature for another 12 hours. After completion, reaction mixture was concentrated and poured into ice-cold water and extracted with ethyl acetate (3×50 mL). The combined organic layers were concentrated under reduced pressure to give a residue. This was purified by preparative HPLC using 100% acetonitrile and 0.1% formic acid in water to give 4-(5-(((5-chlorothiophen-2-yl)methyl)amino)-1-pivaloyl-1H-pyrazol-3-yl)-N,N-dimethylpiperidine-1-carboxamide (Compound 130, 52 mg, yield: 28%) m/z 454.38 [M+1]$^+$; $^1$H NMR (400 MHz, DMSO) δ 7.68 (t, J=6.3 Hz, 1H), 6.96 (t, J=3.0 Hz, 2H), 5.41 (s, 1H), 4.41 (d, J=6.1 Hz, 2H), 3.54 (d, J=13.2 Hz, 2H), 2.79 (t, J=11.4 Hz, 2H), 2.73 (s, 6H), 2.62 (d, J=11.3 Hz, 1H), 1.85 (d, J=11.0 Hz, 2H), 1.52 (dd, J=21.3, 11.6 Hz, 2H), 1.41 (s, 9H) ppm.

Example 181-Preparation of Compound 131

The synthesis of Compound 131 followed the procedure of General Procedure 5a following:

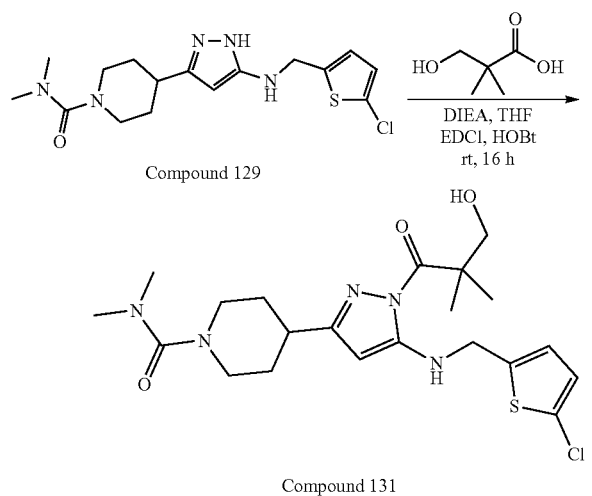

Compound 131

To a solution of hydroxypivalic acid (154 mg, 1.3 mmol, 1.0 eq) in THF (10 mL) was added DIEA (280 mg, 1.6 mmol, 1.5 eq), HOBt (29 mg, 0.22 mmol, 0.2 eq) and finally EDCI.HCl (315 mg, 1.6 mmol, 1.5 eq). After stirring at room temperature for minutes, 4-(5-(((5-chlorothiophen-2-yl)methyl)amino)-1H-pyrazol-3-yl)-N,N-dimethylpiperidine-1-carboxamide (Compound 129, 400 mg, 1.1 mmol, 1.0 eq) was added and the reaction mixture was stirred at room temperature for another 12 hours. After completion, the reaction mixture was concentrated under reduced pressure, poured into ice-cold water and extracted with ethyl acetate (3×50 mL). The combined organic layers were concentrated under reduced pressure to give a residue, which was purified by preparative HPLC using 100% acetonitrile and 0.1% formic acid in water to give 4-(5-(((5-chlorothiophen-2-yl)methyl)amino)-1-(3-hydroxy-2,2-dimethylpropanoyl)-1H-pyrazol-3-yl)-N,N-dimethylpiperidine-1-carboxamide (Compound 131, 56 mg, yield: 11%) m/z 468.63 [M+1]$^+$; $^1$H NMR (400 MHz, DMSO) δ 7.68 (t, J=6.2 Hz, 1H), 6.97 (q, J=3.8 Hz, 2H), 5.40 (s, 1H), 4.83 (t, J=5.3 Hz, 1H), 4.41 (d, J=6.1 Hz, 2H), 3.87 (d, J=5.2 Hz, 2H), 3.55 (d, J=13.0 Hz, 2H), 2.80 (t, J=11.4 Hz, 2H), 2.73 (s, 6H), 2.63 (t, J=11.3 Hz, 1H), 1.85 (d, J=11.3 Hz, 2H), 1.51 (dt, J=15.0, 7.7 Hz, 2H), 1.31 (s, 6H) ppm.

Example 182-Preparation of Compound 132

The synthesis of Compound 132 followed the procedure of General Procedure 15 following:

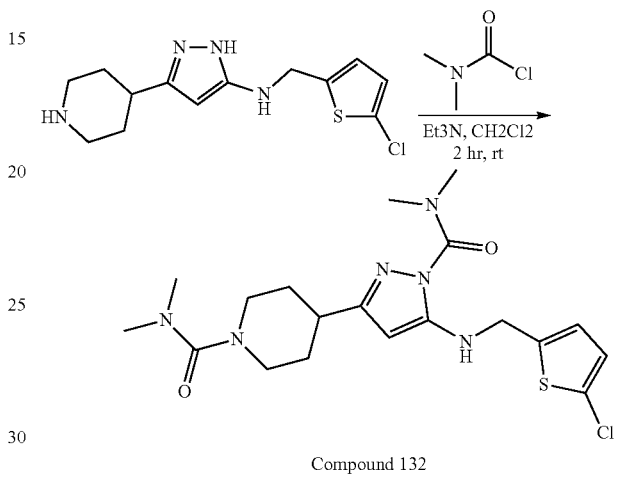

Compound 132

To a cooled solution (0° C.) of N-((5-chlorothiophen-2-yl)methyl)-3-(piperidin-4-yl)-1H-pyrazol-5-amine (100 mg, 2.7 mmol, 1.0 eq) in dichloromethane (10 mL) was added triethylamine (TEA, 200 mg, 1.6 mmol, 6.0 eq). After for 10-15 minutes, N,N-dimethylcarbamic chloride (87 mg, 0.82 mmol, 3.0 eq) was added and the mixture stirred at room temperature for 16 hours. The reaction was monitored by TLC and LC-MS. After completion, solvent was evaporated to give a residue which was purified by column chromatography using silica gel (60-120 mesh), eluting with 5% methanol in dichloromethane to give 4-(5-(((5-chlorothiophen-2-yl)methyl)amino)-1-(dimethylcarbamoyl)-1H-pyrazol-3-yl)-N,N-dimethylpiperidine-1-carboxamide (Compound 132, 0.65 g, yield: 41%); m/z 439.57 [M+1]$^+$; $^1$H NMR (400 MHz, DMSO) δ 7.00-6.91 (m, 2H), 6.75 (t, J=6.0 Hz, 1H), 5.40 (s, 1H), 4.36 (d, J=6.0 Hz, 2H), 3.54 (d, J=13.2 Hz, 2H), 2.98 (d, J=66.8 Hz, 6H), 2.78 (d, J=12.1 Hz, 2H), 2.72 (s, 6H), 2.64-2.53 (m, 1H), 1.80 (d, J=10.9 Hz, 2H), 1.59-1.40 (m, 2H) ppm.

Example 182a—Preparation of Intermediate 53

The synthesis of Intermediate 53 followed the procedure of General Procedure 26 following:

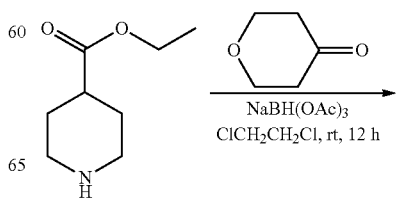

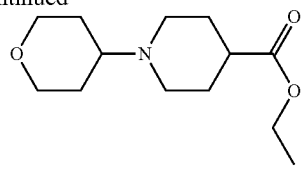

Intermediate 53

To a cooled solution (0° C.) of ethyl piperidine-4-carboxylate (0.93 g, 5.9 mmol, 3.0 eq) in 1,2-dichloroethane (50 mL) was added acetic acid (0.12 g, 2 mmol, 1.0 eq) and tetrahydro-4H-pyran-4-one (0.2 g, 2 mmol, 1 eq). After stirring for 1 hour at room temperature, sodium triacetoxyborohydride (NaBH(OAc)$_3$, 0.63 g, 3 mmol, 1.5 eq.) was added and the mixture stirred at room temperature for another 12 hours. The progress of reaction was monitored by TLC. The reaction mixture was added to water (20 mL), extracted with dichloromethane (3×30 mL), the combined organic layers were dried over anhydrous sodium sulfate, filtered and evaporated under reduced pressure. The crude product was purified by column chromatography (100-200 mesh) eluting with 3% methanol in dichloromethane to give ethyl 1-(tetrahydro-2H-pyran-4-yl)piperidine-4-carboxylate (Intermediate 53, 0.13 g, yield: 42%); $^1$H NMR (400 MHz, CDCl$_3$) δ 4.15 (q, J=7.1 Hz, 2H), 4.05 (dd, J=11.3, 4.3 Hz, 2H), 3.45-3.32 (m, 2H), 3.08-2.96 (m, 2H), 2.68 (s, 1H), 2.41 (dd, J=12.2, 7.1 Hz, 3H), 2.06 (d, J=11.2 Hz, 2H), 1.95-1.80 (m, 4H), 1.67 (ddd, J=24.4, 12.2, 4.4 Hz, 2H), 1.26 (t, J=7.1 Hz, 3H) ppm.

Example 183-Preparation of Intermediate 54

The synthesis of Intermediate 54 followed the procedure of General Procedure 2 following:

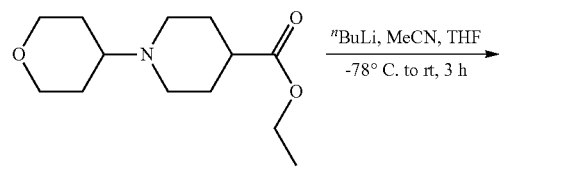

Intermediate 53

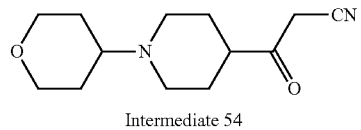

Intermediate 54

To a cooled solution (−78° C.) of acetonitrile (0.97 g, 24 mmol, 1.5 eq) in THF (50 mL) was added n-BuLi (2.5M in n-hexane, 9.5 mL, 2.4 mmol, 1.5 eq) dropwise over a period of 20 minutes. After stirring for 60 minutes at −78° C., ethyl 1-(tetrahydro-2H-pyran-4-yl)piperidine-4-carboxylate (Intermediate 53, 3.8 g, 15.7 mmol, 1.0 eq) was added in one portion. The mixture was then warmed to room temperature over 3 hours. The reaction was quenched with saturated ammonium chloride solution and product was extracted with ethyl acetate (3×20 mL). The combined organic layers were dried over anhydrous sodium sulfate, filtered and concentrated under reduced pressure to obtain a crude product. This was washed with ethyl acetate to yield 3-oxo-3-(1-(tetrahydro-2H-pyran-4-yl)piperidin-4-yl)propanenitrile (Intermediate 54, 1.5 g, yield: 40%) and used 'as is' for the next step; m/z 237.04 [M+H]$^+$; $^1$H NMR (400 MHz, DMSO) δ 4.16 (s, 2H), 3.88 (d, J=11.0 Hz, 2H), 3.25 (t, J=11.0 Hz, 2H), 2.91 (d, J=11.4 Hz, 2H), 2.45 (s, 1H), 2.14 (d, J=10.7 Hz, 2H), 1.81 (d, J=11.9 Hz, 3H), 1.65 (d, J=12.0 Hz, 2H), 1.49-1.33 (m, 4H) ppm.

Example 184-Preparation of Compound 132

The synthesis of Compound 132 followed the procedure of General Procedure 3 following:

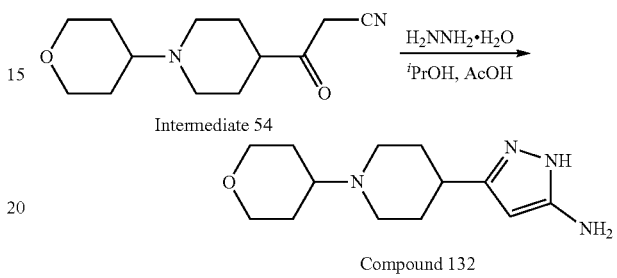

To a solution of 3-oxo-3-(1-(tetrahydro-2H-pyran-4-yl)piperidin-4-yl)propanenitrile (Intermediate 54, 1.3 g, 5.7 mmol, 1.0 eq) in isopropanol (15 mL) and acetic acid (0.34 g, 5.7 mmol, 1.0 eq) was added hydrazine monohydrate (0.31 g, 6.2 mmol, 1.1 eq) dropwise. The reaction mixture was stirred at 80° C. for 12 hours. The reaction mixture was monitored by TLC and LC-MS, and after completion the reaction mixture was concentrated to obtain a crude product. This was purified by column chromatography using silica gel (60-120 mesh), eluting with 10% methanol in dichloromethane to give 3-(1-(tetrahydro-2H-pyran-4-yl)piperidin-4-yl)-1H-pyrazol-5-amine (Compound 132, 1.3 g, yield: 95%) m/z 251.14 [M+1]$^+$ $^1$H NMR (400 MHz, DMSO) δ 8.95 (s, 1H), 5.18 (s, 1H), 3.88 (dd, J=10.8, 3.6 Hz, 2H), 3.26 (t, J=11.1 Hz, 2H), 3.17 (s, 2H), 2.90 (d, J=11.4 Hz, 2H), 2.40 (dd, J=21.3, 11.5 Hz, 2H), 2.15 (t, J=10.6 Hz, 2H), 1.80 (d, J=12.4 Hz, 2H), 1.71-1.60 (m, 2H), 1.57-1.33 (m, 4H) ppm.

Example 185-Preparation of Compound 133

The synthesis of Compound 133 followed the procedure of General Procedure 4 following:

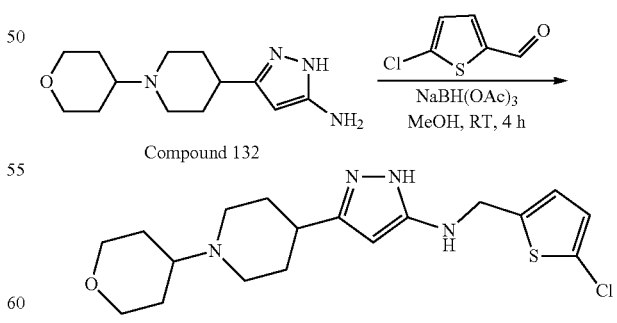

To a cooled solution (0° C.) of 3-(1-(tetrahydro-2H-pyran-4-yl)piperidin-4-yl)-1H-pyrazol-5-amine (Compound 132, 1.7 g, 6.8 mmol, 1.0 eq) in anhydrous methanol (30 mL) was added glacial acetic acid (0.41 g, 6.8 mmol, 1.0 eq) and then 5-chlorothiophene-2-carbaldehyde (1.19 g, 8.2 mmol, 1.2 eq) dropwise. The reaction mixture was slowly brought to room temperature and then stirred for 1 hour. After completion, as monitored by TLC and LC-MS, the mixture was cooled back to 0° C. add to it was added sodium cyanoborohydride (2.16 g, 10 mmol, 1.5 eq). The mixture was stirred at room temperature for 4 hours. The reaction monitored by TLC. The reaction mixture was slowly concentrated under reduced pressure to obtain a yellow residue, which was diluted with ethyl acetate (100 mL) and washed with water (3×25 mL). The organic layer was dried with sodium sulfate, filtered and concentrated under reduced pressure to give a residue, which was purified by column chromatography (silica gel, 60-120 mesh) eluting with 5% methanol in dichloromethane to give N-((5-chlorothiophen-2-yl)methyl)-3-(1-(tetrahydro-2H-pyran-4-yl)piperidin-4-yl)-1H-pyrazol-5-amine (Compound 133, 0.5 g, yield: 19%); m/z 381.36[M+1]+; 1H NMR (400 MHz, DMSO) δ 11.33 (s, 1H), 6.99-6.90 (m, 1H), 6.84 (d, J=3.5 Hz, 1H), 5.66 (s, 1H), 5.28 (s, 1H), 4.28 (d, J=6.2 Hz, 2H), 3.90 (d, J=7.4 Hz, 2H), 3.33-3.22 (m, 4H), 2.98 (s, 2H), 2.31-2.08 (m, 2H), 2.02-1.64 (m, 4H), 1.49 (s, 4H) ppm.

Example 186-Preparation of Compound 134

The synthesis of Compound 134 followed the procedure of General Procedure 5a following:

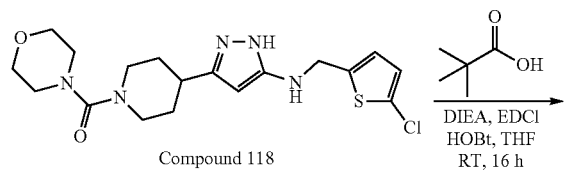

Compound 118

DIEA, EDCl
HOBt, THF
RT, 16 h

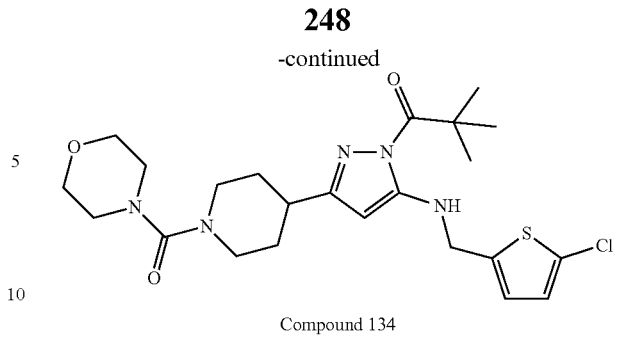

Compound 134

To a solution of pivalic acid (44.7 mg, 0.44 mmol, 1.2 eq) in THF (3 mL) was added DIEA (0.09 mL, 0.55 mmol, 1.5 eq), HOBt (9.8 mg, 0.07 mmol, 0.2 eq.) and then EDCI.HCl (106 mg, 0.55 mmol, 1.5 eq). After stirring for 30 minutes, (4-(5-(((5-chlorothiophen-2-yl)methyl)amino)-1H-pyrazol-3-yl)piperidin-1-yl)(morpholino)methanone (Compound 118, 150 mg, 0.37 mmol, 1.0 eq) was added and the reaction mixture was allowed to stir at room temperature for another 16 hours. After completion, the mixture was concentrated and poured into ice-cold water and extracted with dichloromethane (3×50 mL). The combined organic layers were dried with sodium sulfate, dried and evaporated under reduced pressure. The residue was purified by preparative HPLC using 100% acetonitrile and 0.1% formic acid in water to give 1-(5-(((5-chlorothiophen-2-yl)methyl)amino)-3-(1-(morpholine-4-carbonyl)piperidin-4-yl)-1H-pyrazol-1-yl)-2,2-dimethylpropan-1-one (Compound 134, 53.3 mg, yield-29%) m/z 494.48 [M+1]+; 1H NMR (400 MHz, DMSO) δ 7.69 (d, J=6.1 Hz, 1H), 6.97 (s, 2H), 5.41 (s, 1H), 4.41 (d, J=6.1 Hz, 2H), 3.61 (d, J=13.2 Hz, 2H), 3.60-3.53 (m, 4H), 3.12 (d, J=4.6 Hz, 4H), 2.86 (t, J=11.7 Hz, 2H), 2.66 (d, J=11.7 Hz, 1H), 1.85 (d, J=10.9 Hz, 2H), 1.57-1.44 (m, 2H), 1.40 (s, 9H) ppm.

Example 187-Preparation of Compound 135

The synthesis of Compound 135 followed the procedure of General Procedure 5a following:

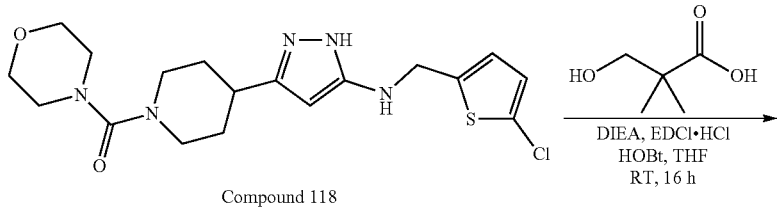

Compound 118

DIEA, EDCI•HCl
HOBt, THF
RT, 16 h

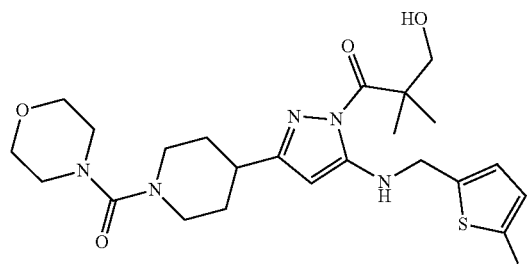

Compound 135

To a solution of hydroxypivalic acid (138 mg, 1.2 mmol, 1.2 eq) in THF (8 mL) was added DIEA (0.25 mL, 1.46 mmol, 1.5 eq), HOBt (26 mg. 0.2 mmol, 0.2 eq) and then EDCI.HCl (282 mg, 1.5 mmol, 1.5 eq). After stirring for another 30 minutes, (4-(5-(((5-chlorothiophen-2-yl)methyl)amino)-1H-pyrazol-3-yl)piperidin-1-yl)(morpholino)methanone (Compound 118, 400 mg, 0.98 mmol, 1.0 eq) was added and the mixture allowed to stir at room temperature for 16 hours. After completion, the reaction mixture was concentrated, poured into ice-cold water and extracted with ethyl acetate (3×50 mL). The combined organic layers were concentrated under reduced pressure to give a residue which was purified by preparative HPLC using 100% acetonitrile and 100% water to give 1-(5-(((5-chlorothiophen-2-yl)methyl)amino)-3-(1-(morpholine-4-carbonyl)piperidin-4-yl)-1H-pyrazol-1-yl)-3-hydroxy-2,2-dimethylpropan-1-one (Compound 135, 58 mg, yield: 12%) m/z 510.53 [M+1]+; 1H NMR (400 MHz, DMSO) δ 7.68 (t, J=6.2 Hz, 1H), 6.96 (d, J=3.8 Hz, 2H), 5.40 (s, 1H), 4.83 (t, J=5.4 Hz, 1H), 4.41 (d, J=6.1 Hz, 2H), 3.87 (d, J=5.3 Hz, 2H), 3.61 (d, J=13.5 Hz, 2H), 3.59-3.53 (m, 4H), 3.15-3.08 (m, 4H), 2.86 (t, J=11.6 Hz, 2H), 2.66 (d, J=11.5 Hz, 1H), 1.85 (d, J=10.6 Hz, 2H), 1.50 (dd, J=21.0, 11.8 Hz, 2H), 1.31 (s, 6H) ppm.

Example 188-Preparation of Compound 136

The synthesis of Compound 136 followed the procedure of General Procedure 15 following:

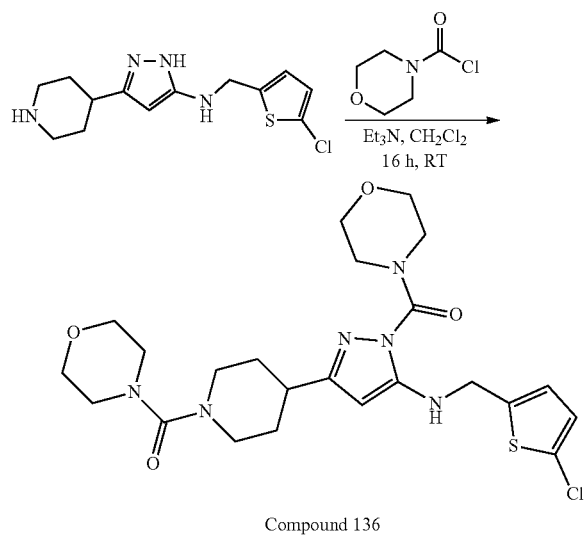

Compound 136

To a cooled solution (0° C.) of N-((5-chlorothiophen-2-yl) methyl)-3-(piperidin-4-yl)-1H-pyrazol-5-amine (0.1 g, 0.24 mmol, 1.0 eq) in dichloromethane (2 mL) was added triethylamine (TEA, 0.2 mL, 1.46 mmol, 6.0 eq). After stirring for 15 minutes, morpholine-4-carbonyl chloride (0.1 g, 0.73 mmol, 3.0 eq) was added and the reaction stirred at room temperature for 16 hours. The reaction was monitored by TLC and LC-MS. After completion, solvent was evaporated to give a residue which was purified by preparative HPLC using 100% acetonitrile and 100% water to give (4-(5-(((5-chlorothiophen-2-yl)methyl)amino)-1-(morpholine-4-carbonyl)-1H-pyrazol-3-yl)piperidin-1-yl)(morpholino)methanone (Compound 136, 15 mg, yield: 2%) m/z 523.63 [M+1]+; 1H NMR (400 MHz, DMSO) δ 6.99-6.93 (m, 2H), 6.85 (t, J=6.2 Hz, 1H), 5.42 (s, 1H), 4.37 (d, J=6.1 Hz, 2H), 3.74-3.54 (m, 14H), 3.15-3.07 (m, 4H), 2.82 (t, J=11.5 Hz, 2H), 2.60 (t, J=11.5 Hz, 1H), 1.80 (d, J=10.9 Hz, 2H), 1.48 (dd, J=21.0, 11.9 Hz, 2H) ppm.

Example 189-Preparation of Compound 137

The synthesis of Compound 137 followed the procedure of General Procedure 15 following:

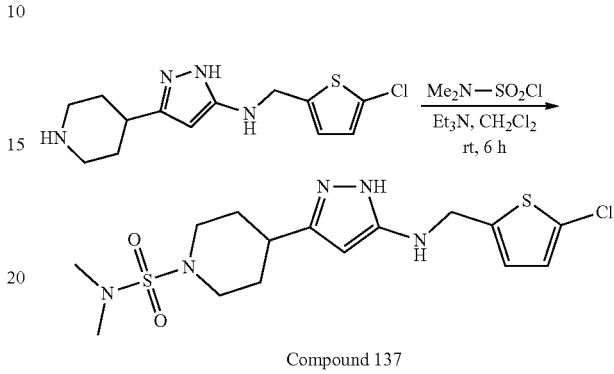

Compound 137

To a cooled solution (0° C.) of N-((5-chlorothiophen-2-yl) methyl)-3-(piperidin-4-yl)-1H-pyrazol-5-amine (0.7 g, 2.4 mmol, 1.0 eq) in dichloromethane (10 mL) was added triethylamine (TEA, 1.2 g. 12 mmol, 5 eq), followed by dimethylsulfamoyl chloride (0.34 g, 2.3 mmol, 1.0 eq). The mixture was stirred at room temperature for 3 hours. The progress of reaction was monitored by TLC. The reaction mixture was added to cold water (10 mL), extracted with dichloromethane (3×25 mL), and the combined organic layers were dried over anhydrous sodium sulfate, filtered and concentrated to give a crude product. This was purified by column chromatography on silica gel (60-120 mesh size) with 45% ethyl acetate in n-hexane to give 4-(5-(((5-chlorothiophen-2-yl)methyl)amino)-1H-pyrazol-3-yl)-N,N-dimethylpiperidine-1-sulfonamide (Compound 137, 0.62 g, yield: 65%) m/z 404.30[M+H]+ 1H NMR (DMSO-d6, 400 MHz, 12092) δ: 11.36 (s, 1H), 7.03-6.76 (m, 2H), 5.65 (s, 1H), 5.31 (s, 1H), 4.29 (d, J=6.3 Hz, 2H), 3.58 (d, J=12.5 Hz, 2H), 2.90 (td, J=12.3, 2.3 Hz, 2H), 2.76 (d, J=5.7 Hz, 6H), 2.64 (s, 1H), 1.89 (d, J=11.2 Hz, 2H), 1.54 (qd, J=12.6, 4.0 Hz, 2H) ppm.

Example 189-Preparation of Compound 138

The synthesis of Compound 138 followed the procedure of General Procedure 5a following:

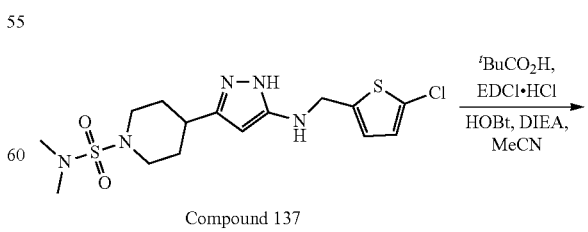

Compound 137

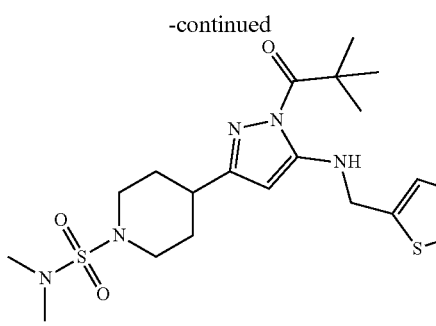

Compound 138

To a cooled solution (0° C.) of pivalic acid (0.085 g, 0.85 mmol, 1.5 eq) in acetonitrile (12 mL) was added EDCI.HCl (0.16 g, 0.85 mmol, 1.5 eq.), HOBt (0.022 g, 0.17 mmol, 0.3 eq) and DIEA (0.23 mL, 1.7 mmol, 3.0 eq). After stirring for 30 minutes, 4-(5-(((5-chlorothiophen-2-yl)methyl)amino)-1H-pyrazol-3-yl)-N,N-dimethylpiperidine-1-sulfonamide (Compound 137, 0.27 g, 0.56 mmol, 1.0 eq) was added and the mixture stirred at room temperature for 16 hours. The reaction was monitored by LC-MS, and after completion of reaction the reaction mixture was added to water (10 mL), extracted with ethyl acetate (3×20 mL), dried with sodium sulfate, filtered and concentrated to give crude product. The residue was purified by Combi-flash chromatography, eluting with 30% ethyl acetate in n-hexane to give 4-(5-(((5-chlorothiophen-2-yl)methyl)amino)-1-pivaloyl-1H-pyrazol-3-yl)-N,N-dimethylpiperidine-1-sulfonamide (Compound 138, 0.09 g, yield: 28%) m/z 488.53 [M+H]+ 1H NMR (DMSO-d6, 400 MHz, 12445) δ: 7.69 (t, J 6.2 Hz, 1H), 6.97 (q, J 3.7 Hz, 2H), 5.42 (s, 1H), 4.42 (d, J 6.1 Hz, 2H), 3.57 (d, J=12.3 Hz, 2H), 2.95 (t, J 10.9 Hz, 2H), 2.75 (s, 6H), 2.69-2.59 (m, 1H), 2.01-1.89 (m, 2H), 1.58 (td, J=15.2, 3.7 Hz, 2H), 1.41 (s, 9H) ppm.

Example 190-Preparation of Compound 139

The synthesis of Compound 139 followed the procedure of General Procedure 5c following:

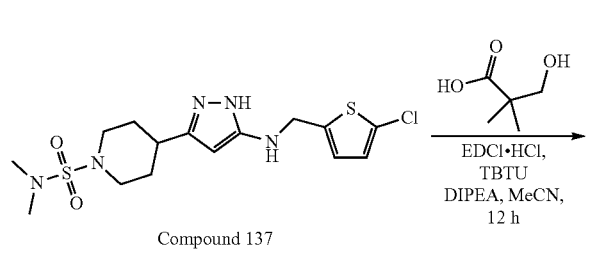

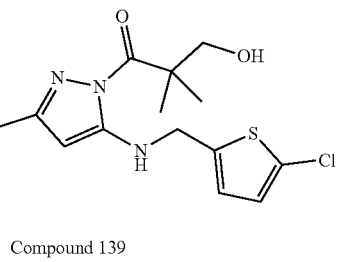

Compound 139

To a cooled solution (0° C.) of 3-hydroxy-2,2-dimethylpropanoic acid (Compound 137, 0.15 g, 1.3 mmol, 1.5 eq) in acetonitrile (12 mL) was added N,N,N',N'-tetramethyl-O-(benzotriazol-1-yl)uronium tetrafluoroborate (TBTU, 0.42 g, 1.3 mmol, 1.5 eq) and then (diisopropyl)ethylamine (DIEA, 0.24 mL, 2.6 mmol, 3.0 eq). After stirring for 30 minutes, to the mixture was added 4-(5-(((5-chlorothiophen-2-yl)methyl)amino)-1-(3-hydroxy-2,2-dimethylpropanoyl)-1H-pyrazol-3-yl)-N,N-dimethylpiperidine-1-sulfonamide (Compound 137, 0.35 g, 0.9 mmol, 1.0 eq), and the mixture stirred at room temperature for 12 hours. The reaction progress was monitored by TLC. After completion, the mixture was poured into water (10 mL) and extracted with ethyl acetate (3×20 mL). The combined organic phases were dried over sodium sulfate, filtered and evaporated to a residue. The crude compound was purified by preparative HPLC eluting with water and acetonitrile as mobile phase on a Sunfire C18, 5 micron column. The purified fractions were lyophilized to give 4-(5-(((5-chlorothiophen-2-yl)methyl)amino)-1-(3-hydroxy-2,2-dimethylpropanoyl)-1H-pyrazol-3-yl)-N,N-dimethylpiperidine-1-sulfonamide (Compound 139, 0.05 g, yield: 11%) m/z 504.48 [M+H]+ 1H NMR (DMSO-d6, 400 MHz, 13050) δ: 7.69 (t, J=6.1 Hz, 1H), 6.97 (d, J=2.3 Hz, 2H), 5.41 (s, 1H), 4.84 (t, J=5.3 Hz, 1H), 4.41 (d, J=6.0 Hz, 2H), 3.87 (d, J=5.3 Hz, 2H), 3.57 (d, J=12.1 Hz, 2H), 2.95 (t, J=10.9 Hz, 2H), 2.75 (s, 6H), 2.62 (dd, J=22.7, 11.4 Hz, 1H), 1.92 (d, J=11.5 Hz, 2H), 1.57 (dd, J=21.0, 11.1 Hz, 2H), 1.31 (s, 6H) ppm.

Example 191-Preparation of Compound 140

The synthesis of Compound 140 followed the procedure of General Procedure 25 following:

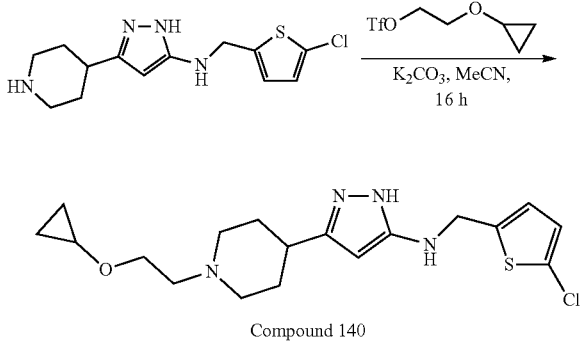

Compound 140

To a solution of N-((5-chlorothiophen-2-yl)methyl)-3-(piperidin-4-yl)-1H-pyrazol-5-amine (1.0 g, 2.5 mmol, 1.0 eq) in acetonitrile (15 mL) was added potassium carbonate (2.0 g, 14.7 mmol, 6.0 eq). After stirring the reaction mixture at room temperature for 30 minutes, 2-cyclopropoxyethyl trifluoromethanesulfonate (0.576 g, 2.5 mmol, 1 eq) was added and the reaction mixture was allowed to stir at room temperature for 16 hours. After completion (as monitored by LC-MS), the reaction mixture was concentrated to give a crude product which was purified by preparative HPLC using water-acetonitrile as mobile phase to give N-((5-chlorothiophen-2-yl)methyl)-3-(1-(2-cyclopropoxyethyl)piperidin-4-yl)-1H-pyrazol-5-amine (Compound 140, 0.61 g, yield: 65%) m/z 381.56[M+1]+ $^1$H NMR (400 MHz, DMSO) δ 11.65 (s, 1H), 6.97-6.81 (m, 2H), 5.80 (s, 1H), 5.35 (d, J=39.2 Hz, 1H), 4.29 (d, J=6.0 Hz, 2H), 3.74 (s, 2H), 3.41-3.31 (m, 5H), 3.23 (s, 2H), 2.98 (s, 1H), 2.08-2.01 (m, 2H), 1.78 (s, 2H), 0.60-0.42 (m, 4H) ppm.

Example 192-Preparation of Compound 141

The synthesis of Compound 141 followed the procedure of General Procedure 5a following:

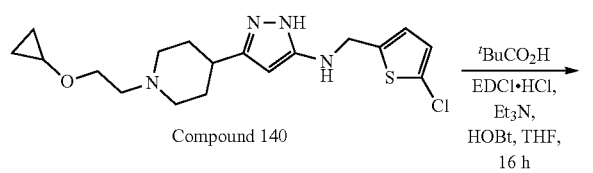

give 1-(5-(((5-chlorothiophen-2-yl)methyl)amino)-3-(1-(2-cyclopropoxyethyl)piperidin-4-yl)-1H-pyrazol-1-yl)-2,2-dimethyl propan-1-one (Compound 141, 0.06 g, yield: 25%) m/z 465.02 [M+H]+ $^1$H NMR (400 MHz, DMSO) δ 7.64 (t, J=6.1 Hz, 1H), 6.96 (q, J=3.8 Hz, 2H), 5.37 (s, 1H), 4.40 (d, J=6.2 Hz, 2H), 3.52 (t, J=6.0 Hz, 2H), 3.26 (ddd, J=9.1, 5.9, 3.2 Hz, 1H), 2.85 (d, J=11.6 Hz, 2H), 2.45-2.31 (m, 3H), 2.13-1.95 (m, 3H), 1.79 (d, J=10.6 Hz, 2H), 1.56 (dd, J=21.1, 11.8 Hz, 2H), 1.39 (s, 9H), 0.46-0.33 (m, 4H) ppm.

Example 193-Preparation of Compound 142

The synthesis of Compound 142 followed the procedure of General Procedure 5b following:

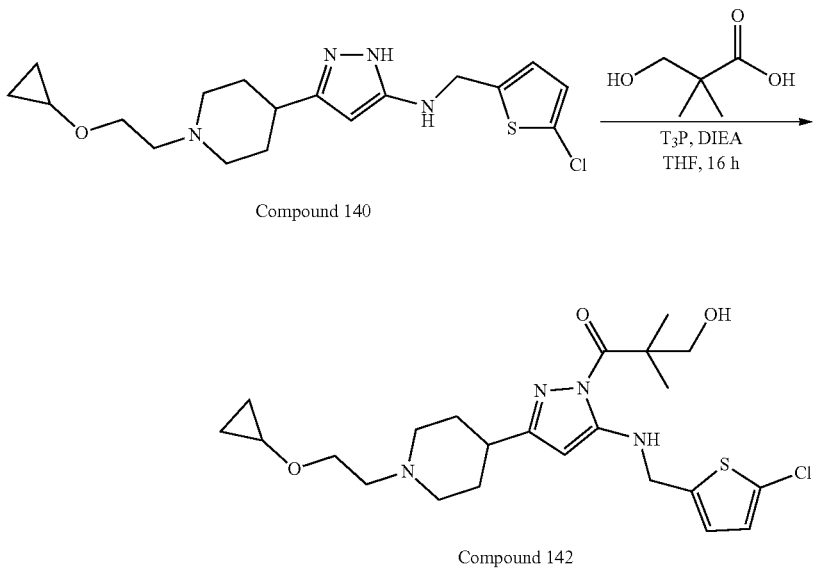

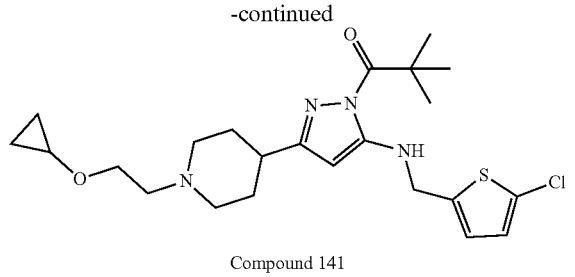

To a cooled solution (0° C.) of pivalic acid (0.2 g, 0.64 mmol, 1.2 eq) in THF (6 mL) was added EDCI.HCl (0.15 g, 0.78 mmol, 1.5 eq) and triethylamine (TEA, 0.16 g, 1.6 mmol, 3.0 eq). After stirring for 30 minutes, HOBt (0.014 g, 0.1 mmol, 0.2 eq) and N-((5-chlorothiophen-2-yl)methyl)-3-(1-(2-cyclopropoxyethyl) piperidin-4-yl)-1H-pyrazol-5-amine (Compound 140, 0.2 g, 0.52 mmol, 1 eq) were added. The reaction mixture was stirred at room temperature for 16 hours. After completion (as monitored by LC-MS), the reaction mixture was poured to water (15 mL) and extracted with ethyl acetate (2×15 mL). The combined organic phases were washed with water, brine, dried over sodium sulfate, filtered and evaporated. The residue was purified by preparative HPLC using water-acetonitrile as mobile phase to To a solution of hydroxypivalic acid (0.093 g, 0.78 mmol, 1.5 eq) in THF (6 mL) were added propylphosphonic anhydride (T$_3$P in 50% solution in ethyl acetate, 0.25 g, 0.8 mmol, 1.5 eq), DIEA (0.2 g, 1.6 mmol, 3 eq), followed by N-((5-chlorothiophen-2-yl)methyl)-3-(1-(2-cyclopropoxyethyl)piperidin-4-yl)-1H-pyrazol-5-amine (Compound 140, 0.2 g, 0.5 mmol, 1.0 eq). The reaction mixture was stirred at room temperature for 16 hours. After completion (as monitored by LC-MS), the reaction mixture was poured into water (10 mL) and extracted with ethyl acetate (2×25 mL). The combined organic phases were washed with water, brine, dried over sodium sulfate, filtered and evaporated under reduced pressure. The residue was purified by preparative HPLC using water-acetonitrile as mobile phase to give 1-(5-(((5-chlorothiophen-2-yl)methyl)amino)-3-(1-(2-cyclopropoxyethyl) piperidin-4-yl)-1H-pyrazol-1-yl)-3-hydroxy-2,2-dimethylpropan-1-one (Compound 142, 0.032 g, yield: 12%) m/z 481.1 [M+H]+ $^1$H NMR (400 MHz, DMSO) δ 7.65 (d, J=6.2 Hz, 1H), 6.96 (t, J=3.4 Hz, 2H), 5.38 (s, 1H), 4.82 (t, J=5.2 Hz, 1H), 4.40 (d, J=6.2 Hz, 2H), 3.86 (d, J=5.3 Hz, 2H), 3.52 (t, J=5.9 Hz, 2H), 3.26 (d, J=3.2 Hz, 1H), 2.87 (d, J=11.1 Hz, 2H), 2.40 (dd, J=28.5, 14.2 Hz, 3H), 2.04 (dd, J=22.2, 11.0 Hz, 3H), 1.78 (s, 2H), 1.56 (d, J=9.6 Hz, 2H), 1.30 (s, 6H), 0.51-0.28 (m, 4H) ppm.

Example 194-Preparation of Compound 143

The synthesis of Compound 143 followed the procedure of General Procedure 25 following:

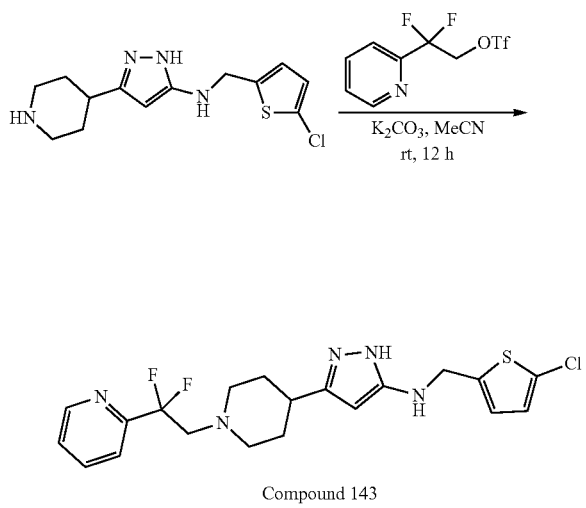

Compound 143

To a solution of N-((5-chlorothiophen-2-yl)methyl)-3-(piperidin-4-yl)-1H-pyrazol-5-amine (1.0 g, 3.4 mmol, 1.0 eq) in acetonitrile (15 mL) was added potassium carbonate (K$_2$CO$_3$, 3.26 g, 23.7 mmol, 7 eq), followed by 2,2-difluoro-2-(pyridin-2-yl)ethyl trifluoromethanesulfonate (1.1 g, 3.7 mmol, 1.1 eq). The mixture was stirred at 80° C. for 12 hours. The progress of reaction was monitored by LC-MS. The reaction mixture was diluted with water (50 mL), extracted with dichloromethane (3×80 mL), and the combined organic phases were dried over anhydrous sodium sulfate, filtered and concentrated to give crude product. This was purified by column chromatography, eluting with 2% methanol in dichloromethane to give N-((5-chlorothiophen-2-yl)methyl)-3-(1-(2,2-difluoro-2-(pyridin-2-yl)ethyl)piperidin-4-yl)-1H-pyrazol-5-amine (Compound 143, 0.4 g, 27%) $^1$H NMR (400 MHz, DMSO) δ 11.26 (s, 1H), 8.68 (d, J=3.9 Hz, 1H), 7.98 (t, J=7.7 Hz, 1H), 7.70 (d, J=7.7 Hz, 1H), 7.59-7.49 (m, 1H), 6.90 (d, J=3.7 Hz, 1H), 6.82 (d, J=3.6 Hz, 1H), 5.62 (s, 1H), 5.23 (s, 1H), 4.26 (d, J=6.1 Hz, 2H), 3.21 (t, J=14.8 Hz, 2H), 2.81 (d, J=11.7 Hz, 2H), 2.32 (dd, J=29.7, 18.6 Hz, 3H), 1.78-1.62 (m, 2H), 1.39 (dd, J=21.2, 12.6 Hz, 2H) ppm.

Example 195-Preparation of Compound 144

The synthesis of Compound 144 followed the procedure of General Procedure 5a following:

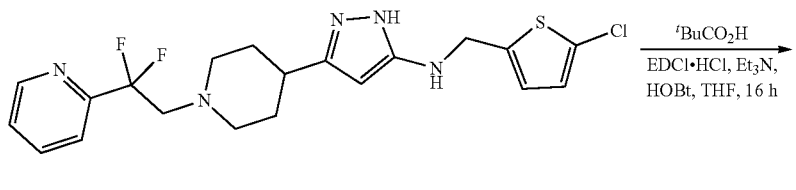

Compound 143

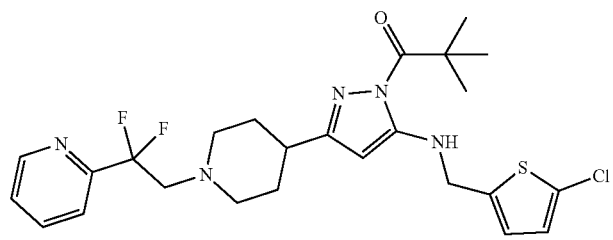

Compound 144

To a cooled solution (0° C.) of pivalic acid (77 mg, 0.76 mmol, 1.1 eq) in THF (10 mL) was added DIPEA (221 mg, 1.7 mmol, 2.5 eq), HOBt (46 mg, 0.34 mmol, 0.5 eq) and then EDCI.HCl (197 mg, 1.0 mmol, 1.5 eq). After stirring at 0° C. for 30 minutes, to the mixture was added N-((5-chlorothiophen-2-yl)methyl)-3-(1-(2,2-difluoro-2-(pyridin-2-yl)ethyl)piperidin-4-yl)-1H-pyrazol-5-amine (Compound 143, 300 mg, 0.7 mmol, 1.0 eq), and the mixture allowed to stir at room temperature for 12 hours. After completion, the reaction mixture was concentrated and poured into ice-cold water and extracted with ethyl acetate (3×50 mL). The combined organic layers were dried over sodium sulfate, filtered and concentrated on reduced pressure. The residue was purified by preparative HPLC using acetonitrile/water to give 1-(5-(((5-chlorothiophen-2-yl)methyl)amino)-3-(1-(2,2-difluoro-2-(pyridin-2-yl)ethyl)piperidin-4-yl)-1H-pyrazol-1-yl)-2,2-dimethylpropan-1-one (Compound 144, 74.5 mg, yield: 17%) m/z 522.10 [M+1]$^+$; $^1$H NMR (400 MHz, DMSO) δ 8.68 (d, J=4.8 Hz, 1H), 7.98 (t, J=7.8 Hz, 1H), 7.70 (d, J=7.8 Hz, 1H), 7.64 (t, J=6.4 Hz, 1H), 7.56-7.49 (m, 1H), 6.95 (d, J=3.8 Hz, 2H), 5.36 (s, 1H), 4.39 (d, J=6.2 Hz, 2H), 3.21 (t, J=14.8 Hz, 2H), 2.81 (d, J=11.5 Hz, 2H), 2.33 (t, J=11.5 Hz, 4H), 1.72 (d, J=12.2 Hz, 2H), 1.51-1.40 (m, 2H), 1.38 (s, 9H) ppm.

Example 196-Preparation of Compound 145

The synthesis of Compound 145 followed the procedure of General Procedure 5a following:

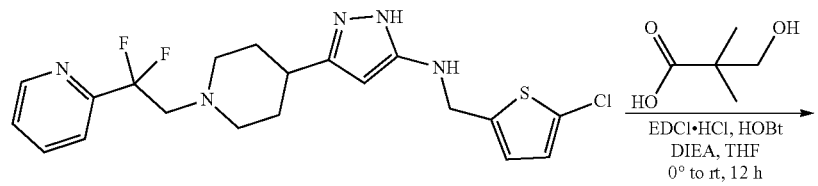

Compound 143

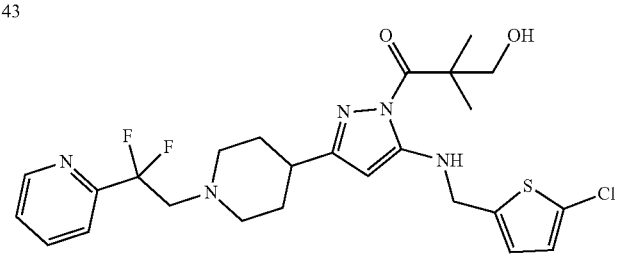

Compound 145

To a cooled solution (0° C.) of hydroxypivalic acid (89 mg, 0.76 mmol, 1.1 eq) in THF (10 mL) was added DIPEA (221 mg, 1.7 mmol, 2.5 eq), HOBt (46 mg, 0.34 mmol, 0.5 eq) and then EDCI.HCl (197 mg, 1.0 mmol, 1.5 eq). After stirring at 0° C. for 30 minutes, to the mixture was added N-((5-chlorothiophen-2-yl)methyl)-3-(1-(2,2-difluoro-2-(pyridin-2-yl)ethyl)piperidin-4-yl)-1H-pyrazol-5-amine (Compound 143, 300 mg, 0.68 mmol, 1.0 eq) and the mixture stirred at room temperature for another 12 hours. After completion, the reaction mixture was concentrated, poured into ice-cold water and extracted with ethyl acetate (3×50 mL). The combined organic layers were concentrated under reduced pressure. The residue was purified by preparative HPLC using 100% acetonitrile and 100% water to give 1-(5-(((5-chlorothiophen-2-yl)methyl)amino)-3-(1-(2, 2-difluoro-2-(pyridin-2-yl)ethyl)piperidin-4-yl)-1H-pyrazol-1-yl)-3-hydroxy-2,2-dimethylpropan-1-one (Compound 145, 76 mg, yield: 21%) m/z 540.63 [M+1]$^+$; $^1$H NMR (400 MHz, DMSO) δ 8.68 (d, J=4.4 Hz, 1H), 7.97 (td, J=7.8, 1.7 Hz, 1H), 7.71 (s, 1H), 7.63 (d, J=6.3 Hz, 1H), 7.54 (dd, J=7.4, 4.8 Hz, 1H), 7.03-6.89 (m, 2H), 5.35 (s, 1H), 4.81 (t, J=5.4 Hz, 1H), 4.39 (d, J=6.2 Hz, 2H), 3.84 (d, J=5.4 Hz, 2H), 3.21 (t, J=14.8 Hz, 2H), 2.82 (d, J=11.5 Hz, 2H), 2.34 (dd, J=23.2, 11.6 Hz, 4H), 1.72 (d, J=11.4 Hz, 2H), 1.50-1.35 (m, 2H), 1.29 (s, 6H) ppm.

Example 197—Preparation of Compound 146

The synthesis of Compound 146 followed the procedure of General Procedure 5 following:

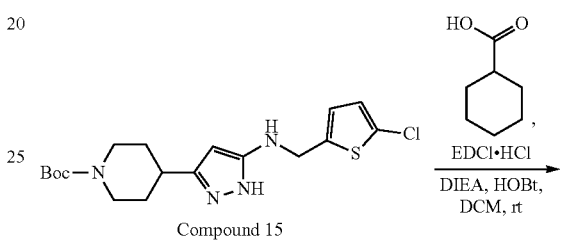

Compound 15

-continued

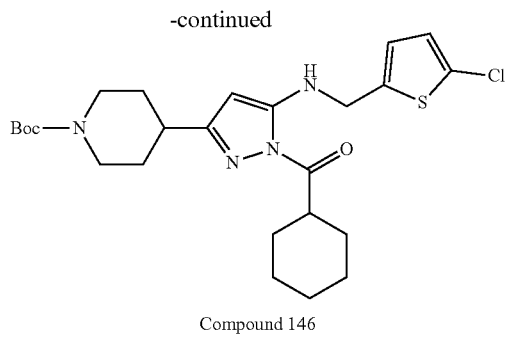

Compound 146

To a cooled (0° C.) solution of cyclohexanecarboxylic acid (181 mg, 1.51 mmol) in dichloromethane (10 mL) under nitrogen was added 1-(3-dimethylaminopropyl)-3-ethylcarbodiimide hydrochloride (EDCI.HCl, 361 mg, 1.89 mmol), followed by hydroxybenzotriazole (HOBt, 511 mg, 3.78 mmol). The reaction mixture was stirred for 10 minutes, then to the mixture was added diisopropylethylamine (DIEA, 0.64 mL, 3.78 mmol), followed by tert-butyl 4-(5-(((5-chlorothiophen-2-yl)methyl)amino)-1H-pyrazol-3-yl)piperidine-1-carboxylate (Compound 15, 500 mg, 1.26 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 30% ethyl acetate/petroleum ether, to afford product tert-butyl 4-(5-(((5-chlorothiophen-2-yl)methyl)amino)-1-(cyclohexanecarbonyl)-1H-pyrazol-3-yl)piperidine-1-carboxylate (Compound 146, 487 mg, yield: 60%) m/z 508.16 [M+1]$^+$; TLC System: 50% Ethyl acetate in hexane. 5 R$_f$-0.7.

Example 198—Preparation of Compound 147

The synthesis of Compound 147 followed the procedure of General Procedure 5 following:

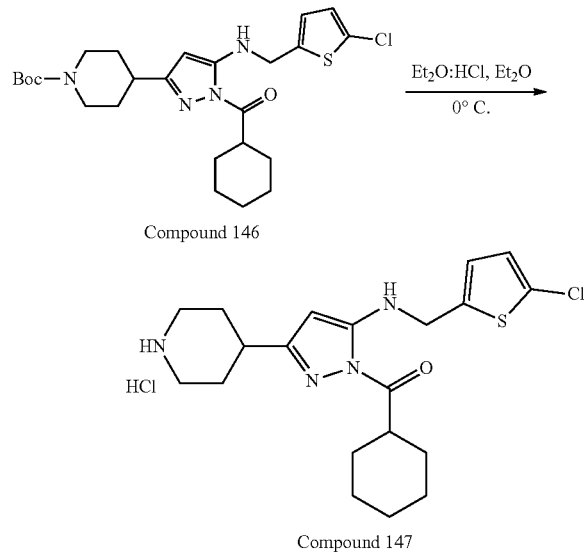

Compound 146

Compound 147

To a cooled (0° C.) solution of tert-butyl 4-(5-(((5-chlorothiophen-2-yl)methyl)amino)-1-(cyclohexanecarbonyl)-1H-pyrazol-3-yl)piperidine-1-carboxylate (200 mg, 0.39 mmol) in diethyl ether (2 mL) was added a solution of hydrogen chloride (1M) in diethyl ether (2 mL). The reaction mixture was stirred for 2 hr, and then evaporated under reduced pressure, triturated with diethyl ether and acetone to afford product (5-(((5-chlorothiophen-2-yl)methyl)amino)-3-(piperidin-4-yl)-1H-pyrazol-1-yl)(cyclohexyl)methanone hydrochloride (Compound 147, 100 mg, yield: 64%) as an off white solid. m/z 407.27 [(M−HCl)+1]$^+$; $^1$H NMR (400 MHz, DMSO-d$_6$) δ 8.70 (br s, 1H), 8.35 (br s, 1H), 7.65-7.63 (m, 1H), 6.95 (s, 2H), 5.39 (s, 1H), 4.43-4.41 (m, 2H), 3.40-3.26 (m, 3H), 2.98-2.77 (m, 3H), 2.01-1.67 (m, 8H), 1.41-1.24 (m, 4H); TLC System: 10% Methanol in dichloromethane. R$_f$-0.15.

Example 199—Preparation of Compound 148

The synthesis of Compound 148 followed the procedure of General

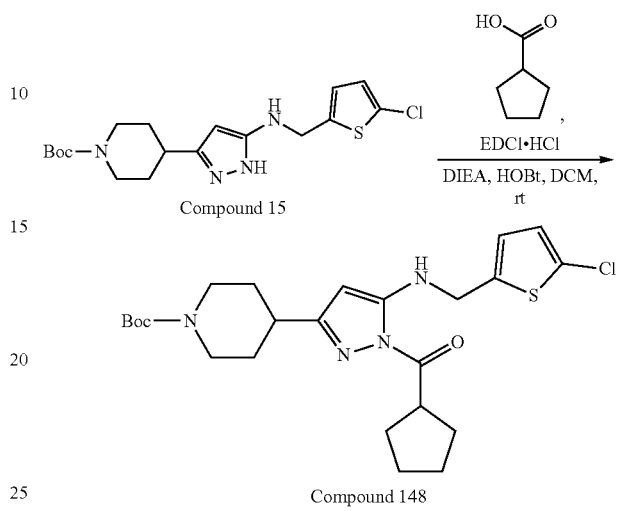

Compound 15

Compound 148

To a cooled (0° C.) solution of cyclopentanecarboxylic acid (172 mg, 1.51 mmol) in dichloromethane (10 mL) under nitrogen was added 1-(3-dimethylaminopropyl)-3-ethylcarbodiimide hydrochloride (EDCI.HCl, 361 mg, 1.89 mmol), followed by hydroxybenzotriazole (HOBt, 511 mg, 3.78 mmol). The reaction mixture was stirred for 10 minutes, then to the mixture was added diisopropylethylamine (DIEA, 0.64 mL, 3.78 mmol), followed by tert-butyl 4-(5-(((5-chlorothiophen-2-yl)methyl)amino)-1H-pyrazol-3-yl)piperidine-1-carboxylate (Compound 15, 500 mg, 1.26 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 30% ethyl acetate/petroleum ether, to afford product tert-butyl 4-(5-(((5-chlorothiophen-2-yl)methyl)amino)-1-(cyclopentanecarbonyl)-1H-pyrazol-3-yl)piperidine-1-carboxylate (Compound 148, 323 mg, yield: 52%) m/z 494.16 [M+1]$^+$; TLC System: 50% Ethyl acetate in hexane. R$_f$-0.7.

Example 200—Preparation of Compound 149

The synthesis of Compound 149 followed the procedure of General Procedure 5 following:

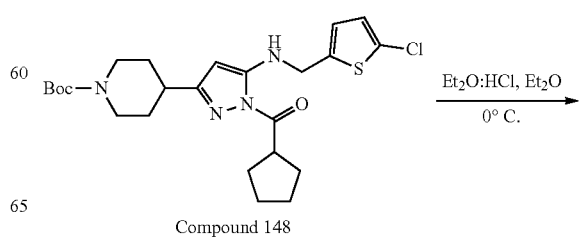

Compound 148

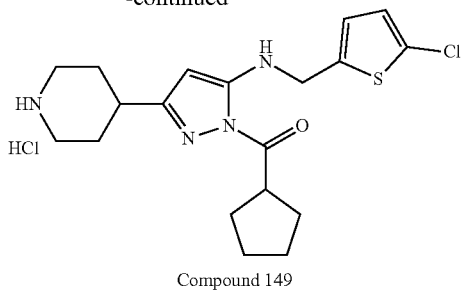

Compound 149

To a cooled (0° C.) solution of tert-butyl 4-(5-(((5-chlorothiophen-2-yl)methyl)amino)-1-(cyclopentanecarbonyl)-1H-pyrazol-3-yl)piperidine-1-carboxylate (200 mg, 0.40 mmol) in diethyl ether (2 mL) was added a solution of hydrogen chloride (1M) in diethyl ether (2 mL). The reaction mixture was stirred for 2 hr, and then evaporated under reduced pressure, triturated with diethyl ether and acetone to afford product (5-(((5-chlorothiophen-2-yl)methyl)amino)-3-(piperidin-4-yl)-1H-pyrazol-1-yl)(cyclopentyl)methanone (Compound 149, 60 mg, yield: 38%) as an off white solid. m/z 393.25 [(M−HCl)+1]⁺; ¹H NMR (400 MHz, DMSO-d₆) δ 8.70 (br s, 1H), 8.35 (br s, 1H), 7.65-7.63 (m, 1H), 6.95 (s, 2H), 5.39 (s, 1H), 4.43-4.41 (m, 2H), 3.40-3.26 (m, 3H), 2.98-2.77 (m, 3H), 2.01-1.67 (m, 8H), 1.41-1.24 (m, 4H); TLC System: 10% Methanol in dichloromethane. R_f-0.15.

Example 201—Preparation of Compound 150

The synthesis of Compound 150 followed the procedure of General Procedure 5 following:

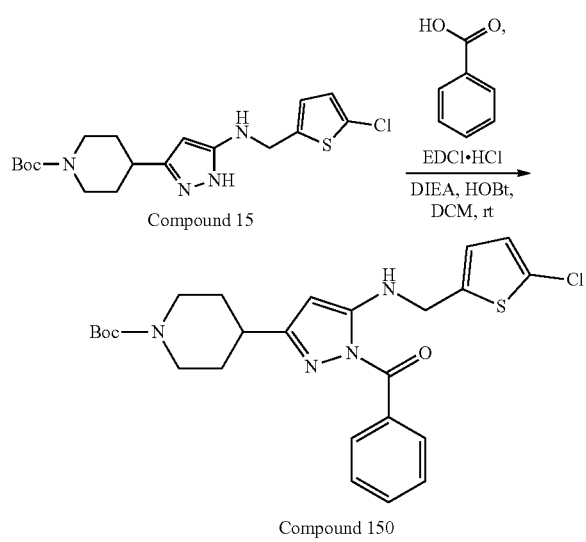

To a cooled (0° C.) solution of benzoic acid (184 mg, 1.51 mmol) in dichloromethane (10 mL) under nitrogen was added 1-(3-dimethylaminopropyl)-3-ethylcarbodiimide hydrochloride (EDCl.HCl, 361 mg, 1.89 mmol), followed by hydroxybenzotriazole (HOBt, 511 mg, 3.78 mmol). The reaction mixture was stirred for 10 minutes, then to the mixture was added diisopropylethylamine (DIEA, 0.64 mL, 3.78 mmol), followed by tert-butyl 4-(5-(((5-chlorothiophen-2-yl)methyl)amino)-1H-pyrazol-3-yl)piperidine-1-carboxylate (Compound 15, 500 mg, 1.26 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 30% ethyl acetate/petroleum ether, to afford product tert-butyl 4-(1-benzoyl-5-(((5-chlorothiophen-2-yl)methyl)amino)-1H-pyrazol-3-yl)piperidine-1-carboxylate (Compound 150, 487 mg, yield: 60%) m/z 502.16 [M+1]⁺; TLC System: 50% Ethyl acetate in hexane. R_f-0.6.

Example 202—Preparation of Compound 151

The synthesis of Compound 151 followed the procedure of General Procedure 5 following:

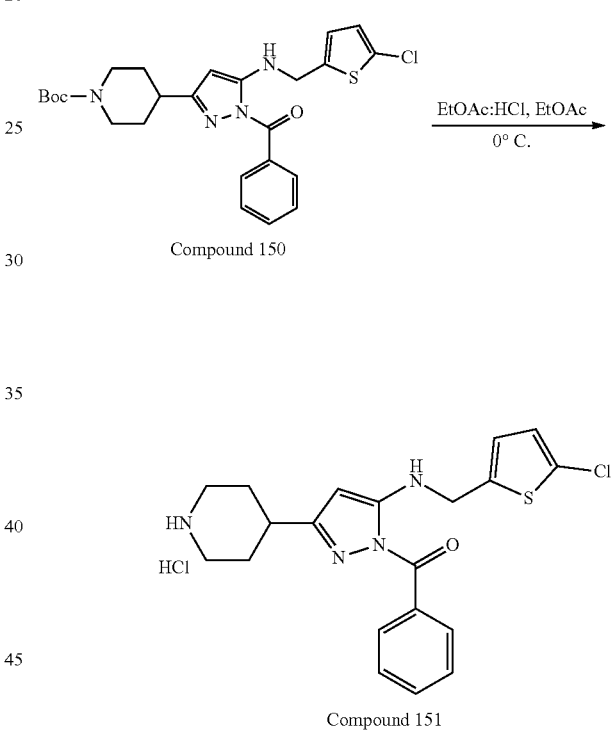

To a cooled (0° C.) solution of tert-butyl 4-(1-benzoyl-5-(((5-chlorothiophen-2-yl)methyl)amino)-1H-pyrazol-3-yl)piperidine-1-carboxylate (200 mg, 0.40 mmol) in ethyl acetate (3 mL) was added a solution of hydrogen chloride (1M) in ethyl acetate (3 mL). The reaction mixture was stirred for 6 hr, and then evaporated under reduced pressure, triturated with diethyl ether and acetone. The residue was recrystallized in isopropyl alcohol to afford product (5-(((5-chlorothiophen-2-yl)methyl)amino)-3-(piperidin-4-yl)-1H-pyrazol-1-yl)(phenyl)methanone hydrochloride (Compound 151, 40 mg, yield: 25%) as an off white solid. m/z 401.26 [(M−HCl)+1]⁺; ¹H NMR (400 MHz, DMSO-d₆) δ 8.79 (br s, 1H), 8.48 (br s, 1H), 7.97-7.94 (m, 2H), 7.81-7.79 (m, 1H), 7.64-6.97 (s, 3H), 5.51 (s, 1H), 4.51-4.49 (m, 2H), 3.31-3.23 (m, 2H), 2.99-2.77 (m, 3H), 2.02-1.96 (m, 2H), 1.78-1.66 (m, 2H); TLC System: 10% Methanol in dichloromethane. R_f-0.15.

Example 203—Preparation of Compound 152

The synthesis of Compound 152 followed the procedure of General

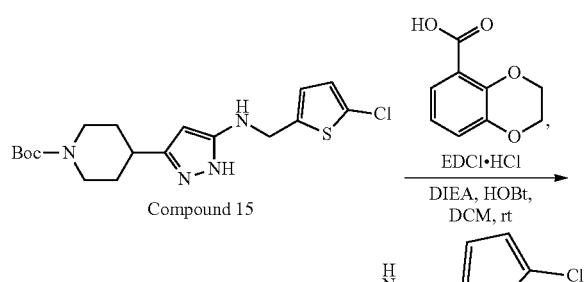

Compound 152

To a cooled (0° C.) solution of 2,3-dihydrobenzo[b][1,4]dioxine-5-carboxylic acid (273 mg, 1.51 mmol) in dichloromethane (10 mL) under nitrogen was added 1-(3-dimethylaminopropyl)-3-ethylcarbodiimide hydrochloride (EDCI.HCl, 361 mg, 1.89 mmol), followed by hydroxybenzotriazole (HOBt, 511 mg, 3.78 mmol). The reaction mixture was stirred for 10 minutes, then to the mixture was added diisopropylethylamine (DIEA, 0.64 mL, 3.78 mmol), followed by tert-butyl 4-(5-(((5-chlorothiophen-2-yl)methyl)amino)-1H-pyrazol-3-yl)piperidine-1-carboxylate (Compound 15, 500 mg, 1.26 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 30% ethyl acetate/petroleum ether, to afford product tert-butyl 4-(5-(((5-chlorothiophen-2-yl)methyl)amino)-1-(2,3-dihydrobenzo[b][1,4]dioxine-5-carbonyl)-1H-pyrazol-3-yl)piperidine-1-carboxylate (Compound 152, 318 mg, yield: 45%) m/z 560.16 [M+1]$^+$; TLC System: 50% Ethyl acetate in hexane. R$_f$-0.6.

Example 204—Preparation of Compound 153

The synthesis of Compound 153 followed the procedure of General Procedure 5 following:

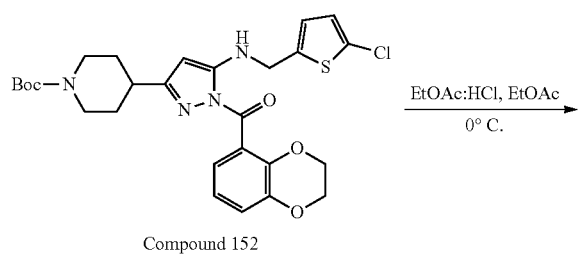

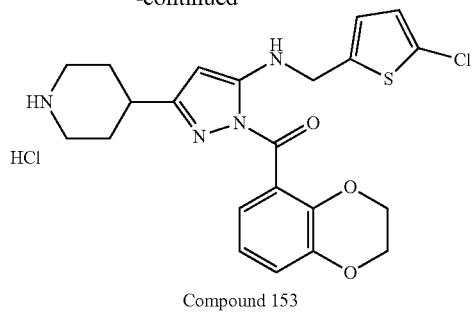

Compound 153

To a cooled (0° C.) solution of tert-butyl 4-(5-(((5-chlorothiophen-2-yl)methyl)amino)-1-(2,3-dihydrobenzo[b][1,4]dioxine-5-carbonyl)-1H-pyrazol-3-yl)piperidine-1-carboxylate (250 mg, 0.45 mmol) in ethyl acetate (3 mL) was added a solution of hydrogen chloride (1M) in ethyl acetate (3 mL). The reaction mixture was stirred for 7 hr, and then evaporated under reduced pressure, triturated with diethyl ether and acetone. The residue was recrystallized in isopropyl alcohol to afford product (5-(((5-chlorothiophen-2-yl)methyl)amino)-3-(piperidin-4-yl)-1H-pyrazol-1-yl)(2,3-dihydrobenzo[b][1,4]dioxin-5-yl)methanone hydrochloride (Compound 153, 150 mg, yield: 67%) as an off white solid. m/z 401.26 [(M−HCl)+1]$^+$; $^1$H NMR (400 MHz, DMSO-d$_6$) δ 8.79 (br s, 1H), 8.48 (br s, 1H), 7.97-7.94 (m, 2H), 7.81-7.79 (m, 1H), 7.04-6.97 (m, 5H), 5.51 (s, 1H), 4.51-4.49 (m, 2H), 3.31-3.23 (m, 2H), 2.99-2.77 (m, 3H), 2.02-1.96 (m, 2H), 1.78-1.66 (m, 2H); TLC System: 5% Methanol in dichloromethane. R$_f$-0.1.

Example 205—Preparation of Compound 154

The synthesis of Compound 154 followed the procedure of General Procedure 5 following:

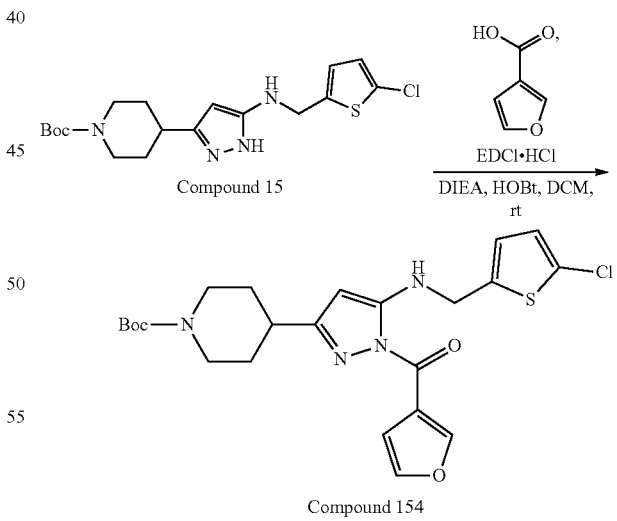

Compound 154

To a cooled (0° C.) solution of furan-3-carboxylic acid (169 mg, 1.51 mmol) in dichloromethane (10 mL) under nitrogen was added 1-(3-dimethylaminopropyl)-3-ethylcarbodiimide hydrochloride (EDCI.HCl, 361 mg, 1.89 mmol), followed by hydroxybenzotriazole (HOBt, 511 mg, 3.78 mmol). The reaction mixture was stirred for 10 minutes, then to the mixture was added diisopropylethylamine (DIEA, 0.64 mL, 3.78 mmol), followed by tert-butyl 4-(5-(((5-chlorothiophen-2-yl)methyl)amino)-1H-pyrazol-3-yl)piperidine-1-carboxylate (Compound 15, 500 mg, 1.26 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 30% ethyl acetate/petroleum ether, to afford product tert-butyl 4-(5-(((5-chlorothiophen-2-yl)methyl)amino)-1-(furan-3-carbonyl)-1H-pyrazol-3-yl)piperidine-1-carboxylate (Compound 154, 235 mg, yield: 38%) m/z 492.16 [M+1]$^+$; TLC System: 50% Ethyl acetate in hexane. $R_f$-0.6.

Example 206—Preparation of Compound 155

The synthesis of Compound 155 followed the procedure of General Procedure 5 following:

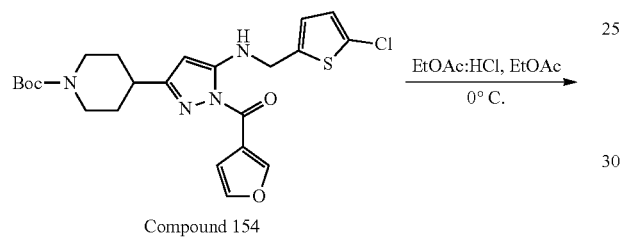

Compound 154

Compound 155

To a cooled (0° C.) solution of tert-butyl 4-(5-(((5-chlorothiophen-2-yl)methyl)amino)-1-(furan-3-carbonyl)-1H-pyrazol-3-yl)piperidine-1-carboxylate (100 mg, 0.20 mmol) in ethyl acetate (3 mL) was added a solution of hydrogen chloride (1M) in ethyl acetate (4 mL). The reaction mixture was stirred for 6 hr, and then evaporated under reduced pressure, triturated with diethyl ether and acetone. The residue was recrystallized in isopropyl alcohol to afford product (5-(((5-chlorothiophen-2-yl)methyl)amino)-3-(piperidin-4-yl)-1H-pyrazol-1-yl)(furan-3-yl)methanone hydrochloride (Compound 155, 30 mg, yield: 34%) as an off white solid. m/z 391.28 [(M−HCl)+1]$^+$; $^1$H NMR (400 MHz, DMSO-d$_6$) δ 8.82 (br s, 1H), 8.75 (s, 1H), 8.52 (br s, 1H), 7.86-7.84 (m, 1H), 7.82-7.77 (m, 1H), 7.04-6.95 (m, 3H), 5.50 (s, 1H), 4.50-4.48 (m, 2H), 3.33-3.27 (m, 2H), 2.99-2.85 (m, 3H), 2.11-2.07 (m, 2H), 1.81-1.77 (m, 2H); TLC System: 5% Methanol in dichloromethane. $R_f$-0.1.

Example 207—Preparation of Compound 156

The synthesis of Compound 156 followed the procedure of General Procedure 5 following:

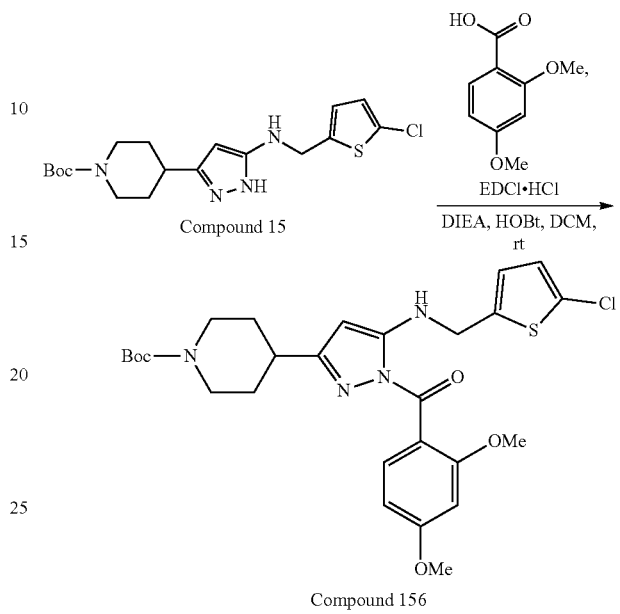

Compound 15

Compound 156

To a cooled (0° C.) solution of 2,4-dimethoxybenzoic acid (274 mg, 1.51 mmol) in dichloromethane (10 mL) under nitrogen was added 1-(3-dimethylaminopropyl)-3-ethylcarbodiimide hydrochloride (EDCI.HCl, 361 mg, 1.89 mmol), followed by hydroxybenzotriazole (HOBt, 511 mg, 3.78 mmol). The reaction mixture was stirred for 10 minutes, then to the mixture was added diisopropylethylamine (DIEA, 0.64 mL, 3.78 mmol), followed by tert-butyl 4-(5-(((5-chlorothiophen-2-yl)methyl)amino)-1H-pyrazol-3-yl)piperidine-1-carboxylate (Compound 15, 500 mg, 1.26 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 30% ethyl acetate/petroleum ether, to afford product tert-butyl 4-(5-(((5-chlorothiophen-2-yl)methyl)amino)-1-(2,4-dimethoxybenzoyl)-1H-pyrazol-3-yl)piperidine-1-carboxylate (Compound 156, 324 mg, yield: 45%) m/z 562.16 [M+1]$^+$; TLC System: 50% Ethyl acetate in hexane. $R_f$-0.6.

Example 208—Preparation of Compound 157

The synthesis of Compound 157 followed the procedure of General Procedure 5 following:

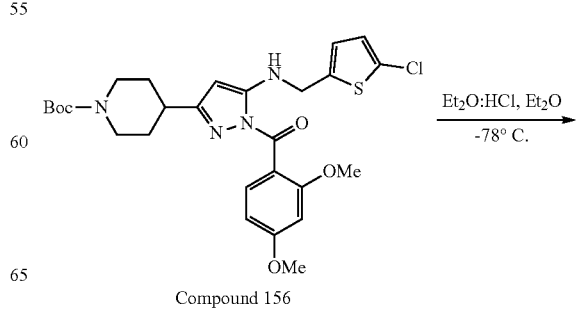

Compound 156

-continued

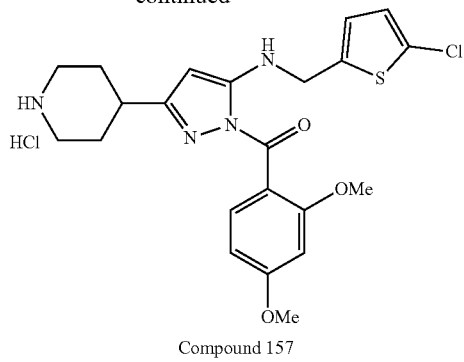

Compound 157

To a cooled (−78° C.) solution of tert-butyl 4-(5-(((5-chlorothiophen-2-yl)methyl)amino)-1-(2,4-dimethoxybenzoyl)-1H-pyrazol-3-yl)piperidine-1-carboxylate (250 mg, 0.45 mmol) in diethyl ether (3 mL) was added a solution of hydrogen chloride (1M) in diethyl ether (3 mL). The reaction mixture was stirred for 1 hr, and then evaporated under reduced pressure, triturated with diethyl ether and acetone. The residue was recrystallized in isopropyl alcohol to afford product (5-(((5-chlorothiophen-2-yl)methyl)amino)-3-(piperidin-4-yl)-1H-pyrazol-1-yl)(2,4-dimethoxyphenyl)methanone hydrochloride (Compound 157, 10 mg, yield: 4%) as an off white solid. m/z 461.26 [(M−HCl)+1]$^+$; $^1$H NMR (400 MHzCDCl$_3$) δ 7.45-7.43 (m, 2H), 6.81-6.76 (m, 2H), 6.53-6.50 (m, 2H), 5.23 (s, 1H), 4.42-4.41 (m, 2H), 3.85 (s, 3H), 3.80 (s, 3H), 3.37-3.33 (m, 2H), 2.99-2.75 (m, 3H), 2.07-2.05 (m, 2H), 1.95-1.92 (m, 2H); TLC System: 5% Methanol in dichloromethane. R$_f$-0.1.

Example 209—Preparation of Compound 158

The synthesis of Compound 158 followed the procedure of General Procedure 5 following:

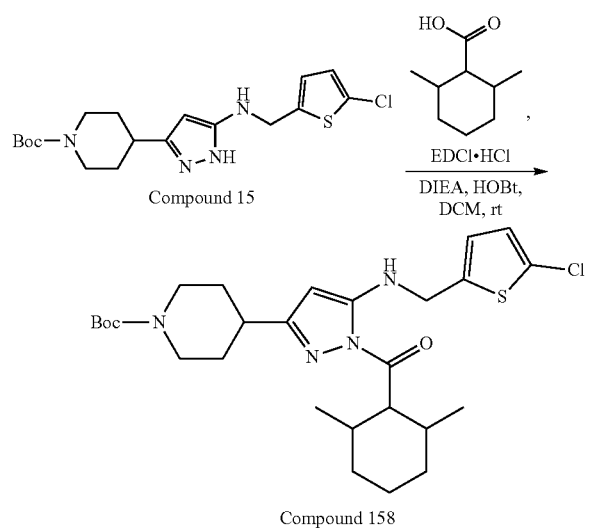

Compound 158

To a cooled (0° C.) solution of 2,6-dimethylcyclohexane-1-carboxylic acid (235 mg, 1.51 mmol) in dichloromethane (10 mL) under nitrogen was added 1-(3-dimethylaminopropyl)-3-ethylcarbodiimide hydrochloride (EDCI.HCl, 361 mg, 1.89 mmol), followed by hydroxybenzotriazole (HOBt, 511 mg, 3.78 mmol). The reaction mixture was stirred for 10 minutes, then to the mixture was added diisopropylethylamine (DIEA, 0.64 mL, 3.78 mmol), followed by tert-butyl 4-(5-(((5-chlorothiophen-2-yl)methyl)amino)-1H-pyrazol-3-yl)piperidine-1-carboxylate (Compound 15, 500 mg, 1.26 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 30% ethyl acetate/petroleum ether, to afford product tert-butyl 4-(5-(((5-chlorothiophen-2-yl)methyl)amino)-1-(2,6-dimethylcyclohexane-1-carbonyl)-1H-pyrazol-3-yl)piperidine-1-carboxylate (Compound 158, 371 mg, yield: 55%) m/z 536.16 [M+1]$^+$; TLC System: 50% Ethyl acetate in hexane. R$_f$-0.8.

Example 210—Preparation of Compound 159

The synthesis of Compound 159 followed the procedure of General Procedure 5 following:

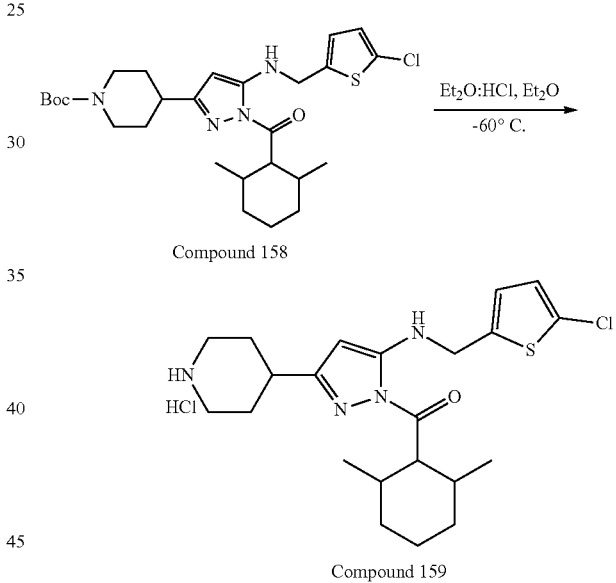

Compound 159

To a cooled (−60° C.) solution of tert-butyl 4-(5-(((5-chlorothiophen-2-yl)methyl)amino)-1-(2,6-dimethylcyclohexane-1-carbonyl)-1H-pyrazol-3-yl)piperidine-1-carboxylate (15 mg, 0.03 mmol) in diethyl ether (3 mL) was added a solution of hydrogen chloride (1M) in diethyl ether (0.5 mL). The reaction mixture was stirred for 1 hr, and then evaporated under reduced pressure, triturated with diethyl ether and acetone to afford product (5-(((5-chlorothiophen-2-yl)methyl)amino)-3-(piperidin-4-yl)-1H-pyrazol-1-yl)(2,6-dimethylcyclohexyl)methanone hydrochloride (Compound 159, 10 mg, yield: 71%) as an off white solid. m/z 435.34 [(M−HCl)+1]$^+$; $^1$H NMR (400 MHz, DMSO-d$_6$) δ 8.66 (br s, 1H), 8.38 (br s, 1H), 7.72-7.69 (m, 1H), 6.96-6.94 (m, 2H), 5.40 (s, 1H), 4.44-4.43 (m, 2H), 3.40-3.26 (m, 3H), 3.00-2.77 (m, 3H), 2.32-2.28 (m, 1H), 2.01-1.87 (m, 3H), 1.75-1.65 (m, 3H), 1.61-1.42 (m, 4H), 0.82 (s, 3H), 0.81 (s, 3H); TLC System: 10% Methanol in dichloromethane. R$_f$-0.15.

Example 211—Preparation of Compound 160

The synthesis of Compound 160 followed the procedure of General Procedure 5 following:

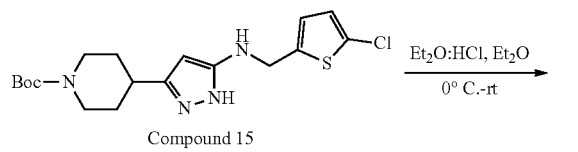

Compound 15

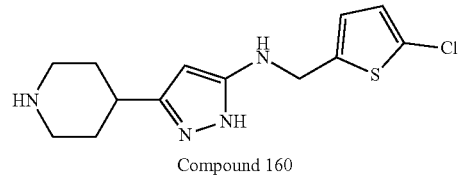

Compound 160

To a cooled (0° C.) solution of tert-butyl 4-(5-(((5-chlorothiophen-2-yl)methyl)amino)-1H-pyrazol-3-yl)piperidine-1-carboxylate (3 g, 7.5 mmol) in diethyl ether (20 mL) was added a solution of hydrogen chloride (1M) in diethyl ether (20 mL). The reaction mixture was stirred for 2 hr, and then evaporated under reduced pressure, triturated with diethyl ether and acetone to afford product N-((5-chlorothiophen-2-yl)methyl)-3-(piperidin-4-yl)-1H-pyrazol-5-amine hydrochloride (Compound 160, 2.8 g, yield: 91%) as an off white solid. m/z 297.21 ((M−HCl)+1]$^+$; TLC System: 10% Methanol in chloroform. R$_f$-0.1.

Example 212—Preparation of Compound 161

The synthesis of Compound 161 followed the procedure of General Procedure 5 following:

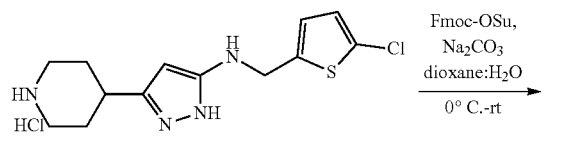

Compound 160

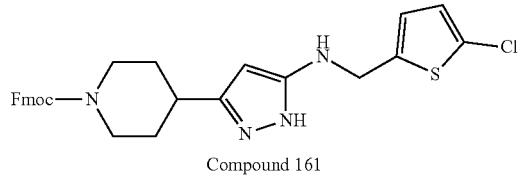

Compound 161

To a cooled (0° C.) solution of N-((5-chlorothiophen-2-yl)methyl)-3-(piperidin-4-yl)-1H-pyrazol-5-amine hydrochloride (2.8 g, 3.01 mmol) in dioxane (70 mL) was added a solution of sodium carbonate (0.63 g, 6.02 mmol) in water (42 mL), followed by Fmoc succinimide (0.81 g, 2.4 mmol). The reaction mixture was stirred for 2 hr and allowed to reach room temperature, then poured into water (100 mL) and extracted with ethyl acetate (2×50 mL). The combined organic phases were dried over anhydrous sodium sulfate, filtered and evaporated under reduced pressure. The residue was purified by silica gel column chromatography (100-200 mesh), eluting with ethyl acetate, to afford product (9H-fluoren-9-yl)methyl 4-(5-(((5-chlorothiophen-2-yl)methyl)amino)-1H-pyrazol-3-yl)piperidine-1-carboxylate (Compound 161, 1.2 g, yield: 76%) as an off white fluffy solid. m/z 505.3 [M+1]$^+$; TLC System: 10% Methanol in dichloromethane. R$_f$-0.5.

Example 213—Preparation of Compound 162

The synthesis of Compound 162 followed the procedure of General Procedure 5 following:

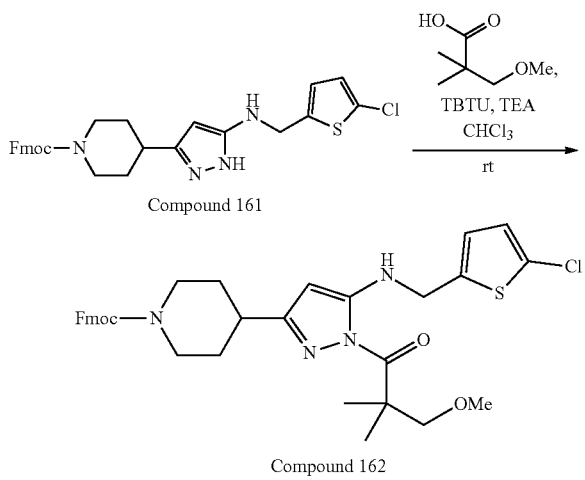

Compound 161

Compound 162

To a solution of (9H-fluoren-9-yl)methyl 4-(5-(((5-chlorothiophen-2-yl)methyl)amino)-1H-pyrazol-3-yl)piperidine-1-carboxylate (Compound 161, 300 mg, 0.48 mmol) and 3-methoxy-2,2-dimethylpropanoic acid (76 mg, 0.58 mmol) in chloroform (5 mL) under nitrogen at room temperature, was added O-(Benzotriazol-1-yl)-N,N,N',N'-tetramethyluronium tetrafluoroborate (TBTU, 171 mg, 0.53 mmol), followed by triethylamine (TEA, 0.1 mL, 0.72 mmol). The reaction mixture was stirred at room temperature for 4 hr, diluted with water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 20% ethyl acetate/petroleum ether, to afford (9H-fluoren-9-yl)methyl 4-(5-(((5-chlorothiophen-2-yl)methyl)amino)-1-(3-methoxy-2,2-dimethylpropanoyl)-1H-pyrazol-3-yl)piperidine-1-carboxylate (Compound 162, 300 mg, yield: 82%). m/z 605.19 [M+1]$^+$; TLC System: 10% Methanol in dichloromethane. R$_f$-0.9.

Example 214—Preparation of Compound 163

The synthesis of Compound 163 followed the procedure of General Procedure 5 following:

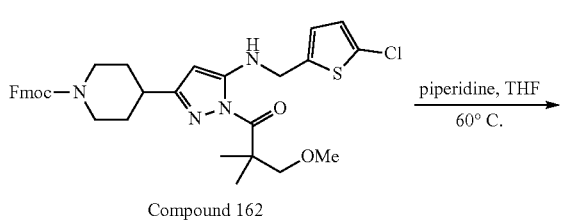

Compound 162

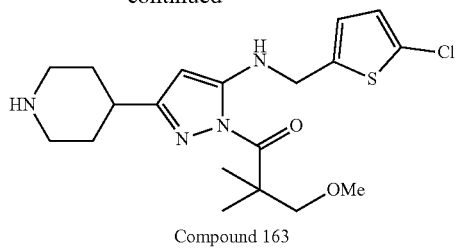

Compound 163

To a solution of (9H-fluoren-9-yl)methyl 4-(5-(((5-chlorothiophen-2-yl)methyl)amino)-1-(3-methoxy-2,2-dimethylpropanoyl)-1H-pyrazol-3-yl)piperidine-1-carboxylate (200 mg, 0.31 mmol) in tetrahydrofurane (2 mL) was added piperidine (0.8 mL). The reaction mixture was stirred for 30 min, and then evaporated under reduced pressure. The residue was purified by silica gel column chromatography (100-200 mesh), eluting with 10% methanol/dichloromethane, to afford product 1-(5-(((5-chlorothiophen-2-yl)methyl)amino)-3-(piperidin-4-yl)-1H-pyrazol-1-yl)-3-methoxy-2,2-dimethylpropan-1-one (Compound 163, 40 mg, yield: 31%) as an off white solid. m/z 411.22 [(M+1)$^+$; $^1$H NMR (400 MHz, CDCl$_3$) δ 9.80 (br s, 1H), 8.38 (br s, 1H), 7.49 (s, 1H), 6.75 (s, 2H), 5.14 (s, 1H), 4.35-4.34 (m, 2H), 3.50-3.47 (m, 2H), 3.27 (s, 3H), 3.10-3.07 (m, 2H), 2.86 (br s, 1H), 2.21-2.00 (m, 4H), 1.41 (s, 6H); TLC System: 10% Methanol in dichloromethane. R$_f$-0.15.

Example 215—Preparation of Compound 164

The synthesis of Compound 164 followed the procedure of General Procedure 5 following:

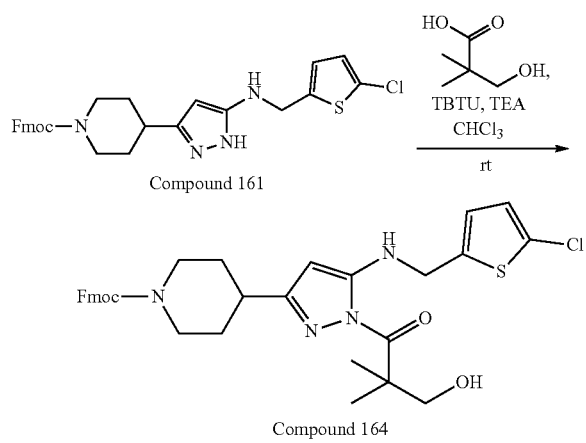

To a solution of (9H-fluoren-9-yl)methyl 4-(5-(((5-chlorothiophen-2-yl)methyl)amino)-1H-pyrazol-3-yl)piperidine-1-carboxylate (Compound 161, 300 mg, 0.48 mmol) and 3-hydroxy-2,2-dimethylpropanoic acid (59 mg, 0.58 mmol) in chloroform (5 mL) under nitrogen at room temperature, was added O-(Benzotriazol-1-yl)-N,N,N',N'-tetramethyluronium tetrafluoroborate (TBTU, 171 mg, 0.53 mmol), followed by triethylamine (TEA, 0.1 mL, 0.72 mmol). The reaction mixture was stirred at room temperature for 4 hr, diluted with water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 20% ethyl acetate/petroleum ether, to afford (9H-fluoren-9-yl)methyl 4-(5-(((5-chlorothiophen-2-yl)methyl)amino)-1-(3-hydroxy-2,2-dimethylpropanoyl)-1H-pyrazol-3-yl)piperidine-1-carboxylate (Compound 164, 250 mg, yield: 71%). m/z 620.19 [M+1]$^+$; TLC System: 10% Methanol in dichloromethane. R$_f$-0.85.

Example 216—Preparation of Compound 165

The synthesis of Compound 165 followed the procedure of General Procedure 5 following:

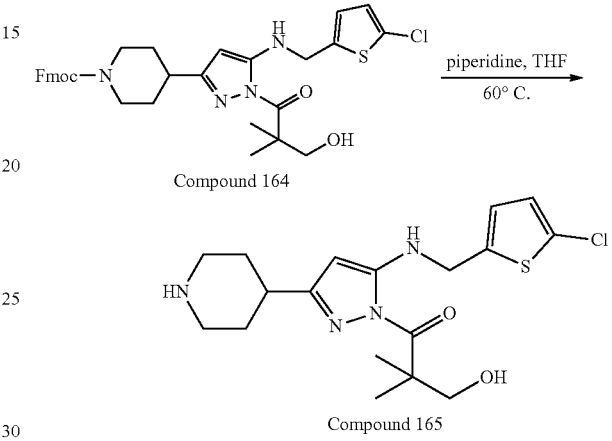

To a solution of (9H-fluoren-9-yl)methyl 4-(5-(((5-chlorothiophen-2-yl)methyl)amino)-1-(3-hydroxy-2,2-dimethylpropanoyl)-1H-pyrazol-3-yl)piperidine-1-carboxylate (250 mg, 0.31 mmol) in tetrahydrofurane (10 mL) was added piperidine (1 mL). The reaction mixture was stirred for 30 min, and then evaporated under reduced pressure. The residue was purified by silica gel column chromatography (100-200 mesh), eluting with 10% methanol/dichloromethane, to afford product 1-(5-(((5-chlorothiophen-2-yl)methyl)amino)-3-(piperidin-4-yl)-1H-pyrazol-1-yl)-3-hydroxy-2,2-dimethylpropan-1-one (Compound 165, 60 mg, yield: 48%) as an off white solid. m/z 397.31 [(M+1)$^+$; $^1$H NMR (400 MHz, CDCl$_3$) δ 9.82 (br s, 1H), 7.49-7.47 (m, 1H), 6.77-6.76 (m, 2H), 5.21 (s, 1H), 4.38-4.36 (m, 2H), 4.00 (br s, 1H), 3.78 (s, 2H), 3.51-3.48 (m, 2H), 3.07-3.02 (m, 2H), 2.87-2.82 (m, 1H), 2.23-2.12 (m, 4H), 1.43 (s, 6H); TLC System: 10% Methanol in dichloromethane. R$_f$-0.15.

Example 217—Characterization of Compound 166

The synthesis of Compound 166 followed the procedure of General Procedure 5.

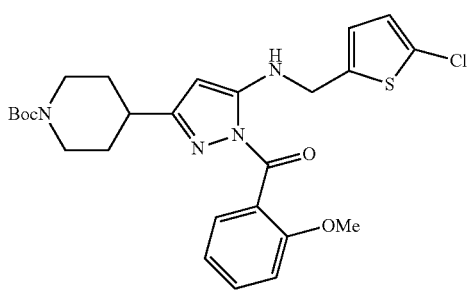 [SMILES: COc1ccccc1C(=O)n1nc(C2CCN(C(=O)OC(C)(C)C)CC2)cc1NCc1ccc(Cl)s1]

m/z 531.30 [M+H]+. 1H NMR (400 MHz, CDCl3) δ 7.4 (m, 3H), 7.0 (m, 2H), 6.8 (m, 2H), 5.2 (s, 1H), 4.4 (m, 2H), 4.1 (m, 2H), 3.8 (s, 3H), 2.8 (m, 2H), 2.6 (m, 2H), 1.8 (m, 2H), 1.4 (s, 9H).

Example 218—Characterization of Compound 167

The synthesis of Compound 167 followed the procedure of General Procedure 6c.

Compound 167

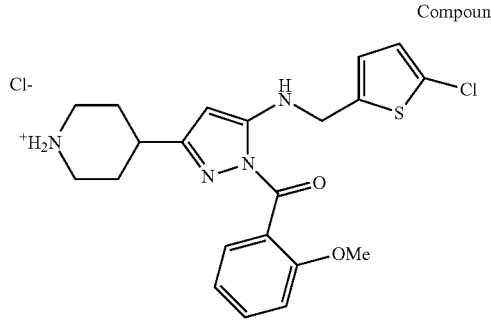

m/z 431.25 [M+H]+. 1H NMR (400 MHz, DMSO-d6) δ 8.2-8.8 (br m, 3H), 7.7 (m, 1H), 7.5 (m, 1H), 7.4 (m, 1H), 7.1 (m, 1H), 7.0 (m, 3H), 5.4 (s, 1H), 4.5 (m, 2H), 3.7 (s, 3H), 3.2 (m, 2H), 2.9 (m, 2H), 2.7 (m, 2H), 1.9 (m, 2H), 1.6 (m, 2H).

Example 219—Characterization of Compound 168

The synthesis of Compound 168 followed the procedure of General Procedure 7.

Compound 168

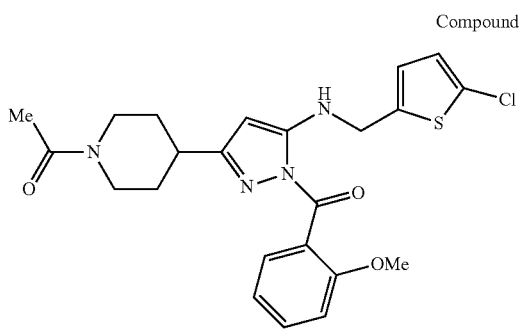

m/z 473.27 [M+H]+. 1H NMR (400 MHz, CDCl3) δ 7.4 (m, 3H), 7.0 (m, 2H), 6.8 (m, 2H), 5.2 (s, 1H), 4.5 (m, 1H), 4.4 (m, 2H), 3.8 (s, 3H), 3.8 (m, 1H), 3.1 (m, 1H), 2.7 (m, 2H), 2.1 (s, 3H), 1.8 (m, 2H), 1.5 (m, 1H).

Example 220—Characterization of Compound 169

The synthesis of Compound 169 followed the procedure of General Procedure 7.

Compound 169

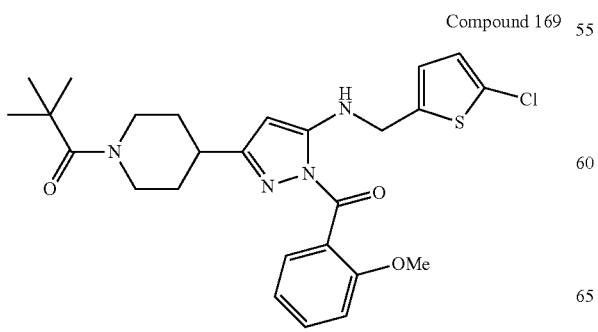

m/z 515.24 [M+H]+. 1H NMR (400 MHz, CDCl3) δ 7.5 (m, 3H), 7.0 (m, 2H), 6.8 (m, 2H), 5.2 (s, 1H), 4.4 (m, 1H), 4.3 (m, 2H), 3.8 (s, 3H), 2.9 (m, 2H), 2.7 (m, 1H), 1.9 (m, 2H), 1.6 (m, 1H), 1.5 (m, 1H), 1.3 (s, 9H).

Example 221—Characterization of Compound 170

The synthesis of Compound 170 followed the procedure of General Procedure 5.

Compound 170

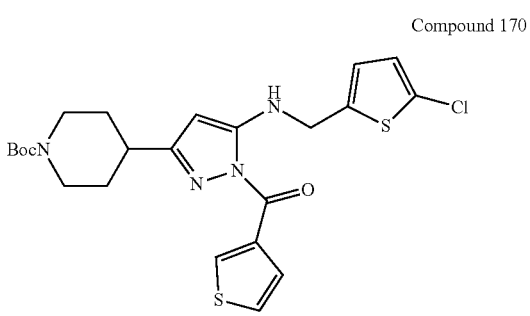 [SMILES: CC(C)(C)OC(=O)N1CCC(c2cc(NCc3ccc(Cl)s3)n(C(=O)c3ccsc3)n2)CC1]

m/z 507.24 [M+H]+. 1H NMR (400 MHz, CDCl3) δ 8.9 (s, 1H), 7.9 (m, 1H), 7.6 (m, 1H), 7.3 (m, 1H), 6.8 (m, 2H), 5.3 (s, 1H), 4.4 (m, 2H), 4.2 (br s, 2H), 2.9 (m, 2H), 2.7 (m, 1H), 1.9 (m, 2H), 1.6 (m, 2H), 1.4 (s, 9H).

Example 222—Characterization of Compound 171

The synthesis of Compound 171 followed the procedure of General Procedure 6c.

Compound 171

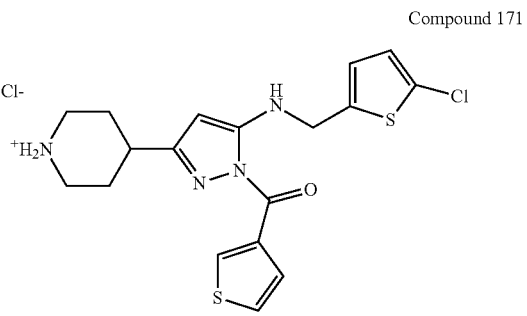 [SMILES: [Cl-] ; O=C(c1ccsc1)n1nc(C2CC[NH2+]CC2)cc1NCc1ccc(Cl)s1]

m/z 407.14 [M+H]+. 1H NMR (400 MHz, DMSO-d6) δ 8.9 (s, 1H), 8.6 (br s, 1H), 8.3 (br s, 1H), 7.9 (m, 1H), 7.8 (m, 1H), 7.6 (m, 1H), 7.0 (m, 2H), 5.5 (s, 1H), 4.5 (m, 2H), 3.2 (m, 2H), 3.0 (m, 2H), 2.8 (m, 1H), 2.1 (m, 2H), 1.8 (m, 2H).

Example 223—Characterization of Compound 172

The synthesis of Compound 172 followed the procedure of General Procedure 7.

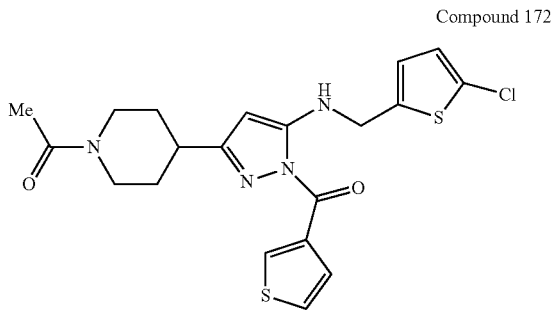 [SMILES: CC(=O)N1CCC(c2cc(NCc3ccc(Cl)s3)n(C(=O)c3ccsc3)n2)CC1]

Compound 172 m/z 449.16 [M+H]+. 1H NMR (400 MHz, CDCl3) δ 8.9 (s, 1H), 7.9 (m, 1H), 7.6 (m, 1H), 7.3 (m, 1H), 6.8 (m, 2H), 5.2 (s, 1H), 4.6 (m, 1H), 4.4 (m, 2H), 3.9 (m, 1H), 3.2 (m, 1H), 2.7-2.9 (m, 2H), 2.1 (s, 3H), 2.0 (m, 2H), 1.7 (m, 3H).

Example 224—Characterization of Compound 173

The synthesis of Compound 173 followed the procedure of General Procedure 7.

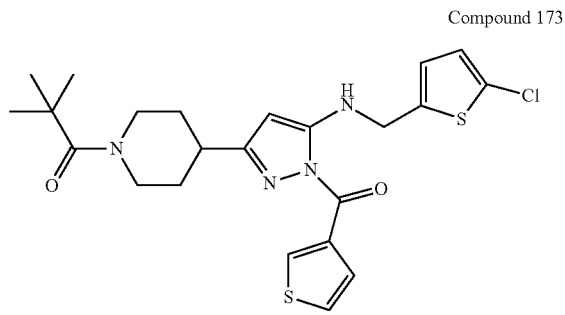 [SMILES: CC(C)(C)C(=O)N1CCC(c2cc(NCc3ccc(Cl)s3)n(C(=O)c3ccsc3)n2)CC1]

Compound 173 m/z 491.18 [M+H]+. 1H NMR (400 MHz, CDCl3) δ 8.9 (s, 1H), 7.9 (m, 1H), 7.6 (m, 1H), 7.3 (m, 1H), 6.8 (m, 2H), 5.2 (s, 1H), 4.4-4.5 (m, 4H), 3.0 (m, 2H), 2.8 (m, 1H), 2.0 (m, 2H), 1.7 (m, 2H), 1.3 (s, 9H).

Example 225—Characterization of Compound 174

The synthesis of Compound 174 followed the procedure of General Procedure 5.

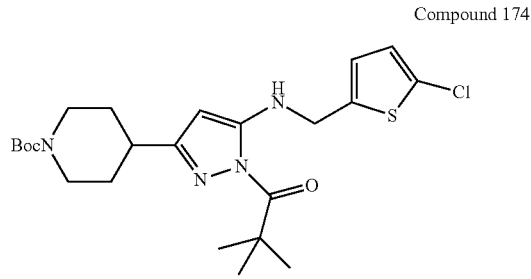 [SMILES: CC(C)(C)OC(=O)N1CCC(c2cc(NCc3ccc(Cl)s3)n(C(=O)C(C)(C)C)n2)CC1]

Compound 174 m/z 481.33 [M+H]+. 1H NMR (400 MHz, DMSO-d6) δ 7.7 (m, 1H), 7.0 (m, 2H), 5.4 (s, 1H), 4.4 (m, 2H), 3.9 (m, 2H), 2.8-2.9 (br s, 2H), 2.7 (m, 1H), 1.8 (m, 2H), 1.4 (m, 18H).

Example 226—Characterization of Compound 175

The synthesis of Compound 175 followed the procedure of General Procedures 6c and 7.

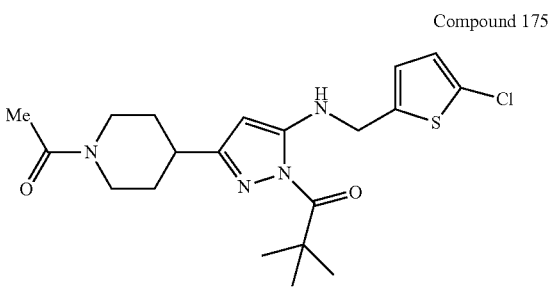 [SMILES: CC(=O)N1CCC(c2cc(NCc3ccc(Cl)s3)n(C(=O)C(C)(C)C)n2)CC1]

Compound 175 m/z 423.26 [M+H]+. 1H NMR (400 MHz, CDCl3) δ 7.5 (m, 1H), 6.8 (m, 2H), 5.1 (s, 1H), 4.5 (m, 1H), 4.4 (m, 2H), 3.8 (m, 1H), 3.2 (m, 1H), 2.7-2.9 (m, 2H), 2.1 (s, 3H), 2.0 (m, 2H), 1.6 (m, 2H), 1.4 (s, 9H).

Example 227—Characterization of Compound 176

The synthesis of Compound 176 followed the procedure of General Procedures 6c and 7.

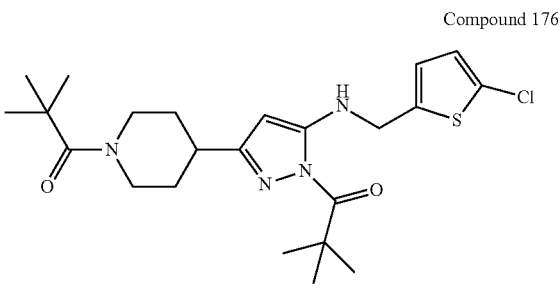 [SMILES: CC(C)(C)C(=O)N1CCC(c2cc(NCc3ccc(Cl)s3)n(C(=O)C(C)(C)C)n2)CC1]

Compound 176 m/z 465.34 [M+H]+. 1H NMR (400 MHz, CDCl3) δ 7.5 (m, 1H), 6.8 (m, 2H), 5.1 (s, 1H), 4.3-4.4 (m, 4H), 3.0 (m, 2H), 2.8 (m, 1H), 2.0 (m, 2H), 1.6 (m, 2H), 1.5 (s, 9H), 1.3 (s, 9H).

Example 228—Preparation of Intermediate 55

The synthesis of Intermediate 55 followed the procedure of General Procedure 7 following:

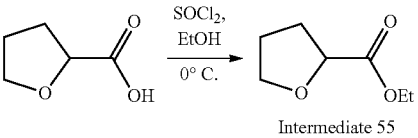 [SMILES: O=C(O)C1CCCO1 ; CCOC(=O)C1CCCO1]

Intermediate 55

To a cooled solution (0° C.) of tetrahydrofuran-2-carboxylic acid (5.8 g, 43 mmol) in Ethanol (40 mL) was added thionyl chloride (9.6 mL, 129 mmol). After stirring at this temperature for 2 hours, the mixture was concentrated under reduced pressure. The mixture was diluted with water (20 mL) and extracted into Diethyl ether (3×100 mL). The combined organic layers were dried over sodium sulfate, filtered and concentrated under reduced pressure to give ethyl tetrahydrofuran-2-carboxylate (Intermediate 55, 6 g, yield: 96%) as an oily residue that was used without further purification into the next step. m/z 145.03 [M+H]$^+$; TLC System: 10% Methanol-dichloromethane; R$_f$-0.6.

Example 229—Preparation of Intermediate 56

The synthesis of Intermediate 56 followed the procedure of General Procedure 2 following:

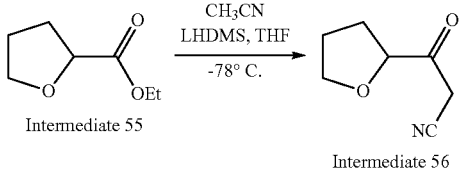 [SMILES: CCOC(=O)C1CCCO1 ; N#CCC(=O)C1CCCO1]

To a cooled (0° C.) solution of ethyl tetrahydrofuran-2-carboxylate (Intermediate 55, 6 g, 41.66 mmol in THF (100 mL), dry acetonitrile (3.4 mL, 83.33 mmol) was added. After 10 min, LHDMS (1M in THF, 13.9 g, 83.3 mmol) was added. After stirring at 0° C. for 2 hours, the mixture was quenched with saturated citric acid solution until pH=5 and extracted into Ethyl acetate (3×200 mL). The combined organic layers were dried over sodium sulfate, filtered and concentrated under reduced pressure to give 3-oxo-3-(tetrahydrofuran-2-yl)propanenitrile (Intermediate 56, 7.5 g, yield: 99%) as an oily residue that was used without further purification into the next step. m/z 140.02 [M+H]$^+$; TLC System: 10% Methanol-dichloromethane; R$_f$-0.4.

Example 230—Preparation of Compound 177

The synthesis of Compound 177 followed the procedure of General Procedure 3 following:

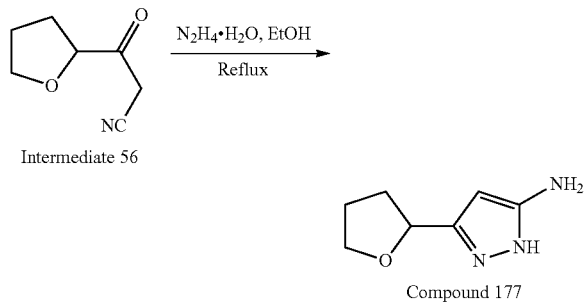

To a solution of 3-oxo-3-(tetrahydrofuran-2-yl)propanenitrile (Intermediate 56, 7.5 g, 53.95 mmol) in ethanol (90 mL) was added hydrazine hydrate (N$_2$H$_4$.H$_2$O, 4.04 mL, 24 mmol) and the reaction mixture was then heated to 90° C. for 5 hours. The reaction mixture was cooled to room temperature and the volatiles were evaporated. The residue was purified by neutral alumina column chromatography (100-300 mesh), eluting with 2% MeOH-dichloromethane, to afford 3-(tetrahydrofuran-2-yl)-1H-pyrazol-5-amine (Compound 177, 2 g, 24%) as an orange liquid; m/z 154.13 [M+H]$^+$; TLC System: 5% Methanol-dichloromethane. R$_f$-0.5.

Example 231—Preparation of Compound 178

The synthesis of Compound 178 followed the procedure of General Procedure 4 following:

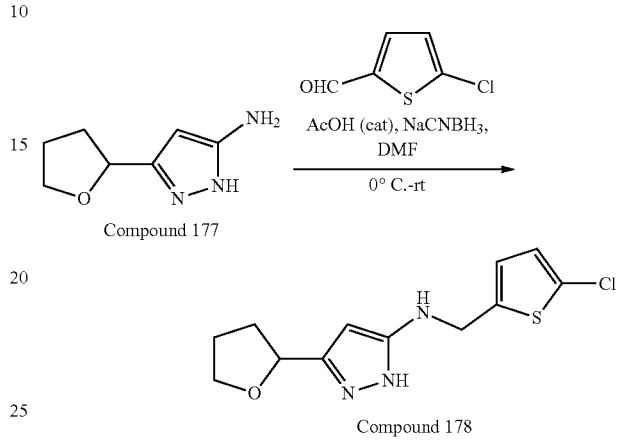

To a cooled solution (0° C.) of 3-(tetrahydrofuran-2-yl)-1H-pyrazol-5-amine (Compound 177, 2 g, 13.1 mmol) in dry DMF (20 mL) was added 5-chlorothiophene-2-carbaldehyde (1.97 mL, 19.6 mmol) and acetic acid (2 mL). The reaction mixture was stirred at room temperature for 2 hours. (Formation of imine was observed as a less polar spot on TLC). The reaction mixture was cooled (0° C.) and sodium cyanoborohydride (1.64 g, 26.1 mmol) was added portionwise and a catalytic amount of acetic acid. After 2 hours, the reaction mixture was quenched with ice-cold water (50 mL), and extracted into Ethyl acetate (3×100 mL). The combined organic layers were washed with saturated NaHCO$_3$ (2×50 mL), water (2×50 mL) and brine (2×50 mL) and dried over sodium sulfate, filtered and concentrated under reduced pressure. The residue was purified by silica gel column chromatography (100-200 mesh), eluting with 10% diethyl ether/dichloromethane, to afford N-((5-chlorothiophen-2-yl)methyl)-3-(tetrahydrofuran-2-yl)-1H-pyrazol-5-amine (Compound 178, 650 mg, 6.2%) as a light yellow gummy liquid; m/z 284.13 [M+H]$^+$. $^1$H NMR (400 MHz, DMSO-d$_6$) δ 11.50 (br s, 1H), 6.91-6.84 (m, 2H), 5.74 (br s, 1H), 5.37 (s, 1H), 4.70 (s, 2H), 4.29 (br s, 2H), 3.84-3.79 (m, 1H), 3.71-3.66 (m, 1H), 2.13-2.11 (m, 1H), 1.91-1.79 (m, 3H) ppm; TLC System: 50% Ethyl acetate in hexane R$_f$-0.5.

Example 232—Preparation of Compound 179

The synthesis of Compound 179 followed the procedure of General Procedure 5 following:

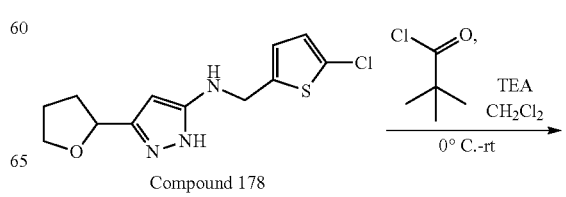

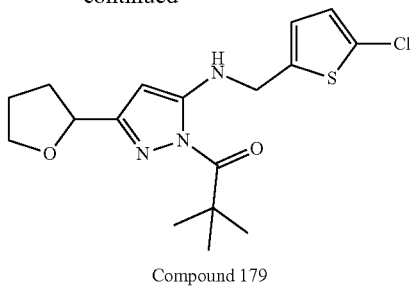

Compound 179

To a cooled solution (0° C.) of N-((5-chlorothiophen-2-yl)methyl)-3-(tetrahydrofuran-2-yl)-1H-pyrazol-5-amine (Compound 178, 200 mg, 0.70 mmol) in dry dichloromethane (8 mL) was added triethylamine (TEA, 0.10 mL, 0.7 mmol), followed by trimethylacetyl chloride (0.06 mL, 0.56 mmol). After stirring at room temperature for 2 hours, the reaction mixture was diluted with water (50 mL) and extracted into dichloromethane (2×25 mL). The combined organic layers were washed with saturated NaHCO₃ (2×10 mL) and water (2×10 mL) and dried over sodium sulfate, filtered and concentrated under reduced pressure. The residue was purified by preparative silica gel TLC (100-200 mesh), eluting with 15% Ethyl acetate/hexanes, to afford 1-(5-(((5-chlorothiophen-2-yl)methyl)amino)-3-(tetrahydrofuran-2-yl)-1H-pyrazol-1-yl)-2,2-dimethylpropan-1-one (Compound 179, 35 mg, 14%) as a colorless liquid. MS (ESI): m/z 368.2 [M+H]⁺. ¹H NMR (400 MHz, DMSO-d₆) δ 7.71 (s, 1H), 6.96 (s, 2H), 5.41 (s, 1H), 4.66 (s, 1H), 4.43 (s, 3H), 3.82-3.80 (m, 1H), 3.73-3.71 (m, 1H), 2.12-2.11 (m, 1H), 1.94-1.89 (m, 3H) ppm; TLC System: 30% Ethyl acetate in hexane. R$_f$-0.6.

Example 233—Preparation of Compound 180

The synthesis of Compound 180 followed the procedure of General Procedure 5 following:

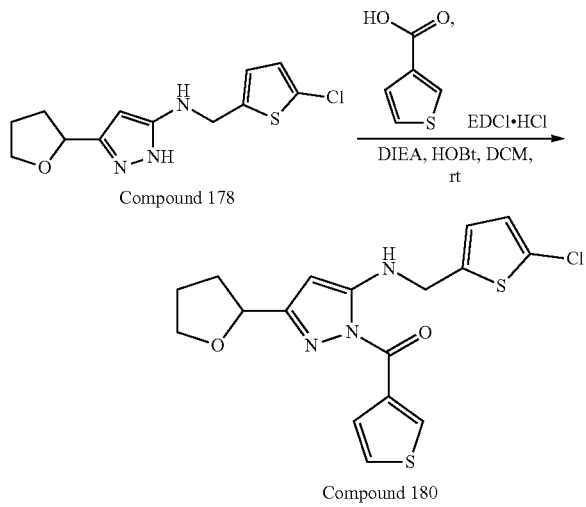

To a cooled (0° C.) solution of thiophene-3-carboxylic acid (95 mg, 0.84 mmol) in dichloromethane (10 mL) under nitrogen was added 1-(3-dimethylaminopropyl)-3-ethylcarbodiimide hydrochloride (EDCI.HCl, 201 mg, 1.05 mmol), followed by hydroxybenzotriazole (HOBt, 283 mg, 2.1 mmol). The reaction mixture was stirred for 10 minutes, then to the mixture was added diisopropylethylamine (DIEA, 0.48 mL, 2.8 mmol), followed by N-((5-chlorothiophen-2-yl)methyl)-3-(tetrahydrofuran-2-yl)-1H-pyrazol-5-amine (Compound 178, 200 mg, 0.7 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by preparative HPLC using acetonitrile-water as mobile phase to give product (5-(((5-chlorothiophen-2-yl)methyl)amino)-3-(tetrahydrofuran-2-yl)-1H-pyrazol-1-yl)(thiophen-3-yl)methanone (Compound 180, 38 mg, yield: 15%) m/z 394.16 [M+1]⁺; ¹H NMR (400 MHz, DMSO) δ 8.87 (s, 1H), 7.84-7.83 (m, 1H), 7.81-7.77 (m, 1H), 7.66-7.64 (m, 1H), 7.00-6.96 (m, 2H), 5.54 (s, 1H), 4.73-4.70 (m, 1H), 4.51 (s, 2H), 3.88-3.83 (m, 1H), 3.77-3.72 (m, 1H), 2.21-2.14 (m, 1H), 1.99-1.87 (m, 3H) ppm; TLC System: 50% Ethyl acetate in hexane. R$_f$-0.6.

Example 234—Preparation of Compound 181

The synthesis of Compound 181 followed the procedure of General Procedure 5 following:

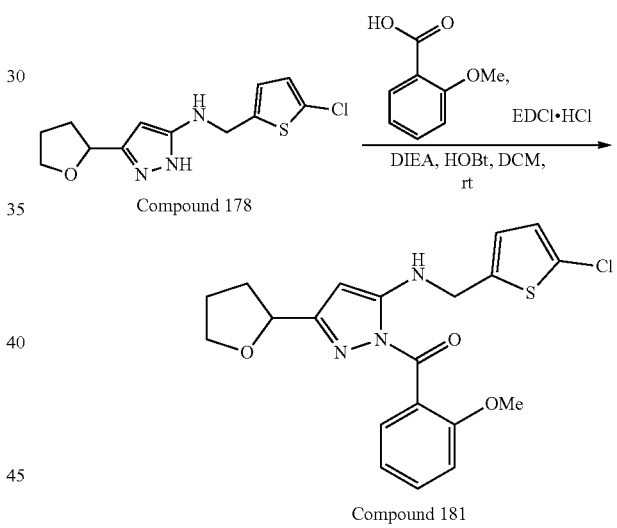

To a cooled (0° C.) solution of 2-methoxybenzoic acid (127 mg, 0.84 mmol) in dichloromethane (10 mL) under nitrogen was added 1-(3-dimethylaminopropyl)-3-ethylcarbodiimide hydrochloride (EDCI.HCl, 201 mg, 1.05 mmol), followed by hydroxybenzotriazole (HOBt, 283 mg, 2.1 mmol). The reaction mixture was stirred for 10 minutes, then to the mixture was added diisopropylethylamine (DIEA, 0.48 mL, 2.8 mmol), followed by N-((5-chlorothiophen-2-yl)methyl)-3-(tetrahydrofuran-2-yl)-1H-pyrazol-5-amine (Compound 178, 200 mg, 0.7 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by preparative HPLC using acetonitrile-water as mobile phase to give product (5-(((5-chlorothiophen-2-yl)methyl)amino)-3-(tetrahydrofuran-2-yl)-1H-pyrazol-1-yl)(2-methoxyphenyl)methanone (Compound 181, 32 mg, yield:

11%) m/z 394.16 [M+1]$^+$; $^1$H NMR (400 MHz, DMSO) δ 7.71-7.68 (m, 1H), 7.49-7.45 (m, 1H), 7.36-7.34 (m, 1H), 7.14-7.12 (m, 2H), 7.03-6.98 (m, 3H), 5.49 (s, 1H), 4.50-4.46 (m, 3H), 3.83-3.77 (m, 1H), 3.73 (s, 3H), 3.69-3.64 (m, 1H), 2.06-2.02 (m, 1H), 1.88-1.68 (m, 3H); TLC System: 50% Ethyl acetate in hexane. R$_f$-0.6.

Example 235—Preparation of Intermediate 57

The synthesis of Intermediate 57 followed the procedure of General Procedure 7 following:

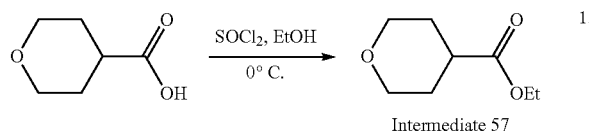

Intermediate 57

To a cooled solution (0° C.) of tetrahydro-2H-pyran-4-carboxylic acid (10 g, 76 mmol) in Ethanol (100 mL) was added thionyl chloride (17.1 mL, 230 mmol). After stirring at this temperature for 3 hours, the mixture was concentrated under reduced pressure. The mixture was diluted with saturated NaHCO$_3$ (20 mL) and extracted into Diethyl ether (3×100 mL). The combined organic layers were dried over sodium sulfate, filtered and concentrated under reduced pressure to give ethyl tetrahydro-2H-pyran-4-carboxylate (Intermediate 57, 11 g, yield: 91%) as an oily residue that was used without further purification into the next step. m/z 145.03 [M+H]$^+$; TLC System: 30% Ethyl acetate in hexane; R$_f$-0.7.

Example 236—Preparation of Intermediate 58

The synthesis of Intermediate 58 followed the procedure of General Procedure 2 following:

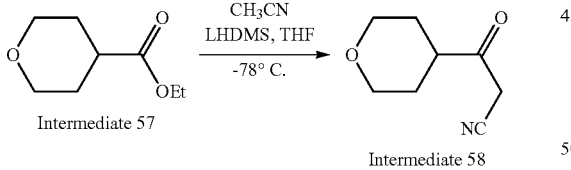

Intermediate 57

Intermediate 58

To a cooled (0° C.) solution of ethyl tetrahydro-2H-pyran-4-carboxylate (Intermediate 57, 3 g, 18.98 mmol) in THF (50 mL), dry acetonitrile (1.5 mL, 37.97 mmol) was added. After 10 min, LHDMS (1M in THF, 63.4 g, 37.9 mmol) was added. After stirring at 0° C. for 2 hours, the mixture was quenched with saturated citric acid solution until pH=5 and extracted into Ethyl acetate (3×100 mL). The combined organic layers were dried over sodium sulfate, filtered and concentrated under reduced pressure to give 3-oxo-3-(tetrahydro-2H-pyran-4-yl)propanenitrile (Intermediate 58, 3.3 g, yield: 99%) as an oily residue that was used without further purification into the next step. m/z 153.12 [M+H]$^+$; TLC System: 50% Ethyl acetate in hexane; R$_f$-0.2.

Example 237—Preparation of Compound 182

The synthesis of Compound 182 followed the procedure of General Procedure 3 following:

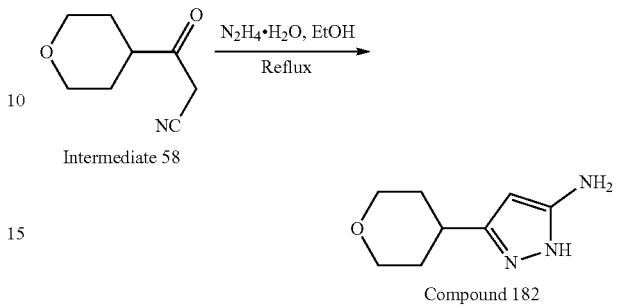

Intermediate 58

Compound 182

To a solution of 3-oxo-3-(tetrahydro-2H-pyran-4-yl)propanenitrile (Intermediate 58, 3.3 g, 21.5 mmol) in ethanol (90 mL) was added hydrazine hydrate (N$_2$H$_4$.H$_2$O, 1.56 mL, 32.3 mmol) and the reaction mixture was then heated to 90° C. for 5 hours. The reaction mixture was cooled to room temperature and the volatiles were evaporated. The residue was purified by neutral alumina column chromatography (100-300 mesh), eluting with 2% MeOH-dichloromethane, to afford 3-(tetrahydro-2H-pyran-4-yl)-1H-pyrazol-5-amine (Compound 182, 1.7 g, 47%) as an orange liquid; m/z 168.15 [M+H]$^+$; TLC System: 10% Methanol-dichloromethane. R$_f$-0.3.

Example 238—Preparation of Compound 183

The synthesis of Compound 183 followed the procedure of General Procedure 4 following:

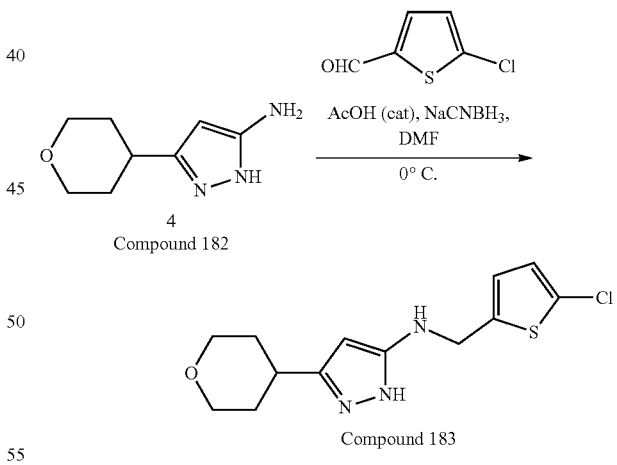

4
Compound 182

Compound 183

To a cooled solution (0° C.) of 3-(tetrahydro-2H-pyran-4-yl)-1H-pyrazol-5-amine (Compound 182, 2.1 g, 12.5 mmol) in dry DMF (20 mL) was added 5-chlorothiophene-2-carbaldehyde (1.96 mL, 18.8 mmol) and acetic acid (2 mL). The reaction mixture was stirred at room temperature for 2 hours. (Formation of imine was observed as a less polar spot on TLC). The reaction mixture was cooled (0° C.) and sodium cyanoborohydride (2.58 g, 25.1 mmol) was added portionwise and a catalytic amount of acetic acid. After 2 hours, the reaction mixture was quenched with ice-cold water (25 mL), and extracted into Ethyl acetate (3×50 mL). The combined organic layers were washed with saturated NaHCO$_3$ (2×50 mL), water (2×50 mL) and brine (2×50 mL) and dried over sodium sulfate, filtered and concentrated under reduced pressure. The residue was purified by silica gel column chromatography (100-200 mesh), eluting with 10% diethyl ether/dichloromethane, to afford N-((5-chlorothiophen-2-yl) methyl)-3-(tetrahydro-2H-pyran-4-yl)-1H-pyrazol-5-amine (Compound 183, 600 mg, 16%) as a light yellow gummy liquid; m/z 298.19 [M+H]$^+$. $^1$H NMR (400 MHz, DMSO-d$_6$) δ 11.50 (br s, 1H), 6.90 (s, 1H), 6.83 (s, 1H), 5.69 (br s, 1H), 5.29 (s, 1H), 4.28 (s, 2H), 3.88-3.84 (m, 2H), 3.39-3.34 (m, 3H), 2.76-2.68 (m, 1H), 1.76-1.72 (m, 2H), 1.60-1.50 (m, 2H) ppm; TLC System: 50% Ethyl acetate in hexane R$_f$-0.5.

Example 239—Preparation of Compound 184

The synthesis of Compound 184 followed the procedure of General Procedure 5 following:

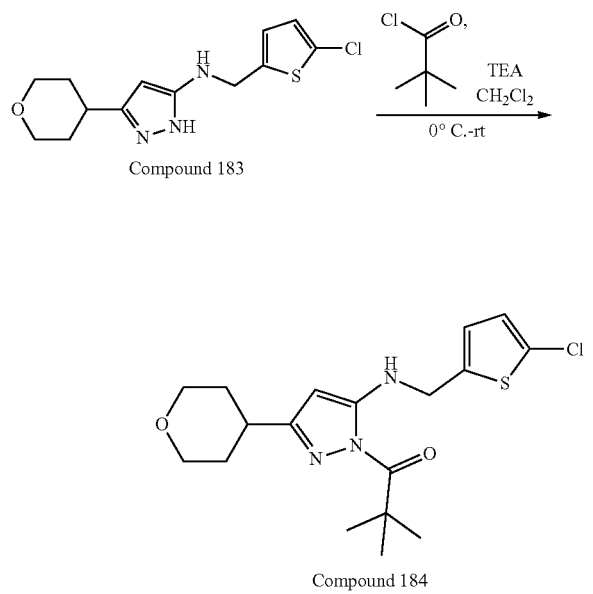

To a cooled solution (0° C.) of N-((5-chlorothiophen-2-yl) methyl)-3-(tetrahydro-2H-pyran-4-yl)-1H-pyrazol-5-amine (Compound 183, 100 mg, 0.33 mmol) in dry dichloromethane (8 mL) was added triethylamine (TEA, 0.06 mL, 0.7 mmol), followed by trimethylacetyl chloride (0.03 mL, 0.26 mmol). After stirring at room temperature for 3 hours, the reaction mixture was diluted with water (50 mL) and extracted into dichloromethane (2×25 mL). The combined organic layers were washed with saturated NaHCO$_3$ (2×10 mL) and water (2×10 mL) and dried over sodium sulfate, filtered and concentrated under reduced pressure. The residue was purified by preparative silica gel TLC (100-200 mesh), eluting with 15% Ethyl acetate/hexanes, to afford 1-(5-(((5-chlorothiophen-2-yl)methyl)amino)-3-(tetrahydrofuran-2-yl)-1H-pyrazol-1-yl)-2,2-dimethylpropan-1-one (Compound 184, 15 mg, 11%) as a colorless liquid. MS (ESI): m/z 382.2 [M+H]$^+$. $^1$H NMR (400 MHz, DMSO-d$_6$) δ 7.69-7.66 (m, 1H), 6.96 (s, 2H), 5.40 (s, 1H), 4.41 (s, 1H), 4.43 (s, 3H), 3.88-3.85 (m, 2H), 3.43-3.34 (m, 2H), 2.74-2.67 (m, 1H), 1.79-1.76 (m, 2H), 1.64-1.54 (m, 2H), 1.40 (s, 9H) ppm; TLC System: 50% Ethyl acetate in hexane. R$_f$-0.7.

Example 240—Preparation of Compound 185

The synthesis of Compound 185 followed the procedure of General Procedure 5 following:

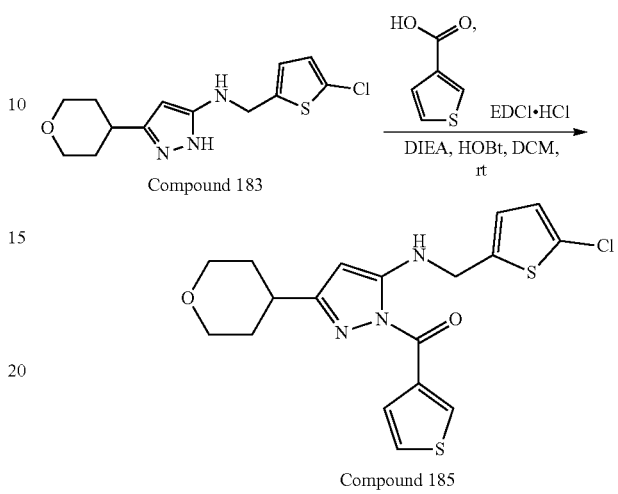

To a cooled (0° C.) solution of thiophene-3-carboxylic acid (103 mg, 0.80 mmol) in dichloromethane (10 mL) under nitrogen was added 1-(3-dimethylaminopropyl)-3-ethylcarbodiimide hydrochloride (EDCI.HCl, 192 mg, 1.00 mmol), followed by hydroxybenzotriazole (HOBt, 271 mg, 2.01 mmol). The reaction mixture was stirred for 10 minutes, then to the mixture was added diisopropylethylamine (DIEA, 0.46 mL, 2.68 mmol), followed by N-((5-chlorothiophen-2-yl)methyl)-3-(tetrahydro-2H-pyran-4-yl)-1H-pyrazol-5-amine (Compound 183, 200 mg, 0.67 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by preparative HPLC using acetonitrile-water as mobile phase to give product (5-(((5-chlorothiophen-2-yl)methyl)amino)-3-(tetrahydrofuran-2-yl)-1H-pyrazol-1-yl)(thiophen-3-yl)methanone (Compound 185, 30 mg, yield: 11%) m/z 408.23 [M+1]$^+$; $^1$H NMR (400 MHz, DMSO) δ 8.90 (s, 1H), 7.81-7.78 (m, 2H), 7.65-7.63 (m, 1H), 7.01-6.96 (m, 2H), 5.54 (s, 1H), 4.49-4.47 (m, 2H), 3.91-3.88 (m, 2H), 3.44-3.41 (m, 2H), 2.80-2.67 (m, 1H), 1.83-1.79 (m, 2H), 1.68-1.58 (m, 2H) ppm; TLC System: 50% Ethyl acetate in hexane. R$_f$-0.5.

Example 241—Preparation of Compound 186

The synthesis of Compound 186 followed the procedure of General Procedure 5 following:

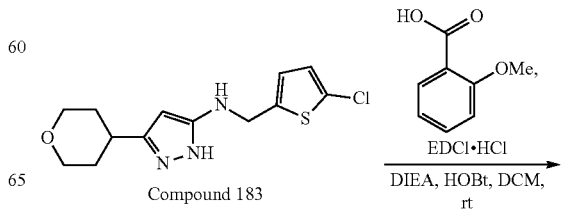

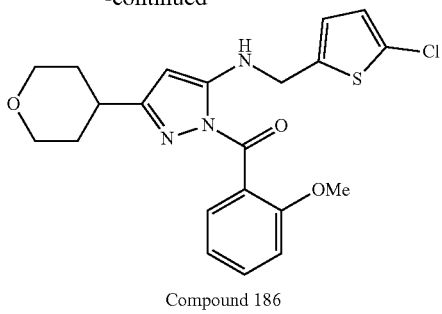

Compound 186

To a cooled (0° C.) solution of 2-methoxybenzoic acid (91 mg, 0.60 mmol) in dichloromethane (10 mL) under nitrogen was added 1-(3-dimethylaminopropyl)-3-ethylcarbodiimide hydrochloride (EDCI.HCl, 144 mg, 0.75 mmol), followed by hydroxybenzotriazole (HOBt, 202 mg, 1.5 mmol). The reaction mixture was stirred for 10 minutes, then to the mixture was added diisopropylethylamine (DIEA, 0.34 mL, 1.5 mmol), followed by N-((5-chlorothiophen-2-yl)methyl)-3-(tetrahydro-2H-pyran-4-yl)-1H-pyrazol-5-amine (Compound 183, 150 mg, 0.50 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by preparative HPLC using acetonitrile-water as mobile phase to give product (5-(((5-chlorothiophen-2-yl)methyl)amino)-3-(tetrahydrofuran-2-yl)-1H-pyrazol-1-yl)(2-methoxyphenyl)methanone (Compound 186, 25 mg, yield: 12%) m/z 432.27 [M+1]$^+$; $^1$H NMR (400 MHz, DMSO) δ 7.67-7.64 (m, 1H), 7.49-7.44 (m, 1H), 7.36-7.33 (m, 1H), 7.13-7.11 (m, 2H), 7.03-6.98 (m, 3H), 5.50 (s, 1H), 4.48-4.47 (m, 2H), 3.82-3.74 (m, 2H), 3.73 (s, 3H), 3.34-3.28 (m, 1H), 2.55-2.49 (m, 1H), 1.61-1.44 (m, 4H); TLC System: 30% Ethyl acetate in hexane. R$_f$-0.5.

Example 242—Preparation of Intermediate 59

The synthesis of Intermediate 59 followed the procedure of General Procedure 2 following:

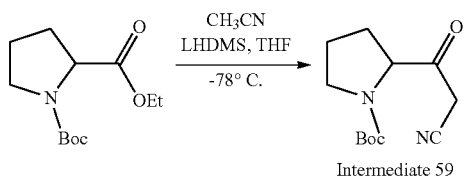 [SMILES: CCOC(=O)C1CCCN1C(=O)OC(C)(C)C ; CC(C)(C)OC(=O)N1CCCC1C(=O)CC#N]

Intermediate 59

To a cooled (−20° C.) solution of 1-(tert-butyl) 2-ethyl pyrrolidine-1,2-dicarboxylate (15 g, 61.7 mmol) in THF (150 mL), dry acetonitrile (2.5 mL, 61.7 mmol) was added. After 10 min, LHDMS (1M in THF, 15 g, 92.5 mmol) was added. After stirring at 0° C. for 2 hours, the mixture was quenched with saturated citric acid solution until pH=5 and extracted into Ethyl acetate (3×100 mL). The combined organic layers were dried over sodium sulfate, filtered and concentrated under reduced pressure to give tert-butyl 2-(2-cyanoacetyl)pyrrolidine-1-carboxylate (Intermediate 59, 15 g, yield: 99%) as an oily residue that was used without further purification into the next step. m/z 238.12 [M+H]$^+$; TLC System: 50% Ethyl acetate in petroleum ether; R$_f$-0.3.

Example 243—Preparation of Compound 187

The synthesis of Compound 187 followed the procedure of General Procedure 3 following:

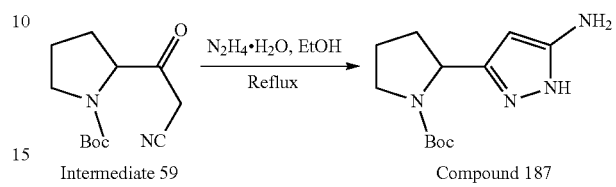

Intermediate 59          Compound 187

To a solution of tert-butyl 2-(2-cyanoacetyl)pyrrolidine-1-carboxylate (Intermediate 59, 15 g, 61.7 mmol) in ethanol (300 mL) was added hydrazine hydrate (N$_2$H$_4$.H$_2$O, 4.68 mL, 32.3 mmol) and the reaction mixture was then heated to 80° C. for 16 hours. The reaction mixture was cooled to room temperature and the volatiles were evaporated. The residue was purified by neutral alumina column chromatography (100-300 mesh), eluting with 3% MeOH-dichloromethane, to afford tert-butyl 2-(5-amino-1H-pyrazol-3-yl)pyrrolidine-1-carboxylate (Compound 187, 5 g, 32%) as a light brown solid; m/z 252.15 [M+H]$^+$; TLC System: 5% Methanol-dichloromethane. R$_f$-0.2.

Example 244—Preparation of Compound 188

The synthesis of Compound 188 followed the procedure of General Procedure 4 following:

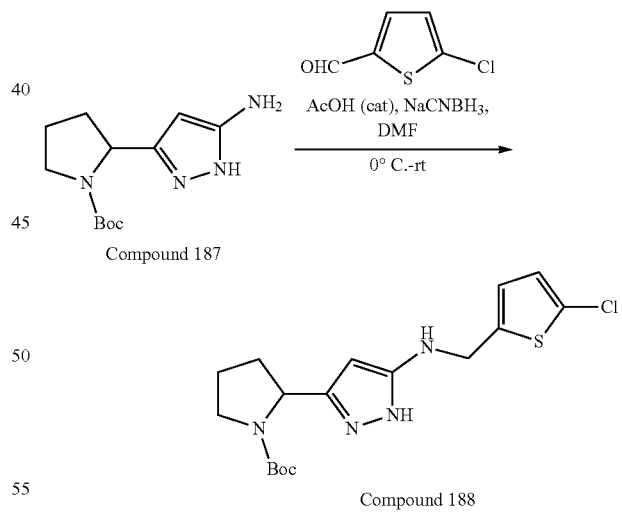

Compound 187

Compound 188

To a cooled solution (0° C.) of tert-butyl 2-(5-amino-1H-pyrazol-3-yl)pyrrolidine-1-carboxylate (Compound 187, 5 g, 19.8 mmol) in dry DMF (10 mL) was added 5-chlorothiophene-2-carbaldehyde (2.75 mL, 25.8 mmol) and acetic acid (1 mL). The reaction mixture was stirred at room temperature for 2 hours. (Formation of imine was observed as a less polar spot on TLC). The reaction mixture was cooled (0° C.) and sodium cyanoborohydride (2.58 g, 25.1 mmol) was added portionwise and a catalytic amount of acetic acid. After 2 hours, the reaction mixture was quenched with ice-cold water (25 mL), and extracted into Ethyl acetate (3×50 mL). The combined organic layers were washed with brine (2×50 mL) and dried over sodium sulfate, filtered and concentrated under reduced pressure. The residue was purified by silica gel column chromatography (100-200 mesh), eluting with 1% dichloromethane/MeOH, to afford tert-butyl 2-(5-(((5-chlorothiophen-2-yl)methyl)amino)-1H-pyrazol-3-yl)pyrrolidine-1-carboxylate (Compound 188, 2.2 g, 27%) as a reddish brown solid; m/z 383.29 [M+H]+. 1H NMR (400 MHz, DMSO-d6) δ 11.34 (br s, 1H), 6.89 (s, 1H), 6.82 (s, 1H), 5.63 (br s, 1H), 5.24 (s, 1H), 4.29-4.27 (m, 2H), 3.38-3.24 (m, 2H), 2.1 (br s, 1H), 1.84 (br s, 3H), 1.38-1.22 (br m, 9H) ppm; TLC System: 5% Methanol-dichloromethane R$_f$-0.5.

Example 245—Preparation of Compound 189

The synthesis of Compound 189 followed the procedure of General Procedure 5 following:

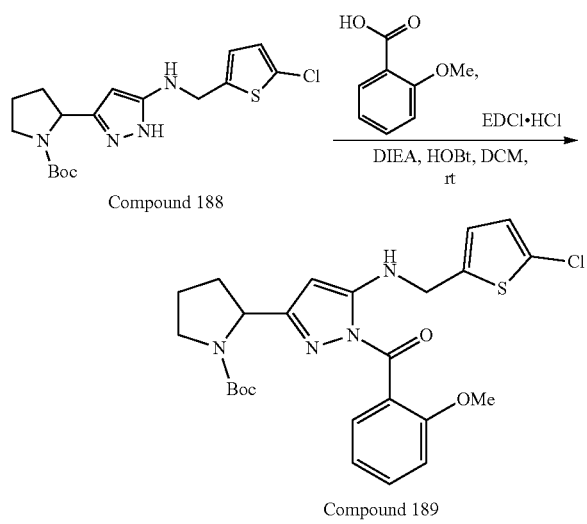

Compound 189

To a cooled (0° C.) solution of 2-methoxybenzoic acid (1 g, 6.59 mmol) in dichloromethane (20 mL) under nitrogen was added 1-(3-dimethylaminopropyl)-3-ethylcarbodiimide hydrochloride (EDCI.HCl, 2.1 g, 10.99 mmol), followed by hydroxybenzotriazole (HOBt, 742 mg, 5.49 mmol). The reaction mixture was stirred for 10 minutes, cooled (0° C.) and then to the mixture was added diisopropylethylamine (DIEA, 2.8 mL, 16.49 mmol), followed by tert-butyl 2-(5-(((5-chlorothiophen-2-yl)methyl)amino)-1H-pyrazol-3-yl)pyrrolidine-1-carboxylate (Compound 188, 2.1 g, 5.49 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 30% ethyl acetate/petroleum ether, to afford tert-butyl 2-(5-(((5-chlorothiophen-2-yl)methyl)amino)-1-(2-methoxybenzoyl)-1H-pyrazol-3-yl)pyrrolidine-1-carboxylate (Compound 189, 1.5 g, yield: 53%) as an off white solid. m/z 417.37 [M+1]+; 1H NMR (400 MHz, CDCl3) δ 7.47-7.40 (m, 3H), 7.02-6.96 (m, 2H), 6.82-6.77 (m, 2H), 5.34 (s, 1H), 4.45-4.43 (m, 2H), 4.03-3.99 (m, 1H), 3.81 (s, 3H), 3.06-3.02 (m, 1H), 2.93- 2.87 (m, 1H), 2.08-2.03 (m, 1H), 1.87-1.72 (m, 3H); TLC System: 70% Ethyl acetate in petroleum ether. R$_f$-0.8.

Example 246—Preparation of Compound 190

The synthesis of Compound 190 followed the procedure of General

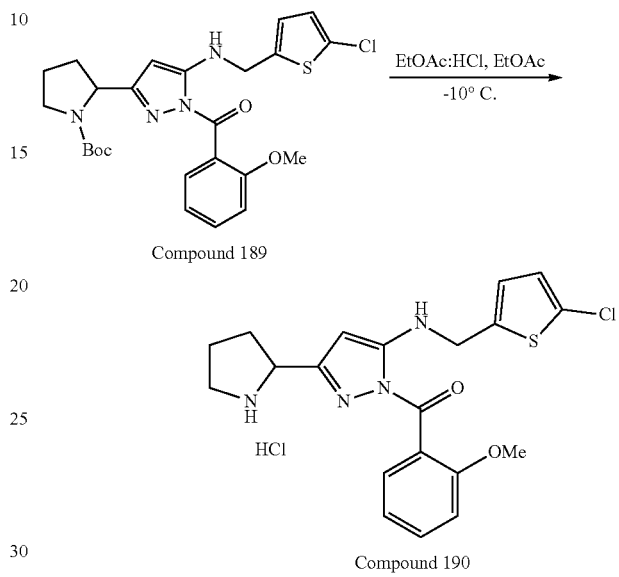

To a cooled (−10° C.) solution of tert-butyl 2-(5-(((5-chlorothiophen-2-yl)methyl)amino)-1-(2-methoxybenzoyl)-1H-pyrazol-3-yl)pyrrolidine-1-carboxylate (500 mg, 0.96 mmol) in ethyl acetate (10 mL) was added a solution of hydrogen chloride (1M) in ethyl acetate (2 mL). The reaction mixture was stirred for 1 hr, and then evaporated under reduced pressure to give product (5-(((5-chlorothiophen-2-yl)methyl)amino)-3-(pyrrolidin-2-yl)-1H-pyrazol-1-yl)(2-methoxyphenyl)methanone hydrochloride (Compound 190, 350 mg, yield: 74%) as an off white solid. m/z 417.37 [(M−HCl)+1]+; 1H NMR (400 MHz, CDCl3) δ 7.47-7.40 (m, 3H), 7.02-6.96 (m, 2H), 6.82-6.77 (m, 2H), 5.34 (s, 1H), 4.45-4.43 (m, 2H), 4.03-3.99 (m, 1H), 3.81 (s, 3H), 3.06-3.02 (m, 1H), 2.93-2.87 (m, 1H), 2.08-2.03 (m, 1H), 1.87-1.72 (m, 3H); TLC System: 70% Ethyl acetate in petroleum ether. R$_f$-0.8.

Example 247—Preparation of Compound 191

The synthesis of Compound 191 followed the procedure of General Procedure 5 following:

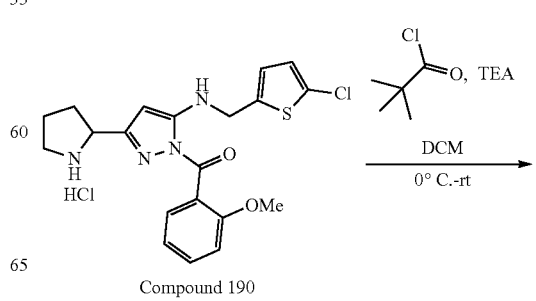

Compound 190

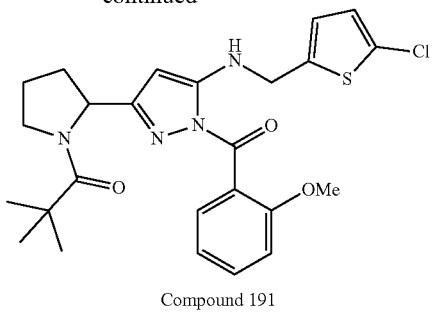

Compound 191

To a cooled (0° C.) solution of (5-(((5-chlorothiophen-2-yl)methyl)amino)-3-(pyrrolidin-2-yl)-1H-pyrazol-1-yl)(2-methoxyphenyl)methanone hydrochloride (170 mg, 0.39 mmol) in dichloromethane (10 mL) was added triethylamine (0.1 mL, 0.74 mmol) followed by pivaloyl chloride (36 mg, 0.29 mmol). The reaction mixture was stirred for 4 hr at room temperature, and then was poured into water (50 mL) and extracted with dichloromethane (2×25 mL). The combined organic phases were washed with brine (2×25 mL), dried over anhydrous sodium sulfate, filtered and evaporated under reduced pressure. The residue was purified by silica gel column chromatography (100-200 mesh), eluting with 50% ethyl acetate/petroleum ether, to afford product 1-(2-(5-(((5-chlorothiophen-2-yl)methyl)amino)-1-(2-methoxybenzoyl)-1H-pyrazol-3-yl)pyrrolidin-1-yl)-2,2-dimethylpropan-1-one (Compound 191, 80 mg, yield: 43%) as an off white solid. m/z 501.29 [M+1]$^+$; $^1$H NMR (400 MHz, CDCl$_3$) δ 7.41-7.32 (m, 3H), 6.99-6.93 (m, 2H), 6.80-6.76 (m, 2H), 5.18 (s, 1H), 5.17-5.13 (m, 1H), 4.42-4.40 (m, 2H), 3.80 (s, 3H), 3.62 (s, 2H), 1.96-1.87 (m, 4H), 1.56 (s, 9H); TLC System: 5% Methanol in chloroform. R$_f$-0.6.

Example 248—Preparation of Compound 192

The synthesis of Compound 192 followed the procedure of General Procedure 5 following:

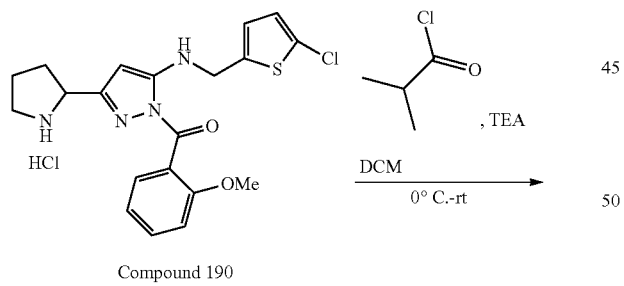

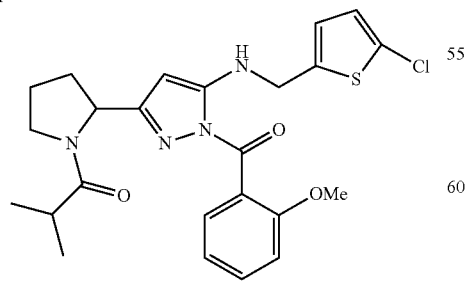

Compound 192

To a cooled (0° C.) solution of (5-(((5-chlorothiophen-2-yl)methyl)amino)-3-(pyrrolidin-2-yl)-1H-pyrazol-1-yl)(2-methoxyphenyl)methanone hydrochloride (150 mg, 0.33 mmol) in dichloromethane (15 mL) was added triethylamine (0.09 mL, 0.66 mmol) followed by isobutyryl chloride (35 mg, 0.33 mmol). The reaction mixture was stirred for 4 hr at room temperature, and then was poured into water (50 mL) and extracted with dichloromethane (2×25 mL). The combined organic phases were washed with brine (2×25 mL), dried over anhydrous sodium sulfate, filtered and evaporated under reduced pressure. The residue was purified by silica gel column chromatography (100-200 mesh), eluting with 60% ethyl acetate/petroleum ether, to afford product 1-(2-(5-(((5-chlorothiophen-2-yl)methyl)amino)-1-(2-methoxybenzoyl)-1H-pyrazol-3-yl)pyrrolidin-1-yl)-2-methylpropan-1-one (Compound 192, 90 mg, yield: 56%) as an off white solid. m/z 487.35 [M+1]$^+$; $^1$H NMR (400 MHz, CDCl$_3$) δ rotamers 7.49-7.32 (m, 3H), 7.04-6.91 (m, 2H), 6.79-6.75 (m, 2H), 5.16 (s, 1H), 4.80-4.78 (m, 1H), 4.42-4.39 (m, 2H), 3.80 (s, 3H), 3.62-3.48 (m, 2H), 2.63-2.53 (m, 1H), 2.02-1.86 (m, 4H), 1.09-0.86 (m, 6H); TLC System: 5% Methanol in chloroform. R$_f$-0.5.

Example 249—Preparation of Compound 193

The synthesis of Compound 193 followed the procedure of General Procedure 5 following:

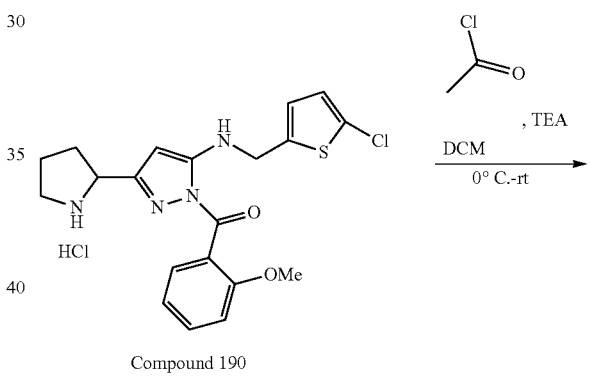

Compound 190

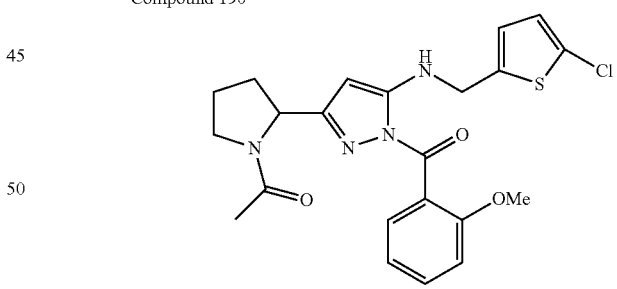

Compound 193

To a cooled (0° C.) solution of (5-(((5-chlorothiophen-2-yl)methyl)amino)-3-(pyrrolidin-2-yl)-1H-pyrazol-1-yl)(2-methoxyphenyl)methanone hydrochloride (130 mg, 0.28 mmol) in dichloromethane (15 mL) was added triethylamine (0.08 mL, 0.57 mmol) followed by acetyl chloride (22 mg, 0.28 mmol). The reaction mixture was stirred for 4 hr at room temperature, and then was poured into water (50 mL) and extracted with dichloromethane (2×25 mL). The combined organic phases were washed with brine (2×25 mL), dried over anhydrous sodium sulfate, filtered and evaporated under reduced pressure. The residue was purified by silica gel column chromatography (100-200 mesh), eluting with 1% Methanol/dichloromethane, to afford product 1-(2-(5-(((5-chlorothiophen-2-yl)methyl)amino)-1-(2-methoxybenzoyl)-1H-pyrazol-3-yl)pyrrolidin-1-yl)ethan-1-one (Compound 193, 15 mg, yield: 12%) as a colorless gummy liquid. m/z 459.27 [M+1]$^+$; $^1$H NMR (400 MHz, CDCl$_3$) δ rotamers 7.52-7.28 (m, 3H), 7.04-6.94 (m, 2H), 6.82-6.77 (m, 2H), 5.31-5.06 (m, 2H), 4.79-4.76 (m, 1H), 4.48-4.38 (m, 2H), 3.81 (s, 3H), 3.62-3.48 (m, 2H), 2.29-2.01 (m, 1H), 1.99-1.86 (m, 6H); TLC System: 5% Methanol in chloroform. R$_f$-0.2.

Example 250—Preparation of Compound 194

The synthesis of Compound 194 followed the procedure of General Procedure 5 following:

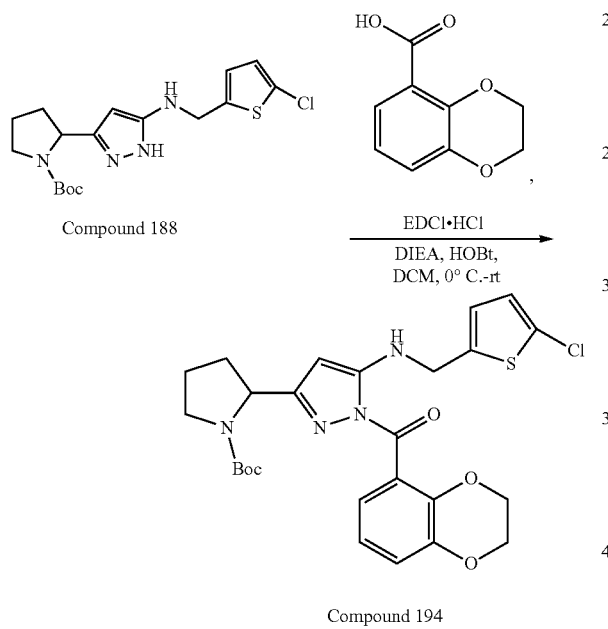

Compound 194

To a cooled (0° C.) solution of 2,3-dihydrobenzo[b][1,4]dioxine-5-carboxylic acid (282 mg, 1.57 mmol) in dichloromethane (15 mL) under nitrogen was added 1-(3-dimethylaminopropyl)-3-ethylcarbodiimide hydrochloride (EDCI.HCl, 191 mg, 3.91 mmol), followed by hydroxybenzotriazole (HOBt, 135 mg, 1.3 mmol). The reaction mixture was stirred for 10 minutes, then to the mixture was added diisopropylethylamine (DIEA, 0.69 mL, 3.91 mmol), followed by tert-butyl 2-(5-(((5-chlorothiophen-2-yl)methyl)amino)-1H-pyrazol-3-yl)pyrrolidine-1-carboxylate (Compound 188, 500 mg, 1.30 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 25% Ethyl acetate/Petroleum ether, to afford product tert-butyl 2-(5-(((5-chlorothiophen-2-yl)methyl)amino)-1-(2,3-dihydrobenzo[b][1,4]dioxine-5-carbonyl)-1H-pyrazol-3-yl)pyrrolidine-1-carboxylate (Compound 194, 200 mg, yield: 32%) m/z 545.16 [M+1]$^+$; TLC System: 70% Ethyl acetate in petroleum ether. R$_f$-0.7.

Example 251—Preparation of Compound 195

The synthesis of Compound 195 followed the procedure of General Procedure 5 following:

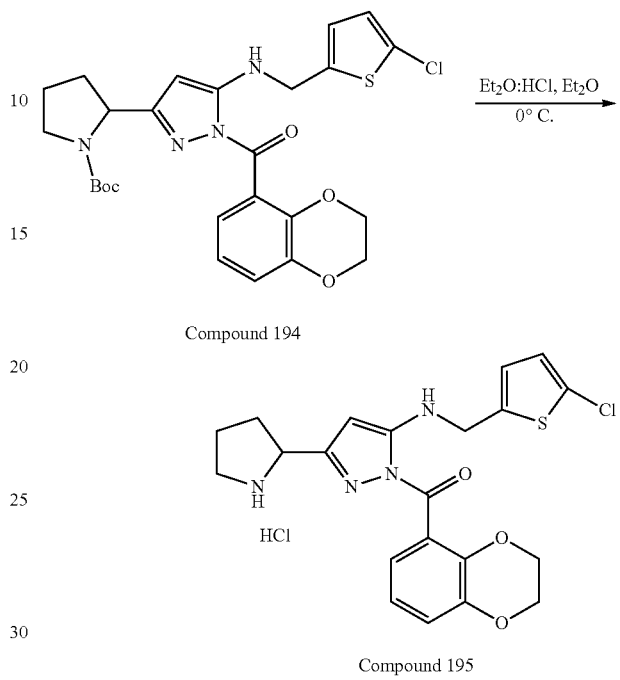

To a cooled (0° C.) solution of tert-butyl 2-(5-(((5-chlorothiophen-2-yl)methyl)amino)-1-(2,3-dihydrobenzo[b][1,4]dioxine-5-carbonyl)-1H-pyrazol-3-yl)pyrrolidine-1-carboxylate (200 mg, 0.96 mmol) in diethyl ether (2 mL) was added a solution of hydrogen chloride (1M) in diethyl ether (2 mL). The reaction mixture was stirred for 2 hr, and then evaporated under reduced pressure, triturated with diethyl ether and acetone to afford product (5-(((5-chlorothiophen-2-yl)methyl)amino)-3-(pyrrolidin-2-yl)-1H-pyrazol-1-yl)(2,3-dihydrobenzo[b][1,4]dioxin-5-yl)methanone hydrochloride (Compound 195, 50 mg, yield: 15%) as an off white solid. m/z 445.19 [(M−HCl)+1]$^+$; $^1$H NMR (400 MHz, DMSO-d$_6$) δ 9.85 (br s, 1H), 8.95 (br s, 1H), 7.86 (s, 1H), 7.03-6.88 (m, 5H), 5.78-5.74 (m, 1H), 4.51-4.49 (m, 1H), 4.41 (s, 1H), 4.27-4.21 (m, 4H), 3.17 (s, 1H), 2.24-2.18 (m, 1H), 1.98-1.88 (m, 3H); TLC System: 10% Methanol in dichloromethane. R$_f$-0.25.

Example 252—Preparation of Compound 196

The synthesis of Compound 196 followed the procedure of General Procedure 5 following:

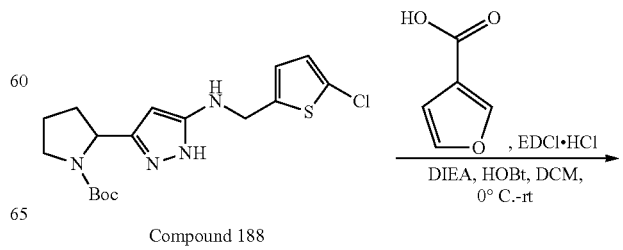

Compound 188

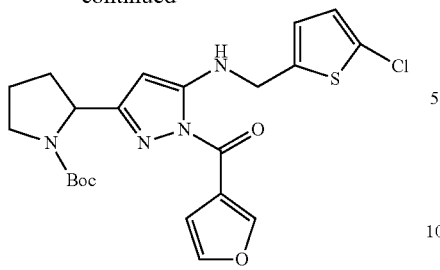

Compound 196

To a cooled (0° C.) solution of furane-3-carboxylic acid (175 mg, 1.57 mmol) in dichloromethane (15 mL) under nitrogen was added 1-(3-dimethylaminopropyl)-3-ethylcarbodiimide hydrochloride (EDCI.HCl, 191 mg, 3.91 mmol), followed by hydroxybenzotriazole (HOBt, 135 mg, 1.3 mmol). The reaction mixture was stirred for 10 minutes, then to the mixture was added diisopropylethylamine (DIEA, 0.69 mL, 3.91 mmol), followed by tert-butyl 2-(5-(((5-chlorothiophen-2-yl)methyl)amino)-1H-pyrazol-3-yl)pyrrolidine-1-carboxylate Compound 188, 500 mg, 1.30 mmol). The reaction was monitored by LC-MS, and after 16 hr at room temperature at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 15% Ethyl acetate/Petroleum ether, to afford product tert-butyl 2-(5-(((5-chlorothiophen-2-yl)methyl)amino)-1-(furan-3-carbonyl)-1H-pyrazol-3-yl)pyrrolidine-1-carboxylate (Compound 196, 280 mg, yield: 45%) m/z 477.16 [M+1]$^+$; TLC System: 70% Ethyl acetate in petroleum ether. R$_f$-0.75.

Example 253—Preparation of Compound 197

The synthesis of Compound 197 followed the procedure of General Procedure 5 following:

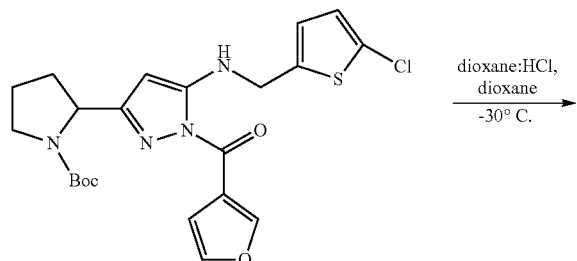

Compound 196

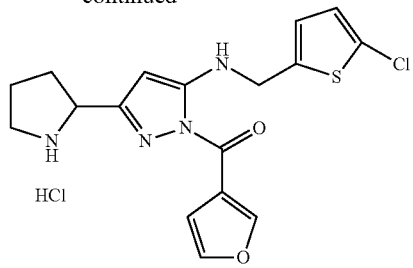

Compound 197

To a cooled (−30° C.) solution of tert-butyl 2-(5-(((5-chlorothiophen-2-yl)methyl)amino)-1-(furan-3-carbonyl)-1H-pyrazol-3-yl)pyrrolidine-1-carboxylate (100 mg, 0.20 mmol) in dioxane (3 mL) was added a solution of hydrogen chloride (1M) in diethyl ether (2 mL). The reaction mixture was stirred for 2 hr, and then evaporated under reduced pressure. The mixture was washed with n-pentane, diethyl ether and n-pentane to afford product (5-(((5-chlorothiophen-2-yl)methyl)amino)-3-(pyrrolidin-2-yl)-1H-pyrazol-1-yl)(furan-3-yl)methanone hydrochloride (Compound 197, 30 mg, yield: 38%) as an off white solid. m/z 377.21 [(M−HCl)+1]$^+$; $^1$H NMR (400 MHz, DMSO-d$_6$) δ 9.64 (br s, 1H), 8.95 (br s, 1H), 9.01 (s, 1H), 8.99 (s, 1H), 8.00-7.98 (m, 1H), 7.88 (s, 1H), 7.06 (s, 1H), 6.99-6.97 (m, 2H), 5.69 (s, 1H), 4.69-4.51 (m, 3H), 3.32-3.29 (m, 2H), 2.39-2.33 (m, 1H), 1.96-1.92 (m, 3H); TLC System: 10% Methanol in chloroform. R$_f$-0.1.

Example 254—Preparation of Compound 198

The synthesis of Compound 198 followed the procedure of General Procedure 5 following:

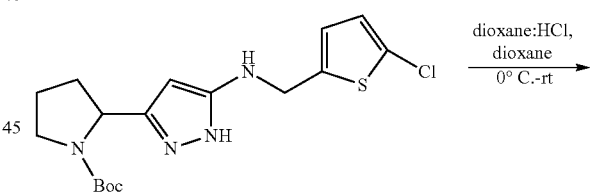

Compound 188

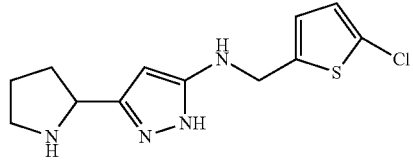

Compound 198

To a cooled (0° C.) solution of tert-butyl 2-(5-(((5-chlorothiophen-2-yl)methyl)amino)-1H-pyrazol-3-yl)pyrrolidine-1-carboxylate (200 mg, 0.52 mmol) in dioxane (5 mL) was added a solution of hydrogen chloride (1M) in dioxane (5 mL). The reaction mixture was stirred for 8 hr at room temperature, and then evaporated under reduced pressure. The mixture was diluted with saturated NaHCO$_3$ (20 mL) and extracted into ethyl acetate (3×50 mL). The combined organic layers were washed with brine (50 mL), dried over sodium sulfate, filtered and concentrated under reduced pressure. The residue was purified by silica gel column chromatography (100-200 mesh), eluting with 5% Methanol/dichloromethane, to afford product N-((5-chlorothiophen-2-yl)methyl)-3-(pyrrolidin-2-yl)-1H-pyrazol-5-amine (Compound 198, 130 mg, yield: 91%) as an off white solid. m/z 283.21 (M+1)$^+$; TLC System: 10% Methanol in chloroform. R$_f$-0.2.

Example 255—Preparation of Compound 199

The synthesis of Compound 199 followed the procedure of General Procedure 5 following:

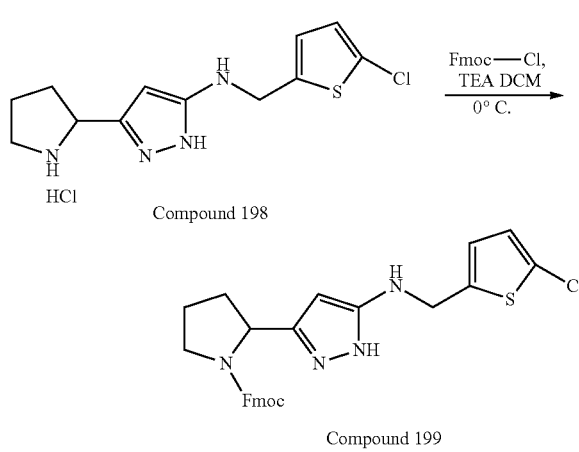

To a cooled (0° C.) solution of N-((5-chlorothiophen-2-yl)methyl)-3-(pyrrolidin-2-yl)-1H-pyrazol-5-amine hydrochloride (3.5 g, 11.0 mmol) in dichloromethane (20 mL) was added triethylamine (0.72 mL, 16.5 mmol) followed by Fmoc chloride (3.13 g, 12.1 mmol). The reaction mixture was stirred for 2 hr, and then was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 5% Methanol/dichloromethane, to afford product (9H-fluoren-9-yl)methyl-2-(5-(((5-chlorothiophen-2-yl)methyl)amino)-1H-pyrazol-3-yl)pyrrolidine-1-carboxylate (Compound 199, 3.5 g, yield: 63%) as an off white fluffy solid. m/z 505.3 [M+1]$^+$; TLC System: 10% Methanol in chloroform. R$_f$-0.4.

Example 256—Preparation of Compound 200

The synthesis of Compound 200 followed the procedure of General Procedure 5 following:

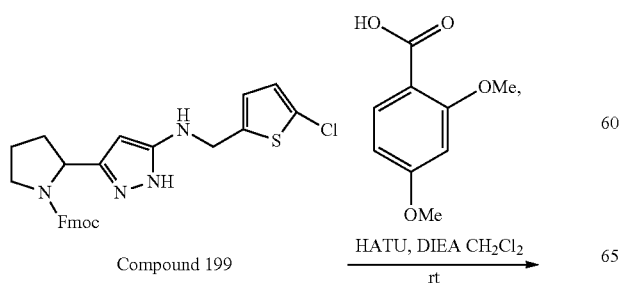

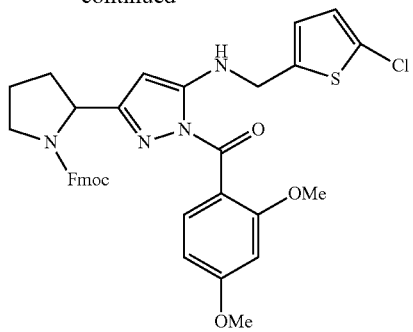

Compound 200

To a solution of tert-butyl 2-(5-(((5-chlorothiophen-2-yl)methyl)amino)-1H-pyrazol-3-yl)pyrrolidine-1-carboxylate (Compound 199, 500 mg, 0.99 mmol) and 3-methoxy-2,2-dimethylpropanoic acid (180 mg, 1.18 mmol) in dichloromethane (5 mL) under nitrogen at room temperature, was added 1-[Bis(dimethylamino)methylene]-1H-1,2,3-triazolo[4,5-b]pyridinium 3-oxid hexafluorophosphate (HATU, 564 mg, 1.48 mmol), followed by diisopropylethylamine (DIEA, 0.32 mL, 1.48 mmol). The reaction 5 mixture was stirred at room temperature for 16 hr, diluted with water (50 mL) and extracted with dichloromethane (2×25 mL). The combined organic phases were dried over anhydrous sodium sulfate, filtered and evaporated under reduced pressure. The residue was purified by preparative HPLC using acetonitrile-water as mobile phase to give product (9H-fluoren-9-yl)methyl 2-(5-(((5-chlorothiophen-2-yl)methyl)amino)-1-(2,4-dimethoxybenzoyl)-1H-pyrazol-3-yl)pyrrolidine-1-carboxylate (Compound 200, 140 mg, yield: 21%). m/z 669.19 [M+1]$^+$; TLC System: 10% Acetone in dichloromethane. R$_f$-0.85.

Example 257—Preparation of Compound 201

The synthesis of Compound 201 followed the procedure of General Procedure 5 following:

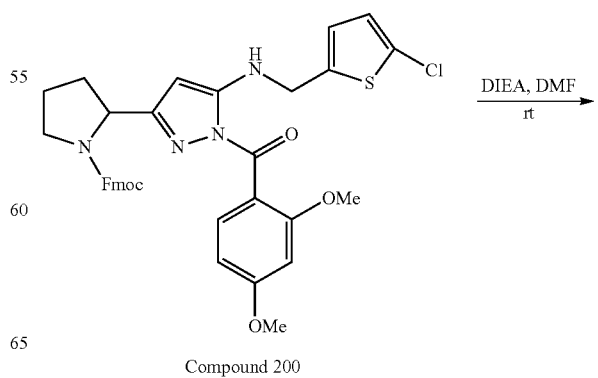

-continued

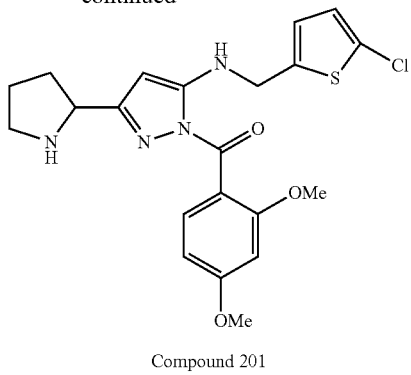

Compound 201

To a solution of (9H-fluoren-9-yl)methyl 2-(5-(((5-chlorothiophen-2-yl)methyl)amino)-1-(2,4-dimethoxybenzoyl)-1H-pyrazol-3-yl)pyrrolidine-1-carboxylate (140 mg, 0.20 mmol) in dimethylformamide (2 mL) was added diisopropylethylamine (DIEA, 142 mg, 1.70 mmol). The reaction mixture was stirred for 2 hr, and then evaporated under reduced pressure. The mixture was diluted with water and extracted with ethyl acetate. The combined organic phases were dried over anhydrous sodium sulfate, filtered and evaporated under reduced pressure. The residue was purified by silica gel column chromatography (100-200 mesh), eluting with 5% Methanol/dichloromethane, to afford product (5-(((5-chlorothiophen-2-yl)methyl)amino)-3-(pyrrolidin-2-yl)-1H-pyrazol-1-yl)(2,4-dimethoxyphenyl)methanone (Compound 201, 45 mg, yield: 48%) as gummy liquid. m/z 447.24 [(M+1]$^+$; $^1$H NMR (400 MHz, DMSO-d$_6$) δ 9.64 (br s, 1H), 8.95 (br s, 1H), 9.11 (s, 1H), 7.84-7.81 (m, 1H), 7.39-7.37 (m, 1H), 7.02-6.98 (m, 2H), 6.67 (s, 1H), 6.60-6.57 (m, 1H), 5.72 (s, 1H), 4.50-4.37 (m, 3H), 3.83 (s, 3H), 3.74 (m, 3H), 3.19-3.14 (m, 2H), 2.22-2.17 (m, 1H), 1.96-1.88 (m, 3H); TLC System: 10% Methanol in chloroform. R$_f$-0.3.

Example 258—Preparation of Compound 202

The synthesis of Compound 202 followed the procedure of General Procedure 5 following:

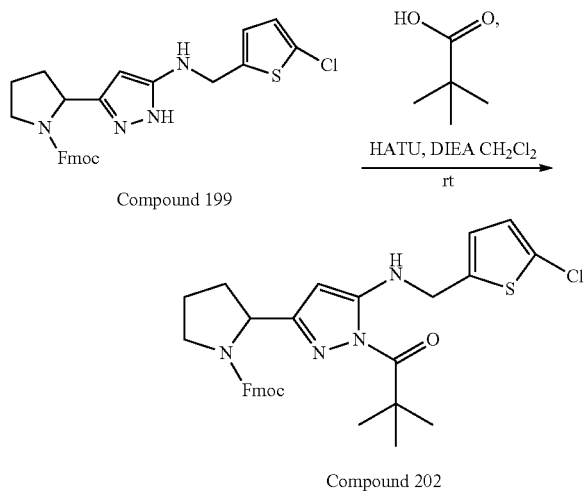

To a solution of tert-butyl 2-(5-(((5-chlorothiophen-2-yl)methyl)amino)-1H-pyrazol-3-yl)pyrrolidine-1-carboxylate (Compound 199, 500 mg, 0.99 mmol) and pivalic acid (121 mg, 1.18 mmol) in dichloromethane (5 mL) under nitrogen at room temperature, was added 1-[Bis(dimethylamino)methylene]-1H-1,2,3-triazolo[4,5-b]pyridinium 3-oxid hexafluorophosphate (HATU, 564 mg, 1.48 mmol), followed by diisopropylethylamine (DIEA, 0.32 mL, 1.48 mmol). The reaction mixture was stirred at room temperature for 16 hr, diluted with water (50 mL) and extracted with dichloromethane (2×25 mL). The combined organic phases were dried over anhydrous sodium sulfate, filtered and evaporated under reduced pressure. The residue was purified by preparative HPLC using acetonitrile-water as mobile phase to give product (9H-fluoren-9-yl)methyl 2-(5-(((5-chlorothiophen-2-yl)methyl)amino)-1-pivaloyl-1H-pyrazol-3-yl)pyrrolidine-1-carboxylate (Compound 202, 200 mg, yield: 35%). m/z 590.19 [M+1]$^+$; TLC System: 10% Acetone in dichloromethane. R$_f$-0.8.

Example 259—Preparation of Compound 203

The synthesis of Compound 203 followed the procedure of General Procedure 5 following:

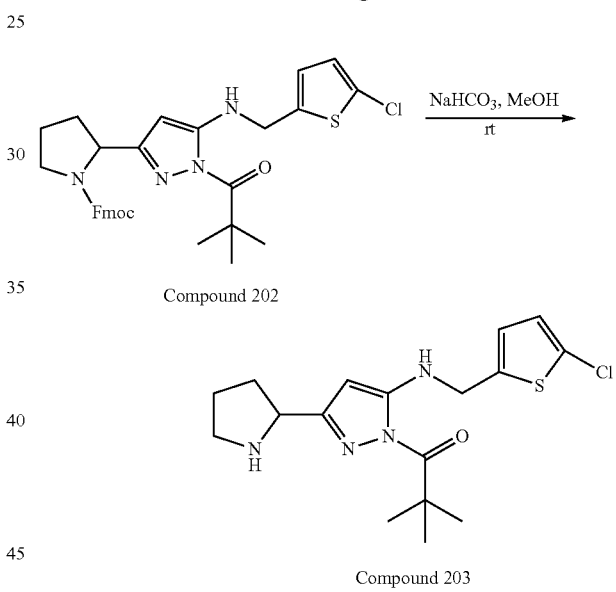

To a solution of (9H-fluoren-9-yl)methyl 2-(5-(((5-chlorothiophen-2-yl)methyl)amino)-1-pivaloyl-1H-pyrazol-3-yl)pyrrolidine-1-carboxylate (100 mg, 0.17 mmol) in methanol (2 mL) was added sodium bicarbonate (142 mg, 1.70 mmol). The reaction mixture was stirred for 16 hr, and then evaporated under reduced pressure. The mixture was diluted with water and extracted with ethyl acetate. The combined organic phases were dried over anhydrous sodium sulfate, filtered and evaporated under reduced pressure. The residue was purified by silica gel column chromatography (100-200 mesh), eluting with 8% Methanol/dichloromethane, to afford product 1-(5-(((5-chlorothiophen-2-yl)methyl)amino)-3-(pyrrolidin-2-yl)-1H-pyrazol-1-yl)-2,2-dimethylpropan-1-one (Compound 203, 35 mg, yield: 56%) as a gummy liquid. m/z 367.23 [(M+1]$^+$; $^1$H NMR (400 MHz, DMSO-d$_6$) δ 7.72-7.62 (m, 1H), 6.99 (s, 1H), 5.4 (s, 1H), 4.45-4.38 (m, 2H), 3.93-3.82 (m, 1H), 2.85-2.97 (m, 2H), 1.98-1.88 (m, 1H), 1.78-1.62 (m, 3H), 1.42 (s, 9H); TLC System: 10% Methanol in chloroform. R$_f$-0.35.

Example 260—Preparation of Compound 204

The synthesis of Compound 204 followed the procedure of General Procedure 5 following:

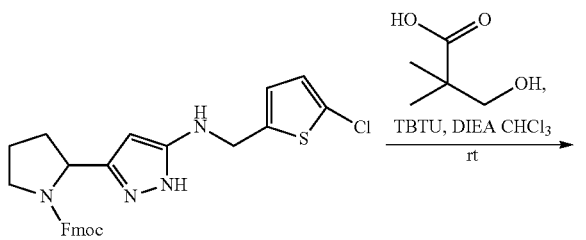

Compound 199

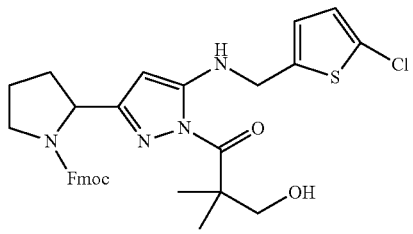

Compound 204

To a solution of (9H-fluoren-9-yl)methyl 2-(5-(((5-chlorothiophen-2-yl)methyl)amino)-1H-pyrazol-3-yl)pyrrolidine-1-carboxylate (Compound 199, 500 mg, 0.99 mmol) and 3-hydroxy-2,2-dimethylpropanoic acid (146 mg, 1.2 mmol) in chloroform (25 mL) under nitrogen at room temperature, was added O-(Benzotriazol-1-yl)-N,N,N',N'-tetramethyluronium tetrafluoroborate (TBTU, 365 mg, 1.1 mmol), followed by diisopropylethylamine (DIEA, 0.3 mL, 7.4 mmol). The reaction mixture was stirred at room temperature for 4 hr, diluted with water (50 mL) and extracted with chloroform (2×25 mL). The combined organic phases were dried over anhydrous sodium sulfate, filtered and evaporated under reduced pressure. The residue was purified by preparative HPLC using acetonitrile-water as mobile phase to give product (9H-fluoren-9-yl)methyl 2-(5-(((5-chlorothiophen-2-yl)methyl)amino)-1-(3-hydroxy-2,2-dimethylpropanoyl)-1H-pyrazol-3-yl)pyrrolidine-1-carboxylate (Compound 204, 250 mg, yield: 42%). m/z 605.19 [M+1]$^+$; TLC System: 10% Methanol in dichloromethane. $R_f$-0.9.

Example 261—Preparation of Compound 205

The synthesis of Compound 205 followed the procedure of General Procedure 5 following:

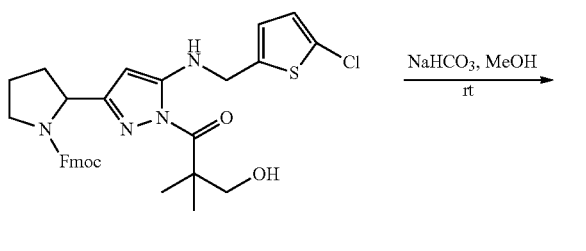

Compound 204

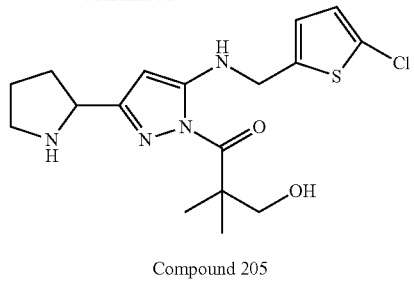

Compound 205

To a solution of (9H-fluoren-9-yl)methyl 2-(5-(((5-chlorothiophen-2-yl)methyl)amino)-1-(3-hydroxy-2,2-dimethylpropanoyl)-1H-pyrazol-3-yl)pyrrolidine-1-carboxylate (100 mg, 0.16 mmol) in methanol (2 mL) was added sodium bicarbonate (139 mg, 1.65 mmol). The reaction mixture was stirred for 16 hr, and then evaporated under reduced pressure. The mixture was diluted with water and extracted with ethyl acetate. The combined organic phases were dried over anhydrous sodium sulfate, filtered and evaporated under reduced pressure. The residue was purified by silica gel column chromatography (100-200 mesh), eluting with 5% Methanol/dichloromethane, to afford product 1-(5-(((5-chlorothiophen-2-yl)methyl)amino)-3-(pyrrolidin-2-yl)-1H-pyrazol-1-yl)-3-hydroxy-2,2-dimethylpropan-1-one (Compound 205, 15 mg, yield: 24%) as a semi solid. m/z 383.23 [(M+1]$^+$; $^1$H NMR (400 MHz, DMSO-d$_6$) δ 7.72-7.62 (m, 1H), 6.99 (s, 1H), 5.4 (s, 1H), 4.84-4.83 (m, 1H), 4.45-4.38 (m, 2H), 3.93-3.82 (m, 1H), 2.85-2.97 (m, 2H), 2.78-2.81 (m, 1H), 1.98-1.88 (m, 1H), 1.78-1.62 (m, 3H), 1.42 (s, 6H); TLC System: 5% Methanol in chloroform. $R_f$-0.3.

Example 262—Preparation of Compound 206

The synthesis of Compound 206 followed the procedure of General Procedure 5 following:

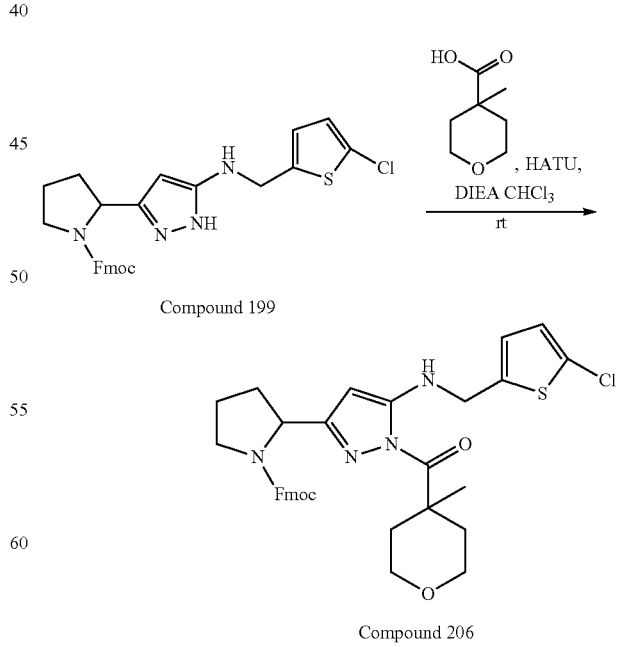

To a solution of (9H-fluoren-9-yl)methyl 2-(5-(((5-chlorothiophen-2-yl)methyl)amino)-1H-pyrazol-3-yl)pyrrolidine- 1-carboxylate (Compound 199, 500 mg, 0.99 mmol) and 4-methyltetrahydro-2H-pyran-4-carboxylic acid (143 mg, 0.99 mmol) in dichloromethane (5 mL) under nitrogen at room temperature, was added 1-[Bis(dimethylamino)methylene]-1H-1,2,3-triazolo[4,5-b]pyridinium 3-oxid hexafluorophosphate (HATU, 564 mg, 1.48 mmol), followed by diisopropylethylamine (DIEA, 0.32 mL, 1.48 mmol). The reaction mixture was stirred at room temperature for 16 hr, diluted with water (50 mL) and extracted with dichloromethane (2×25 mL). The combined organic phases were dried over anhydrous sodium sulfate, filtered and evaporated under reduced pressure. The residue was purified by preparative HPLC using acetonitrile-water as mobile phase to give product (9H-fluoren-9-yl)methyl 2-(5-(((5-chlorothiophen-2-yl)methyl)amino)-1-(4-methyltetrahydro-2H-pyran-4-carbonyl)-1H-pyrazol-3-yl)pyrrolidine-1-carboxylate (Compound 206, 110 mg, yield: 18%). m/z 632.19 [M+1]⁺; TLC System: 10% Acetone in dichloromethane. $R_f$-0.9.

Example 263—Preparation of Compound 207

The synthesis of Compound 207 followed the procedure of General Procedure 5 following:

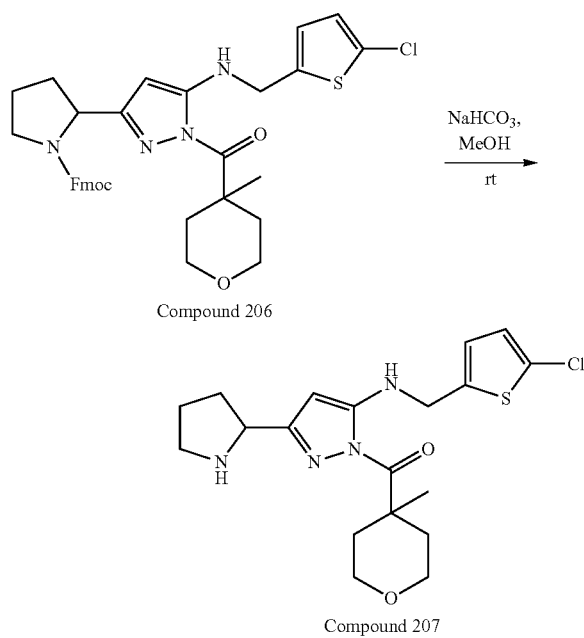

Compound 206

Compound 207

To a solution of (9H-fluoren-9-yl)methyl 2-(5-(((5-chlorothiophen-2-yl)methyl)amino)-1-(4-methyltetrahydro-2H-pyran-4-carbonyl)-1H-pyrazol-3-yl)pyrrolidine-1-carboxylate (100 mg, 0.16 mmol) in methanol (2 mL) was added sodium bicarbonate (139 mg, 1.65 mmol). The reaction mixture was stirred for 16 hr, and then evaporated under reduced pressure. The mixture was diluted with water and extracted with ethyl acetate. The combined organic phases were dried over anhydrous sodium sulfate, filtered and evaporated under reduced pressure. The residue was purified by silica gel column chromatography (100-200 mesh), eluting with 5% Methanol/dichloromethane, to afford product (5-(((5-chlorothiophen-2-yl)methyl)amino)-3-(pyrrolidin-2-yl)-1H-pyrazol-1-yl)(4-methyltetrahydro-2H-pyran-4-yl) methanone (Compound 207, 15 mg, yield: 24%) as a semi solid. m/z 410.31 [(M+1]⁺; ¹H NMR (400 MHz, DMSO-d₆) δ 8.81 (br s, 1H), 7.85 (br s, 1H), 6.96 (s, 2H), 5.60 (s, 1H), 4.54-4.43 (m, 2H), 3.78 (br s, 2H), 3.45 (br s, 2H), 3.22 (br s, 2H), 2.43-2.21 (br s, 3H), 1.98-1.89 (m, 3H), 1.75 (br s, 2H), 1.54-1.50 (m, 3H); TLC System: 10% Methanol in chloroform. $R_f$-0.35.

Example 264—Preparation of Compound 208

The synthesis of Compound 208 followed the procedure of General Procedure 5 following:

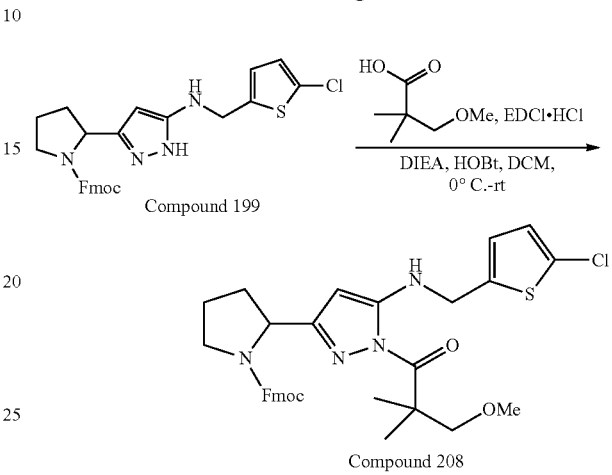

Compound 199

Compound 208

To a cooled (0° C.) solution of 3-methoxy-2,2-dimethylpropanoic acid (200 mg, 1.57 mmol) in dichloromethane (15 mL) under nitrogen was added 1-(3-dimethylaminopropyl)-3-ethylcarbodiimide hydrochloride (EDCI.HCl, 191 mg, 3.91 mmol), followed by hydroxybenzotriazole (HOBt, 135 mg, 1.3 mmol). The reaction mixture was stirred for 10 minutes, then to the mixture was added diisopropylethylamine (DIEA, 0.69 mL, 3.91 mmol), followed by (9H-fluoren-9-yl)methyl 2-(5-(((5-chlorothiophen-2-yl)methyl)amino)-1H-pyrazol-3-yl)pyrrolidine-1-carboxylate (Compound 199, 500 mg, 1.30 mmol). The reaction was monitored by LC-MS, and after 16 hr at room temperature the reaction mixture was poured into water (50 mL) and extracted with dichloromethane (2×25 mL). The combined organic phases were dried over anhydrous sodium sulfate, filtered and evaporated under reduced pressure. The residue was purified by silica gel column chromatography (100-200 mesh), eluting with 20% Ethyl acetate/Petroleum ether, to afford product (9H-fluoren-9-yl)methyl 2-(5-(((5-chlorothiophen-2-yl)methyl)amino)-1-(3-methoxy-2,2-dimethylpropanoyl)-1H-pyrazol-3-yl)pyrrolidine-1-carboxylate (Compound 208, 200 mg, yield: 31%) m/z 497.26 [M+1]⁺; TLC System: 70% Ethyl acetate in petroleum ether. $R_f$-0.7.

Example 265—Preparation of Compound 209

The synthesis of Compound 209 followed the procedure of General Procedure 5 following:

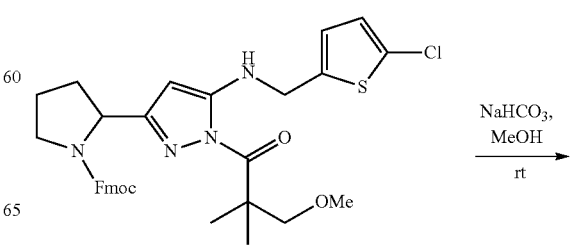

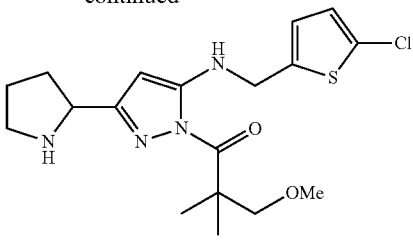

To a solution of (9H-fluoren-9-yl)methyl 2-(5-(((5-chlorothiophen-2-yl)methyl)amino)-1-(3-methoxy-2,2-dimethylpropanoyl)-1H-pyrazol-3-yl)pyrrolidine-1-carboxylate (180 mg, 0.29 mmol) in methanol (2 mL) was added sodium bicarbonate (200 mg, 2.91 mmol). The reaction mixture was stirred for 16 hr, and then evaporated under reduced pressure. The mixture was diluted with water and extracted with ethyl acetate. The combined organic phases were dried over anhydrous sodium sulfate, filtered and evaporated under reduced pressure. The residue was purified by silica gel column chromatography (100-200 mesh), eluting with 8% Methanol/dichloromethane, to afford product 1-(5-(((5-chlorothiophen-2-yl)methyl)amino)-3-(pyrrolidin-2-yl)-1H-pyrazol-1-yl)-3-methoxy-2,2-dimethylpropan-1-one (Compound 209, 15 mg, yield: 24%) as a semi solid. m/z 397.25 [(M+1)]$^+$; $^1$H NMR (400 MHz, CDCl$_3$) δ 7.51-7.50 (m, 1H), 6.80-6.79 (m, 1H), 6.76-6.75 (m, 1H), 5.42 (s, 1H), 4.64-4.61 (m, 1H), 4.36-4.35 (m, 2H), 3.79 (s, 2H), 3.41-3.40 (m, 1H), 3.27 (s, 3H), 2.37-2.32 (m, 1H), 2.17-1.97 (m, 4H), 1.42 (s, 6H); TLC System: 10% Methanol in chloroform. R$_f$-0.2.

Example 266—Preparation of Intermediate 60

The synthesis of Intermediate 60 followed the procedure of General Procedure 7 following:

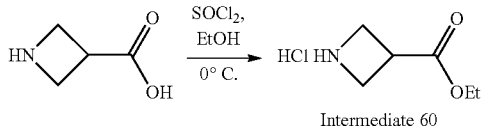

To a cooled solution (0° C.) of azetidine-3-carboxylic acid (50 g, 494 mmol) in Ethanol (500 mL) was added thionyl chloride (110 mL, 1483 mmol) dropwise. After stirring at this temperature for 2 hours, the mixture was concentrated under reduced pressure. The mixture was co-distilled with benzene (3×50 mL) and concentrated under reduced pressure to give ethyl azetidine-3-carboxylate hydrochloride (Intermediate 60, 70 g, yield: 96%) as a gummy liquid that was used without further purification into the next step. m/z 130.03 [(M−HCl)+1]$^+$; TLC System: 10% Methanol-chloroform; R$_f$-0.6.

Example 267—Preparation of Intermediate 61

The synthesis of Intermediate 61 followed the procedure of General Procedure 7 following:

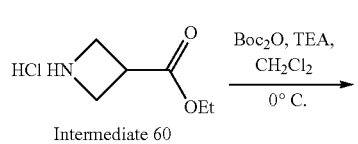

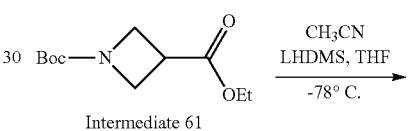

To a cooled solution (0° C.) of ethyl azetidine-3-carboxylate hydrochloride (70 g, 424 mmol) in dichloromethane (700 mL) was added triethylamine (119 mL, 848 mmol) dropwise over 30 min, followed by di-tert butyl dicarbonate (111 g, 509 mmol). After stirring at this temperature for 3 hours, the mixture was concentrated under reduced pressure. The mixture was diluted with water (20 mL) and extracted into dichloromethane (3×100 mL). The combined organic layers were washed with brine (2×10 mL), dried over sodium sulfate, filtered and concentrated under reduced pressure to give 1-(tert-butyl) 3-ethyl azetidine-1,3-dicarboxylate (Intermediate 61, 40 g, yield: 42%) as an oily residue that was used without further purification into the next step. m/z 230.23 [M+H]$^+$; TLC System: 10% Methanol-dichloromethane; R$_f$-0.7.

Example 268—Preparation of Intermediate 62

The synthesis of Intermediate 62 followed the procedure of General Procedure 2 following:

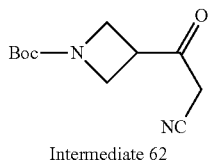

To a cooled (0° C.) solution of 1-(tert-butyl) 3-ethyl azetidine-1,3-dicarboxylate (Intermediate 61, 1 g, 4.36 mmol in THF (50 mL), dry acetonitrile (0.32 mL, 8.7 mmol) was added. After 10 min, LHDMS (1M in THF, 8.7 mL, 8.7 mmol) was added. After stirring at 0° C. for 2 hours, the mixture was quenched with saturated citric acid solution until pH=5 and extracted into Ethyl acetate (3×50 mL). The combined organic layers were dried over sodium sulfate, filtered and concentrated under reduced pressure to give tert-butyl 3-(2-cyanoacetyl)azetidine-1-carboxylate (Intermediate 62, 1.2 g, yield: 99%) as an oily residue that was used without further purification into the next step. m/z 225.02 [M+H]$^+$; TLC System: 10% Methanol-dichloromethane; R$_f$-0.5.

Example 269—Preparation of Compound 210

The synthesis of Compound 210 followed the procedure of General Procedure 3 following:

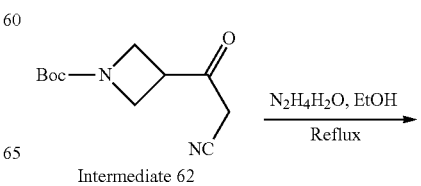

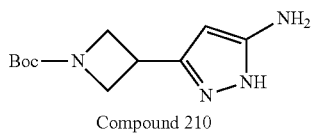

Compound 210

To a solution of tert-butyl 3-(2-cyanoacetyl)azetidine-1-carboxylate (Intermediate 62, 1.2 g, 5.35 mmol) in ethanol (12 mL) was added hydrazine hydrate (N$_2$H$_4$.H$_2$O, 1.34 mL, 8.0 mmol) and the reaction mixture was then heated to 90° C. for 5 hours. The reaction mixture was cooled to room temperature and the volatiles were evaporated. The residue was purified by neutral alumina column chromatography (100-300 mesh), eluting with 2% MeOH-dichloromethane, to afford tert-butyl 3-(5-amino-1H-pyrazol-3-yl)azetidine-1-carboxylate (Compound 210, 600 mg, 47%) as an off white solid; m/z 239.13 [M+H]+; TLC System: 10% Methanol-dichloromethane. R$_f$-0.4.

Example 270—Preparation of Compound 211

The synthesis of Compound 211 followed the procedure of General Procedure 4 following:

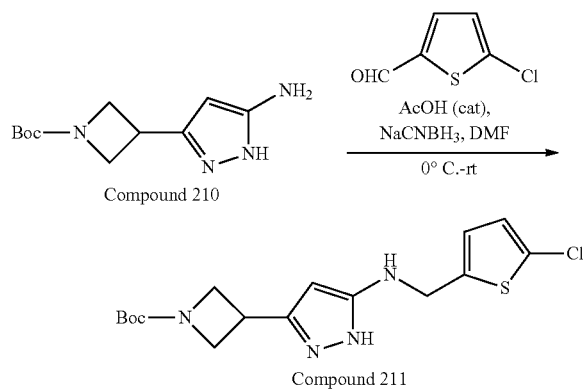

To a cooled solution (0° C.) of tert-butyl 3-(5-amino-1H-pyrazol-3-yl)azetidine-1-carboxylate (Compound 210, 11 g, 46.2 mmol) in dry DMF (40 mL) was added 5-chlorothiophene-2-carbaldehyde (7.12 mL, 69.3 mmol) and acetic acid (12 mL). The reaction mixture was stirred at room temperature for 2 hours. (Formation of imine was observed as a less polar spot on TLC). The reaction mixture was cooled (0° C.) and sodium cyanoborohydride (6.18 g, 92.4 mmol) was added portionwise and a catalytic amount of acetic acid. After 2 hours, the reaction mixture was quenched with ice-cold water (50 mL), and extracted into Ethyl acetate (3×100 mL). The combined organic layers were washed with saturated NaHCO$_3$ (2×50 mL), water (2×50 mL) and brine (2×50 mL) and dried over sodium sulfate, filtered and concentrated under reduced pressure. The residue was purified by silica gel column chromatography (100-200 mesh), eluting with 2% methanol/dichloromethane, to afford tert-butyl 3-(5-(((5-chlorothiophen-2-yl)methyl)amino)-1H-pyrazol-3-yl)azetidine-1-carboxylate (Compound 211, 7 g, 41%); m/z 368.13 [M+H]+; TLC System: 10% Methanol in dichloromethane R$_f$-0.5.

Example 271—Preparation of Compound 212

The synthesis of Compound 212 followed the procedure of General Procedure 5 following:

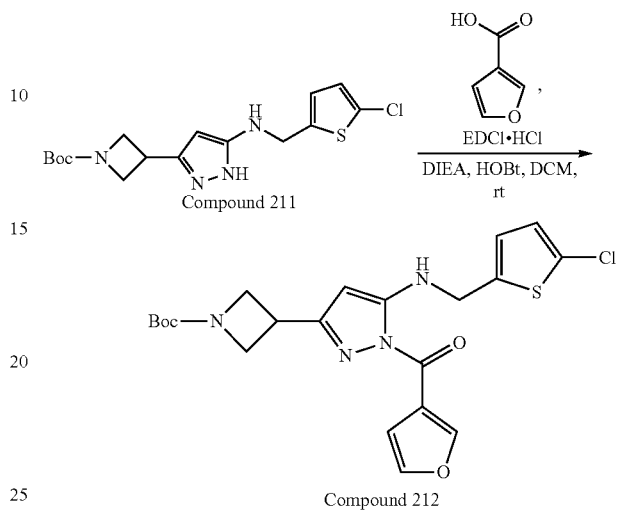

To a cooled (0° C.) solution of furan-3-carboxylic acid (182 mg, 1.63 mmol) in dichloromethane (10 mL) under nitrogen was added 1-(3-dimethylaminopropyl)-3-ethylcarbodiimide hydrochloride (EDCI.HCl, 388 mg, 2.0 mmol), followed by hydroxybenzotriazole (HOBt, 135 mg, 4 mmol). The reaction mixture was stirred for 10 minutes, cooled (0° C.) and then to the mixture was added diisopropylethylamine (DIEA, 0.9 mL, 5.4 mmol), followed by tert-butyl 3-(5-(((5-chlorothiophen-2-yl)methyl)amino)-1H-pyrazol-3-yl)azetidine-1-carboxylate (Compound 211, 500 mg, 1.35 mmol). The reaction was monitored by LC-MS, and after 16 hr at room temperature the reaction mixture was poured into water (25 mL) and extracted with dichloromethane (2×10 mL). The combined organic phases were dried over anhydrous sodium sulfate, filtered and evaporated under reduced pressure. The residue was purified by silica gel column chromatography (100-200 mesh), eluting with 10% ethyl acetate/hexane, to afford tert-butyl 3-(5-(((5-chlorothiophen-2-yl)methyl)amino)-1-(furan-3-carbonyl)-1H-pyrazol-3-yl)azetidine-1-carboxylate (Compound 212, 230 mg, yield: 35%) as an off white solid. m/z 463.37 [M+1]+; TLC System: 30% Ethyl acetate in hexane. R$_f$-0.5.

Example 272—Preparation of Compound 213

The synthesis of Compound 213 followed the procedure of General Procedure 5 following:

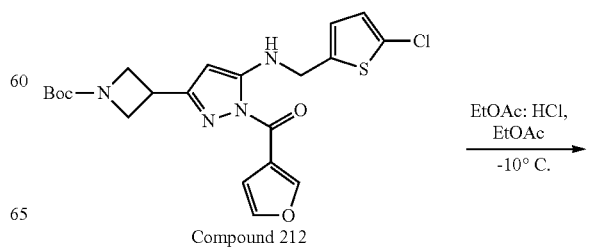

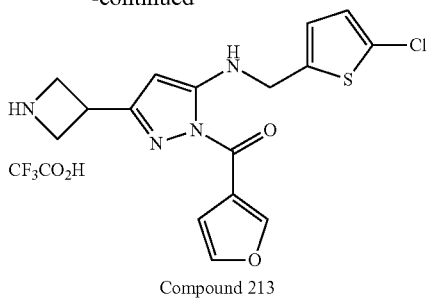

Compound 213

To a cooled (−10° C.) solution of tert-butyl 3-(5-(((5-chlorothiophen-2-yl)methyl)amino)-1-(furan-3-carbonyl)-1H-pyrazol-3-yl)azetidine-1-carboxylate (230 mg, 0.49 mmol) in ethyl acetate (5 mL) was added a solution of hydrogen chloride (1M) in ethyl acetate (8 mL). The reaction mixture was stirred for 2 hr, and then evaporated under reduced pressure, triturated with diethyl ether and acetone and the residue was purified by preparative HPLC using acetonitrile-water-TFA as mobile phase to give product (3-(azetidin-3-yl)-5-(((5-chlorothiophen-2-yl)methyl)amino)-1H-pyrazol-1-yl)(furan-3-yl)methanone 2,2,2-trifluoroacetate (Compound 213, 10 mg, yield: 8%) as an off white solid. m/z 363.14 [(M-TFA)+1]$^+$; $^1$H NMR (400 MHz, DMSO-$d_6$) δ 8.94 (s, 1H), 8.74 (br s, 1H), 7.96-7.92 (m, 1H), 7.89-7.88 (m, 1H), 7.07 (s, 1H), 6.98-6.96 (m, 2H), 5.58 (s, 1H), 4.50-4.49 (m, 2H), 4.26-4.22 (m, 2H), 4.13-3.95 (m, 3H); TLC System: 10% Ethyl acetate in petroleum ether. $R_f$-0.1.

Example 273—Preparation of Compound 214

The synthesis of Compound 214 followed the procedure of General Procedure 5 following:

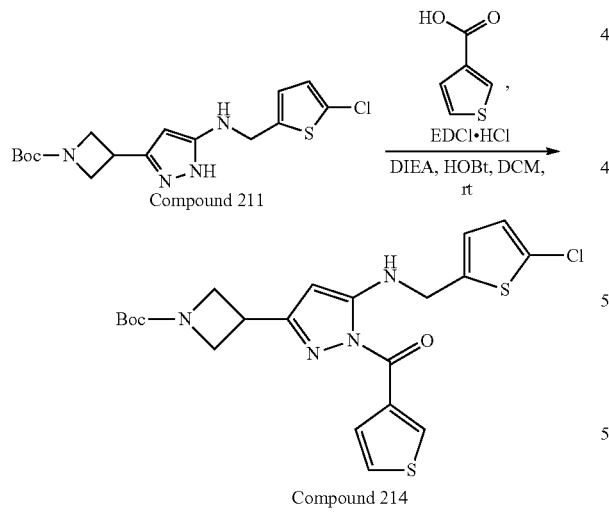

To a cooled (0° C.) solution of thiophene-3-carboxylic acid (208 mg, 1.63 mmol) in dichloromethane (10 mL) under nitrogen was added 1-(3-dimethylaminopropyl)-3-ethylcarbodiimide hydrochloride (EDCI.HCl, 388 mg, 2.0 mmol), followed by hydroxybenzotriazole (HOBt, 135 mg, 4 mmol). The reaction mixture was stirred for 10 minutes, cooled (0° C.) and then to the mixture was added diisopropylethylamine (DIEA, 0.9 mL, 5.4 mmol), followed by tert-butyl 3-(5-(((5-chlorothiophen-2-yl)methyl)amino)-1H-pyrazol-3-yl)azetidine-1-carboxylate (Compound 211, 500 mg, 1.35 mmol). The reaction was monitored by LC-MS, and after 16 hr at room temperature the reaction mixture was poured into water (25 mL) and extracted with dichloromethane (2×10 mL). The combined organic phases were dried over anhydrous sodium sulfate, filtered and evaporated under reduced pressure. The residue was purified by silica gel column chromatography (100-200 mesh), eluting with 10% ethyl acetate/hexane, to afford tert-butyl 3-(5-(((5-chlorothiophen-2-yl)methyl)amino)-1-(thiophene-3-carbonyl)-1H-pyrazol-3-yl)azetidine-1-carboxylate (Compound 214, 230 mg, yield: 36%) as an off white solid. m/z 479.37 [M+1]$^+$; TLC System: 30% Ethyl acetate in hexane. $R_f$-0.5.

Example 274—Preparation of Compound 215

The synthesis of Compound 215 followed the procedure of General Procedure 5 following:

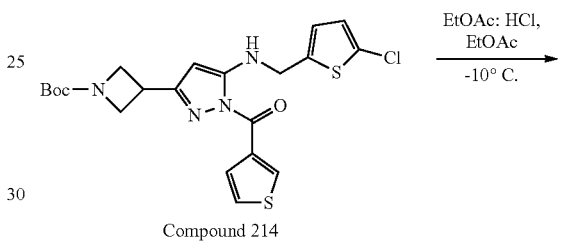

Compound 214

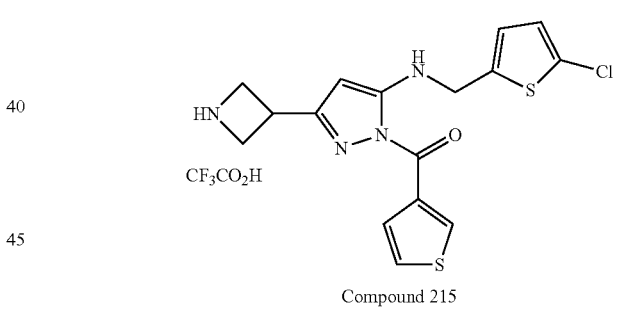

Compound 215

To a cooled (−10° C.) solution of tert-butyl 3-(5-(((5-chlorothiophen-2-yl)methyl)amino)-1-(thiophene-3-carbonyl)-1H-pyrazol-3-yl)azetidine-1-carboxylate (230 mg, 0.48 mmol) in ethyl acetate (5 mL) was added a solution of hydrogen chloride (1M) in ethyl acetate (8 mL). The reaction mixture was stirred for 2 hr, and then evaporated under reduced pressure, triturated with diethyl ether and acetone and the residue was purified by preparative HPLC using acetonitrile-water-TFA as mobile phase to give product (3-(azetidin-3-yl)-5-(((5-chlorothiophen-2-yl)methyl)amino)-1H-pyrazol-1-yl)(thiophene-3-yl)methanone 2,2,2-trifluoroacetate (Compound 215, 10 mg, yield: 7%) as an off white solid. m/z 379.13 [(M-TFA)+1]$^+$; $^1$H NMR (400 MHz, DMSO-$d_6$) δ 9.01 (s, 1H), 9.00 (br s, 1H), 7.98-7.94 (m, 1H), 7.81-7.79 (m, 1H), 7.68-7.67 (m, 1H), 7.09-6.97 (m, 2H), 5.63 (s, 1H), 4.51-4.49 (m, 2H), 4.26-4.21 (m, 2H), 4.12-3.93 (m, 3H); TLC System: 10% Ethyl acetate in petroleum ether. $R_f$-0.1.

Example 275—Preparation of Compound 216

The synthesis of Compound 216 followed the procedure of General Procedure 5 following:

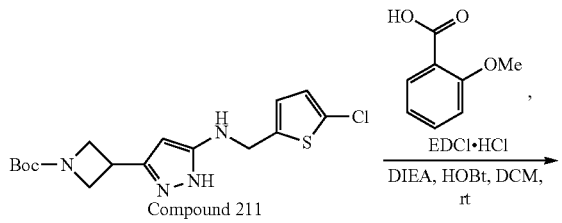

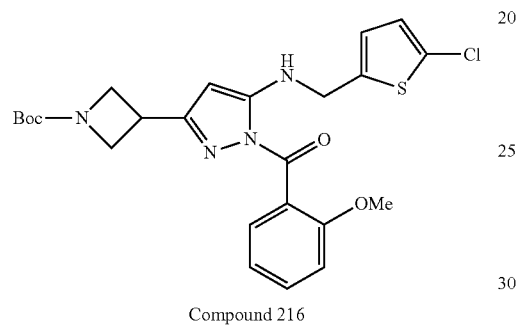

Compound 216

To a cooled (0° C.) solution of 2-methoxybenzoic acid (247 mg, 1.63 mmol) in dichloromethane (10 mL) under nitrogen was added 1-(3-dimethylaminopropyl)-3-ethylcarbodiimide hydrochloride (EDCI.HCl, 388 mg, 2.0 mmol), followed by hydroxybenzotriazole (HOBt, 135 mg, 4 mmol). The reaction mixture was stirred for 10 minutes, cooled (0° C.) and then to the mixture was added diisopropylethylamine (DIEA, 0.9 mL, 5.4 mmol), followed by tert-butyl 3-(5-(((5-chlorothiophen-2-yl)methyl)amino)-1H-pyrazol-3-yl)azetidine-1-carboxylate (Compound 211, 500 mg, 1.35 mmol). The reaction was monitored by LC-MS, and after 16 hr at room temperature the reaction mixture was poured into water (25 mL) and extracted with dichloromethane (2×10 mL). The combined organic phases were dried over anhydrous sodium sulfate, filtered and evaporated under reduced pressure. The residue was purified by silica gel column chromatography (100-200 mesh), eluting with 10% ethyl acetate/hexane, to afford tert-butyl 3-(5-(((5-chlorothiophen-2-yl)methyl)amino)-1-(2-methoxybenzoyl)-1H-pyrazol-3-yl)azetidine-1-carboxylate (Compound 216, 150 mg, yield: 25%) as an off white solid. m/z 503.37 [M+1]$^+$; TLC System: 30% Ethyl acetate in hexane. $R_f$-0.5.

Example 276—Preparation of Compound 217

The synthesis of Compound 217 followed the procedure of General Procedure 5 following:

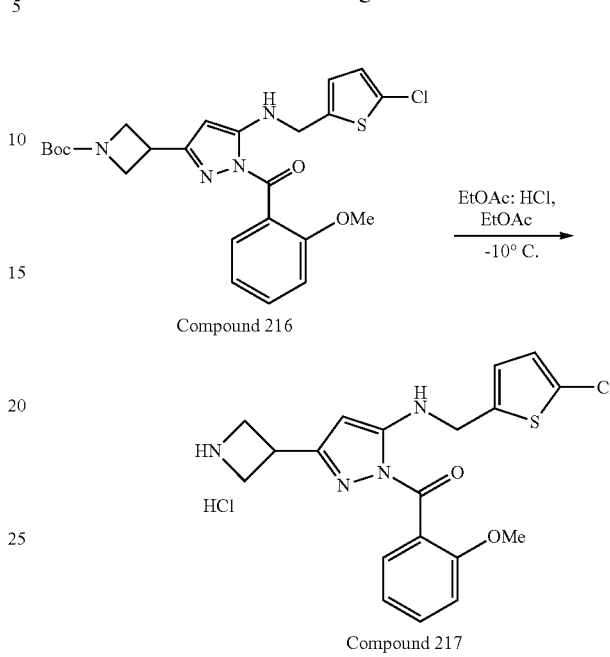

Compound 217

To a cooled (−10° C.) solution of tert-butyl 3-(5-(((5-chlorothiophen-2-yl)methyl)amino)-1-(2-methoxybenzoyl)-1H-pyrazol-3-yl)azetidine-1-carboxylate (150 mg, 0.29 mmol) in ethyl acetate (5 mL) was added a solution of hydrogen chloride (1M) in ethyl acetate (8 mL). The reaction mixture was stirred for 2 hr, and then evaporated under reduced pressure, triturated with diethyl ether and acetone and the residue was purified by preparative HPLC using acetonitrile-water as mobile phase to give product (3-(azetidin-3-yl)-5-(((5-chlorothiophen-2-yl)methyl)amino)-1H-pyrazol-1-yl)(2-methoxyphenyl)methanone hydrochloride (Compound 217, 8 mg, yield: 5%) as an off white solid. m/z 403.24 [(M−HCl)+1]$^+$; $^1$H NMR (400 MHz, CDCl$_3$) δ 7.51-7.38 (m, 3H), 7.06-6.94 (m, 2H), 6.86 (s, 1H), 6.78 (s, 1H), 5.51 (s, 1H), 4.46-4.43 (m, 2H), 4.25-4.16 (m, 4H), 3.82 (s, 3H), 3.81-3.76 (m, 1H); TLC System: 50% Ethyl acetate in petroleum ether. R-0.1.

Example 277—Preparation of Compound 218

The synthesis of Compound 218 followed the procedure of General Procedure 5 following:

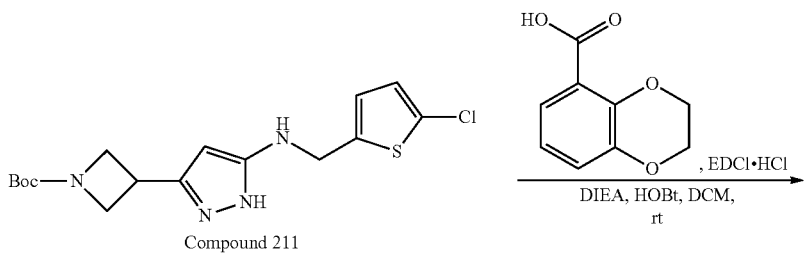

Compound 211

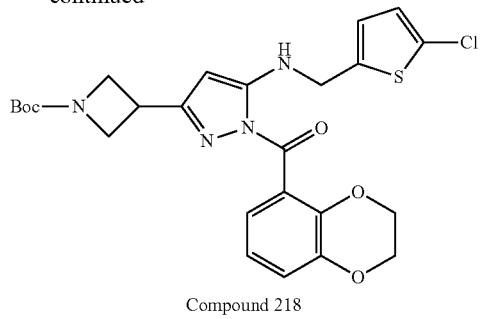

Compound 218

To a cooled (0° C.) solution of 2-methoxybenzoic acid (293 mg, 1.63 mmol) in dichloromethane (10 mL) under nitrogen was added 1-(3-dimethylaminopropyl)-3-ethylcarbodiimide hydrochloride (EDCI.HCl, 388 mg, 2.0 mmol), followed by hydroxybenzotriazole (HOBt, 135 mg, 4 mmol). The reaction mixture was stirred for 10 minutes, cooled (0° C.) and then to the mixture was added diisopropylethylamine (DIEA, 0.9 mL, 5.4 mmol), followed by tert-butyl 3-(5-(((5-chlorothiophen-2-yl)methyl)amino)-1H-pyrazol-3-yl)azetidine-1-carboxylate (Compound 211, 500 mg, 1.35 mmol). The reaction was monitored by LC-MS, and after 16 hr at room temperature the reaction mixture was poured into water (25 mL) and extracted with dichloromethane (2×10 mL). The combined organic phases were dried over anhydrous sodium sulfate, filtered and evaporated under reduced pressure. The residue was purified by silica gel column chromatography (100-200 mesh), eluting with 10% ethyl acetate/hexane, to afford tert-butyl 3-(5-(((5-chlorothiophen-2-yl)methyl)amino)-1-(2-methoxybenzoyl)-1H-pyrazol-3-yl)azetidine-1-carboxylate (Compound 218, 100 mg, yield: 18%) as an off white solid. m/z 531.37 [M+1]$^+$; TLC System: 30% Ethyl acetate in hexane. R$_f$-0.5.

Example 278—Preparation of Compound 219

The synthesis of Compound 219 followed the procedure of General Procedure 5 following:

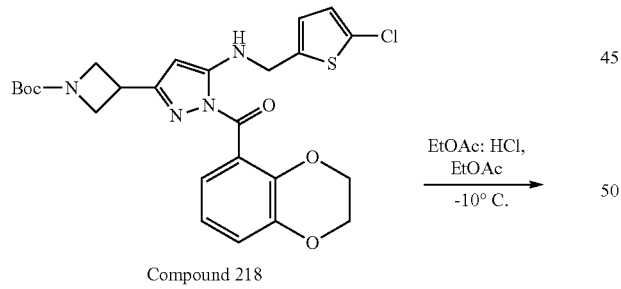

Compound 218

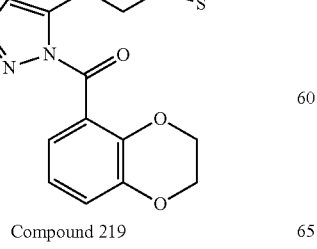

Compound 219

To a cooled (−10° C.) solution of tert-butyl 3-(5-(((5-chlorothiophen-2-yl)methyl)amino)-1-(2-methoxybenzoyl)-1H-pyrazol-3-yl)azetidine-1-carboxylate (100 mg, 0.19 mmol) in ethyl acetate (5 mL) was added a solution of hydrogen chloride (1M) in ethyl acetate (8 mL). The reaction mixture was stirred for 2 hr, and then evaporated under reduced pressure, triturated with diethyl ether and acetone and the residue was purified by preparative HPLC using acetonitrile-water-TFA as mobile phase to give product (3-(azetidin-3-yl)-5-(((5-chlorothiophen-2-yl)methyl)amino)-1H-pyrazol-1-yl)(2-methoxyphenyl)methanone 2,2,2-trifluoroacetate (Compound 219, 2 mg, yield: 2%) as an oily liquid. m/z 431.2 [(M-TFA)+1]$^+$; $^1$H NMR (400 MHz, DMSO-d$_6$) δ 7.84-7.81 (m, 1H), 7.02-6.87 (m, 5H), 5.63 (s, 1H), 4.50-4.49 (m, 4H), 4.14-4.09 (m, 2H), 3.94-3.85 (m, 2H); TLC System: 50% Ethyl acetate in petroleum ether. R$_f$-0.1.

The contents of all references, patents, and published applications cited herein are hereby incorporated by reference in their entirety and for all purposes.

While the invention has been described in detail with reference to certain preferred embodiments thereof, it will be understood that modifications and variations are within the spirit and scope of that which is described and claimed.

What is claimed is:
1. A compound with the following structure:

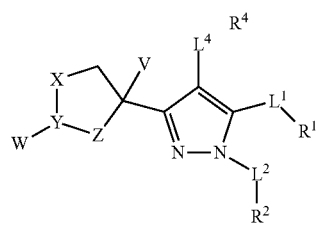

or pharmaceutically acceptable salt or ester thereof, wherein:
  $L^1$ is —NR$^5$—;
  $L^2$ is bond or —C(O)—, provided that when $L^2$ is bond, $R^2$ is hydrogen;
  $L^4$ is a bond;
  $R^1$ is substituted $C_1$-$C_4$ having one or more substituent groups selected from the group consisting of substituted or unsubstituted heteroaryl and substituted or unsubstituted heterocycloalkyl;
  $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, substituted or unsubstituted fused ring aryl, or substituted or unsubstituted heteroaryl;

$R^4$ is hydrogen, substituted or unsubstituted $C_1$-$C_4$ alkyl, or substituted or unsubstituted $C_1$-$C_4$ heteroalkyl;

$R^5$ is hydrogen, or substituted or unsubstituted $C_1$-$C_4$ alkyl;

V is hydrogen or substituted or unsubstituted alkyl;

W is absent, hydrogen, substituted or unsubstituted alkyl, substituted or unsubstituted heteroalkyl, substituted or unsubstituted alkenyl, substituted or unsubstituted heteroalkenyl, —C(O)$R^6$, —C(O)N$^6R^7$, —SO$_2R^6$, —SO$_2$NR$^6R^7$, where $R^6$ and $R^7$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted alkenyl, substituted or unsubstituted heteroalkenyl, substituted or unsubstituted cycloalkenyl, substituted or unsubstituted heterocycloalkenyl, substituted or unsubstituted aryl, or substituted or unsubstituted heteroaryl, wherein $R^6$ and $R^7$ can be combined if both are present to form a substituted or unsubstituted alkylene, or substituted or unsubstituted heteroalkylene;

X is a bond, substituted or unsubstituted methylene, substituted or unsubstituted ethylene, substituted or unsubstituted propylene, substituted or unsubstituted butylene, substituted or unsubstituted pentylene, —O—, or —NR$^8$—;

Y is a bond, substituted or unsubstituted methylene, substituted or unsubstituted ethylene, substituted or unsubstituted propylene, substituted or unsubstituted butylene, substituted or unsubstituted pentylene, —O—, or —N—, provided that when Y is —O—, W is absent; and Z is a bond, —C(O)—, substituted or unsubstituted methylene, substituted or unsubstituted ethylene, substituted or unsubstituted propylene, substituted or unsubstituted butylene, substituted or unsubstituted pentylene, —O—, or —NR$^9$—;

wherein $R^8$ and $R^9$ are independently hydrogen, substituted or unsubstituted alkyl, substituted or unsubstituted heteroalkyl, substituted or unsubstituted alkenyl, substituted or unsubstituted heteroalkenyl, —C(O)$R^6$, —C(O)NR$^6R^7$, —SO$_2R^6$, or —SO$_2$NR$^6R^7$, wherein $R^6$ and $R^7$ are as defined above; and provided that either at least one of X is —NR$^8$—, Y is —N—, or Z is —NR$^9$—; and wherein for any substituted or unsubstituted cycloalkyl, substituted or unsubstituted heterocycloalkyl, substituted or unsubstituted cycloalkenyl, or substituted or unsubstituted heterocycloalkenyl a monocyclic ring has 3-8 ring members, a bicyclic ring has 4-16 ring members, and a tricyclic ring has 5-24 ring members; and wherein for any substituted or unsubstituted aryl, substituted or unsubstituted fused ring aryl, or substituted or unsubstituted heteroaryl, each ring contains between 4-20 atoms.

2. The compound of claim 1, wherein X is selected from the group consisting of a bond, substituted or unsubstituted methylene, substituted or unsubstituted ethylene, substituted or unsubstituted propylene, substituted or unsubstituted butylene, and substituted or unsubstituted pentylene.

3. The compound of claim 2, wherein Z is selected from the group consisting of a bond, substituted or unsubstituted methylene, or substituted or unsubstituted ethylene, substituted or unsubstituted propylene, substituted or unsubstituted butylene, and substituted or unsubstituted pentylene.

4. The compound of claim 3, wherein Y is —N—, and W is hydrogen, substituted or unsubstituted alkyl, substituted or unsubstituted heteroalkyl, substituted or unsubstituted aryl, —C(O)$R^6$, —C(O)NR$^6R^7$, —SO$_2R^6$, or SO$_2$NR$^6R^7$, wherein $R^6$ and $R^7$ are independently substituted or unsubstituted alkyl, substituted or unsubstituted cycloalkyl, or substituted or unsubstituted heterocycloalkyl, or $R^6$ and $R^7$ can be combined if both are present to form a substituted or unsubstituted alkylene, or substituted or unsubstituted heteroalkylene.

5. The compound of claim 4, wherein X is selected from the group consisting of substituted or unsubstituted methylene, substituted or unsubstituted ethylene, substituted or unsubstituted propylene, substituted or unsubstituted butylene, and substituted or unsubstituted pentylene, and Z is a bond.

6. The compound of claim 4, wherein X is a bond, and Z is selected from the group consisting of substituted or unsubstituted methylene, substituted or unsubstituted ethylene, substituted or unsubstituted propylene, substituted or unsubstituted butylene, and substituted or unsubstituted pentylene.

7. The compound of claim 4, wherein X is selected from the group consisting of substituted or unsubstituted methylene, substituted or unsubstituted ethylene, substituted or unsubstituted propylene, substituted or unsubstituted butylene, and substituted or unsubstituted pentylene, and wherein Z is selected from the group consisting of substituted or unsubstituted methylene, substituted or unsubstituted ethylene, substituted or unsubstituted propylene, substituted or unsubstituted butylene, and substituted or unsubstituted pentylene.

8. The compound of claim 7, wherein X and Z are both branched alkylene and X and Z are covalently attached.

9. The compound of claim 4, wherein Z is selected from the group consisting of substituted methylene, substituted ethylene, substituted propylene, substituted butylene, and substituted pentylene, having one or more substituent groups selected from the group consisting of —OH, —NH$_2$, —SH, —CN, —CF$_3$, —NO$_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

10. The compound of claim 4, wherein X is selected from the group consisting of substituted or unsubstituted methylene, substituted or unsubstituted ethylene, substituted or unsubstituted propylene, substituted or unsubstituted butylene, and substituted or unsubstituted pentylene, and wherein Z is —C(O)—.

11. The compound of claim 4, wherein W is hydrogen.

12. The compound of claim 4, wherein W is selected from the group consisting of substituted or unsubstituted alkyl, substituted or unsubstituted heteroalkyl, substituted or unsubstituted alkenyl, substituted or unsubstituted heteroalkenyl, substituted or unsubstituted cycloalkyl, substituted or unsubstituted heterocycloalkyl, —C(O)$R^6$, —C(O)NR$^6R^7$, —SO$_2R^6$, and —SO$_2$NR$^6R^7$.

13. The compound of claim 12, wherein W is substituted alkyl, substituted heteroalkyl, substituted alkenyl, or substituted heteroalkenyl, having one or more substituent groups selected from the group consisting of —OH, —NH$_2$, —SH, —CN, —CF$_3$, —NO$_2$, oxo, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

14. The compound of claim 12, wherein W is —$COR^6$, —$C(O)NR^6R^7$, —$SO_2R^6$ or —$SO_2NR^6R^7$, and wherein $R^6$ and $R^7$ are selected from the group consisting of substituted or unsubstituted alkyl, substituted or unsubstituted heteroalkyl, substituted or unsubstituted aryl, and substituted or unsubstituted heteroaryl, or $R^6$ and $R^7$ combine to form a substituted or unsubstituted alkylene.

15. The compound of claim 1, wherein W is absent, X is —$NR^8$—, Y is a bond or substituted or unsubstituted alkylene, and Z is —$NR^9$—.

16. The compound of claim 15, wherein Y is selected from the group consisting of substituted or unsubstituted methylene, substituted or unsubstituted ethylene, substituted or unsubstituted propylene, substituted or unsubstituted butylene, and substituted or unsubstituted pentylene.

17. The compound of claim 16, wherein $R^8$ is selected from the group consisting of substituted or unsubstituted alkyl, substituted or unsubstituted heteroalkyl, substituted or unsubstituted alkenyl, substituted or unsubstituted heteroalkenyl, —$COR^6$, —$C(O)NR^6R^7$, —$SO_2R^6$, and —$SO_2NR^6R^7$, and wherein $R^9$ is selected from the group consisting of substituted or unsubstituted alkyl, substituted or unsubstituted heteroalkyl, substituted or unsubstituted alkenyl, substituted or unsubstituted heteroalkenyl, —$COR^6$, —$C(O)NR^6R^7$, $SO_2R^6$, and —$SO_2NR^6R^7$.

18. The compound of claim 1, wherein V is hydrogen or substituted or unsubstituted methyl.

19. The compound according to claim 1, wherein $R^1$ is substituted alkyl having one or more substituent groups selected from the group consisting of substituted or unsubstituted thiophenyl and substituted or unsubstituted phenyl.

20. The compound according to claim 19, wherein $R^1$ is substituted alkyl substituted by chloro-substituted thiophenyl.

21. The compound according to claim 1, wherein $R^2$ is hydrogen, substituted or unsubstituted alkyl, substituted or unsubstituted heteroalkyl, substituted or unsubstituted cycloalkyl, substituted or unsubstituted aryl, substituted or unsubstituted fused ring aryl, substituted or unsubstituted heteroaryl, or substituted or unsubstituted heterocycloalkyl.

22. The compound according to claim 21, wherein $L^2$ is bond, and $R^2$ is hydrogen.

23. The compound according to claim 21, wherein $L^2$ is —C(O)—, and $R^2$ is substituted or unsubstituted alkyl, substituted or unsubstituted heteroalkyl, substituted or unsubstituted cycloalkyl, substituted or unsubstituted aryl, substituted or unsubstituted fused ring aryl, substituted or unsubstituted heteroaryl, or substituted or unsubstituted heterocycloalkyl.

24. The compound according to claim 1, wherein $L^4$ is a bond, and $R^4$ is hydrogen.

25. The compound according to claim 1 as set forth in Table A, Table B, Table C, or Table D.

26. A pharmaceutical composition comprising a compound according to claim 1, or a compound as set forth in Table A, Table B, Table C, or Table D and a pharmaceutically acceptable excipient.

27. A method for treating a kallikrein-related disease or disorder in a subject, comprising administering a compound according to claim 1 to a subject in need thereof in an amount effective to treat said disease or disorder, wherein said kallikrein-related disorder is an ophthalmic disease selected from the group consisting of diabetic macular edema, age-related macular degeneration, and diabetic retinopathy.

28. The method according to claim 27, wherein said compound or pharmaceutical composition is administered in the form of an ophthalmic composition applied topically to the eye.

29. The method according to claim 28, wherein the ophthalmic composition is in the form of eye drops.

30. The method according to claim 27, wherein said compound or pharmaceutical composition is administered in the form of an ophthalmic composition via intravitreal injection.

31. The compound according to claim 23, wherein $R^2$ is substituted or unsubstituted aryl, substituted or unsubstituted fused ring aryl, or substituted or unsubstituted heteroaryl.

32. The compound according to claim 31, wherein $R^2$ is substituted or unsubstituted phenyl.

33. The compound according to claim 32, wherein $R^2$ is substituted phenyl having at least one halogen and one carboxylic acid substituent group.

34. The compound according to claim 33, wherein the halogen is selected from the group consisting of chlorine and fluorine.

35. The compound according to claim 34, wherein the halogen is chlorine.

36. The compound according to claim 24, wherein $L^4$ is a bond, and $R^4$ is substituted or unsubstituted alkyl, or substituted or unsubstituted heteroalkyl.

37. The compound according to claim 36, wherein $R^4$ is selected from the group consisting of methyl, cyano, and methoxy.

* * * * *